US011746157B2

(12) United States Patent
Anderson et al.

(10) Patent No.: US 11,746,157 B2
(45) Date of Patent: Sep. 5, 2023

(54) PSMA BINDING AGENTS AND USES THEREOF

(71) Applicant: Janssen Biotech, Inc., Horsham, PA (US)

(72) Inventors: Glenn Mark Anderson, Eagleville, PA (US); Tammy Bush, Perkasie, PA (US); Rosa Maria Fernandes Cardoso, Berwyn, PA (US); Ellen Chi, Del Mar, CA (US); Judith Ann Connor, Vista, CA (US); Thai Quang Dinh, Solana Beach, CA (US); Derrick Lemon Domingo, Carlsbad, CA (US); John Michael Jones, Ambler, PA (US); Colleen Kane, Flourtown, PA (US); Bethany Kay Mattson, Conoshohocken, PA (US); Theresa Marie McDevitt, Warminster, PA (US); Jill Marie Mooney, San Diego, CA (US); Richard Stephen Tawadros, Norristown, PA (US); Hong Mimi Zhou, San Diego, CA (US)

(73) Assignee: JANSSEN BIOTECH, INC., Horsham, PA (US)

( * ) Notice: Subject to any disclaimer, the term of this patent is extended or adjusted under 35 U.S.C. 154(b) by 313 days.

(21) Appl. No.: 16/418,328

(22) Filed: May 21, 2019

(65) Prior Publication Data

US 2020/0024360 A1 Jan. 23, 2020

Related U.S. Application Data

(60) Provisional application No. 62/676,099, filed on May 24, 2018.

(51) Int. Cl.
*C07K 16/30* (2006.01)
*C07K 16/28* (2006.01)

(52) U.S. Cl.
CPC ...... *C07K 16/3069* (2013.01); *C07K 16/2809* (2013.01); *C07K 2317/21* (2013.01); *C07K 2317/31* (2013.01); *C07K 2317/515* (2013.01); *C07K 2317/565* (2013.01); *C07K 2317/76* (2013.01); *C07K 2317/92* (2013.01)

(58) Field of Classification Search
CPC ............ C07K 16/2809; C07K 2317/31; C07K 2317/515; C07K 2317/565; C07K 2317/92
See application file for complete search history.

(56) References Cited

U.S. PATENT DOCUMENTS

| 541,606 A | 6/1895 | Fellows |
|---|---|---|
| 4,683,195 A | 7/1987 | Mullis et al. |
| 5,208,020 A | 5/1993 | Chari et al. |
| 5,223,409 A | 6/1993 | Ladner et al. |
| 5,225,539 A | 7/1993 | Winter |
| 5,403,484 A | 4/1995 | Ladner et al. |
| 5,427,908 A | 6/1995 | Dower et al. |
| 5,571,698 A | 11/1996 | Ladner et al. |
| 5,580,717 A | 12/1996 | Dower et al. |
| 5,635,483 A | 6/1997 | Pettit et al. |
| 5,712,374 A | 1/1998 | Kuntsmann et al. |
| 5,714,586 A | 2/1998 | Kunstmann et al. |
| 5,739,116 A | 4/1998 | Hamann et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,877,296 A | 3/1999 | Hamann et al. |
| 5,885,793 A | 3/1999 | Griffiths et al. |
| 5,969,108 A | 10/1999 | McCafferty et al. |
| 6,054,297 A | 4/2000 | Carter et al. |
| 6,150,584 A | 11/2000 | Kucherlapati et al. |
| 6,172,197 B1 | 1/2001 | McCafferty et al. |
| 6,521,404 B1 | 2/2003 | Griffiths et al. |
| 6,521,427 B1 | 2/2003 | Evans |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,582,959 B2 | 6/2003 | Kim |
| 6,593,081 B1 | 7/2003 | Griffiths et al. |
| 6,630,579 B2 | 10/2003 | Chari et al. |
| 6,670,127 B2 | 12/2003 | Evans |
| 6,703,020 B1 | 3/2004 | Thorpe et al. |
| 6,818,749 B1 | 11/2004 | Kashmiri et al. |
| 6,884,879 B1 | 4/2005 | Baca et al. |
| 7,060,269 B1 | 6/2006 | Baca et al. |
| 7,498,298 B2 | 3/2009 | Doronina et al. |

(Continued)

FOREIGN PATENT DOCUMENTS

| CL | 201802063 | 11/2018 |
|---|---|---|
| CL | 202003033 | 4/2021 |

(Continued)

OTHER PUBLICATIONS

Lloyd et al, Protein Engineering Design & Selection (2009) 22:159-168. (Year: 2009).*
Edwards et al, J Mol Biol (2003) 14;334(1):103-118. (Year: 2003).*
Goel et al., The Journal of Immunology (2004) 173(12):7358-7367. (Year: 2004).*
Malia et al., Proteins (2016) 84;427-434 (Year: 2016).*
Abhinandan, K.R., et al., "Analysis and improvements to Kbat and structurally correct numbering of antibody variable domains", Molecular Immunology, (2008), vol. 45, pp. 3832-3839.
Adan, A., et al., "Flow cytometry: basic principles and applications", Crit Rev Biotechnol, (2017), vol. 37, No. 2, pp. 163-176.

(Continued)

*Primary Examiner* — Meera Natarajan
*Assistant Examiner* — Cheom-Gil Cheong
(74) *Attorney, Agent, or Firm* — Riverside Law LLP

(57) ABSTRACT

The present invention relates to antibodies specifically binding PSMA or PSMA and CD3, polynucleotides encoding the antibodies or fragments, and methods of making and using the foregoing.

81 Claims, 61 Drawing Sheets

Specification includes a Sequence Listing.

(56) References Cited

U.S. PATENT DOCUMENTS

| | | | |
|---|---|---|---|
| 7,709,226 | B2 | 5/2010 | Foote |
| 8,748,356 | B2 | 6/2014 | Raghunathan |
| 10,844,122 | B2* | 11/2020 | Anderson .......... C07K 16/2809 |
| 2003/0190317 | A1 | 10/2003 | Baca et al. |
| 2003/0203409 | A1 | 10/2003 | Kim |
| 2003/0206899 | A1 | 11/2003 | Ferrara et al. |
| 2005/0112126 | A1 | 5/2005 | Baca et al. |
| 2005/0186208 | A1 | 8/2005 | Fyfe et al. |
| 2006/0009360 | A1 | 1/2006 | Pifer et al. |
| 2007/0287170 | A1 | 12/2007 | Davis et al. |
| 2009/0182127 | A1 | 7/2009 | Kjaergaard et al. |
| 2010/0015133 | A1 | 1/2010 | Igawa et al. |
| 2010/0028637 | A1 | 2/2010 | Tavsanli et al. |
| 2010/0261620 | A1 | 10/2010 | Almagro et al. |
| 2011/0123532 | A1 | 5/2011 | Gurney et al. |
| 2014/0141000 | A1 | 5/2014 | Chiu et al. |
| 2016/0068605 | A1 | 3/2016 | Nemeth et al. |
| 2016/0347840 | A1* | 12/2016 | Anderson .......... C07K 16/3069 |
| 2019/0352421 | A1* | 11/2019 | Adams .................. C07K 16/30 |

FOREIGN PATENT DOCUMENTS

| | | |
|---|---|---|
| EP | 0 666 868 B1 | 8/1995 |
| EP | 0 666 868 B2 | 8/1995 |
| JP | 2012504403 | 2/2012 |
| WO | WO 88/01649 A1 | 3/1988 |
| WO | WO 90/04036 A1 | 4/1990 |
| WO | WO 90/07861 A1 | 7/1990 |
| WO | WO 92/01047 A1 | 1/1992 |
| WO | WO 92/22653 A1 | 12/1992 |
| WO | WO 94/10202 A1 | 5/1994 |
| WO | WO 94/11026 A2 | 5/1994 |
| WO | WO 94/11026 A3 | 5/1994 |
| WO | WO 94/13804 A1 | 6/1994 |
| WO | WO 96/30046 A1 | 10/1996 |
| WO | WO 98/44001 A1 | 10/1998 |
| WO | WO 98/45332 A3 | 10/1998 |
| WO | WO 99/45962 A1 | 9/1999 |
| WO | WO 02/43478 A2 | 6/2002 |
| WO | WO 02/43478 A3 | 6/2002 |
| WO | WO 02/43478 A8 | 6/2002 |
| WO | WO 02/066470 A1 | 8/2002 |
| WO | WO 02/066630 A1 | 8/2002 |
| WO | WO 03/077914 A1 | 9/2003 |
| WO | WO 2004/106380 A2 | 12/2004 |
| WO | WO 2004/106380 A3 | 12/2004 |
| WO | WO 2005/012359 A2 | 2/2005 |
| WO | WO 2005/012359 A3 | 2/2005 |
| WO | WO 2005/044853 A2 | 5/2005 |
| WO | WO 2005/044853 A3 | 5/2005 |
| WO | WO 2005/048935 A2 | 6/2005 |
| WO | WO 2005/113556 A1 | 12/2005 |
| WO | WO 2005/121142 A1 | 12/2005 |
| WO | WO 2006/028936 A2 | 3/2006 |
| WO | WO 2006/028936 A3 | 3/2006 |
| WO | WO 2007/004415 A1 | 1/2007 |
| WO | WO 2008/024725 A1 | 2/2008 |
| WO | WO 2009/018386 A1 | 2/2009 |
| WO | WO 2009/080251 A1 | 7/2009 |
| WO | WO 2009/080252 A1 | 7/2009 |
| WO | WO 2009/080254 A1 | 7/2009 |
| WO | WO 2009/085462 A1 | 7/2009 |
| WO | WO 2009/085983 A1 | 7/2009 |
| WO | WO 2009/114870 A2 | 9/2009 |
| WO | WO 2009/114870 A3 | 9/2009 |
| WO | WO 2010/006086 A2 | 1/2010 |
| WO | WO 2010/006086 A3 | 1/2010 |
| WO | 2010037836 A2 | 4/2010 |
| WO | WO 2010/036380 A1 | 4/2010 |
| WO | WO 2010/136172 A1 | 12/2010 |
| WO | WO 2011/131746 A2 | 10/2011 |
| WO | WO 2011/131746 A3 | 10/2011 |
| WO | WO 2013/019906 A1 | 2/2013 |
| WO | WO 2013/019906 A9 | 2/2013 |
| WO | WO 2013/174873 A1 | 11/2013 |
| WO | WO 2015/095392 A1 | 6/2015 |
| WO | WO 2015/158636 A1 | 10/2015 |
| WO | WO 2015/158636 A8 | 10/2015 |
| WO | WO 2015/184207 A1 | 12/2015 |
| WO | 2016179518 | 11/2016 |
| WO | 2016179534 | 11/2016 |
| WO | 2017023761 | 2/2017 |
| WO | 2019125982 | 6/2019 |

OTHER PUBLICATIONS

Bostwick, D.G., et al., "Prostate Specific Membrane Antigen Expression in Prostatic Intraepithelial Neoplasia and Adenocarcinoma", Cancer, (1998), vol. 82, pp. 2256-2261.

Brüggemann, M., et al., "Human antibody production in transgenic mice: expression from 100 kb of the human IgH locus", Eur. J. Immunol., (1991), vol. 21, pp. 1323-1326.

Brüggemann, M., et al., "Production of human antibody repertoires in transgenic mice", Current Opinion in Biotechnology, (1997), vol. 8, pp. 455-458.

Chames, P., et al., "Bispecific antibodies for cancer therapy", Current Opinion in Drug Discovery & Development, (2009), vol. 12, No. 2, pp. 276-283.

Chari, R.V.J., et al., "Immunoconjugates Containing Novel Maytansinoids Promising Anticancer Drugs", Cancer Research, (1992), vol. 52, pp. 127-131.

Chothia, C., et al., "Canonical Structures for the Hypervariable Regions of Immunoglobulins", J. Mol. Biol., (1987), vol. 196, pp. 901-917.

Cline, M.J., et al., "Perspectives for Gene Therapy: inserting new genetic information into mammalian cells by physical techniques and viral vectors", Pharmac. Ther., (1985), vol. 29, pp. 69-92.

Dranoff, G., et al., "Vaccination with irradiated tumor cells engineered to secrete murine granulocyte-macrophage colony-stimulating factor stimulates potent, specific, and long-lasting anti-tumor immunity", Proc. Natl. Acad. Sci., (1993), vol. 90, pp. 3539-3543.

Dubowchik, G.M., et al., "Doxorubicin Immunoconjugates Containing Bivalent, Lysosomally-Cleavable Dipeptide Linkages", Bioorganic & Medicinal Chemistry Letters, (2002), vol. 12, pp. 1529-1532.

Fishwild, D.M., et al., "High-avidity human IgGk monoclonal antibodies from a novel strain of minilocus transgenic mice", Nature Biotechnology, (1996), vol. 14, pp. 845-851.

Freshney, R.I., et al., "Culture of Animal Cells: A Manual of Basic Technique, 3rd edition", Journal of Immunological Methods, (1995), vol. 183, pp. 291-292.

Gadi, V.K., et al., "In vivo sensitization of ovarian tumors to chemotherapy by expression of E. coli purine nucleoside phosphorylase in a small fraction of cells", Gene Therapy, (2000), vol. 7, pp. 1738-1743.

Green, L.L., "Antibody engineering via genetic engineering of the mouse: XenoMouse strains are a vehicle for the facile generation of therapeutic human monoclonal antibodies", Journal of Immunological Methods, (1999), vol. 231, pp. 11-23.

Green, L.L., et al., "Regulation of B Cell Development by Variable Gene Complexity in Mice Reconstituted with Human Immunoglobulin Yeast Artificial Chromosomes", J. Exp. Med., (1998), vol. 188, No. 3, pp. 483-495.

Green, L.L., et al., "Antigen-specific human monoclonalo antibodies from mice engineered with human Ig heavy and light chain YACs", Nature Genetics, (1994), vol. 7, pp. 13-21.

Hinman, L.M., et al., "Preparation and Characterization of Monoclonal Antibody Conjugates of the Calicheamicins: A Novel and Potent Family of Antitumor Antibiotics", Cancer Research, (1993), vol. 53, pp. 3336-3342.

Hoogenboom, H.R., et al., "By-passing Immunisation Human Antibodies from Synthetic Repertoires of Germline $V_H$ Gene Segments Rearranged in Vitro", J. Mol. Biol., (1992), vol. 227, pp. 381-388.

Hudes, G., et al., "Temsirolimus, Interferon Alfa, or Both for Advanced Renal-Cell Carcinoma", N Engl J Med, (2007), vol. 356, No. 22, pp. 2271-2281.

(56) References Cited

OTHER PUBLICATIONS

Jeffrey, S.C., et al., "Dipeptide-based highly potent doxorubicin antibody conjugates", Bioorg. Med. Chem. Lett., (2006), vol. 16, pp. 358-362.
Kawakami, M., et al., "Enhanced Expression of Prostate-specific Membrane Antigen Gene in Prostate Cancer as Revealed by in Situ Hybridization", Cancer Research, (1997), vol. 57, pp. 2321-2324.
Kenter, M.J.H., et al., "TGN1412 and the Lancet's solicitation of reports of phase I trials", Lancet, (2006), vol. 368, pp. 2206-2207.
Kim, N.W., et al., "Specific Association of Human Telomerase Activity with Immortal Cells and Cancer", Science, (1994), vol. 266, pp. 2011-2013.
King, H.D., et al., "Monoclonal Antibody Conjugates of Doxorubicin Prepared with Branched Peptide Linkers: Inhibition of Aggregation by Methoxytriethyleneglycol Chains", J. Med. Chem., (2002), vol. 45, pp. 4336-4343.
Knappik, A., et al., "Fully Synthetic Human Combinatorial Antibody Libraries (HuCAL) Based on Modular Consensus Frameworks and CDRs Randomized with Trinucleotides", J. Mol. Biol., (2000), vol. 296, pp. 57-86.
Kohler, et al., "Continuous cultures of fused cells secreting antibody of predefined specificity", Nature, (1975), vol. 256, pp. 495-497.
Kratz, F., et al., "Prodrugs of Anthracyclines in Cancer Chemotherapy", Current Medicinal Chemistry, (2006), vol. 13, pp. 477-523.
Krebs, B., et al., "High-throughput generation and engineering of recombinant human antibodies", Journal of Immunological Methods, (2001), vol. 254, pp. 67-84.
Kugler, A., et al., "Regression of human metastatic renal cell carcinoma after vaccination with tumor cell-dendritic cell hybrids", Nature Medicine, (2000), vol. 6, No. 3, pp. 332-336.
Lathey, J.L., et al., "Production and characterization of an anti-idiotypic antibody specific for a monoclonal antibody to glycoprotein D of herpes simplex virus", Immunology, (1986), vol. 57, pp. 29-35.
Lefranc, M.P., et al., "IMGT unique numbering for immunoglobulin and T cell receptor variable domains and Ig superfamily V-like domains", Developmental and Comparative Immunology, (2003), vol. 27, pp. 55-77.
Li, P., et al., "Design and Synthesis of Paclitaxel Conjugated with an ErbB2-Recognizing Peptide, EC-1", Biopolymers, (2007), vol. 87, No. 4, pp. 225-230.
Liu, D.Z., et al., "Synthesis of 2'-paclitaxel methyl 2-glucopyranosyl succinate for specific targeted delivery to cancer cells", Bioorganic & Medicinal Chemistry Letters, (2007), vol. 17, pp. 617-620.
Lode, H.N., et al., "Targeted Therapy with a Novel Enediyene Antibiotic Calicheamicin $\Theta^I_1$ Effectively Suppresses Growth and dissemination of Liver Metastases in a Syngeneic Model of Murine Neuroblastoma", Cancer Research, (1998), vol. 58, pp. 2925-2928.
Lonberg, N., et al., "Human Antibodies from Transgenic Mice", Intern. Rev. Immunol., (1995), vol. 13, pp. 65-93.
Lonberg, N., et al., "Antigen-specific human antibodies from mice comprising four distinct genetic modifications", Nature, (1994), vol. 368, pp. 856-859.
MacLennan, D.H., et al., "Structure-Function Relationships in the $Ca^{2+}$ Binding and Translocation Domain of SERCA1: physiological correlates in Brody disease", Acta Physiol Scand, (1998), vol. 163, suppl. 643, pp. 55-67.
Marks, J.D., et al., "By-passing Immunization Human Antibodies from V-gene Libraries Displayed on Phase", J. Mol. Biol., (1991), vol. 222, pp. 581-597.
Mendez, M.J., et al., "Functional transplant of megabase human immunoglobulin loci recapitulates human antibody response in mice", Nature Genetics, (1997), vol. 15, pp. 146-156.
Mitsiades, C.S., et al., "Molecular staging by RT-PCR analysis for PSA and PSMA in peripheral blood and bone marrow samples is an independent predictor of time to biochemical failure following radical prostatectomy for clinically localized prostate cancer", Clinical & Experimental Metastasis, (2004), vol. 21, pp. 495-505.

Mokyr, M.B., et al., "Realization of the Therapeutic Potential of CTLA-4 Blockade in Low-Dose Chemotherapy-treated Tumor-bearing Mice", Cancer Research, (1998), vol. 58, pp. 5301-5304.
Motzer, R.J., et al., "Efficacy of everolimus in advanced renal cell carcinoma: a double-blind, randomized, placebo-controlled phase III trial", Lancet, (2008), vol. 372, pp. 449-456.
Nagy, A., et al., "Stability of cytotoxic luteinizing hormone-releasing hormone conjugate (AN-152) containing doxorubicin 14-O-hemiglutarate in mouse and human serum in vitro: Implications for the design of preclinical studies", PNAS, (2000), vol. 97, No. 2, pp. 829-834.
Nestle, F.O., et al., "Vaccination of melanoma patients with peptide- or tumor lysate-pulsed dendritic cells", Nature Medicine, (1998), vol. 4, No. 3, pp. 328-332.
Nunez-Prado, N., et al., "The coming of age of engineered multivalent antibodies", Drug Discovery Today, (2015), vol. 20, No. 5, pp. 588-594.
Okayama, H., et al., "A cDNA Cloning Vector That Permits Expression of cDNA Inserts in Mammalian Cells", Molecular and Cellular Biology, (1983), vol. 3, No. 2, pp. 280-289.
Padlan, E.A., "A Possible Procedure for Reducing the Immunogenicity of Antibody Variable Domains While Preserving Their Ligand-Binding Properties", Molecular Immunology, (1991), vol. 28, Nos. 4/5, pp. 489-498.
Pal, S.K., et al., "Programmed Death-1 Inhibition in Renal Cell Carcinoma: Clinical Insights and Future Directions", Clinical Advances in Hematology & Oncology, (2014), vol. 12, No. 2, pp. 90-99.
Presta, L.G., et al., "Humanization of an Anti-Vascular Endothelial Growth Factor Monoclonal Antibody for the Therapy of Solid Tumors and Other Disorders", Cancer Research, (1997), vol. 57, pp. 4593-4599.
Popkov, M., et al., "Human/mouse cross-reactive anti-VEGF receptor 2 recombinant antibodies selected from an immune b9 allotype rabbit antibody library", Journal of Immunological Methods, (2004), vol. 288, pp. 149-164.
Troy, D.B., "Remington: The Science and Practice of Pharmacy", $21^{st}$ Edition, Lippincott, Williams & Wilkins, (2006), Table of Contents.
Restifo, N.P., et al., "Cancer Vaccines", Chapter 61, Cancer: Principles & Practice of Oncology, Fifth Edition (1997), pp. 3023-3043.
Rini, B.I., et al., "Phase III Trial of Bevacizumab Plus Interferon Alfa Versus Interferon Alfa Monotherapy in Patients With Metastatic Renal Cell Carcinoma: Final Results of CALGB 90206", Journal of Clinical Oncology, (2010), vol. 28, No. 13, pp. 2137-2143.
Rosenberg, S.A., "Development of Cancer Vaccines", American Society of Clinical Oncology, (2000), pp. 60-62.
Sasaki, N., et al., "Structure-Mutation Analysis of the ATPase Site of Dictyostelium Discoideum Myosin II", Adv. Biophys., (1998), vol. 35, pp. 1-24.
Sheets, M.D., et al., "Efficient construction of a large nonimmune phage antibody library: The production of high-affinity human single-chain antibodies to protein antigens", Proc. Natl. Acad. Sci., (1998), vol. 95, pp. 6157-6162.
Shi, L., et al., "De Novo Selection of High-Affinity Antibodies from Synthetic Fab Libraries Displayed on Phage as pIX Fusion Proteins", J. Mol. Biol., (2010), vol. 397, pp. 385-396.
Suto, R., et al., "A Mechanism for the Specific Immunogenicity of Heat Shock Protein-Chaperoned Peptides", Science, (1995), vol. 269, pp. 1585-1588.
Tamura, Y., et al., "Immunotherapy of Tumors with Autologous Tumor-Derived Heat Shock Protein Preparations", Science, (1997), vol. 278, pp. 117-120.
Thalmann, G.N., et al., "Androgen-independent Cancer Progression and Bone Metastasis in the LNCaP Model of Human Prostate Cancer", Cancer Research, (1994), vol. 54, pp. 2577-2581.
Torgov, M.Y., et al., "Generation of an Intensely Potent Anthracycline by a Monoclonal Antibody-ß-Galactosidase Conjugate", Bioconjugate Chem., (2005), vol. 16, pp. 717-721.
Vaughan, T.J., et al., "Human Antibodies with Sub-nanomolar Affinities Isolated from a Large Non-immunized Phage Display Library", Nature Biotechnology, (1996), vol. 14, pp. 309-314.

(56) References Cited

OTHER PUBLICATIONS

Vitetta, E.S., et al., "Redesigning Nature's Poisons to Create Anti-Tumor Reagents", Science, (1987), vol. 238, p. 1098.

Wildman, D.E., et al., "Implications of natural selection in shaping 99.4% nonsynonymous DNA identity between humans and chimpanzees: Enlarging genus *Homo*", PNAS, (2003), vol. 100, No. 12, p. 7181.

Wranik, B.J., et al., "LUZ-Y, a Novel Platform for the Mammalian Cell Production of Full-length IgG-bispecific Antibodies", Journal of Biological Chemistry, (2012), vol. 287, 52, pp. 43331-43339.

Wright, G.L., et al., "Upregulation of Prostate-Specific Membrance Antigen After Androgen-Deprivation Therapy", Urology, (1996), vol. 48, pp. 326-334.

Yang, X.D., et al., "Eradication of Established Tumors by a Fully Human Monoclonal Antibody to the Epidermal Growth Factor Receptor without Concomitant Chemotherapy", Cancer Research, (1999), vol. 59, pp. 1236-1243.

Goding, "Monoclonal Antibodies: Principles and Practice", Academic Press, (1996), pp. 59-103.

"FOLH1_Human", Jun. 1, 1994, retrieved from internet, https://www.uniprot.org/uniprot/Q04609.

* cited by examiner

Fig. 4

Light Chain (SEQ ID NO:114)

```
         10        20        30        40        50        60
          .         .         .         .         .         .
          |         |         |         |         |         |
QAVVTQESALTTSPGETVTLTCRSSTGAVTTSNYANWVQEKPDHLFTGLIGGTNKRAPGV 70        80        90       100       110       120
          .         .         .         .         .         .
          |         |         |         |         |         |
PARFSGSLIGDKAALTITGAQTEDEAIYFCALWYSNLWVFGGGTKLTVLGQPKSSPSVTL 130       140       150       160       170       180
          .         .         .         .         .         .
          |         |         |         |         |         |
FPPSSEELETNKATLVCTITDFYPGVVTVDWKVDGTPVTQGMETTQPSKQSNNKYMASSY 190       200       210
          .         .         .
          |         |         |
LTLTARAWERHSSYSCQVTHEGHTVEKSLSRADCS
```

Heavy Chain (SEQ ID NO:113)

```
         10        20        30        40        50        60
          .         .         .         .         .         .
          |         |         |         |         |         |
EVKLLESGGGLVQPKGSLKLSCAASGFTFNTYAMNWVRQAPGKGLEWVARIRSKYNNYAT 70        80        90       100       110       120
          .         .         .         .         .         .
          |         |         |         |         |         |
YYADSVKDRFTISRDDSQSILYLQMNNLKTEDTAMYYCVRHGNFGNSYVSWFAYWGQGTL 130       140       150       160       170       180
          .         .         .         .         .         .
          |         |         |         |         |         |
VTVSAATTTAPSVYPLVPGCSDTSGSSVTLGCLVKGYFPEPVTVKWNYGALSSGVRTVSS 190       200       210       220       230       240
          .         .         .         .         .         .
          |         |         |         |         |         |
VLQSAFYSLSSLVTVPSSTWPSQTVICNVAHPASKTELIKRIEPRIPKPSTPPGSSCPPG 250       260       270       280       290       300
          .         .         .         .         .         .
          |         |         |         |         |         |
NILGGPSVFIFPPKPKDALMISLTPKVTCVVVDVSEDDPDVHVSWFVDNKEVHTAWTQPR 310       320       330       340       350       360
          .         .         .         .         .         .
          |         |         |         |         |         |
EAQYNSTFRVVSALPIQHQDWMRGKEFKCKVNNKALPAPIERTISKPKGRAQTPQVYTIP 370       380       390       400       410       420
          .         .         .         .         .         .
          |         |         |         |         |         |
PPREQMSKKKVSLTCLVTNFFSEAISVEWERNGELEQDYKNTPPILDSDGTYFLYSKLTV 430       440
          .         .
          |         |
DTDSWLQGEIFTCSVVHEALHNHHTQKNLSRSPGK
```

Fig. 5

```
VH              10         20         30         40         50         60
                 .    |    .    |    .    |    .    |    .    |    .    |
sp34    EVKLLESGGGLVQPKGSLKLSCAASGFTFNTYAMNWVRQAPGKGLEWVARIRSKYNNYATY
CD3H141 EVQLVESGGGLVQPGGSLRLSCAASGFTFNTYAMNWVRQAPGKGLEWVARIRSKYNNYATY
CD3H142 EVQLLESGGGLVQPGGSLRLSCAASGFTFNTYAMNWVRQAPGKGLEWVARIRSKYNNYATY
CD3H143 EVQLLESGGGLVQPGGSLRLSCAASGFTFNTYAMNWVRQAPGKGLEWVARIRSKYNNYATY
CD3H144 EVQLVESGGGLVQPGGSLKLSCAASGFTFNTYAMNWVRQASGKGLEWVGRIRSKYNGYATY 70         80         90        100        110        120
                 .    |    .    |    .    |    .    |    .    |    .    |
sp34    YADSVKDRFTISRDDSQSILYLQMNNLKTEDTAMYYCVRHGNFGNSYVSWFAYWGQGTLVTVSA
CD3H141 YAASVKGRFTISRDDSKNSLYLQMNSLKTEDTAVYYCARHGNFGNSYVSWFAYWGQGTLVTVSS
CD3H142 YADSVKGRFTISRDNSKNTLYLQMNSLRAEDTAVYYCAKHGNFGNSYVSWFAYWGQGTLVTVSS
CD3H143 YADSVKGRFTISRDNSKNTLYLQMNSLRAEDTAVYYCVKHGNFGNSYVSWFAYWGQGTLVTVSS
CD3H144 YAASVKGRFTISRDDSKNTAYLQMNSLKTEDTAVYYCTRHGNFGNSYVSWFAYWGQGTLVTVSS

VL              10         20         30         40         50         60
                 .    |    .    |    .    |    .    |    .    |    .    |
sp34    QAVVTQES-ALTTSPGETVTLTCRSSTGAVTTSNYANWVQEKPDHLFTGLIGGTNKRAPGV
CD3L63  QAVVTQEP-SLTVSPGGTVTLTCRSSTGAVTTSNYANWVQQKPGQAPRGLIGGTNKRAPGT
CD3L64  QSVLTQPP-SVSAAPGQKVTISCRSSTGAVTTSNYANWVQQLPGTAPKGLIGGTNKRAPGI
CD3L66  QTVVTQEP-SLTVSPGGTVTLTCRSSTGAVTTSNYANWVQQKPGQAPRGLIGGTNKRAPGT 70         80         90        100        110
                 .    |    .    |    .    |    .    |    .    |
sp34    PARFSGSLIGDKAALTITGAQTEDEAIYFCALWYSNLWVFGGGTKLTVL
CD3L63  PARFSGSLLGGKAALTLSGAQPEDEAEYYCALWYSNLWVFGGGTKLTVL...
CD3L64  PDRFSGSKSGTSATLGITGLQTGDEADYYCALWYSNLWVFGGGTKLTVL...
CD3L66  PARFSGSLLGGKAALTLSGVQPEDEAEYYCALWYSNLWVFGGGTKLTVL...
```

PSMAxCD3 Bispecific antibody binding of PSMG9(Chimp-HEK)

PSMAxCD3 Bispecific antibody binding of PSMG5(Cyno-HEK)

PSMAxCD3 Bispecific antibody binding of Human PSMA-HEK

Human PSMA-HEK T-cell mediated cytotoxicity assay

Comparison of CD3 arms in cytotoxicity assay in human –PSMA HEK

LNCAP cells in T-cell mediated cytotoxicity assay

Cyno PSMA-HEK cells in T-cell mediated cytotoxicity assay

ELM Caspase 3/7 T Cell Dependent Apoptosis of PSMA Over Expressing HEK Cell lines Human PSMA-HEK Cyno PSMA-HEK (PSMG5)

LNCaP

T-cell activation by PS3B27

Prevention of tumorigenesis of HEK293-PSMA xenografts treated with PS3B27 in PBMC humanized NSG mice.

Mean body weights of PBMC-humanized NSG mice bearing HEK293-PSMA xenografts with treatment Efficacy of PS3B27 in tumorigenesis prevention of admixture HEK293-PSMA/T cell xenografts in male CD1 nude mice.

Body Weight of CD1 male nude mice bearing Admixture HEK293-PSMA/T cell Xenografts Treated with PS3B27

Overall structure of PSMB83 (AKA "PSMM84") Fab bound to PSMA

Close view of PSMA main interactions with the PSMB83 (AKA "PSMM84") Light Chain Close view of PSMA main interactions with the PSMB83 (AKA "PSMM84") Heavy Chain

Fig.28

Epitope residues of PSMB83 (AKA PSMM84)

```
humanPSMA  (93)   AKQIQSQWKEFGLDSVELAHYDVLLSYPNKTHPNYISIINEDGNEIF
mousePSMA  (95)   AKQIHDQWKEFGLDLVELSHYDVLLSYPNKTHPNYISIINEDGNEIF
cynoPSMA   (93)   AKQIQSQWKEFGLDSVELTHYDVLLSYPNKTHPNYISIINEDGNEIF humanPSMA  (140)  NTSLFEPPPPGYENVSDIVPPFSAFSPQGMPEGDLVYVNYARTEDFF
mousePSMA  (142)  KTSLSEQPPPGYENISDVVPPYSAFSPQGTPEGDLVYVNYARTEDFF
cynoPSMA   (140)  NTSLFEPPPAGYENVSDIVPPFSAFSPQGMPEGDLVYVNYARTEDFF humanPSMA  (187)  KLERDMKINCSGKIVIARYGKVFRGNKVKNAQLAGAKGVILYSDPAD
mousePSMA  (189)  KLEREMKISCSGKIVIARYGKVFRGNMVKNAQLAGAKGMILYSDPAD
cynoPSMA   (187)  KLERDMKINCSGKIVIARYGKVFRGNKVKNAQLAGATGVILYSDPDD humanPSMA  (234)  YFAPGVKSYPDGWNLPGGGVQRGNILNLNGAGDPLTPGYPANEYAYR
mousePSMA  (236)  YFVPAVKSYPDGWNLPGGGVQRGNVLNLNGAGDPLTPGYPANEHAYR
cynoPSMA   (234)  YFAPGVKSYPDGWNLPGGGVQRGNILNLNGAGDPLTPGYPANEYAYR humanPSMA  (281)  RGIAEAVGLPSIPVHPIGYYDAQKLLEKMGGSAPPDSSWRGSLKVPY
mousePSMA  (283)  HELTNAVGLPSIPVHPIGYDDAQKLLEHMGGPAPPDSSWKGGLKVPY
cynoPSMA   (281)  RGMAEAVGLPSIPVHPIGYYDAQKLLEKMGGSASPDSSWRGSLKVPY
```

Epitope residues are shaded. Sequence divergence shown by underline

Fig. 29
Paratope of PSMM84

PSMM84 HC

| | | |
|---|---|---|
| (1) | EVQLLESGGGLVQPGGSLRLSCAASGFTFKSDAMHWVRQAPGKGLE | (46) |
| (47) | WVSEISGSGGYTNYADSVKGRFTISRDNSKNTLYLQMNSLRAEDTA | (92) |
| (93) | VYYCARDSYDSSLYVGDYFDYWGQGTLVTVSSASTKGPSVFPLAPS | (138) |
| (139) | SKSTSGGTAALGCLVKDYFPEPVTVSWNSGALTSGVHTFPAVLQSS | (184) |
| (185) | GLYSLSSVVTVPSSSLGTQTYICNVNHKPSNTKVDKKVEPKSC | (227) |

PSMM84 LC

| | | |
|---|---|---|
| (1) | EIVLTQSPATLSLSPGERATLSCRASQSVSSYLAWYQQKPGQAPRL | (46) |
| (47) | LIYDASNRATGIPARFSGSGSGTDFTLTISSLEPEDFAVYYCQQRS | (92) |
| (93) | NWPLTFGQGTKVEIKRTVAAPSVFIFPPSDEQLKSGTASVVCLLNN | 138) |
| (139) | FYPREAKVQWKVDNALQSGNSQESVTEQDSKDSTYSLSSTLTLSKA | (184) |
| (185) | DYEKHKVYACEVTHQGLSSPVTKSFNRGEC | (214) |

CDR regions underlined. Paratope residues shaded.

Interaction map showing direct contacts between PSMA and PSMB83 (AKA "PSMM84").

Van der Waals interactions are shown as dashed lines and H-bonds are solid lines with arrows pointing to the backbone atoms. A distance cut-off of 4 Å was used to identify the contact residues.

Fab expression levels

Human PSMA binding

Cynomolgus PSMA binding

Human PSMA binding – normalized by Fab expression

Cyno PSMA binding – normalized by Fab expression

PSMA BINDING AGENTS AND USES THEREOF

CROSS-REFERENCE TO RELATED APPLICATIONS

This application claims the benefit of U.S. Provisional Application Ser. No. 62/676,099, filed 24 May 2018. The entire content of the aforementioned application is incorporated herein by reference in its entirety.

SEQUENCE LISTING

The instant application contains a Sequence Listing which has been submitted electronically in ASCII format and is hereby incorporated by reference in its entirety. Said ASCII copy, created on Apr. 30, 2019, is named PRD3342USNP1_SL.txt and is 269,122 bytes in size.

TECHNICAL FIELD

The disclosure provided herein relates to monoclonal antibodies that immunospecifically bind Prostate specific membrane antigen (PSMA), multispecific antibodies that immunospecifically bind PSMA and cluster of differentiation 3 (CD3), and methods of producing and using the described antibodies.

BACKGROUND

Prostate cancer is the second most common cancer in men worldwide, and the sixth leading cause of cancer-related death. Globally, there are approximately 1,100,000 new cases and 300,000 mortalities every year, comprising 4 percent of all cancer deaths. It is estimated that 1 in every 6 men will be diagnosed with the disease during his lifetime. In the U.S., more than 90% of prostate cancers are found in local or regional stages. At these early stages, the 5-year survival rate nears 100%. When the cancer has metastasized, however, the 5-year survival rate drops to 28%, and there remains a need for effective treatments for advanced-stage prostate cancer.

Prostate specific membrane antigen (PSMA), is a type II membrane protein that is highly expressed in prostatic intraepithelial neoplasia (PIN), a condition in which some prostate cells have begun to look and behave abnormally, and in primary and metastatic prostate cancers [Bostwick D G, Pacelli A, Blute M, Roche P, Murphy G P. Prostate specific membrane antigen expression in prostatic intraepithelial neoplasia and adenocarcinoma: A study of 184 cases. Cancer 1998; 82 (11):2256-2261.]. Expression of PSMA in cancer tissues correlates with the stage of disease and Gleason score [Kawakami M, Nakayama J. Enhanced expression of prostate-specific membrane antigen gene in prostate cancer as revealed by in situ hybridization. Cancer Res 1997; 57(12):2321-2324.]. PSMA expression is also higher in prostate cancer cells from hormone-refractory patients [Wright G L Jr, Grob B M, Haley C, Grossman K, Newhall K, Petrylak D, Troyer J, Konchuba A, Schellhammer P F, Moriarty R. Upregulation of prostate-specific membrane antigen after androgen-deprivation therapy. Urology 1996; 48(2):326-334.] and increased PSMA expression has been shown to be an independent marker of disease recurrence [Mitsiades C S, Lembessis P, Sourla A, Milathianakis C, Tsintavis A, Koutsilieris M. Molecular staging by RT-pCR analysis for PSA and PSMA in peripheral blood and bone marrow samples is an independent predictor of time to biochemical failure following radical prostatectomy for clinically localized prostate cancer. Clin Exp Metastasis 2004; 21(6):495-505.]. High-level PSMA expression is correlated with early prostate-specific antigen (PSA) recurrence in surgically treated prostate cancer. PSMA expression levels correlate with the aggressiveness of the disease, and thereby strongly support PSMA as an excellent target for prostate cancer characterization and subsequent therapy.

Current treatments for prostate cancer include surgery, radiation and hormone therapies. When prostate cancers grow despite the lowering of testosterone levels by hormone therapy, treatment options are limited. Typically, the cancer vaccine sipuleucel-T, a radiopharmaceutical agent (such as radium-223 chloride), secondary hormone therapies (such as abiraterone or enzalutamide), and/or chemotherapies (docetaxel and cabazitaxel) are added to the hormonal therapy in sequence. While each of these treatments can delay growth of the cancer for several months and palliate symptoms produced by the disease, the disease ultimately becomes resistant to them. This underscores the need for more improved treatment and effective therapies for PSMA-expressing advanced prostate cancer.

SUMMARY

Provided herein are antibodies that immunospecifically bind to *Pan troglodytes* (chimpanzee, chimp), *Macaca fascicularis* (cynomolgus monkey, macaque, cyno) and/or human, PSMA and antigen-binding fragments thereof. Also described are related polynucleotides capable of encoding the provided PSMA-specific antibodies and antigen-binding fragments, cells expressing the provided antibodies and antigen-binding fragments, as well as associated vectors and detectably labeled antibodies and antigen-binding fragments. In addition, methods of using the provided antibodies and antigen-binding fragments are described. For example, the PSMA-specific antibodies and antigen-binding fragments may be used to diagnose or monitor PSMA-expressing cancer progression, regression, or stability; to determine whether or not a patient should be treated for cancer; or to determine whether or not a subject is afflicted with PSMA-expressing cancer and thus may be amenable to treatment with a PSMA-specific anti-cancer therapeutic, such as the multispecific (bispecific, trispecific, etc) antibodies against PSMA and CD3 described herein.

Further provided herein are multispecific antibodies that immunospecifically bind to PSMA and CD3 and multispecific antigen-binding fragments thereof. Also described are related polynucleotides capable of encoding the provided PSMA×CD3-multispecific antibodies, cells expressing the provided antibodies, as well as associated vectors and detectably labeled multispecific antibodies. In addition, methods of using the provided multispecific antibodies are described. For example, the PSMA×CD3-multispecific antibodies may be used to diagnose or monitor PSMA-expressing cancer progression, regression, or stability; to determine whether or not a patient should be treated for cancer; or to determine whether or not a subject is afflicted with PSMA-expressing cancer and thus may be amenable to treatment with a PSMA-specific anti-cancer therapeutic, such as the PSMA×CD3-multispecific antibodies described herein.

PSMA-Specific Antibodies

The invention provides an isolated antibody and fragments thereof, specifically binding *Pan troglodytes*, *Macaca fascicularis* (cynomolgus monkey, macaque, cyno) and/or human PSMA, comprising a heavy chain complementarity determining region 1 (HCDR1), a HCDR2 and a HCDR3 of SEQ ID NOs: 31, 42 and 43, respectively.

The invention provides an isolated antibody and fragments thereof, specifically binding *Pan troglodytes, Macaca fascicularis* and/or human PSMA, comprising a HCDR1, a HCDR2 and a HCDR3 of SEQ ID NOs: 31, 42, 43, respectively, and a light chain complementarity determining region 1 (LCDR1), a LCDR2 and a LCDR3 of SEQ ID NOs: 11, 12 and 13 respectively.

The invention provides an isolated antibody and fragments thereof, specifically binding *Pan troglodytes, Macaca fascicularis* and/or human PSMA, comprising a HCDR1, a HCDR2 and a HCDR3 of SEQ ID NOs: 25, 26 and 27, respectively.

The invention provides an isolated antibody and fragments thereof, specifically binding *Pan troglodytes, Macaca fascicularis* and/or human PSMA, comprising a HCDR1, a HCDR2 and a HCDR3 of SEQ ID NOs: 25, 26, 27, respectively, and a LCDR1, a LCDR2 and a LCDR3 of SEQ ID NOs: 28, 29 and 30 respectively.

The invention provides an isolated antibody and fragments thereof, specifically binding *Pan troglodytes, Macaca fascicularis* and/or human PSMA, comprising a HCDR1, a HCDR2 and a HCDR3 of SEQ ID NOs: 20, 21 and 22, respectively.

The invention provides an isolated antibody and fragments thereof, specifically binding *Pan troglodytes, Macaca fascicularis* and/or human PSMA, comprising a HCDR1, a HCDR2 and a HCDR3 of SEQ ID NOs: 20, 21, and 22, respectively, and a LCDR1, a LCDR2 and a LCDR3 of SEQ ID NOs: 23, 12 and 24 respectively.

The invention provides an isolated antibody and fragments thereof, specifically binding *Pan troglodytes, Macaca fascicularis* and/or human PSMA, comprising a HCDR1, a HCDR2 and a HCDR3 of SEQ ID NOs: 14, 15 and 16, respectively, or SEQ ID NOs: 14, 15 and 16 respectively.

The invention provides an isolated antibody and fragments thereof, specifically binding *Pan troglodytes, Macaca fascicularis* and/or human PSMA, comprising a HCDR1, a HCDR2 and a HCDR3 of SEQ ID NOs: 14, 15, and 16, respectively, and a LCDR1, a LCDR2 and a LCDR3 of SEQ ID NOs: 17, 18 and 19 respectively.

The invention provides an isolated antibody and fragments thereof, specifically binding *Pan troglodytes, Macaca fascicularis* and/or human PSMA, comprising a HCDR1, a HCDR2 and a HCDR3 of SEQ ID NOs: 36, 37 and 38, respectively.

The invention provides an isolated antibody and fragments thereof, specifically binding *Pan troglodytes, Macaca fascicularis* and/or human PSMA, comprising a HCDR1, a HCDR2 and a HCDR3 of SEQ ID NOs: 36, 37, and 38, respectively, and a LCDR1, a LCDR2 and a LCDR3 of SEQ ID NOs: 39, 40 and 41 respectively.

The invention provides an isolated antibody and fragments thereof, specifically binding *Pan troglodytes, Macaca fascicularis* and/or human PSMA, comprising a HCDR1, a HCDR2 and a HCDR3 of SEQ ID NOs: 122, 123 and 124, respectively.

The invention provides an isolated antibody and fragments thereof, specifically binding *Pan troglodytes, Macaca fascicularis* and/or human PSMA, comprising a HCDR1, a HCDR2 and a HCDR3 of SEQ ID NOs: 122, 123, and 124, respectively, and a LCDR1, a LCDR2 and a LCDR3 of SEQ ID NOs: 23, 12, and 24, respectively.

The invention provides an isolated antibody and fragments thereof, specifically binding *Pan troglodytes, Macaca fascicularis* (cynomolgus monkey, macaque, cyno) and/or human PSMA, comprising a heavy chain complementarity determining region 1 (HCDR1), a HCDR2 and a HCDR3 of SEQ ID NOs: 31, 44 and 45, respectively.

The invention provides an isolated antibody and fragments thereof, specifically binding *Pan troglodytes, Macaca fascicularis* and/or human PSMA, comprising a HCDR1, a HCDR2 and a HCDR3 of SEQ ID NOs: 31, 44, and 45, respectively, and a light chain complementarity determining region 1 (LCDR1), a LCDR2 and a LCDR3 of SEQ ID NOs: 46, 29 and 27, respectively.

The invention provides an isolated antibody and fragments thereof, specifically binding *Pan troglodytes, Macaca fascicularis* (cynomolgus monkey, macaque, cyno) and/or human PSMA, comprising a heavy chain complementarity determining region 1 (HCDR1), a HCDR2 and a HCDR3 of SEQ ID NOs: 36, 37 and 48, respectively.

The invention provides an isolated antibody and fragments thereof, specifically binding *Pan troglodytes, Macaca fascicularis* and/or human PSMA, comprising a HCDR1, a HCDR2 and a HCDR3 of SEQ ID NOs: 36, 37, and 48, respectively, and a light chain complementarity determining region 1 (LCDR1), a LCDR2 and a LCDR3 of SEQ ID NOs: 49, 50 and 51, respectively.

The invention provides an isolated antibody and fragments thereof, specifically binding *Pan troglodytes, Macaca fascicularis* (cynomolgus monkey, macaque, cyno) and/or human PSMA, comprising a heavy chain complementarity determining region 1 (HCDR1), a HCDR2 and a HCDR3 of SEQ ID NOs: 36, 37 and 52, respectively.

The invention provides an isolated antibody and fragments thereof, specifically binding *Pan troglodytes, Macaca fascicularis* and/or human PSMA, comprising a HCDR1, a HCDR2 and a HCDR3 of SEQ ID NOs: 36, 37, and 52, respectively, and a light chain complementarity determining region 1 (LCDR1), a LCDR2 and a LCDR3 of SEQ ID NOs: 49, 50 and 51, respectively.

The invention provides an isolated antibody and fragments thereof, specifically binding *Pan troglodytes, Macaca fascicularis* (cynomolgus monkey, macaque, cyno) and/or human PSMA, comprising a heavy chain complementarity determining region 1 (HCDR1), a HCDR2 and a HCDR3 of SEQ ID NOs: 8, 9 and 10, respectively.

The invention provides an isolated antibody and fragments thereof, specifically binding *Pan troglodytes, Macaca fascicularis* and/or human PSMA, comprising a HCDR1, a HCDR2 and a HCDR3 of SEQ ID NOs: 8, 9, and 10, respectively, and a light chain complementarity determining region 1 (LCDR1), a LCDR2 and a LCDR3 of SEQ ID NOs: 11, 12 and 13, respectively.

The invention provides an isolated antibody and fragments thereof, specifically binding *Pan troglodytes, Macaca fascicularis* (cynomolgus monkey, macaque, cyno) and/or human PSMA, comprising a heavy chain complementarity determining region 1 (HCDR1), a HCDR2 and a HCDR3 of SEQ ID NOs: 31, 32 and 33, respectively.

The invention provides an isolated antibody and fragments thereof, specifically binding *Pan troglodytes, Macaca fascicularis* and/or human PSMA, comprising a HCDR1, a HCDR2 and a HCDR3 of SEQ ID NOs: 31, 32, and 33, respectively, and a light chain complementarity determining region 1 (LCDR1), a LCDR2 and a LCDR3 of SEQ ID NOs: 34, 12 and 35, respectively.

The invention provides an isolated antibody and fragments thereof, specifically binding *Pan troglodytes, Macaca fascicularis* (cynomolgus monkey, macaque, cyno) and/or human PSMA, comprising a heavy chain complementarity determining region 1 (HCDR1), a HCDR2 and a HCDR3 of SEQ ID NOs: 53, 54 and 55, respectively.

The invention provides an isolated antibody and fragments thereof, specifically binding Pan troglodytes, Macaca fascicularis and/or human PSMA, comprising a HCDR1, a HCDR2 and a HCDR3 of SEQ ID NOs: 53, 54, and 55, respectively, and a light chain complementarity determining region 1 (LCDR1), a LCDR2 and a LCDR3 of SEQ ID NOs: 23, 12 and 35, respectively.

The invention also provides an isolated antibody and fragments thereof, specifically binding Pan troglodytes, Macaca fascicularis and/or human PSMA, comprising certain HCDR1, HCDR2, HCDR3, LCDR1, LCDR2 and LCDR3 amino acid sequences as described herein.

The invention also provides an isolated antibody and fragments thereof, specifically binding Pan troglodytes, Macaca fascicularis and/or human PSMA, comprising certain variable heavy chain region (VH) and variable light chain region (VL) amino acid sequences as described herein.

The invention also provides an isolated bispecific PSMA/CD3 antibody specifically binding Pan troglodytes, Macaca fascicularis and/or human PSMA and fragments thereof, comprising a first domain specifically binding PSMA and a second domain specifically binding CD3.

The invention also provides an isolated bispecific PSMA/CD3 antibody specifically binding Pan troglodytes, Macaca fascicularis and/or human PSMA and fragments thereof, comprising a first domain specifically binding PSMA and a second domain specifically binding CD3, comprising certain HCDR1, HCDR2, HCDR3, LCDR1, LCDR2, LCDR3, VH, VL, heavy chain or light chain amino acids sequences as described herein.

The invention also provides an isolated bispecific PSMA/CD3 antibody and fragments thereof, comprising a first domain specifically binding PSMA and a second domain specifically binding CD3, wherein the first domain comprises the HCDR1, the HCDR2, the HCDR3, the LCDR1, the LCDR2 and the LCDR3 of SEQ ID NOs: 31, 42, 43, 11, 12 and 13, respectively.

The invention also provides an isolated bispecific PSMA/CD3 antibody and fragments thereof, comprising a first domain specifically binding PSMA and a second domain specifically binding CD3, wherein the first domain comprises the HCDR1, the HCDR2, the HCDR3, the LCDR1, the LCDR2 and the LCDR3 of SEQ ID NOs: 25, 26, 27, 28, 29 and 30, respectively.

The invention also provides an isolated bispecific PSMA/CD3 antibody and fragments thereof, comprising a first domain specifically binding PSMA and a second domain specifically binding CD3, wherein the first domain comprises the HCDR1, the HCDR2, the HCDR3, the LCDR1, the LCDR2 and the LCDR3 of SEQ ID NOs: 36, 37, 38, 39, 40 and 41, respectively.

The invention also provides an isolated bispecific PSMA/CD3 antibody and fragments thereof, comprising a first domain specifically binding PSMA and a second domain specifically binding CD3, wherein the first domain comprises the HCDR1, the HCDR2, the HCDR3, the LCDR1, the LCDR2 and the LCDR3 of SEQ ID NOs: 20, 21, 22, 23, 12 and 24, respectively.

The invention also provides an isolated bispecific PSMA/CD3 antibody and fragments thereof, comprising a first domain specifically binding PSMA and a second domain specifically binding CD3, wherein the first domain comprises the HCDR1, the HCDR2, the HCDR3, the LCDR1, the LCDR2 and the LCDR3 of SEQ ID NOs: 14, 15, 16, 17, 18 and 19, respectively.

The invention also provides an isolated bispecific PSMA/CD3 antibody and fragments thereof, comprising a first domain specifically binding PSMA and a second domain specifically binding CD3, wherein the first domain comprises the HCDR1, the HCDR2, the HCDR3, the LCDR1, the LCDR2 and the LCDR3 of SEQ ID NOs: 122, 123, 124, 23, 12, and 24, respectively.

The invention also provides an isolated bispecific PSMA/CD3 antibody and fragments thereof, comprising a first domain specifically binding PSMA and a second domain specifically binding CD3, wherein the first domain comprises the HCDR1, the HCDR2, the HCDR3, the LCDR1, the LCDR2 and the LCDR3 of SEQ ID NOs: 31, 44, 45, 46, 29, and 47, respectively.

The invention also provides an isolated bispecific PSMA/CD3 antibody and fragments thereof, comprising a first domain specifically binding PSMA and a second domain specifically binding CD3, wherein the first domain comprises the HCDR1, the HCDR2, the HCDR3, the LCDR1, the LCDR2 and the LCDR3 of SEQ ID NOs: 36, 37, 48, 49, 50, and 51, respectively.

The invention also provides an isolated bispecific PSMA/CD3 antibody and fragments thereof, comprising a first domain specifically binding PSMA and a second domain specifically binding CD3, wherein the first domain comprises the HCDR1, the HCDR2, the HCDR3, the LCDR1, the LCDR2 and the LCDR3 of SEQ ID NOs: 36, 37, 52, 49, 50, and 51, respectively.

The invention also provides an isolated bispecific PSMA/CD3 antibody and fragments thereof, comprising a first domain specifically binding PSMA and a second domain specifically binding CD3, wherein the first domain comprises the HCDR1, the HCDR2, the HCDR3, the LCDR1, the LCDR2 and the LCDR3 of SEQ ID NOs: 8, 9, 10, 11, 12, and 13, respectively.

The invention also provides an isolated bispecific PSMA/CD3 antibody and fragments thereof, comprising a first domain specifically binding PSMA and a second domain specifically binding CD3, wherein the first domain comprises the HCDR1, the HCDR2, the HCDR3, the LCDR1, the LCDR2 and the LCDR3 of SEQ ID NOs: 31, 32, 33, 34, 12, and 35, respectively.

The invention also provides an isolated bispecific PSMA/CD3 antibody and fragments thereof, comprising a first domain specifically binding PSMA and a second domain specifically binding CD3, wherein the first domain comprises the HCDR1, the HCDR2, the HCDR3, the LCDR1, the LCDR2 and the LCDR3 of SEQ ID NOs: 53, 54, 55, 23, 12, and 35, respectively.

The invention also provides an isolated bispecific PSMA/CD3 antibody and fragments thereof, comprising a first domain specifically binding PSMA and a second domain specifically binding CD3, wherein the first domain comprises the HCDR1, the HCDR2, the HCDR3, the LCDR1, the LCDR2 and the LCDR3 of SEQ ID NOs: 25, 130, 27, 28, 29, and 30, respectively.

The invention also provides an isolated bispecific PSMA/CD3 antibody and fragments thereof, comprising a first domain specifically binding PSMA and a second domain specifically binding CD3, wherein the first domain comprises the HCDR1, the HCDR2, the HCDR3, the LCDR1, the LCDR2 and the LCDR3 of SEQ ID NOs: 25, 130, 27, 131, 29, and 132, respectively.

The invention also provides an isolated bispecific PSMA/CD3 antibody and fragments thereof, comprising a first domain specifically binding PSMA and a second domain specifically binding CD3, wherein the first domain comprises the HCDR1, the HCDR2, the HCDR3, the LCDR1, the LCDR2 and the LCDR3 of SEQ ID NOs: 25, 130, 27, 28, 133, and 132, respectively.

The invention also provides an isolated bispecific PSMA/CD3 antibody and fragments thereof, comprising a first domain specifically binding PSMA and a second domain specifically binding CD3, wherein the first domain comprises the HCDR1, the HCDR2, the HCDR3, the LCDR1, the LCDR2 and the LCDR3 of SEQ ID NOs: 25, 134, 27, 28, 29, and 30, respectively.

The invention also provides an isolated bispecific PSMA/CD3 antibody and fragments thereof, comprising a first domain specifically binding PSMA and a second domain specifically binding CD3, wherein the first domain comprises the HCDR1, the HCDR2, the HCDR3, the LCDR11, the LCDR2 and the LCDR3 of SEQ ID NOs: 25, 135, 27, 28, 29, and 136, respectively.

The invention also provides an isolated bispecific PSMA/CD3 antibody and fragments thereof, comprising a first domain specifically binding PSMA and a second domain specifically binding CD3, wherein the first domain comprises the HCDR1, the HCDR2, the HCDR3, the LCDR11, the LCDR2 and the LCDR3 of SEQ ID NOs: 25, 135, 27, 28, 29, and 30, respectively.

The invention also provides an isolated bispecific PSMA/CD3 antibody and fragments thereof, comprising a first domain specifically binding PSMA and a second domain specifically binding CD3, wherein the first domain comprises the HCDR1, the HCDR2, the HCDR3, the LCDR1, the LCDR2 and the LCDR3 of SEQ ID NOs: 25, 135, 27, 131, 29, and 132, respectively.

The invention also provides an isolated bispecific PSMA/CD3 antibody and fragments thereof, comprising a first domain specifically binding PSMA and a second domain specifically binding CD3, wherein the first domain comprises the HCDR1, the HCDR2, the HCDR3, the LCDR1, the LCDR2 and the LCDR3 of SEQ ID NOs: 25, 135, 27, 28, 133, and 132, respectively.

The invention also provides an isolated bispecific PSMA/CD3 antibody and fragments thereof, comprising a first domain specifically binding PSMA and a second domain specifically binding CD3, wherein the first domain comprises the HCDR1, the HCDR2, the HCDR3, the LCDR1, the LCDR2 and the LCDR3 of SEQ ID NOs: 25, 134, 27, 28, 29, and 136, respectively.

The invention also provides an isolated bispecific PSMA/CD3 antibody and fragments thereof, comprising a first domain specifically binding PSMA and a second domain specifically binding CD3, wherein the first domain comprises the HCDR1, the HCDR2, the HCDR3, the LCDR1, the LCDR2 and the LCDR3 of SEQ ID NOs: 25, 134, 27, 131, 29, and 132, respectively.

The invention also provides an isolated bispecific PSMA/CD3 antibody and fragments thereof, comprising a first domain specifically binding PSMA and a second domain specifically binding CD3, wherein the first domain comprises the HCDR1, the HCDR2, the HCDR3, the LCDR11, the LCDR2 and the LCDR3 of SEQ ID NOs: 25, 134, 27, 28, 133, and 132, respectively.

The invention also provides an isolated bispecific PSMA/CD3 antibody and fragments thereof, comprising a first domain specifically binding PSMA and a second domain specifically binding CD3, wherein the first domain comprises the HCDR1, the HCDR2, the HCDR3, the LCDR11, the LCDR2 and the LCDR3 of SEQ ID NOs: 25, 137, 27, 28, 133, and 132, respectively.

The invention also provides an isolated bispecific PSMA/CD3 antibody and fragments thereof, comprising a first domain specifically binding PSMA and a second domain specifically binding CD3, wherein the first domain comprises a heavy chain variable region (VH) of SEQ ID NO: 74 and a light chain variable region (VL) of SEQ ID NO: 61, and the second domain comprises the VH of SEQ ID NO: 104 and the VL of SEQ ID NO: 105.

The invention also provides an isolated bispecific PSMA/CD3 antibody and fragments thereof, comprising a first domain specifically binding PSMA and a second domain specifically binding CD3, wherein the first domain comprises a heavy chain variable region (VH) of SEQ ID NO: 74 and a light chain variable region (VL) of SEQ ID NO: 61, and the second domain comprises the VH of SEQ ID NO: 152 and the VL of SEQ ID NO: 153.

The invention also provides an isolated bispecific PSMA/CD3 antibody and fragments thereof, comprising a first domain specifically binding PSMA and a second domain specifically binding CD3, wherein the first domain comprises a heavy chain variable region (VH) of SEQ ID NO: 66 and a light chain variable region (VL) of SEQ ID NO: 67, and the second domain comprises the VH of SEQ ID NO: 104 and the VL of SEQ ID NO: 105.

The invention also provides an isolated bispecific PSMA/CD3 antibody and fragments thereof, comprising a first domain specifically binding PSMA and a second domain specifically binding CD3, wherein the first domain comprises a heavy chain variable region (VH) of SEQ ID NO: 66 and a light chain variable region (VL) of SEQ ID NO: 67, and the second domain comprises the VH of SEQ ID NO: 152 and the VL of SEQ ID NO: 153.

The invention also provides an isolated bispecific PSMA/CD3 antibody and fragments thereof, comprising a first domain specifically binding PSMA and a second domain specifically binding CD3, wherein the first domain comprises a heavy chain variable region (VH) of SEQ ID NO: 64 and a light chain variable region (VL) of SEQ ID NO: 65, and the second domain comprises the VH of SEQ ID NO: 104 and the VL of SEQ ID NO: 105.

The invention also provides an isolated bispecific PSMA/CD3 antibody and fragments thereof, comprising a first domain specifically binding PSMA and a second domain specifically binding CD3, wherein the first domain comprises a heavy chain variable region (VH) of SEQ ID NO: 64 and a light chain variable region (VL) of SEQ ID NO: 65, and the second domain comprises the VH of SEQ ID NO: 152 and the VL of SEQ ID NO: 153.

The invention also provides an isolated bispecific PSMA/CD3 antibody and fragments thereof, comprising a first domain specifically binding PSMA and a second domain specifically binding CD3, wherein the first domain comprises a heavy chain variable region (VH) of SEQ ID NO: 62 and a light chain variable region (VL) of SEQ ID NO: 63, and the second domain comprises the VH of SEQ ID NO: 104 and the VL of SEQ ID NO: 105.

The invention also provides an isolated bispecific PSMA/CD3 antibody and fragments thereof, comprising a first domain specifically binding PSMA and a second domain specifically binding CD3, wherein the first domain comprises a heavy chain variable region (VH) of SEQ ID NO: 62 and a light chain variable region (VL) of SEQ ID NO: 63, and the second domain comprises the VH of SEQ ID NO: 152 and the VL of SEQ ID NO: 153.

The invention also provides an isolated bispecific PSMA/CD3 antibody and fragments thereof, comprising a first domain specifically binding PSMA and a second domain specifically binding CD3, wherein the first domain comprises a heavy chain variable region (VH) of SEQ ID NO: 75 and a light chain variable region (VL) of SEQ ID NO: 76, and the second domain comprises the VH of SEQ ID NO: 104 and the VL of SEQ ID NO: 105.

The invention also provides an isolated bispecific PSMA/CD3 antibody and fragments thereof, comprising a first domain specifically binding PSMA and a second domain specifically binding CD3, wherein the first domain comprises a heavy chain variable region (VH) of SEQ ID NO: 75 and a light chain variable region (VL) of SEQ ID NO: 76, and the second domain comprises the VH of SEQ ID NO: 152 and the VL of SEQ ID NO: 153.

The invention also provides an isolated bispecific PSMA/CD3 antibody and fragments thereof, comprising a first domain specifically binding PSMA and a second domain specifically binding CD3, wherein the first domain comprises a heavy chain variable region (VH) of SEQ ID NO: 160 and a light chain variable region (VL) of SEQ ID NO: 65, and the second domain comprises the VH of SEQ ID NO: 104 and the VL of SEQ ID NO: 105.

The invention also provides an isolated bispecific PSMA/CD3 antibody and fragments thereof, comprising a first domain specifically binding PSMA and a second domain specifically binding CD3, wherein the first domain comprises a heavy chain variable region (VH) of SEQ ID NO: 160 and a light chain variable region (VL) of SEQ ID NO: 65, and the second domain comprises the VH of SEQ ID NO: 152 and the VL of SEQ ID NO: 153.

The invention also provides an immunoconjugate comprising the antibody or antigen-binding portion thereof of the invention linked to a therapeutic agent or to an imaging agent.

The invention also provides a pharmaceutical composition comprising the antibody of the invention and a pharmaceutically accepted carrier.

The invention also provides a polynucleotide encoding the antibody VH, the antibody VL or the antibody VH and the antibody VL of the invention.

The invention also provides a vector comprising the polynucleotide encoding the antibody VH, the antibody VL or the antibody VH and the VL of the invention.

The invention also provides a host cell comprising the vector of the invention.

The invention also provides a method of producing the antibody of the invention, comprising culturing the host cell of the invention in conditions that the antibody is expressed, and recovering the antibody produced by the host cell.

The invention also provides a method of treating a PSMA-overexpressing disease and/or cancer in a subject, comprising administering a therapeutically effective amount of the isolated antibody of the invention to the subject in need thereof for a time sufficient to treat the cancer.

The invention also provides a kit comprising the antibody of the invention.

BRIEF DESCRIPTION OF THE DRAWINGS

FIG. 4 shows the amino acid sequence of SP34 with sequential numbering. CDRs in AbM definition (K. R. Abhinandan and A. C. Martin, 2008. Mol. Immunol. 45, 3832-3839) are underlined. Ser230 is the last HC residue present in papain-cleaved Fab. Residues 231-455 are from IGHG3_MOUSE (mouse IgG3, isoform 2).

FIG. 5 shows the Human Framework Adaptation ("HFA") variants for $V_H$ (SEQ ID NOS: 104, 102, 115, and 116, respectively, in order of appearance) and $V_L$ (SEQ ID NOS: 103, 117, and 105, respectively, in order of appearance). The numbering is sequential; CDRs in the AbM definition are underlined; residues that differ from SP34 are highlighted in bold; back mutations in HFA variants are bold and underlined. Figure discloses the sp34 VH and VL sequences as SEQ ID NOS 128 and 129, respectively.

FIG. 28 shows the comparison of epitope residues of PSMB83 (AKA "PSMM84") within the sequences of human (SEQ ID NO: 3), mouse (SEQ ID NO: 157) and Cynomolgus monkey (cyno) (SEQ ID NO: 2) PSMA. Epitope residues are shaded and sequence divergence is shown by underline.

FIG. 29 shows the paratope residues of PSMB83 (AKA "PSMM84"). CDRs are underlined and paratope residues are shaded. Figure discloses SEQ ID NOS 158 and 159, respectively, in order of appearance.

DETAILED DESCRIPTION OF THE INVENTION

Figure 1A:
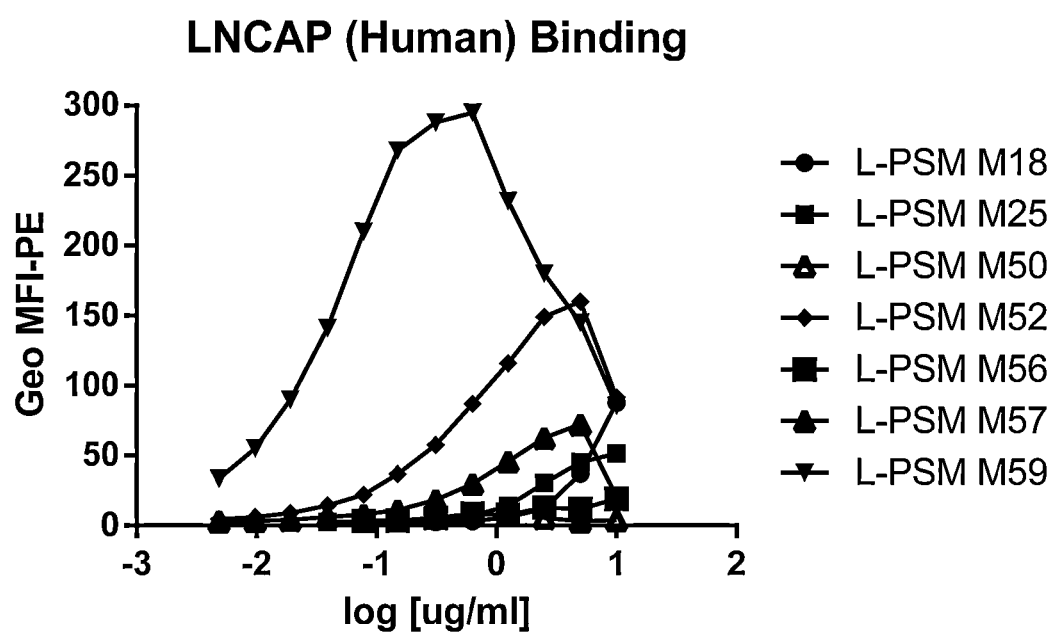
FIGS. 1A-1D show mammalian Fab supernatant titration curves for Anti-PSMA phage panning hits binding to LNCaP cells.
Figure 1B:
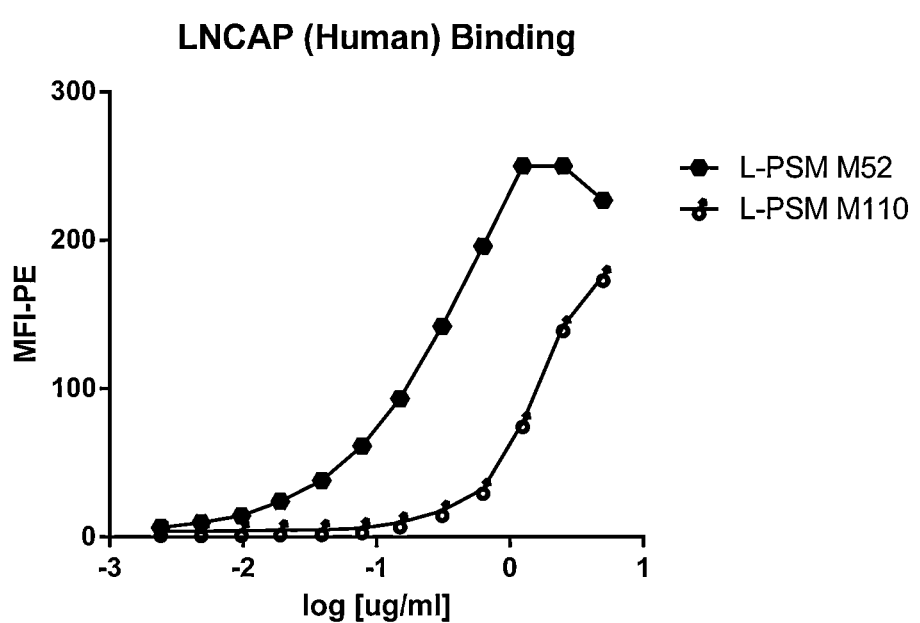
Figure 1C:
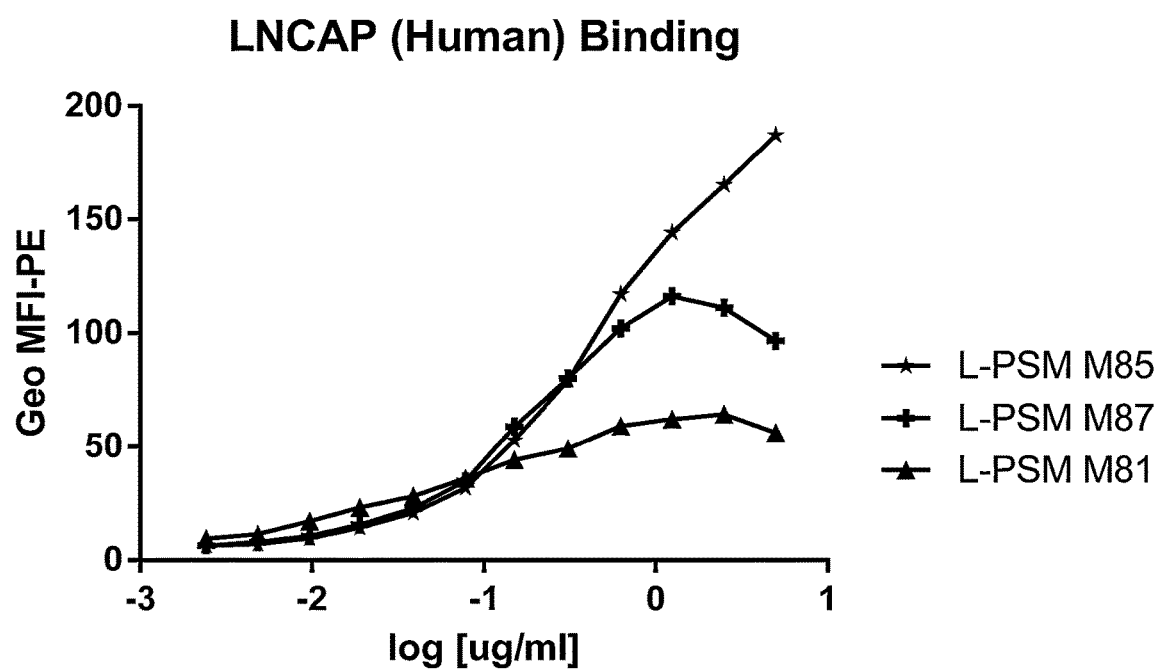

All publications, including but not limited to patents and patent applications, cited in this specification are herein incorporated by reference as though fully set forth.

It is to be understood that the terminology used herein is for the purpose of describing particular embodiments only and is not intended to be limiting. Unless defined otherwise, all technical and scientific terms used herein have the same meaning as commonly understood by one of ordinary skill in the art to which the invention pertains.

Although any methods and materials similar or equivalent to those described herein may be used in the practice for testing of the present invention, exemplary materials and methods are described herein. In describing and claiming the present invention, the following terminology will be used.

As used in this specification and the appended claims, the singular forms "a," "an," and "the" include plural referents unless the content clearly dictates otherwise. Thus, for example, reference to "a cell" includes a combination of two or more cells, and the like.

"Specific binding" or "specifically binds" or "binds" refers to an antibody binding to an antigen or an epitope within the antigen with greater affinity than for other antigens. Typically, the antibody binds to the antigen or the epitope within the antigen with an equilibrium dissociation constant ($K_D$) of about $5×10^{-8}$ M or less, for example about $1×10^{-9}$ M or less, about $1×10^{-10}$ M or less, about $1×10^{-11}$ M or less, or about $1×10^{-2}$ M or less, typically with the $K_D$ that is at least one hundred fold less than its $K_D$ for binding to a non-specific antigen (e.g., BSA, casein). The dissociation constant may be measured using standard procedures. Antibodies that specifically bind to the antigen or the epitope within the antigen may, however, have cross-reactivity to other related antigens, for example to the same antigen from other species (homologs), such as human or monkey, for example *Macaca fascicularis* (cynomolgus, cyno) or *Pan troglodytes* (chimpanzee, chimp). While a monospecific antibody specifically binds one antigen or one epitope, a bispecific antibody specifically binds two distinct antigens or two distinct epitopes.

"Antibodies" is meant in a broad sense and includes immunoglobulin molecules including monoclonal antibodies including murine, human, humanized and chimeric monoclonal antibodies, antibody fragments, bispecific or multispecific antibodies, dimeric, tetrameric or multimeric antibodies, single chain antibodies, domain antibodies and any other modified configuration of the immunoglobulin molecule that comprises an antigen binding site of the required specificity. "Full length antibody molecules" are comprised of two heavy chains (HC) and two light chains (LC) inter-connected by disulfide bonds as well as multimers thereof (e.g. IgM). Each heavy chain is comprised of a heavy chain variable region (VH) and a heavy chain constant region (comprised of domains CH1, hinge, CH2 and CH3). Each light chain is comprised of a light chain variable region (VL) and a light chain constant region (CL). The VH and the VL regions may be further subdivided into regions of hypervariability, termed complementarity determining regions (CDR), interspersed with framework regions (FR). Each VH and VL is composed of three CDRs and four FR segments, arranged from amino-to-carboxy-terminus in the following order: FR1, CDR1, FR2, CDR2, FR3, CDR3 and FR4.

"Complementarity determining regions (CDR)" are "antigen binding sites" in an antibody. CDRs may be defined using various terms: (i) Complementarity Determining Regions (CDRs), three in the VH (HCDR1, HCDR2, HCDR3) and three in the VL (LCDR1, LCDR2, LCDR3) are based on sequence variability (Wu and Kabat, (1970) J Exp Med 132:211-50; Kabat et al., Sequences of Proteins of Immunological Interest, 5th Ed. Public Health Service, National Institutes of Health, Bethesda, Md., 1991). (ii) "Hypervariable regions", "HVR", or "HV", three in the VH (H1, H2, H3) and three in the VL (L1, L2, L3) refer to the regions of an antibody variable domains which are hypervariable in structure as defined by Chothia and Lesk (Chothia and Lesk, (1987) Mol Biol 196:901-17). The International ImMunoGeneTics (IMGT) database (www_imgt_org) provides a standardized numbering and definition of antigen-binding sites. The correspondence between CDRs, HVs and IMGT delineations is described in Lefranc et al., (2003) Dev Comparat Immunol 27:55-77. The term "CDR", "HCDR1", "HCDR2", "HCDR3", "LCDR1", "LCDR2" and "LCDR3" as used herein includes CDRs defined by any of the methods described supra, Kabat, Chothia or IMGT, unless otherwise explicitly stated in the specification.

Immunoglobulins may be assigned to five major classes, IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Antibody light chains of any vertebrate species may assigned to one of two clearly distinct types, namely kappa (κ) and lambda (λ), based on the amino acid sequences of their constant domains.

"Antibody fragments" or "antigen-binding fragments" refer to a portion of an immunoglobulin molecule that retains the heavy chain and/or the light chain antigen binding site, such as heavy chain complementarity determining regions (HCDR) 1, 2 and 3, light chain complementarity determining regions (LCDR) 1, 2 and 3, a heavy chain variable region (VH), or a light chain variable region (VL). Antibody or antigen-binding fragments include well known Fab, F(ab')2, Fd and Fv fragments as well as domain antibodies (dAb) consisting of one VH domain. VH and VL domains may be linked together via a synthetic linker to form various types of single chain antibody designs where the VH/VL domains may pair intramolecularly, or intermolecularly in those cases when the VH and VL domains are expressed by separate single chain antibody constructs, to form a monovalent antigen binding site, such as single chain Fv (scFv) or diabody; described for example in Int. Patent Publ. Nos. WO1998/44001, WO1988/01649, WO1994/13804 and WO1992/01047.

"Monoclonal antibody" refers to an antibody population with single amino acid composition in each heavy and each light chain, except for possible well known alterations such as removal of C-terminal lysine from the antibody heavy chain. Monoclonal antibodies typically bind one antigenic epitope, except that bispecific monoclonal antibodies bind two distinct antigenic epitopes. Monoclonal antibodies may have heterogeneous glycosylation within the antibody population. Monoclonal antibody may be monospecific or multispecific, or monovalent, bivalent or multivalent. A bispecific antibody is included in the term monoclonal antibody.

"Isolated antibody" refers to an antibody or antibody fragment that is substantially free of other antibodies having different antigenic specificities (e.g., an isolated antibody specifically binding PSMA is substantially free of antibodies that specifically bind antigens other than PSMA). In the case of bispecific PSMA×CD3 antibodies, the bispecific antibody specifically binds both PSMA and CD3, and is substantially free of antibodies that specifically bind antigens other that PSMA and CD3. "Isolated antibody" encompasses antibodies that are isolated to a higher purity, such as antibodies that are 800/%, 81%, 82%, 83%, 84%, 85%, 86%, 87%, 88%, 89%, 90%, 91%, 92%, 93%, 94%, 95%, 960%, 97%, 98%, 99% or 100% pure.

"Humanized antibody" refers to an antibody in which the antigen binding sites are derived from non-human species and the variable region frameworks are derived from human immunoglobulin sequences. Humanized antibody may include substitutions in the framework so that the framework may not be an exact copy of expressed human immunoglobulin or human immunoglobulin germline gene sequences.

"Human antibody" refers to an antibody having heavy and light chain variable regions in which both the framework and the antigen binding site are derived from sequences of human origin. If the antibody contains a constant region or a portion of the constant region, the constant region also is derived from sequences of human origin.

Human antibody comprises heavy or light chain variable regions that are "derived from" sequences of human origin if the variable regions of the antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci as described herein. "Human antibody" may contain amino acid differences when compared to the human germline immunoglobulin or rearranged immunoglobulin genes due to for example naturally occurring somatic mutations or intentional introduction of substitutions into the framework or antigen binding site, or both. Typically, "human antibody" is at least about 80%, 81%, 82%/0, 83%, 84%, 85%, 86%, 87%, 88%, 89%, 90%, 91%, 92%, 93%, 94%, 95%, 96%, 97%, 98%, 99% or 100% identical in amino acid sequence to an amino acid sequence encoded by human germline immunoglobulin or rearranged immunoglobulin genes. In some cases, "human antibody" may contain consensus framework sequences derived from human framework sequence analyses, for example as described in Knappik et al., (2000) J Mol Biol 296:57-86, or synthetic HCDR3 incorporated into human immunoglobulin gene libraries displayed on phage, for example as described in Shi et al., (2010) J Mol Biol 397:385-96, and in Int. Patent Publ. No. WO2009/085462.

Human antibodies derived from human immunoglobulin sequences may be generated using systems such as phage display incorporating synthetic CDRs and/or synthetic frameworks, or may be subjected to in vitro mutagenesis to improve antibody properties, resulting in antibodies that are not expressed by the human antibody germline repertoire in vivo.

Antibodies in which antigen binding sites are derived from a non-human species are not included in the definition of "human antibody".

"Recombinant" refers to DNA, antibodies and other proteins that are prepared, expressed, created or isolated by recombinant means when segments from different sources are joined to produce recombinant DNA, antibodies or proteins.

"Epitope" refers to a portion of an antigen to which an antibody specifically binds. Epitopes typically consist of chemically active (such as polar, non-polar or hydrophobic) surface groupings of moieties such as amino acids or polysaccharide side chains and may have specific three-dimensional structural characteristics, as well as specific charge characteristics. An epitope may be composed of contiguous and/or discontinuous amino acids that form a conformational spatial unit. For a discontiguous epitope, amino acids from differing portions of the linear sequence of the antigen come in close proximity in 3-dimensional space through the folding of the protein molecule. Antibody "epitope" depends on the methodology used to identify the epitope.

"Paratope" refers to a portion of an antibody to which an antigen specifically binds. A paratope may be linear in nature or may be discontinuous, formed by a spatial relationship between non-contiguous amino acids of an antibody rather than a linear series of amino acids. A "light chain paratope" and a "heavy chain paratope" or "light chain paratope amino acid residues" and "heavy chain paratope amino acid residues" refer to antibody light chain and heavy chain residues in contact with an antigen, respectively, or in general, "antibody paratope residues" refer to those antibody amino acids that are in contact with antigen.

"Bispecific" refers to an antibody that specifically binds two distinct antigens or two distinct epitopes within the same antigen. The bispecific antibody may have cross-reactivity to other related antigens, for example to the same antigen from other species (homologs), such as human or monkey, for example *Macaca fascicularis* (cynomolgus, cyno) or *Pan troglodytes*, or may bind an epitope that is shared between two or more distinct antigens.

"Multispecific" refers to an antibody that specifically binds two or more distinct antigens or two or more distinct epitopes within the same antigen. The multispecific antibody may have cross-reactivity to other related antigens, for example to the same antigen from other species (homologs), such as human or monkey, for example *Macaca fascicularis* (cynomolgus, cyno) or *Pan troglodytes*, or may bind an epitope that is shared between two or more distinct antigens.

"Variant" refers to a polypeptide or a polynucleotide that differs from a reference polypeptide or a reference polynucleotide by one or more modifications, for example one or more substitutions, insertions or deletions.

"Vector" refers to a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system, such as a cell, virus, animal, plant, and reconstituted biological systems utilizing biological components capable of duplicating a vector. The vector polynucleotide may be DNA or RNA molecules or a hybrid of these, single stranded or double stranded.

"Expression vector" refers to a vector that can be utilized in a biological system or in a reconstituted biological system to direct the translation of a polypeptide encoded by a polynucleotide sequence present in the expression vector.

"Polynucleotide" refers to a molecule comprising a chain of nucleotides covalently linked by a sugar-phosphate backbone or other equivalent covalent chemistry. Double and single-stranded DNA and RNA are typical examples of polynucleotides. "Polypeptide" or "protein" refers to a molecule that comprises at least two amino acid residues linked by a peptide bond to form a polypeptide. Small polypeptides of less than 50 amino acids may be referred to as "peptides".

"Flow cytometry" is a technology that is used to analyze the physical and chemical characteristics of particles in a fluid as it passes through at least one laser. Cell components are fluorescently labelled and then excited by the laser to emit light at varying wavelengths (Adan, et al, Critical Reviews in Biotechnology (2016) 1549-7801).

"Anti-idiotypic (anti-Id) antibody" is an antibody which recognizes the antigenic determinants (e.g. the paratope or CDRs) of the antibody. It is generally known in the art the process of producing or preparing an anti-idiotypic antibody. (Lathey, J. et al Immunology 1986 57(1):29-35). The anti-Id antibody may be antigen-blocking or non-blocking. The antigen-blocking anti-Id antibody may be used to detect the free antibody in a sample (e.g. anti-PSMA, anti-CD3 or the bispecific PSMAxCD3 antibody of the invention described herein). The non-blocking anti-Id antibody may be used to detect the total antibody (free, partially bound to antigen, or fully bound to antigen) in a sample. An anti-Id antibody may be prepared by immunizing an animal with the antibody to which an anti-Id antibody is being prepared. In some embodiments described herein, the anti-idiotypic antibody is used for detecting the level of the therapeutic antibodies (e.g. anti-PSMA, anti-CD3 or the bispecific PSMAxCD3 antibody of the invention described herein) in a sample.

An anti-Id antibody may also be used as an immunogen to induce an immune response in yet another animal, producing a so-called anti-anti-Id antibody. An anti-anti-Id may be epitopically identical to the original mAb, which induced the anti-Id antibody. Thus, by using antibodies to the idiotypic determinants of a mAb, it is possible to identify other clones expressing antibodies of identical specificity. Anti-Id antibodies may be varied (thereby producing anti-Id antibody variants) and/or derivatized by any suitable technique, such as those described elsewhere herein with respect to the antibodies specifically binding PSMA or CD3, or the bispecific PSMAxCD3 antibodies.

PSMA refers to Prostate Specific Membrane Antigen. The amino acid sequence of the *Pan troglodytes* (also referred to as chimpanzee or chimp) PSMA is shown in SEQ ID NO: 1. The extracellular domain spans residues 44-750, the transmembrane domain spans residues 20-43 and the cytoplasmic domain spans residues 1-19 of SEQ ID NO: 1. The amino acid sequence of the *Macaca fascicularis* (also referred to as cynomolgus monkey, macaque or cyno) PSMA is shown in SEQ ID NO: 2. The extracellular domain spans residues 44-750, the transmembrane domain spans residues 20-43 and the cytoplasmic domain spans residues 1-19 of SEQ ID NO: 2. The amino acid sequence of the human PSMA is shown in SEQ ID NO: 3. The extracellular domain spans residues 44-750, the transmembrane domain spans residues 20-43 and the cytoplasmic domain spans residues 1-19 of SEQ ID NO: 3.

CD3 refers to the T-cell antigen receptor. Throughout the specification, "CD3-specific" refers to antibodies that bind specifically to the T-cell receptor complex. More specifically, the antibodies bind to the CD3-epsilon polypeptide, which together with CD3-gamma, -delta and -zeta, and the T-cell receptor alpha/beta and gamma/delta heterodimers, forms the T-cell receptor-CD3 complex. This complex plays an important role in coupling antigen recognition to several intracellular signal-transduction pathways. The CD3 complex mediates signal transduction, resulting in T cell activation and proliferation. CD3 is required for the immune response.

"In combination with" means that two or more therapeutics are administered to a subject together in a mixture, concurrently as single agents or sequentially as single agents in any order.

"Overexpress", "overexpressed" and "overexpressing" interchangeably refers to a sample such as a cancer cell, malignant cell or cancer tissue that has measurably higher levels of PSMA when compared to a reference sample. The overexpression may be caused by gene amplification or by increased transcription or translation. Expression and overexpression of protein in the sample may be measured using well known assays using, for example ELISA, immunofluorescence, flow cytometry or radioimmunoassay on live or lysed cells. Expression and overexpression of a polynucleotide in the sample may be measured, for example, using fluorescent in situ hybridization, Southern blotting, or PCR techniques. A protein or a polynucleotide is overexpressed when the level of the protein or the polynucleotide in the sample is at least 1.5-fold higher when compared to the reference sample. Selection of the reference sample is well known.

"Sample" refers to a collection of similar fluids, cells, or tissues isolated from a subject, as well as fluids, cells, or tissues present within a subject. Exemplary samples are of biological fluids such as blood, serum and serosal fluids, plasma, lymph, urine, saliva, cystic fluid, tear drops, feces, sputum, mucosal secretions of the secretory tissues and organs, vaginal secretions, ascites fluids such as those associated with non-solid tumors, fluids of the pleural, pericardial, peritoneal, abdominal and other body cavities, fluids collected by bronchial lavage, liquid solutions contacted with a subject or biological source, for example, cell and organ culture medium including cell or organ conditioned medium, lavage fluids and the like, tissue biopsies, fine needle aspirations or surgically resected tumor tissue.

A "cancer cell" or a "tumor cell" as used herein refers to a cancerous, precancerous or transformed cell, either in vivo, ex vivo, or in tissue culture, that has spontaneous or induced phenotypic changes. These changes do not necessarily involve the uptake of new genetic material. Although transformation may arise from infection with a transforming virus and incorporation of new genomic nucleic acid or uptake of exogenous nucleic acid, it can also arise spontaneously or following exposure to a carcinogen, thereby mutating an endogenous gene. Transformation/cancer is exemplified by morphological changes, immortalization of cells, aberrant growth control, foci formation, proliferation, malignancy, modulation of tumor specific marker levels, invasiveness, tumor growth in suitable animal hosts such as nude mice, and the like, in vitro, in vivo, and ex vivo (Freshney, Culture of Animal Cells: A Manual of Basic Technique (3rd ed. 1994)). Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

"Effector antigens" are antigens from cells of the immune system which can stimulate or trigger cytotoxicity, phagocytosis, antigen presentation, cytokine release. Such effector antigens are from, for example but not limited to, T cells and natural killer (NK) cells. Examples of suitable specificities for effector antigens include but are not limited to CD3 or CD3 subunits such as CD3ε for T cells and CD16 for NK cells. Such cell surface molecules of effector cells are suitable for mediating cell killing. Effector cells are cells of the immune system which can stimulate or trigger cytotoxicity, phagocytosis, antigen presentation, cytokine release. Such effector cells are, for example but not limited to, T-cells, natural killer (NK) cells, granulocytes, monocytes, macrophages, dendritic cells, and antigen-presenting cells. Examples of suitable specificities for effector cells include but are not limited to CD2, CD3 and CD3 subunits such as CD3e, CD5, CD28 and other components of the T-cell receptor (TCR) for T cells; CD16, CD16A, CD25, CD38, CD44, CD56, CD69, CD94, CD335 (NKp46), CD336, (NKp44), CD337 (NKp30), NKp80, NKG2C and NKG2D, DNAM, NCRs for NK cells; CD18, CD64 and CD89 for granulocytes; CD18, CD32, CD64, CD89 and mannose receptor for monocytes and macrophages; CD64 and mannose receptor for dendritic cells; as well as CD35. In certain embodiments of the inventions, those specificities, i. e. cell surface molecules, of effector cells are suitable for mediating cell killing upon binding of a bispecific or multispecific molecules to such cell surface molecule and, thereby, inducing cytolysis or apoptosis.

"Bispecific PSMA×CD3 antibody", "PSMA/CD3 antibody", "bispecific anti-PSMA×CD3 antibody" or "anti-PSMA/CD3 antibody" refers to a molecule comprising at least one binding domain specifically binding PSMA and at least one binding domain specifically binding CD3. The domains specifically binding PSMA and CD3 are typically VH/VL pairs. The bispecific anti-PSMA×CD3 antibody may be monovalent in terms of its binding to either PSMA or CD3.

"Valent" refers to the presence of a specified number of binding sites specific for an antigen in a molecule. As such, the terms "monovalent", "bivalent", "tetravalent", and "hexavalent" refer to the presence of one, two, four and six binding sites, respectively, specific for an antigen in a molecule. "Multivalent" refers to the presence of two or more binding sites specific for an antigen in a molecule.

"An antigen specific CD4+ or CD8+ T cell" refers to a CD4+ or CD8+ T cell activated by a specific antigen, or immunostimulatory epitope thereof.

"Subject" includes any human or nonhuman animal. "Nonhuman animal" includes all vertebrates, e.g., mammals and non-mammals, such as nonhuman primates, sheep, dogs, cats, horses, cows chickens, amphibians, reptiles, etc. Except when noted, the terms "patient" or "subject" are used interchangeably.

The numbering of amino acid residues in the antibody constant region throughout the specification is according to the EU index as described in Kabat et al., Sequences of Proteins of Immunological Interest, 5th Ed. Public Health Service, National Institutes of Health, Bethesda, Md. (1991), unless otherwise explicitly stated.

Conventional one and three-letter amino acid codes are used herein as shown in Table 1.

TABLE 1

| Amino acid | Three-letter code | One-letter code |
|---|---|---|
| Alanine | Ala | A |
| Arginine | Arg | R |
| Asparagine | Asn | N |
| Aspartate | Asp | D |
| Cysteine | Cys | C |
| Glutamate | Gln | E |
| Glutamine | Glu | Q |
| Glycine | Gly | G |
| Histidine | His | H |
| Isoleucine | Ile | I |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Compositions of Matter

The present invention provides antibodies and fragments thereof that specifically bind PSMA and multispecific antibodies that specifically bind PSMA and CD3 and fragments thereof. The present invention provides polypeptides and polynucleotides encoding the antibodies of the invention or complementary nucleic acids thereof, vectors, host cells, and methods of making and using them.

The antibodies and fragments thereof that bind to PSMA bind to the chimpanzee target antigen. In one embodiment, the antibodies and fragments thereof bind to the human and macaque PSMA target antigens with affinities within 5-fold of each other. In other words, the difference in antibody binding is less than a multiple of 5. In this case, the identical antibody molecule can be used both for preclinical evaluation of safety, activity and/or pharmacokinetic profile of PSMA in primates and as a drug in humans. Put in other words, the same PSMA-specific molecule can be used in preclinical animal studies as well as in clinical studies in humans. This leads to highly comparable results and a much-increased predictive power of the animal studies compared to species-specific surrogate molecules. Since the PSMA domain is cross-species specific, i.e. reactive with the human and macaque antigens, the antibody or fragments thereof of the invention can be used both for preclinical evaluation of safety, activity and/or pharmacokinetic profile of these binding domains in primates and—in the identical form—as drug in humans.

The present invention also provides for multispecific antibodies that specifically bind to PSMA. According to the invention, a bispecific, i. e. bifunctional, antibody can be used to engage two different therapeutic targets or perform two distinct functions. Such antibodies can be used for example to recruit an immune effector cell, e.g. T- or NK-cell, towards a particular target cell. Various antibody-fragment based molecules are known and under investigation, for example for cancer therapy. A multispecific antibody of the invention may be a trispecific antibody for dual targeting of tumor cells—these are trifunctional structures that can be designed to target two different targets/epitopes on the tumor cell and with the third functionality bind with high affinity to either T-cells or NK-cells. Trispecific antibodies targeting two distinct tumor epitopes and engaging T- or NK-cells lyse the tumor cells that express both targets. Such molecules can be generated by antibody formats known in the art and are fully described. (WO20151842071, WO2015158636, WO2010136172, WO2013174873). In a trispecific antibody embodiment of the invention, the multispecific antibody may be specific for PSMA and a second distinct antigen on the same or another tumor cell and additionally specific for an effector cell, in particular a T cell or an NK cell.

The present invention also provides for a PSMAx"effector antigen" bispecific antibody. In one embodiment, the effector antigen of the PSMAx"effector antigen" bispecific antibody is CD3. It has been found in the present invention that it is possible to generate a PSMAxCD3 bispecific antibody wherein the identical molecule can be used in preclinical animal testing, as well as clinical studies and even in therapy in human. This is due to the identification of the PSMAxCD3 bispecific antibody, which, in addition to binding to human PSMA and human CD3, respectively, also binds to the homologs of antigens of chimpanzee and macaques. The PSMAxCD3 bispecific antibody of the invention can be used as a therapeutic agent against various diseases, including, but not limited to cancer. In view of the above, the need to construct a surrogate target PSMAxCD3 bispecific antibody for testing in a phylogenetically distant (from humans) species disappears. As a result, the identical molecule can be used in animal preclinical testing as is intended to be administered to humans in clinical testing as well as following market approval and therapeutic drug administration. The ability to use the same molecule for preclinical animal testing as in later administration to humans virtually eliminates, or at least greatly reduces, the danger that the data obtained in preclinical animal testing have limited applicability to the human case. In short, obtaining preclinical safety data in animals using the same molecule as will actually be administered to humans does much to ensure the applicability of the data to a human-relevant scenario. In contrast, in conventional approaches using surrogate molecules, said surrogate molecules have to be molecularly adapted to the animal test system used for preclinical safety assessment. Thus, the molecule to be used in human therapy in fact differs in sequence and also likely in structure from the surrogate molecule used in preclinical testing in pharmacokinetic parameters and/or biological activity, with the consequence that data obtained in preclinical animal testing have limited applicability/transferability to the human case. The use of surrogate molecules requires the construction, production, purification and characterization of a completely new construct. This leads to additional development costs and time necessary to obtain that molecule. In sum, surrogates have to be developed separately in addition to the actual drug to be used in human therapy, so that two lines of development for two molecules have to be carried out. Therefore, a major advantage of the PSMAx CD3 bispecific antibody of the invention exhibiting cross-species specificity described herein is that the identical molecule can be used for therapeutic agents in humans and in preclinical animal testing.

Another major advantage of the antibody and multispecific antibody of the invention is its applicability for preclinical testing in various primates. The behavior of a drug candidate in animals should ideally be indicative of the expected behavior of this drug candidate upon administration to humans. As a result, the data obtained from such preclinical testing should therefore generally have a highly predictive power for the human case. However, as learned from the tragic outcome of the recent Phase I clinical trial on TGN1412 (a CD28 monoclonal antibody), a drug candidate may act differently in a primate species than in humans: Whereas in preclinical testing of said antibody, no or only limited adverse effects have been observed in animal studies performed with cynomolgus monkeys, six human patients developed multiple organ failure upon administration of said antibody (Lancet 368 (2006), 2206-7). The results of these dramatic, non-desired negative events suggest that it may not be sufficient to limit preclinical testing to only one (non-chimpanzee primate) species. The fact that the described antibody and multispecific antibody specifically bind PSMA of chimpanzee and cynomolgus monkey may help to overcome the problems faced in the case mentioned above. Accordingly, the present invention provides means and methods for minimizing species differences in effects when drugs for human therapy are being developed and tested.

With the antibody and multi specific antibody of the invention it is also no longer necessary to adapt the test animal to the drug candidate intended for administration to humans, such as e.g. the creation of transgenic animals. The cross-species specificity of the PSMA antibody or multispecific antibody of the invention allows the antibody to be directly used for preclinical testing in non-chimpanzee primates without any genetic manipulation of the animals. As well known to those skilled in the art, approaches in which the test animal is adapted to the drug candidate always bear the risk that the results obtained in the preclinical safety testing are less representative and predictive for humans due to the modification of the animal. For example, in transgenic animals, the proteins encoded by the transgenes are often highly overexpressed. Thus, data obtained for the biological activity of an antibody against this protein antigen may be limited in their predictive value for humans in which the protein is expressed at much lower, more physiological levels.

A further advantage of the uses of the antibody of the invention exhibiting cross-species specificity is the fact that the use of chimpanzees, an endangered species, can be avoided for animal testing. Chimpanzees are the closest relatives to humans and were recently grouped into the family of hominids based on the genome sequencing data (Wildman et al., PNAS 100 (2003), 7181). Therefore, data obtained with chimpanzee is generally considered to be highly predictive for humans. However, due to their status as endangered species, the number of chimpanzees, which can be used for medical experiments, is highly restricted. As stated above, maintenance of chimpanzees for animal testing is therefore both costly and ethically problematic. The uses of the antibody of the invention avoid both ethical objections and financial burden during preclinical testing without prejudicing the quality, i.e. applicability, of the animal testing data obtained. In light of this, the uses of the antibody or multispecific antibody specifically binding PSMA of the invention provide for a reasonable alternative for studies in chimpanzees.

A still further advantage of the antibody or multispecific antibody specifically binding PSMA of the invention is the ability of extracting multiple blood samples when using it as part of animal preclinical testing, for example in the course of pharmacokinetic animal studies. Multiple blood extractions can be much more readily obtained with a non-chimpanzee primate than with lower animals, e.g. a mouse. The extraction of multiple blood samples allows continuous testing of blood parameters for the determination of the biological effects induced by the antibody or multispecific antibody specifically binding PSMA of the invention. Furthermore, the extraction of multiple blood samples enables the researcher to evaluate the pharmacokinetic profile of the antibody or multispecific antibody specifically binding PSMA of the invention as defined herein. In addition, potential side effects, which may be induced by said antibody or multispecific antibody specifically binding PSMA of the invention reflected in blood parameters can be measured in different blood samples extracted during the course of the administration of said antibody.

This allows the determination of the potential toxicity profile of antibody or multispecific antibody binding PSMA of the invention as defined herein.

In some embodiments of the invention described herein, and in some embodiments of each and every one of the numbered embodiments listed below, the isolated antibody or antibody fragment thereof specifically binding PSMA has one, two, three, four or five of the following properties:

a) binds *Pan troglodytes* PSMA extracellular domain (ECD) with an equilibrium dissociation constant ($K_D$) of 25 nM or less, wherein the $K_D$ is measured using ProteOn XPR36 system at +25° C., b) binds LNCaP cells with a calculated $EC_{50}$ of 20 nM or less and binds *Macaca fascicularis* PSMA-expressing HEK cells with a calculated $EC_{50}$ of 40 nM or less, wherein the difference in calculated $EC_{50}$ between binding LNCaP cells and binding *Macaca fascicularis* PSMA-expressing HEK cells is less than 5-fold, and wherein the calculated $EC_{50}$ is measured in a whole cell binding assay at 0° C. using flow cytometry, c) binds recombinant PSMA ECD from human (SEQ ID NO: 7), *Pan troglodytes* (SEQ ID NO:4) and *Macaca fascicularis* (SEQ ID NO: 5) with an equilibrium dissociation constant ($K_D$) of 12 nM or less, wherein the $K_D$ is measured using Proteon surface plasmon resonance assay ProteOn XPR36 system at +25° C.;

d) displays T-cell mediated killing of LNCaP cells, C42 cells, human PSMA-expressing HEK cells or *Macaca fascicularis* PSMA-expressing HEK cells when paired in a bispecific antibody with anti-CD3 antibody CD3B219, wherein the T-cell mediated killing is measured by Chromium-51 or by caspase 3/7 activation assay, or e) recognizes a conformational epitope wherein the epitope is comprised of residues I138, F235, P237, G238, D244, Y299, Y300, Q303, K304, E307, and K324-P326 of human PSMA (SEQ ID NO:3)

Exemplary such antibodies or fragments thereof are PSMA antibodies PSMB119, PSMB120, PSMB121, PSMB122, PSMB123, PSMB87, PSMB126, PSMB127, PSMB128, PSMB129, PSMB130, PSMB120, PSMB121, PSMB122, PSMB123, PSMB127, PSMB128, PSMB130, PSMB344, PSMB345, PSMB346, PSMB347, PSMB349, PSMB358, PSMB359, PSMB360, PSMB361, PSMB362, PSMB363, and PSMB365 described herein.

In some embodiments of the invention described herein, and in some embodiments of each and every one of the numbered embodiments listed below, the isolated PSMA antibody or antibody fragment thereof specifically binding PSMA binds Chimpanzee PSMA ECD with an equilibrium dissociation constant ($K_D$) of about 30 nM or less, wherein the $K_D$ is measured using ProteOn XPR36 system at +25° C. as described in Example 8. Assays for measuring affinity by SPR using Proteon include assays where the assay is performed at room temperature (e.g. at or near 25° C.), wherein the antibody capable of binding to chimp PSMA ECD is captured on the Proteon sensor chip by an anti-Fc antibody (e.g. (Jackson ImmunoResearch Laboratory, cat #109-005-098) to a level around 100RUs, followed by injection of recombinant PSMA ECD, and the collection of association and dissociation data at a flow rate of 50 μl/min.

In some embodiments of the invention described herein, and in some embodiments of each and every one of the numbered embodiments listed below, the isolated PSMA antibody or antibody binding fragment thereof specifically binding PSMA binds LNCaP cells with an $EC_{50}$ of 20 nM or less and binds cyno PSMA expressing HEK cells with an $EC_{50}$ of 40 nM or less, wherein the difference in calculated $EC_{50}$ between binding LNCaP cells and binding cyno PSMA-expressing HEK cells is less than 5-fold, wherein the cell binding is measure using FACS as described in Example 7. Assays for measuring whole cell binding by FACS are performed at a density of 200,000 cells per well for 1 hour on ice. The amount of antibody bound to whole cells is detected with a labelled secondary antibody, for example, with a mouse anti-human kappa-RPE antibody (Life Technologies cat #MH10514) by a FACS Array flow cytometer.

In some embodiments of the invention described herein, and in some embodiments of each and every one of the numbered embodiments listed below, the isolated antibody or antibody fragment thereof specifically binding PSMA binds human, chimp and cyno PSMA ECDs with an equilibrium dissociation constant ($K_D$) of 12 nM or less, wherein the $K_D$ is measured using ProteOn XPR36 system at +25° C. as described in Example 8. Assays for measuring affinity by SPR using Proteon include assays where the assay is performed at room temperature (e.g. at or near 25° C.), wherein the antibody capable of binding to chimp PSMA ECD is captured on the Proteon sensor chip by an anti-Fc antibody (e.g. (Jackson ImmunoResearch Laboratory, cat #109-005-098) to a level around 100RUs, followed by injection of recombinant PSMA ECD, and the collection of association and dissociation data at a flow rate of 50 µl/min.

The measured affinity of a particular antibody/PSMA interaction may vary if measured under different conditions (e.g., osmolarity, pH). Thus, measurements of affinity and other binding parameters (e.g., $K_D$, $K_{on}$, $K_{off}$) are typically made with standardized conditions and a standardized buffer, such as the buffer described herein. Skilled in the art will appreciate that the internal error for affinity measurements for example using Biacore 3000 or ProteOn (measured as standard deviation, SD) may typically be within 5-33% for measurements within the typical limits of detection. Therefore the term "about" in the context of $K_D$ reflects the typical standard deviation in the assay. For example, the typical SD for a $K_D$ of $1\times10^{-9}$ M is up to $+0.33\times10^{-9}$ M.

In some embodiments of the invention described herein, and in some embodiments of each and every one of the numbered embodiments listed below, the isolated antibody or antibody fragment thereof specifically binding PSMA show T-cell mediated killing of human PSMA-expressing LNCaP cells, C42 cells, human PSMA-expressing HEK cells or cyno PSMA-expressing HEK cells when paired in a bispecific antibody with anti-CD3 antibody CD3B219, wherein the T-cell mediated killing is measured by Chromium-51 release and target cells are cultured with pre-activated T-cells at 5:1 ratio for 18-24 hours or by caspase 3/7 activation assay as in Example 6. In some embodiments, the isolated antibody or antibody fragment thereof specifically binding PSMA show T-cell mediated killing of human PSMA-expressing LNCaP and C42 cells with an $EC_{50}$ of about 0.3-0.5 nM or less and 0.12-0.03 nM or less, respectively, when paired in a bispecific antibody with anti-CD3 antibody CD3B219, wherein the T-cell mediated killing is measured by caspase 3/7 activation assay as in Example 9. Target PSMA-expressing cells are cultured with pre-activated T-cells at 1:3 ratio for 18-24 hours and cleavage of the added Caspase 3/7 substrate results in a fluorescent DNA dye, with fluorescence restricted to the cell nucleus.

In some embodiments of the invention described herein, and in some embodiments of each and every one of the numbered embodiments listed below, the isolated antibody or antibody fragment thereof specifically binding PSMA recognizes a conformational epitope wherein the epitope is comprised of residues I138, F235, P237, G238, D244, Y299, Y300, Q303, K304, E307, and K324-P326 as determined by X-ray crystallography as described in Example 13.

In some embodiments of the invention described herein, and in some embodiments of each and every one of the numbered embodiments listed below, the antibody or fragment thereof specifically binding PSMA of the invention comprises the HCDR1, the HCDR2 and the HCDR3 contained within a heavy chain variable region (VH) of SEQ ID NOs: 60, 62, 64, 66, 68, 70, 72, 74, 75, 77, 79, 160, 138, 139, or 140, wherein the HCDR1, the HCDR2 and the HCDR3 are defined by Chothia, Kabat, or IMGT.

In some embodiments of the invention described herein, and in some embodiments of each and every one of the numbered embodiments listed below, the antibody or fragments thereof specifically binding PSMA of the invention comprises the LCDR1, the LCDR2 and the LCDR3 contained within a light chain variable region (VL) of SEQ ID NOs: 61, 63, 65, 67, 69, 71, 73, 76, 78, 142, 143, or 144, wherein the LCDR1, the LCDR2 and the LCDR are defined by Chothia, Kabat, or IMGT.

In some embodiments of the invention described herein, and in some embodiments of each and every one of the numbered embodiments listed below, the antibody specifically binding PSMA of the invention comprises
the HCDR1 of SEQ ID NOs: 8, 14, 20, 25, 31, 36, 46, 53, or 122;
the HCDR2 of SEQ ID NOs: 9, 15, 21, 26, 32, 37, 42, 44, 54, 123, 130, 134, 135, or 137; and
the HCDR3 of SEQ ID NOs: 10, 16, 22, 27, 33, 38, 43, 45, 48, 52, 55, 124.

In some embodiments of the invention described herein, and in some embodiments of each and every one of the numbered embodiments listed below, the antibody specifically binding PSMA of the invention comprises
the LCDR1 of SEQ ID NOs: 11, 17, 23, 28, 34, 39, 46, 49, or 131;
the LCDR2 of SEQ ID NOs: 12, 18, 29, 40, 50, or 133; and
the LCDR3 of SEQ ID NOs: 13, 19, 24, 30, 35, 41, 47, 51, 132, or 136.

In some embodiments of the invention described herein, and in some embodiments of each and every one of the numbered embodiments listed below, the antibody specifically binding PSMA of the invention comprises
the HCDR1 of SEQ ID NOs: 8, 14, 20, 25, 31, 36, 53, or 122;
the HCDR2 of SEQ ID NOs: 9, 15, 21, 26, 32, 37, 42, 44, 54, 123, 130, 134, 135, or 137;
the HCDR3 of SEQ ID NOs: 10, 16, 22, 27, 33, 38, 43, 45, 48 51, 52, 55, or 124;
the LCDR1 of SEQ ID NOs: 11, 17, 23, 28, 34, 39, 46, 49, or 131;
the LCDR2 of SEQ ID NOs: 12, 18, 29, 40, 50, or 133; and
the LCDR3 of SEQ ID NOs: 13, 19, 24, 30, 35, 41, 47, 51, 132, or 136.

In some embodiments of the invention described herein, and in some embodiments of each and every one of the numbered embodiments listed below, the antibody specifically binding PSMA of the invention comprises the HCDR1, the HCDR2 and the HCDR3 of
SEQ ID NOs: 8, 9 and 10, respectively;
SEQ ID NOs: 14, 15 and 16, respectively;
SEQ ID NOs: 20, 21 and 22, respectively,
SEQ ID NOs: 25, 26 and 27, respectively;
SEQ ID NOs: 25, 130 and 27, respectively;
SEQ ID NOs: 25, 134 and 27, respectively;
SEQ ID NOs: 25, 135 and 27, respectively;
SEQ ID NOs: 25, 137 and 27, respectively;
SEQ ID NOs: 31, 32 and 33, respectively;
SEQ ID NOs: 36, 37 and 38, respectively;
SEQ ID NOs: 31, 42 and 43, respectively;
SEQ ID NOs: 31, 44 and 45, respectively,
SEQ ID NOs: 36, 37 and 48, respectively;
SEQ ID NOs: 36, 37 and 52, respectively;
SEQ ID NOs: 53, 54 and 55, respectively; or
SEQ ID NOs: 122, 123, and 124, respectively.

In some embodiments of the invention described herein, and in some embodiments of each and every one of the numbered embodiments listed below, the antibody specifically binding PSMA of the invention comprises the LCDR1, the LCDR2 and the LCDR3 of
SEQ ID NOs: 11, 12 and 13, respectively;
SEQ ID NOs: 17, 18 and 19, respectively;
SEQ ID NOs: 23, 12 and 24, respectively;
SEQ ID NOs: 28, 29 and 30, respectively;
SEQ ID NOs: 28, 29 and 136, respectively;
SEQ ID NOs: 28, 133 and 132, respectively;
SEQ ID NOs: 34, 12 and 35, respectively;
SEQ ID NOs: 39, 40 and 41, respectively;
SEQ ID NOs: 46, 29 and 47, respectively;
SEQ ID NOs: 49, 50 and 51, respectively;
SEQ ID NOs: 23, 12 and 35, respectively; or
SEQ ID NOs: 131, 29 and 132, respectively;

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 8, 9, 10, 11, 12 and 13, respectively.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 14, 15, 16, 17, 18 and 19, respectively.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 20, 21, 22, 23, 12 and 24, respectively.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 122, 123, 124, 23, 12, and 24, respectively.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 26, 27, 28, 29 and 30, respectively.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 31, 32, 33, 34, 12 and 35, respectively.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 36, 37, 38, 39, 40 and 41, respectively.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 36, 37, 38, 49, 50 and 51, respectively.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 31, 42, 43 11, 12 and 13, respectively.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 31, 44, 45, 46, 29 and 47, respectively.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 36, 37, 52, 49, 50 and 51, respectively.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 53, 54, 55, 23, 12 and 35, respectively.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 130, 27, 28, 29, and 30, respectively.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 130, 27, 131, 29, and 132, respectively.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 130, 27, 28, 133, and 132, respectively.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 134, 27, 28, 29, and 30, respectively.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 135, 27, 131, 29, and 132, respectively.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 135, 27, 28, 29, and 136, respectively.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 135, 27, 28, 29, and 30, respectively.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 135, 27, 131, 29, and 132, respectively.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 134, 27, 28, 29, and 136, respectively.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 134, 27, 131, 29, and 132, respectively.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 134, 27, 28, 133, and 132, respectively.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 137, 27, 28, 133, and 132, respectively. In some embodiments of the invention described herein, and in some embodiments of each and every one of the numbered embodiments listed below, the antibody specifically binding PSMA of the invention comprises a heavy chain variable region (VH) of SEQ ID NOs: 60, 62, 64, 66, 68, 70, 72, 74, 75, 77, 79, 160, 138, 139, or 140.

In some embodiments of the invention described herein, and in some embodiments of each and every one of the numbered embodiments listed below, the antibody specifically binding PSMA of the invention comprises a light chain variable region (VL) or SEQ ID NOs: 61, 63, 65, 67, 69, 71, 73, 76, 78, 142, 143, or 144.

The VH, the VL, the HCDR and the LCDR sequences of exemplary antibodies specifically binding PSMA of the invention are shown in Table 2.

Table 2 provides a summary of examples of some PSMA-specific antibodies described herein:

TABLE 2

CDR sequences (as defined by Kabat) of mAbs generated from phage panning against human PSMA (SEQ ID NO:)

| FAB ID | | CDR1 | CDR2 | CDR3 |
|---|---|---|---|---|
| PSMB129 | HC | NAWIS (8) | WINPESGRA NYAQKFQG (9) | ELYYLVYSTY YYAFDY (10) |
| | LC | RASQSIDRWLN (11) | AASSLQS (12) | QQSPRYPLT (13) |
| PSMB130 | HC | SYDIS (14) | GIIPIEGTA NYAQKFQG (15) | DYPAGYGFDY (16) |
| | LC | RASQSVSS-SYLA (17) | GASSRAT (18) | QQYGSSPLT (19) |
| PSMB128 | HC | SDWMS (20) | AISGNGGST EYADSVKG (21) | DPYYYDGDSY YGMDV (22) |
| | LC | RASQSISSYLN (23) | AASSLQS (12) | QQSYSTP (24) |
| PSMB127 | HC | SDAMH (25) | EISGSGGYT NYADSVKG (26) | DSYDSSLYVG DYFDY (27) |
| | LC | RASQSVSSYLA (28) | DASNRAT (29) | QQRSNWPLT (30) |
| PSMB124 | HC | SYAIS (31) | WISPYNGNA NYAQKFQG (32) | DSDRSYNLDY (33) |
| | LC | RASQSISGWLN (34) | AASSLQS (12) | QQSYSTPLT (35) |
| PSMB123 | HC | SYWIG (36) | IIYPGDSDT RYSPSFQG (37) | GLPIWYLDY (38) |
| | LC | RASQSVASDLA (39) | FASNRAT (40) | QQSITWPFT (41) |
| PSMB122 | HC | SYAIS (31) | WIIPYNGNA NYAQKFQG (42) | VNSAALVWE RLDY (43) |
| | LC | RASQSIDRWLN (11) | AASSLQS (12) | QQSPRYPLT (13) |
| PSMB123 | HC | SYAIS (31) | GIIPIFGTA NYAQKFQG (44) | ASRVWHASY GYLDY (45) |

TABLE 2-continued

CDR sequences (as defined by Kabat) of mAbs generated from phage panning against human PSMA (SEQ ID NO:)

| FAB ID | | CDR1 | CDR2 | CDR3 |
|---|---|---|---|---|
| | LC | RASQSVSKWLA (46) | DASNRAT (29) | QQRFTAPWT (47) |
| PSMB120 | HC | SYWIG (36) | IIYPGDSDT RYSPSFQG (37) | GWAYDRGLDY (48) |
| | LC | KSSQSVLYSSN NKNYLA (49) | WASTRES (50) | QQYYSTPLT (51) |
| PSMB119 | HC | SYWIG (36) | IIYPGDSDT RYSPSFQG (37) | AYHYSKGLDY (52) |
| | LC | KSSQSVLYSSN NKNYLA (49) | WASTRES (50) | QQYYSTPLT (51) |
| PSMB126 | HC | DYAIS (53) | RIDPIEGTA NYAQKFQG (54) | DRYYYDGVYW YSDYFDY (55) |
| | LC | RASQSISSYLN (23) | AASSLQS (12) | QQSYSTPLT (35) |
| PSMB87 | HC | SYWIS (122) | IITPGDSYT RYSPSFQG (123) | DYEWELFDSR LDY (124) |
| | LC | RASQSISSYLN (23) | AASSLQS (12) | QQSYSTP (24) |
| PSMB344 | HC | SDAMH (25) | EISGSGGYT NYADSMKG (130) | DSYDSSLYVG DYFDY (27) |
| | LC | RASQSVSSYLA (28) | DASNRAT (29) | QQRSNWPLT (30) |
| PSMB345 | HC | SDAMH (25) | EISGSGGYT NYADSMKG (130) | DSYDSSLYVG DYFDY (27) |
| | LC | RASQSVSNYLA (131) | DASNRAT (29) | QQRRNWPLT (132) |
| PSMB346 | HC | SDAMH (25) | EISGSGGYT NYADSMKG (130) | DSYDSSLYVG DYFDY (27) |
| | LC | RASQSVSSYLA (28) | DASYRAT (133) | QQRRNWPLT (132) |
| PSMB347 | HC | SDAMH (25) | EISGSGGYT NYADSMKS (134) | DSYDSSLYVG DYFDY (27) |
| | LC | RASQSVSSYLA (28) | DASNRAT (29) | QQRSNWPLT (30) |
| PSMB349 | HC | SDAMH (25) | EISGSGGYT NYADSLKG (135) | DSYDSSLYVG DYFDY (27) |
| | LC | RASQSVSSYLA (28) | DASNRAT (29) | QQRGNWPLT (136) |
| PSMB358 | HC | SDAMH (25) | EISGSGGYT NYADSLKG (135) | DSYDSSLYVG DYFDY (27) |
| | LC | RASQSVSSYLA (28) | DASNRAT (29) | QQRSNWPLT (30) |
| PSMB359 | HC | SDAMH (25) | EISGSGGYT NYADSLKG (135) | DSYDSSLYVG DYFDY (27) |
| | LC | RASQSVSNYLA (131) | DASNRAT (29) | QQRRNWPLT (132) |
| PSMB360 | HC | SDAMH (25) | EISGSGGYT NYADSLKG (135) | DSYDSSLYVG DYFDY (27) |
| | LC | RASQSVSSYLA (28) | DASYRAT (133) | QQRRNWPLT (132) |
| PSMB361 | HC | SDAMH (25) | EISGSGGYT NYADSMKS (134) | DSYDSSLYVG DYFDY (27) |
| | LC | RASQSVSSYLA (28) | DASNRAT (29) | QQRGNWPLT (136) |
| PSMB362 | HC | SDAMH (25) | EISGSGGYT NYADSMKS (134) | DSYDSSLYVG DYFDY (27) |
| | LC | RASQSVSNYLA (131) | DASNRAT (29) | QQRRNWPLT (132) |
| PSMB363 | HC | SDAMH (25) | EISGSGGYT NYADSMKS (134) | DSYDSSLYVG DYFDY (27) |
| | LC | RASQSVSSYLA (28) | DASYRAT (133) | QQRRNWPLT (132) |
| PSMB365 | HC | SDAMH (25) | EISGSGGYT NYADSLKS (137) | DSYDSSLYVG DYFDY (27) |
| | LC | RASQSVSSYLA (28) | DASYRAT (133) | QQRRNWPLT (132) |

In some embodiments are provided a PSMA-specific antibody, or an antigen-binding fragment thereof, comprising a heavy chain comprising a CDR1, a CDR2, and a CDR3 of any one of the antibodies described in Table 2. In some embodiments are provided a PSMA-specific antibody, or an antigen-binding fragment thereof, comprising a heavy chain comprising a CDR1, a CDR2, and a CDR3 of any one of the antibodies described in Table 2 and a light chain comprising a CDR1, a CDR2, and a CDR3 of any one of the antibodies described in Table 2. In some embodiments described herein, the PSMA-specific antibody or antigen-binding fragment thereof competes for binding to PSMA with an antibody or antigen-binding comprising a heavy chain comprising a CDR1, a CDR2, and a CDR3 of any one of the antibodies described in Table 2 and a light chain comprising a CDR1, a CDR2, and a CDR3 of any one of the antibodies described in Table 2.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 14, 15, 16, 17, 18 and 19, respectively.

In some embodiments, the antibody comprises the VH of SEQ ID NO: 62 and the VL of SEQ ID NO: 63.

In some embodiments, the antibody comprises a heavy chain (HC) having of SEQ ID NO: 84 and a light chain (LC) of SEQ ID NO: 85.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 20, 21, 22, 23, 12 and 24, respectively.

In some embodiments, the antibody comprises the VH of SEQ ID NO: 64 and the VL of SEQ ID NO: 65.

In some embodiments, the antibody comprises a heavy chain (HC) of SEQ ID NO: 86 and a light chain (LC) of SEQ ID NO: 87.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 31, 42, 43, 11, 12 and 13, respectively.

In some embodiments, the antibody comprises the VH of SEQ ID NO: 74 and the VL of SEQ ID NO: 61.

In some embodiments, the antibody comprises a heavy chain (HC) of SEQ ID NO: 96 and a light chain (LC) of SEQ ID NO: 83.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs 25, 26, 27, 28, 29 and 30, respectively.

In some embodiments, the antibody comprises the VH of SEQ ID NO: 66 and the VL of SEQ ID NO: 67.

In some embodiments, the antibody comprises a heavy chain (HC) of SEQ ID NO: 88 and a light chain (LC) of SEQ ID NO: 89.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs 122, 123, 124, 23, 12, and 24, respectively.

In some embodiments, the antibody comprises the VH of SEQ ID NO: 160 and the VL of SEQ ID NO: 65.

In some embodiments, the antibody comprises a heavy chain (HC) of SEQ ID NO: 125 and a light chain (LC) of SEQ ID NO: 91.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs 8, 9, 10, 11, 12, and 13, respectively.

In some embodiments, the antibody comprises the VH of SEQ ID NO: 60 and the VL of SEQ ID NO: 61.

In some embodiments, the antibody comprises a heavy chain (HC) of SEQ ID NO: 82 and a light chain (LC) of SEQ ID NO: 83.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs 31, 32, 33, 34, 12, and 35, respectively.

In some embodiments, the antibody comprises the VH of SEQ ID NO: 70 and the VL of SEQ ID NO: 71.

In some embodiments, the antibody comprises a heavy chain (HC) of SEQ ID NO: 92 and a light chain (LC) of SEQ ID NO: 93.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs 36, 37, 38, 39, 40, and 41, respectively.

In some embodiments, the antibody comprises the VH of SEQ ID NO: 72 and the VL of SEQ ID NO: 73.

In some embodiments, the antibody comprises a heavy chain (HC) of SEQ ID NO: 94 and a light chain (LC) of SEQ ID NO: 95.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs 31, 44, 45, 46, 29, and 47, respectively.

In some embodiments, the antibody comprises the VH of SEQ ID NO: 75 and the VL of SEQ ID NO: 76.

In some embodiments, the antibody comprises a heavy chain (HC) of SEQ ID NO: 97 and a light chain (LC) of SEQ ID NO: 98.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs 36, 37, 48, 49, 50, and 51, respectively.

In some embodiments, the antibody comprises the VH of SEQ ID NO: 77 and the VL of SEQ ID NO: 78.

In some embodiments, the antibody comprises a heavy chain (HC) of SEQ ID NO: 99 and a light chain (LC) of SEQ ID NO: 100.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs 36, 37, 52, 49, 50, and 51, respectively.

In some embodiments, the antibody comprises the VH of SEQ ID NO: 79 and the VL of SEQ ID NO: 78.

In some embodiments, the antibody comprises a heavy chain (HC) of SEQ ID NO: 101 and a light chain (LC) of SEQ ID NO: 100.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs 53, 54, 55, 23, 12, and 35, respectively.

In some embodiments, the antibody comprises the VH of SEQ ID NO: 68 and the VL of SEQ ID NO: 69.

In some embodiments, the antibody comprises a heavy chain (HC) of SEQ ID NO: 90 and a light chain (LC) of SEQ ID NO: 91.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs 25, 130, 27, 28, 29, and 30, respectively.

In some embodiments, the antibody comprises the VH of SEQ ID NO: 138 and the VL of SEQ ID NO: 67.

In some embodiments, the antibody comprises a heavy chain (HC) of SEQ ID NO: 145 and a light chain (LC) of SEQ ID NO: 89.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs 25, 130, 27, 131, 29, and 132, respectively.

In some embodiments, the antibody comprises the VH of SEQ ID NO: 138 and the VL of SEQ ID NO: 142.

In some embodiments, the antibody comprises a heavy chain (HC) of SEQ ID NO: 145 and a light chain (LC) of SEQ ID NO: 148.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs 25, 130, 27, 28, 133, and 132, respectively.

In some embodiments, the antibody comprises the VH of SEQ ID NO: 138 and the VL of SEQ ID NO: 143.

In some embodiments, the antibody comprises a heavy chain (HC) of SEQ ID NO: 145 and a light chain (LC) of SEQ ID NO: 149.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs 25, 134, 27, 28, 29, and 30, respectively.

In some embodiments, the antibody comprises the VH of SEQ ID NO: 139 and the VL of SEQ ID NO: 67.

In some embodiments, the antibody comprises a heavy chain (HC) of SEQ ID NO: 146 and a light chain (LC) of SEQ ID NO: 89.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs 25, 135, 27, 28, 29, and 136, respectively.

In some embodiments, the antibody comprises the VH of SEQ ID NO: 140 and the VL of SEQ ID NO: 144.

In some embodiments, the antibody comprises a heavy chain (HC) of SEQ ID NO: 147 and a light chain (LC) of SEQ ID NO: 150.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs 25, 135, 27, 28, 29, and 30, respectively.

In some embodiments, the antibody comprises the VH of SEQ ID NO: 140 and the VL of SEQ ID NO: 67.

In some embodiments, the antibody comprises a heavy chain (HC) of SEQ ID NO: 147 and a light chain (LC) of SEQ ID NO: 89.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs 25, 135, 27, 131, 29, and 132, respectively.

In some embodiments, the antibody comprises the VH of SEQ ID NO: 140 and the VL of SEQ ID NO: 143.

In some embodiments, the antibody comprises a heavy chain (HC) of SEQ ID NO: 147 and a light chain (LC) of SEQ ID NO: 148.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs 25, 135, 27, 28, 133, and 132, respectively.

In some embodiments, the antibody comprises the VH of SEQ ID NO: 140 and the VL of SEQ ID NO: 67.

In some embodiments, the antibody comprises a heavy chain (HC) of SEQ ID NO: 147 and a light chain (LC) of SEQ ID NO: 149.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs 25, 134, 27, 28, 29, and 136, respectively.

In some embodiments, the antibody comprises the VH of SEQ ID NO: 139 and the VL of SEQ ID NO: 144.

In some embodiments, the antibody comprises a heavy chain (HC) of SEQ ID NO: 146 and a light chain (LC) of SEQ ID NO: 150.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs 25, 134, 27, 131, 29, and 132, respectively.

In some embodiments, the antibody comprises the VH of SEQ ID NO: 140 and the VL of SEQ ID NO: 67.

In some embodiments, the antibody comprises a heavy chain (HC) of SEQ ID NO: 139 and a light chain (LC) of SEQ ID NO: 142.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs 25, 134, 27, 28, 133, and 132, respectively.

In some embodiments, the antibody comprises the VH of SEQ ID NO: 139 and the VL of SEQ ID NO: 143.

In some embodiments, the antibody comprises a heavy chain (HC) of SEQ ID NO: 146 and a light chain (LC) of SEQ ID NO: 149.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs 25, 137, 27, 28, 133, and 132, respectively.

In some embodiments, the antibody comprises the VH of SEQ ID NO: 141 and the VL of SEQ ID NO: 143.

In some embodiments, the antibody comprises a heavy chain (HC) of SEQ ID NO: 151 and a light chain (LC) of SEQ ID NO: 149.

In some embodiments, the antibody binds human PSMA ECD with an equilibrium dissociation constant ($K_D$) of less than about 100 nM, optionally less than about 50 nM, for example less than about 12 nM, wherein the $K_D$ is measured using ProteOn XPR36 system at +25° C.

In some embodiments, the antibody binds cynomolgus PSMA ECD with an equilibrium dissociation constant ($K_D$) of less than about 100 nM, optionally less than about 50 nM, for example less than about 12 nM, wherein the $K_D$ is measured using ProteOn XPR36 system at +25° C.

In some embodiments, the antibody is of IgG4 isotype, optionally comprising a heavy chain substitution S228P, F234A, and L235A when compared to the wild type IgG4.

In some embodiments, the antibody comprises the VH of SEQ ID NO: 74 and the VL of SEQ ID NO: 61 and is of IgG4 isotype, optionally comprising a heavy chain substitution S228P, F234A, and L235A when compared to the wild type IgG4.

In some embodiments, the antibody is a multispecific antibody, such as a bispecific PSMA/CD3 antibody.

The antibody is suitable for use in therapy, for example in treating cancer.

The antibody is suitable for use in therapy, for example in treating a solid tumor.

The antibody is suitable for use in therapy, for example in treating a prostate cancer or castration-resistant prostate cancer.

The antibody is suitable for use in therapy, for example in treating a prostatic intraepithelial neoplasia.

The antibody is suitable for use in therapy, for example in treating colorectal cancer.

The antibody is suitable for use in therapy, for example in treating a clear cell renal carcinoma.

The antibody is suitable for use in therapy, for example in treating gastric cancer.

The antibody is suitable for use in therapy, for example in treating a renal cell carcinoma (RCC) (e.g., a kidney clear cell carcinoma or a kidney papillary cell carcinoma), or a metastatic lesion thereof.

The antibody is suitable for use in therapy, for example in treating a bladder cancer.

The antibody is suitable for use in therapy, for example in treating a breast cancer The antibody is suitable for use in therapy, for example in treating a kidney cancer.

The antibody is suitable for use in therapy, for example in treating a neovascular disorder such as, for example, a cancer characterized by solid tumor growth.

The antibody is suitable for use in therapy, for example in treating a neovascular disorder such as, for example, clear cell renal carcinoma (CCRCC colorectal cancer, breast cancer, bladder cancer, lung cancer, and pancreatic cancer and various other non-prostate cancers, including but not limited to renal, urothelial, lung, colon, breast, and adenocarcinaoma to the liver.

The IgG class is divided in four isotypes: IgG1, IgG2, IgG3 and IgG4 in humans. They share more than 95% homology in the amino acid sequences of the Fc regions but show major differences in the amino acid composition and structure of the hinge region. The Fc region mediates effector functions, such as antibody-dependent cellular cytotoxicity (ADCC) and complement-dependent cytotoxicity (CDC). In ADCC, the Fc region of an antibody binds to Fc receptors (FcgRs) on the surface of immune effector cells such as natural killers and macrophages, leading to the phagocytosis or lysis of the targeted cells. In CDC, the antibodies kill the targeted cells by triggering the complement cascade at the cell surface. The antibodies described herein include antibodies with the described features of the variable domains in combination with any of the IgG isotypes, including modified versions in which the Fc sequence has been modified to effect different effector functions.

For many applications of therapeutic antibodies, Fc-mediated effector functions are not part of the mechanism of action. These Fc-mediated effector functions can be detrimental and potentially pose a safety risk by causing off-mechanism toxicity. Modifying effector functions can be achieved by engineering the Fc regions to reduce their binding to FcgRs or the complement factors. The binding of IgG to the activating (FcgRI, FcgRIIa, FcgRIIIa and FcgRIIIb) and inhibitory (FcgRIIb) FcgRs or the first component of complement (C1q) depends on residues located in the hinge region and the CH2 domain. Mutations have been introduced in IgG1, IgG2 and IgG4 to reduce or silence Fc functionalities. The antibodies described herein may include these modifications.

In one embodiment, the antibody comprises an Fc region with one or more of the following properties: (a) reduced effector function when compared to the parent Fc; (b) reduced affinity to Fcg RI, Fcg RIIa, Fcg RIIb, Fcg RIIIb and/or Fcg RIIIa, (c) reduced affinity to FcgRI (d) reduced affinity to FcgRIIa (e) reduced affinity to FcgRIIb, (f) reduced affinity to Fcg RIIIb or (g) reduced affinity to FcgRIIIa.

In some embodiments, the antibodies or antigen-binding fragments are IgG, or derivatives thereof, e.g., IgG1, IgG2, IgG3, and IgG4 isotypes. In some embodiments wherein the antibody has an IgG4 isotype, the antibody contains S228P, L234A, and L235A substitutions in its Fc region. In some embodiments wherein the antibody has an IgG1 isotype, the antibody contains S228P, L234A, and L235A substitutions in its Fc region. The antibodies described herein may include these modifications. In some embodiments, the antibody has an IgG1 isotype In some embodiments, the antibody is of IgG4 isotype, optionally comprising a heavy chain substitution S228P when compared to the wild type IgG4.

In some embodiments, the antibody is of IgG isotype, optionally comprising heavy chain substitutions L234A, G237A, P238S, H268A, V309L, A330S and P331S when compared to the wild type IgG1.

In addition to the described PSMA-specific antibodies and antigen-binding fragments, also provided are polynucleotide sequences capable of encoding the described antibodies and antigen-binding fragments. Vectors comprising the described polynucleotides are also provided, as are cells expressing the PSMA-specific antibodies or antigen-binding fragments provided herein. Also described are cells capable of expressing the disclosed vectors. These cells may be mammalian cells (such as 293F cells, CHO cells), insect cells (such as Sf7 cells), yeast cells, plant cells, or bacteria cells (such as *E. coli*). The described antibodies may also be produced by hybridoma cells.

Homologous Antibodies

Variants of the antibodies specifically binding PSMA of the invention described herein, and in some embodiments of each and every one of the numbered embodiments listed below, comprising the VH, the VL or the VH and the VL amino acid sequences shown in Table 3 are within the scope of the invention. For example, variants may comprise one, two, three, four, five, six, seven, eight, nine, ten, eleven, twelve, thirteen, fourteen or fifteen amino acid substitutions in the VH and/or the VL as long as the homologous antibodies retain or have improved functional properties when compared to the parental antibodies. In some embodiments, the sequence identity may be about 90%, 91%, 92%, 93%, 94%, 95%, 96%, 97%, 98% or 99% to a VH or the VL amino acid sequence of the invention. Optionally, any variation of the variant compared to the parental antibody is not within the CDRs of the variant.

In some embodiments of the invention described herein, and in some embodiments of each and every one of the numbered embodiments listed below, the antibody specifically binding PSMA of the invention comprises the VH of SEQ ID NOs: 60, 62, 64, 66, 68, 70, 72, 74, 75, 77, 79, 160, 138, 139, or 140, the VH optionally having one, two, three, four, five, six, seven, eight, nine, ten, eleven, twelve, thirteen, fourteen or fifteen amino acid substitutions. Optionally, any substitutions are not within the CDRs.

In some embodiments of the invention described herein, and in some embodiments of each and every one of the numbered embodiments listed below, the antibody specifically binding PSMA of the invention comprises the VL of SEQ ID NOs: 61, 63, 65, 67, 69, 71, 73, 76, 78, 142, 143, or 144, the VL optionally having one, two, three, four, five, six, seven, eight, nine, ten, eleven, twelve, thirteen, fourteen or fifteen amino acid substitutions. Optionally, any substitutions are not within the CDRs.

In some embodiments of the invention described herein, and in some embodiments of each and every one of the numbered embodiments listed below, the antibody specifically binding PSMA of the invention comprises the VH of SEQ ID NO: 60 and the VL of SEQ ID NO: 61, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

In some embodiments of the invention described herein, and in some embodiments of each and every one of the numbered embodiments listed below, the antibody specifically binding PSMA of the invention comprises the VH of SEQ ID NO: 62 and the VL of SEQ ID NO: 63, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

In some embodiments of the invention described herein, and in some embodiments of each and every one of the numbered embodiments listed below, the antibody specifically binding PSMA of the invention comprises the VH of SEQ ID NO: 64 and the VL of SEQ ID NO: 65, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

In some embodiments of the invention described herein, and in some embodiments of each and every one of the numbered embodiments listed below, the antibody specifically binding PSMA of the invention comprises the VH of SEQ ID NO: 66 and the VL of SEQ ID NO: 67, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

In some embodiments of the invention described herein, and in some embodiments of each and every one of the numbered embodiments listed below, the antibody specifically binding PSMA of the invention comprises the VH of SEQ ID NO: 68 and the VL of SEQ ID NO: 69, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

In some embodiments of the invention described herein, and in some embodiments of each and every one of the numbered embodiments listed below, the antibody specifically binding PSMA of the invention comprises the VH of SEQ ID NO: 70 and the VL of SEQ ID NO: 71, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

In some embodiments of the invention described herein, and in some embodiments of each and every one of the numbered embodiments listed below, the antibody specifically binding PSMA of the invention comprises the VH of SEQ ID NO: 72 and the VL of SEQ ID NO: 73, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

In some embodiments of the invention described herein, and in some embodiments of each and every one of the numbered embodiments listed below, the antibody specifically binding PSMA of the invention comprises the VH of SEQ ID NO: 74 and the VL of SEQ ID NO: 61, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

In some embodiments of the invention described herein, and in some embodiments of each and every one of the numbered embodiments listed below, the antibody specifically binding PSMA of the invention comprises the VH of SEQ ID NO: 75 and the VL of SEQ ID NO: 76, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

In some embodiments of the invention described herein, and in some embodiments of each and every one of the numbered embodiments listed below, the antibody specifically binding PSMA of the invention comprises the VH of SEQ ID NO: 77 and the VL of SEQ ID NO: 78, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

In some embodiments of the invention described herein, and in some embodiments of each and every one of the numbered embodiments listed below, the antibody specifically binding PSMA of the invention comprises the VH of SEQ ID NO: 79 and the VL of SEQ ID NO: 78, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

In some embodiments of the invention described herein, and in some embodiments of each and every one of the numbered embodiments listed below, the antibody specifically binding PSMA of the invention comprises the VH of SEQ ID NO: 160 and the VL of SEQ ID NO: 65, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

In some embodiments of the invention described herein, and in some embodiments of each and every one of the numbered embodiments listed below, the antibody specifically binding PSMA of the invention comprises the VH of SEQ ID NO: 138 and the VL of SEQ ID NO: 67, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

In some embodiments of the invention described herein, and in some embodiments of each and every one of the numbered embodiments listed below, the antibody specifically binding PSMA of the invention comprises the VH of SEQ ID NO: 138 and the VL of SEQ ID NO: 142, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

In some embodiments of the invention described herein, and in some embodiments of each and every one of the numbered embodiments listed below, the antibody specifically binding PSMA of the invention comprises the VH of SEQ ID NO: 138 and the VL of SEQ ID NO: 143, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

In some embodiments of the invention described herein, and in some embodiments of each and every one of the numbered embodiments listed below, the antibody specifically binding PSMA of the invention comprises the VH of SEQ ID NO: 139 and the VL of SEQ ID NO: 67, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

In some embodiments of the invention described herein, and in some embodiments of each and every one of the numbered embodiments listed below, the antibody specifically binding PSMA of the invention comprises the VH of SEQ ID NO: 140 and the VL of SEQ ID NO: 144, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

In some embodiments of the invention described herein, and in some embodiments of each and every one of the numbered embodiments listed below, the antibody specifically binding PSMA of the invention comprises the VH of SEQ ID NO: 140 and the VL of SEQ ID NO: 67, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

In some embodiments of the invention described herein, and in some embodiments of each and every one of the numbered embodiments listed below, the antibody specifically binding PSMA of the invention comprises the VH of SEQ ID NO: 140 and the VL of SEQ ID NO: 142, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

In some embodiments of the invention described herein, and in some embodiments of each and every one of the numbered embodiments listed below, the antibody specifically binding PSMA of the invention comprises the VH of SEQ ID NO: 140 and the VL of SEQ ID NO: 143, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

In some embodiments of the invention described herein, and in some embodiments of each and every one of the numbered embodiments listed below, the antibody specifically binding PSMA of the invention comprises the VH of SEQ ID NO: 139 and the VL of SEQ ID NO: 144, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

In some embodiments of the invention described herein, and in some embodiments of each and every one of the numbered embodiments listed below, the antibody specifically binding PSMA of the invention comprises the VH of SEQ ID NO: 139 and the VL of SEQ ID NO: 142, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

In some embodiments of the invention described herein, and in some embodiments of each and every one of the numbered embodiments listed below, the antibody specifically binding PSMA of the invention comprises the VH of SEQ ID NO: 139 and the VL of SEQ ID NO: 143, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

In some embodiments of the invention described herein, and in some embodiments of each and every one of the numbered embodiments listed below, the antibody specifically binding PSMA of the invention comprises the VH of SEQ ID NO: 141 and the VL of SEQ ID NO: 143, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

The homologous antibodies specifically binding PSMA of the invention described herein, and in some embodiments of each and every one of the numbered embodiments listed below, have one, two, three, four or five of the following properties:
  a) binds *Pan troglodyte* PSMA ECD with an equilibrium dissociation constant ($K_D$) of 25 nM or less, wherein the $K_D$ is measured using ProteOn XPR36 system at +25° C.,
  b) binds LNCaP cells with a calculated $EC_{50}$ of 20 nM or less and binds *Macaca fascicularis* PSMA-expressing HEK cells with a calculated $EC_{50}$ of 40 nM or less, wherein the difference in calculated $EC_{50}$ between binding LNCaP cells and binding *Macaca fascicularis* PSMA-expressing HEK cells is less than 5-fold, and wherein the calculated $EC_{50}$ is measured in a whole cell binding assay at 0° C. using flow cytometry, c) binds recombinant PSMA ECD from human (SEQ ID NO: 7), *Pan troglodytes* (SEQ ID NO:4) and *Macaca fascicularis* (SEQ ID NO: 5) with an equilibrium dissociation constant ($K_D$) of 12 nM or less, wherein the $K_D$ is measured using Proteon surface plasmon resonance assay ProteOn XPR36 system at +25° C.;

d) displays T-cell mediated killing of LNCaP cells, C42 cells, human PSMA-expressing HEK cells or *Macaca fascicularis* PSMA-expressing HEK cells when paired in a bispecific antibody with anti-CD3 antibody CD3B219, wherein the T-cell mediated killing is measured by Chromium-51 or by caspase 3/7 activation assay or e) recognizes a conformational epitope wherein the epitope is comprised of residues I138, F235, P237, G238, D244, Y299, Y300, Q303, K304, E307, and K324-P326 of human PSMA (SEQ ID NO:3)

Antibodies with Conservative Modifications

In some embodiments described herein, and in some embodiments of each and every one of the numbered embodiments listed below, the antibody specifically binding PSMA of the invention comprises the VH comprising the HCDR1, the HCDR2 and the HCDR3 sequences and the VL comprising the LCDR1, the LCDR2 and the LCDR3 sequences, wherein one or more of the CDR sequences comprise specified amino acid sequences based on the antibodies described herein (e.g., antibodies shown in Table 2, or conservative modifications thereof, and wherein the antibodies retain the desired functional properties of the parental antibodies specifically binding PSMA of the invention.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 8, 9, 10, 11, 12 and 13, respectively, and conservative modifications thereof.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 14, 15, 16, 17, 18 and 19, respectively, and conservative modifications thereof.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 20, 21, 22, 23, 12 and 24, respectively, and conservative modifications thereof.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 26, 27, 28, 29 and 30, respectively, and conservative modifications thereof.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 31, 32, 33, 34, 12 and 35, respectively, and conservative modifications thereof.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 36, 37, 38, 39, 40 and 41, respectively, and conservative modifications thereof.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 31, 42, 43 11, 12 and 13, respectively, and conservative modifications thereof.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 31, 44, 45, 46, 29 and 47, respectively, and conservative modifications thereof.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 36, 37, 48, 49, 50 and 51, respectively, and conservative modifications thereof.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 36, 37, 52, 49, 50 and 51, respectively, and conservative modifications thereof.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 53, 54, 55, 23, 12 and 35, respectively, and conservative modifications thereof.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 130, 27, 28, 29, and 30, respectively and conservative modifications thereof.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 130, 27, 131, 29, and 132, respectively and conservative modifications thereof.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 130, 27, 28, 133, and 132, respectively and conservative modifications thereof.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 134, 27, 28, 29, and 30, respectively and conservative modifications thereof.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 135, 27, 28, 29, and 136, respectively and conservative modifications thereof.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 135, 27, 28, 29, and 30, respectively and conservative modifications thereof.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 135, 27, 131, 29, and 132, respectively and conservative modifications thereof.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 135, 27, 131, 29, and 132, respectively and conservative modifications thereof.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 134, 27, 28, 29, and 136, respectively and conservative modifications thereof.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 134, 27, 131, 29, and 132, respectively and conservative modifications thereof.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 134, 27, 28, 133, and 132, respectively and conservative modifications thereof.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 25, 137, 27, 28, 133, and 132, respectively and conservative modifications thereof.

In some embodiments of the invention described herein, and in some embodiments of each and every one of the numbered embodiments listed below, the antibody specifically binding PSMA of the invention comprises the HCDR1, the HCDR2, the HCDR3, the LCDR1, the LCDR2 and the LCDR3 of SEQ ID NOs: 122, 123, 124, 23, 12 and 24, respectively, and conservative modifications thereof.

The antibodies with conservative modifications of the invention described herein, and in some embodiments of each and every one of the numbered embodiments listed below, have one, two, three, four or five of the following properties:

a) binds *Pan troglodyte* PSMA ECD with an equilibrium dissociation constant ($K_D$) of 25 nM or less, wherein the $K_D$ is measured using ProteOn XPR36 system at +25° C., b) binds LNCaP cells with a calculated $EC_{50}$ of 20 nM or less and binds *Macaca fascicularis* PSMA-expressing HEK cells with a calculated $EC_{50}$ of 40 nM or less, wherein the difference in calculated $EC_{50}$ between binding LNCaP cells and binding *Macaca fascicularis* PSMA-expressing HEK cells is less than 5-fold, and wherein the calculated $EC_{50}$ is measured in a whole cell binding assay at 0° C. using flow cytometry, c) binds recombinant PSMA ECD from human (SEQ ID NO: 7), *Pan troglodytes* (SEQ ID NO:4) and *Macaca fascicularis* (SEQ ID NO: 5) with an equilibrium dissociation constant ($K_D$) of 12 nM or less, wherein the $K_D$ is measured using Proteon surface plasmon resonance assay ProteOn XPR36 system at +25° C.;

d) displays T-cell mediated killing of LNCaP cells, C42 cells, human PSMA-expressing HEK cells or *Macaca fascicularis* PSMA-expressing HEK cells when paired in a bispecific antibody with anti-CD3 antibody CD3B219, wherein the T-cell mediated killing is measured by Chromium-51 or by caspase 3/7 activation assay or e) recognizes a conformational epitope wherein the epitope is comprised of residues I138, F235, P237, G238, D244, Y299, Y300, Q303, K304, E307, and K324-P326 of human PSMA (SEQ ID NO:3)

"Conservative modifications" refer to amino acid modifications that do not significantly affect or alter the binding characteristics of the antibody containing the amino acid sequences. Conservative modifications include amino acid substitutions, additions and deletions. Conservative substitutions are those in which the amino acid is replaced with an amino acid residue having a similar side chain. The families of amino acid residues having similar side chains are well defined and include amino acids with acidic side chains (e.g., aspartic acid, glutamic acid), basic side chains (e.g., lysine, arginine, histidine), nonpolar side chains (e.g., alanine, valine, leucine, isoleucine, proline, phenylalanine, methionine), uncharged polar side chains (e.g., glycine, asparagine, glutamine, cysteine, serine, threonine, tyrosine, tryptophan), aromatic side chains (e.g., phenylalanine, tryptophan, histidine, tyrosine), aliphatic side chains (e.g., glycine, alanine, valine, leucine, isoleucine, serine, threonine), amide (e.g., asparagine, glutamine), beta-branched side chains (e.g., threonine, valine, isoleucine) and sulfur-containing side chains (cysteine, methionine). Furthermore, any native residue in the polypeptide may also be substituted with alanine, as has been previously described for alanine scanning mutagenesis (MacLennan et al., (1988) Acta Physiol Scand Suppl 643:55-67, Sasaki et al., (1988) Adv Biophys 35:1-24). Amino acid substitutions to the antibodies of the invention may be made by known methods for example by PCR mutagenesis (U.S. Pat. No. 4,683,195). Alternatively, libraries of variants may be generated for example using random (NNK) or non-random codons, for example DVK codons, which encode 11 amino acids (Ala, Cys, Asp, Glu, Gly, Lys, Asn, Arg, Ser, Tyr, Trp). The resulting antibody variants may be tested for their characteristics using assays described herein.

Immunoconjugates

An "immunoconjugate" refers to the antibody of the invention conjugated to one or more heterologous molecule(s).

In some embodiments, the antibody of the invention described herein, and in some embodiments of each and every one of the numbered embodiments listed below, is conjugated to one or more cytotoxic agents. Exemplary such cytotoxic agents include chemotherapeutic agents or drugs, growth inhibitory agents, toxins (e.g., protein toxins, enzymatically active toxins of bacterial, fungal, plant, or animal origin, or fragments thereof), and radioactive isotopes.

In some embodiments, an immunoconjugate is an antibody-drug conjugate (ADC) in which the antibody of the invention is conjugated to one or more drugs, such as to a maytansinoid (see, e.g., U.S. Pat. Nos. 5,208,020, 5,416, 06)); an auristatin such as monomethylauristatin drug moieties DE and DF (MMAE and MMAF) (see, e.g., U.S. Pat. Nos. 5,635,483 and 5,780,588, and 7,498,298), a dolastatin, a calicheamicin or derivative thereof (see, e.g., U.S. Pat. Nos. 5,712,374, 5,714,586, 5,739, 116, 5,767,285, 5,770, 701, 5,770,710, 5,773,001, and 5,877,296; Hinman et al., (1993) Cancer Res 53:3336-3342; and Lode et al., (1998) Cancer Res 58:2925-2928); an anthracycline such as daunomycin or doxorubicin (see, e.g., Kratz et al., (2006) Current Med. Chem 13:477-523; Jeffrey et al., (2006) Bioorganic & Med Chem Letters 16:358-362; Torgov et al., (2005) Bioconj Chem 16:717-721; Nagy et al., (2000) Proc Natl Acad Sci USA 97:829-834; Dubowchik et al, Bioorg. & Med. Chem. Letters 12: 1529-1532 (2002); King et al., (2002) J Med Chem 45:4336-4343; and U.S. Pat. No. 6,630,579), methotrexate, vindesine, a taxane such as docetaxel, paclitaxel, larotaxel, tesetaxel, and ortataxel.

In some embodiments, the immunoconjugate comprises the antibody of the invention described herein conjugated to an enzymatically active toxin or fragment thereof, such as diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In some embodiments described herein, and in some embodiments of each and every one of the numbered embodiments listed below, the antibody is conjugated to a radioactive atom to form a radioconjugate. A variety of radioactive isotopes are available for the production of radioconjugates. Examples include At211, 1131, I125, Y90, Re186, Re188, Sm153, Bi212, P32, Pb212 and radioactive isotopes of Lu. When the radioconjugate is used for detection, it may comprise a radioactive atom for scintigraphic studies, for example tc99m or 1123, or a spin label for nuclear magnetic resonance (NMR) imaging (also known as magnetic resonance imaging, mri), such as iodine-123 again, iodine-131, indium-I1, fluorine-19, carbon-13, nitrogen-15, oxygen-17, gadolinium, manganese or iron.

Conjugates of the antibody of the invention described herein and the cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HQ), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin may be prepared as described in Vitetta et al., (1987) Science 238: 1098. Carbon-14-labeled I-isothiocyanatobenzyl-3-methyldiethylene triaminepentaacetic acid (MX-DTPA) is an exemplary chelating agent for conjugation of radionucleotide to the antibody. See, e.g., WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., (1992) Cancer Res 52: 127-131; U.S. Pat. No. 5,208,020) may be used.

The immunoconjugates or ADCs may be prepared with cross-linker reagents such as BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

One embodiment of the invention, and in some embodiments of each and every one of the numbered embodiments listed below, is an immunoconjugate comprising the antibody specifically binding PSMA of the invention linked to a therapeutic agent or an imaging agent.

Another embodiment of the invention, and in some embodiments of each and every one of the numbered embodiments listed below, is an immunoconjugate comprising the antibody specifically binding CD3 of the invention linked to a therapeutic agent or an imaging agent.

Another embodiment of the invention, and in some embodiments of each and every one of the numbered embodiments listed below, is an immunoconjugate comprising the bispecific PSMA/CD3 antibody of the invention linked to a therapeutic agent or an imaging agent.

Generation of Monospecific Antibodies of the Invention

In some embodiments described herein, and in some embodiments of each and every one of the numbered embodiments listed below, the antagonistic antibodies specifically binding PSMA of the invention are human.

In some embodiments described herein, and in some embodiments of each and every one of the numbered embodiments listed below, the antagonistic antibodies specifically binding PSMA of the invention are humanized.

Monospecific antibodies of the invention described herein (e.g. antibodies specifically binding PSMA) may be generated using various technologies. For example, the hybridoma method of Kohler and Milstein, Nature 256:495, 1975 may be used to generate monoclonal antibodies. In the hybridoma method, a mouse or other host animal, such as a hamster, rat or monkey, is immunized with human chimpanzee or macaque PSMA or CD3 or fragments of PSMA or CD3, such as the extracellular domain of PSMA or CD3, followed by fusion of spleen cells from immunized animals with myeloma cells using standard methods to form hybridoma cells (Goding, Monoclonal Antibodies: Principles and Practice, pp. 59-103 (Academic Press, 1986)). Colonies arising from single immortalized hybridoma cells are screened for production of antibodies with desired properties, such as specificity of binding, cross-reactivity or lack thereof, and affinity for the antigen.

Various host animals may be used to produce the PSMA antibodies of the invention described herein, and in some embodiments of each and every one of the numbered embodiments listed below. For example, Balb/c mice may be used to generate mouse anti-human PSMA antibodies. The antibodies made in Balb/c mice and other non-human animals may be humanized using various technologies to generate more human-like sequences.

Exemplary humanization techniques including selection of human acceptor frameworks are known and include CDR grafting (U.S. Pat. No. 5,225,539), SDR grafting (U.S. Pat. No. 6,818,749), Resurfacing (Padlan, (1991) Mol Immunol 28:489-499), Specificity Determining Residues Resurfacing (U.S. Patent Publ. No. 2010/0261620), human framework adaptation (U.S. Pat. No. 8,748,356) or superhumanization (U.S. Pat. No. 7,709,226). In these methods, CDRs of parental antibodies are transferred onto human frameworks that may be selected based on their overall homology to the parental frameworks, based on similarity in CDR length, or canonical structure identity, or a combination thereof.

Humanized antibodies may be further optimized to improve their selectivity or affinity to a desired antigen by incorporating altered framework support residues to preserve binding affinity (backmutations) by techniques such as those described in Int. Patent Publ. Nos. WO1090/007861 and WO1992/22653, or by introducing variation at any of the CDRs for example to improve affinity of the antibody.

Transgenic animals, such as mice or rat carrying human immunoglobulin (Ig) loci in their genome may be used to generate human antibodies against a target protein, and are described in for example U.S. Pat. No. 6,150,584, Int. Patent Publ. No. WO99/45962, Int. Patent Publ. Nos. WO2002/066630, WO2002/43478, WO2002/043478 and WO1990/04036, Lonberg et al (1994) Nature 368:856-9; Green et al (1994) Nature Genet. 7:13-21; Green & Jakobovits (1998) Exp. Med. 188:483-95; Lonberg and Huszar (1995) Int Rev Immunol 13:65-93; Bruggemann et al., (1991) Eur J Immunol 21:1323-1326; Fishwild et al., (1996) Nat Biotechnol 14:845-851; Mendez et al., (1997) Nat Genet 15:146-156; Green (1999) J Immunol Methods 231:11-23; Yang et al., (1999) Cancer Res 59:1236-1243; Bruggemann and Taussig (1997) Curr Opin Biotechnol 8:455-458. The endogenous immunoglobulin loci in such animal may be disrupted or deleted, and at least one complete or partial human immunoglobulin locus may be inserted into the genome of the animal using homologous or non-homologous recombination, using transchromosomes, or using minigenes. Companies such as Regeneron (www_regeneron_com), Harbour Antibodies (www_harbourantibodies_com), Open Monoclonal Technology, Inc. (OMT) (www_omtinc_net), KyMab (www_kymab_com), Trianni (www.trianni_com) and Ablexis (www_ablexis_com) may be engaged to provide human antibodies directed against a selected antigen using technologies as described above.

Human antibodies may be selected from a phage display library, where the phage is engineered to express human immunoglobulins or portions thereof such as Fabs, single chain antibodies (scFv), or unpaired or paired antibody variable regions (Knappik et al., (2000) J Mol Biol 296:57-86; Krebs et al., (2001) J Immunol Meth 254:67-84; Vaughan et al., (1996) Nature Biotechnology 14:309-314; Sheets et al., (1998) PITAS (USA) 95:6157-6162; Hoogenboom and Winter (1991) J Mol Biol 227:381; Marks et al., (1991) J Mol Biol 222:581). The antibodies of the invention may be isolated for example from phage display library expressing antibody heavy and light chain variable regions as fusion proteins with bacteriophage pIX coat protein as described in Shi et al., (2010) J Mol Biol 397:385-96, and Int. Patent Publ. No. WO09/085462). The libraries may be screened for phage binding to human and/or cyno PSMA or CD3 and the obtained positive clones may be further characterized, the Fabs isolated from the clone lysates, and expressed as full length IgGs. Such phage display methods for isolating human antibodies are described in for example: U.S. Pat. Nos. 5,223,409, 5,403,484, 5,571,698, 5,427,908, 5,580,717, 5,969,108, 6,172,197, 5,885,793; 6,521,404; 6,544,731; 6,555,313; 6,582,915 and 6,593,081.

Preparation of immunogenic antigens and monoclonal antibody production may be performed using any suitable technique, such as recombinant protein production. The immunogenic antigens may be administered to an animal in the form of purified protein, or protein mixtures including whole cells or cell or tissue extracts, or the antigen may be formed de novo in the animal's body from nucleic acids encoding said antigen or a portion thereof.

Generation of Multispecific PSMA×CD3 Antibodies of the Invention

The multispecific PSMA×CD3 antibodies of the invention (e.g. the bispecific antibodies comprising a first domain specifically binding PSMA and a second domain specifically binding CD3) may be generated by combining PSMA binding VH/VL domains with CD3 binding VH/VL domains isolated and characterized herein. Alternatively, the bispecific PSMA×CD3 antibodies may be engineered using VH/VL domains from publicly available monospecific anti-PSMA and anti-CD3 antibodies, and/or by mix-matching the PSMA or CD3 binding VH/VL domains identified herein with publicly available PSMA or CD3 binding VH/VL domains.

Exemplary anti-PSMA antibodies that may be used to engineer bispecific PSMA×CD3 molecules are for example those herein and in Table 2. For example, the VH/VL domains of the PSMA antibodies of the invention may be incorporated into bispecific antibodies comprising CD3 binding VH/VL domains described herein and in Table 5. For example, the VH/VL domains of the CD3 antibodies CD3B217 and CD3B219 described herein may be used to generate bispecific PSMA×CD3 antibodies. In addition to the description and characterization of antibodies CD3B217 and CD3B219 provided herein, a more detailed description of the antibodies may be found in U.S. patent application publication number 2016-0068605 A1, which is incorporated by reference herein.

Similarly, exemplary anti-CD3 antibodies that may be used to engineer bispecific PSMA×CD3 molecules are for example those described in Int. Patent Publ. Nos. WO2005/048935, WO2004/106380 and WO2015095392. These CD3 VH/VL domains may be incorporated into bispecific antibodies comprising PSMA binding VH/VL domains described herein and in Table 2. For example, the VH/VL domains of the PSMA antibodies PSMB119, PSMB120, PSMB121, PSMB122, PSMB123, PSMB87, PSMB126, PSMB127, PSMB128, PSMB129, PSMB130, PSMB120, PSMB121, PSMB122, PSMB123, PSMB127, PSMB128, PSMB130, PSMB344, PSMB345, PSMB346, PSMB347, PSMB349, PSMB358, PSMB359, PSMB360, PSMB361, PSMB362, PSMB363, and PSMB365 described herein may be used to generate bispecific PSMA×CD3 antibodies.

The generated bispecific PSMA×CD3 antibodies may be tested for their binding to PSMA and CD3, and for their desired functional characteristics, such as T-cell mediated killing of PSMA-expressing cells (eg, LNCaP).

Bispecific antibodies of the invention comprise antibodies having a full length antibody structure.

"Full length antibody" refers to an antibody having two full length antibody heavy chains and two full length antibody light chains. A full length antibody heavy chain (HC) consists of well-known heavy chain variable and constant domains VH, CH1, hinge, CH2, and CH3. A full length antibody light chain (LC) consists of well-known light chain variable and constant domains VL and CL. The full length antibody may be lacking the C-terminal lysine (K) in either one or both heavy chains.

"Fab-arm" or "half molecule" refers to one heavy chain-light chain pair that specifically binds an antigen.

Full length bispecific antibodies of the invention described herein and in some embodiments of each and every one of the numbered embodiments listed below, may be generated for example using Fab arm exchange (or half molecule exchange) between two monospecific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy chain disulfide bonds in the hinge regions of the parental monospecific antibodies are reduced. The resulting free cysteines of one of the parental monospecific antibodies form an inter heavy-chain disulfide bond with cysteine residues of a second parental monospecific antibody molecule and simultaneously CH3 domains of the parental antibodies release and reform by dissociation-association. The CH3 domains of the Fab arms may be engineered to favor heterodimerization over homodimerization. The resulting product is a bispecific antibody having two Fab arms or half molecules which each bind a distinct epitope, i.e. an epitope on PSMA and an epitope on CD3.

"Homodimerization" refers to an interaction of two heavy chains having identical CH3 amino acid sequences. "Homodimer" refers to an antibody having two heavy chains with identical CH3 amino acid sequences.

"Heterodimerization" refers to an interaction of two heavy chains having non-identical CH3 amino acid sequences. "Heterodimer" refers to an antibody having two heavy chains with non-identical CH3 amino acid sequences.

In some embodiments, the bispecific antibodies include designs such as the Triomab/Quadroma (Trion Pharma/Fresenius Biotech), Knob-in-Hole (Genentech), CrossMAbs (Roche) and the electrostatically-matched (Chugai, Amgen, NovoNordisk, Oncomed), the LUZ-Y (Genentech), the Strand Exchange Engineered Domain body (SEEDbody) (EMD Serono), the Biclonic (Merus) and the DuoBody (Genmab A/S).

The Triomab quadroma technology may be used to generate full length bispecific antibodies of the invention. Triomab technology promotes Fab arm exchange between two parental chimeric antibodies, one parental mAb having IgG2a and the second parental mAb having rat IgG2b constant regions, yielding chimeric bispecific antibodies.

The "knob-in-hole" strategy (see, e.g., Intl. Publ. No. WO 2006/028936) may be used to generate full length bispecific antibodies of the invention. Briefly, selected amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob". Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S_L368A_Y407V.

The CrossMAb technology may be used to generate full length bispecific antibodies of the invention. CrossMAbs, in addition to utilizing the "knob-in-hole" strategy to promoter Fab arm exchange, have in one of the half arms the CH1 and the CL domains exchanged to ensure correct light chain pairing of the resulting bispecific antibody (see e.g. U.S. Pat. No. 8,242,247).

Other cross-over strategies may be used to generate full length bispecific antibodies of the invention by exchanging variable or constant, or both domains between the heavy chain and the light chain or within the heavy chain in the bispecific antibodies, either in one or both arms. These exchanges include for example VH-CH1 with VL-CL, VH with VL, CH3 with CL and CH3 with CH1 as described in Int. Patent Publ. Nos. WO2009/080254, WO2009/080251, WO2009/018386 and WO2009/080252.

Other strategies such as promoting heavy chain heterodimerization using electrostatic interactions by substituting positively charged residues at one CH3 surface and negatively charged residues at a second CH3 surface may be used, as described in US Patent Publ. No. US2010/0015133; US Patent Publ. No. US2009/0182127; US Patent Publ. No. US2010/028637 or US Patent Publ. No. US2011/0123532. In other strategies, heterodimerization may be promoted by following substitutions (expressed as modified position in the first CH3 domain of the first heavy chain/modified position in the second CH3 domain of the second heavy chain): L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F, or T350V_L351Y_F405A_Y407V/T350V_T366L_K392L_T394W as described in U.S. Patent Publ. No. US2012/0149876 or U.S. Patent Publ. No. US2013/0195849.

LUZ-Y technology may be utilized to generate bispecific antibodies of the invention. In this technology, a leucine zipper is added into the C terminus of the CH3 domains to drive the heterodimer assembly from parental mAbs that is removed post-purification as described in Wranik et al., (2012) J Biol Chem 287(52): 42221-9.

SEEDbody technology may be utilized to generate bispecific antibodies of the invention. SEEDbodies have, in their constant domains, select IgG residues substituted with IgA residues to promote heterodimerization as described in U.S. Patent No. US20070287170.

The present invention also provides for a multispecific, multifunctional antibody that specifically binds to PSMA.

According to the invention such a multispecific, multifunctional antibody that specifically binds to PSMA may be a trispecific antibody for dual targeting of tumor cells—these are trifunctional structures that can be designed to target two different targets/epitopes on the tumor cell and with the third functionality bind with high affinity to either T-cells or NK-cells. Trispecific antibodies targeting two distinct tumor epitopes and engaging T- or NK-cells lyse the tumor cells that express both targets. Such molecules can be generated by antibody formats known in the art and are fully described. (WO20151842071, WO2015158636, WO2010136172, WO2013174873). In a trispecific embodiment of the invention the antigen-binding polypeptide is bispecific for PSMA and a second distinct antigen on a tumor cell and additionally specific for an effector cell, in particular a T cell or a NK cell.

Bispecific antibodies of the invention described herein, and in some embodiments of each and every one of the numbered embodiments listed below, may be generated in vitro in a cell-free environment by introducing asymmetrical mutations in the CH3 regions of two monospecific homodimeric antibodies and forming the bispecific heterodimeric antibody from two parent monospecific homodimeric antibodies in reducing conditions to allow disulfide bond isomerization according to methods described in Int. Patent Publ. No. WO2011/131746 (DuoBody technology). In the methods, the first monospecific bivalent antibody (e.g., anti-PSMA antibody) and the second monospecific bivalent antibody (e.g., anti-CD3 antibody) are engineered to have certain substitutions at the CH3 domain that promoter heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Exemplary reducing agents that may be used are 2-mercaptoethylamine (2-MEA), dithiothreitol (DTT), dithioerythritol (DTE), glutathione, tris(2-carboxyethyl)phosphine (TCEP), L-cysteine and beta-mercaptoethanol. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

In some embodiments described herein, and in some embodiments of each and every one of the numbered embodiments listed below, the isolated bispecific antibody comprising a first domain specifically binding PSMA and a second domain specifically binding CD3 comprises at least one substitution in an antibody CH3 constant domain.

In some embodiments described herein, and in some embodiments of each and every one of the numbered embodiments listed below, the at least one substitution in the antibody CH3 constant domain is 409R, F405L or F405L and R409K substitution, wherein residue numbering is according to the EU Index.

Antibody domains and numbering are well known. "Asymmetrical" refers to non-identical substitutions in the two CH3 domains in two separate heavy chains in an antibody. An IgG1 CH3 region typically consists of residues 341-446 on IgG1 (residue numbering according to the EU index).

In some embodiments described herein, and in some embodiments of each and every one of the numbered embodiments listed below, the isolated bispecific PSMA× CD3 antibody comprises a F405L substitution in an antibody first heavy chain (HC1) and a 409R substitution in an antibody second heavy chain (HC2).

In some embodiments described herein, and in some embodiments of each and every one of the numbered embodiments listed below, the isolated bispecific PSMA× CD3 antibody comprises a S228P substitution in the HC1 and S228P, F405L and R409K substitutions in the HC2, wherein the antibody is of IgG4 isotype.

In some embodiments described herein, and in some embodiments of each and every one of the numbered embodiments listed below, the HC1 contains the first domain specifically binding PSMA and the HC2 contains the second domain specifically binding CD3.

In some embodiments described herein, the bispecific antibody of the invention comprises at least one, two, three, four, five, six, seven or eight asymmetrical substitutions in the HC1 and the HC2 at residue positions 350, 366, 368, 370, 399, 405, 407 or 409, when residue numbering is according to the EU index.

In some embodiments described herein, the bispecific antibody of the invention comprises at least one, two, three or four asymmetrical substitutions in the HC1 and the HC2 at residue positions 350, 370, 405 or 409, when residue numbering is according to the EU index.

In some embodiments described herein, the bispecific antibody of the invention comprises at least one asymmetrical substitution in the HC1 and the HC2 at residue positions 405 or 409, when residue numbering is according to the EU index.

In some embodiments described herein, the bispecific antibody of the invention comprises a 409R or a F405L substitution in the HC1 and a 409R or a F405L substitution in the HC2, wherein residue numbering is according to the EU index.

In some embodiments described herein, the bispecific antibody of the invention comprises the F405L substitution in the HC1 and the 409R substitution in the HC2.

In some embodiments described herein, the bispecific antibody of the invention comprises at least one asymmetrical substitution in the HC1 and the HC2 at residue positions 366, 368, 370, 399, 405, 407 or 409, wherein residue numbering is according to the EU index.

In some embodiments described herein, the HC1 position 409 has an amino acid substitution other than Lys, Leu or Met and the HC2 position 405 has an amino acid substitution other than Phe.

In some embodiments described herein, the HC1 position 405 has an amino acid substitution other than Phe and the HC2 position 409 has an amino acid substitution other than Lys, Leu or Met.

In some embodiments described herein, the HC1 position 409 has an amino acid substitution other than Lys, Leu or Met and the HC2 position 405 has an amino acid substitution other than Phe, Arg or Gly.

In some embodiments described herein, the HC1 position 405 has an amino acid substitution other than Phe, Arg or Gly and the HC2 CH3 position 409 has an amino acid substitution other than Lys, Leu or Met In some embodiments described herein, the HC1 CH3 has Phe at position 405 and an amino acid other than Lys, Leu or Met at position 409 and the HC2 has an amino acid other than Phe at position 405 and a Lys at position 409.

In some embodiments described herein, the HC1 has an amino acid other than Phe at position 405 and Lys at position 409 and the HC2 has Phe at position 405 and an amino acid other than Lys, Leu or Met at position 409.

In some embodiments described herein, the HC1 has Phe at position 405 and an amino acid other than Lys, Leu or Met at position 409 and the HC2 has a substitution other than Phe, Arg or Gly at position 405 and Lys at position 409.

In some embodiments described herein, the HC1 has a substitution other than Phe, Arg or Gly at position 405 and Lys at position 409 and the HC2 has Phe at position 405 and an amino acid other than Lys, Leu or Met at position 409.

In some embodiments described herein, the HC1 has Phe at position 405 and an amino acid other than Lys, Leu or Met at position 409 and the HC2 has Leu at position 405 and Lys at position 409.

In some embodiments described herein, the HC1 has Leu at position 405 and Lys at position 409 and the HC2 has Phe at position 405 and an amino acid other than Lys, Leu or Met at position 409.

In some embodiments described herein, the HC1 has Phe at position 405 and Arg at position 409 and the HC2 has an amino acid other than Phe, Arg or Gly at position 405 and Lys at position 409.

In some embodiments described herein, the HC has an amino acid other than Phe, Arg or Gly at position 405 and Lys at position 409 and the HC2 has Phe at position 405 and Arg at position 409.

In some embodiments described herein, the HC1 has Phe at position 405 and Arg at position 409 and the HC2 has Leu at position 405 and Lys at position 409.

In some embodiments described herein, the HC1 has Leu at position 405 and Lys at position 409 and the HC2 has Phe at position 405 and Arg at position 409.

In some embodiments described herein, the HC1 has Phe at position 405 and Lys at position 409 and the HC2 has Leu at position 405 and Arg at position 409.

In some embodiments described herein, the HC1 has Leu at position 405 and Arg at position 409 and the HC2 has Phe at position 405 and Lys at position 409.

In some embodiments described herein, the HC1 has an amino acid other than Lys, Leu or Met at position 409 and the HC2 has Lys at position 409, Thr at position 370 and Leu at position 405.

In some embodiments described herein, the HC1 has Lys at position 409, Thr at position 370 and Leu at position 405 and the HC2 has an amino acid other than Lys, Leu or Met at position 409.

In some embodiments described herein, the HC1 has Arg at position 409 and the HC2 has Lys at position 409, Thr at position 370 and Leu at position 405.

In some embodiments described herein, the HC1 has Lys at position 409, Thr at position 370 and Leu at position 405 and the HC2 has Arg at position 409.

In some embodiments described herein, the HC1 has Lys at position 370, Phe at position 405 and Arg at position 409 and the HC2 has Lys at position 409, Thr at position 370 and Leu at position 405.

In some embodiments described herein, the HC1 has Lys at position 409, Thr at position 370 and Leu at position 405 and the HC2 has Lys at position 370, Phe at position 405 and Arg at position 409.

In some embodiments described herein, the HC1 has an amino acid other than Lys, Leu or Met at position 409 and the HC2 has an amino acid other than Tyr, Asp, Glu, Phe, Lys, Gln, Arg, Ser or Thr at position 407.

In some embodiments described herein, the HC1 has an amino acid other than Tyr, Asp, Glu, Phe, Lys, Gln, Arg, Ser or Thr at position 407 and the HC2 has an amino acid other than Lys, Leu or Met at position 409.

In some embodiments described herein, the HC1 has an amino acid other than Lys, Leu or Met at position 409 and the HC2 has Ala, Gly, His, Ile, Leu, Met, Asn, Val or Trp at position 407.

In some embodiments described herein, the HC1 has Ala, Gly, His, Ile, Leu, Met, Asn, Val or Trp at position 407 and the HC2 has an amino acid other than Lys, Leu or Met at position 409.

In some embodiments described herein, the HC1 has an amino acid other than Lys, Leu or Met at position 409 and the HC2 has Gly, Leu, Met, Asn or Trp at position 407.

In some embodiments described herein, the HC1 has Gly, Leu, Met, Asn or Trp at position 407 and the HC2 has an amino acid other than Lys, Leu or Met at position 409.

In some embodiments described herein, the HC1 has Tyr at position 407 and an amino acid other than Lys, Leu or Met at position 409 and the HC2 has an amino acid other than Tyr, Asp, Glu, Phe, Lys, Gln, Arg, Ser or Thr at position 407 and Lys at position 409.

In some embodiments described herein, the HC1 has an amino acid other than Tyr, Asp, Glu, Phe, Lys, Gln, Arg, Ser or Thr at position 407 and Lys at position 409 and the HC2 has Tyr at position 407 and an amino acid other than Lys, Leu or Met at position 409.

In some embodiments described herein, the HC1 has Tyr at position 407 and an amino acid other than Lys, Leu or Met at position 409 and the HC2 has Ala, Gly, His, Ile, Leu, Met, Asn, Val or Trp at position 407 and Lys at position 409.

In some embodiments described herein, the HC1 has Ala, Gly, His, Ile, Leu, Met, Asn, Val or Trp at position 407 and Lys at position 409 and the HC2 CH3 has Tyr at position 407 and an amino acid other than Lys, Leu or Met at position 409.

In some embodiments described herein, the HC1 CH3 has Tyr at position 407 and an amino acid other than Lys, Leu or Met at position 409 and the HC2 has Gly, Leu, Met, Asn or Trp at position 407 and Lys at position 409.

In some embodiments described herein, the HC1 has Gly, Leu, Met, Asn or Trp at position 407 and Lys at position 409 and the HC2 has Tyr at position 407 and an amino acid other than Lys, Leu or Met at position 409.

In some embodiments described herein, the HC1 has Tyr at position 407 and Arg at position 409 and the HC2 has an amino acid other than Tyr, Asp, Glu, Phe, Lys, Gln, Arg, Ser or Thr at position 407 and Lys at position 409.

In some embodiments described herein, the HC1 has an amino acid other than Tyr, Asp, Glu, Phe, Lys, Gln, Arg, Ser or Thr at position 407 and Lys at position 409 and the HC2 has Tyr at position 407 and Arg at position 409.

In some embodiments described herein, the HC1 has Tyr at position 407 and Arg at position 409 and the HC2 has Ala, Gly, His, Ile, Leu, Met, Asn, Val or Trp at position 407 and Lys at position 409.

In some embodiments described herein, the HC1 has Ala, Gly, His, Ile, Leu, Met, Asn, Val or Trp at position 407 and Lys at position 409 and the HC2 has Tyr at position 407 and Arg at position 409.

In some embodiments described herein, the HC1 CH3 has Tyr at position 407 and Arg at position 409 and the HC2 CH3 has Gly, Leu, Met, Asn or Trp at position 407 and Lys at position 409.

In some embodiments described herein, the HC1 has Gly, Leu, Met, Asn or Trp at position 407 and Lys at position 409 and the HC2 has Tyr at position 407 and Arg at position 409.

In some embodiments described herein, the HC1 has an amino acid other than Lys, Leu or Met at position 409, and the HC2 has (i) an amino acid other than Phe, Leu and Met at position 368, or (ii) a Trp at position 370, or (iii) an amino acid other than Asp, Cys, Pro, Glu or Gln at position 399.

In some embodiments described herein, the HC1 has (i) an amino acid other than Phe, Leu and Met at position 368, or (ii) a Trp at position 370, or (iii) an amino acid other than Asp, Cys, Pro, Glu or Gln at position 399 and the HC2 has an amino acid other than Lys, Leu or Met at position 409.

In some embodiments described herein, the HC1 has Arg, Ala, His or Gly at position 409, and the HC2 has (i) Lys, Gln, Ala, Asp, Glu, Gly, His, Ile, Asn, Arg, Ser, Thr, Val, or Trp at position 368, or (ii) Trp at position 370, or (iii) Ala, Gly, Ile, Leu, Met, Asn, Ser, Thr, Trp, Phe, His, Lys, Arg or Tyr at position 399.

In some embodiments described herein, the HC1 has (i) Lys, Gln, Ala, Asp, Glu, Gly, His, Ile, Asn, Arg, Ser, Thr, Val, or Trp at position 368, or (ii) Trp at position 370, or (iii) Ala, Gly, lie, Leu, Met, Asn, Ser, Thr, Trp, Phe, His, Lys, Arg or Tyr at position 399 and the HC2 has Arg, Ala, His or Gly at position 409.

In some embodiments described herein, the HC1 has Arg at position 409, and the HC2 has (i) Asp, Glu, Gly, Asn, Arg, Ser, Thr, Val, or Trp at position 368, or (ii) Trp at position 370, or (iii) Phe, His, Lys, Arg or Tyr at position 399.

In some embodiments described herein, the HC1 has (i) Asp, Glu, Gly, Asn, Arg, Ser, Thr, Val, or Trp at position 368, or (ii) Trp at position 370, or (iii) Phe, His, Lys, Arg or Tyr at position 399 and the HC2 has Arg at position 409.

In some embodiments described herein, the HC1 comprises a 409R substitution or a F405L substitution and the HC2 comprises a 409R substitution or a F405L substitution, wherein residue numbering is according to the EU index.

In some embodiments described herein, the HC1 comprises the F405L substitution and the HC2 comprises the 409R substitution.

Substitutions are typically made at the DNA level to a molecule such as the constant domain of the antibody using standard methods.

The antibodies of the invention may be engineered into various well-known antibody forms.

In some embodiments, the bispecific antibody of the present invention is a diabody or a cross-body.

In some embodiments, the bispecific antibodies include recombinant IgG-like dual targeting molecules, wherein the two sides of the molecule each contain the Fab fragment or part of the Fab fragment of at least two different antibodies; IgG fusion molecules, wherein full length IgG antibodies are fused to an extra Fab fragment or parts of Fab fragment; Fc fusion molecules, wherein single chain Fv molecules or stabilized diabodies are fused to heavy-chain constant-domains, Fc-regions or parts thereof; Fab fusion molecules, wherein different Fab-fragments are fused together; ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule.

In some embodiments, recombinant IgG-like dual targeting molecules include Dual Targeting (DT)-Ig (GSK/Domantis), Two-in-one Antibody (Genentech) and mAb2 (F-Star).

In some embodiments, IgG fusion molecules include Dual Variable Domain (DVD)-Ig (Abbott), Ts2Ab (MedImmune/AZ) and BsAb (Zymogenetics), HERCULES (Biogen Idec) and TvAb (Roche).

In some embodiments, Fc fusion molecules include to ScFv/Fc Fusions (Academic Institution), SCORPION (Emergent BioSolutions/Trubion, Zymogenetics/BMS) and Dual Affinity Retargeting Technology (Fc-DART) (MacroGenics).

In some embodiments, Fab fusion bispecific antibodies include F(ab)2 (Medarex/AMGEN), Dual-Action or Bis-Fab (Genentech), Dock-and-Lock (DNL) (ImmunoMedics), Bivalent Bispecific (Biotecnol) and Fab-Fv (UCB-Celltech). ScFv-, diabody-based and domain antibodies include Bispecific T Cell Engager (BITE) (Micromet), Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), dual targeting heavy chain only domain antibodies. Various formats of bispecific antibodies have been described, for example in Chames and Baty (2009) Curr Opin Drug Disc Dev 12: 276 and in Nunez-Prado et al., (2015) Drug Discovery Today 20(5):588-594.

Polynucleotides, Vectors and Host Cells

Also disclosed are isolated polynucleotides that encode the antibodies or antigen-binding fragments that immunospecifically bind to PSMA. The isolated polynucleotides capable of encoding the variable domain segments provided herein may be included on the same, or different, vectors to produce antibodies or antigen-binding fragments.

Polynucleotides encoding recombinant antigen-binding proteins also are within the scope of the disclosure. In some embodiments, the polynucleotides described (and the peptides they encode) include a leader sequence. Any leader sequence known in the art may be employed. The leader sequence may include, but is not limited to, a restriction site or a translation start site.

The PSMA-specific antibodies or antigen-binding fragments described herein include variants having single or multiple amino acid substitutions, deletions, or additions that retain the biological properties (e.g., binding affinity or immune effector activity) of the described PSMA-specific antibodies or antigen-binding fragments. In the context of the present invention the following notations are, unless otherwise indicated, used to describe a mutation; i) substitution of an amino acid in a given position is written as e.g. K409R which means a substitution of a Lysine in position 409 with an Arginine; and ii) for specific variants the specific three or one letter codes are used, including the codes Xaa and X to indicate any amino acid residue. Thus, the substitution of Arginine for Lysine in position 409 is designated as: K409R, or the substitution of any amino acid residue for Lysine in position 409 is designated as K409X. In case of deletion of Lysine in position 409 it is indicated by K409*. Where a particular amino acid residue may vary among peptide isotypes or variants, and a substitution affects that residue in each isotype or variant or any of the isotypes or variants, the substitution is designated as, e.g., 409R, meaning the amino acid corresponding to position 409 is substituted with Arginine. The skilled person may produce variants having single or multiple amino acid substitutions, deletions, or additions.

These variants may include: (a) variants in which one or more amino acid residues are substituted with conservative or nonconservative amino acids. (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies or antigen-binding fragments described herein may include variants in which amino acid residues from one species are substituted for the corresponding residue in another species, either at the conserved or nonconserved positions. In other embodiments, amino acid residues at nonconserved positions are substituted with conservative or nonconservative residues. The techniques for obtaining these variants, including genetic (deletions, mutations, etc.), chemical, and enzymatic techniques, are known to persons having ordinary skill in the art.

The PSMA-specific antibodies or antigen-binding fragments described herein may embody several antibody isotypes, such as IgM, IgD, IgG, IgA and IgE. In some embodiments the antibody isotype is IgG1, IgG2, IgG3, or IgG4 isotype, preferably IgG1 or IgG4 isotype. Antibody or antigen-binding fragment thereof specificity is largely determined by the amino acid sequence, and arrangement, of the CDRs. Therefore, the CDRs of one isotype may be transferred to another isotype without altering antigen specificity. Alternatively, techniques have been established to cause hybridomas to switch from producing one antibody isotype to another (isotype switching) without altering antigen specificity. Accordingly, such antibody isotypes are within the scope of the described antibodies or antigen-binding fragments.

Also provided, are vectors comprising the polynucleotides described herein. The vectors can be expression vectors. Recombinant expression vectors containing a sequence encoding a polypeptide of interest are thus contemplated as within the scope of this disclosure. The expression vector may contain one or more additional sequences such as but not limited to regulatory sequences (e.g., promoter, enhancer), a selection marker, and a polyadenylation signal. Vectors for transforming a wide variety of host cells are well known and include, but are not limited to, plasmids, phagemids, cosmids, baculoviruses, bacmids, bacterial artificial chromosomes (BACs), yeast artificial chromosomes (YACs), as well as other bacterial, yeast and viral vectors.

Recombinant expression vectors within the scope of the description include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated.

The transcriptional and translational control sequences in expression vectors to be used in transforming vertebrate cells may be provided by viral sources. Exemplary vectors may be constructed as described by Okayama and Berg, 3 *Mol. Cell. Biol.* 280 (1983).

In some embodiments, the antibody- or antigen-binding fragment-coding sequence is placed under control of a powerful constitutive promoter, such as the promoters for the following genes: hypoxanthine phosphoribosyl transferase (HPRT), adenosine deaminase, pyruvate kinase, beta-actin, human myosin, human hemoglobin, human muscle creatine, and others. In addition, many viral promoters function constitutively in eukaryotic cells and are suitable for use with the described embodiments. Such viral promoters include without limitation, Cytomegalovirus (CMV) immediate early promoter, the early and late promoters of SV40, the Mouse Mammary Tumor Virus (MMTV) promoter, the long terminal repeats (LTRs) of Maloney leukemia virus, Human Immunodeficiency Virus (HIV), Epstein Barr Virus (EBV), Rous Sarcoma Virus (RSV), and other retroviruses, and the thymidine kinase promoter of Herpes Simplex Virus. In one embodiment, the PSMA-specific antibody or antigen-binding fragment thereof coding sequence is placed under control of an inducible promoter such as the metallothionein promoter, tetracycline-inducible promoter, doxycycline-inducible promoter, promoters that contain one or more interferon-stimulated response elements (ISRE) such as protein kinase R 2',5'-oligoadenylate synthetases, Mx genes, ADAR1, and the like.

Vectors described herein may contain one or more Internal Ribosome Entry Site(s) (IRES). Inclusion of an IRES sequence into fusion vectors may be beneficial for enhancing expression of some proteins. In some embodiments the vector system will include one or more polyadenylation sites (e.g., SV40), which may be upstream or downstream of any of the aforementioned nucleic acid sequences. Vector components may be contiguously linked, or arranged in a manner that provides optimal spacing for expressing the gene products (i.e., by the introduction of "spacer" nucleotides between the ORFs), or positioned in another way. Regulatory elements, such as the IRES motif, may also be arranged to provide optimal spacing for expression.

The vectors may comprise selection markers, which are well known in the art. Selection markers include positive and negative selection markers, for example, antibiotic resistance genes (e.g., neomycin resistance gene, a hygromycin resistance gene, a kanamycin resistance gene, a tetracycline resistance gene, a penicillin resistance gene), glutamate synthase genes, HSV-TK, HSV-TK derivatives for ganciclovir selection, or bacterial purine nucleoside phosphorylase gene for 6-methylpurine selection (Gadi et al., 7 *Gene Ther.* 1738-1743 (2000)). A nucleic acid sequence encoding a selection marker or the cloning site may be upstream or downstream of a nucleic acid sequence encoding a polypeptide of interest or cloning site.

The vectors described herein may be used to transform various cells with the genes encoding the described antibodies or antigen-binding fragments. For example, the vectors may be used to generate PSMA-specific antibody or antigen-binding fragment-producing cells. Thus, another aspect features host cells transformed with vectors comprising a nucleic acid sequence encoding an antibody or antigen-binding fragment thereof that specifically binds PSMA, such as the antibodies or antigen-binding fragments described and exemplified herein.

Numerous techniques are known in the art for the introduction of foreign genes into cells and may be used to construct the recombinant cells for purposes of carrying out the described methods, in accordance with the various embodiments described and exemplified herein. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome mediated gene transfer, micro cell mediated gene transfer), physical methods (e.g., transfection, spheroplast fusion, microinjection, electroporation, liposome carrier), viral vector transfer (e.g., recombinant DNA viruses, recombinant RNA viruses and the like (described in Cline, 29 *Pharmac. Ther.* 69-92 (1985)). Calcium phosphate precipitation and polyethylene glycol (PEG)-induced fusion of bacterial protoplasts with mammalian cells may also be used to transform cells.

Cells suitable for use in the expression of the PSMA-specific antibodies or antigen-binding fragments described herein are preferably eukaryotic cells, more preferably cells of plant, rodent, or human origin, for example but not limited to NSO, CHO, CHOK1, perC.6, Tk-ts13, BHK, HEK293 cells, COS-7, T98G, CV-1/EBNA, L cells, C127, 3T3, HeLa, NS1, Sp2/0 myeloma cells, and BHK cell lines, among others. In addition, expression of antibodies may be accomplished using hybridoma cells. Methods for producing hybridomas are well established in the art.

Cells transformed with expression vectors described herein may be selected or screened for recombinant expression of the antibodies or antigen-binding fragments described herein. Recombinant-positive cells are expanded and screened for subclones exhibiting a desired phenotype, such as high level expression, enhanced growth properties, or the ability to yield proteins with desired biochemical characteristics, for example, due to protein modification or altered post-translational modifications. These phenotypes may be due to inherent properties of a given subclone or to mutation. Mutations may be effected through the use of chemicals, UV-wavelength light, radiation, viruses, insertional mutagens, inhibition of DNA mismatch repair, or a combination of such methods.

Pharmaceutical Compositions/Administration

The invention provides for pharmaceutical compositions comprising the antibodies of the invention described herein and a pharmaceutically acceptable carrier. For therapeutic use, the antibodies of the invention may be prepared as pharmaceutical compositions containing an effective amount of the antibody as an active ingredient in a pharmaceutically acceptable carrier. "Carrier" refers to a diluent, adjuvant, excipient, or vehicle with which the antibody of the invention is administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine may be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the antibodies of the invention in such pharmaceutical formulation may vary, from less than about 0.5%, usually to at least about 1% to as much as 15 or 20% by weight and may be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21st Edition, Troy, D. B. ed., Lippincott Williams and Wilkins, Philadelphia, Pa. 2006, Part 5, Pharmaceutical Manufacturing pp 691-1092, See especially pp. 958-989.

The mode of administration for therapeutic use of the antibodies of the invention may be any suitable route that delivers the antibody to the host, such as parenteral administration, e.g., intradermal, intramuscular, intraperitoneal, intravenous or subcutaneous, pulmonary, transmucosal (oral, intranasal, intravaginal, rectal), using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intratumoral, intrarticular, intrabronchial, intraabdominal, intracapsular, intracartilaginous, intracavitary, intracelial, intracelebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

The antibodies of the invention described herein, and in some embodiments of each and every one of the numbered embodiments listed below, may be administered to a subject by any suitable route, for example parentally by intravenous (i.v.) infusion or bolus injection, intramuscularly or subcutaneously or intraperitoneally. i.v. infusion may be given over for example 15, 30, 60, 90, 120, 180, or 240 minutes, or from 1, 2, 3, 4, 5, 6, 7, 8, 9, 10, 11 or 12 hours.

The dose given to a subject is sufficient to alleviate or at least partially arrest the disease being treated ("therapeutically effective amount") and may be sometimes 0.005 mg to about 100 mg/kg, e.g. about 0.05 mg to about 30 mg/kg or about 5 mg to about 25 mg/kg, or about 4 mg/kg, about 8 mg/kg, about 16 mg/kg or about 24 mg/kg, or for example about 1, 2, 3, 4, 5, 6, 7, 8, 9 or 10 mg/kg, but may even higher, for example about 15, 16, 17, 18, 19, 20, 21, 22, 23, 24, 25, 30, 40, 50, 60, 70, 80, 90 or 100 mg/kg.

A fixed unit dose may also be given, for example, 50, 100, 200, 500 or 1000 mg, or the dose may be based on the patient's surface area, e.g., 500, 400, 300, 250, 200, or 100 mg/m2. Usually between 1 and 8 doses, (e.g., 1, 2, 3, 4, 5, 6, 7 or 8) may be administered to treat the patient, but 9, 10, 11, 12, 13, 14, 15, 16, 17, 18, 19, 20 or more doses may be given.

The administration of the antibodies of the invention described herein, and in some embodiments of each and every one of the numbered embodiments listed below, may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose. For example, the antibodies of the invention described herein may be administered at 8 mg/kg or at 16 mg/kg at weekly interval for 8 weeks, followed by administration at 8 mg/kg or at 16 mg/kg every two weeks for an additional 16 weeks, followed by administration at 8 mg/kg or at 16 mg/kg every four weeks by intravenous infusion.

For example, the antibodies in the methods of the invention described herein, and in some embodiments of each and every one of the numbered embodiments listed below, may be provided as a daily dosage in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

The antibodies in the methods of the invention described herein, and in some embodiments of each and every one of the numbered embodiments listed below, may also be administered prophylactically in order to reduce the risk of developing cancer, delay the onset of the occurrence of an event in cancer progression, and/or reduce the risk of recurrence when a cancer is in remission.

The antibodies of the invention may be lyophilized for storage and reconstituted in a suitable carrier prior to use. This technique has been shown to be effective with conventional protein preparations and well known lyophilization and reconstitution techniques can be employed.

Methods of Using PSMA-Specific Antibodies

PSMA is a prostate-cancer related cell membrane antigen frequently overexpressed in prostatic intraepithelial neoplasia (PIN), a condition in which some prostate cells have begun to look and behave abnormally; primary and metastatic prostate cancers; and the neovasculature of other solid tumors (e.g. breast, lung, bladder, kidney). PSMA expression correlates with disease progression and Gleason score. PSMA expression is increased in metastatic disease, hormone refractory cases, and higher-grade lesions, and it is further upregulated in androgen-insensitive tumors Blockade of PSMA may inhibit or decrease the growth of PSMA-expressing cancerous cells and tumors in a subject. It may also have antiangiogenic activity owing to expression of PSMA in tumor neovasculature (Milowsky, et al. 2007). PSMA is highly expressed in prostatic intraepithelial neoplasia, the most established precursor of prostatic carcinoma, and therefore blockade of PSMA may modulate progression of PIN to prostate cancer One embodiment of the invention described herein, and in some embodiments of each and every one of the numbered embodiments listed below is a method of inhibiting growth of tumor cells in a subject, comprising administering to the subject a therapeutically effective amount of the antibody specifically binding PSMA of the invention.

Another embodiment of the invention described herein, and in some embodiments of each and every one of the numbered embodiments listed below is a method of inhibiting the formation or growth of neovasculature of a tumor in a subject, comprising administering to the subject a therapeutically effective amount of the antibody specifically binding PSMA of the invention.

Another embodiment of the invention described herein, and in some embodiments of each and every one of the numbered embodiments listed below is a method of inhibiting progression of a precancerous state in a subject, comprising administering to the subject a therapeutically effective amount of the antibody specifically binding PSMA of the invention.

One embodiment of the invention described herein, and in some embodiments of each and every one of the numbered embodiments listed below is a method of treating a cancer by administering to the subject in need thereof the antibody specifically binding PSMA of the invention described herein.

One embodiment of the invention described herein, and in some embodiments of each and every one of the numbered embodiments listed below is a method of inhibiting growth of tumor cells in a subject, comprising administering to the subject a therapeutically effective amount of the bispecific antibody specifically binding PSMA×CD3 of the invention.

Another embodiment of the invention described herein, and in some embodiments of each and every one of the numbered embodiments listed below is a method of inhibiting the formation or growth of neovasculature of a tumor in a subject, comprising administering to the subject a therapeutically effective amount of the bispecific antibody specifically binding PSMA×CD3 of the invention.

Another embodiment of the invention described herein, and in some embodiments of each and every one of the numbered embodiments listed below is a method of inhibiting progression of a precancerous state in a subject, comprising administering to the subject a therapeutically effective amount of the bispecific antibody specifically binding PSMA×CD3 of the invention.

One embodiment of the invention described herein, and in some embodiments of each and every one of the numbered embodiments listed below is a method of treating a cancer by administering to the subject in need thereof the bispecific antibody specifically binding PSMA×CD3 of the invention.

Exemplary antibodies that may be used in the methods of the invention are antibodies specifically binding PSMA and bispecific PSMA×CD3 antibodies as described herein.

Exemplary PSMA antibodies that can be monospecific or can be part of a CD3 bispecific are antibodies PSMB19, PSMB120, PSMB121, PSMB122, PSMB123, PSMB87, PSMB126, PSMB127, PSMB128, PSMB129, PSMB130, PSMB120, PSMB121, PSMB122, PSMB123, PSMB127, PSMB128, PSMB130, PSMB344, PSMB345, PSMB346, PSMB347, PSMB349, PSMB358, PSMB359, PSMB360, PSMB361, PSMB362, PSMB363, and PSMB365, having the VH and the VL amino acid sequence and characteristics as described herein.

In some embodiments, the antibody specifically binding PSMA used in the methods of the invention described herein is PSMB119, PSMB120, PSMB121, PSMB122, PSMB123, PSMB87, PSMB126, PSMB127, PSMB128, PSMB129, PSMB130, PSMB120, PSMB121, PSMB122, PSMB123, PSMB127, PSMB128, PSMB130, PSMB344, PSMB345, PSMB346, PSMB347, PSMB349, PSMB358, PSMB359, PSMB360, PSMB361, PSMB362, PSMB363, and PSMB365. The VH and the VL amino acid sequences of these antibodies are shown in Table 2.

In some embodiments, the antibody specifically binding PSMA used in the methods of the invention described herein comprises the VH of SEQ ID NO: 160 and the VL of SEQ ID NO: 65.

In some embodiments, the antibody specifically binding PSMA used in the methods of the invention described herein comprises the VH of SEQ ID NO: 79 and the VL of SEQ ID NO: 78.

In some embodiments, the antibody specifically binding PSMA used in the methods of the invention described herein comprises the VH of SEQ ID NO: 77 and the VL of SEQ ID NO: 78.

In some embodiments, the antibody specifically binding PSMA used in the methods of the invention described herein comprises the VH of SEQ ID NO: 75 and the VL of SEQ ID NO: 76.

In some embodiments, the antibody specifically binding PSMA used in the methods of the invention described herein comprises the VH of SEQ ID NO: 74 and the VL of SEQ ID NO: 61.

In some embodiments, the antibody specifically binding PSMA used in the methods of the invention described herein comprises the VH of SEQ ID NO: 72 and the VL of SEQ ID NO: 73.

In some embodiments, the antibody specifically binding PSMA used in the methods of the invention described herein comprises the VH of SEQ ID NO: 66 and the VL of SEQ ID NO: 67.

In some embodiments, the antibody specifically binding PSMA used in the methods of the invention described herein comprises the VH of SEQ ID NO: 64 and the VL of SEQ ID NO: 65.

In some embodiments, the antibody specifically binding PSMA used in the methods of the invention described herein comprises the VH of SEQ ID NO: 62 and the VL of SEQ ID NO: 63.

In some embodiments, the antibody specifically binding PSMA used in the methods of the invention described herein comprises the VH of SEQ ID NO: 60 and the VL of SEQ ID NO: 61

In some embodiments, the antibody specifically binding PSMA used in the methods of the invention described herein comprises the VH of SEQ ID NO: 68 and the VL of SEQ ID NO: 69.

In some embodiments, the antibody specifically binding PSMA used in the methods of the invention described herein comprises the VH of SEQ ID NO: 70 and the VL of SEQ ID NO: 71.

In some embodiments, the antibody specifically binding PSMA used in the methods of the invention described herein comprises the VH of SEQ ID NO: 138 and the VL of SEQ ID NO: 67.

In some embodiments, the antibody specifically binding PSMA used in the methods of the invention described herein comprises the VH of SEQ ID NO: 138 and the VL of SEQ ID NO: 142.

In some embodiments, the antibody specifically binding PSMA used in the methods of the invention described herein comprises the VH of SEQ ID NO: 138 and the VL of SEQ ID NO: 143.

In some embodiments, the antibody specifically binding PSMA used in the methods of the invention described herein comprises the VH of SEQ ID NO: 62 and the VL of SEQ ID NO: 63.

In some embodiments, the antibody specifically binding PSMA used in the methods of the invention described herein comprises the VH of SEQ ID NO: 139 and the VL of SEQ ID NO: 67.

In some embodiments, the antibody specifically binding PSMA used in the methods of the invention described herein comprises the VH of SEQ ID NO: 140 and the VL of SEQ ID NO: 144.

In some embodiments, the antibody specifically binding PSMA used in the methods of the invention described herein comprises the VH of SEQ ID NO: 140 and the VL of SEQ ID NO: 67.

In some embodiments, the antibody specifically binding PSMA used in the methods of the invention described herein comprises the VH of SEQ ID NO: 140 and the VL of SEQ ID NO: 142.

In some embodiments, the antibody specifically binding PSMA used in the methods of the invention described herein comprises the VH of SEQ ID NO: 140 and the VL of SEQ ID NO: 143.

In some embodiments, the antibody specifically binding PSMA used in the methods of the invention described herein comprises the VH of SEQ ID NO: 139 and the VL of SEQ ID NO: 144.

In some embodiments, the antibody specifically binding PSMA used in the methods of the invention described herein comprises the VH of SEQ ID NO: 139 and the VL of SEQ ID NO: 142.

In some embodiments, the antibody specifically binding PSMA used in the methods of the invention described herein comprises the VH of SEQ ID NO: 139 and the VL of SEQ ID NO: 143.

In some embodiments, the antibody specifically binding PSMA used in the methods of the invention described herein comprises the VH of SEQ ID NO: 141 and the VL of SEQ ID NO: 143. In some embodiments, the bispecific PSMA/CD3 antibody comprising a first domain specifically binding PSMA and a second domain specifically binding CD3 used in the methods of the invention described herein, comprises the VH of SEQ ID NO: 62 and the VL of SEQ ID NO: 63 in the first domain, and the VH of SEQ ID NO: 104 and the VL of SEQ ID NO: 105 in the second domain.

In some embodiments, the bispecific PSMA/CD3 antibody comprising a first domain specifically binding PSMA and a second domain specifically binding CD3 used in the methods of the invention described herein, comprises the VH of SEQ ID NO: 64 and the VL of SEQ ID NO: 65 in the first domain, and the VH of SEQ ID NO: 104 and the VL of SEQ ID NO: 105 in the second domain.

In some embodiments, the bispecific PSMA/CD3 antibody comprising a first domain specifically binding PSMA and a second domain specifically binding CD3 used in the methods of the invention described herein, comprises the VH of SEQ ID NO: 66 and the VL of SEQ ID NO: 67 in the first domain, and the VH of SEQ ID NO: 104 and the VL of SEQ ID NO: 105 in the second domain.

In some embodiments, the bispecific PSMA/CD3 antibody comprising a first domain specifically binding PSMA and a second domain specifically binding CD3 used in the methods of the invention described herein, comprises the VH of SEQ ID NO: 75 and the VL of SEQ ID NO: 76 in the first domain, and the VH of SEQ ID NO: 104 and the VL of SEQ ID NO: 105 in the second domain.

In some embodiments, the bispecific PSMA/CD3 antibody comprising a first domain specifically binding PSMA and a second domain specifically binding CD3 used in the methods of the invention described herein, comprises the VH of SEQ ID NO: 74 and the VL of SEQ ID NO: 61 in the first domain, and the VH of SEQ ID NO: 104 and the VL of SEQ ID NO: 105 in the second domain.

In some embodiments, the bispecific PSMA/CD3 antibody comprising a first domain specifically binding PSMA and a second domain specifically binding CD3 used in the methods of the invention described herein, comprises the VH of SEQ ID NO: 160 and the VL of SEQ ID NO: 65 in the first domain, and the VH of SEQ ID NO: 104 and the VL of SEQ ID NO: 105 in the second domain.

Cancer may be a hyperproliferative condition or disorder, a solid tumor, a neovasculature, a soft tissue tumor, or a metastatic lesion.

"Cancer" is meant to include all types of cancerous growths or oncogenic processes, metastatic tissues or malignantly transformed cells, tissues, or organs, irrespective of histopathology type or stage of invasiveness. Examples of cancers include solid tumors, hematological malignancies, soft tissue tumors, and metastatic lesions. Exemplary solid tumors include malignancies, e.g., sarcomas, and carcinomas (including adenocarcinomas and squamous cell carcinomas) of the various organ systems, such as those affecting prostate, liver, lung, breast, lymphoid, gastrointestinal (e.g., colon), genitourinary tract (e.g., renal, urothelial cells), prostate and pharynx. Adenocarcinomas include malignancies such as most colon cancers, a rectal cancer, a renal-cell carcinoma, a liver cancer, a non-small cell carcinoma of the lung, a cancer of the small intestine and a cancer of the esophagus. Squamous cell carcinomas include malignancies, e.g., in the lung, esophagus, skin, head and neck region, oral cavity, anus, and cervix.

In one embodiment, the cancer is a prostate cancer.

Metastatic lesions of the aforementioned cancers may also be treated or prevented using the methods and antibodies of the invention described herein.

Exemplary cancers whose growth may be inhibited or reduced using the antibodies of the invention described herein include cancers that may overexpress PSMA. Exemplary such cancers include a prostate cancer or a prostatic intraepithelial neoplasia, a colorectal cancer, a gastric cancer, a clear cell renal carcinoma, a bladder cancer, a lung cancer, a squamous cell carcinoma, a glioma, a breast cancer, a kidney cancer, a neovascular disorder, a clear cell renal carcinoma (CCRCC), and a pancreatic cancer and various other non-prostate cancers, including but not limited to a renal cancer, a urothelial cancer and an adenocarcinaoma to the liver. Refractory or recurrent malignancies may be treated using the antibodies of the invention described herein.

Exemplary other cancers that may be treated with the antibodies of the invention described herein are anal cancer, a basal cell carcinoma, a biliary tract cancer, a bladder cancer, a bone cancer, brain and CNS cancers, a carcinoma of the fallopian tubes, carcinoma of the vagina, a carcinoma of the vulva, a cutaneous or intraocular malignant melanoma, a astro-esophageal cancer, a testicular cancer, an ovarian cancer, a pancreatic cancer, a rectal cancer, an uterine cancer, a primary CNS lymphoma; a neoplasm of the central nervous system (CNS), a cervical cancer, a choriocarcinoma, a rectum cancer, a connective tissue cancer, a cancer of the digestive system, an endometrial cancer, an eye cancer; an intra-epithelial neoplasm, a kidney cancer, a larynx cancer, a liver cancer; a small cell lung cancer, a neuroblastoma, an oral cavity cancer (e.g., lip, tongue, mouth, and pharynx), a nasopharyngeal cancer, a retinoblastoma, a rhabdomyosarcoma, a cancer of the respiratory system, a sarcoma, a thyroid cancer, a cancer of the urinary system, a hepatocarcinoma, a cancer of the anal region, a carcinoma of the fallopian tubes, a carcinoma of the vagina, a carcinoma of the vulva, a cancer of the small intestine, a cancer of the endocrine system, a cancer of the parathyroid gland, a cancer of the adrenal gland, a sarcoma of soft tissue, a cancer of the urethra, a cancer of the penis, solid tumors of childhood, a tumor angiogenesis, a spinal axis tumor, a brain stem glioma, a pituitary adenoma, Kaposi's sarcoma, Merkel cell cancer, an epidermoid cancer, a squamous cell cancer, an environmentally induced cancers including those induced by asbestos, as well as other carcinomas and sarcomas, and combinations of said cancers.

Patients having cancer including metastatic cancer that express PSMA may be treated with the antibodies of the invention described herein. The cancer may be a prostate cancer or a prostatic intraepithelial neoplasia, a colorectal cancer, a gastric cancer, a clear cell renal carcinoma, a bladder cancer, a lung cancer, a squamous cell carcinoma, a glioma, a breast cancer, a kidney cancer, a neovascular disorder, a clear cell renal carcinoma (CCRCC), and a pancreatic cancer and various other non-prostate cancers, including but not limited to a renal cancer, a urothelial cancer and an adenocarcinaoma to the liver.

In some embodiments of the invention described herein, and in some embodiments of each and every one of the numbered embodiments listed below, the subject has a solid tumor.

In some embodiments of the invention described herein, and in some embodiments of each and every one of the numbered embodiments listed below, the subject has a prostate tumor.

In some embodiments of the invention described herein, and in some embodiments of each and every one of the numbered embodiments listed below, the solid tumor is a colorectal cancer.

In some embodiments of the invention described herein, and in some embodiments of each and every one of the numbered embodiments listed below, the solid tumor is a gastric cancer.

In some embodiments of the invention described herein, and in some embodiments of each and every one of the numbered embodiments listed below, the solid tumor is a lung cancer.

In some embodiments of the invention described herein, and in some embodiments of each and every one of the numbered embodiments listed below, the solid tumor is a bladder cancer.

In some embodiments of the invention described herein, and in some embodiments of each and every one of the numbered embodiments listed below, the solid tumor is a squamous cell carcinoma.

In some embodiments of the invention described herein, and in some embodiments of each and every one of the numbered embodiments listed below, the cancer is clear cell renal carcinoma (CCRCC).

In some embodiments of the invention described herein, and in some embodiments of each and every one of the numbered embodiments listed below, the solid tumor is a breast cancer.

In some embodiments of the invention described herein, and in some embodiments of each and every one of the numbered embodiments listed below, the solid tumor is glioma.

In some embodiments of the invention described herein, and in some embodiments of each and every one of the numbered embodiments listed below, the solid tumor is a prostate cancer or castration-resistant prostate cancer.

In some embodiments of the invention described herein, and in some embodiments of each and every one of the numbered embodiments listed below, the solid tumor is a kidney cancer.

In some embodiments of the invention described herein, and in some embodiments of each and every one of the numbered embodiments listed below, the solid tumor is a pancreatic cancer.

In some embodiments of the invention described herein, and in some embodiments of each and every one of the numbered embodiments listed below, the solid tumor is an adenocarcinoma to the liver.

In some embodiments of the invention described herein, and in some embodiments of each and every one of the numbered embodiments listed below, the cancer is a neovascular.

In some embodiments of the invention described herein, and in some embodiments of each and every one of the numbered embodiments listed below, the cancer is renal cancer.

In some embodiments of the invention described herein, and in some embodiments of each and every one of the numbered embodiments listed below, the solid tumor is a urothelial cancer.

In some embodiments of the invention described herein, and in some embodiments of each and every one of the numbered embodiments listed below, the solid tumor is a brain cancer.

In some embodiments described herein, the subject has a tumor that expresses PSMA.

In some embodiments described herein, the subject has tumor-infiltrating T lymphocytes (TILs) in the tumor tissue.

"Increased number" refers to statistically significant increase in a subject when compared to a control. "Increased number" for example refers to statistically significant increase in the number of TILs in a subject (e.g. patient) pre- and post-treatment with a PSMA antibody or other therapeutic.

In some embodiments described herein, the subject has increased expression or activity of interferon-gamma (IFN-γ).

In some embodiments described herein the subject has been treated with an anti-PSMA antibody.

In some embodiments described herein, the subject is refractory to treatment with the anti-PSMA antibody.

Any of the PSMA or bispecific PSMA×CD3 antibodies of the invention described herein may be used in the methods of the invention.

The antibodies and fragments thereof as described herein may also be administered in combination therapy, i.e., combined with other therapeutic agents relevant for the disease or condition to be treated. Accordingly, in one embodiment, the antibody-containing medicament is for combination with one or more further therapeutic agent, such as a chemotherapeutic agent. In some embodiments, the other therapeutic agent is a radiopharmaceutical agent (such as radium-223 chloride), secondary hormone therapies (such as abiraterone or enzalutamide), and/or chemotherapies (docetaxel and cabazitaxel). Such combined administration may be simultaneous, separate or sequential, in any order. For simultaneous administration the agents may be administered as one composition or as separate compositions, as appropriate. a chemotherapeutic agent (e.g., docetaxel, carboplatin, fludarabine), abiraterone, hormonal therapy (e.g., flutamide, bicalutamide, nilutamide, cyproterone acetate, ketoconazole, aminoglutethimide, abarelix, degarelix, leuprolide, goserelin, triptorelin, buserelin, ARN-509), serine or tyrosine kinase inhibitor (e.g., PI3 kinase inhibitor SF1126) (e.g., lapatanib), multikinase inhibitor (e.g., sorafenib, sunitinib), VEGF inhibitor (e.g., bevacizumab), TAK-700, cancer vaccine (e.g., BPX-101, PEP223), *Listeria*-based vaccine, lenalidomide, TOK-001, IGF-1 receptor inhibitor (e.g., cixutumumab), TRC105, Aurora A kinase inhibitor (e.g., MLN8237), proteasome inhibitor (e.g., bortezomib), OGX-011, radioimmunotherapy (e.g., HuJ591-GS), HDAC inhibitor (e.g., valproic acid, SB939, LBH589), hydroxychloroquine, mTOR inhibitor (e.g., everolimus), dovitinib lactate, diindolylmethane, efavirenz, OGX-427, genistein, IMC-3G3, bafetinib, CP-675,206, radiation therapy, surgery, or a combination thereof.

In one embodiment, a method for treating a disorder involving cells expressing PSMA in a subject, which method comprises administration of a therapeutically effective amount of a bispecific antibody or fragment, such as a PSMA×CD3 bispecific antibody described herein, and radiotherapy to a subject in need thereof is provided. In one embodiment is provided a method for treating or preventing cancer, which method comprises administration of a therapeutically effective amount of a bispecific antibody or fragment, such as a PSMA×CD3 antibody described herein, and radiotherapy to a subject in need thereof. Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

Antibodies of the invention described herein may be administered in combination with a vaccine.

Exemplary vaccines are immunogenic agents, such as cancerous cells, purified tumor antigens (including recombinant proteins, antigen epitopes, peptides and carbohydrate molecules), tumor antigens delivered to a patient via gene therapy, cells, and cells transfected with genes encoding immune stimulating cytokines. Exemplary vaccines that may be used include peptides of melanoma antigens, such as peptides of gp100, MAGE antigens, Trp-2, MART1 and/or tyrosinase, or tumor cells transfected to express the cytokine GM-CSF, DNA-based vaccines, RNA-based vaccines, *Listeria*-based vaccines and viral transduction-based vaccines, peptides or prostate antigens (eg PSMA, STEAP1, PSCA), the cancer vaccine sipuleucel-T or peptides of lung cancer antigens. The cancer vaccine may be prophylactic or therapeutic.

Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al., (1993) Proc Natl Acad Sci U.S.A. 90: 3539-43).

The antibodies of the invention described herein may be administered in combination with one or a collection of recombinant proteins and/or peptides expressed in or on a tumor in order to generate an immune response to these proteins. These proteins are normally viewed by the immune system as self-antigens and are therefore tolerant to them. The tumor antigen may also include the protein telomerase, which is required for the synthesis of telomeres of chromosomes and which is expressed in more than 85% of human cancers and in only a limited number of somatic tissues (Kim et al., (1994) Science 266: 2011-2013). Tumor antigens may also be "neo-antigens" expressed in or on cancer cells as a result of somatic mutations that alter protein sequence or create fusion proteins between two unrelated sequences (e.g., bcr-abl in the Philadelphia chromosome), or idiotype from B cell tumors. The tumor antigens may be antigen epitopes of prostate specific antigen (PSA), mesothelin, prostate-specific membrane antigen (PSMA), synovial sarcoma X2 (SSX2), NKX3.1, prostatic acidic phosphatase (PAP), or epidermal growth factor receptors, or peptides specific for variants of EGFR such as the well-known EGFRvIII overexpressed on tumor cells.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV), and Epstein-Barr virus (EBV). Another form of tumor specific antigens which may be used in combination with the antibodies of the invention described herein is purified heat shock proteins (HSP) isolated from the tumor tissue itself. HSP contain fragments of proteins from the tumor cells and are highly efficient at delivery to antigen presenting cells for eliciting tumor immunity (Suot and Srivastava (1995) Science 269: 1585-1588; Tamura et al., (1997) Science 278:117-120).

Dendritic cells (DC) are potent antigen presenting cells that may be used to prime antigen-specific responses. DC's may be produced ex vivo and loaded with various protein and peptide antigens as well as tumor cell extracts (Nestle et al., (1998) Nature Medicine 4: 328-332). DCs may also be transduced by genetic means to express these tumor antigens. DCs have also been fused directly to tumor cells for the purposes of immunization (Kugler et al., (2000) Nature Medicine 6:332-336). As a method of vaccination, DC immunization may be effectively combined with the antibodies of the invention described herein to activate more potent anti-tumor responses.

In some embodiments described herein, the antibodies specifically binding PSMA of the invention or the bispecific PSMA×CD3 antibodies of the invention are administered in combination with a tumor vaccine comprising a peptide fragment of a prostate specific antigen, or a vector encoding the peptide fragment of a prostate specific antigen.

The antibodies of the invention described herein may be administered in combination with a standard of care cancer treatment.

The antibodies of the invention described herein may be administered in combination with a standard of care cancer chemotherapeutic regimes. In these instances, it may be possible to reduce the dose of chemotherapeutic reagent administered (Mokyr et al., (1998) Cancer Research 58: 5301-5304).

In some embodiments described herein, the antibodies of the invention may be administered in combination with one or more of other antibody molecules, chemotherapy, other anti-cancer therapy (e.g., targeted anti-cancer therapies, or oncolytic drugs), cytotoxic agents, cytokines, surgical and/or radiation procedures.

Exemplary cytotoxic agents that may be administered in combination with the antibodies of the invention described herein include hormone inhibitors, antimicrotubule agents, topoisomerase inhibitors, anti-metabolites, mitotic inhibitors, alkylating agents, anthracyclines, *vinca* alkaloids, intercalating agents, agents capable of interfering with a signal transduction pathway, agents that promote apoptosis, proteosome inhibitors, and radiation (e.g., local or whole body irradiation).

Standard of care therapeutics include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), vinorelbine (Navelbine®), Ibrutinib, idelalisib, and brentuximab vedotin.

Exemplary alkylating agents include, nitrogen mustards, ethylenimine derivatives, alkyl sulfonates, nitrosoureas and triazenes: uracil mustard (Aminouracil Mustard®, Chlorethaminacil®, Demethyldopan®, Desmethyldopan®, Haemanthamine®, Nordopan®, Uracil Nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune®), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®) Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HC1 (Treanda®).

Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary *vinca* alkaloids that may be used in combination with the antibodies of the invention include vinorelbine tartrate (Navelbine®), Vincristine (Oncovin®), and Vindesine (Eldisine®); vinblastine (also known as vinblastine sulfate, vincaleukoblastine and VLB, Alkaban-AQ® and Velban®); and vinorelbine (Navelbine®).

Exemplary proteosome inhibitors that may be used in combination with the antibodies of the invention, alone or in combination with another immunomodulator are bortezomib (Velcade®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

In some embodiments described herein, the antibodies of the invention are administered in combination with a serine or tyrosine kinase inhibitor (e.g., a receptor tyrosine kinase (RTK) inhibitor). Exemplary tyrosine kinase inhibitor include an epidermal growth factor (EGF) pathway inhibitor (e.g., an epidermal growth factor receptor (EGFR) inhibitor), a vascular endothelial growth factor (VEGF) pathway inhibitor (e.g., a vascular endothelial growth factor receptor (VEGFR) inhibitor (e.g., a VEGFR-1 inhibitor, a VEGFR-2 inhibitor, a VEGFR-3 inhibitor), a platelet derived growth factor (PDGF) pathway inhibitor (e.g., a platelet derived growth factor receptor (PDGFR) inhibitor (e.g., a PDGFR-P3 inhibitor), a RAF-1 inhibitor, a KIT inhibitor and a RET inhibitor. In some embodiments, the second therapeutic is axitinib (AG013736), bosutinib (SKI-606), cediranib (RE-CENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), alemtuzumab (CAMPATH®), gemtuzumab ozogamicin (MYLOTARG®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, XL228, AEE788, AG-490, AST-6, BMS-599626, CUDC-101, PD153035, pelitinib (EKB-569), vandetanib (zactima), WZ3146, WZ4002, WZ8040, ABT-869 (linifanib), AEE788, AP24534 (ponatinib), AV-951 (tivozanib), axitinib, BAY 73-4506 (regorafenib), brivanib alaninate (BMS-582664), brivanib (BMS-540215), cediranib (AZD2171), CHIR-258 (dovitinib), CP 673451, CYC116, E7080, Ki8751, masitinib (AB1010), MGCD-265, motesanib diphosphate (AMG-706), MP-470, OSI-930, Pazopanib Hydrochloride, PD173074, Sorafenib Tosylate (Bay 43-9006), SU 5402, TSU-68 (SU6668), vatalanib, XL880 (GSK1363089, EXEL-2880). Selected tyrosine kinase inhibitors are chosen from sunitinib, erlotinib, gefitinib, or sorafenib. In some embodiments, the EGFR inhibitor os a bispecific EGFRc-Met antibody (EM-1 mAb) comprising the heavy and the light chains of SEQ DI NO:s 249, 250, 251 and 252 (US2014/0141000).

In some embodiments, the antibodies of the invention are administered in combination with Vascular Endothelial Growth Factor (VEGF) receptor inhibitors, including Bevacizumab (Avastin®), axitinib (Inlyta®); Brivanib alaninate (BMS-582664, (S)—((R)-1-(4-(4-Fluoro-2-methyl-1H-indol-5-yloxy)-5-methylpyrrolo[2,1-f][1,2,4]triazin-6-yloxy) propan-2-yl)2-aminopropanoate); Sorafenib (Nexavar®); Pazopanib (Votrient®); Sunitinib malate (Sutent®); Cediranib (AZD2171, CAS 288383-20-1); Vargatef (BIBF1120, CAS 928326-83-4); Foretinib (GSK1363089); Telatinib (BAY57-9352, CAS 332012-40-5); Apatinib (YN968D1, CAS 811803-05-1); Imatinib (Gleevec®); Ponatinib (AP24534, CAS 943319-70-8); Tivozanib (AV951, CAS 475108-18-0); Regorafenib (BAY73-4506, CAS 755037-03-7); Vatalanib dihydrochloride (PTK787, CAS 212141-51-0); Brivanib (BMS-540215, CAS 649735-46-6); Vandetanib (Caprelsa® or AZD6474); Motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); Dovitinib dilactic acid (TKI258, CAS 852433-84-2); Linfanib (ABT869, CAS 796967-16-3); Cabozantinib (XL184, CAS 849217-68-1); Lestaurtinib (CAS 111358-88-4); N-[5-[[[5-(1,1-Dimethylethyl)-2-oxazolyl]methyl]thio]-2-thiazolyl]-4-piperidinecarboxamide (BMS38703, CAS 345627-80-7); (3R,4R)-4-Amino-1-((4-((3-methoxyphenyl)amino)pyrrolo[2,1-f][1,2,4]triazin-5-yl)methyl)piperidin-3-ol (BMS690514); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); 4-Methyl-3-[[1-methyl-6-(3-pyridinyl)-1H-pyrazolo[3,4-d]pyrimidin-4-yl]amino]-N-[3-(trifluoromethyl)phenyl]-benzamide (BHG712, CAS 940310-85-0); and Aflibercept (Eylea®).

Exemplary VEGF inhibitors include a monoclonal antibody that binds to the same epitope as the monoclonal anti-VEGF antibody A4.6.1 produced by hybridoma ATCC HB 10709; a recombinant humanized anti-VEGF monoclonal antibody generated according to Presta et al., (1997) Cancer Res 57:4593-4599. In one embodiment, the anti-VEGF antibody is Bevacizumab (BV), also known as rhuMAb VEGF or AVASTIN®. It comprises mutated human IgG1 framework regions and antigen-binding complementarity-determining regions from the murine anti-hVEGF monoclonal antibody A.4.6.1 that blocks binding of human VEGF to its receptors. Bevacizumab and other humanized anti-VEGF antibodies are further described in U.S. Pat. No. 6,884,879. Additional anti-VEGF antibodies include the G6 or B20 series antibodies (e.g., G6-31, B20-4.1), as described in Int. Patent Publication Nos. WO2005/012359 and WO2005/044853, For additional antibodies see U.S. Pat. Nos. 7,060,269, 6,582,959, 6,703,020, 6,054,297, WO98/45332, WO 96/30046, WO94/10202, EP 0666868B1, U.S. Patent Application Publication Nos. US2006009360, US20050186208, US20030206899, US20030190317, US20030203409, and US20050112126; and Popkov et al., (2004) Journal of Immunological Methods 288: 149-164. Other antibodies include those that bind to a functional epitope on human VEGF comprising of residues F17, M18, D19, Y21, Y25, Q89, 191, K101, E103, and C104 or, alternatively, comprising residues F17, Y21, Q22, Y25, D63, 183 and Q89.

In some embodiments described herein, the antibodies of the invention are administered in combination with a PI3K inhibitor. In one embodiment, the PI3K inhibitor is an inhibitor of delta and gamma isoforms of PI3K. In another embodiment, the PI3K inhibitor is an inhibitor of beat isoforms of PI3K. Exemplary PI3K inhibitors that may be used are described in, e.g., WO 2010/036380, WO 2010/006086, WO 09/114870, WO 05/113556, GSK 2126458, GDC-0980, GDC-0941, Sanofi XL147, XL756, XL147, PF-46915032, BKM 120, CAL-101, CAL 263, SF1126, PX-886, and a dual PI3K inhibitor (e.g., Novartis BEZ235).

In some embodiments described herein, the antibodies of the invention are administered in combination with a mTOR inhibitor, e.g., one or more mTOR inhibitors chosen from one or more of rapamycin, temsirolimus (TORISEL®), AZD8055, BEZ235, BGT226, XL765, PF-4691502, GDC0980, SF1126, OSI-027, GSK1059615, KU-0063794, WYE-354, Palomid 529 (P529), PF-04691502, or PKI-587. ridaforolimus (formally known as deferolimus, (1R,2R,4S)-4-[(2R)-2 [(1R,9S,12S,15R,16E,18R,19R,21R,23S,24E, 26E,28Z,30S,32S,35R)-1,18-dihydroxy-19,30-dimethoxy-15,17,21,23,29,35-hexamethyl-2,3,10,14,20-pentaoxo-11, 36-dioxa-4-azatricyclo[30.3.1.04,9] hexatriaconta-16,24,26, 28-tetraen-12-yl]propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS 164301-51-3); emsirolimus, (5-{2,4-Bis[(3S)-3-methylmorpholin-4-yl] pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d] pyrimidin-7(8H)-one (PF04691502, CAS 1013101-36-4); and N2-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-(SEQ ID NO: 237), inner salt (SF1126, CAS 936487-67-1), and XL765.

In some embodiments described herein, the antibodies of the invention are administered in combination with a BRAF inhibitor, e.g., GSK2118436, RG7204, PLX4032, GDC-0879, PLX4720, and sorafenib tosylate (Bay 43-9006).

In some embodiments described herein, the antibodies of the invention are administered in combination with an immunomodulatory agent. Targeting immune checkpoints such as programmed cell death protein 1 (PD1), programmed cell death 1 ligand 1 (PDL1) and cytotoxic T lymphocyte antigen 4 (CTLA4) has achieved noteworthy benefit in multiple cancers by blocking immunoinhibitory signals and enabling patients to produce an effective anti-tumour response. In some embodiments, the antibodies of the invention are administered in combination with an anti-PD1 (eg. nivolumab), anti-PDL (eg. MDX-1105) or anti-CTLA4 (eg. Ipilimumab). The ability of agonistic CD40 antibodies (referred to as αCD40) or CD40 ligand to stimulate immune responses and target tumors suggests such reagents have promise as cancer immunotherapeutics. In some embodiments, the antibodies of the invention are administered in combination with an anti-CD40 (eg. SGN-40, CP-870,893) or anti-CD40L (eg. BG9588).

In some embodiments described herein, the antibodies of the invention are administered in combination with a MEK inhibitor.

In some embodiments described herein, the antibodies of the invention administered in combination with the MEK inhibitor are used in the treatment of a prostate cancer, a melanoma, a colorectal cancer, a non-small cell lung cancer, an ovarian cancer, a breast cancer, a prostate cancer, a pancreatic cancer, a hematological malignancy or a renal cell carcinoma. In certain embodiments, the tumor tissue or cancer cell has a BRAF mutation (e.g., a BRAF V600E mutation), a BRAF wildtype, a KRAS wildtype or an activating KRAS mutation. The cancer may be at an early, intermediate or late stage. Any MEK inhibitor may be used in combination including, ARRY-142886, G02442104 (also known as GSK1120212), RDEA436, RDEA119/BAY 869766, AS703026, G00039805 (also known as AZD-6244 or selumetinib), BIX 02188, BIX 02189, CI-1040 (PD-184352), PD0325901, PD98059, U0126, GDC-0973 (Methanone, [3,4-difluoro-2-[(2-fluoro-4-iodophenyl) amino]phenyl][3-hydroxy-3-(25)-2-piperidinyl-1-azetidinyl]-), G-38963, G02443714 (also known as AS703206), or a pharmaceutically acceptable salt or solvate thereof. Additional examples of MEK inhibitors are disclosed in WO 2013/019906, WO 03/077914, WO 2005/121142, WO 2007/04415, WO 2008/024725 and WO 2009/085983.

In some embodiments described herein, the antibodies of the invention are administered in combination with a JAK2 inhibitor, e.g., CEP-701, INCB18424, CP-690550 (tasocitinib).

In some embodiments described herein, the antibodies of the invention are administered in combination with paclitaxel or a paclitaxel agent, e.g., TAXOL®, protein-bound paclitaxel (e.g., ABRAXANE®). Exemplary paclitaxel agents include nanoparticle albumin-bound paclitaxel (ABRAXANE, marketed by Abraxis Bioscience), docosahexaenoic acid bound-paclitaxel (DHA-paclitaxel, Taxoprexin, marketed by Protarga), polyglutamate bound-paclitaxel (PG-paclitaxel, paclitaxel poliglumex, CT-2103, XYOTAX, marketed by Cell Therapeutic), the tumor-activated prodrug (TAP), ANG105 (Angiopep-2 bound to three molecules of paclitaxel, marketed by ImmunoGen), paclitaxel-EC-1 (paclitaxel bound to the erbB2-recognizing peptide EC-1; see Li et al., Biopolymers (2007) 87:225-230), and glucose-conjugated paclitaxel (e.g., 2'-paclitaxel methyl 2-glucopyranosyl succinate, see Liu et al., (2007) Bioorganic & Medicinal Chemistry Letters 17:617-620).

In some embodiments described herein, the antibodies of the invention are administered in combination with a cellular immunotherapy (e.g., Provenge (e.g., Sipuleucel)), and optionally in combination with cyclophosphamide.

Exemplary therapeutic agents that may be used in combination with the antibodies of the invention for treatment of a prostate cancer include a chemotherapeutic agent (e.g., docetaxel, carboplatin, fludarabine), abiraterone, hormonal therapy (e.g., flutamide, bicalutamide, nilutamide, cyproterone acetate, ketoconazole, aminoglutethimide, abarelix, degarelix, leuprolide, goserelin, triptorelin, buserelin), tyrosine kinase inhibitor (e.g., dual kinase inhibitor (e.g., lapatanib), multikinase inhibitor (e.g., sorafenib, sunitinib), VEGF inhibitor (e.g., bevacizumab), TAK-700, cancer vaccine (e.g., BPX-101, PEP223), lenalidomide, TOK-001, IGF-1 receptor inhibitor (e.g., cixutumumab), TRC105, Aurora A kinase inhibitor (e.g., MLN8237), proteasome inhibitor (e.g., bortezomib), OGX-011, radioimmunotherapy (e.g., HuJ591-GS), HDAC inhibitor (e.g., valproic acid, SB939, LBH589), hydroxychloroquine, mTOR inhibitor (e.g., everolimus), dovitinib lactate, diindolylmethane, efavirenz, OGX-427, genistein, IMC-3G3, bafetinib, CP-675,206, ARN-509, radiation therapy, surgery, or a combination thereof.

Exemplary therapeutic agents that may be used in combination with the antibodies of the invention for treatment of pancreatic cancer include a chemotherapeutic agent, e.g., paclitaxel or a paclitaxel agent (e.g., a paclitaxel formulation such as TAXOL, an albumin-stabilized nanoparticle paclitaxel formulation (e.g., ABRAXANE) or a liposomal paclitaxel formulation); gemcitabine (e.g., gemcitabine alone or in combination with AXP107-11); other chemotherapeutic agents such as oxaliplatin, 5-fluorouracil, capecitabine, rubitecan, epirubicin hydrochloride, NC-6004, cisplatin, docetaxel (e.g., TAXOTERE), mitomycin C, ifosfamide; interferon; tyrosine kinase inhibitor (e.g., EGFR inhibitor (e.g., erlotinib, panitumumab, cetuximab, nimotuzumab);

HER2/neu receptor inhibitor (e.g., trastuzumab); dual kinase inhibitor (e.g., bosutinib, saracatinib, lapatinib, vandetanib); multikinase inhibitor (e.g., sorafenib, sunitinib, XL184, pazopanib); VEGF inhibitor (e.g., bevacizumab, AV-951, brivanib); radioimmunotherapy (e.g., XR303); cancer vaccine (e.g., GVAX, survivin peptide); COX-2 inhibitor (e.g., celecoxib); IGF-1 receptor inhibitor (e.g., AMG 479, MK-0646); mTOR inhibitor (e.g., everolimus, temsirolimus); IL-6 inhibitor (e.g., CNTO 328); cyclin-dependent kinase inhibitor (e.g., P276-00, UCN-01); Altered Energy Metabolism-Directed (AEMD) compound (e.g., CPI-613); HDAC inhibitor (e.g., vorinostat); TRAIL receptor 2 (TR-2) agonist (e.g., conatumumab); MEK inhibitor (e.g., AS703026, selumetinib, GSK1120212); Raf/MEK dual kinase inhibitor (e.g., RO5126766); Notch signaling inhibitor (e.g., MK0752); monoclonal antibody-antibody fusion protein (e.g., L19IL2); curcumin; HSP90 inhibitor (e.g., tanespimycin, STA-9090); rIL-2; denileukin diftitox; topoisomerase 1 inhibitor (e.g., irinotecan, PEP02); statin (e.g., simvastatin); Factor VIla inhibitor (e.g., PCI-27483); AKT inhibitor (e.g., RX-0201); hypoxia-activated prodrug (e.g., TH-302); metformin hydrochloride, gamma-secretase inhibitor (e.g., R04929097); ribonucleotide reductase inhibitor (e.g., 3-AP); immunotoxin (e.g., HuC242-DM4); PARP inhibitor (e.g., KU-0059436, veliparib); CTLA-4 inhibitor (e.g., CP-675,206, ipilimumab); AdV-tk therapy; proteasome inhibitor (e.g., bortezomib (Velcade), NPI-0052); thiazolidinedione (e.g., pioglitazone); NPC-1C; Aurora kinase inhibitor (e.g., R763/AS703569), CTGF inhibitor (e.g., FG-3019); siG12D LODER; and radiation therapy (e.g., tomotherapy, stereotactic radiation, proton therapy), surgery, and a combination thereof. In certain embodiments, a combination of paclitaxel or a paclitaxel agent, and gemcitabine can be used with the antibodies of the invention.

Exemplary therapeutic agents that may be used in combination with the antibodies of the invention for treatment of small cell lung cancer include a chemotherapeutic agent, e.g., etoposide, carboplatin, cisplatin, oxaliplatin, irinotecan, topotecan, gemcitabine, liposomal SN-38, bendamustine, temozolomide, belotecan, NK012, FR901228, flavopiridol); tyrosine kinase inhibitor (e.g., EGFR inhibitor (e.g., erlotinib, gefitinib, cetuximab, panitumumab); multikinase inhibitor (e.g., sorafenib, sunitinib); VEGF inhibitor (e.g., bevacizumab, vandetanib); cancer vaccine (e.g., GVAX); Bcl-2 inhibitor (e.g., oblimersen sodium, ABT-263); proteasome inhibitor (e.g., bortezomib (Velcade), NPI-0052), paclitaxel or a paclitaxel agent; docetaxel; IGF-1 receptor inhibitor (e.g., AMG 479); HGF/SF inhibitor (e.g., AMG 102, MK-0646); chloroquine; Aurora kinase inhibitor (e.g., MLN8237); radioimmunotherapy (e.g., TF2); HSP90 inhibitor (e.g., tanespimycin, STA-9090); mTOR inhibitor (e.g., everolimus); Ep-CAM/CD3-bispecific antibody (e.g., MTI10); CK-2 inhibitor (e.g., CX-4945); HDAC inhibitor (e.g., belinostat); SMO antagonist (e.g., BMS 833923); peptide cancer vaccine, and radiation therapy (e.g., intensity-modulated radiation therapy (IMRT), hypofractionated radiotherapy, hypoxia-guided radiotherapy), surgery, and combinations thereof.

Exemplary therapeutic agents that may be used in combination with the antibodies of the invention for treatment of non-small cell lung cancer include a chemotherapeutic agent, e.g., vinorelbine, cisplatin, docetaxel, pemetrexed disodium, etoposide, gemcitabine, carboplatin, liposomal SN-38, TLK286, temozolomide, topotecan, pemetrexed disodium, azacitidine, irinotecan, tegafur-gimeracil-oteracil potassium, sapacitabine); tyrosine kinase inhibitor (e.g., EGFR inhibitor (e.g., erlotinib, gefitinib, cetuximab, panitumumab, necitumumab, PF-00299804, nimotuzumab, RO5083945), MET inhibitor (e.g., PF-02341066, ARQ 197), PI3K kinase inhibitor (e.g., XL147, GDC-0941), Raf/MEK dual kinase inhibitor (e.g., RO5126766), PI3K/mTOR dual kinase inhibitor (e.g., XL765), SRC inhibitor (e.g., dasatinib), dual inhibitor (e.g., BIBW 2992, GSK1363089, ZD6474, AZD0530, AG-013736, lapatinib, MEHD7945A, linifanib), multikinase inhibitor (e.g., sorafenib, sunitinib, pazopanib, AMG 706, XL184, MGCD265, BMS-690514, R935788), VEGF inhibitor (e.g., endostar, endostatin, bevacizumab, cediranib, BIBF 1120, axitinib, tivozanib, AZD2171), cancer vaccine (e.g., BLP25 liposome vaccine, GVAX, recombinant DNA and adenovirus expressing L523S protein), Bcl-2 inhibitor (e.g., oblimersen sodium), proteasome inhibitor (e.g., bortezomib, carfilzomib, NPI-0052, MLN9708), paclitaxel or a paclitaxel agent, docetaxel, IGF-1 receptor inhibitor (e.g., cixutumumab, MK-0646, OSI 906, CP-751,871, BIIB022), hydroxychloroquine, HSP90 inhibitor (e.g., tanespimycin, STA-9090, AUY922, XL888), mTOR inhibitor (e.g., everolimus, temsirolimus, ridaforolimus), Ep-CAM/CD3-bispecific antibody (e.g., MT110), CK-2 inhibitor (e.g., CX-4945), HDAC inhibitor (e.g., MS 275, LBH589, vorinostat, valproic acid, FR901228), DHFR inhibitor (e.g., pralatrexate), retinoid (e.g., bexarotene, tretinoin), antibody-drug conjugate (e.g., SGN-15), bisphosphonate (e.g., zoledronic acid), cancer vaccine (e.g., belagenpumatucel-L), low molecular weight heparin (LMWH) (e.g., tinzaparin, enoxaparin), GSK1572932A, melatonin, talactoferrin, dimesna, topoisomerase inhibitor (e.g., amrubicin, etoposide, karenitecin), nelfinavir, cilengitide, ErbB3 inhibitor (e.g., MM-121, U3-1287), survivin inhibitor (e.g., YM155, LY2181308), eribulin mesylate, COX-2 inhibitor (e.g., celecoxib), pegfilgrastim, Polo-like kinase 1 inhibitor (e.g., BI 6727), TRAIL receptor 2 (TR-2) agonist (e.g., CS-1008), CNGRC peptide (SEQ ID NO: 225)-TNF alpha conjugate, dichloroacetate (DCA), HGF inhibitor (e.g., SCH 900105), SAR240550, PPAR-gamma agonist (e.g., CS-7017), gamma-secretase inhibitor (e.g., RO4929097), epigenetic therapy (e.g., 5-azacitidine), nitroglycerin, MEK inhibitor (e.g., AZD6244), cyclin-dependent kinase inhibitor (e.g., UCN-01), cholesterol-Fus1, antitubulin agent (e.g., E7389), farnesyl-OH-transferase inhibitor (e.g., lonafarnib), immunotoxin (e.g., BB-10901, SSI (dsFv) PE38), fondaparinux, vascular-disrupting agent (e.g., AVE8062), PD-L1 inhibitor (e.g., MDX-1105, MDX-1106), beta-glucan, NGR-hTNF, EMD 521873, MEK inhibitor (e.g., GSK1120212), epothilone analog (e.g., ixabepilone), kinesin-spindle inhibitor (e.g., 4SC-205), telomere targeting agent (e.g., KML-001), P70 pathway inhibitor (e.g., LY2584702), AKT inhibitor (e.g., MK-2206), angiogenesis inhibitor (e.g., lenalidomide), Notch signaling inhibitor (e.g., OMP-21M18), EGFR/c-Met bispecific antibody EM-1 as described in US2014/0141000A1, radiation therapy, surgery, and combinations thereof.

Exemplary therapeutic agents that may be used in combination with the antibodies of the invention for treatment of ovarian cancer include a chemotherapeutic agent (e.g., paclitaxel or a paclitaxel agent; docetaxel; carboplatin; gemcitabine; doxorubicin; topotecan; cisplatin; irinotecan, TLK286, ifosfamide, olaparib, oxaliplatin, melphalan, pemetrexed disodium, SJG-136, cyclophosphamide, etoposide, decitabine); ghrelin antagonist (e.g., AEZS-130), immunotherapy (e.g., APC8024, oregovomab, OPT-821), tyrosine kinase inhibitor (e.g., EGFR inhibitor (e.g., erlotinib), dual inhibitor (e.g., E7080), multikinase inhibitor (e.g., AZD0530, JI-101, sorafenib, sunitinib, pazopanib), ON 01910.Na), VEGF inhibitor (e.g., bevacizumab, BIBF 1120, cediranib, AZD2171), PDGFR inhibitor (e.g., IMC-3G3), paclitaxel, topoisomerase inhibitor (e.g., karenitecin, Irinotecan), HDAC inhibitor (e.g., valproate, vorinostat), folate receptor inhibitor (e.g., farletuzumab), angiopoietin inhibitor (e.g., AMG 386), epothilone analog (e.g., ixabepilone), proteasome inhibitor (e.g., carfilzomib), IGF-1 receptor inhibitor (e.g., OSI 906, AMG 479), PARP inhibitor (e.g., veliparib, AG014699, iniparib, MK-4827), Aurora kinase inhibitor (e.g., MLN8237, ENMD-2076), angiogenesis inhibitor (e.g., lenalidomide), DHFR inhibitor (e.g., pralatrexate), radioimmunotherapeutic agent (e.g., Hu3S193), statin (e.g., lovastatin), topoisomerase 1 inhibitor (e.g., NKTR-102), cancer vaccine (e.g., p53 synthetic long peptides vaccine, autologous OC-DC vaccine), mTOR inhibitor (e.g., temsirolimus, everolimus), BCR/ABL inhibitor (e.g., imatinib), ET-A receptor antagonist (e.g., ZD4054), TRAIL receptor 2 (TR-2) agonist (e.g., CS-1008), HGF/SF inhibitor (e.g., AMG 102), EGEN-001, Polo-like kinase 1 inhibitor (e.g., BI 6727), gamma-secretase inhibitor (e.g., RO4929097), Wee-1 inhibitor (e.g., MK-1775), antitubulin agent (e.g., vinorelbine, E7389), immunotoxin (e.g., denileukin diftitox), SB-485232, vascular-disrupting agent (e.g., AVE8062), integrin inhibitor (e.g., EMD 525797), kinesin-spindle inhibitor (e.g., 4SC-205), revlimid, HER2 inhibitor (e.g., MGAH22), ErrB3 inhibitor (e.g., MM-121), radiation therapy, and combinations thereof.

Exemplary therapeutics agents that may be used in combination with the antibodies of the invention for treatment of a renal cancer, e.g., a renal cell carcinoma (RCC) or metastatic RCC include an immune-based strategy (e.g., interleukin-2 or interferon-α), a targeted agent (e.g., a VEGF inhibitor such as a monoclonal antibody to VEGF, e.g., bevacizumab (Rini et al., (2010) J Clin Oncol 28(13):2137-2143)); a VEGF tyrosine kinase inhibitor such as sunitinib, sorafenib, axitinib and pazopanib (reviewed in Pal et al., (2014) Clin Advances in Hematology & Oncology 12(2): 90-99); an RNAi inhibitor, or an inhibitor of a downstream mediator of VEGF signaling, e.g., an inhibitor of the mammalian target of rapamycin (mTOR), e.g., everolimus and temsirolimus (Hudes et al., (2007) N Engl J Med 356(22): 2271-2281, Motzer et al., (2008) Lancet 372: 449-456).

PSMA-Specific Antibody Kits

Described herein are kits including the disclosed PSMA-specific antibodies or antigen-binding fragments thereof. The described kits may be used to carry out the methods of using the PSMA-specific antibodies or antigen-binding fragments provided herein, or other methods known to those skilled in the art. In some embodiments the described kits may include the antibodies or antigen-binding fragments described herein and reagents for use in detecting the presence of PSMA in a biological sample. Accordingly, the described kits may include one or more of the antibodies, or an antigen-binding fragment(s) thereof, described herein and a vessel for containing the antibody or fragment when not in use, instructions for use of the antibody or fragment, the antibody or fragment affixed to a solid support, and/or detectably labeled forms of the antibody or fragment, as described herein.

One embodiment of the invention is a kit comprising the antibody specifically binding PSMA of the invention.

Another embodiment of the invention is a kit comprising the bispecific PSMA×CD3 antibody comprising a first domain specifically binding PSMA and a second domain specifically binding CD3 of the invention.

The kit may be used for therapeutic uses and as diagnostic kits.

The kit may be used to detect the presence of PSMA, CD3 or PSMA and CD3 in a biological sample.

In some embodiments, the kit comprises the antibody of the invention described herein and reagents for detecting the antibody. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody for administration; pharmaceutically acceptable carriers; and devices or other materials for administration to a subject.

In some embodiments, the kit comprises the antibody of the invention in a container and instructions for use of the kit.

In some embodiments, the antibody in the kit is labeled.

In some embodiments, the kit comprises the anti-PSMA antibody PSMB119, PSMB120, PSMB121, PSMB122, PSMB123, PSMB87, PSMB126, PSMB127, PSMB128, PSMB129, PSMB130, PSMB120, PSMB121, PSMB122, PSMB123, PSMB127, PSMB128, PSMB130, PSMB344, PSMB345, PSMB346, PSMB347, PSMB349, PSMB358, PSMB359, PSMB360, PSMB361, PSMB362, PSMB363, and PSMB365.

In some embodiments, the kit comprises the bispecific PSMA×CD3 antibody, PS3B22, PS3B23, PS3B25, PS3B27, PS3B28, or PS3B30.

Methods of Detecting PSMA or PSMA and CD3

One embodiment of the invention described herein is a method of detecting PSMA in a sample, comprising obtaining the sample, contacting the sample with the antagonistic antibody specifically binding PSMA of the invention, and detecting the antibody bound to PSMA in the sample.

One embodiment of the invention described herein is a method of detecting PSMA and CD3 in a sample, comprising obtaining the sample, contacting the sample with the bispecific antibody comprising a first domain specifically binding PSMA and a second domain specifically binding CD3 of the invention, and detecting the antibody bound to PSMA and CD3 in the sample.

In some embodiments described herein, the sample may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like.

The antibodies of the invention described herein bound to PSMA or PSMA and CD3 may be detected using known methods. Exemplary methods include direct labeling of the antibodies using fluorescent or chemiluminescent labels, or radiolabels, or attaching to the antibodies of the invention a moiety which is readily detectable, such as biotin, enzymes or epitope tags. Exemplary labels and moieties are ruthenium, 111In-DOTA, 111In-diethylenetriaminepentaacetic acid (DTPA), horseradish peroxidase, alkaline phosphatase and beta-galactosidase, poly-histidine (HIS tag), acridine dyes, cyanine dyes, fluorone dyes, oxazin dyes, phenanthridine dyes, rhodamine dyes and Alexafluor® dyes.

The antibodies of the invention may be used in a variety of assays to detect PSMA or PSMA and CD3 in the sample. Exemplary assays are western blot analysis, radioimmunoassay, surface plasmon resonance, immunoprecipitation, equilibrium dialysis, immunodiffusion, electrochemiluminescence (ECL) immunoassay, immunohistochemistry, fluorescence-activated cell sorting (FACS) or ELISA assay.

EMBODIMENTS

1) An isolated recombinant anti-PSMA antibody or antigen-binding fragment thereof, wherein the antibody or antigen binding fragment (i) binds to cells expressing recombinant *Pan troglodytes* PSMA, wherein the binding to cells is measured by flow cytometry and (ii) binds recombinant *Pan troglodytes* PSMA extracellular domain (SEQ ID NO:4) with an affinity of about 30 nM or less, wherein the affinity is measured by Proteon XPR36 surface plasmon resonance assay.

2) The antibody of embodiment 1, wherein the antibody has one, two, three or four of the following properties:
   a) binds LNCaP cells with a calculated $EC_{50}$ of 20 nM or less and binds *Macaca fascicularis* PSMA-expressing HEK cells with a calculated $EC_{50}$ of 40 nM or less, wherein the difference in calculated $EC_{50}$ between binding LNCaP cells and binding *Macaca fascicularis* PSMA-expressing HEK cells is less than 5-fold, and wherein the calculated $EC_{50}$ is measured in a whole cell binding assay at 0° C. using flow cytometry,
   b) binds recombinant PSMA ECD from human (SEQ ID NO: 7), *Pan troglodytes* (SEQ ID NO:4) and *Macaca fascicularis* (SEQ ID NO: 5) with an equilibrium dissociation constant ($K_D$) of 12 nM or less, wherein the $K_D$ is measured using Proteon surface plasmon resonance assay ProteOn XPR36 system at +25° C.;
   c) displays T-cell mediated killing of LNCaP cells, C42 cells, human PSMA-expressing HEK cells or *Macaca fascicularis* PSMA-expressing HEK cells when paired in a bispecific antibody with anti-CD3 antibody CD3B219, wherein the T-cell mediated killing is measured by Chromium-51 or by caspase 3/7 activation assay or
   d) recognizes a conformational epitope wherein the epitope is comprised of residues I138, F235, P237, G238, D244, Y299, Y300, Q303, K304, E307, and K324-P326 of human PSMA (SEQ ID NO:3)
3) The antibody of embodiment 2, comprising the HCDR1, the HCDR2, the HCDR3, the LCDR1, the LCDR2 and the LCDR3 of SEQ ID NOs: 14, 15, 16, 17, 18 and 19, respectively.
4) The antibody of embodiment 2, comprising the HCDR1, the HCDR2, the HCDR3, the LCDR1, the LCDR2 and the LCDR3 of SEQ ID NOs: 20, 21, 22, 23, 12 and 24, respectively.
5) The antibody of embodiment 2, comprising the HCDR1, the HCDR2, the HCDR3, the LCDR1, the LCDR2 and the LCDR3 of SEQ ID NOs: 25, 26, 27, 28, 29 and 30, respectively.
6) The antibody of embodiment 2, comprising the HCDR1, the HCDR2, the HCDR3, the LCDR1, the LCDR2 and the LCDR3 of SEQ ID NOs: 36, 37, 38, 39, 40 and 41, respectively.
7) The antibody of embodiment 2, comprising the HCDR1, the HCDR2, the HCDR3, the LCDR1, the LCDR2 and the LCDR3 of SEQ ID NOs: 31, 42, 43, 11, 12 and 13, respectively.
8) The antibody of embodiment 2, comprising the HCDR1, the HCDR2, the HCDR3, the LCDR1, the LCDR2 and the LCDR3 of SEQ ID NOs: 31, 44, 45, 46, 29 and 47, respectively.
9) The antibody of embodiment 2, comprising the HCDR1, the HCDR2, the HCDR3, the LCDR1, the LCDR2 and the LCDR3 of SEQ ID NOs: 36, 37, 48, 49, 50 and 51, respectively.
10) The antibody of embodiment 2, comprising the HCDR1, the HCDR2, the HCDR3, the LCDR1, the LCDR2 and the LCDR3 of SEQ ID NOs: 36, 37, 52, 49, 50 and 51, respectively.
11) The antibody of embodiment 2, comprising the HCDR1, the HCDR2, the HCDR3, the LCDR1, the LCDR2 and the LCDR3 of SEQ ID NOs: 8, 9, 10, 11, 12 and 13, respectively.
12) The antibody of embodiment 2, comprising the HCDR1, the HCDR2, the HCDR3, the LCDR1, the LCDR2 and the LCDR3 of SEQ ID NOs: 31, 32, 33, 34, 12 and 35, respectively.
13) The antibody of embodiment 2, comprising the HCDR1, the HCDR2, the HCDR3, the LCDR1, the LCDR2 and the LCDR3 of SEQ ID NOs: 53, 54, 55, 23, 12 and 35, respectively.
14) The antibody of embodiment 2, comprising the HCDR1, the HCDR2, the HCDR3, the LCDR1, the LCDR2 and the LCDR3 of SEQ ID NOs: 122, 123, 124, 23, 12 and 24, respectively.
15) The antibody of embodiment 2, comprising a heavy chain variable region (VH) of SEQ ID NO: 60, 62, 64, 66, 68, 70, 72, 74, 75, 77, 79, or 160.
16) The antibody of embodiment 15, comprising a light chain variable region (VL) of SEQ ID NOs: 61, 63, 65, 67, 69, 71, 73, 61, 76, or 78.
17) The antibody of embodiment 15, comprising the VH of SEQ ID NO: 62 and the VL of SEQ ID NO: 63.
18) The antibody of embodiment 15, comprising the VH of SEQ ID NO: 64 and the VL of SEQ ID NO: 65.
19) The antibody of embodiment 15, comprising the VH of SEQ ID NO: 66 and the VL of SEQ ID NO: 67.
20) The antibody of embodiment 15, comprising the VH of SEQ ID NO: 72 and the VL of SEQ ID NO: 73.
21) The antibody of embodiment 15, comprising the VH of SEQ ID NO: 74 and the VL of SEQ ID NO: 61.
22) The antibody of embodiment 15, comprising the VH of SEQ ID NO: 75 and the VL of SEQ ID NO: 76.
23) The antibody of embodiment 15, comprising the VH of SEQ ID NO: 77 and the VL of SEQ ID NO: 78.
24) The antibody of embodiment 15, comprising the VH of SEQ ID NO: 79 and the VL of SEQ ID NO: 78.
25) The antibody of embodiment 15, comprising the VH of SEQ ID NO: 160 and the VL of SEQ ID NO: 65.
26) The antibody of embodiment 15, comprising the VH of SEQ ID NO: 60 and the VL of SEQ ID NO: 61.
27) The antibody of embodiment 15, comprising the VH of SEQ ID NO: 68 and the VL of SEQ ID NO: 69.
    The antibody of embodiment 15, comprising the VH of SEQ ID NO: 70 and the VL of SEQ ID NO: 71.
28) An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 31, 42, 43, 11, 12 and 13, respectively.
29) The antibody of embodiment 28, wherein the antibody comprises the VH of SEQ ID NO: 74 and the VL of SEQ ID NO: 61.
30) An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 14, 15, 16, 17, 18 and 19, respectively.
31) The antibody of embodiment 30, wherein the antibody comprises the VH of SEQ ID NO: 62 and the VL of SEQ ID NO: 63.
32) An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 25, 26, 27, 28, 29 and 30, respectively.

33) The antibody of embodiment 32, wherein the antibody comprises the VH of SEQ ID NO: 66 and the VL of SEQ ID NO: 67.
34) An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 36, 37, 38, 39, 40 and 41, respectively
35) The antibody of embodiment 34, wherein the antibody comprises the VH of SEQ ID NO: 72 and the VL of SEQ ID NO: 73.
36) An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 122, 123, 124, 23, 12, and 24, respectively.
37) The antibody of embodiment 36, wherein the antibody comprises the VH of SEQ ID NO: 160 and the VL of SEQ ID NO: 65.
38) An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 8, 9, 10, 11, 12, and 13, respectively.
39) The antibody of embodiment 38, wherein the antibody comprises the VH of SEQ ID NO:60 and the VL of SEQ ID NO:61.
40) An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 20, 21, 22, 23, 12, and 24, respectively.
41) The antibody of embodiment 40, wherein the antibody comprises the VH of SEQ ID NO:64 and the VL of SEQ ID NO:65.
42) An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 31, 32, 33, 34, 12, and 35, respectively.
43) The antibody of embodiment 42, wherein the antibody comprises the VH of SEQ ID NO:70 and the VL of SEQ ID NO:71.
44) An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 31, 44, 45, 46, 29, and 47, respectively.
45) The antibody of embodiment 44, wherein the antibody comprises the VH of SEQ ID NO:75 and the VL of SEQ ID NO:76.
46) An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 36, 37, 48, 49, 50, and 51, respectively.
47) The antibody of embodiment 46, wherein the antibody comprises the VH of SEQ ID NO:77 and the VL of SEQ ID NO:78.
48) An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 36, 37, 52, 49, 50, and 51, respectively.
49) The antibody of embodiment 48, wherein the antibody comprises the VH of SEQ ID NO:79 and the VL of SEQ ID NO:78.
50) An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 53, 54, 55, 23, 12, and 35, respectively.
51) The antibody of embodiment 50, wherein the antibody comprises the VH of SEQ ID NO:68 and the VL of SEQ ID NO:69.
52) An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 25, 130, 27, 28, 29, and 30, respectively.
53) The antibody of embodiment 52, wherein the antibody comprises the VH of SEQ ID NO:138 and the VL of SEQ ID NO:67.
54) An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 25, 130, 27, 131, 29, and 132, respectively.
55) The antibody of embodiment 54, wherein the antibody comprises the VH of SEQ ID NO: 138 and the VL of SEQ ID NO: 142.
56) An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 25, 130, 27, 28, 133, and 132, respectively.
57) The antibody of embodiment 56, wherein the antibody comprises the VH of SEQ ID NO: 138 and the VL of SEQ ID NO:143.
58) An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 25, 134, 27, 28, 29, and 30, respectively.
59) The antibody of embodiment 58, wherein the antibody comprises the VH of SEQ ID NO: 139 and the VL of SEQ ID NO: 167.
60) An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 25, 135, 27, 28, 29, and 136, respectively.
61) The antibody of embodiment 60, wherein the antibody comprises the VH of SEQ ID NO: 140 and the VL of SEQ ID NO:144.
62) An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 25, 135, 27, 28, 29, and 30, respectively.
63) The antibody of embodiment 62, wherein the antibody comprises the VH of SEQ ID NO: 140 and the VL of SEQ ID NO: 167.
64) An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 25, 135, 27, 131, 29, and 132, respectively.
65) The antibody of embodiment 64, wherein the antibody comprises the VH of SEQ ID NO: 140 and the VL of SEQ ID NO: 142.
66) An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 25, 135, 27, 28, 133, and 132, respectively.
67) The antibody of embodiment 66, wherein the antibody comprises the VH of SEQ ID NO: 140 and the VL of SEQ ID NO:143.
68) An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 25, 134, 27, 28, 29, and 136, respectively.
69) The antibody of embodiment 68, wherein the antibody comprises the VH of SEQ ID NO: 139 and the VL of SEQ ID NO:144.
70) An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 25, 134, 27, 131, 29, and 132, respectively.
71) The antibody of embodiment 70, wherein the antibody comprises the VH of SEQ ID NO: 139 and the VL of SEQ ID NO: 142.
72) An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 25, 134, 27, 28, 133, and 132, respectively.
73) The antibody of embodiment 72, wherein the antibody comprises the VH of SEQ ID NO: 139 and the VL of SEQ ID NO:143.
74) An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 25, 137, 27, 28, 133, and 132, respectively.
75) The antibody of embodiment 74, wherein the antibody comprises the VH of SEQ ID NO: 141 and the VL of SEQ ID NO: 143.
76) The antibody of any one of embodiments 1-75, wherein the antibody is human or humanized.
77) The antibody of embodiment 76, wherein the antibody is of IgG4 or IgG1 isotype.
78) The antibody of embodiment 77, comprising one, two, three, four, five, six, seven, eight, nine or ten substitutions in the antibody Fc.
79) The antibody of embodiment 77, comprising
   a) L234A, L235A, G237A, P238S, H268A, A330S and P331S substitutions;
   b) V234A, G237A, P238S, H268A, V309L, A330S and P331S substitutions;
   c) F234A, L235A, G237A, P238S and Q268A substitutions,
   d) L234A, L235A or L234A and L235A substitutions;
   e) F234A, L235A or F234A and L235A substitutions; or
   f) V234A substitution, wherein residue numbering is according to the EU Index.
80) The antibody of embodiment 79, comprising S228P, F234A and L235A substitutions, wherein residue numbering is according to the EU Index.
81) The antibody of any one of embodiments 1-80, wherein the antibody is bispecific.
82) The antibody of embodiment 76, wherein the antibody specifically binds PSMA and specifically binds CD3, CD5, CD28, CD16, CD16A, CD25, CD38, CD44, CD56, CD69, CD94, CD335 (NKp46), CD336, (NKp44), CD337 (NKp30), NKp80, NKG2C and NKG2D, DNAM, NCRs, CD18, CD89, CD18, CD32, CD64, CD64 and CD35.
83) A pharmaceutical composition comprising the antibody of any one of embodiments 1-82 and a pharmaceutically accepted carrier.
84) A polynucleotide encoding the antibody VH of embodiment 15, the antibody VL of embodiment 16, or the antibody VH and the antibody VL of embodiment 15 and 16.
85) A polynucleotide encoding the antibody VH, the antibody VL, or the antibody VH and the antibody VL of any one of embodiments 28-75.
86) A vector comprising the polynucleotide of embodiment 84.
87) A vector comprising the polynucleotide of embodiment 85.
88) A host cell comprising the vector of embodiment 86.
89) A host cell comprising the vector of embodiment 87.
90) A method of producing the antibody of embodiment 1, comprising culturing the host cell of embodiment 89 in conditions that the antibody is expressed, and recovering the antibody produced by the host cell.
91) A method of treating a cancer in a subject, comprising administering a therapeutically effective amount of the isolated antibody of any one of embodiments 1-82 to the subject in need thereof for a time sufficient to treat the cancer.
92) The method of embodiment 91, wherein the cancer is a solid tumor, malignancy or a tumor neovasculature.
93) The method of embodiment 92, wherein the solid tumor is a prostate cancer or a colorectal cancer, a gastric cancer, a clear cell renal carcinoma, a bladder cancer, a lung cancer, a squamous cell carcinoma, a glioma, a breast cancer, a kidney cancer, a neovascular disorder, a clear cell renal carcinoma (CCRCC), a pancreatic cancer, a renal cancer, a urothelial cancer and an adenocarcinaoma to the liver.
94) The method of embodiment 93, wherein the prostate cancer is a refractory prostate cancer, a prostatic intraepithelial neoplasia, an androgen independent prostate cancer, a malignant prostate cancer.
95) The method of any one of embodiments 90-94, wherein the antibody is administered in combination with a second therapeutic agent.
96) The method of embodiment 95, wherein the second therapeutic agent is a standard of care drug for treatment of the solid tumor or malignancy or a tumor neovasculature.
97) The method of embodiment 96, wherein the second therapeutic agent is an hormone inhibitor, an antimicrotubule agent, a kinase inhibitor, an immunomodulating agent, a topoisomerase inhibitor, an anti-metabolite, a mitotic inhibitor, an alkylating agent, an anthracycline, a vinca alkaloid, an intercalating agent, an agent capable of interfering with a signal transduction pathway, an agent that promotes apoptosis, a proteosome inhibitor or radiation.
98) The method of embodiment 96, wherein the second therapeutic agent is a vaccine.
99) The method of embodiment 98, wherein the vaccine is a polypeptide or fragment thereof, or a DNA or a RNA encoding the polypeptide or fragment thereof expressed on tumor cells.
100) The method of embodiment 99, wherein the polypeptide is PSMA, mesothelin, EGFR or EGFRvIII.

101) The method of embodiment 95, wherein the second therapeutic agent is administered simultaneously, sequentially or separately.
102) The method of any one of embodiments 91-101, wherein the subject is treated or is being treated with radiation therapy.
103) The method of any one of embodiments 91-101 wherein the subject has had or will undergo surgery.
104) The method of any one of embodiments 46-58, wherein the isolated antibody comprises the VH of SEQ ID NO: 66 and the VL of SEQ ID NO: 67.
105) The antibody of any one of embodiments 1-82 for use in therapy.
106) An anti-idiotypic antibody binding to the antibody of any one of embodiments 1-82.
107) A bispecific antibody comprising a first domain that specifically binds PSMA and a second domain that specifically binds CD3, wherein the first domain comprises:
  a) the HCDR1, the HCDR2, the HCDR3, the LCDR1, the LCDR2 and the LCDR3 of SEQ ID NOs: 31, 42, 43, 11, 12 and 13, respectively;
  b) the HCDR1, the HCDR2, the HCDR3, the LCDR1, the LCDR2 and the LCDR3 of SEQ ID NOs: 14, 15, 16, 17, 18 and 19, respectively;
  c) the HCDR1, the HCDR2, the HCDR3, the LCDR1, the LCDR2 and the LCDR3 of SEQ ID NOs: 25, 26, 27, 28, 29 and 30, respectively;
  d) the HCDR1, the HCDR2, the HCDR3, the LCDR1, the LCDR2 and the LCDR3 of SEQ ID NOs: 36, 37, 38, 39, 40 and 41, respectively;
  e) the HCDR1, the HCDR2, the HCDR3, the LCDR1, the LCDR2 and the LCDR3 of SEQ ID NOs: 122, 123, 124, 23, 12, and 24, respectively;
  f) the HCDR1, the HCDR2, the HCDR3, the LCDR1, the LCDR2 and the LCDR3 of SEQ ID NOs: 8, 9, 10, 11, 12, and 13, respectively;
  g) the HCDR1, the HCDR2, the HCDR3, the LCDR1, the LCDR2 and the LCDR3 of SEQ ID NOs: 14, 15, 16, 17, 18, and 19, respectively;
  h) the HCDR1, the HCDR2, the HCDR3, the LCDR1, the LCDR2 and the LCDR3 of SEQ ID NOs: 20, 21, 22, 23, 12, and 24, respectively;
  i) the HCDR1, the HCDR2, the HCDR3, the LCDR1, the LCDR2 and the LCDR3 of SEQ ID NOs: 31, 32, 33, 34, 12, and 35, respectively;
  j) the HCDR1, the HCDR2, the HCDR3, the LCDR1, the LCDR2 and the LCDR3 of SEQ ID NOs: 31, 44, 45, 46, 29, and 47, respectively;
  k) the HCDR1, the HCDR2, the HCDR3, the LCDR1, the LCDR2 and the LCDR3 of SEQ ID NOs: 36, 37, 48, 49, 50, and 51, respectively;
  l) the HCDR1, the HCDR2, the HCDR3, the LCDR1, the LCDR2 and the LCDR3 of SEQ ID NOs: 53, 54, 55, 23, 12, and 35, respectively;
  m) the HCDR1, the HCDR2, the HCDR3, the LCDR1, the LCDR2 and the LCDR3 of SEQ ID NOs: 25, 130, 27, 28, 29, and 30, respectively;
  n) the HCDR1, the HCDR2, the HCDR3, the LCDR1, the LCDR2 and the LCDR3 of SEQ ID NOs: 25, 130, 27, 131, 29, and 132, respectively;
  o) the HCDR1, the HCDR2, the HCDR3, the LCDR1, the LCDR2 and the LCDR3 of SEQ ID NOs: 25, 130, 27, 28, 133, and 132, respectively;
  p) the HCDR1, the HCDR2, the HCDR3, the LCDR1, the LCDR2 and the LCDR3 of SEQ ID NOs: 25, 134, 27, 28, 29, and 30, respectively;
  q) the HCDR1, the HCDR2, the HCDR3, the LCDR1, the LCDR2 and the LCDR3 of SEQ ID NOs: 25, 135, 27, 28, 29, and 136, respectively;
  r) the HCDR1, the HCDR2, the HCDR3, the LCDR1, the LCDR2 and the LCDR3 of SEQ ID NOs: 25, 135, 27, 28, 29, and 30, respectively;
  s) the HCDR1, the HCDR2, the HCDR3, the LCDR1, the LCDR2 and the LCDR3 of SEQ ID NOs: 25, 135, 27, 131, 29, and 132, respectively;
  t) the HCDR1, the HCDR2, the HCDR3, the LCDR1, the LCDR2 and the LCDR3 of SEQ ID NOs: 25, 135, 27, 28, 133, and 132, respectively;
  u) the HCDR1, the HCDR2, the HCDR3, the LCDR1, the LCDR2 and the LCDR3 of SEQ ID NOs: 25, 134, 27, 28, 29, and 136, respectively;
  v) the HCDR1, the HCDR2, the HCDR3, the LCDR1, the LCDR2 and the LCDR3 of SEQ ID NOs: 25, 134, 27, 131, 29, and 132, respectively;
  w) the HCDR1, the HCDR2, the HCDR3, the LCDR1, the LCDR2 and the LCDR3 of SEQ ID NOs: 25, 134, 27, 28, 133, and 132, respectively; or
  x) the HCDR1, the HCDR2, the HCDR3, the LCDR1, the LCDR2 and the LCDR3 of SEQ ID NOs: 25, 137, 27, 28, 133, and 132, respectively.
108) The bispecific antibody of embodiment 107, wherein the first domain comprises:
  a) the HCDR1, the HCDR2, the HCDR3, the LCDR1, the LCDR2 and the LCDR3 of SEQ ID NOs: 31, 42, 43, 11, 12 and 13, respectively, and the VH of SEQ ID NO: 74 and the VL of SEQ ID NO: 61;
  b) the HCDR1, the HCDR2, the HCDR3, the LCDR1, the LCDR2 and the LCDR3 of SEQ ID NOs: 14, 15, 16, 17, 18 and 19, respectively, and the VH of SEQ ID NO: 62 and the VL of SEQ ID NO: 63;
  c) the HCDR1, the HCDR2, the HCDR3, the LCDR1, the LCDR2 and the LCDR3 of SEQ ID NOs: 25, 26, 27, 28, 29 and 30, respectively, and the VH of SEQ ID NO: 66 and the VL of SEQ ID NO: 67;
  d) the HCDR1, the HCDR2, the HCDR3, the LCDR1, the LCDR2 and the LCDR3 of SEQ ID NOs: 36, 37, 38, 39, 40 and 41, respectively, and the VH of SEQ ID NO: 72 and the VL of SEQ ID NO: 73;
  e) the HCDR1, the HCDR2, the HCDR3, the LCDR1, the LCDR2 and the LCDR3 of SEQ ID NOs: 122, 123, 124, 23, 12, and 24, respectively, and the VH of SEQ ID NO: 160 and the VL of SEQ ID NO: 65;
  f) the HCDR1, the HCDR2, the HCDR3, the LCDR1, the LCDR2 and the LCDR3 of SEQ ID NOs: 8, 9, 10, 11, 12, and 13, respectively, and the VH of SEQ ID NO:60 and the VL of SEQ ID NO:61;
  g) the HCDR1, the HCDR2, the HCDR3, the LCDR1, the LCDR2 and the LCDR3 of SEQ ID NOs: 14, 15, 16, 17, 18, and 19, respectively, and the VH of SEQ ID NO:62 and the VL of SEQ ID NO:63;
  h) the HCDR1, the HCDR2, the HCDR3, the LCDR1, the LCDR2 and the LCDR3 of SEQ ID NOs: 20, 21, 22, 23, 12, and 24, respectively, and VH of SEQ ID NO:64 and the VL of SEQ ID NO:65;
  i) the HCDR1, the HCDR2, the HCDR3, the LCDR1, the LCDR2 and the LCDR3 of SEQ ID NOs: 31, 32, 33, 34, 12, and 35, respectively, and the VH of SEQ ID NO:70 and the VL of SEQ ID NO:71;
  j) the HCDR1, the HCDR2, the HCDR3, the LCDR1, the LCDR2 and the LCDR3 of SEQ ID NOs: 31, 44, 45, 46, 29, and 47, respectively, the VH of SEQ ID NO:75 and the VL of SEQ ID NO:76;

k) the HCDR1, the HCDR2, the HCDR3, the LCDR1, the LCDR2 and the LCDR3 of SEQ ID NOs: 36, 37, 48, 49, 50, and 51, respectively, and the VH of SEQ ID NO:77 and the VL of SEQ ID NO:78;

l) the HCDR1, the HCDR2, the HCDR3, the LCDR1, the LCDR2 and the LCDR3 of SEQ ID NOs: 53, 54, 55, 23, 12, and 35, respectively, and the VH of SEQ ID NO:68 and the VL of SEQ ID NO:69;

m) the HCDR1, the HCDR2, the HCDR3, the LCDR1, the LCDR2 and the LCDR3 of SEQ ID NOs: 25, 130, 27, 28, 29, and 30, respectively, and the VH of SEQ ID NO:138 and the VL of SEQ ID NO:67;

n) the HCDR1, the HCDR2, the HCDR3, the LCDR1, the LCDR2 and the LCDR3 of SEQ ID NOs: 25, 130, 27, 131, 29, and 132, respectively, and the VH of SEQ ID NO:138 and the VL of SEQ ID NO: 142;

o) the HCDR1, the HCDR2, the HCDR3, the LCDR1, the LCDR2 and the LCDR3 of SEQ ID NOs: 25, 130, 27, 28, 133, and 132, respectively, and the VH of SEQ ID NO:138 and the VL of SEQ ID NO:143;

p) the HCDR1, the HCDR2, the HCDR3, the LCDR1, the LCDR2 and the LCDR3 of SEQ ID NOs: 25, 134, 27, 28, 29, and 30, respectively, and the VH of SEQ ID NO:139 and the VL of SEQ ID NO:167;

q) the HCDR1, the HCDR2, the HCDR3, the LCDR1, the LCDR2 and the LCDR3 of SEQ ID NOs: 25, 135, 27, 28, 29, and 136, respectively, and the VH of SEQ ID NO:140 and the VL of SEQ ID NO:144;

r) the HCDR1, the HCDR2, the HCDR3, the LCDR1, the LCDR2 and the LCDR3 of SEQ ID NOs: 25, 135, 27, 28, 29, and 30, respectively, and the VH of SEQ ID NO: 140 and the VL of SEQ ID NO: 167;

s) the HCDR1, the HCDR2, the HCDR3, the LCDR1, the LCDR2 and the LCDR3 of SEQ ID NOs: 25, 135, 27, 131, 29, and 132, respectively and the VH of SEQ ID NO:140 and the VL of SEQ ID NO: 142;

t) the HCDR1, the HCDR2, the HCDR3, the LCDR1, the LCDR2 and the LCDR3 of SEQ ID NOs: 25, 135, 27, 28, 133, and 132, respectively, and the VH of SEQ ID NO:140 and the VL of SEQ ID NO:143;

u) the HCDR1, the HCDR2, the HCDR3, the LCDR1, the LCDR2 and the LCDR3 of SEQ ID NOs: 25, 134, 27, 28, 29, and 136, respectively; and the VH of SEQ ID NO:139 and the VL of SEQ ID NO: 144;

v) the HCDR1, the HCDR2, the HCDR3, the LCDR1, the LCDR2 and the LCDR3 of SEQ ID NOs: 25, 134, 27, 131, 29, and 132, respectively, and the VH of SEQ ID NO:139 and the VL of SEQ ID NO: 142;

w) the HCDR1, the HCDR2, the HCDR3, the LCDR1, the LCDR2 and the LCDR3 of SEQ ID NOs: 25, 134, 27, 28, 133, and 132, respectively, and the VH of SEQ ID NO:139 and the VL of SEQ ID NO:143; or x) the HCDR1, the HCDR2, the HCDR3, the LCDR1, the LCDR2 and the LCDR3 of SEQ ID NOs: 25, 137, 27, 28, 133, and 132, respectively and the VH of SEQ ID NO:141 and the VL of SEQ ID NO: 143.

109) An isolated bispecific PSMA/CD3 antibody comprising a first domain that (i) binds to cells expressing recombinant *Pan troglodytes* PSMA, wherein the binding to cells is measured by flow cytometry and (ii) binds recombinant *Pan troglodytes* PSMA extracellular domain (SEQ ID NO:4) with an affinity of about 30 nM or less, wherein the affinity is measured by Proteon surface plasmon resonance assay specifically binding PSMA, and a second domain specifically binding CD3.

110) The bispecific PSMA×CD3 antibody of embodiment 109, wherein the antibody
a) binds LNCaP cells with a calculated $EC_{50}$ of 20 nM or less and binds *Macaca fascicularis* PSMA-expressing HEK cells with a calculated $EC_{50}$ of 40 nM or less, wherein the difference in calculated $EC_{50}$ between binding LNCaP cells and binding *Macaca fascicularis* PSMA-expressing HEK cells is less than 5-fold, and wherein the calculated $EC_{50}$ is measured in a whole cell binding assay at 0° C. using flow cytometry,
b) binds recombinant PSMA ECD from human (SEQ ID NO:7), *Pan troglodytes* (SEQ ID NO:4) and *Macaca fascicularis* (SEQ ID NO:5) with an equilibrium dissociation constant ($K_D$) of 12 nM or less, wherein the $K_D$ is measured using Proteon surface plasmon resonance assay ProteOn XPR36 system at +25° C.;
c) displays T-cell mediated killing of LNCaP cells, C42 cells, human PSMA-expressing HEK cells or *Macaca fascicularis* PSMA-expressing HEK cells, wherein the T-cell mediated killing is measured by Chromium-51 or by caspase 3/7 activation assay or
d) recognizes a conformational epitope wherein the epitope is comprised of residues I138, F235, P237, G238, D244, Y299, Y300, Q303, K304, E307, and K324-P326 of human PSMA (SEQ ID NO:3).

111) The bispecific PSMA×CD3 antibody of embodiment 109, wherein the antibody binds to T-cells.

112) The bispecific PSMA×CD3 antibody of embodiment 109, wherein the first domain comprises
a) the heavy chain complementarity determining region 1 (HCDR1), a HCDR2 and a HCDR3 of SEQ ID NOs: 14, 15 and 16, respectively; and the light chain complementarity determining region 1 (LCDR1), a LCDR2 and a LCDR3 of SEQ ID NOs: 17, 18 and 19, respectively;
b) the HCDR1, the HCDR2 and the HCDR3 of SEQ ID NOs: 20, 21 and 22, respectively, and the LCDR1, the LCDR2 and the LCDR3 of SEQ ID NOs: 23, 12 and 24, respectively;
c) the HCDR1, the HCDR2 and the HCDR3 of SEQ ID NOs: 25, 26 and 27, respectively, and the LCDR1, the LCDR2 and the LCDR3 of SEQ ID NOs: 28, 29 and 30, respectively,
d) the HCDR1, the HCDR2 and the HCDR3 of SEQ ID NOs: 31, 44 and 45, respectively, and the LCDR1, the LCDR2 and the LCDR3 of SEQ ID NOs: 46, 29 and 47, respectively;
e) the HCDR1, the HCDR2 and the HCDR3 of SEQ ID NOs: 31, 42 and 43, respectively, and the LCDR1, the LCDR2 and the LCDR3 of SEQ ID NOs: 11, 12 and 13, respectively; or
f) the HCDR1, the HCDR2 and the HCDR3 of SEQ ID NOs: 122, 123 and 124, respectively, and the LCDR1, the LCDR2 and the LCDR3 of SEQ ID NOs: 23, 12 and 24, respectively.

113) The bispecific PSMA×CD3 antibody of embodiment 109, wherein the first domain comprises the HCDR1, the HCDR2 and the HCDR3 of
a) SEQ ID NOs: 14, 15 and 16, respectively;
b) SEQ ID NOs: 20, 21 and 22, respectively;
c) SEQ ID NOs: 25, 26 and 27, respectively;
d) SEQ ID NOs: 31, 44 and 45, respectively;
e) SEQ ID NOs: 31, 42 and 43, respectively; or
f) SEQ ID NOs: 122, 123 and 124, respectively.

114) The bispecific PSMA×CD3 antibody of embodiment 109, wherein the first domain comprises the LCDR1, the LCDR2 and the LCDR3 of a) SEQ ID NOs: 17, 18 and 19, respectively;
b) SEQ ID NOs: 23, 12 and 24, respectively;
c) SEQ ID NOs: 28, 29 and 30, respectively;
d) SEQ ID NOs: 46, 29 and 47, respectively;
e) SEQ ID NOs: 11, 12 and 13, respectively; or
f) SEQ ID NOs: 23, 12 and 24, respectively.

115) The bispecific PSMAxCD3 antibody of embodiment 109, wherein
a) the first domain comprises a heavy chain variable region (VH) of SEQ ID NO: 62 and a light chain variable region (VL) of SEQ ID NO: 63, and the second domain comprises the VH of SEQ ID NO: 104 and the VL of SEQ ID NO: 105
b) the first domain comprises the VH of SEQ ID NO: 64 and the VL of SEQ ID NO: 65, and the second domain comprises the VH of SEQ ID NO: 104 and the VL of SEQ ID NO: 105;
c) the first domain comprises the VH of SEQ ID NO: 66 and the VL of SEQ ID NO: 67, and the second domain comprises the VH of SEQ ID NO: 104 and the VL of SEQ ID NO: 105;
d) the first domain comprises the VH of SEQ ID NO: 75 and the VL of SEQ ID NO: 76, and the second domain comprises the VH of SEQ ID NO: 104 and the VL of SEQ ID NO: 105;
e) the first domain comprises the VH of SEQ ID NO: 74 and the VL of SEQ ID NO: 61, and the second domain comprises the VH of SEQ ID NO: 104 and the VL of SEQ ID NO: 105;
f) the first domain comprises the VH of SEQ ID NO: 160 and the VL of SEQ ID NO: 65, and the second domain comprises the VH of SEQ ID NO: 104 and the VL of SEQ ID NO: 105.

116) The bispecific PSMAxCD3 antibody of embodiment 109, comprising a first heavy chain (HC1), a first light chain (LC1), a second heavy chain (HC2) and a second light chain (LC2), wherein the HC1 and the LC1 comprise the amino acid sequences of
a) SEQ ID NOs: 84 and 85, respectively;
b) SEQ ID NOs: 86 and 87, respectively;
c) SEQ ID NOs: 88 and 89, respectively;
d) SEQ ID NOs: 125 and 91, respectively;
e) SEQ ID NOs: 94 and 95, respectively; or
f) SEQ ID NOs: 96 and 83, respectively.

117) The bispecific PSMAxCD3 antibody of embodiment 116, wherein the HC2 and the LC2 comprises SEQ ID NOs: 110 and 111, respectively.

118) The bispecific PSMAxCD3 antibody of embodiment 109, comprising the HC1, the LC1, the HC2 and the LC2 of
a) SEQ ID NOs: 84, 85, 110 and 111, respectively;
b) SEQ ID NOs: 86, 87, 110 and 111, respectively;
c) SEQ ID NOs: 88, 89, 110, 111, respectively;
d) SEQ ID NOs: 125, 91, 110 and 111, respectively;
e) SEQ ID NOs: 94, 95, 110 and 111, respectively;
f) SEQ ID NOs: 96, 83, 110 and 111, respectively.

119) The bispecific PSMAxCD3 antibody of any one of embodiments 109-118, wherein the antibody is human or humanized.

120) The bispecific PSMAxCD3 antibody of embodiment 119, wherein the antibody is of IgG1, IgG2, IgG3 or IgG4 isotype.

121) The bispecific PSMAxCD3 antibody of embodiment 120, wherein the antibody is of IgG1 or IgG4 isotype.

122) The bispecific PSMAxCD3 antibody of embodiment 120 or 121, having one, two, three, four, five, six, seven, eight, nine or ten substitutions in an antibody Fc.

123) The bispecific PSMAxCD3 antibody of embodiment 121, comprising:
a) L234A, L235A, G237A, P238S, H268A, A330S and P331S substitutions;
b) V234A, G237A, P238S, H268A, V309L, A330S and P331S substitutions;
c) F234A, L235A, G237A, P238S and Q268A substitutions;
d) L234A, L235A or L234A and L235A substitutions;
e) F234A, L235A or F234A and L235A substitutions;
f) V234A substitution; or
g) S228P, F234A and L235A substitutions, wherein residue numbering is according to the EU Index.

124) The bispecific PSMAxCD3 antibody of any one of embodiments 109-123, comprising at least one substitution in an antibody CH3 constant domain.

125) The bispecific PSMAxCD3 antibody of embodiment 124, wherein the substitution in the antibody CH3 constant domain is 409R, F405L or F405L/R409K substitution, wherein residue numbering is according to the EU Index.

126) The bispecific PSMAxCD3 antibody of embodiment 124, wherein the antibody comprises
a) F405L substitution in the HC1 and 409R substitution in the HC2, wherein the antibody is of IgG1 isotype; b) V234A, G237A, P238S, H268A, V309L, A330S, P331S and F405L substitutions in the HC1 and V234A, G237A, P238S, H268A, V309L, A330S, P331S and 409R substitutions in the HC2, wherein the antibody is of IgG1 isotype; or
b) S228P substitution in the HC1 and S228P, F405L and R409K substitution in the HC2, wherein the antibody is of IgG4 isotype.

127) A pharmaceutical composition comprising the bispecific PSMAxCD3 antibody of any one of embodiments 109-126 and a pharmaceutically accepted carrier.

128) A polynucleotide encoding the bispecific PSMAxCD3 antibody HC1, LC1, HC2 or LC2 of embodiment 118.

129) A vector comprising the polynucleotide encoding the HC1, the LC1, the HC2, the LC2, the HC1 and the LC1 or the HC2 and the LC2 of embodiment 128.

130) An isolated host cell comprising the vector of embodiment 129.

131) A method of producing the bispecific PSMAxCD3 antibody of embodiment 118, comprising culturing the host cell of embodiment 130 in conditions that the antibody is expressed, and recovering and purifying the bispecific PSMAxCD3 antibody produced by the host cell.

132) A method of producing the bispecific PSMAxCD3 antibody of embodiment 118, comprising:
a) combining a monospecific bivalent PSMA antibody having two identical HC1 and two identical LC1 and a monospecific bivalent CD3 antibody having two identical HC2 and two identical LC2 in a mixture of about 1:1 molar ratio;
b) introducing a reducing agent into the mixture;
c) incubating the mixture about ninety minutes to about six hours;
d) removing the reducing agent; and
e) purifying the bispecific PSMAxCD3 antibody that comprises the HC1, the LC1, the HC2 and the LC2.

133) The method of embodiment 132, wherein the reducing agent is 2-mercaptoethanolamine (2-MEA).

134) The method of embodiment 133, wherein
h) the 2-MEA is present at a concentration of about 25 mM to about 75 mM; and i) the incubating step is performed at a temperature of about 25° C. to about 37° C.

135) A method of treating a cancer in a subject, comprising administering a therapeutically effective amount of the isolated PSMA×CD3 bispecific antibody of any one of embodiments 109-126 to the subject in need thereof for a time sufficient to treat the cancer.

136) The method of embodiment 135, wherein the cancer is a solid tumor, malignancy or a tumor neovasculature.

137) The method of embodiment 136, wherein the solid tumor is a prostate cancer or a colorectal cancer, a gastric cancer, a clear cell renal carcinoma, a bladder cancer, a lung cancer, a squamous cell carcinoma, a glioma, a breast cancer, a kidney cancer, a neovascular disorder, a clear cell renal carcinoma (CCRCC), a pancreatic cancer, a renal cancer, a urothelial cancer and an adenocarcinaoma to the liver.

138) The method of embodiment 137, wherein the prostate cancer is a refractory prostate cancer, a prostatic intraepithelial neoplasia, an androgen independent prostate cancer, a malignant prostate cancer.

139) The method of any one of embodiments 135-138, wherein the antibody is administered in combination with a second therapeutic agent.

140) The method of embodiment 139, wherein the second therapeutic agent is a standard of care drug for treatment of the solid tumor or malignancy or a tumor neovasculature.

141) The method of embodiment 139, wherein the second therapeutic agent is a hormone inhibitor, an antimicrotubule agent, a topoisomerase inhibitor, an anti-metabolite, a mitotic inhibitor, an alkylating agent, an anthracycline, a *vinca* alkaloid, an intercalating agent, an agent capable of interfering with a signal transduction pathway, an agent that promotes apoptosis, a proteosome inhibitor or radiation.

142) The method of embodiment 139, wherein the second therapeutic agent is a vaccine.

143) The method of embodiment 142, wherein the vaccine is a polypeptide or fragment thereof, or a DNA or a RNA encoding the polypeptide or fragment thereof expressed on tumor cells.

144) The method of embodiment 143, wherein the polypeptide is PSMA, mesothelin, EGFR or EGFRvIII.

145) The method of embodiment 139, wherein the second therapeutic agent is administered simultaneously, sequentially or separately.

146) The method of any one of embodiments 135-145, wherein the subject is treated or is being treated with radiation therapy.

147) The method of any one of embodiments 135-145 wherein the subject has had or will undergo surgery.

148) The method of any one of embodiments 135-145, wherein the first domain of the bispecific PSMA×CD3 antibody comprises the VH of SEQ ID NO:66 and the VL or SEQ ID NO:67, and the second domain of the bispecific PSMA×CD3 antibody comprises the VH of SEQ ID NO:104 and the VL of SEQ ID NO:105.

149) The antibody of any one of embodiments 109-126 for use in therapy.

150) An anti-idiotypic antibody binding to the antibody of any one of embodiments 109-126.

Example 1: Materials

Generation of PSMA Cell Lines

Expression vectors presenting full-length chimpanzee PSMA (H2Q3K5_PANTR, SEQ ID NO: 1) or full length Cynomolgous monkey PSMA (EHH56646.1, SEQ ID NO: 2) were generated for use as screening tools to assess the anti-PSMA leads using an in-house expression vector with the CMV promoter using standard molecular biology techniques. Vectors were transiently transfected into HEK293F cells in suspension using standard methods. Transfected 293F suspension cells were plated in growth medium plus serum to become adherent and selected for stable plasmid integration. Single cell populations were selected by serial dilution and the PSMA surface receptor expression was quantified by FACS using the (PSMAL antibody (Center) affinity Purified Rabbit Polyclonal Antibody (Catalog #OAAB02483, Aviva Systems Biology) as the primary antibody with a R-PE anti-rabbit secondary antibody (Catalog #111-116-144, Jackson ImmunoResearch Laboratories, Inc.) and a rabbit polyclonal IgG (Catalog #SC-532, Santa Cruz Biotechnology) as the isotype control).

Human PSMA expressing cell lines were generated using lentivirus (Genecopoeia, cat #EX-G0050-Lv105-10) containing full length human PSMA (FOLH1_HUMAN, SEQ ID NO:3) and puromycin for selection of PSMA positive cells. HEK293F cells (ATCC), negative for PSMA, were transduced with Lentiviral particles to overexpress human PSMA. Following transduction, cells positively expressing PSMA and the resistance marker were selected by treating pooled cells, grown in DMEM+10% HI FBS (Life Technologies) and supplemented with varying concentrations of Puromycin (Life Technologies).

In addition to the HEK generated cell lines, several commercial cell lines were used for phage panning and binding and cellular toxicity assays. LNCaP clone FGC cells (ATCC cat #CRL-1740) are a commercially available human prostate cancer cell lines. C4-2B cells were originally developed at MD Anderson and are derived from LNCaP FGC grown in vivo and metastasize to bone marrow (Thalmann, et al 1994, Cancer Research 54, 2577-81).

Generation of Soluble PSMA ECD Proteins

Recombinant chimpanzee PSMA Extra Cellular Domain (ECD) protein (Chimp PSMA ECD, SEQ ID NO:4) was generated for panning and to assess the anti-PSMA leads using an in-house expression vector with the CMV promoter using standard molecular biology techniques. The chimp PSMA ECD gene fragment (amino acid 44-750 of SEQ ID NO: 1) with N-terminal signal sequence (SEQ ID NO:56), N-terminal Avitag (SEQ ID NO:57) and 6-His tags (SEQ ID NO:58) was cloned using an in-house expression vector with the CMV promoter using standard molecular biology techniques and transiently expressed in 293Expi cells (Invitrogen). cDNA was prepared using gene synthesis techniques (U.S. Pat. Nos. 6,670,127; 6,521,427). Supernatants were harvested and clarified by centrifugation. The proteins were purified using a two-step purification process: 1) IMAC purification with a HisTrap HP column (GE Healthcare) and 2) size exclusion purification (Superdex 200, Ge Healthcare) where the elution buffer is Dulbecco's phosphate-buffered saline, calcium, magnesium (Thermofisher, #14040) containing 0.5 mM $ZnCl_2$ to stabilize PSMA dimerization. Fractions containing the protein of interest were pooled and protein concentration was determined by A280. This material was used for binding and affinity measurements and is referred to as PSMG8.

Chimp PSMA ECD was also biotinylated for panning. The BirA plasmid that was co-transfected into mammalian cells to biotinylate proteins containing the Avi tag was created in-house. The BirA coding region (SEQ ID NO:59) was fused to the signal peptide from mouse IgG heavy chain (SEQ ID NO:80), and an ER retention signal (KDEL ("KDEL" disclosed as SEQ ID NO: 156) was added to the C-terminus to generate the BirA (SEQ ID NO:112). The constructed gene was cloned into an expression vector under the control of the CMV promoter. To produce biotinylated PSMA antigen, the PSMA plasmid DNA was added in a 4-fold excess (w/w) to the BirA plasmid into the transfection mix.

Biotinylation of the Chimp PSMA ECD protein was performed via the Avi tag by cotransfection of a BirA expression construct and the resulting secreted protein was purified using a two-step purification process: 1) IMAC purification with a HisTrap HP column (GE Healthcare) and 2) size exclusion purification (Superdex 200, Ge Healthcare) where the elution buffer is Dulbecco's phosphate-buffered saline, calcium, magnesium (Thermofisher, #14040) containing 0.5 mM ZnCl2 to stabilize PSMA dimerization. The protein was tested for endotoxin prior to use in phage panning studies.

Recombinant cynomolgous monkey PSMA extracellular domain (ECD) protein (cyno PSMA ECD, SEQ ID NO:5), corresponding to amino acids 44-750 of SEQ ID NO:2 with N-terminal signal (SEQ ID NO:56), N-terminal Avi-(SEQ ID NO:57) and 6His (SEQ ID NO:58) tags was cloned and expressed as described previously for the chimp PSMA ECD. Biotinylation of the cyno PSMA ECD protein was performed via the Avi tag by cotransfection of a BirA expression construct and the resulting secreted protein was purified by a two-step purification using IMAC HisTrap HP column (GE Healthcare) and MonoAvidin columns. The protein was tested for endotoxin prior to use in phage panning studies. This material was also used for binding and affinity measurements and is referred to as PSMG1.

A second recombinant cyno PSMA ECD protein (Cyno PSMA Fc, SEQ ID NO:6) with an IgG1 Fc (SEQ ID NO:81) was cloned and expressed using an in-house expression vector with the CMV promoter using standard molecular biology techniques. CynoPSMA Fc protein was transiently expressed in 293HEK-expi cells. Transient transfection of PSMG3 in HEK293 Expi cells were harvested 5 days after transfection, clarified by centrifugation (30 min, 6000 rpm) and filtered (0.2µ PES membrane, Corning). The relative amount of IgG was determined with the Octet instrument (ForteBio) using a purified known IgG (same isotype) spiked into spent medium to generate the standard curve.

Clarified Cyno PSMA Fc supernatant was loaded onto an equilibrated (dPBS, pH 7.2) HiTrap MabSelect Sure Protein A column (GE Healthcare) at a relative concentration of ~30 mg protein per ml of resin. After loading, the column was washed with dPBS, pH7.2 and protein eluted with 10 column volumes of 0.1 M Na-Acetate, pH 3.5. Peak fractions were pooled, neutralized with 2M Tris, pH 7, and filtered (0.2p). The neutralized protein sample was dialyzed against 3 changes of dPBS containing Ca2+, Mg2+, and 0.5 mM ZnCl2, pH 7.2 overnight at 4° C. The next day, sample was removed from dialysis, filtered (0.2p) and the protein concentration determined by absorbance at 280 nm on a BioTek SynergyHT™ spectrophotometer. The quality of the purified proteins was assessed by SDS-PAGE and analytical size exclusion HPLC (Dionex HPLC system). Endotoxin levels were measured using a LAL assay (Pyrotell-T, Associates of Cape Cod). Purified proteins were stored at 4° C.

Recombinant human PSMA extracellular domain (ECD) protein (human PSMA ECD, SEQ ID NO:7), corresponding to amino acids 44-750 of SEQ ID NO:3 with N-terminal Avi- and 6His (SEQ ID NO: 58) tags was cloned, expressed and purified as described previously for the chimp and cyno PSMA ECD proteins.

Example 2: Identification of Anti-Chimp and Anti-Human PSMA Fabs

Panning with recombinant protein. A first solution panning of the de novo Human Fab-pIX libraries [Shi, L., et al J Mol Biol, 2010. 397(2): p. 385-396. WO 2009/085462], consisting of VH1-69, 3-23 and 5-51 heavy chain libraries paired with four human VL germline genes (A27, B3, L6, O12) libraries, was performed using an alternating panning approach with one round of phage capture on Strepavidin beads (Invitrogen Cat #112.05D, Lot #62992920) coated with biotinylated Chimp PSMA ECD according to the manufacturer's protocol, followed by phage capture on ProtG beads (Invitrogen, Cat #10003D) coated with Cyno-PSMA-Fc according to the manufacturer's protocol followed by phage capture on Sera-mag Double Speed magnetic Neutravidin beads (Thermo, Cat #7815-2104-011150) coated with biotinylated Chimp PSMA ECD according to the manufacturer's protocol. This panning yielded two hits: PSMB18 and PSMB25.

Whole cell panning for anti-PSMA Fabs. Additional panning experiments were performed on whole cells using the Round #1 output from the chimpanzee ECD panning experiments described above or fresh de novo phage libraries, as input. Briefly, phage was produced by helper phage infection and concentrated by PEG/NaCl precipitation according to standard protocols known in the art. The phage libraries were pre-cleared on untransfected parental HEK293F cells overnight at 4° C. with gentle rocking. Following PEG/NaCl precipitation, the pre-cleared libraries were incubated with chimp PSMA expressing HEK293 cells or LNCAP cells with gentle rocking for 2 hr at 4° C. The removal of unbound phage and the recovery of phage-bound cells was performed by Ficoll gradient, and following several wash steps with, cells carrying bound phage were incubated with 1 mL of TG-1 E. coli culture at 37° C. for 30 minutes without agitation. The resulting mixture was plated on LB-Carbenicillin-1% Glucose plates and grown over night at 37° C. The process was then repeated for subsequent panning rounds.

Conversion of phage Fab-pIX to Fab-His for generating E. coli supernatants. The resulting phage Fab-pIX hits were converted to Fab-His using a standard procedure. Plasmid DNA was isolated from phage panned E. coli (Plasmid Plus Maxi Kit, Qiagen cat #12963) and subjected to NheI/SpeI restriction digest. The resulting 5400 and 100 bp fragments were separated on a 0.8% agarose gel and the 5400 bp fragment was gel purified (MinElute PCR purification kit, Qiagen cat #28006). The purified 5400 bp band was self-ligated using T4 ligase and the resulting product (encoding the Fab-his fusion) was transformed back into the TG-1 E. coli strain and clonally isolated. Fab-His supernatants were generated from clones by overnight induction of cultures with 1 mM IPTG. Following centrifugation of the overnight culture, clarified supernatants were ready for use in downstream assays. To determine the relative expression levels of different Fab-his supernatants, an anti-kappa (Southern Biotech cat #2061-05) ELISA on serially diluted supernatants was performed. All of the clones tested exhibited similar Fab-his expression (data not shown).

Cell binding of Fab-his fusions from E. coli. A cell-based binding assay was designed to assess the binding capabilities of individual Fab-his fusions from E. coli supernatants to PSMA-expressing cells. Individual Fab clones were isolated from the round 3 output of all panning experiments following pIX excision. Fab clones were tested for binding to chimp and cyno PSMA expressing HEK cells, as well as to human PSMA on LNCaP cells. Briefly, PSMA expressing cells were aliquoted into a V-bottom plate (CoStar 3357) at a density of 200,000 per well and incubated with (100 µl) supernatants expressing Fab fragments for 1 hour on ice. Cells were washed twice with PBS containing 2% FBS, and stained with a mouse anti-human kappa-RPE antibody (Life Technologies cat #MH10514) for 1 hour on ice. Cells were washed twice with PBS containing 2% FBS and resuspended in 100 L of the same wash buffer. Plates were read on a BD FACS Array flow cytometer. FACS data was analyzed in FlowJo software by live gating the healthy population of cells using forward scatter and side scatter, and then analyzing the cells within this gate for PE staining. Mean fluorescence intensity (MFI) was calculated and exported into Microsoft Excel. Fab clones that exhibited binding≥3 times background for all three species of PSMA (cyno, chimp and human), and exhibited no binding to the HEK293 cell line, were labeled as "preliminary positive". Fabs were sequenced and moved forward for cloning into mammalian expression vector for rescreening. True positives were selected from the binding of mammalian cell expressed Fab supernatants to PSMA-expressing cell lines.

Preparation of Mammalian Fabs. For conversion of E. coli Fab to mammalian-expressed Fab, In-Fusion HD cloning (ClonTech cat #638918) was utilized according to the manufacturer's protocol. Briefly, nucleotide sequences of clones that have passed the primary screen and are to be moved into mammalian Fab format, are loaded into the "InFu Primer Finder v1.2.3" program (software developed in-house), which generates a list of isotype-specific PCR primers used to generate PCR fragments for In-Fusion cloning into the huKappa_muIgGSP and huG1 Fab expression vectors. These vectors are in-house vectors with CMV promotors based off of pcDNA3.1. Following the In-fusion process, E. coli clones were isolated, sequence verified and transfected into HEK293 cells using standard protocols. Mammalian PSMA Fabs for confirming binding to PSMA expressing cell lines were prepared by harvesting 20 ml of supernatants from transfection after 5 days.

Rescreening hits from whole cell panning in mammalian sup format. Confirmation of mammalian expressed Fab supernatants was performed using the whole cell binding assay described previously. Binding of Fabs to Chimpanzee, Cynomolgous monkey and human PSMA (LNCaP cells) was tested, as well as counter screening for no binding to the parental HEK cell line. Table 3 shows the hit profile of mammalian Fab supernatant binding to PSMA-expressing cells. Many of the hits from E. coli supernatants did not confirm with mammalian expressed proteins. PSMB47 showed high binding to cyno PSMA-expressing cells and some binding to chimp-PSMA expressing cells, but no binding to LNCaP cells expressing human PSMA. PSMB55 showed a similar profile, but with some binding to LNCaP cells. PSMB68-PSMB79 bound to LNCaP cells, but not to chimp- or cyno-PSMA expressing cells. Mammalian Fab sups PSMB51, PSMB55 and PSMB56, bound all three cell lines. PSMB49, PSMB50, and PSMB53, show more chimp or cyno binding. M58 showed slight chimp and cyno binding.

TABLE 3

Hit profile of Mammalian Fab protein binding to PSMA-expressing cells measured by Geo-MFI (Mean Fluoresent Instensity)

| Fab protein ID (Fab DNA ID) | cyno | chimp | LNCaP | Parent HEK |
|---|---|---|---|---|
| PSMB10 (PSMM10) | 244 | 81.6 | — | 248 |
| PSMB11 (PSMM11) | 19 | 6.6 | — | 8.14 |
| PSMB12 (PSMM12) | 31.6 | 8.05 | — | 12.6 |
| PSMB13 (PSMM13) | 57.8 | 18.2 | — | 50.5 |
| PSMB14 (PSMM14) | 32.6 | 13.1 | — | 22.2 |
| PSMB15 (PSMM15) | 40.4 | 18.5 | — | 38 |
| PSMB16 (PSMM16) | 175 | 220 | — | 6.39 |
| PSMB17 (PSMM17) | 34.9 | 22.4 | — | 40.1 |
| PSMB18 (PSMM18) | 696 | 439 | — | 8.71 |
| PSMB19 (PSMM19) | 53.7 | — | 5.15 | 4.47 |
| PSMB20 (PSMM20) | 5.75 | — | 5.85 | 41.3 |
| PSMB21 (PSMM21) | 94.4 | — | 20.7 | 372 |
| PSMB22 (PSMM22) | 9.07 | — | 7.92 | 54.9 |
| PSMB23 (PSMM23) | 16.4 | — | 6.66 | 164 |
| PSMB24 (PSMM24) | 14.6 | 9.6 | 4.09 | 3.96 |
| PSMB25 (PSMM25) | 15.2 | 11.3 | 16.9 | 4.09 |
| PSMB26 (PSMM26) | 9.48 | — | 7.26 | 114 |
| PSMB27 (PSMM27) | 20 | — | 7.56 | 136 |
| PSMB28 (PSMM28) | 29.7 | — | 8.88 | 302 |
| PSMB29 (PSMM29) | 6.87 | — | 5.7 | 72.8 |
| PSMB30 (PSMM30) | 5.16 | — | 4.58 | 45 |
| PSMB31 (PSMM31) | 5.99 | — | — | 25.5 |
| PSMB32 (PSMM32) | 4.81 | — | — | 27.1 |
| PSMB33 (PSMM33) | 5.14 | — | — | 40.1 |
| PSMB34 (PSMM34) | 17.9 | — | — | 107 |
| PSMB35 (PSMM35) | 58.5 | — | — | 231 |
| PSMB36 (PSMM36) | 5.05 | — | — | 6.96 |
| PSMB37 (PSMM37) | 23.4 | — | — | 178 |
| PSMB38 (PSMM38) | 4.05 | — | — | 7.7 |
| PSMB39 (PSMM39) | 10.2 | — | — | 166 |
| PSMB40 (PSMM40) | 66.9 | — | — | 348 |
| PSMB41 (PSMM41) | 5.39 | — | — | 12 |
| PSMB42 (PSMM42) | 7.35 | — | — | 25.8 |
| PSMB43 (PSMM43) | 8.73 | — | — | 7.18 |
| PSMB44 (PSMM44) | 12.6 | — | — | 48.9 |
| PSMB45 (PSMM45) | 22.4 | — | — | 43.1 |
| PSMB46 (PSMM46) | 3.88 | — | — | 5.29 |
| PSMB47 (PSMM48) | 101 | 25.5 | 3.46 | 2.85 |
| PSMB48 (PSMM49) | 2.72 | 3.18 | 2.68 | 2.72 |
| PSMB49 (PSMM50) | 51.6 | 22 | 3.22 | 3.48 |
| PSMB51 (PSMM52) | 285 | 231 | 41.5 | 2.68 |
| PSMB52 (PSMM53) | 39.2 | 6.89 | 2.67 | 2.56 |
| PSMB53 (PSMM54) | 27.6 | 17.8 | 4 | 2.6 |
| PSMB54 (PSMM55) | 2.7 | 2.75 | 2.65 | 2.79 |
| PSMB55 (PSMM56) | 226 | 180 | 17.2 | 2.58 |
| PSMB56 (PSMM57) | 95.6 | 34.7 | 24.5 | 2.52 |
| PSMB57 (PSMM58) | 19.8 | 11 | 3.26 | 2.68 |
| PSMB58 (PSMM59) | 121 | 192 | 25.3 | 2.67 |
| PSMB59 (PSMM60) | 4.96 | 9.69 | 6.04 | 3 |
| PSMB60 (PSMM61) | 2.28 | 3.07 | 87.3 | 4.64 |
| PSMB61 (PSMM62) | 2.1 | 3.16 | 135 | 2.98 |
| PSMB62 (PSMM63) | 7.17 | 4.43 | 54.9 | 9.09 |
| PSMB63 (PSMM64) | 2.07 | 2.95 | 27 | 2.82 |
| PSMB64 (PSMM65) | 2.39 | 3.26 | 70.5 | 3.05 |
| PSMB65 (PSMM66) | 2.3 | 3.13 | 32.4 | 4.25 |
| PSMB66 (PSMM67) | 2.14 | 3 | 24.6 | 2.83 |
| PSMB67 (PSMM68) | 2.23 | 2.95 | 21 | 2.95 |
| PSMB68 (PSMM69) | 5.44 | — | 134 | 35.3 |
| PSMB69 (PSMM70) | 2.29 | 3.38 | 25.5 | 3.35 |
| PSMB70 (PSMM71) | 2.22 | 3.49 | 15.5 | 3.26 |
| PSMB71 (PSMM72) | 2.54 | 4.4 | 18.5 | 3.07 |
| PSMB72 (PSMM73) | 2.13 | 3.53 | 227 | 3.02 |
| PSMB73 (PSMM74) | 2.97 | 4.13 | 125 | 11.1 |
| PSMB74 (PSMM75) | 120 | — | 178 | 132 |
| PSMB75 (PSMM76) | 2.99 | 3.04 | 173 | 7.89 |
| PSMB76 (PSMM77) | 3.75 | 3.99 | 138 | 3.95 |
| PSMB77 (PSMM78) | 4.68 | 3.96 | 144 | 4.71 |
| PSMB78 (PSMM79) | 25.2 | — | 378 | 24.4 |
| PSMB79 (PSMM80) | 38.4 | — | 512 | 157 |
| PSMB80 (PSMM81) | 19.6 | 18.6 | 20.9 | 6.61 |
| PSMB81 (PSMM82) | 2.63 | 2.06 | 4.07 | 2.69 |
| PSMB82 (PSMM83) | 2.79 | 2.23 | 4.11 | 2.76 |
| PSMB83 (PSMM84) | 2.59 | 2.28 | 4.09 | 2.74 |
| PSMB84 (PSMM85) | 750 | 729 | 192 | 3.15 |
| PSMB85 (PSMM86) | 2.84 | 2.59 | 2.33 | 3.24 |

TABLE 3-continued

Hit profile of Mammalian Fab protein binding to PSMA-expressing cells measured by Geo-MFI (Mean Fluoresent Instensity)

| Fab protein ID (Fab DNA ID) | cyno | chimp | LNCaP | Parent HEK |
|---|---|---|---|---|
| PSMB86 (PSMM87) | 224 | 176 | 31.7 | 2.82 |
| PSMB87 (PSMM88) | 2.63 | 2.27 | 4.23 | 2.91 |
| PSMB88 (PSMM89) | 37.7 | 29.7 | 30.3 | 7.6 |
| PSMB89 (PSMM90) | 27.1 | 27.3 | 53.2 | 39.5 |
| PSMB90 (PSMM91) | 26.7 | 24.7 | 47.1 | 36.4 |
| PSMB91 (PSMM92) | 8.97 | 6.16 | 13 | 6.63 |
| PSMB92 (PSMM93) | 20 | 16.5 | 57.1 | 50 |
| PSMB93 (PSMM94) | 5.13 | 9.62 | 2.5 | 3.66 |
| PSMB94 (PSMM95) | 5.12 | 2.67 | 2.22 | 3.57 |
| PSMB95 (PSMM96) | 8.9 | 8.82 | 13.4 | 11.4 |
| PSMB96 (PSMM97) | 2.4 | 3.25 | 2.53 | 4.03 |
| PSMB97 (PSMM98) | 2.57 | 4.73 | 2.52 | 3.7 |
| PSMB99 (PSMM100) | 9.95 | 2.4 | 2.39 | 4.03 |
| PSMB100 (PSMM101) | 4.03 | 2.52 | 2.33 | 3.37 |
| PSMB100 (PSMM101) | 3.5 | 2.86 | 2.48 | 4.57 |
| PSMB101 (PSMM102) | 5.49 | 3.18 | 2.23 | 3.33 |
| PSMB102 (PSMM103) | 2.4 | 2.42 | 2.16 | 3.2 |
| PSMB103 (PSMM104) | 3.52 | 3.26 | 2.58 | 4.44 |
| PSMB104 (PSMM105) | 2.15 | 2.5 | 2.34 | 3.95 |
| PSMB105 (PSMM106) | 2.03 | 2.39 | 2.18 | 3.39 |
| PSMB106 (PSMM107) | 2 | 2.4 | 2.27 | 3.59 |
| PSMB107 (PSMM108) | 9 | 2.47 | 2.33 | 3.49 |
| PSMB108 (PSMM109) | 2 | 2.58 | 2.28 | 3.46 |
| PSMB109 (PSMM110) | 321 | 326 | 34.9 | 6.11 |
| PSMB110 (PSMM111) | 2.3 | 2.31 | 2.31 | 3.4 |
| PSMB111 (PSMM112) | 2.32 | 2.31 | — | 3.21 |
| PSMB112 (PSMM113) | 6.28 | 5.7 | 2.71 | 3.28 |
| PSMB113 (PSMM114) | 2.82 | 2.95 | 2.32 | 3.29 |
| PSMB114 (PSMM115) | 2.78 | 2.47 | 4.3 | 3.14 |
| PSMB115 (PSMM116) | 2.66 | 2.59 | 2.2 | 3.14 |
| PSMB46 (PSMM117) | 4.54 | 3.18 | 2.21 | 4.79 |
| PSMB67 (PSMM118) | 3.95 | 4.3 | 3 | 6.13 |
| PSMB74 (PSMM119) | 7.94 | 13 | 3.16 | 12.5 |
| PSMB78 (PSMM120) | 5.08 | 4.79 | 22.3 | 6.82 |
| PSMB81 (PSMM121) | 3.66 | 3.83 | 3.05 | 5.11 |
| PSMB82 (PSMM122) | 15.1 | 28.4 | 10.8 | 24.3 |
| PSMB83 (PSMM123) | 37.5 | 42.1 | 3.04 | 4.88 |
| PSMB85 (PSMM124) | 34.6 | 52.9 | 20.7 | 46.8 |
| PSMB87 (PSMM125) | 4.23 | 3.74 | 2.26 | 4.73 |
| PSMB89 (PSMM126) | 51.8 | 53.1 | 11.7 | 6.27 |
| PSMB90 (PSMM127) | 42.8 | 30.2 | 7.74 | 5.99 |
| PSMB91 (PSMM128) | 3.9 | 27.6 | 2.37 | 4.32 |
| PSMB92 (PSMM129) | 45.7 | 37.3 | 12.1 | 7.4 |
| PSMB93 (PSMM130) | 5.13 | 7.85 | 4.11 | 7.82 |
| PSMB94 (PSMM131) | 3.67 | 3.23 | 2.32 | 4.72 |
| PSMB95 (PSMM132) | 4.05 | 3.64 | 2.56 | 5.57 |
| PSMB96 (PSMM133) | 3.91 | 4.54 | 2.37 | 4.65 |
| PSMB97 (PSMM134) | 3.22 | 3.16 | 4.08 | 4.22 |
| PSMB98 (PSMM135) | 15.6 | 12.7 | 2.22 | 4.21 |
| PSMB99 (PSMM136) | 4.08 | 3.26 | 2.22 | 5.04 |
| PSMB100 (PSMM137) | 5.24 | 3.82 | 2.16 | 4.83 |
| PSMB101 (PSMM138) | 3.84 | 3.14 | 2.23 | 4.52 |
| PSMB102 (PSMM139) | 4.51 | 3.82 | 2.23 | 4.59 |
| PSMB103 (PSMM140) | 6.81 | 4.27 | 2.21 | 5.41 |
| PSMB104 (PSMM141) | 7.52 | 4.35 | 2.26 | 4.39 |
| PSMB105 (PSMM142) | 5.03 | 11.2 | 4.87 | 7.28 |
| PSMB106 (PSMM143) | 3.87 | 3.8 | 2.73 | 4.9 |
| PSMB107 (PSMM144) | 3.3 | 3.35 | 2.3 | 4.64 |
| PSMB108 (PSMM145) | 6.78 | 3.83 | 2.33 | 4.98 |
| PSMB110 (PSMM146) | 4.03 | 3.23 | 2.28 | 5.3 |
| PSMB111 (PSMM147) | 3.71 | 3.26 | 2.36 | 5.11 |
| PSMB112 (PSMM148) | 4.54 | 3.26 | 2.26 | 4.86 |
| PSMB113 (PSMM149) | 84.3 | 104 | 51.7 | 94.2 |
| PSMB114 (PSMM150) | 3.31 | 3.26 | 2.21 | 5.14 |
| PSMB115 (PSMM151) | 3.55 | 3.43 | 2.3 | 4.21 |

Figure 1:
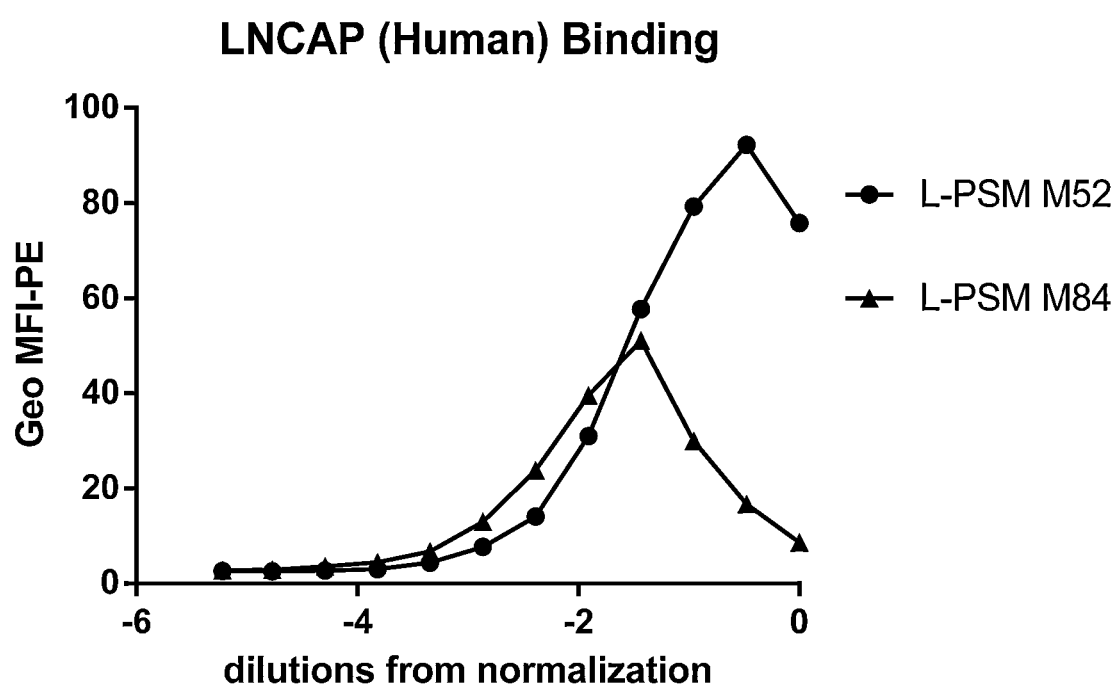
Figure 2A:
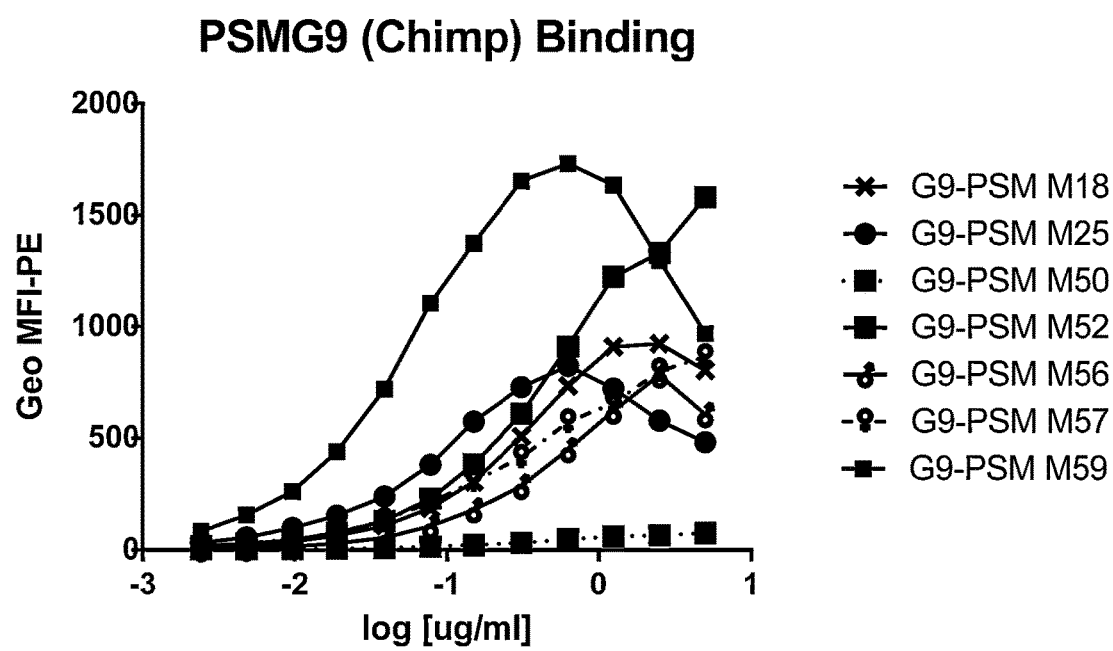
FIGS. 2A-2D show mammalian Fab supernatant titration curves for Anti-PSMA phage panning hits binding to Chimpanzee-PSMA expressing HEK cells.
Figure 2B:
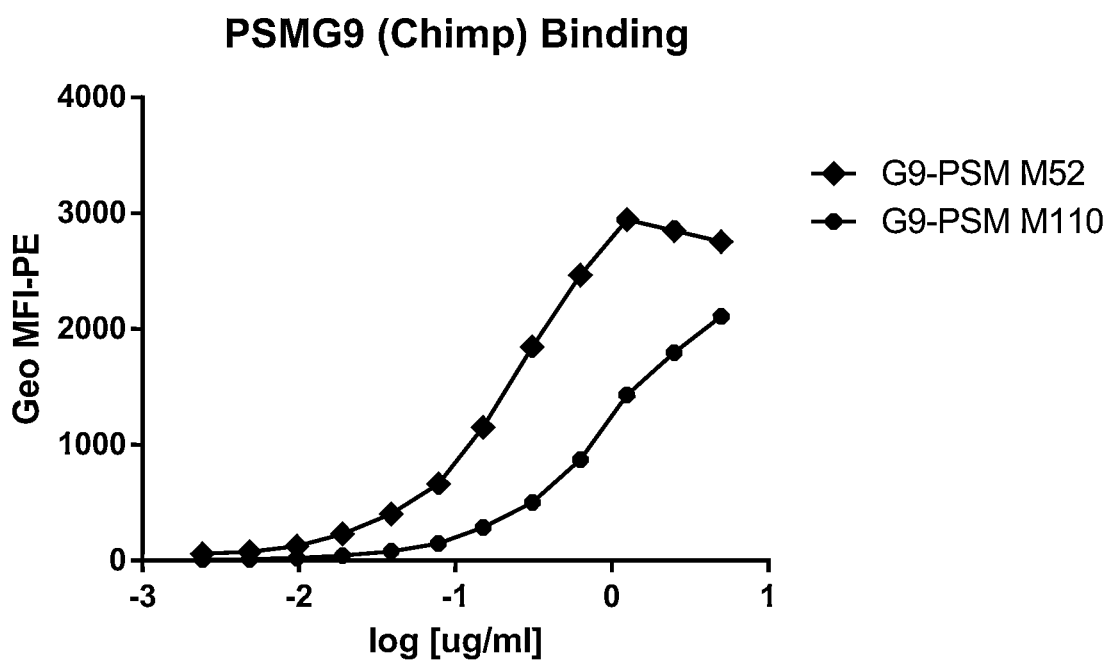
Figure 2C:
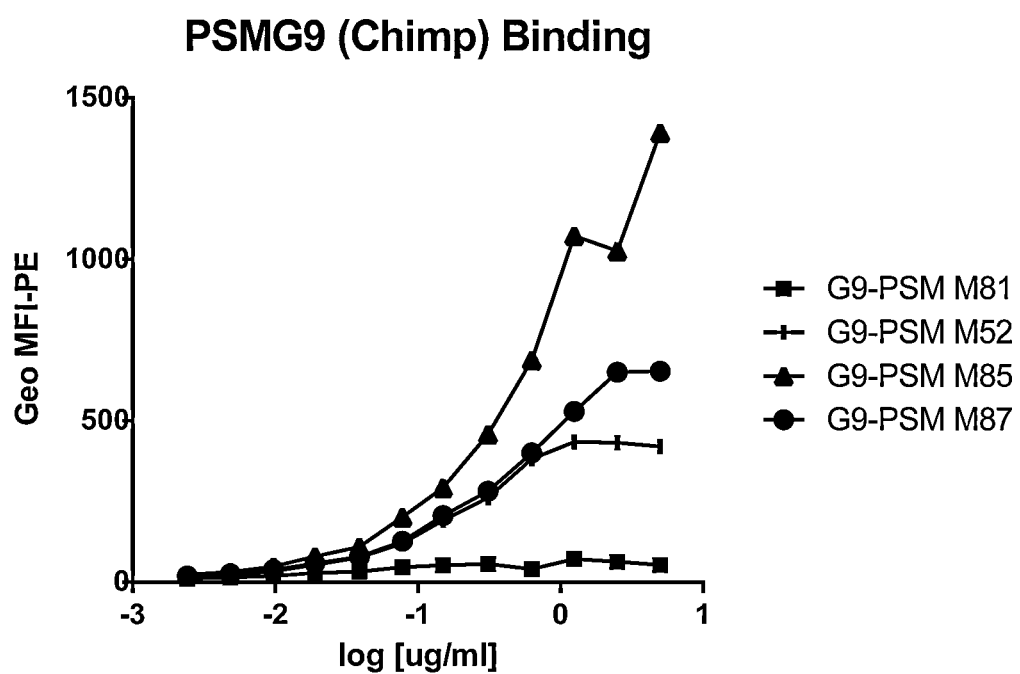
Figure 2D:
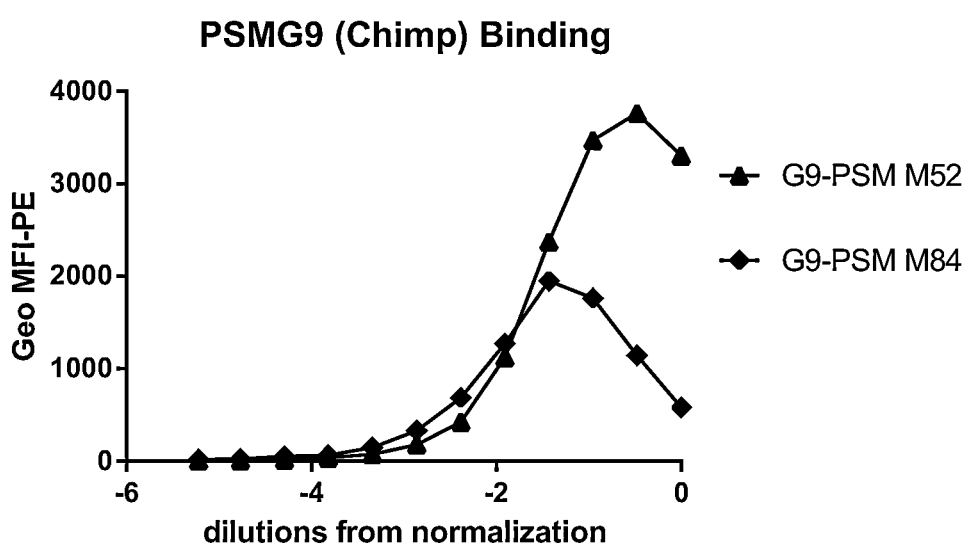
Figure 3A:
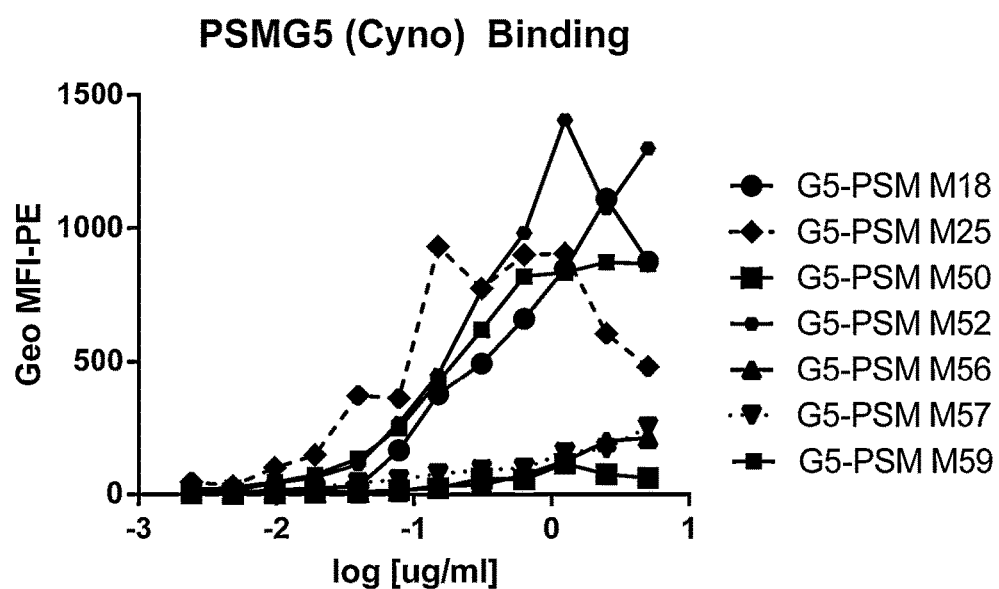
FIGS. 3A-3D shows mammalian Fab supernatant titration curves for Anti-PSMA phage panning hits binding to Cynomolgus monkey PSMA-expressing HEK cells.
Figure 3B:
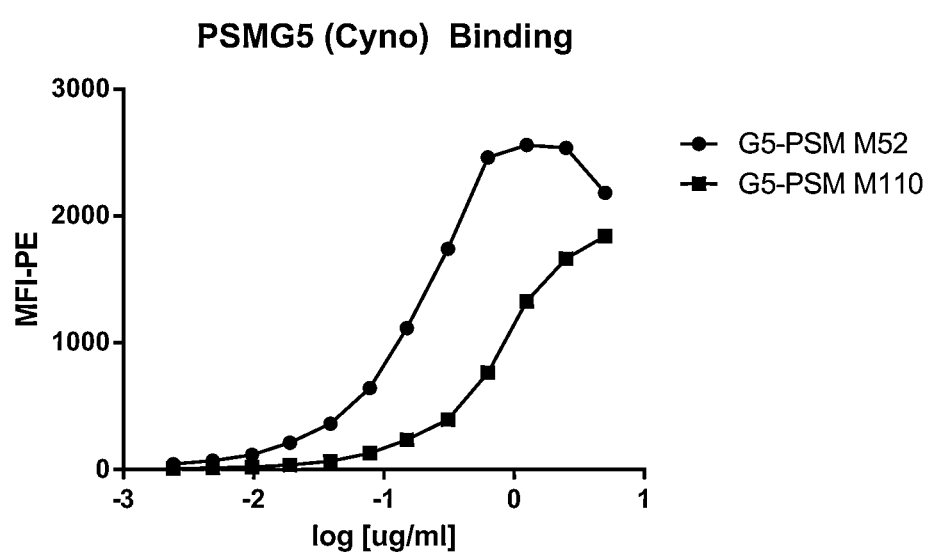
Figure 3C:
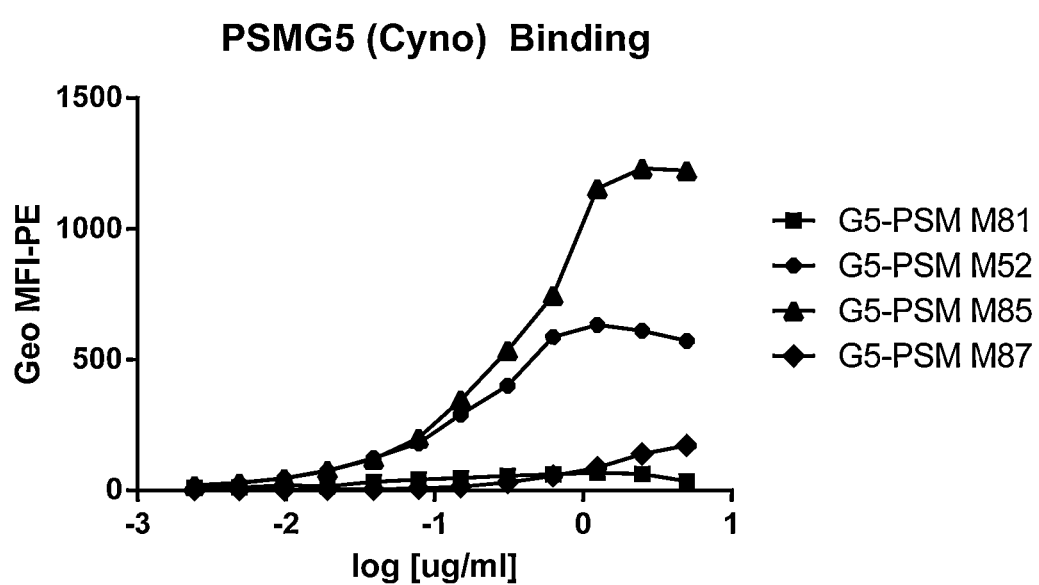
Figure 3D:
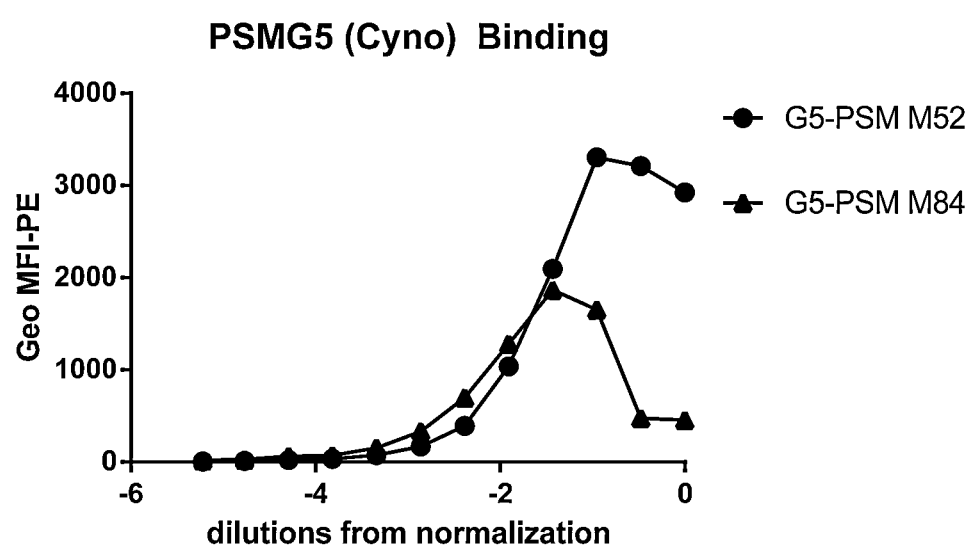

Dose response curves of mammalian expressed Fabs. Once mammalian expressed Fab clones were confirmed for positive binding as neat Fab supernatants to PSMA expressing cell lines, the supernatants were normalized for protein concentration by Octet or protein gel, and dose-response curves were completed to confirm PSMA binding using the protocol described previously. FIGS. 1-3 show titration curves for hits that demonstrated binding to all three PSMA-expressing cells. FIGS. 1A-D show the titration curves for anti-PSMA panning hits vs. LNCaP cells. FIGS. 2A-D show the titration curves for anti-PSMA panning hits vs Chimp-PSMA HEK cells. FIGS. 3A-D show the titration curves for anti-PSMA panning hits vs Cyno-PSMA HEK cells. PSMG5 (Cyno PSMA, GenBank: EHH56646.1) or PSMG9 (Chimp PSMA, NCBI Reference Sequence: XP_016777253.1) were cloned into a mammalian expression vector between HindII and EcoRI sites under control of CMV promoter for cell line generation. Engineered DNA was transfected into 293F cells using lipofectamine LTX reagent followed by geneticin selection to select for PSMA (PSMG5 or PSMG9) positive cells. Following selection, cells were screened and sorted using anti-PSMA antibody (Aviva Cat #OAAB02483-PSMG9) or anti-PSMA Fab (PSMB18-Janssen Internal) using FACS. FACS sorted PSMG5 clones 11, 23, 25 and 32 and PSMG9 clones 2, 10, 11, 12, 20 and 24 were selected and handed off for screening. PSMG5 and PSMG9 sequences are provided below. Binding profiles among hits were compared across cell lines expressing different species of PSMA. PSMB51 supernatant was used as a positive control across experiments. Several hits were deprioritized because of N-linked glycosylation sites in CDRs, binding to the PSMA negative parental HEK cell line, or lack of binding to PSMA positive cell lines. Eleven Fab hits remained and 10 hits were cloned into human IgG4-PAA heavy chain constructs and used to generate PSMA×CD3 bispecific antibodies. These hits showed cross-species binding within 3-fold of each other and were moved into a bispecific antibody format to be tested for T cell redirection killing of PSMA positive targets. The panning antigens for each hit is shown in Table 4.

PSMG5
(SEQ ID NO: 126)
MWNLLHETDSAVATARRPRWLCAGALVLAGGFFLLGFLFGWFIKSSSE

ATNITPKHNMKAFLDELKAENIKKFLHNFTQIPHLAGTEQNFQLAKQIQS

QWKEFGLDSVELTHYDVLLSYPNKTHPNYISIINEDGNEIFNTSLFEPPP

AGYENVSDIVPPFSAFSPQGMPEGDLVYVNYARTEDFFKLERDMKINCSG

KIVIARYGKVFRGNKVKNAQLAGATGVILYSDPDDYFAPGVKSYPDGW

NLPGGGVQRGNILNLNGAGDPLTPGYPANEYAYRRGMAEAVGLPSIPV

HPIGYYDAQKLLEKMGGSASPDSSWRGSLKVPYNVGPGFTGNFSTQKV

KMHIHSTSEVTRIYNVIGTLRGAVEPDRYVILGGHRDSWVFGGIDPQSG

AAVVHEIVRSFGMLKKEGWRPRRTILFASWDAEEFGLLGSTEWAEENS

RLLQERGVAYINADSSIEGNYTLRVDCTPLMYSLVYNLTKELESPDEGF

EGKSLYESTWKKSPSPEFSGMPRISKLGSGNDFEVFFQRLGIASGRARYT

KNWETNKFSSYPLYHSVYETYELVEKFYDPMFKYHLTVAQVRGGMVF

ELANSVVLPFDCRDYAVVLRKYADKIYNISMKHPQEMKTYSVSFDSLFS

AVKNFTEIASKFSERLRDFDKSNPILLRMMNDQLMFLERAFIDPLGLPDR

PFYRHVIYAPSSHNKYAGESFPGIYDALFDIESKVDPSQAWGEVKRQISI

ATFTVQAAAETLSEVA

PSMG9
(SEQ ID NO: 127)
MWNLLHETDSAVATARRPRWLCAGALVLAGGFFLLGFLFGWFIKSSNEA

TNITPKHNMKAFLDELKAENIKKFLYNFTQIPHLAGTEQNFQLAKQIQSQ

-continued
WKEFGLDSVELAHYDVLLSYPNKTHPNYISIINEDGNEIFNTSLFEPPPP

GYENVLDIVPPFSAFSPQGMPEGDLVYVNYARTEDFFKLERDMKINCSGK

IVIARYGKVFRGNKVKNAQLAGAKGVILYSDPADYFAPGVKSYPDGWNLP

GGGVQRGNILNLNGAGDPLTPGYPANEYAYRHGIAEAVGLPSIPVHPIGY

YDAQKLLEKMGGSAPPDSSWRGSLKVPYNVGPGFTGNFSTQKVKMHIHST

NEVTRIYNVIGTLRGAVEPDRYVILGGHRDSWVFGGIDPQSGAAVVHEIV

RSFGTLKKEGWRPRRTILFASWDAEEFGLLGSTEWAEENSRLLQERGVAY

INADSSIEGNYTLRVDCTPLMYSLVYNLTKELKSPDEGFEGKSLYESWTK

KSPSPEFSGMPRISKLGSGNDFEVFFQRLGIASGRARYTKNWETNKFSGY

PLYHSVYETYELVEKFYDPMFKYHLTVAQVRGGMVFELANSIVLPFDCRD

YAVVLRKYADKIYNISMKHPQEMKTYSVSFDSLFSAVKNFTEIASKFTER

LQDFDKSNPILLRMMNDQLMFLERAFIDPLGLPDRPFYRHVIYAPSSHNK

YAGESFPGIYDALFDIESKVDPSKAWGDVKRQISVAAFTVQAAAETLSEV

A

TABLE 4

Antigen for each of the panning hits

| Round 1 antigen | Round 2-3 antigen | Hits | Hit identification |
|---|---|---|---|
| Chimp PSMA ECD | Cyno PSMA ECD | 2 | PSMB18, PSMB25 |
| Chimp PSMA ECD | Chimp PSMA HEK | 9 | PSMB49, PSMB51, PSMB56, PSMB58, PSMB109, PSMB55, PSMB84, PSMB83 |
| LNCaP | Chimp PSMA HEK | 2 | PSMB86, PSMB80 |

Preparation of anti-PSMA mAbs. A total of 12 clones that demonstrated binding to all three PSMA-expressing cells were ultimately converted to mAb IgG4 having Fc substitutions S228P, F234A, and L235A (PAA) isotype by restriction cloning. Briefly, constructs corresponding to Fab clones that have passed initial screens were digested with HindIII and ApaI. Gel purified fragments were ligated into an in-house expression vector with CMV promoter for generation of human IgG4-PAA expression. This allowed for rapid generation of bispecific antibodies. The in-house expression vector previously described was used to express the Heavy and Light Chains for each PSMA mab, where both vectors were co-transfected transiently into 293Expi or CHO cell lines for expression of the mAb. CDR sequences of cross-species positive PSMA Fabs generated from phage panning are shown below in Table 5. VH and VL sequences of the selected Fabs are shown below in Table 6. Heavy and light chain sequences of mAbs generated from the Fabs are shown in Table 7.

TABLE 5

CDR sequences (defined according to Kabat) of FAbs from phage panning (corresponding SEQ ID NOs are listed in parentheses)

| FAB ID | | CDR1 | CDR2 | CDR3 |
|---|---|---|---|---|
| PSMB58 | HC | SYWIS (122) | IIPGDSYTR YSPSFQG (123) | DYEWELFDSR LDY (124) |
| | LC | RASQSISSYLN (23) | AASSLQS (12) | QQSYSTP (24) |
| PSMB109 | HC | NAWIS (8) | WINPESGRA NYAQKFQG (9) | ELYYLVYSTY YYAFDY (10) |
| | LC | RASQSIDRWLN (11) | AASSLQS (12) | QQSPRYPLT (13) |
| PSMB86 | HC | SYDIS (14) | GIIPIEGTA NYAQKFQG (15) | DYPAGYGFDY (16) |
| | LC | RASQSVSSSYLA (17) | GASSRAT (18) | QQYGSSPLT (19) |
| PSMB84 | HC | SDWMS (20) | AISGNGGST EYADSVKG (21) | DPYYYYDGDS YYGMDV (22) |
| | LC | RASQSISSYLN (23) | AASSLQS (12) | QQSYSTP (24) |
| PSMB83 | HC | SDAMH (25) | EISGSGGYT NYADSVKG (26) | DSYDSSLYVG DYFDY (27) |
| | LC | RASQSVSSYLA (28) | DASNRAT (29) | QQRSNWPLT (30) |
| PSMB56 | HC | SYAIS (31) | WISPYNGNA NYAQKFQG (32) | DSDRSYNLDY (33) |
| | LC | RASQSISGWLN (34) | AASSLQS (12) | QQSYSTPLT (35) |
| PSMB55 | HC | SYWIG (36) | IIYPGDSDT RYSPSFQG (37) | GLPIWYLDY (38) |
| | LC | RASQSVASDLA (39) | FASNRAT (40) | QQSITWPFT (41) |
| PSMB51 | HC | SYAIS (31) | WIIPYNGNA NYAQKFQG (42) | VNSAALVWER LDY (43) |
| | LC | RASQSIDRWLN (11) | AASSLQS (12) | QQSPRYPLT (13) |
| PSMB49 | HC | SYAIS (31) | GIIPIFGTA NYAQKFQG (44) | ASRVMHASYG YLDY (45) |
| | LC | RASQSVSKWLA (46) | DASNRAT (29) | QQRFTAPWT (47) |
| PSMB25 | HC | SYWIG (36) | IIYPGDSDT RYSTSFQG (37) | GWAYDRGLDY (48) |
| | LC | KSSQSVLYSSN NKNYLA (49) | WASTRES (50) | QQYYSTPLT (51) |
| PSMB18 | HC | SYWIG (36) | IIYPGDSDT RYSPSFQG (37) | AYHYSKGLDY (52) |
| | LC | KSSQSVLYSSN NKNYLA (49) | WASTRES (50) | QQYYSTPLT (51) |
| PSMB80 | HC | DYAIS (53) | RIDPIEGTA NYAQKFQG (54) | DRYYYDGVYW YSDYFDY (55) |
| | LC | RASQSISSYLN (23) | AASSLQS (12) | QQSYSTPLT (35) |

A monospecific anti-PSMA antibody PSMB119 was generated comprising the VH and VL regions having the VH of SEQ ID NO: 79 and the VL of SEQ ID NO: 78 and an IgG4 constant region with S228P, F234A, and L235A substitutions. A monospecific anti-PSMA antibody PSMB120 was generated comprising the VH and VL regions having the VH of SEQ ID NO: 77 and the VL of SEQ ID NO: 78 and an IgG4 constant region with S228P, F234A, and L235A substitutions. A monospecific anti-PSMA antibody PSMB121 was generated comprising the VH and VL regions having the VH of SEQ ID NO: 75 and the VL of SEQ ID NO: 76 and an IgG4 constant region with S228P, F234A, and L235A substitutions. A monospecific anti-PSMA antibody PSMB122 was generated comprising the VH and VL regions having the VH of SEQ ID NO: 74 and the VL of SEQ ID NO: 61 and an IgG4 constant region with S228P, F234A, and L235A substitutions. A monospecific anti-PSMA antibody PSMB123 was generated comprising the VH and VL regions having the VH of SEQ ID NO: 72 and the VL of SEQ ID NO: 73 and an IgG4 constant region with S228P, F234A, and L235A substitutions. A monospecific anti-PSMA antibody PSMB124 was generated comprising the VH and VL regions having the VH of SEQ ID NO: 70 and the VL of SEQ ID NO: 71 and an IgG4 constant region with S228P, F234A, and L235A substitutions. A monospecific anti-PSMA antibody PSMB126 was generated comprising the VH and VL regions having the VH of SEQ ID NO: 68 and the VL of SEQ ID NO: 69 and an IgG4 constant region with S228P, F234A, and L235A substitutions. A monospecific anti-PSMA antibody PSMB127 was generated comprising the VH and VL regions having the VH of SEQ ID NO: 66 and the VL of SEQ ID NO: 67 and an IgG4 constant region with S228P, F234A, and L235A substitutions. A monospecific anti-PSMA antibody PSMB128 (Alt. Fab ID: PSMB84) was generated comprising the VH and VL regions having the VH of SEQ ID NO: 64 and the VL of SEQ ID NO: 65 and an IgG4 constant region with S228P, F234A, and L235A substitutions. A monospecific anti-PSMA antibody PSMB129 was generated comprising the VH and VL regions having the VH of SEQ ID NO: 60 and the VL of SEQ ID NO: 61 and an IgG4 constant region with S228P, F234A, and L235A substitutions. A monospecific anti-PSMA antibody PSMB130 was generated comprising the VH and VL regions having the VH of SEQ ID NO: 62 and the VL of SEQ ID NO: 63 and an IgG4 constant region with S228P, F234A, and L235A substitutions.

TABLE 6

VH and VL sequences of PSMA Fabs

| FAB ID | VH Amino acid sequence | SEQ ID NO | VL Amino Acid Sequence | SEQ ID NO |
|---|---|---|---|---|
| PSMB109 | QVQLVQSGAEVKKPGSSVKVSCKASGGTFSSYAISWVRQAPGQGLEWMGWISPYNGNANYAQKFQGRVTITADESTSTAYMELSSLRSEDTAVYYCARVNSAALVWERLDYWGQGTLVTVSS | 60 | DIQMTQSPSSLSASVGDRVTITCRASQSIDRWLNWYQQKPGKAPKLLIYAASSLQSGVPSRESGSGSGTDFTLTISSLQPEDFATYYCQQSPRYPLTFGQGTKVEIK | 61 |
| PSMB86 | QVQLVQSGAEVKKPGSSVKVSCKASGTFKSYDISWVRQAPGQGLEWMGGIIPIEGTANYAQKFQGRVTITADESTSTAYMELSSLRSEDTAVYYCARDYPAGYGFDYWGQGTLVTVSS | 62 | EIVLTQSPGTLSLSPGERATLSCPASQSVSSSYLAWYQQKPGQAPRLLIYGASSRATGIPDRFSGSGSGTDFTLTISRLEPEDFAVYYCQQYGSSPLTFGQGTKVEIK | 63 |

TABLE 6-continued

VH and VL sequences of PSMA Fabs

| FAB ID | VH Ammo acid sequence | SEQ ID NO | VL Amino Acid Sequence | SEQ ID NO |
|---|---|---|---|---|
| PSMB84 | EVQLLESGGGLVQPGGSLRLSCAASGFTFDSDWMSWVRQAPGKGLEWVSAISGNGGSTEYADSVKGRFTISRDNSKNTLYLQMNSLRAEDTAVYYCARDPYYYDGDSYYGMDVWGQGTLVTVSS | 64 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 65 |
| PSMB83 | EVQLLESGGGLVQPGGSLRLSCAASGFTFKSDAMHWVRQAPGKGLEWVSEISGSGGYTNYADSVKGRFTISRDNSKNTLYLQMNSLRAEDTAVYYCARDSYDSSLYVGDYEDYWGQGTLVTVSS | 66 | EIVITQSPATLSLSPGERATLSCRASQSVSSYLAWYQQKPGQAPPLLIYDASNRATGIPARFSGSGSGTDFTLTISSLEPEDFAVYYCQQRSNWPLTFGQGTKVEIK | 67 |
| PSMB80 | QVQLVQSGAEVKKPGSSVKVSCKASGGTFDDYAISWVRQAPGQGLEWMGRIDPIEGTANYAQKFQGRVTITADESTSTAYMELSSLRSEDTAVYYCARDRYYYDGVYWYSDYFDYWGQGTLVTVSS | 68 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 69 |
| PSMB58 | EVQLVQSGAEVKKPGESLKISCKGSGYSFTSYWISWVRQMPGKGLEWMGIIYPGDSYTRYSPSFQGQVTISADKSISTAYLQWSSLKASDTAMYYCARDYEWELFDSRLDYWGQGTLVTVSS | 160 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 65 |
| PSMB56 | QVQLVQSGAEVKKPGSSVKVSCKASGGTFSSYAISWVRQAPGQGLEWMGWISPYNGNANYAQKFQGRVTITADESTSTAYMELSSLRSEDTAVYYCARDSDRSYNLDYWGQGTLVTVSS | 70 | DIQMTQSPSSLSASVGDRVTITCRASQSISGWLNWYQQKPGKAPKLLIYAASSLQSGVPSRFSGSGSGTDFTLTISSLQPEDFATYYCQQSYSTPLTFGQGTKVEIK | 71 |
| PSMB55 | EVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARGLPIWYLDYWGQGTLVTVSS | 72 | EIVLTQSPATLSLSPGERATLSCRASQSVASDLAWYQQKPGQAPRLLIYFASNRATGIPARFSGSGSGTDFTLTISSLEPEDFAVYYCQQSITWPFTFGQGTKVEIK | 73 |
| PSMB51 | QVQLVQSGAEVKKPGSSVKVSCKASGGTFSSYAISWVRQAPGQGLEWMGWIIPYNGNANYAQKFQGRVTITADESTSTAYMELSSLRSEDTAVYYCARVNSAALVWERLDYWGQGTLVTVSS | 74 | DIQMTQSPSSLSASVGDRVTITCRASQSIDRWLNWYQQKPGKAPKLLIYAASSLQSGVPSRFSGSGSGTDFTLTISSLQPEDFATYYCQQSPRYPLTFGQGTKVEIK | 61 |
| PSMB49 | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARASRVWHASYGYLDYWGQGTLVTVSS | 75 | EIVLTQSPATLSLSPGERATLSCRASQSVSKWLAWYQQKPGQAPRLLIYDASNRATGIPARFSGSGSGTDFTLTISSLEPEDFAVYYCQQRFTAPWTFGQGTKVEIK | 76 |
| PSMB25 | EVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARGWAYDRGLDYWGQGTLVTVSS | 77 | DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQYYSTPLTFGQGTKVEIK | 78 |

TABLE 6-continued

VH and VL sequences of PSMA Fabs

| FAB ID | VH Amino acid sequence | SEQ ID NO | VL Amino Acid Sequence | SEQ ID NO |
|---|---|---|---|---|
| PSMB18 | EVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARAYHYSKGLDYWGQGTLVTVSS | 79 | DIVMTQSPDSLAVSLGERATINCKSSQSVLYSSNNKYLAWYQQKPGQPPKLLIYWASTRESGVPDRFSGSGSGTDFTLTISSLQAEDVAVYYCQQYYSTPLTFGQGTKVEIK | 78 |

TABLE 7

Heavy and Light chain sequences of Mabs with corresponding SEQ ID NOs

| mAb ID | Heavy Chain Amino acid sequence | SEQ ID NO | Light Chain Amino Acid Sequence | SEQ ID NO |
|---|---|---|---|---|
| PSMB129 (FAB PSMB109) | QVQLVQSGAEVKKPGSSVKVSCKASGGTFSSYAISWVRQAPGQGLEWMGWISPYNGNANYAQKFQGRVTITADESTSTAYMELSSLRSEDTAVYYCARVNSAALVWERLDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK | 82 | DIQMTQSPSSLSASVGDRVTITCRASQSIDRWLNWYQQKPGKAPKLLIYAASSLQSGVPSRFSGSGSGTDFTLTISSLQPEDFATYYCQQSPRYPLTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 83 |
| PSMB130 (FAB PSMB86) | QVQLVQSGAEVKKPGSSVKVSCKASGGTFKSYDISWVRQAPGQGLEWMGGIIPIEGTANYAQKFQGRVTITADESTSTAYMELSSLRSEDTAVYYCARDYPAGYGFDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK | 84 | EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPLTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 85 |
| PSMB128 (FAB PSMB84) | EVQLLESGGGLVQPGGSLRLSCAASGFTFDSDWMSWVRQAPGKGLEWVSAISGNGGSTEYADSVKGRFTISRDNSKNTLYLQMNSLRAEDTAVYYCARDPYYYYDGDSYYGMDVWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGS | 86 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 87 |

TABLE 7-continued

Heavy and Light chain sequences of Mabs with corresponding SEQ ID NOs

| mAb ID | Heavy Chain Amino acid sequence | SEQ ID NO | Light Chain Amino Acid Sequence | SEQ ID NO |
|---|---|---|---|---|
| | FFLYSRLTVDKSRWQEGNVFSCSV<br>MHEALHNHYTQKSLSLSLGK | | | |
| PSMB127<br>(FAB<br>PSMB83) | EVQLLESGGGLVQPGGSLRLSCAA<br>SCFTFKSDAMHWVRQAPGKGLEWV<br>SEISGSGGYTNYADSVKGRFTISR<br>DNSKNTLYLQMNSLRAEDTAVYYC<br>ARDSYDSSLYVGDYFDYWGQGTLV<br>TVSSASTKGPSVFPLAPCSRSTSE<br>STAALGCLVKDYFPEPVTVSWNSG<br>ALTSGVHTFPAVLQSSGLYSLSSV<br>VTVPSSLGTKTYTCNVDHKPSNT<br>KVDKRVESKYGPPCPPCPAPEAAG<br>GPSVFLFPPKPKDTLMISRTPEVT<br>CVVVDVSQEDPEVQFNWYVDGVEV<br>HNAKTKPREEQFNSTYRVVSVLTV<br>LHQDWLNGKEYKCKVSNKGLPSSI<br>EKTISKAKGQPREPQVYTLPPSQE<br>EMTKNQVSLTCLVKGFYPSDIAVE<br>WESNGQPENNYKTTPPVLDSDGSF<br>FLYSRLTVDKSRWQEGNVFSCSVM<br>HEALHNHYTQKSLSLSLGK | 88 | EIVLTQSPATLSLSPGERATLS<br>CRASQSVSSYLAWYQQKPGQAP<br>RLLIYDASNRATGIPARFSGSG<br>SGTDFTLTISSLEPEDFAVYYC<br>QQRSNWPLTFGQGTKVEIKRTV<br>AAPSVFIFPPSDEQLKSGTASV<br>VCLLNNFYPREAKVQWKVDNAL<br>QSGNSQESVTEQDSKDSTYSLS<br>STLTLSKADYEKHKVYACEVTH<br>QGLSSPVTKSFNRGEC | 89 |
| PSMB127<br>DNA | atggcttgggtgtggaccttgc<br>tattcctgatggcagctgccca<br>aagtatacaggccgaggttcag<br>ctgctggaatctggcggaggat<br>tggttcagcctggcggctctct<br>gagactgtcttgtgccgcttct<br>ggcttcaccttcaagtccgacg<br>ctatgcactgggtccgacaggc<br>ccctggaaaaggactggaatgg<br>gtgtccgagatctctggctctg<br>gcggctacaccaactacgccga<br>ctccatgaagtcccggttcacc<br>atctctcgggacaactccaaga<br>acaccctgtacctgcagatgaa<br>ctccctgagagccgaggacacc<br>gccgtgtactactgcgccgagag<br>actcctacgactccagcctgta<br>cgtgggcgactacttagattat<br>tggggccagggcaccctggtca<br>ccgtttcttctgcttccaccaa<br>gggcccatccgtcttccccctg<br>gcgcctgctccaggagcacct<br>ccgagagcacagccgccctggg<br>ctgcctggtcaaggactacttc<br>cccgaaccggtgacggtgtcgt<br>ggaactcaggcgccctgaccag<br>cggcgtgcacaccttcccggct<br>gtcctacagtcctcaggactct<br>actccctcagcagcgtggtgac<br>cgtgccctccagcagcttgggc<br>acgaaaacctacacctgcaacg<br>tagatcacaagcccagcaacac<br>caaggtggacaagagagttgag<br>tccaaatatggtccccatgcc<br>caccatgcccagcacctgaggc<br>cgccgggggaccatcagtcttc<br>ctgttccccccaaaacccaagg<br>acactctcatgatctcccggac<br>ccctgaggtcacgtgcgtggtg<br>gtggacgtgagccaggaagacc<br>ccgaggtccagttcaactggta<br>cgtggatggcgtggaggtgcat<br>aatgccaagacaaagccgcggg<br>aggagcagttcaacagcacgta<br>ccgtgtggtcagcgtcctcacc<br>gtcctgcaccaggactggctga<br>acggcaaggagtacaagtgcaa<br>ggtctccaacaaaggcctcccg<br>tcctccatcgagaaaaccatct<br>ccaaagccaaagggcagccccg | 161 | atggcctgggtgtggaccct<br>gctgttcctgatggccgccg<br>cccagagcatccaggccgag<br>atcgtgctgacccagagccc<br>cgccaccctgagcctgagcc<br>ccggcgagcgggccaccctg<br>agctgccgggccagcagag<br>cgtgagcagctacctggcct<br>ggtaccagcagaagcccggc<br>caggccccccggctgctgat<br>ctacgacgccagcaaccggg<br>ccaccggcatccccgcccgg<br>ttcagcggcagcggcagcgg<br>caccgacttcaccctgacca<br>tcagcagcctggagcccgag<br>gacttcgccgtgtactactg<br>ccagcagcggagcaactggc<br>ccctgaccttcggccagggc<br>accaaggtggagatcaagcg<br>tacggtggctgcaccatctg<br>tcttcatcttcccgccatct<br>gatgagcagttgaaatctgg<br>aactgcctctgttgtgtgcc<br>tgctgaataacttctatccc<br>agagaggccaaagtacagtg<br>gaaggtggataacgccctcc<br>aatcgggtaactcccaggag<br>agtgtcacagagcaggacag<br>caaggacagcacctacagcc<br>tcagcagcaccctgacgctg<br>agcaaagcagactacgagaa<br>acacaaagtctacgcctgcg<br>aagtcacccatcagggcctg<br>agctcgcccgtcacaaagag<br>cttcaacaggggagagtgt | 162 |

TABLE 7-continued

Heavy and Light chain sequences of Mabs with corresponding SEQ ID NOs

| mAb ID | Heavy Chain Amino acid sequence | SEQ ID NO | Light Chain Amino Acid Sequence | SEQ ID NO |
|---|---|---|---|---|
| | agagccacaggtgtacaccctg ccccccatcccaggaggagatga ccaagaaccaggtcagcctgac ctgcctggtcaaaggcttctac cccagcgacatcgccgtggagt gggagagcaatgggcagccga gaacaactacaagaccacgcct cccgtgctggactccgacggct ccttcttcctctacagcaggct aaccgtggacaagagcaggtgg caggaggggaatgtcttctcat gctccgtgatgcatgaggctct gcacaaccactacacacagaag agcctctccctgtctctgggta aa | | | |
| PSMB126 (FAB PSMB80) | QVQLVQSGAEVKKPGSSVKVSCKA SGGTFDDYAISWVRQAPGQGLEWM GRIDPIEGTANYAQKFQGRVITA DESTSTAYMELSSLRSEDTAVYYC ARDRYYYDGVYWYSDYFDYWGQGT LVTVSSASTKGPSVFPLAPCSRST SESTAALGCLVKDYFPEPVTVSWN SGALTSGVHTFPAVLQSSGLYSLS SVVTVPSSSLGTKTYTCNVDHKPS NTKVDKRVESKYGPPCPPCPAPEA AGGPSVFLFPPKPKDTLMISRTPE VTCVVVDVSQEDPEVQFNWYVDGV EVHNAKTKPREEQFNSTYRVVSVL TVLHQDWLNGKEYKCKVSNRGLPS SIERTISKAKGQPREPQVYTLPPS QEEMTKNQVSLTCLVKGFYPSDIA VEWESNEQPENNYKTTPPVLDSDG SFELYSRLTVDKSRWQEGNVFSCS VMHEALHNHYTQKSLSLSLGK | 90 | DIQMTQSPSSLSASVGDRVTIT CRASQSISSYLNWYQQKPGKAP KLLIYAASSLQSGVPSRESGSG SGTDFTLTISSLQPEDFATYYC QQSYSTPLTFGQGTKVEIKRTV AAPSVFIFPPSDEQLKSGTASV VCLLNNFYPREAKVQWKVDNAL QSGNSQESVTEQDSKDSTYSLS STLTLSKADYEKHKVYACEVTH QGLSSPVTKSFNRGEC | 91 |
| PSMB124 (FAB PSMB56) | QVQLVQSGAEVKKPGSSVKVSCKA SGGTFSSYAISWVRQAPGQGLEWM GWISPYNGNANYAQKFQGRVTITA DESTSTAYMELSSLRSEDTAVYYC ARDSDRSYNLDYWGQGTLVTVSSA STKGPSVFPLAPCSRSTSESTAAL GCLVKDYFPEPVTVSWNSGALTSG VHTFPAVLQSSGLYSLSSVVTVPS SSLGTKTYTCNVDHKPSNTKVDKR VESKYGPPCPPCPAPEAAGGPSVF LFPPKPKDTLMISPTPEVTCVVVD VSQEDPEVQFNWYVDEVEVHNAKT KPREEQFNSTYRVVSVLTVLHQDW LNGKEYKCKVSNKGLPSSIEKTIS KAKGQPREPQVYTLPPSQEEMTKN QVSLTCLVKGFYPSDIAVEWESNG QPENNYKTTPPVLDSDGSFFLYSR LTVDKSRWQEGNVFSCSVMHEALH NHYTQRSLSLSLGK | 92 | DIQMTQSPSSLSASVGDRVTIT CRASQSISGWLNWYQQKPGKAP KLLIYAASSLQSGVPSRFSGSG SGTDFTLTISSLQPEDFATYYC QQSYSTPLTFGQGTKVEIKRTV AAPSVFIFPPSDEQLKSGTASV VCLLNNFYPREAKVQWKVDNAL QSGNSQESVTEQDSKDSTYSLS STLTLSKADYEKHKVYACEVTH QGLSSPVTKSFNRGEC | 93 |
| PSMB123 (FAB PSMB55) | EVQLVQSGAEVKKPGESLKISCKG SGYSFTSYWIGWVRQMPGKGLEWM GIIYPGDSDTRYSPSFQGQVTISA DKSISTAYLQWSSLKASDTAMYYC ARGLPIWYLDYWGQGTLVTVSSAS TKGPSVFPLAPCSRSTSESTAALG CLVKDYFPEPVTVSWNSGALTSGV HTFPAVLQSSGLYSLSSVVTVPSS SLGTKTYTCNVDHKPSNTKVDKRV ESKYGPPCPPCPAPEAAGGPSVFL FPPKPKDTLMISRTPEVTCVVVDV SQEDPEVQFNWYVDGVEVHNAKTK PREEQFNSTYRVVSVLTVLHQDWL NGKEYKCKVSNKGLPSSIEKTISK AKGQPREPQVYTLPPSQEEMTKNQ VSLTCLVKGFYPSDIAVEWESNGQ PENNYKTTPPVLDSDGSFFLYSRL | 94 | EIVLTQSPATLSLSPGERATLS CRASQSVASDLAWYQQKPGQAP RLLIYFASNRATGIPARFSGSG SGTDFTLTISSLEPEDFAVYYC QQSITWPFTFGQGTKVEIKRTV AAPSVFIFPPSDEQLKSGTASV VCLLNNFYPREAKVQWKVDNAL QSGNSQESVTEQDSKDSTYSLS STLTLSKADYEKHKVYACEVTH QGLSSPVTKSFNRGEC | 95 |

TABLE 7-continued

Heavy and Light chain sequences of Mabs with corresponding SEQ ID NOs

| mAb ID | Heavy Chain Amino acid sequence | SEQ ID NO | Light Chain Amino Acid Sequence | SEQ ID NO |
|---|---|---|---|---|
| | TVDKSRWQEGNVFSCSVMHEALHN HYTQKSLSLSLGK | | | |
| PSMB122 (FAB PSMB51) | QVQLVQSGAEVKKPGSSVKVSCKA SGGTFSSYAISWVRQAPGQGLEWM GWIIPYNGNANYAQKFQGRVTITA DESTSTAYMELSSLRSEDTAVYYC ARVNSAALVWERLDYWGQGTLVTV SSASTKGPSVFPLAPCSRSTSEST AALGCLVKDYFPEPVTVSWNSGAL TSGVHTFPAVLQSSGLYSLSSVVT VPSSSLGTKTYTCNVDHKPSNTKV DKRVESKYGPPCPPCPAPEAAGGP SVFLFPPKPKDTLMISRTPEVTCV VVDVSQEDPEVQFNWYVDGVEVHN AKTKPREEQFNSTYRVVSVLTVLH QDWLNGKEYKCKVSNKGLPSSIEK TISKAKGQPREPQVYTLPPSQEEM TKNQVSLTCLVKGFYPSDIAVEWE SNGQPENNYKTTPPVLDSDGSFFL YSRLTVDKSRWQEGNVFSCSVMHE ALHNHYTQKSLSLSLGK | 96 | DIQMTQSPSSLSASVGDRVTIT CRASQSIDRWLNWYQQKPGKAP KLLIYAASSLQSGVPSRFSGSG SGTDFTLTISSLQPEDFATYYC QQSPRYPLTFGQGTKVEIKRTV AAPSVFIFPPSDEQLKSGTASV VCLLNNFYPREAKVQWKVDNAL QSGNSQESVTEQDSKDSTYSLS STLTLSKADYEKHKVYACEVTH QGLSSPVTKSFNRGEC | 83 |
| PSMB121 (FAB PSMB49) | QVQLVQSGAEVKKPGSSVKVSCKA SGGTFSSYAISWVRQAPGQGLEWM GGIIPIFGTANYAQKFQGPVTITA DESTSTAYMELSSLRSEDTAVYYC ARASRVWHASYGYLDYWGQGTLVT VSSASTKGPSVFPLAPCSRSTSES TAALGCLVKDYFPEPVTVSWNSGA LTSGVHTFPAVLQSSGLYSLSSVV TVPSSSLGTKTYTCNVDHKPSNTK VDKRVESKYGPPCPPCPAPEAAGG PSVFLFPPKPKDTLMISRTPEVTC VVVDVSQEDPEVQFNWYVDGVEVH NAKTKPREEQFNSTYRVVSVLTVL HQDWLNGKEYKCKVSNKGLPSSIE KTISKAKGQPREPQVYTLPPSQEE MTKNQVSLTCLVKGFYPSDIAVEW ESNGQPENNYKTTPPVLDSDGSFF LYSRLTVDKSRWQEGNVFSCSVMH EALHNHYTQKSLSLSLGK | 97 | EIVLTQSPATLSLSPGERATLS CRASQSVSKWLAWYQQKPGQAP RLLIYDASNRATGIPARFSGSG SGTDFTLTISSLEPEDFAVYYC QQRFTAPWTFGQGTKVEIKRTV AAPSVFIFPPSDEQLKSGTASV VCLLNNFYPREAKVQWKVDNAL QSGNSQESVTEQDSKDSTYSLS STLTLSKADYEKHKVYACEVTH QGLSSPVTKSFNRGEC | 98 |
| PSMB120 (FAB PSMB25) | EVQLVQSGAEVKKPGESLKISCKG SGYSFTSYWIGWVRQMPGKGLEWM GIIYPGDSDTRYSPSFQGQVTISA DKSISTAYLQWSSLKASDTAMYYC ARGWAYDRGLDYWGQGTLVTVSSA STKGPSVFPLAPCSRSTSESTAAL GCLVKDYFPEPVTVSWNSGALTSG VHTFPAVLQSSGLYSLSSVVTVPS SSLGTKTYTCNVDHKPSNTKVDKR VESKYGPPCPPCPAPEAAGGPSVF LFPPKPKDTLMISRTPEVTCVVVD VSQEDPEVQFNWYVDGVEVHNAKT NPREEQFNSTYRVVSVLTVLHQDW LNGKEYKCKVSNKGLPSSIEKTIS KAKGQPREPQVYTLPPSQEEMTKN QVSLTCLVKGFYPSDIAVEWESNG QPENNYKTTPPVLDSDGSFFLYSR LTVDKSRWQEGNVFSCSVMHEALH NHYTQKSLSLSLGK | 99 | DIVMTQSPDSLAVSLGERATIN CKSSQSVLYSSNNKNYLAWYQQ KPGQPPKLLIYWASTRESGVPD RFSGSGSGTDFTLTISSLQAED VAVYYCQQYYSTPLTFGQGTKV EIKRTVAAPSVFIFPPSDEQLK SGTASVVCLLNNFYPREAKVQW KVDNALQSGNSQESVTEQDSKD STYSLSSTLTLSKADYEKHKVY ACEVTHQGLSSPVTKSFNRGEC | 100 |
| PSMB119 (FAB PSMB18) | EVQLVQSGAEVKKPGESLKISCKG SGYSFTSYWIGWVRQMPGKGLEWM GIIYPGDSDTRYSPSFQGQVTISA DKSISTAYLQWSSLKASDTAMYYC ARAYHYSKGLDYWGQGTLVTVSSA STKGPSVFPLAPCSRSTSESTAAL GCLVKDYFPEPVTVSWNSGALTSG VHTFPAVLQSSGLYSLSSVVTVPS SSLGTKTYTCNVDHKPSNTKVDKR VESKYGPPCPPCPAPEAAGGPSVF | 101 | DIVMTQSPDSLAVSLGERATIN CKSSQSVLYSSNNKNYLAWYQQ KPGQPPKLLIYWASTRESGVPD RFSGSGSGTDFTLTISSLQAED VAVYYCQQYYSTPLTFGQGTKV EIKRTVAAPSVFIFPPSDEQLK SGTASVVCLLNNFYPREAKVQW KVDNALQSGNSQESVTEQDSKD STYSLSSTLTLSKADYEKHKVY ACEVTHQGLSSPVTKSFNRGEC | 100 |

TABLE 7-continued

Heavy and Light chain sequences of Mabs with corresponding SEQ ID NOs

| mAb ID | Heavy Chain Amino acid sequence | SEQ ID NO | Light Chain Amino Acid Sequence | SEQ ID NO |
|---|---|---|---|---|
| | LFPPKPKDTLMISRTPEVTCVVVD<br>VSQEDPEVQFNWYVDGVEVHNAKT<br>KPREEQFNSTYRVVSVLTVLHQDW<br>LNGKEYKCKVSNKGLPSSIEKTIS<br>KAKGQPREPQVYTLPPSQEEMTKN<br>QVSLTCLVKGFYPSDIAVEWESNG<br>QPENNYKTTPPVLDSDGSFFLYSR<br>LTVDKSRWQEGNVFSCSVMHEALH<br>NHYTQKSLSLSLGK | | | |
| PSMB87<br>(FAB<br>PSMB58) | EVQLVQSGAEVKKPGESLKISCKG<br>SGYSFTSYWISWVRQMPGKGLEWM<br>GIIYPGDSYTRYSPSFQGQVTISA<br>DKSISTAYLQWSSLKASDTAMYYC<br>ARDYEWELFDSRLDYWGQGTLVTV<br>SSASTKGPSVFPLAPCSRSTSEST<br>AALGCLVKDYFPEPVTVSWNSGAL<br>TSGVHTFPAVLQSSGLYSLSSVVT<br>VPSSSLGTKTYTCNVDHKPSNTKV<br>DKRVESKYGPPCPPCPAPEAAGGP<br>SVFLFPPKPKDTLMISRTPEVTCV<br>VVDVSQEDPEVQFNWYVDGVEVHN<br>AKTKPREEQFNSTYRVVSVLTVLH<br>QDWLNGKEYKCKVSNKGLPSSIEK<br>TISKAKGQPREPQVYTLPPSQEEM<br>TKNQVSLTCLVKGFYPSDIAVEWE<br>SNGQPENNYKTTPPVLDSDGSFFL<br>YSRLTVDKSRWQEGNVFSCSVMHE<br>ALHNHYTQKSLSLSLGK | 125 | DIQMTQSPSSLSASVGDRVTIT<br>CRASQSISSYLNWYQQKPGKAP<br>KLLIYAASSLQSGVPSRFSGSG<br>SGTDFTLTISSLQPEDFATYYC<br>QQSYSTPLTFGQGTKVEIKRTV<br>AAPSVFIFPPSDEQLKSGTASV<br>VCLLNNFYPREAKVQWKVDNAL<br>QSGNSQESVTEQDSKDSTYSLS<br>STLTLSKADYEKHKVYACEVTH<br>QGLSSPVTKSFNRGEC | 91 |

The interactions of parent PSMA mAbs PSMB123 (Fab PSMB55), PSMB127 (Fab PSMB83), and PSMB130 (Fab PSMB86) with human, chimp, and cyno PSMA ECDs were measured by Surface Plasmon Resonance (SPR) using a ProteOn XPR36 system (BioRad) as described previously for recombinant chimp PSMA ECD. The summary of binding affinities for each of these mabs to human, chimp, and cyno PSMA ECD are shown in Table 18. These mAbs bind targets with similar affinities to the bispecific antibodies.

TABLE 18

Binding of monoclonal antibodies to recombinant human, chimp, and cyno PSMA ECD by Proteon

| | Human KD (nM) | Chimp KD (nM) | Cyno KD (nM) |
|---|---|---|---|
| PSMB123 (Fab PSMB55) | 9.03 ± 1.20 | 14.3 ± 3.33 | 66.7 ± 8.60 |
| PSMB127 (Fab PSMB83) | 12.0 ± 2.05 | 12.8 ± 1.83 | 6.68 ± 0.45 |
| PSMB130 (Fab PSMB86) | 29.6 ± 2.43 | 31.7 ± 7.48 | >300 |

Example 3: Human Framework Adaptation of Anti-CD3 Antibody SP34

Anti-CD3 murine antibody SP34 was humanized by the Human Framework Adaptation method (Fransson, et al, JMB, 2010 398(2):214-31). The VH and VL sequences of SP34 are shown below and in FIG. 4, with residues 1-215 of the light chain and residues 1-230 of the heavy chain derived directly from the electron density map, and with residues 231-455 derived from IGHG3_MOUSE (mouse IgG3, isoform 2).

VH of SP34
(SEQ ID NO: 128)
EVKLLESGGGLVQPKGSLKLSCAASGFTFNTYAMNWVRQAPGKGLEWV

ARIRSKYNNYATYYADSVKDRFTISRDDSQSILYLQMNNLKTEDTAMYY

CVRHGNFGNSYVSWFAYWGQGTLVTVSA

VL of SP34
(SEQ ID NO: 129)
QAVVTQESALTTSPGETVTLTCRSSTGAVTTSNYANWVQEKPDHLFTGLI

GGTNKRAPGVPARFSGSLIGDKAALTITGAQTEDEAIYFCALWYSNLWVF

GGGTKLTVL

Four different heavy chains were combined with three different light chains to produce 12 humanized variants.
SP34 Humanization and Affinity Maturation
Selection of Human Germlines A matrix of four human heavy and three light variable region sequences were selected for testing. Selection of human germlines were based solely on the overall sequence similarity to SP34 in the framework region (FR). Neither the CDR sequences, nor their length or canonical structures, were considered in this selection.

The closest matches for the heavy chain are human GLs IGHV3-72 and IGHV3-73. Another GL, IGHV3-23 was selected because of its high frequency of occurrence in the human B-cell repertoire.

The closest matches for the light chain are human lambda GLs IGLV7-43 (aka 7a), IGLV7-46 (aka 7b) and IGLV1-51 (aka 1b). IGLV7-46 is virtually identical to IGLV7-43, but has an advantage of Ala at position 2, i.e. as in SP34.

Selected J-regions are the following: IGHJ1 for the heavy chain; IGLJ3 for the lambda light chain

Back Mutations

To preserve the conformation of CDR-H3, residues in several framework positions in VL, most notably positions Val38, Gly48 and Gly51 must be retained. These 'back mutations' were added into the humanization plan.

The Asn at position 57 of the heavy chain was truncated to Gly in the maturation plan to allow necessary flexibility and potentially improve stability (by reducing non-glycine related local structural strain) while not impacting binding.

There were several other considerations made in the humanization design. First, human GLs IGLV7-46 and IGLV7-43 introduce a Trp at position 59 with an unwanted oxidation potential. Two other GLs have Gly at this position, which corresponds to the mouse sequence. Therefore, Gly59 was preserved in both IGLV7-46 and IGLV7-43 variants. Finally, Ala at position 49 of VH may be essential. Also, the residue at position 99 (Val in SP34) may impact antigen binding. To test these positions, back mutations were introduced in some variants (FIG. 5)

HFA Matrix

The HFA matrix (Table 8) is composed of four variants of VH and three variants of VL (FIG. 5). For the purpose of HFA, AbM CDR definition (K. R. Abhinandan and A. C. Martin, 2008. Mol. Immunol. 45, 3832-3839) is used.

The variants for VH:

CD3H141 (SEQ ID NO: 104): EGHV3-72*01 with mouse CDRs + Gly49Ala
EVQLVESGGGLVQPGGSLRLSCAASGFTFNTYAMNWVRQAPGKGLEWVAR
IRSKYNNYATYYAASVKGRFTISRDDSKNSLYLQMNSLKTEDTAVYYCAR
HGNFGNSYVSWFAYWGQGTLVTVSS CD3H142 (SEQ ID NO: 102): IGHV3-23*01 with mouse CDRs + Ser49Ala
EVQLLESGGGLVQPGGSLRLSCAASGFTFNTYAMNWVRQAPGKGLEWVAR
IRSKYNNYATYYADSVKGRFTISRDNSKNTLYLQMNSLRAEDTAVYYCAK
HGNFGNSYVSWFAYWGQGTLVTVSS CD3H143 (SEQ ID NO: 115): IGHV3-23*01 with mouse CDRs + Ser49Ala, Ala99Val
EVQLLESGGGLVQPGGSLRLSCAASGFTFNTYAMNWVRQAPGKGLEWVAR
IRSKYNNYATYYADSVKGRFTISRDNSKNTLYLQMNSLRAEDTAVYYCVK
HGNFGNSYVSWFAYWGQGTLVTVSS CD3H144 (SEQ ID NO: 116): IGHV3-73*01 with mouse CDRs + Asn57Gly
EVQLVESGGGLVQPGGSLKLSCAASGFTFNTYAMNWVRQASGKGLEWVGR
IRSKYNGYATYYAASVKGRFTISRDDSKNTAYLQMNSLKTEDTAVYYCTR
HGNFGNSYVSWFAYWGQGTLVTVSS The variants for VL:

CD3L63 (SEQ ID NO: 103): IGLV7-46*01 with mouse CDRs + Ser49Ala
QAVVTQEPSLTVSPGGTVTLTCRSSTGAVTTSNYANWVQQKPGQAPRGLI
GGTNKRAPGRPARFSGSLLGGKAALTLSGAQPEDEAEYYCALWYSNLWVF
GGGTLKTVL CD3L64 (SEQ ID NO: 117): IGLV1-51*01 with mouse CDRs + Y38V, L48G, Y51G
QSVLTQPPSVSAAPGQKVTISCRSSTGAVTTSNYANWVQQLPGTAPKGLI
GGTNKRAPGIPDRFSGSKSGTSATLGITGLQTGDEADYYCALWYSNLWVF
GGGTLKTVL CD3L66 (SEQ ID NO: 105): IGLV7-43*01 with mouse CDRs + F38V, A48G, Y51G, W59G
QTVVTQEPSLTVSPGGTVTLTCRSSTGAVTTSNYANWVQQKPGQAPRGLI
GGTNKRAPGTPARFSGSLLGGKAALTLSGVQPFDFAEYYCALWYSNLWVF
GGGTKLTVL

TABLE 8

Matrix of CD3 Heavy and Light chains
(All were prepared with IgG1-AA Fc
containing L234A, L235A, and F405L)

|  | CD3L63 (LV7-46/W59G) SEQ ID NO: 103 | CD3L64 (LV1-51) SEQ ID NO: 117 | CD3L66 (LV7-43/W59G) SEQ ID NO: 105 |
|---|---|---|---|
| CD3H141 (HV3-72 + G49A) SEQ ID NO: 104 | CD3B143 | CD3B144 | CD3B146 |
| CD3H142 (HV3-23 + S49A) SEQ ID NO: 102 | CD3B147 | CD3B148 | CD3B150 |
| CD3H143 (HV3-23 + S49A, A99V) SEQ ID NO: 115 | CD3B151 | CD3B152 | CD3B154 |
| CD3H144 (VH3-73 with G49) SEQ ID NO: 116 | CD3B155 | CD3B156 | CD3B158 |

Amino acid sequences were back-translated to DNA and cDNA was prepared using gene synthesis techniques (U.S. Pat. Nos. 6,670,127; 6,521,427). Heavy chain (HC) variable regions were subcloned onto human IgG1-AA Fc containing L234A, L235A, and F405L mutations using an in-house expression vector with the CMV promoter using standard molecular biology techniques. Light chain (LC) variable regions were subcloned onto a human Lambda (λ) constant regions using an in-house expression vector with the CMV promoter using standard molecular biology techniques. Resulting plasmids were transfected into Expi293F cells (Invitrogen) and mAbs were expressed. Purification was by standard methods using a Protein A column (hiTrap MAb-Select SuRe column). After elution, the pools were dialyzed into D-PBS, pH 7.2. The VH and VL sequence of the antibodies are shown in Table 9.

TABLE 9

The VH and VL sequences of anti-CD3 antibodies

| mAb | HC | VH Amino Acid sequence | SEQ ID NO: | LC | VL Amino Acid sequence | SEQ ID NO: |
|---|---|---|---|---|---|---|
| CD3B1 | CD3H 143 | EVQLVESGGGLVQPG GSLRLSCAASGFTFN TYAMNWVRQAPGKGL EWVARIRSKYNNYAT YYAASVKGRFTISRD DSKNSLYLQMNSLKT EDTAVYYCARHGNFG NSYVSWFAYWGQGTL VTVSS | 104 | CD3L 63 | QAVVTQEPSLTVSP GGTVTLTCRSSTGA VTTSNYANWVQQKP GQAPRGLIGGTNKR APGTPARFSGSLLG GKAALTLSGAQPED EAEYYCALWYSNLW VFGGGTKLTVL | 103 |

TABLE 9-continued

The VH and VL sequences of anti-CD3 antibodies

| mAb | HC | VH Amino Acid sequence | SEQ ID NO: | LC | VL Amino Acid sequence | SEQ ID NO: |
|---|---|---|---|---|---|---|
| CD3B1CD3H44 | 141 | EVQLVESGGGLVQPGGSLRLSCAASGFTFNTYAMNWVRQAPGKGLEWVARIRSKYNNYATYYAASVKGRFTISRDDSKNSLYLQMNSLKTEDTAVYYCARHGNFGNSYVSWFAYWGQGTLVTVSS | 104 | CD3L64 | QSVLTQPPSVSAAPGQKVTISCRSSTGAVTTSNYANWVQQLPGTAPKGLIGGTNKRAPGIPDRFSGSKSGTSATLGITGLQTGDEADYYCALWYSNLWVFGGGTKLTVL | 117 |
| CD3B1CD3H46 | 141 | EVQLVESGGGLVQPGGSLRLSCAASGFTFNTYAMNWVRQAPGKGLEWVARIRSKYNNYATYYAASVKGRFTISRDDSKNSLYLQMNSLKTEDTAVYYCARHGNFGNSYVSWFAYWGQGTLVTVSS | 104 | CD3L66 | QTVVTQEPSLTVSPGGTVTLTCRSSTGAVTTSNYANWVQQKPGQAPRGLIGGTNKRAPGTPARFSGSLLGGKAALTLSGVQPEDEAEYYCALWYSNLWVFGGGTKLTVL | 105 |
| CD3B1CD3H47 | 142 | EVQLLESGGGLVQPGGSLRLSCAASGFTFNTYAMNWVRQAPGKGLEWVARIRSKYNNYATYYADSVKGRFTISRDNSKNTLYLQMNSLRAEDTAVYYCAKHGNFGNSYVSWFAYWGQGTLVTVSS | 102 | CD3L63 | QAVVTQEPSLTVSPGGTVTLTCRSSTGAVTTSNYANWVQQKPGQAPRGLIGGTNKRAPGTPARFSGSLLGGKAALTLSGAQPEDEAEYYGALWYSNLWVFGGGTKLTVL | 103 |
| CD3B1CD3H48 | 142 | EVQLLESGGGLVQPGGSLRLSCAASGFTFNTYAMNWVRQAPGKGLEWVARIRSKYNNYATYYADSVKGRFTISRDNSKNTLYLQMNSLRAEDTAVYYCAKHGNFGNSYVSWFAYWGQGTLVTVSS | 102 | CD3L64 | QSVLTQPPSVSAAPGQKVTISCRSSTGAVTTSNYANWVQQLPGTAPKGLIGGTNKRAPGIPDRFSGSKSGTSATLGITGLQTGDEADYYCALWYSNLWVFGGGTKLTVL | 117 |
| CD3B1CD3H50 | 142 | EVQLLESGGGLVQPGGSLRLSCAASGFTFNTYAMNWVRQAPGKGLEWVARIRSKYNNYATYYADSVKGRFTISRDNSKNTLYLQMNSLRAEDTAVYYCAKHGNFGNSYVSWFAYWGQGTLVTVSS | 102 | CD3L66 | QTVVTQEPSLTVSPGGTVTLTCRSSTGAVTTSNYANWVQQKPGQAPRGLIGGTNKRAPGTPARFSGSLLGGKAALTLSGVQPEDEAEYYCALWYSNLWVFGGGTKLTVL | 105 |
| CD3B1CD3H51 | 143 | EVQLVESGGGLVQPGGSLRLSCAASGFTFNTYAMNWVRQAPGKGLEWVARIRSKYNNYATYYADSVKGRFTISRDNSKNTLYLQMNSLRAEDTAVYYCVKHGNFGNSYVSWFAYWGQGTLVTVSS | 115 | CD3L63 | QAVVTQEPSLTVSPGGTVTLTCRSSTGAVTTSNYANWVQQKPGQAPRGLIGGTNKRAPGTPARFSGSLLGGKAALTLSGAQPEDEAEYYCALWYSNLWVFGGGTKLTVL | 103 |
| CD3B1CD3H52 | 143 | EVQLLESGGGLVQPGGSLRLSCAASGFTFNTYAMNWVRQAPGKGLEWVARIRSKYNNYATYYADSVKGRFTISRDNSKNTLYLQMNSLRAEDTAVYYCVKHGNFGNSYVSWFAYWGQGTLVTVSS | 115 | CD3L64 | QSVLTQPPSVSAAPGQKVTISCRSSTGAVTTSNYANWVQQLPGTAPKGLIGGTNKRAPGIPDRFSGSKSGTSATLGITGLQTGDEADYYCALWYSNLWVFGGGTKLTVL | 117 |
| CD3B1CD3H54 | 143 | EVQLLESGGGLVQPGGSLRLSCAASGFTFNTYAMNWVRQAPGKGLEWVARIRSKYNNYATYYADSVKGRFTISRDNSKNTLYLQMNSLRAEDTAVYYCVKHGNFGNSYVSWFAYWGQGTLVTVSS | 115 | CD3L66 | QTVVTQEPSLTVSPGGTVTLTCRSSTGAVTTSNYANWVQQKP... | 105 |
| CD3B1CD3H55 | 144 | EVQLLESGGGLVQPGGSLKLSCAASGFTFNTYAMNWVRQASGKGLEWVGRIRSKYNGYATYYAASVKGRFTISRDDSKNTAYLQMNSLKTEDTAVYYCTRHGNFGNSYVSWFAYWGQGTLVTVSS | 116 | CD3L63 | QAVVTQEPSLTVSPGGTVTLTCRSSTGAVTTSNYANWVQQKPGQAPRGLIGGTNKRAPGTPARFSGSLLGGKAALTLSGAQPEDEAEYYCALWYSNLWVFGGGTKLTVL | 103 |
| CD3B1CD3H56 | 144 | EVQLVESGGGLVQPGGSLKLSCAASGFTFNTYAMNWVRQASGKGLEWVGRIRSKYNGYATYYAASVKGRFTISRDDSKNTAYLQMNSLKTEDTAVYYCTRHGNFGNSYVSWFAYWGQGTLVTVSS | 116 | CD3L64 | QSVLTQPPSVSAAPGQKVTISCRSSTGAVTTSNYANWVQQLPGTAPKGLIGGTNKRAPGIPDRFSGSKSGTSATLGITGLQTGDEADYYCALWYSNLWVFGGGTKLTVL | 117 |
| CD3B1CD3H58 | 144 | EVQLVESGGGLVQPGGSLKLSCAASGFTFNTYAMNWVRQASGKGLEWVGRIRSKYNGYATYYAASVKGRFTISRDDSKNTAYLQMNSLKTEDTAVYYCTRHGNFGNSYVSWFAYWGQGTLVTVSS | 116 | CD3L66 | QTVVTQEPSLTVSPGGTVTLTCRSSTGAVTTSNYANWVQQKPGQAPRGLIGGTNKRAPGTPARFSGSLLGGKAALTLSGVQPEDEAEYYCALWYSNLWVFGGGTKLTVL | 105 |

Example 4: Endogenous Cell Binding of the Humanized Anti-CD3 Hits to Primary T Cells The resulting panel of anti-CD3 antibodies was tested for binding against cell-surface CD3ε on primary human T cells. To do this, binding of antibodies from expression supernatants was visualized using a polyclonal anti-human secondary antibody and analyzed by flow cytometry. Briefly, binding of anti-CD3 antibodies to cell-surface CD3ε was assessed by flow cytometry using primary Human T lymphocytes purified by negative selection (Biological Specialty, Colmar, USA). Expression supernatants or purified antibodies were normalized to 10 μg/ml in media or FACS buffer (BD BioSciences), respectively. 2×10⁵ cells were aliquoted into wells of a 96 well round-bottomed plate (CoStar) for labeling. Antibodies in expression supernatant were added to cells and incubated for 45 min at 4° C. Following centrifugation at 1300 rpm for 3 min and removal of supernatant, 50 μL of anti-human IgG (H+L) Alexa Fluor 647 secondary antibody (Life technologies Inc.) was incubated with the cells at a final concentration of 10 μg/mL for 30 min at 4° C. away from direct light. Following washing and resuspension in 30 μL FACs buffer (BD BioSciences). Sample collection was performed on an Intellicyt HTFC system using ForeCyt software. Viable single cells were gated prior to analysis of binding using the green or red fixable live/dead dyes (Life Technologies Inc.) and forward/side scatter area and height parameters, respectively. Graphs were generated in GraphPad Prism version 5 using mean fluorescence intensity values.

Figure 6:
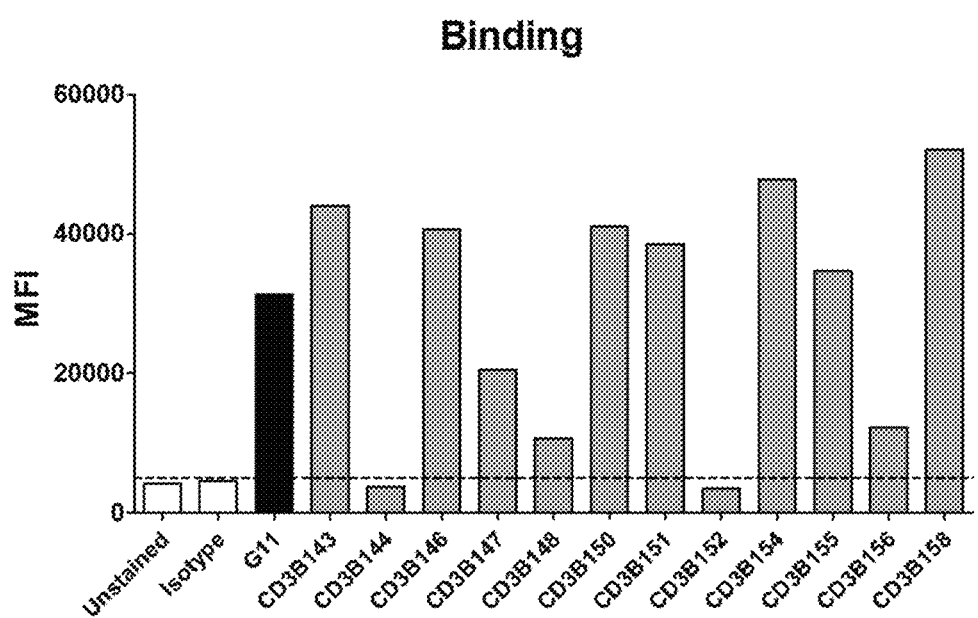
FIG. 6 shows binding of SP34 HFA variants to primary Human T cells.

Although a titration series was run, an intermediate concentration is presented in FIG. 6 for clarity. Two in-house phage-derived antibodies with the same Fc region as the therapeutic antibodies were used as controls: GI (HC SEQ ID NO: 118, LC SEQ ID NO: 119), a non-cyno cross-reactive, agonistic antibody was used as a positive control and CD3B94 (HC-SEQ ID NO: 120, LC-SEQ ID NO: 121) a non-binder/non-agonistic antibody was used to assess non-specific binding. The commercial SP34 antibody was not used as a comparator in this assay since it is a mouse antibody and the use of a different secondary detection reagent would have prohibited direct comparison with the variants tested.

The data demonstrates an array of binding potential within the panel of humanized anti-CD3 hits, with two antibodies (CD3B144, CD3B152) showing complete loss of binding to human T cells The remaining antibodies showed a range of binding potential that could be broadly split into strong and weak binders using G11 binding as an arbitrary threshold. Using these parameters, seven strong binders and seven weak binders were identified from the panel of variants (FIG. 6).

Figure 7:
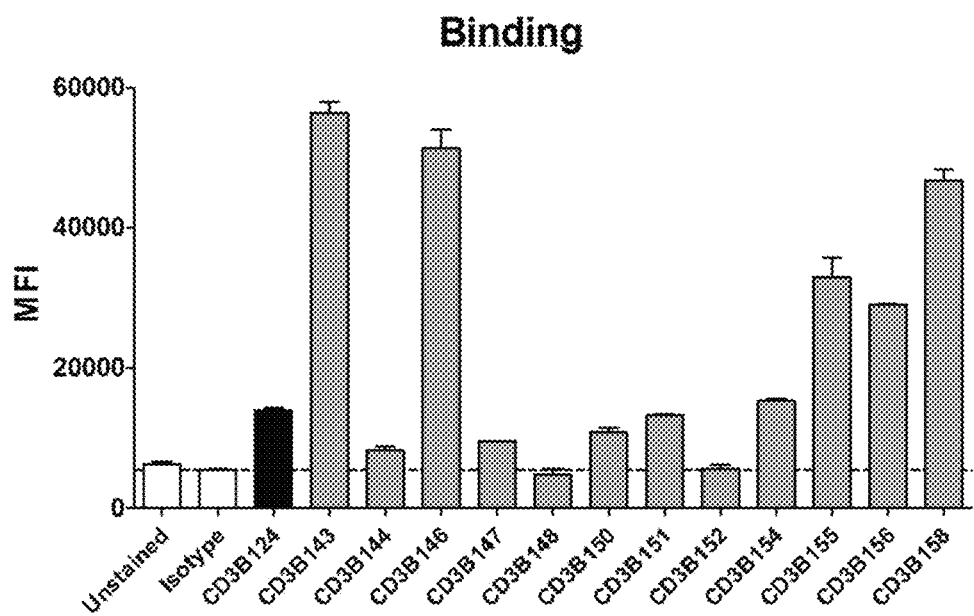
FIG. 7 shows binding of SP34 HFA variants to Cynomolgus primary T cells.

Binding analysis of the anti-CD3 hits to primary cynomolgus CD4+ T cells was then tested in order to assess the retention of cross-reactivity. Purified CD4+ T cells from the peripheral blood of cynomolgus monkeys (Zen Bio, Triangle Research Park, USA were used). Assay protocols were similar to those described above. Since G11 does not cross-react with cynomolgus CD3ε, CD3B124, an in-house chimeric SP34-derived antibody having the VH and VL of SP34 with murine framework and a human IgG1 Fc was used as a positive control in this assay (FIG. 7). Interestingly, several variants showed decreased binding potential compared to that seen with human cells. This included the strong binders CD3B50, CD3B151 and CD3B154, in which binding was reduced, and several weak binders where binding could no longer be detected over background. This loss of binding was not related to a specific immunoglobulin chain, suggesting that the combination of heavy and light chains played a role in the loss of cross-reactivity. Together, these assays allowed the identification of variants that retained species cross-reactivity between human and cynomolgus CD3ε.

Figure 8:
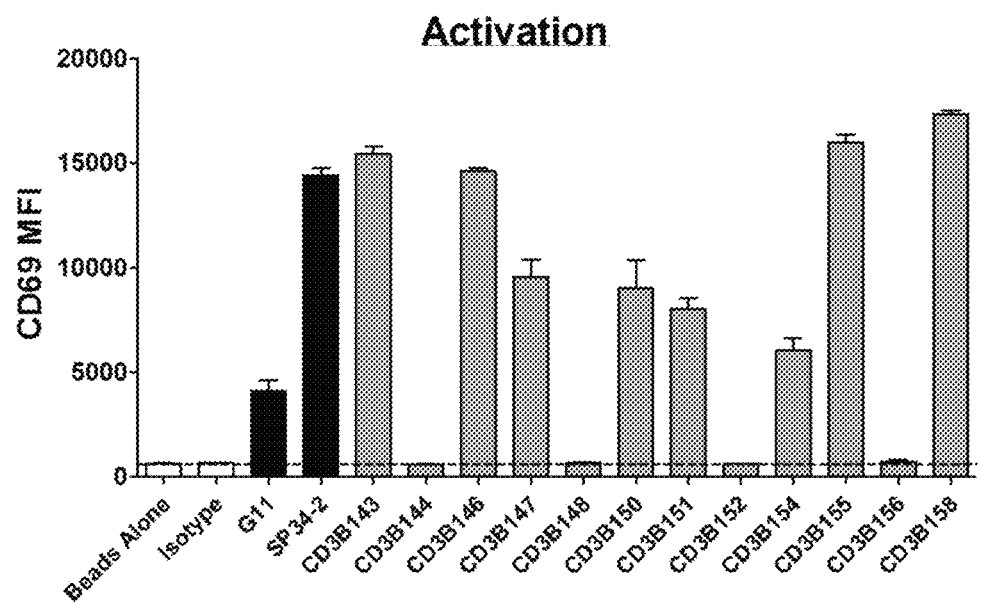
FIG. 8 shows that SP34 HFA variants activate primary human T cells in vitro. Negative controls are shown in white and positive controls are shown in black.

Example 5: Functional Analysis of the Humanized Anti-CD3 Hits in Primary T Cells Binding analysis demonstrated that the panel of humanized anti-CD3 hits showed a range of binding potential to human and cynomolgus T-cells. To investigate the capacity of each variant to induce activation via CD3ε crosslinking, primary T-cells were cultured overnight in the presence of bead-conjugated antibody. The following day, cells were harvested and labeled with an anti-CD69 antibody to measure activation (FIG. 8). Humanized anti-CD3 antibodies were bound to protein A coated magnetic beads (Sphero-Tech, Lake forest, USA) by overnight incubation with antibody at 10 μg/mL. The following day, 2×10$^5$ primary human T cells were plated in round-bottomed cell culture plates in triplicate and 2×10$^5$ coated beads were added. Following overnight culture at 37° C., cells were harvested and labeled with anti-CD69 Alexa Fluor® 488 antibody (clone FN50; Biolegend) to assess the up-regulation of this activation marker. Sample collection and analysis was performed as described above for binding. Several negative controls were run, including T-cells alone, T-cells with non-coated beads, and T-cells with isotype control (CD3B94)-coated beads. All of these showed similar mean fluorescence intensity values comparable to unstained T-cells indicating that background was low in this assay. Several positive controls were run for comparison, including OKT3 (U.S. Pat. No. 5,929,212) and commercially available SP34-2 antibody.

Figure 9:
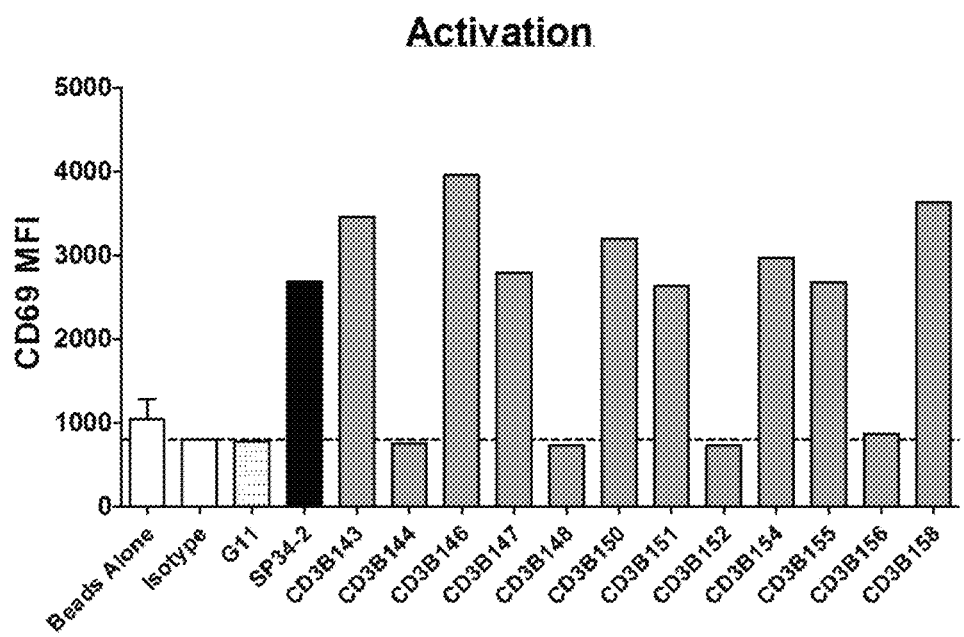
FIG. 9 shows that SP34 HFA variants activate primary cynomolgus T cells in vitro. Negative controls are shown in white and positive controls are shown in black. Non-CD3e-cross-reactive antibody G11 served as an additional negative control.

The humanized anti-CD3 hits were then tested for their capacity to activate primary cynomolgus CD4+ T cells (Zen Bio, Triangle Research Park, USA) in the same assay (FIG. 9). The FN50 anti-CD69 antibody has been described as being cross-reactive with non-human protein and could therefore be used to test activation of these cells.

Figure 10A:
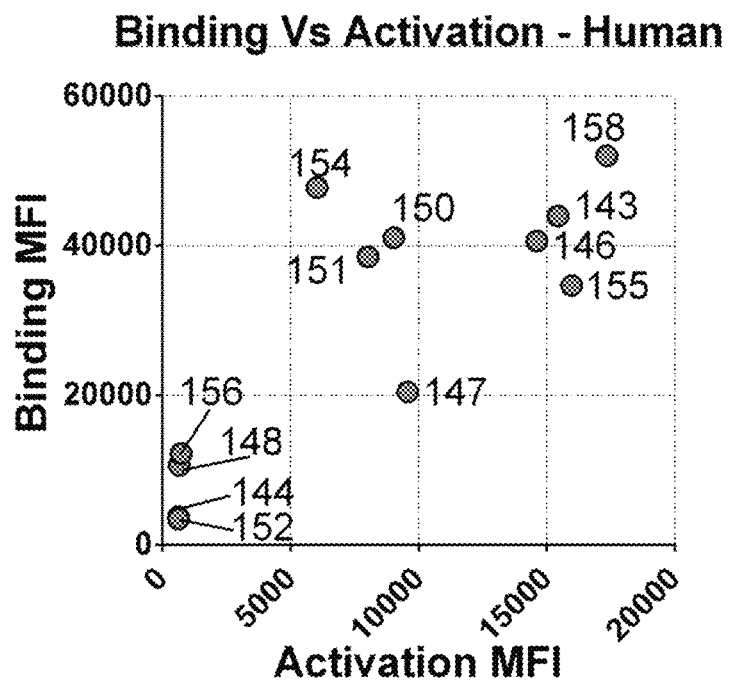
FIGS. 10A and 10B show the correlation of binding and activation by SP34 HFA variants. Average binding and CD69 Mean Fluorescence Intensity ("MFI") values for human (FIG. 10A) and cynomolgus (FIG. 10B) were plotted against each other.
Figure 10B:
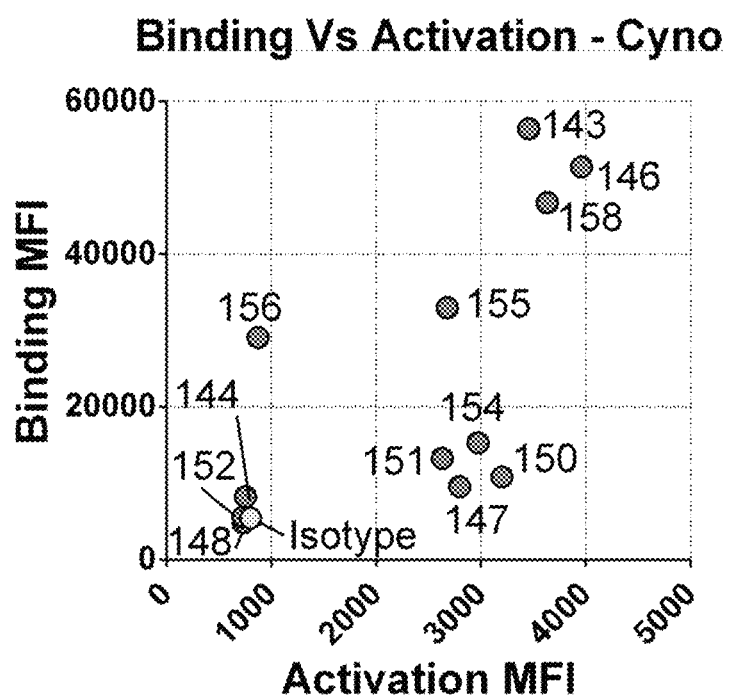
Figure 11A:
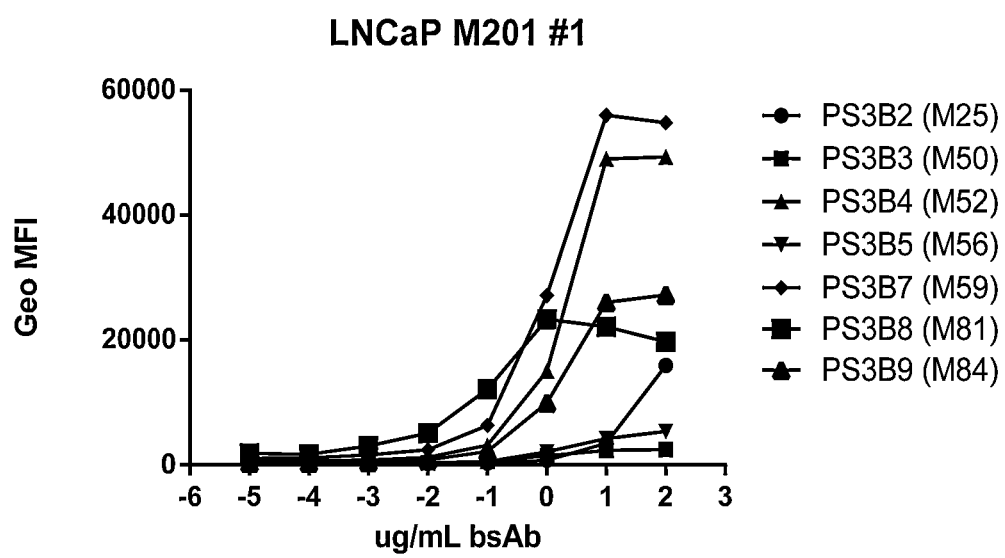
FIGS. 11A-11F show titration curves for PSMA×CD3 bispecific antibodies binding to LNCaP cells.
Figure 11B:
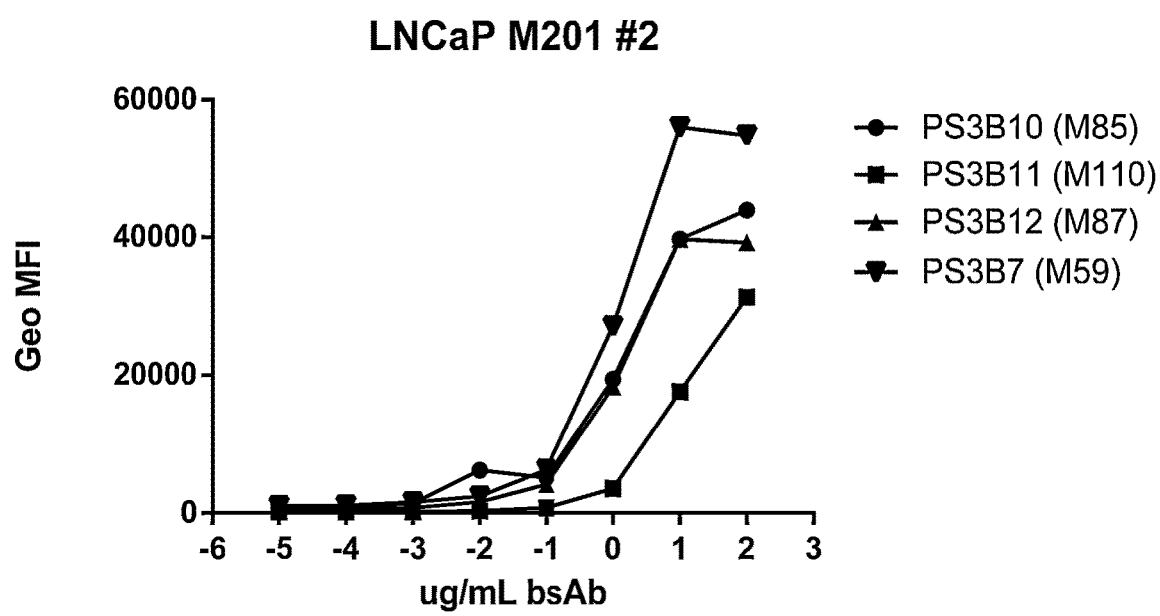
Figure 11C:
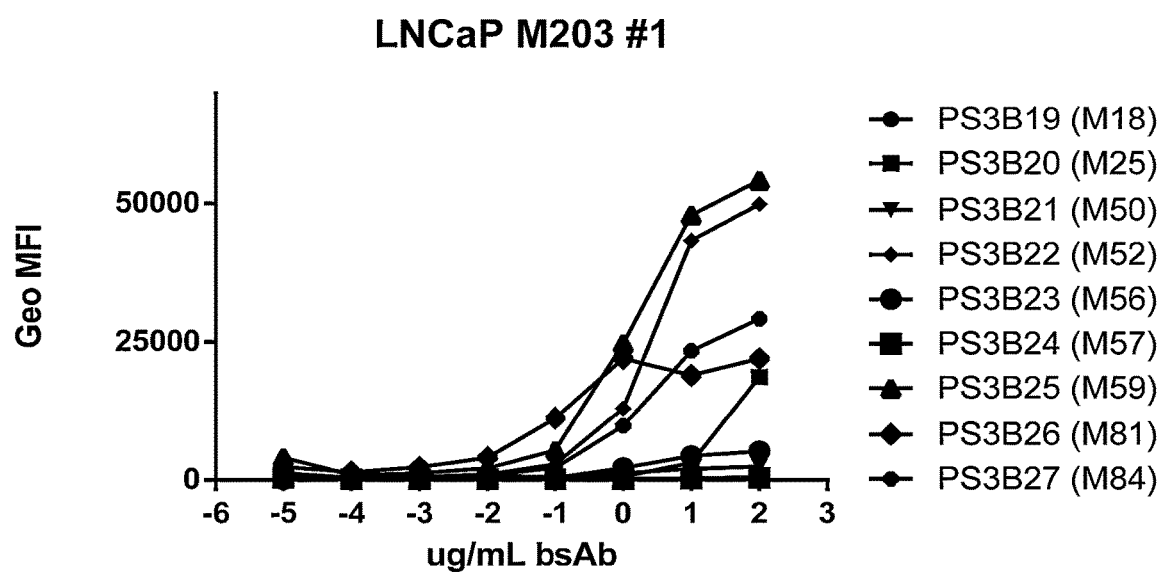
Figure 11D:
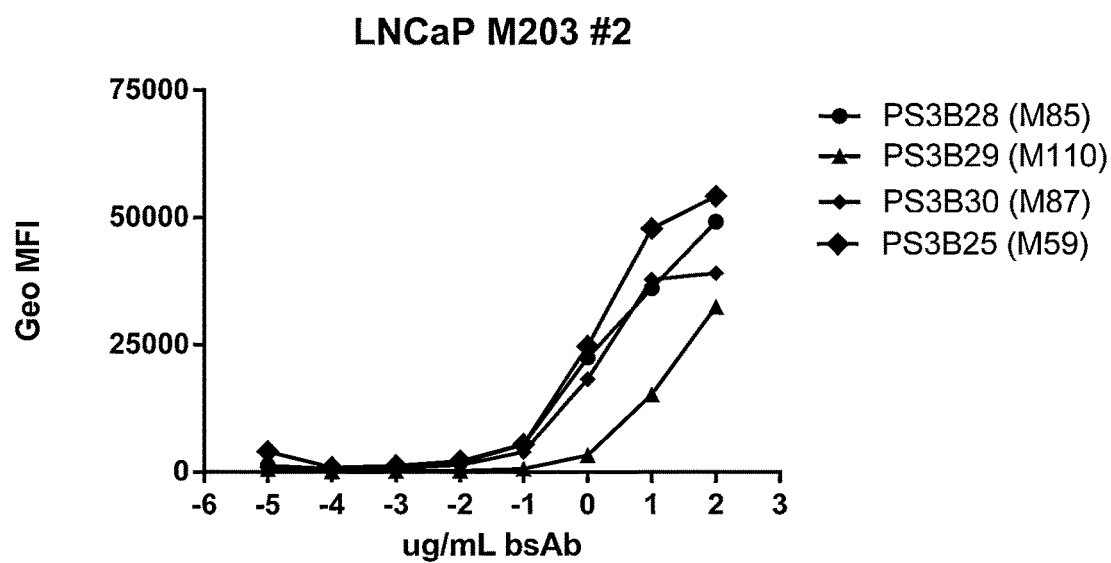
Figure 11E:
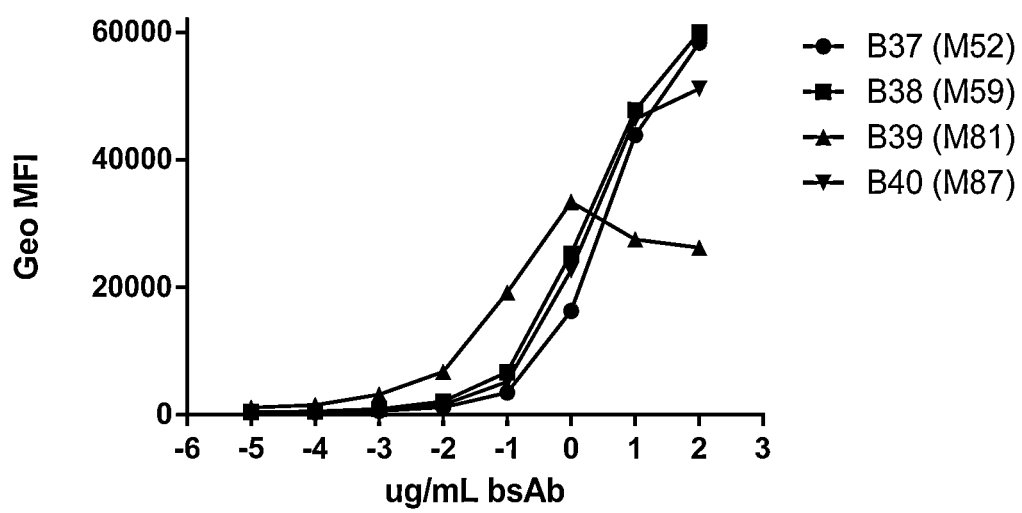
Figure 11F:
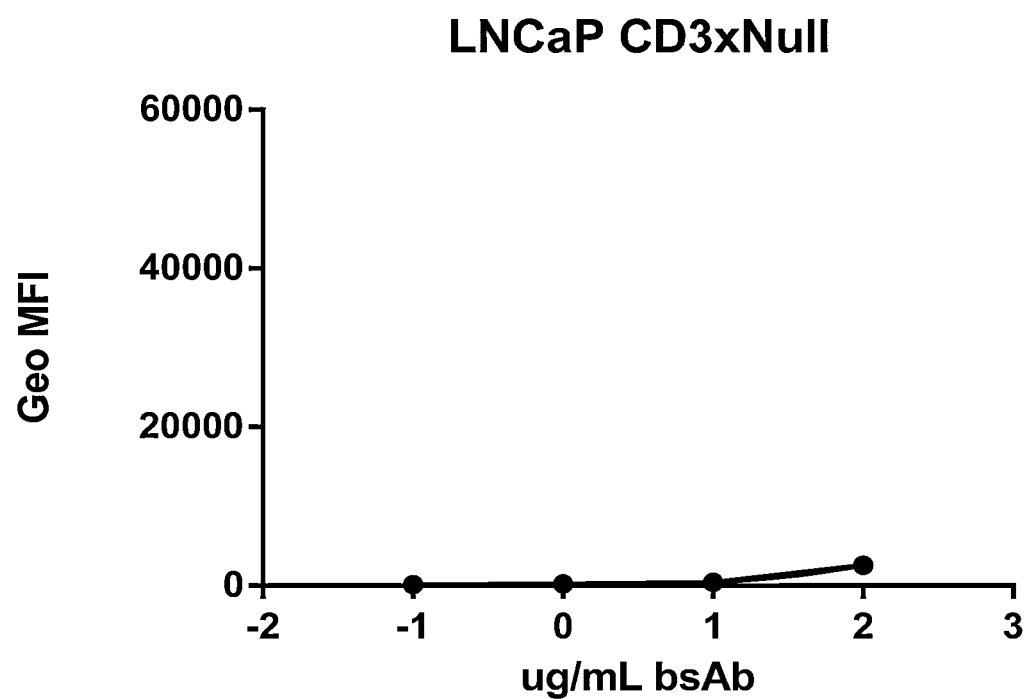

The human and cynomolgus activation data correlated with the binding data in that the panel of hits displayed a range of activation potentials. A number of the strong binders showed the capacity to activate human T-cells to an equivalent or greater extent when compared to commercially available SP34-2. Several variants showed activation potential that was lower compared SP34-2, whereas some binders did not show evidence of CD69 stimulation. The inability to activate was only seen in the variants that showed no or weak binding and all strong binders showed some level of activation, suggesting a correlation between binding and activation potentials for both human (FIG. 10A) and cynomolgus (FIG. 10B).

Two anti-CD3 antibodies, CD3B146 and CD3B147, with high and medium affinity respectively, were selected for preparation of bispecific antibodies with the PSMA specific antibodies. These two anti-CD3 antibodies were prepared in the IgG4 PAA GenMab format (Labrijn et al, 2013) where the targeting parent (PSMA) contains the 409R GenMab mutation (native amino acid for IgG4), while the killing parent (CD3) contains the F405L GenMab mutation and R409K. The monospecific anti-CD3 antibody was expressed as IgG4, having Fc substitutions S228P, F234A, L235A, F405L, and R409K (CD3 arm) (numbering according to EU index) in their Fc regions. Heavy chain (HC) variable regions were subcloned onto human IgG4-PAA Fc containing S228P, F234A, L235A, F405L, and R409K mutations using an in-house expression vector with the CMV promoter using standard molecular biology techniques. Light chain (LC) variable regions were subcloned onto a human Lambda (λ) constant regions using an in-house expression vector with the CMV promoter using standard molecular biology techniques. Resulting plasmids were transfected into Expi293F cells (Invitrogen) and mAbs were expressed. The anti-CD3 antibodies were purified using standard purification methods: a protein A column with an elution buffer of 100 mM NaAc pH3.5 and a neutralization puffer of 2M Tris pH 7.5 and 150 mM NaCl. The mabs were desalted using PD10 (Sephadex G25M) column and the pools were dialyzed into D-PBS, pH 7.2.

A monospecific anti-CD3 antibody CD3B217 was generated comprising the VH and VL regions having the VH of SEQ ID NO:102 and the VL of SEQ ID NO:103 and an IgG4 constant region with S228P, F234A, L235A, F405L, and R409K substitutions. CD3B217 comprises a heavy chain of SEQ ID NO: 108 and a light chain of SEQ ID NO:109. A monospecific anti-CD3 antibody CD3B219 was generated comprising the VH and VL regions having the VH of SEQ ID NO:104 and the VL of SEQ ID NO:105 and an IgG4 constant region with S228P, F234A, L235A, F405L, and R409K substitutions. CD3B219 comprises a heavy chain of SEQ ID NO: 110 and a light chain of SEQ ID NO:111.

Example 6. Preparation of PSMA×CD3 Bispecific Antibodies

The formation of the PSMA×CD3 Bispecific antibodies requires two parental mAbs, one specific for the targeting arm (e.g. PSMA) and one specific for the effector arm (e.g. CD3). PSMA mAbs were recombined with a medium affinity CD3B217 (VH SEQ ID NO: 102, VL SEQ ID NO:103) and a high affinity CD3B219 (VH SEQ ID NO:104, VL SEQ ID NO:105) CD3 arms. These parental mAbs are in the GenMab format (Labrijn et al, 2013) where the targeting parent (PSMA) contains the 409R GenMab mutation (native amino acid for IgG4), while the killing parent (CD3) contains the F405L GenMab mutation and R409K mutation. The monospecific anti-CD3 antibody was expressed as IgG4, having Fc substitutions S228P, F234A, L235A, F405L, and R409K (CD3 arm) (numbering according to EU index) in their Fc regions. The monospecific antibodies were expressed in HEK cell lines under CMV promoters.

The parental PSMA and CD3 antibodies were purified using a protein A column with an elution buffer of 100 mM NaAc pH3.5 and a neutralization puffer of 2M Tris pH 7.5 and 150 mM NaCl. The mabs were desalted using PD10 (Sephadex G25M) column and dialyzed into D-PBS, pH 7.2 buffer.

Post purification the parental PSMA antibodies were mixed with the desired parental CD3 antibody under reducing conditions in 75 mM cystamine-HC1 and incubated at 31° C. for 4 h. The recombination reactions were based on molar ratios, where a set amount of PSMA (eg, 10 mg, or ~67.8 nanomoles) was combined with CD3 antibody (eg, ~71.8 nanomoles), where the CD3 antibody was added in a 6% excess of the PSMA antibody. The concentrations of the PSMA antibody stocks varied from 0.8 to 6 mg/mL, and the volumes the recombination reactions varied for each pairing. The recombinations were subsequently dialyzed against PBS to remove the reductant. The bispecific antibody reactions were performed with an excess of the CD3 antibody (ratio) to minimize the amount of unreacted PSMA parental antibody remaining after recombination. Following the partial reduction of the parental mAbs, the reductant was removed via overnight dialysis into PBS.

The final bispecific antibodies produced, along with the parental mAbs (i.e. PSMA, CD3, or Null) used in the recombination reactions are listed in Table 10, with sequences listed in Tables 11 and 12.

Selected PSMA hits were also paired with a non-killing arm (Null) to create negative controls for testing purposes. For control bispecific antibodies, B2M1, an RSV antibody in the IgG4 PAA format (VH SEQ ID NO: 106, VL SEQ ID NO: 107) was generated, purified and, combined with either the CD3 arm CD3B219-F405L, R409K to generate CD3B288 (CD3×null) or PSMA arms, PSMB162, PSMB126, PSMB130 to generate PS3B37, PS3B39 and PS3B40 respectively (PSMA×null).

TABLE 10

PSMA × CD3 Bispecific antibodies generated

| Bispecific antibody | ARM 1 | SEQ ID NO: HC | LC | ARM 2 | SEQ ID NO: (VH; VL IgG4PAA F405L, R409K) HC | LC |
|---|---|---|---|---|---|---|
| PS3B2 | PSMB120 (FAB PSMB25) | 99 | 100 | CD3B217 | 108 | 109 |
| PS3B3 | PSMB121 (FAB PSMB49) | 97 | 98 | CD3B217 | 108 | 109 |

TABLE 10-continued

PSMA × CD3 Bispecific antibodies generated

| Bispecific antibody | ARM 1 | SEQ ID NO: HC | LC | ARM 2 | SEQ ID NO: (VH; VL IgG4PAA F405L, R409K) HC | LC |
|---|---|---|---|---|---|---|
| PS3B4 | PSMB122 (FAB PSMB51) | 96 | 83 | CD3B217 | 108 | 109 |
| PS3B5 | PSMB123 (FAB PSMB55) | 94 | 95 | CD3B217 | 108 | 109 |
| PS3B7 | PSMB87 (FAB PSMB58) | 125 | 91 | CD3B217 | 108 | 109 |
| PS3B8 | PSMB126 (FAB PSMB80) | 90 | 91 | CD3B217 | 108 | 109 |
| PS3B9 | PSMB127 (FAB PSMB83) | 88 | 89 | CD3B217 | 108 | 109 |
| PS3B10 | PSMB128 (FAB PSMB84) | 86 | 87 | CD3B217 | 108 | 109 |
| PS3B11 | PSMB129 (FAB PSMB109) | 82 | 83 | CD3B217 | 108 | 109 |
| PS3B12 | PSMB130 (FAB PSMB86) | 84 | 85 | CD3B217 | 108 | 109 |
| PS3B19 | PSMB119 (FAB PSMB18) | 101 | 100 | CD3B219 | 110 | 111 |
| PS3B20 | PSMB120 (FAB PSMB25) | 99 | 100 | CD3B219 | 110 | 111 |
| PS3B21 | PSMB121 (FAB PSMB49) | 97 | 98 | CD3B219 | 110 | 111 |
| PS3B22 | PSMB122 (FAB PSMB51) | 96 | 83 | CD3B219 | 110 | 111 |
| PS3B23 | PSMB123 (FAB PSMB55) | 94 | 95 | CD3B219 | 110 | 111 |
| PS3B24 | PSMB124 (FAB PSMB56) | 92 | 93 | CD3B219 | 110 | 111 |
| PS3B25 | PSMB87 (FAB PSMB58) | 125 | 91 | CD3B219 | 110 | 111 |
| PS3B26 | PSMB126 (FAB PSMB80) | 90 | 91 | CD3B219 | 110 | 111 |
| PS3B27 | PSMB127 (FAB PSMB83) | 88 | 89 | CD3B219 | 110 | 111 |
| PS3B28 | PSMB128 (FAB PSMB84) | 86 | 87 | CD3B219 | 110 | 111 |
| PS3B29 | PSMB129 (FAB PSMB109) | 82 | 83 | CD3B219 | 110 | 111 |
| PS3B30 | PSMB130 (FAB PSMB86) | 84 | 85 | CD3B219 | 110 | 111 |

A monospecific anti-CD3 antibody CD3B217 was generated comprising the VH and VL regions having the VH of SEQ ID NO:102 and the VL of SEQ ID NO:103 and an IgG4 constant region with S228P, F234A, L235A, F405L, and R409K substitutions. CD3B217 comprises a heavy chain of SEQ ID NO: 108 and a light chain of SEQ ID NO:109. A monospecific anti-CD3 antibody CD3B219 was generated comprising the VH and VL regions having the VH of SEQ ID NO:104 and the VL of SEQ ID NO:105 and an IgG4 constant region with S228P, F234A, L235A, F405L, and R409K substitutions. CD3B219 comprises a heavy chain of SEQ ID NO: 110 and a light chain of SEQ ID NO: 111. As a control, a monospecific anti-RSV antibody, derived from B21M, was generated comprising the VH and VL regions having the VH of SEQ ID NO: 106 and the VL of SEQ ID NO:107 and an IgG4 constant region with S228P, F234A, L235A, or F234A, L235A, R409K, F405L to partner as the null arm with either the CD3 or PSMA arm of a bispecific antibody.

The bispecific antibody PS3B2 comprises the CD3 binding arm of mAb CD3B217-F405L, R409K and the PSMA binding arm of mAb PSMB120. The bispecific antibody PS3B3 comprises the CD3 binding arm of mAb CD3B217-F405L, R409K and the PSMA binding arm of mAb PSMB121-R409. The bispecific antibody PS3B4 comprises the CD3 binding arm of mAb CD3B217-F405L, R409K and the PSMA binding arm of mAb PSMB122-R409. The bispecific antibody PS3B5 comprises the CD3 binding arm of mAb CD3B217-F405L, R409K and the PSMA binding arm of mAb PSMB123-R409. The bispecific antibody PS3B7 comprises the CD3 binding arm of mAb CD3B217-F405L, R409K and the PSMA binding arm of mAb PSMB58-R409. The bispecific antibody PS3B8 comprises the CD3 binding arm of mAb CD3B217-F405L, R409K and the PSMA binding arm of mAb PSMB126-R409. The bispecific antibody PS3B9 comprises the CD3 binding arm of mAb CD3B217-F405L, R409K and the PSMA binding arm of mAb PSMB127-R409. The bispecific antibody PS3B10 comprises the CD3 binding arm of mAb CD3B217-F405L, R409K and the PSMA binding arm of mAb PSMB128-R409. The bispecific antibody PS3B11 comprises the CD3 binding arm of CD3B217-F405L, R409K and the PSMA binding arm of mAb PSMB129-R409. The bispecific antibody PS3B12 comprises the CD3 binding arm of CD3B217-F405L, R409K and the PSMA binding arm of mAb PSMB130-R409.

The bispecific antibody PS3B19 comprises the CD3 binding arm of mAb CD3B219-F405L, R409K and the PSMA binding arm of mAb PSMB119-R409. The bispecific antibody PS3B20 comprises the CD3 binding arm of mAb CD3B219-F405L, R409K and the PSMA binding arm of mAb PSMB120-R409. The bispecific antibody PS3B21 comprises the CD3 binding arm of mAb CD3B219-F405L, R409K and the PSMA binding arm of mAb PSMB121-R409. The bispecific antibody PS3B22 comprises the CD3 binding arm of mAb CD3B219-F405L, R409K and the PSMA binding arm of mAb PSMB122-R409. The bispecific antibody PS3B23 comprises the CD3 binding arm of mAb CD3B219-F405L, R409K and the PSMA binding arm of mAb PSMB123-R409. The bispecific antibody PS3B24 comprises the CD3 binding arm of mAb CD3B219-F405L, R409K and the PSMA binding arm of mAb PSMB124-R409. The bispecific antibody PS3B25 comprises the CD3 binding arm of mAb CD3B219-F405L, R409K and the PSMA binding arm of mAb PSMB165-R409. The bispecific antibody PS3B26 comprises the CD3 binding arm of mAb CD3B219-F405L, R409K and the PSMA binding arm of mAb PSMB126-R409. The bispecific antibody PS3B27 comprises the CD3 binding arm of CD3B219-F405L, R409K and the PSMA binding arm of mAb PSMB127-R409. The bispecific antibody PS3B28 comprises the CD3 binding arm of CD3B219-F405L, R409K and the PSMA binding arm of mAb PSMB128-R409. The bispecific antibody PS3B29 comprises the CD3 binding arm of CD3B219-F405L, R409K and the PSMA binding arm of mAb PSMB129-R409. The bispecific antibody PS3B30 comprises the CD3 binding arm of CD3B219-F405L, R409K and the PSMA binding arm of mAb PSMB130-R409.

TABLE 11

Sequences of PSMA X CD3 bispecific antibodies

| Bispecific Ab ID | Heavy Chain Amino acid sequences: PSMA Arm CD3 Arm | SEQ ID NO | Light Chain Amino Acid Sequences: PSMA Arm CD3 Arm | SEQ ID NO |
|---|---|---|---|---|
| PS3B2 (PSMB120 X CD3B217) | EVQLVQSGAEVKKPGESLKISCK GSGYSFTSYWIGWVRQMPGKGL EWMGIIYPGDSDTRYSPSFQGQVT ISADKSISTAYLQWSSLKASDTAM YYCARGWAYDRGLDYWGQGTL VTVSSASTKGPSVFPLAPCSRSTSE STAALGCLVKDYFPEPVTVSWNS GALTSGVHTFPAVLQSSGLYSLSS VVTVPSSSLGTKTYTCNVDHKPS NTKVDKRVESKYGPPCPPCPAPE AAGGPSVFLIPPKPKDTLMISRTP EVTCVVVDVSQEDPEVQFNWYV DGVEVHNAKTKPREEQFNSTYRV VSVLTVLHQDWLNGKEYKCKVS NKGLPSSIEKTISKAKGQPREPQV YTLPPSQEEMTKNQVSLTCLVKG FYPSDIAVEWESNGQPENNYKTT PPVLDSDGSFFLYSRLTVDKSRW QEGNVFSCSVMHEALHNHYTQK SLSLSLGK | 99 | DIVMTQSPDSLAVSLGERATI NCKSSQSVINSSNNKNYLA WYQQKPGQPPKILIYWAST RESGVPDRFSGSGSGTDFTL TISSLQAEDVAVYYCQQYYS TPLTFGQGTKVEIKRTVAAP SVFIFPPSDEQLKSGTASVVC LLNNFYPREAKVQWKVDNA LQSGNSQESVTEQDSKDSTY SLSSTLTLSKADYEKHKVYA CEVTHQGLSSPVTKSFNRGE C | 100 |
| | EVQLLESGGGLVQPGGSLRLSCA ASGFTFNTYAMNWVRQAPGKGL EWVARIRSKYNNYATYYADSVK GRFTISRDNSKNTLYLQMNSLRA EDTAVYYCVKHGNFGNSYVSWF AYWGQGTLVTVSSASTKGPSVFP LAPCSRSTSESTAALGCLVKDYFP EPVTVSWNSGALTSGVHTFPAVL | 108 | QAVVTQEPSLTVSPGGTVTL TCRSSTGAVTTSNYANWVQ QKPGQAPRGLIGGTNKRAPG TPARFSGSLLGGKAATLTLSG AQPEDEAEYYCALWYSNLW VFGGGTKLTVLGQPKAAPS VTLFPPSSEELQANKATLVC LISDFYPGAVTVAWKADSSP | 109 |

TABLE 11-continued

Sequences of PSMA X CD3 bispecific antibodies

| Bispecific Ab ID | Heavy Chain Amino acid sequences: PSMA Arm CD3 Arm | SEQ ID NO | Light Chain Amino Acid Sequences: PSMA Arm CD3 Arm | SEQ ID NO |
|---|---|---|---|---|
| | QSSGLYSLSSVVTVPSSSLGTKTY TCNVDHKPSNTKVDKRVESKYGP PCPPCPAPEAAGGPSVFLFPPKPK DTLMISRTPEVTCVVVDVSQEDPE VQFNWYVDGVEVHNAKTKPREE QFNSTYRVVSVLTVLHQDWLNG KEYKCKVSNKGLPSSIEKTISKAK GQPREPQVYTLPPSQEEMTKNQV SLTCLVKGFYPSDIAVEWESNGQP ENNYKTTPPVLDSDGSFLLYSKLT VDKSRWQEGNVFSCSVMHEALH NHYTQKSLSLSLGK | | VKAGVETTTPSKQSNNKYA ASSYLSLTPEQWKSHRSYSC QVTHEGSTVEKTVAPTECS | |
| PS3B3 (PSMB121 X CD3B217) | QVQLVQSGAEVKKPGSSVKVSCK ASGGTFSSYAISWVRQAPGQGLE WMGGIIPIFGTANYAQKFQGRVTI TADESTSTAYMELSSLRSEDTAV YYCARASRVWHASYGYLDYWG QGTLVTVSSASTKGPSVFPLAPCS RSTSESTAALGCLVKDYFPEPVTV SWNSGALTSGVHTFPAVLQSSGL YSLSSVVTVPSSSLGTKTYTCNVD HKPSNTKVDKRVESKYGPPCPPC PAPEAAGGPSVFLFPPKPKDTLMI SRTPEVTCVVVDVSQEDPEVQFN WYVDGVEVHNAKTKPREEQFNS TYRVVSVLTVLHQDWLNGKEYK CKVSNKGLPSSIEKTISKAKGQPR EPQVYTLPPSQEEMTKNQVSLTC LVKGFYPSDIAVEWESNGQPENN YKTTPPVLDSDGSFFLYSRLTVDK SRWQEGNVFSCSVMHEALHNHY TQKSLSLSLGK | 97 | EIVLTQSPATLSLSPGERATL SCRASQSVSKWLAWYQQKP GQAPRLLIYDASNRATGIPA RFSGSGSGTDFTLTISSLEPE DFAVYYCQQRFTAPWTFGQ GTKVEIKRTVAAPSVFIFPPS DEQLKSGTASVVCLLNNFYP REAKVQWKVDNALQSGNS QESVTEQDSKDSTYSLSSTLT LSKADYEKHKVYACEVTHQ GLSSPVTKSENRGEC | 98 |
| | EVQLLESGGGLVQPGGSLRLSCA ASGFTFNTYAMNWVRQAPGKGL EWVARIRSKYNNYATYYADSVK GRFTISRDNSKNTLYLQMNSLRA EDTAVYYCVKHGNFGNSYVSWF AYWGQGTLVTVSSASTKGPSVFP LAPCSRSTSESTAALGCLVKDYFP EPVTVSWNSGALTSGVHTFPAVL QSSGLYSLSSVVTVPSSSLGTKTY TCNVDHKPSNTKVDKRVESKYGP PCPPCPAPEAAGGPSVFLFPPKPK DTLMISRTPEVTCVVVDVSQEDPE VQFNWYVDGVEVHNAKTKPREE QFNSTYRVVSVLTVLHQDWLNG KEYKCKVSNKGLPSSIEKTISKAK GQPREPQVYTLPPSQEEMTKNQV SLTCLVKGFYPSDIAVEWESNGQP ENNYKTTPPVLDSDGSFLLYSKLT VDKSRWQEGNVFSCSVMHEALH NHYTQKSLSLSLGK | 108 | QAVVTQFPSLTVSPGGTVTL TCRSSTGAVTTSNYANWVQ QKPGQAPRGLIGGTNKRAPG TPARFSGSLLGGKAALTLSG AQPEDEAEYYCALWYSNLW VFGGGTKLTVLGQPKAAPS VTLFPPSSEELQANKATLVC LISDFYPGAVTVAWKADSSP VKAGVETTTPSKQSNNKYA ASSYLSLTPEQWKSHRSYSC QVTHEGSTVEKTVAPTECS | 109 |
| PS3B4 (PSMB122 X CD3B217) | QVQLVQSGAEVKKPGSSVKVSCK ASGGTFSSYAISWVRQAPGQGLE WMGWIIPYNGNANYAQKFQGRV TITADESTSTAYMELSSLRSEDTA VYYCARVNSAALVWERLDYWG QGTLVTVSSASTKGPSVFPLAPCS RSTSESTAALGCLVKDYFPEPVTV SWNSGALTSGVHTFPAVLQSSGL YSLSSVVTVPSSSLGTKTYTCNVD HKPSNTKVDKRVESKYGPPCPPC PAPEAAGGPSVFLFPPKPKDTLMI SRTPEVTCVVVDVSQEDPEVQFN WYVDGVEVHNAKTKPREEQFNS TYRVVSVLTVLHQDWLNGKEYK CKVSNKGLPSSIEKTISKAKGQPR EPQVYTLPPSQEEMTKNQVSLTC LVKGFYPSDIAVEWESNGQPENN YKTTPPVLDSDGSFFLYSRLTVDK | 96 | DIQMTQSPSSLSASVGDRVTI TCRASQSIDRWLNWYQQKP GKAPKLLIYAASSLQSGVPS RFSGSGSGTDFTLTISSLQPE DFATYYCQQSPRYPLTFGQG TKVEIKRTVAAPSVFIFPPSD EQLKSGTASVVCLLNNFYPR EAKVQWKVDNALQSGNSQE SVTEQDSKDSTYSLSSTLTLS KADYEKHKVYACEVTHQGL SSPVTKSFNRGEC | 83 |

TABLE 11-continued

Sequences of PSMA X CD3 bispecific antibodies

| Bispecific Ab ID | Heavy Chain Amino acid sequences: PSMA Arm CD3 Arm | SEQ ID NO | Light Chain Amino Acid Sequences: PSMA Arm CD3 Arm | SEQ ID NO |
|---|---|---|---|---|
| | SRWQEGNVESCSVMHEALHNHY TQKSLSLSLGK | | | |
| | EVQLLESGGGLVQPGGSLRLSCA ASGFTFNTYAMNWVRQAPGKGL EWVARIRSKYNNYATYYADSVK GRFTISRDNSKNTLYLQMNSLRA EDTAVYYCVKHGNFGNSYVSWF AYWGQGTLVTVSSASTKGPSVFP LAPCSRSTSESTAALGCLVKDYFP EPVTVSWNSGALTSGVHTFPAVL QSSGLYSLSSVVTVPSSSLGTKTY TCNVDHKPSNTKVDKRVESKYGP PCPPCPAPEAAGGPSVFLFPPKPK DTLMISRTPEVTCVVVDVSQEDPE VQFNWYVDGVEVHNAKTKPREE QFNSTYRVVSVLTVLHQDWLNG KEYKCKVSNKGLPSSIEKTISKAK GQPREPQVYTLPPSQEEMTKNQV SLTCLVKGFYPSDIAVEWESNGQP ENNYKTTPPVLDSDGSFLLYSKLT VDKSRWQEGNVFSCSVMHEALH NHYTQKSLSLSLGK | 108 | QAVVTQEPSLTVSPGGTVTL TCRSSTGAVTTSNYANWVQ QKPGQAPRGLIGGINKRAPG TPARFSGSLLGGKAALTLSG AQPEDEAEYYCALWYSNLW VFGGGTKLTVLGQPKAAPS VTLFPPSSEELQANKATLVC LISDFYPGAVTVAWKADSSP VKAGVETTTPSKQSNNKYA ASSYLSLTPEQWKSHRSYSC QVTHEGSTVEKTVAPTECS | 109 |
| PS3B5 (PSMB123 X CD3B217) | EVQLVQSGAEVKKPGESLKISCK GSGYSFTSYWIGWVRQMPGKGL EWMGIIYPGDSDTRYSPSFQGQVT ISADKSISTAYLQWSSLKASDTAM YYCARGLPIWYLDYWGQGTLVT VSSASTKGPSVFPLAPCSRSTSEST AALGCLVKDYFPEPVTVSWNSGA LTSGVHTFPAVLQSSGLYSLSSVV TVPSSSLGTKTYTCNVDHKPSNT KVDKRVESKYGPPCPPCPAPEAA GGPSVFLFPPKPKDTLMISRTPEV TCVVVDVSQEDPEVQFNWYVDG VEVHNAKTKPREEQFNSTYRVVS VLTVLHQDWLNGKEYKCKVSNK GLPSSIEKTISKAKGQPREPQVYTL PPSQEEMTKNQVSLTCLVKGFYP SDIAVEWESNGQPENNYKTTPPV LDSDGSFFLYSRLTVDKSRWQEG NVFSCSVMHEALHNHYTQKSLSL SLGK | 94 | EIVLTQSPATLSLSPGERATL SCRASQSVASDLAWYQQKP GQAPRLLIYFASNRATGIPAR FSGSGSGTDFTLTISSLEPEDF AVYYCQQSITWPFTFGQGTK VEIKRTVAAPSVFIFPPSDEQ LKSGTASVVCLLNNFYPREA KVQWKVDNALQSGNSQESV TEQDSKDSTYSLSSTLTLSKA DYEKHKVYACEVTHQGLSS PVTKSFNRGEC | 95 |
| | EVQLLESGGGLVQPGGSLRLSCA ASGFTFNTYAMNWVRQAPGKGL EWVARIRSKYNNYATYYADSVK GRFTISRDNSKNTLYLQMNSLRA EDTAVYYCVKHGNFGNSYVSWF AYWGQGTLVTVSSASTKGPSVFP LAPCSRSTSESTAALGCLVKDYFP EPVTVSWNSGALTSGVHTFPAVL QSSGLYSLSSVVTVPSSSLGTKTY TCNVDHKPSNTKVDKRVESKYGP PCPPCPAPEAAGGPSVFLFPPKPK DTLMISRTPEVTCVVVDVSQEDPE VQFNWYVDGVEVHNAKTKPREE QFNSTYRVVSVLTVLHQDWLNG KEYKCKVSNKGLPSSIEKTISKAK GQPREPQVYTLPPSQEEMTKNQV SLTCLVKGFYPSDIAVEWESNGQP ENNYKTTPPVLDSDGSFLLYSKLT VDKSRWQEGNVFSCSVMHEALH NHYTQKSLSLSLGK | 108 | QAVVTQEPSLTVSPGGTVTL TCRSSTGAVTTSNYANWVQ QKPGQAPRGLIGGINKRAPG TPARFSGSLLGGKAALTLSG AQPEDEAEYYCALWYSNLW VFGGGTKLTVLGQPKAAPS VTLFPPSSEELQANKATLVC LISDFYPGAVTVAWKADSSP VKAGVETTTPSKQSNNKYA ASSYLSLTPEQWKSHRSYSC QVTHEGSTVEKTVAPTECS | 109 |
| PS3B (PSMB87 X CD3B217) | EVQLLESGGGLVQPGGSLRLSCA ASGFTFNTYAMNWVRQAPGKGL EWVARIRSKYNNYATYYADSVK GRFTISRDNSKNTLYLQMNSLRA EDTAVYYCVKHGNFGNSYVSWF AYWGQGTLVTVSSASTKGPSVFP LAPCSRSTSESTAALGCLVKDYFP | 108 | QAVVTQEPSLTVSPGGTVTL TCRSSTGAVTTSNYANWVQ QKPGQAPRGLIGGINKRAPG TPARFSGSLLGGKAALTLSG AQPEDEAEYYCALWYSNLW VFGGGTKLTVLGQPKAAPS VTLFPPSSEELQANKATLVC | 109 |

TABLE 11-continued

Sequences of PSMA X CD3 bispecific antibodies

| Bispecific Ab ID | PSMA Arm CD3 Arm | Heavy Chain Amino acid sequences: | SEQ ID NO | Light Chain Amino Acid Sequences: PSMA Arm CD3 Arm | SEQ ID NO |
|---|---|---|---|---|---|
| | | EPVTVSWNSGALTSGVHTFPAVL QSSGLYSLSSVVTVPSSSLGTKTY TCNVDHKPSNTKVDKRVESKYGP PCPPCPAPEAAGGPSVFLFPPKPK DTLMISRTPEVTCVVVDVSQEDPE VQFNWYVDGVEVHNAKTKPREE QFNSTYRVVSVLTVLHQDWLNG KEYKCKVSNKGLPSSIEKTISKAK GQPREPQVYTLPPSQEEMTKNQV SLTCLVKGFYPSDIAVEWESNGQP ENNYKTTPPVLDSDGSFLLYSKLT VDKSRWQEGNVFSCSVMHEALH NHYTQKSLSLSLGK | | LISDFYPGAVTVAWKADSSP VKAGVETTTPSKQSNNKYA ASSYLSLTPEQWKSHRSYSC QVTHEGSTVEKTVAPTECS | |
| | | EVQLVQSGAEVKKPGESLKISCK GSGYSFTSYWISWVRQMPGKGLE WMGIIYPGDSYTRYSTSFQGQVTI SADKSISTAYLQWSSLKASDTAM YYCARDYEWELFDSRLDYWGQG TLVTVSSASTKGPSVFPLAPCSRS TSESTAALGCLVKDYFPEPVTVS WNSGALTSGVHTFPAVLQSSGLY SLSSVVTVPSSSLGTKTYTCNVDH KPSNTKVDKRVESKYGPPCPPCP APEAAGGPSVFLFPPKPKDTLMIS RTPEVTCVVVDVSQEDPEVQFNW YVDGVEVHNAKTKPREEQFNSTY RVVSVLTVLHQDWLNGKEYKCK VSNKGLPSSIEKTISKAKGQPREP QVYTLPPSQEEMTKNQVSLTCLV KGFYPSDIAVEWESNGQPENNYK TTPPVLDSDGSFFLYSRLTVDKSR WQEGNVFSCSVMHEALHNHYTQ KSLSLSLGK | 125 | DIQMTQSPSSLSASVGDRVTI TCRASQSISSYLNWYQQKPG KAPKLLIYAASSLQSGVPSRF SGSGSGTDFTLTISSLQPEDF ATYYCQQSYSTPLTFGQGTK VEIKRTVAAPSVFIFPPSDEQ LKSGTASVVCLLNNFYPREA KVQWKVDNALQSGNSQESV TEQDSKDSTYSLSSTLTLSKA DYEKHKVYACEVTHQGLSS PVTKSFNRGEC | 91 |
| PS3B8 (PSMB126 X CD3B217) | | QVQLVQSGAEVKKPGSSVKVSCK ASGGTFDDYAISWVRQAPGQGLE WMGRIDPIEGTANYAQKFQGRVT ITADESTSTAYMELSSERSEDTAV YYCARDRYYYDGVYWYSDYFD YWGQGTLVTVSSASTKGPSCFPP APCSRSTSESTAALGCLVKDYFPE PVTVSWNSGALTSGVHTFPAVLQ SSGLYSLSSVVTVPSSSLGTKTYT CNVDHKPSNTKVDKRVESKYGPP CPPCPAPEAAGGPSVFLFPPKPKD TLMISRTPEVTCVVVDVSQEDPEV QFNWYVDGVEVHNAKTKPREEQ FNSTYRVVSVLTVLHQDWENGK EYKCKVSNKGLPSSIEKTISKAKG QPREPQVYTLPPSQEEMTKNQVS LTCLVKGFYPSDIAVEWESNGQP ENNYKTTPPVLDSDGSFFLYSRLT VDKSRWQEGNVFSCSVMHEALH NHYTQKSLSLSLGK | 90 | DIQMTQSPSSLSASVGDRVTI TCRASQSISSYLNWYQQKPG KAPKLLIYAASSLQSGVPSRF SGSGSGTDFTLTLSSLQPEDF ATYYCQQSYSTPLTFGQGTK VEIKRTVAAPSVFIFPPSDEQ LKSGTASVVCLLNNFYPREA KVQWKVDNALQSGNSQESV TEQDSKDSTYSLSSTLTLSKA DYEKHKVYACEVTHQGLSS PVTKSFNRGEC | 91 |
| | | EVQLLESGGGLVQPGGSLRLSCA ASGFTFNTYAMNWVRQAPGKGL EWVARIRSKYNNYATYYADSVK GRFTISRDNSKNTLYLQMNSLRA EDTAVYYCVKHGNFGNSYVSWF AYWGQGTLVTVSSASTKGPSVFP LAPCSRSTSESTAALGCLVKDYFP EPVTVSWNSGALTSGVHTFPAVL QSSGLYSLSSVVTVPSSSLGTKTY TCNVDHKPSNTKVDKRVESKYGP PCPPCPAPEAAGGPSVFLFPPKPK DTLMISRTPEVTCVVVDVSQEDPE VQFNWYVDGVEVHNAKTKPREE QFNSTYRVVSVLTVLHQDWLNG KEYKCKVSNKGLPSSIEKTISKAK GQPREPQVYTLPPSQEEMTKNQV SLTCLVKGFYPSDIAVEWESNGQP | 108 | QAVVTQEPSLTVSPGGTVTL TCRSSTGAVTTSNYANWVQ QKPGQAPRGLIGGINKRAPG TPARFSGSLLGGKAALTLSG AQPEDEAEYYCALWYSNLW VFGGGTKLTVLGQPKAAPS VTLFPPSSEELQANKATLVC LISDFYPGAVTVAWKADSSP VKAGVETTTPSKQSNNKYA ASSYLSLTPEQWKSHRSYSC QVTHEGSTVEKTVAPTECS | 109 |

TABLE 11-continued

Sequences of PSMA X CD3 bispecific antibodies

| Bispecific Ab ID | Heavy Chain Amino acid sequences: PSMA Arm CD3 Arm | SEQ ID NO | Light Chain Amino Acid Sequences: PSMA Arm CD3 Arm | SEQ ID NO |
|---|---|---|---|---|
| | ENNYKTTPPVLDSDGSFLLYSKLT VDKSRWQEGNVFSCSVMHEALH NHYTQKSLSLSLGK | | | |
| PS3B9 (PSMB127 X CD3B217) | EVQLLESGGGLVQPGGSLRLSCA ASGFTFKSDAMHWVRQAPGKGL EWVSEISGSGGYTNYADSVKGRF TISRDNSKNTLYLQMNSLRAEDT AVYYCARDSYDSSLYVGDYFDY WGQGTLVTVSSASTKGPSVFPLA PCSRSTSESTAALGCLVKDYFPEP VTVSWNSGALTSGVHTFPAVLQS SGLYSLSSVVTVPSSSLGTKTYTC NVDHKPSNTKVDKRVESKYGPPC PPCPAPEAAGGPSVFLFPPKPKDT LMISRTPEVTCVVVDVSQEDPEV QFNWYVDGVEVHNAKTKPREEQ FNSTYRVVSVLTVLHQDWLNGK EYKCKVSNKGLPSSIEKTISKAKG QPREPQVYTLPPSQEEMTKNQVS LTCLVKGFYPSDIAVEWESNGQP ENNYKTTPPVLDSDGSFFLYSRLT VDKSRWQEGNVFSCSVMHEALH NHYTQKSLSLSLGK | 88 | EIVLTQSPATLSLSPGERATL SCRASQSVSSYLAWYQQKP GQAPRLLIYDASNRATGIPA RFSGSGSGTDFTLTISSSEEPE DFAVYYCQQRSNWPLTFGQ GTKVEIKRTVAAPSVFIFPPS DEQLKSGTASVVCLLNNFYP REAKVQWKVDNALQSGNS QESVTEQDSKDSTYSLSSTLT LSKADYEKHKVYACEVTHQ GLSSPVTKSFNRGEC | 89 |
| | EVQLLESGGGLVQPGGSLRLSCA ASGFTFNTYAMNWVRQAPGKGL EWVARIRSKYNNYATYYADSVK GRFTISRDNSKNTLYLQMNSLRA EDTAVYYCVKHGNFGNSYVSWF AYWGQGTLVTVSSASTKGPSVFP LAPCSRSTSESTAALGCLVKDYFP EPVTVSWNSGALTSGVHTFPAVL QSSGLYSLSSVVTVPSSSLGTKTY TCNVDHKPSNTKVDKRVESKYGP PCPPCPAPEAAGGPSVFLFPPKPK DTLMISRTPEVTCVVVDVSQEDPE VQFNWYVDGVEVHNAKTKPREE QFNSTYRVVSVLTVLHQDWLNG KEYKCKVSNKGLPSSIEKTISKAK GQPREPQVYTLPPSQEEMTKNQV SLTCLVKGFYPSDIAVEWESNGQP ENNYKTTPPVLDSDGSFLLYSKLT VDKSRWQEGNVFSCSVMHEALH NHYTQKSLSLSLGK | 108 | QAVVTQEPSLTVSPGGTVTL TCRSSTGAVTTSNYANWVQ QKPGQAPRGLIGGTNKRAPG TPARFSGSLLGGKAATLTLSG AQPEDEAEYYCALWYSNLW VFGGGTKLTVLGQPKAAPS VTLFPPSSEELQANKATLVC LISDFYPGAVTVAWKADSSP VKAGVETTTPSKQSNNKYA ASSYLSLTPEQWKSHRSYSC QVTHEGSTVEKTVAPTECS | 109 |
| PS3B10 (PSMB128 X CD3B217) | EVQLLESGGGLVQPGGSLRLSCA ASGFTFDSDWMSWVRQAPGKGL EWVSAISGNGGSTEYADSVKGRF TISRDNSKNTLYLQMNSLRAEDT AVYYCARDPYYYDGDSYYGM DVWGQGTLVTVSSASTKGPSVFP LAPCSRSTSESTAALGCLVKDYFP EPVTVSWNSGALTSGVHTFPAVL QSSGLYSLSSVVTVPSSSLGTKTY TCNVDHKPSNTKVDKRVESKYGP PCPPCPAPEAAGGPSVFLFPPKPK DTLMISRTPEVTCVVVDVSQEDPE VQFNWYVDGVEVHNAKTKPREE QFNSTYRVVSVLTVLHQDWLNG KEYKCKVSNKGLPSSIEKTISKAK GQPREPQVYTLPPSQEEMTKNQV SLTCLVKGFYPSDIAVEWESNGQP ENNYKTTPPVLDSDGSFFLYSRLT VDKSRWQEGNVFSCSVMHEALH NHYTQKSLSLSLGK | 86 | DIQMTQSPSSLSASVGDRVTI TCRASQSISSYLNWYQQKPG KAPKLLIYAASSLQSGVPSRF SGSGSGTDFTLTISSLQPEDF ATYYCQQSYSTPLTFGQGTK VEIKRTVAAPSVFIFPPSDEQ LKSGTASVVCLLNNFYPREA KVQWKVDNALQSGNSQESV TEQDSKDSTYSLSSTLTLSKA DYEKHKVYACEVTHQGLSS PVTKSFNRGEC | 87 |
| | EVQLLESGGGLVQPGGSLRLSCA ASGFTFNTYAMNWVRQAPGKGL EWVARIRSKYNNYATYYADSVK GRFTISRDNSKNTLYLQMNSLRA EDTAVYYCVKHGNFGNSYVSWF AYWGQGTLVTVSSASTKGPSVFP | 108 | QAVVTQEPSLTVSPGGTVTL TCRSSTGAVTTSNYANWVQ QKPGQAPRGLIGGTNKRAPG TPARFSGSLLGGKAATLTLSG AQPEDEAEYYCALWYSNLW VFGGGTKLTVLGQPKAAPS | 109 |

TABLE 11-continued

Sequences of PSMA X CD3 bispecific antibodies

| Bispecific Ab ID | Heavy Chain Amino acid sequences: PSMA Arm CD3 Arm | SEQ ID NO | Light Chain Amino Acid Sequences: PSMA Arm CD3 Arm | SEQ ID NO |
|---|---|---|---|---|
| | LAPCSRSTSESTAALGCLVKDYFP EPVTVSWNSGALTSGVHTFPAVL QSSGLYSLSSVVTVPSSSLGTKTY TCNVDHKPSNTKVDKRVESKYGP PCPPCPAPEAAGGPSVFLFPPKPK DTLMISRTPEVTCVVVDVSQEDPE VQFNWYVDGVEVHNAKTKPREE QFNSTYRVVSVLTVLHQDWLNG KEYKCKVSNKGLPSSIEKTISKAK GQPREPQVYTLPPSQEEMTKNQV SLTCLVKGFYPSDIAVEWESNGQP ENNYKTTPPVLDSDGSFFLYSKLT VDKSRWQEGNVFSCSVMHEALH NHYTQKSLSLSLGK | | VTLFPPSSEELQANKATLVC LISDFYPGAVTVAWKADSSP VKAGVETTTPSKQSNNKYA ASSYLSLTPEQWKSHRSYSC QVTHEGSTVEKTVAPTECS | |
| PS3B11 (PSMB129 X CD3B217) | QVQLVQSGAEVKKPGSSVKVSCK ASGGTFSSYAISWVRQAPGQGLE WMGWISPYNGNANYAQKFQGRV TITADESTSTAYMELSSLRSEDTA VYYCARVNSAALVWERLDYWG QGTLVTVSSASTKGPSVFPLAPCS RSTSESTAALGCLVKDYFPEPVTV SWNSGALTSGVHTFAVLQSSGL YSLSSVVTVPSSSLGTKTYTCNVD HKPSNTKVDKRVESKYGPPCPPC PAPEAAGGPSVFLFPPKPKDTLMI SRTPEVTCVVVDVSQEDPEVQFN WYVDGVEVHNAKTKPRELQFNS TYRVVSVLTVLHQDWLNGKEYK CKVSNKGLPSSIEKTISKAKGQPR EPQVYTLPPSQREMTKNQVSLTC LVKGFYPSDIAVEWESNGQPENN YKTTPPVLDSDGSFFLYSRLTVDK SRWQEGNVFSCSVMHEALEINHY TQKSLSLSLGK | 82 | DIQMIQSPSSLSASVGDRVTI TCRASQSIDRWLNWYQQKP GKAPKLLIYAASSLQSGVPS RFSGSGSGTDFTLTISSLQPE DFATYYCQQSPRYPLTFGQG TKVEIKRTVAAPSVFIFPPSD EQLKSGTASVVCLLNNFYPR EAKVQWKVDNALQSGNSQE SVTEQDSKDSTYSLSSTLTLS KADYEKHKVYACEVTHQGL SSPVTKSFNRGEC | 83 |
| | EVQLLESGGGLVQPGGSLRLSCA ASGFTFNTYAMNWVRQAPGKGL EWVARIRSKYNNYATYYADSVK GRFTISRDNSKNTLYLQMNSLRA EDTAVYYCVKHGNFGNSYVSWF AYWGQGTLVTVSSASTKGPSVFP LAPCSRSTSESTAALGCLVKDYFP EPVTVSWNSGALTSGVHTFPAVL QSSGLYSLSSVVTVPSSSLGTKTY TCNVDHKPSNTKVDKRVESKYGP PCPPCPAPEAAGGPSVFLFPPKPK DTLMISRTPEVTCVVVDVSQEDPE VQFNWYVDGVEVHNAKTKPREE QFNSTYRVVSVLTVLHQDWLNG KEYKCKVSNKGLPSSIEKTISKAK GQPREPQVYTLPPSQEEMTKNQV SLTCLVKGFYPSDIAVEWESNGQP ENNYKTTPPVLDSDGSFFLYSKLT VDKSRWQEGNVFSCSVMHEALH NHYTQKSLSLSLGK | 108 | QAVVTQEPSLTVSPGGTVTL TCRSSTGAVTTSNYANWVQ QKPGQAPRGLIGGTNKRAPG TPARFSGSLLGGKAATLTLSG AQPEDEAEYYCALWYSNLW VFGGGTKLTVLGQPKAAPS VTLFPPSSEELQANKATLVC LISDFYPGAVTVAWKADSSP VKAGVETTTPSKQSNNKYA ASSYLSLTPEQWKSHRSYSC QVTHEGSTVEKTVAPTECS | 109 |
| PS3B12 (PSMB130 X CD3B217) | QVQLVQSGAEVKKPGSSVKVSCK ASGGTFKSYDISWVRQAPGQGLE WMGGIIPIEGTANYAQKFQGRVTI TADESTSTAYMELSSLRSEDTAV YYCARDYPAGYGFDYWGQGTLV TVSSASTKGPSVFPLAPCSRSTSES TAALGCLVKDYFPEPVTVSWNSG ALTSGVHTFPAVLQSSGLYSLSSV VTVPSSSLGTKTYTCNVDHKPSN TKVDKRVESKYGPPCPPCPAPEA AGGPSVFLFPPKPKDTLMISRTPE VTCVVVDVSQEDPEVQFNWVVD GVEVHNAKTKPREEQFNSTYRVV SVLTVLHQDWLNGKEYKCKVSN KGLPSSIEKTISKAKGQPREPQVY TLPPSQEEMTKNQVSLTCLVKGF | 84 | EIVLTQSPGTLSLSPGERATL SCRASQSVSSSYLAWYQQKP GQAPRLLIYGASSRATGIPDR FSGSGSGTDFTLTISRLEPED FAVYYCQQYGSSPLTFGQGT KVEIKRTVAAPSVFIFPPSDE QLKSGTASVVCLLNNGYPRE AKVQWKVDNALQSGNSQES VTEQDSKDSTYSLSSTLTLSK ADYRKHKVYACEVTHQGLS SPVTKSFNRGEC | 85 |

TABLE 11-continued

Sequences of PSMA X CD3 bispecific antibodies

| Bispecific Ab ID | Heavy Chain Amino acid sequences: PSMA Arm CD3 Arm | SEQ ID NO | Light Chain Amino Acid Sequences: PSMA Arm CD3 Arm | SEQ ID NO |
|---|---|---|---|---|
| | YPSDIAVEWESNGQPENNYKTTP PVLDSDGSFFLYSRLTVDKSRWQ EGNVFSCSVMEEALHNHYTQKSL SLSLGK | | | |
| | EVQLLESGGGLVQPGGSLRLSCA ASGFTFNTYAMNWVRQAPGKGL EWVARIRSKYNNYATYYADSVK GRFTISRDNSKNTLYLQMNSLRA EDTAVYYCVKHGNFGNSYVSWF AYWGQGTLVTVSSASTKGPSVFP LAPCSRSTSESTAALGCLVKDYFP EPVTVSWNSGALTSGVHTFPAVL QSSGLYSLSSVVTVPSSSLGTKTY TCNVDHKPSNTKVDKRVESKYGP PCPPCPAPEAAGGPSVFLFPPKPK DTLMISRTPEVTCVVVDVSQEDPE VQFNWYVDGVEVHNAKTKPREE QFNSTYRVVSVLTVLHQDWLNG KEYKCKVSNKGLPSSIEKTISKAK GQPREPQVYTLPPSQEEMTKNQV SLTCLVKGFYPSDIAVEWESNGQP ENNYKTTPPVLDSDGSFLLYSKLT VDKSRWQEGNVFSCSVMHEALH NHYTQKSLSLSLGK | 108 | QAVVTQEPSLTVSPGGTVTL TCRSSTGAVTTSNYANWVQ QKPGQAPRGLIGGTNKRAPG TPARFSGSLLGGKAATLTLSG AQPEDEAEYYCALWYSNLW VFGGGTKLTVLGQPKAAPS VTLFPPSSEELQANKATLVC LISDFYPGAVTVAWKADSSP VKAGVETTTPSKQSNNKYA ASSYLSLTPEQWKSHRSYSC QVTHEGSTVEKTVAPTECS | 109 |
| PS3B11 (PSMB129 X CD3B217) | QVQLVQSGAEVKKPGSSVKVSCK ASGGTFSSYAISWVRQAPGQGLE WMGWISPYNGNANYAQKFQGRV TITADESTSTAYMELSSLRSEDTA VYYCARVNSAALVWERLDYWG QGTLVTVSSASTKGPSVFPLAPCS RSTSESTAALGCLVKDYFPEPVTV SWNSGALTSGVHTFAVLQSSGL YSLSSVVTVPSSSLGTKTYTCNVD HKPSNTKVDKRVESKYGPPCPPC PAPEAAGGPSVFLFPPKPKDTLMI SRTPEVTCVVVDVSQEDPEVQFN WYVDGVEVHNAKTKPRELQFNS TYRVVSVLTVLHQDWLNGKEYK CKVSNKGLPSSIEKTISKAKGQPR EPQVYTLPPSQREMTKNQVSLTC LVKGFYPSDIAVEWESNGQPENN YKTTPPVLDSDGSFFLYSRLTVDK SRWQEGNVFSCSVMHEALEINHY TQKSLSLSLGK | 82 | DIQMIQSPSSLSASVGDRVTI TCRASQSIDRWLNWYQQKP GKAPKLLIYAASSLQSGVPS RFSGSGSGTDFTLTISSLQPE DFATYYCQQSPRYPLTFGQG TKVEIKRTVAAPSVFIFPPSD EQLKSGTASVVCLLNNFYPR EAKVQWKVDNALQSGNSQE SVTEQDSKDSTYSLSSTLTLS KADYEKHKVYACEVTHQGL SSPVTKSFNRGEC | 83 |
| | EVQLVESGGGLVQPGGSLRLSCA ASGFTFNTYAMNWVRQAPGKGL EWVARIRSKYNNYATYYAASVK GRFTISRDDSKNSLYLQMNSLKTE DTAVYYCARHGNFGNSYVSWFA YWGQGTLVTVSSASTKGPSVFPL APCSRSTSESTAALGCLVKDYFPE PVTVSWNSGALTSGVHTFPAVLQ SSGLYSLSSVVTVPSSSLGTKTYT CNVDHKPSNTKVDKRVESKYGPP CPPCPAPEAAGGPSVFLFPPKPKD TLMISRTPEVTCVVVDVSQEDPEV QFNWYVDGVEVHNAKTKPREEQ FNSTYRVVSVLTVLHQDWLNGK EYKCKVSNKGLPSSIEKTISKAKG QPREPQVYTLPPSQEEMTKNQVS LTCLVKGFYPSDIAVEWESNGQP ENNYKTTPPVLDSDGSFLLYSKLT VDKSRWQEGNVFSCSVMHEALH NHYTQKSLSLSLGK | 110 | QTVVTQEPSLTVSPGGTVTL TCRSSTGAVTTSNYANWVQ QKPGQAPRGLIGGTNKRAPG TPARFSGSLLGGKAALTLSG VQPEDEAEYYCALWYSNLW VFGGGTKLTVLGQPKAAPS VTLFPPSSEELQANKATLVC LISDFYPGAVTVAWKADSSP VKAGVETTTPSKQSNNKYA ASSYLSLTPEQWKSHRSYSC QVTHEGSTVEKTVAPTECS | 111 |
| PS3B30 (PSMB130 X CD3B219) | QVQLVQSGAEVKKPGSSVKVSCK ASGGTFKSYDISWVRQAPGQGLE WMGGIIPIEGTANYAQKFQGRVTI TADESTSTAYMELSSLRSEDTAV YYCARDYPAGYGFDYWGQGTLV | 84 | EIVLTQSPGTLSLSPGERATL SCRASQSVSSSYLAWYQQKP GQAPRLLIYGASSRATGIPDR FSGSGSGTDFTLTISRLEPED FAVYYCQQYGSSPLTFGQGT | 85 |

TABLE 11-continued

Sequences of PSMA X CD3 bispecific antibodies

| Bispecific Ab ID | Heavy Chain Amino acid sequences: PSMA Arm CD3 Arm | SEQ ID NO | Light Chain Amino Acid Sequences: PSMA Arm CD3 Arm | SEQ ID NO |
|---|---|---|---|---|
| | TVSSASTKGPSVFPLAPCSRSTSES TAALGCLVKDYFPEPVTVSWNSG ALTSGVHTFPAVLQSSGLYSLSSV VTVPSSSLGTKTYTCNVDHKPSN TKVDKRVESKYGPPCPPCPAPEA AGGPSVFLFPPKPKDTLMISRTPE VTCVVVDVSQEDPEVQFNWYVD GVEVHNAKTKPREEQFNSTYRVV SVLTVLHQDWLNGKEYKCKVSN KGLPSSIEKTISKAKGQPREPQVY TLPPSQEEMTKNQVSLTCLVKGF YPSDIAVEWESNGQPENNYKTTP PVLDSDGSFFLYSRLTVDKSRWQ EGNVFSCSVMHEALHNHYTQKSL SLSLGK | | KVEIKRTVAAPSVFIFPPSDE QLKSGTASVVCLLNNFYPRE AKVQWKVDNALQSGNSQES VTEQDSKDSTYSLSSTLTLSK ADYEKHKVYACEVTHQGLS SPVTKSFNRGEC | |
| | EVQLVESGGGLVQPGGSLRLSCA ASGFTFNTYAMNWVRQAPGKGL EWVARIRSKYNNYATYYAASVK GRFTISRDDSKNSLYLQMNSLKTE DTAVYYCARHGNFGNSYVSWFA YWGQGTLVTVSSASTKGPSVFPL APCSRSTSESTAALGCLVKDYFPE PVTVSWNSGALTSGVHTFPAVLQ SSGLYSLSSVVTVPSSSLGTKTYT CNVDHKPSNTKVDKRVESKYGPP CPPCPAPEAAGGPSVFLFPPKPKD TLMISRTPEVTCVVVDVSQEDPEV QFNWYVDGVEVHNAKTKPREEQ FNSTYRVVSVLTVLHQDWLNGK EYKCKVSNKGLPSSIEKTISKAKG QPREPQVYTLPPSQEEMTKNQVS LTCLVKGFYPSDIAVEWESNGQP ENNYKTTPPVLDSDGSFLLYSKLT VDKSRWQEGNVFSCSVMHEALH NHYTQKSLSLSLGK | 110 | QTVVTQEPSLTVSPGGTVTL TCRSSTGAVTTSNYANWVQ QKPGQAPRGLIGGTNKRAPG TPARFSSGSLLGGKAALTLSG VQPEDEAEYYCALWYSNLW VFGGGTKLTVLGQPKAAPS VTLFPPSSEELQANKATLVC LISDFYPGAVTVAWKADSSP VKAGVETTTPSKQSNNKYA ASSYLSLTPEQWKSHRSYSC QVTHEGSTVEKTVAPTECS | 111 |
| PS3B28 (PSMB128 X CD3B219) | EVQLLESGGGLVQPGGSLRLSCA ASGFTFDSDWMSWVRQAPGKGL EWVSAISGNGGSTEYADSVKGRF TISRDNSKNTLYLQMNSLRAEDT AVYYCARDPYYYYDGDSYYGM DVWGQGTLVTVSSASTKGPSVFP LAPCSRSTSESTAALGCLVKDYFP EPVTVSWNSGALTSGVHTFPAVL QSSGLYSLSSVVTVPSSSLGTKTY TCNVDHKPSNTKVDKRVESKYGP PCPPCPAPEAAGGPSVFLFPPKPK DTLMISRTREVTCVVVDVSQEDPE VQFNWYVDGVEVHNAKTKPREE QFNSTYRVVSVLTVLHQDWLNG KEYKCKVSNKGLPSSIEKTISKAK GQPREPQVYTLPPSQEEMTKNQV SLTCLVKGFYPSDIAVEWESNGQP ENNYKTTPPVLDSDGSFFLYSRLT VDKSRWQEGNVFSCSVMHEALH NHYTQKSLSLSLGK | 86 | DIQMTQSPSSLSASVGDRVTI TCRASQSISSYLNWYQQKPG KAPKLLIYAASSLQSGVPSRF SGSGSGTDFTLTISSLQPEDF ATYYCQQSYSTPLTFGQGTK VEIKRTVAAPSVFIEPPSDEQ LKSGTASVVCLLNNFYPREA KVQWKVDNALQSGNSQESV TEQDSKDSTYSLSSTLTLSKA DYEKHKVYACEVTHQGLSS PVTKSFNRGEC | 87 |
| | EVQLVESGGGLVQPGGSLRLSCA ASGFTFNTYAMNWVRQAPGKGL EWVARIRSKYNNYATYYAASVK GRFTISRDDSKNSLYLQMNSLKTE DTAVYYCARHGNFGNSYVSWFA YWGQGTLVTVSSASTKGPSVFPL APCSRSTSESTAALGCLVKDYFPE PVTVSWNSGALTSGVHTFPAVLQ SSGLYSLSSVVTVPSSSLGTKTYT CNVDHKPSNTKVDKRVESKYGPP CPPCPAPEAAGGPSVFLFPPKPKD TLMISRTPEVTCVVVDVSQEDPEV QFNWYVDGVEVHNAKTKPREEQ FNSTYRVVSVLTVLHQDWLNGK EYKCKVSNKGLPSSIEKTISKAKG | 110 | QTVVTQEPSLTVSPGGTVTL TCRSSTGAVTTSNYANWVQ QKPGQAPRGLIGGTNKRAPG TPARFSSGSLLGGKAALTLSG VQPEDEAEYYCALWYSNLW VFGGGTKLTVLGQPKAAPS VTLFPPSSEELQANKATLVC LISDFYPGAVTVAWKADSSP VKAGVETTTPSKQSNNKYA ASSYLSLTPEQWKSHRSYSC QVTHEGSTVEKTVAPTECS | 111 |

TABLE 11-continued

Sequences of PSMA X CD3 bispecific antibodies

| Bispecific Ab ID | Heavy Chain Amino acid sequences: PSMA Arm CD3 Arm | SEQ ID NO | Light Chain Amino Acid Sequences: PSMA Arm CD3 Arm | SEQ ID NO |
|---|---|---|---|---|
| | QPREPQVYTLPPSQEEMTKNQVS LTCLVKGFYPSDIAVEWESNGQP ENNYKTTPPVLDSDGSFLLYSKLT VDKSRWQEGNVFSCSVMHEALH NHYTQKSLSLSLGK | | | |
| PS3B27 (PSMB127 X CD3B219) | EVQLLESGGGLVQPGGSLRLSCA ASGFTFKSDAMEWVRQAPGKGL EWVSEISGSGGYTNYADSVKGRF TISRDNSKNTLYQMNSLRAEDT AVYYCARDSYDSSLYVGDYFDY WGQGTLVTVSSASTKGPSVFPLA PCSRSTSESTAALGCLVKDYFPEP VTVSWNSGALTSGVHTFPAVLQS SGLYSLSSVVTVPSSSLGTKTYTC NVDHKPSNTKVDKRVESKYGPPC PPCPAPEAAGGPSVFLFPPKPKDT LMISRTPEVTCVVVDVSQEDPEV QFNWYVDGVEVHNAKTKPREEQ FNSTYRVVSVLTVLHQDWLNGK EYKCKVSNKGLPSSIEKTISKAKG QPREPQVYTLPPSQEEMTKNQVS LTCLVKGFYPSDIAVEWESNGQP ENNYKTTPPVLDSDGSFFLYSRLT VDKSRWQEGNVFSCSVMHEALH NHYTQKSLSLSLGK | 88 | EIVLTQSPATLSLSPGERATL SCRASQSVSSYLAWYQQKP GQAPRLLIYDASNRATGIPA RFSGSGSGTDFTLTISSLEPE DFAVYYCQQRSNWPLTFGQ GTKVEIKRTVAAPSVFIFPPS DEQLKSGTASVVCLLNNFYP REAKVQWKVDNALQSGNS QESVTEQDSKDSTYSLSSTLT LSKADYEKHKVYACEVTHQ GLSSPVTKSFNRGEC | 89 |
| | EVQLVESGGGLVQPGGSLRLSCA ASGFTFNTYAMNWVRQAPGKGL EWVARIRSKYNNYATYYAASVK GRFTISRDDSKNSLYLQMNSLKTE DTAVYYCARHGNFGNSYVSWFA YWGQGTLVTVSSASTKGPSVFPL APCSRSTSESTAALGCLVKDYFPE PVTVSWNSGALTSGVHTFPAVLQ SSGLYSLSSVVTVPSSSLGTKTYT CNVDHKPSNTKVDKRVESKYGPP CPPCPAPEAAGGPSVFLFPPKPKD TLMISRTPEVTCVVVDVSQEDPEV QFNWYVDGVEVHNAKTKPREEQ FNSTYRVVSVLTVLHQDWLNGK EYKCKVSNKGLPSSIEKTISKAKG QPREPQVYTLPPSQEEMTKNQVS LTCLVKGFYPSDIAVEWESNGQP ENNYKTTPPVLDSDGSFLLYSKLT VDKSRWQEGNVFSCSVMHEALH NHYTQKSLSLSLGK | 110 | QTVVTQEPSLTVSPGGTVTL TCRSSTGAVTTSNYANWVQ QKPGQAPRGLIGGTNKRAPG TPARFSSGSLLGGKAALTLSG VQPEDEAEYYCALWYSNLW VFGGGTKLTVLGQPKAAPS VTLFPPSSEELQANKATLVC LISDFYPGAVTVAWKADSSP VKAGVETTTPSKQSNNKYA ASSYLSLTPEQWKSHRSYSC QVTHEGSTVEKTVAPTECS | 111 |
| PS3B26 (PSMB126 X CD3B219) | QVQLVQSGAEVKKPGSSVKVSCK ASGGTFDDYAISWVRQAPGQGLE WMGRIDPIEGTANYAQKFQGRVT ITADESTSTAYMELSSLRSEDTAV YYCARDRYYYDGVYWYSDYFD YWGQGTLVTVSSASTKGPSVFPL APCSRSTSESTAALGCLVKDYFPE PVTVSWNSGALTSGVHTFPAVLQ SSGLYSLSSVVTVPSSSLGTKTYT CNVDHKPSNTKVDKRVESKYGPP CPPCPAPEAAGGPSVFLEPPKPKD TLMISRTPEVTCVVVDVSQEDPEV QFNWYVDGVEVHNAKTKPREEQ FNSTYRVVSVLTVLHQDWLNGK EYKCKVSNKGLPSSIEKTISKAKG QPREPQVYTLPPSQEEMTKNQVS LTCLVKGFYPSDIAVEWESNGQP ENNYKTTPPVLDSDGSFFLYSRLT VDKSRWQEGNVFSCSVMHEALH NHYTQKSLSLSLGK | 90 | DIQMTQSPSSLSASVGDRVTI TCRASQSISSYLNWYQQKPG KAPKILIYAASSLQSGVPSRF SGSGSGTDFTLTISSLQPEDF ATYYCQQSYSTPLTFGQGTK VEIKRTVAAPSVFIFPPSDEQ LKSGTASVVCLLNNFYPREA KVQWKVDNALQSGNSQESV TEQDSKDSTYSLSSTLTLSKA DYEKHKVYACEVTHQGLSS PVTKSFNRGEC | 91 |
| | EVQLVESGGGLVQPGGSLRLSCA ASGFTFNTYAMNWVRQAPGKGL EWVARIRSKYNNYATYYAASVK GRFTISRDDSKNSLYLQMNSLKTE | 110 | QTVVTQEPSLTVSPGGTVTL TCRSSTGAVTTSNYANWVQ QKPGQAPRGLIGGTNKRAPG TPARFSSGSLLGGKAALTLSG | 111 |

TABLE 11-continued

Sequences of PSMA X CD3 bispecific antibodies

| Bispecific Ab ID | Heavy Chain Amino acid sequences: PSMA Arm CD3 Arm | SEQ ID NO | Light Chain Amino Acid Sequences: PSMA Arm CD3 Arm | SEQ ID NO |
|---|---|---|---|---|
| | DTAVYYCARHGNFGNSYVSWFA YWGQGTLVTVSSASTKGPSVFPL APCSRSTSESTAALGCLVKDYFPE PVTVSWNSGALTSGVHTFPAVLQ SSGLYSLSSVVTVPSSSLGTKTYT CNVDHKPSNTKVDKRVESKYGPP CPPCPAPEAAGGPSVFLFPPKPKD TLMISRTPEVTCVVVDVSQEDPEV QFNWYVDGVEVHNAKTKPREEQ FNSTYRVVSVLTVLHQDWLNGK EYKCKVSNKGLPSSIEKTISKAKG QPREPQVYTLPPSQEEMTKNQVS LTCLVKGFYPSDIAVEWESNGQP ENNYKTTPPVLDSDGSFLLYSKLT VDKSRWQEGNVFSCSVMHEALH NHYTQKSLSLSLGK | | VQPEDEAEYYCALWYSNLW VFGGGTKLTVLGQPKAAPS VTLFPPSSEELQANKATLVC LISDFYPGAVTVAWKADSSP VKAGVETTTPSKQSNNKYA ASSYLSLTPEQWKSHRSYSC QVTHEGSTVEKTVAPTECS | |
| PS3B25 (PSMB87 X CD3B219) | EVQLVQSGAEVKKPGESLKISCK GSGYSFTSYWISWVRQMPGKGLE WMGITYPGDSYTRYSPSFQGQVTI SADKSISTAYLQWSSLKASDTAM YYCARDYEWELFDSRLDYWGQG TLVTVSSASTKGPSVFPLAPCSRS TSESTAALGCLVKDYFPEPVTVS WNSGALTSGVHTFPAVLQSSGLY SLSSVVTVPSSSLGTKTYTCNVDH KPSNTKVDKRVESKYGPPCPPCP APEAAGGPSVFLFPPKPKDTLMIS RTPEVTCVVVDVSQEDPEVQFNW YVDGVEVHNAKTKPREEQFNSTY RVVSVLTVLHQDWLNGKEYKCK VSNKGLPSSIEKTISKAKGQPREP QVYTLPPSQEEMTKNQVSLTCLV KGFYPSDIAVEWESNGQPENNYK TTPPVLDSDGSFFLYSRLTVDKSR WQEGNVFSCSVMHEALHNHYTQ KSLSLSLGK | 125 | DIQMTQSPSSLSASVGDRVTI TCRASQSISSYLNWYQQKPG KAPKILIYAASSLQSGVPSRF SGSGSGTDFTLTISSLQPEDF ATYYCQQSYSTPLTFGQGTK VEIKRTVAAPSVFIFPPSDEQ LKSGTASVVCLLNNFYPREA KVQWKVDNALQSGNSQESV TEQDSKDSTYSLSSTLTLSKA DYEKHKVYACEVTHQGLSS PVTKSFNRGEC | 91 |
| | EVQLVESGGGLVQPGGSLRLSCA ASGFTFNTYAMNWVRQAPGKGL EWVARIRSKYNNYATYYAASVK GRFTISRDDSKNSLYLQMNSLKTE DTAVYYCARHGNFGNSYVSWFA YWGQGTLVTVSSASTKGPSVFPL APCSRSTSESTAALGCLVKDYFPE PVTVSWNSGALTSGVHTFPAVLQ SSGLYSLSSVVTVPSSSLGTKTYT CNVDHKPSNTKVDKRVESKYGPP CPPCPAPEAAGGPSVFLFPPKPKD TLMISRTPEVTCVVVDVSQEDPEV QFNWYVDGVEVHNAKTKPREEQ FNSTYRVVSVLTVLHQDWLNGK EYKCKVSNKGLPSSIEKTISKAKG QPREPQVYTLPPSQEEMTKNQVS LTCLVKGFYPSDIAVEWESNGQP ENNYKTTPPVLDSDGSFLLYSKLT VDKSRWQEGNVFSCSVMHEALH NHYTQKSLSLSLGK | 110 | QTVVTQEPSLTVSPGGTVTL TCRSSTGAVTTSNYANWVQ QKPGQAPRGLIGGTNKRAPG TPARFSSGSLLGGKAALTLSG VQPEDEAEYYCALWYSNLW VFGGGTKLTVLGQPKAAPS VTLFPPSSEELQANKATLVC LISDFYPGAVTVAWKADSSP VKAGVETTTPSKQSNNKYA ASSYLSLTPEQWKSHRSYSC QVTHEGSTVEKTVAPTECS | 111 |
| PS3B24 (PSMB124 X CD3B219) | QVQLVQSGAEVKKPGSSVKVSCK ASGGTFSSYAISWVRQAPGQGLE WMGWISPYNGNANYAQKFQGRV TITADESTSTAYMELSSLRSEDTA VYYCARDSDRSYNLDYWGQGTL VTVSSASTKGPSVFPLAPCSRSTSE STAALGCLVKDYFPEPVTVSWNS GALTSGVHTFPAVLQSSGLYSLSS VVTVPSSSLGTKTYTCNVDHKPS NTKVDKRVESKYGPPCPPCPAPE AAGGPSVFLFPPKPKDTLMISRTP EVTCVVVDVSQEDPEVQFNWYV DGVEVHNAKTKPREEQFNSTYRV VSVLTVLHQDWLNGKEYKCKVS | 92 | DIQMTQSPSSLSASVGDRVTI TCRASQSISGWLNWYQQKP GKAPKLLIYAASSLQSGVPS RFSGSGSGTDFTLTISSLQPE DFATYYCQQSYSTPLTFGQG TKVEIKRTVAAPSVFIFPPSD EQLKSGTASVVCLLNNFYTR EAKVQWKVDNALQSGNSQE SVTEQDSKDSTYSLSSTLTLS KADYEKHKVYACEVTHQGL SSPVTKSFNRGEC | 93 |

TABLE 11-continued

Sequences of PSMA X CD3 bispecific antibodies

| Bispecific Ab ID | Heavy Chain Amino acid sequences: PSMA Arm CD3 Arm | SEQ ID NO | Light Chain Amino Acid Sequences: PSMA Arm CD3 Arm | SEQ ID NO |
|---|---|---|---|---|
| | NKGLPSSIEKTISKAKGQPREPQV YTLPPSQEEMTKNQVSLTCLVKG FYPSDIAVEWESNGQPENNYKTT PPVLDSDGSFFLYSRLTVDKSRW QEGNVFSCSVMHEALHNHYTQK SLSLSLGK | | | |
| | EVQLVESGGGLVQPGGSLRLSCA ASGFTFNTYAMNWVRQAPGKGL EWVARIRSKYNNYATYYAASVK GRFTISRDDSKNSLYLQMNSLKTE DTAVYYCARHGNFGNSYVSWFA YWGQGTLVTVSSASTKGPSVFPL APCSRSTSESTAALGCLVKDYFPE PVTVSWNSGALTSGVHTFPAVLQ SSGLYSLSSVVTVPSSSLGTKTYT CNVDHKPSNTKVDKRVESKYGPP CPPCPAPEAAGGPSVFLFPPKPKD TLMISRTPEVTCVVVDVSQEDPEV QFNWYVDGVEVHNAKTKPREEQ FNSTYRVVSVLTVLHQDWLNGK EYKCKVSNKGLPSSIEKTISKAKG QPREPQVYTLPPSQEEMTKNQVS LTCLVKGFYPSDIAVEWESNGQP ENNYKTTPPVLDSDGSFLLYSKLT VDKSRWQEGNVFSCSVMHEALH NHYTQKSLSLSLGK | 110 | QTVVTQEPSLTVSPGGTVTL TCRSSTGAVTTSNYANWVQ QKPGQAPRGLIGGTNKRAPG TPARFSGSLLGGKAALTLSG VQPEDEAEYYCALWYSNLW VFGGGTKLTVLGQPKAAPS VTLFPPSSEELQANKATLVC LISDFYPGAVTVAWKADSSP VKAGVETTTPSKQSNNKYA ASSYLSLTPEQWKSHRSYSC QVTHEGSTVEKTVAPTECS | 111 |
| PS3B23 (PSMB123 X (D3B219) | EVQLVQSGAEVKKPGESLKISCK GSGYSFTSYWIGWVRQMPGKGL EWMGIIYPGDSDTRYSPSFQGQVT ISADKSISTAYLQWSSLKASDTAM YYCARGLPIWYLDYWGQGTLVT VSSASTKGPSVFPLAPCSRSTSEST AALGCLVKDYTPEPVTVSWNSGA LTSGVHTFPAVLQSSGLYSLSSVV TVPSSSLGTKTYTCNVDHKPSNT KVDKRVESKYGPPCPPCPAPEAA GGPSVFLFPPKPKDTLMISRTPEV TCVVVDVSQEDREVQFNWYVDG VEVHNAKTKPREEQFNSTYRVVS VLTVLHWDWLNGKEYKCKVSNK GLPSSIEKTISKAKGQPREPQVYTL PPSQEEMTKNQVSLTCLVKGFYP SDIAVEWESNGQPENNYKTTPPV LDSDGSFFLYSRLTVDKSRWQEG NVFSCSVMHEALHNHYTQKSLSL SLGK | 94 | EIVLTQSPATLSLSPGERATL SCRASQSVASDLAWYQQKP GQAPRLLIYFASNRATGIPAR FSGSGSGTDFTLTISSLEPEDF AVVYCQQSITWPFTFGQGTK VEIKRTVAAPSVFIFPPSDEQ LKSGTASVVCLLNNFYPREA KVQWKVDNALQSGNSQESV TEQDSKDSTYSLSSTLTLSKA DYEKHKVYACEVTHQGLSS PVTKSFNRGEC | 95 |
| | EVQLVESGGGLVQPGGSLRLSCA ASGFTFNTYAMNWVRQAPGKGL EWVARIRSKYNNYATYYAASVK GRFTISRDDSKNSLYLQMNSLKTE DTAVYYCARHGNFGNSYVSWFA YWGQGTLVTVSSASTKGPSVFPL APCSRSTSESTAALGCLVKDYFPE PVTVSWNSGALTSGVHTFPAVLQ SSGLYSLSSVVTVPSSSLGTKTYT CNVDHKPSNTKVDKRVESKYGPP CPPCPAPEAAGGPSVFLFPPKPKD TLMISRTPEVTCVVVDVSQEDPEV QFNWYVDGVEVHNAKTKPREEQ FNSTYRVVSVLTVLHQDWLNGK EYKCKVSNKGLPSSIEKTISKAKG QPREPQVYTLPPSQEEMTKNQVS LTCLVKGFYPSDIAVEWESNGQP ENNYKTTPPVLDSDGSFLLYSKLT VDKSRWQEGNVFSCSVMHEALH NHYTQKSLSLSLGK | 110 | QTVVTQEPSLTVSPGGTVTL TCRSSTGAVTTSNYANWVQ QKPGQAPRGLIGGTNKRAPG TPARFSGSLLGGKAALTLSG VQPEDEAEYYCALWYSNLW VFGGGTKLTVLGQPKAAPS VTLFPPSSEELQANKATLVC LISDFYPGAVTVAWKADSSP VKAGVETTTPSKQSNNKYA ASSYLSLTPEQWKSHRSYSC QVTHEGSTVEKTVAPTECS | 111 |
| PS3B22 (PSMB123 X | QVQLVQSGAEVKKPGSSVKVSCK ASGGTFSSYAISWVRQAPGQGLE WMGWIIPYNGNANYAQKFQGRV | 96 | DIQMTQSPSSLSASVGDRVTI TCRASQSIDRWLNWYQQKP GKAPKLLIYAASSLQSGVPS | 83 |

TABLE 11-continued

Sequences of PSMA X CD3 bispecific antibodies

| Bispccific Ab ID | Heavy Chain Amino acid sequences: PSMA Arm CD3 Arm | SEQ ID NO | Light Chain Amino Acid Sequences: PSMA Arm CD3 Arm | SEQ ID NO |
|---|---|---|---|---|
| CD3B219) | TITADESTSTAYMELSSLRSEDTA VYYCARVNSAALVWERLDYWG QGTLVTVSSASTKGPSVFPLAPCS RSTSESTAALGCLVKDYFPEPVTV SWNSGALTSGVHTFPAVLQSSGL YSLSSVVTVPSSSLGTKTYTCNVD HKPSNTKVDKRVESKYGPPCPPC PAPEAAGGPSVFLFPPKPKDTLMI SRTPEVTCVVVDVSQEDPEVQFN WYVDGVEVHNAKTKPREEQFNS TYRVVSVLTVLHQDWLNGKEYK CKVSNKGLPSSIEKTISKAKGQPR EPQVYTLPPSQEEMTKNQVSLTC LVKGFYPSDIAVEWESNGQPENN YKTTPPVLDSDGSFFLYSRLTVDK SRWQEGNVFSCSVMHEALHNHY TQKSLSLSLGK | | RFSGSGSGTDFTLTISSLQPE DFATYYCQQSPRYPLTFGQG TKVEIKRTVAAPSVFIFPPSD EQLKSGTASVVCLLNNFYPR EAKVQWKVDNALQSGNSQE SVTEQDSKDSTYSLSSTLTLS KADYEKHKVYACEVTHQGL SSPVTKSFNRGEC | |
| | EVQLVESGGGLVQPGGSLRLSCA ASGFTFNTYAMNWVRQAPGKGL EWVARIRSKYNNYATYYAASVK GRFTISRDDSKNSLYLQMNSLKTE DTAVYYCARHGNFGNSYVSWFA YWGQGTLVTVSSASTKGPSVFPL APCSRSTSESTAALGCLVKDYFPE PVTVSWNSGALTSGVHTFPAVLQ SSGLYSLSSVVTVPSSSLGTKTYT CNVDHKPSNTKVDKRVESKYGPP CPPCPAPEAAGGPSVFLFPPKPKD TLMISRTPEVTCVVVDVSQEDPEV QFNWYVDGVEVHNAKTKPREEQ FNSTYRVVSVLTVLHQDWLNGK EYKCKVSNKGLPSSIEKTISKAKG QPREPQVYTLPPSQEEMTKNQVS LTCLVKGFYPSDIAVEWESNGQP ENNYKTTPPVLDSDGSFLLYSKLT VDKSRWQEGNVFSCSVMHEALH NHYTQKSLSLSLGK | 110 | QTVVTQEPSLTVSPGGTVTL TCRSSTGAVTTSNYANWVQ QKPGQAPRGLIGGTNKRAPG TPARFSSGSLLGGKAALTLSG VQPEDEAEYYCALWYSNLW VFGGGTKLTVLGQPKAAPS VTLFPPSSEELQANKATLVC LISDFYPGAVTVAWKADSSP VKAGVETTTPSKQSNNKYA ASSYLSLTPEQWKSHRSYSC QVTHEGSTVEKTVAPTECS | 111 |
| PS3B21 (PSMB121 X CD3B219) | QVQLVQSGAEVKKPGSSVKVSCK ASGGTFSSYAISWVRQAPGQGLE WMGGIIPIFGTANYAQKFQGRVTI TADESTSTAYMELSSLRSEDTAV YYCARASRVWHASYGYLDYWG QGTLVTVSSASTKGPSVFPLAPCS RSTSESTAALGCLVKDYFPEPVTV SWNSGALTSGVHTFPAVLQSSGL YSLSSVVTVPSSSLGTKTYTCNVD HKPSNTKVDKRVESKYGPPCPPC PAPEAAGGPSVFLYPPKPKDTLMI SRTPEVTCVVVDVSQEDPEVQFN WYVDGVEVHNAKTKPREEQFNS TYRVVSVLTVLHQDWLNGKEYK CKVSNKGLPSSIEKTISKAKGQPR EPQVYTLPPSQEEMTKNQVSLTC LVKGFYPSDIAVEWESNGQPENN YKTTPPVLDSDGSFFLYSRLTVDK SRWQEGNVFSCSVMHEALHNHY TQKSLSLSLGK | 97 | EIVLTQSPATLSLSPGERATL SCRASQSVSKWLAWYQQKP GQAPRLLIYDASNRATGIPA RFSGSGSGTDFTLTISSLEPE DFAVYYCQQRFTAPWTFGQ GTKVEIKRTVAAPSVFIFPPS DEQLKSGTASVVCLLNNFYP REAKVQWKVDNALQSGNS QESVTEQDSKDSTYSLSSTLT LSKADYEKHKVYACEVTHQ GLSSPVTKSFNRGEC | 98 |
| | EVQLVESGGGLVQPGGSLRLSCA ASGFTFNTYAMNWVRQAPGKGL EWVARIRSKYNNYATYYAASVK GRFTISRDDSKNSLYLQMNSLKTE DTAVYYCARHGNFGNSYVSWFA YWGQGTLVTVSSASTKGPSVFPL APCSRSTSESTAALGCLVKDYFPE PVTVSWNSGALTSGVHTFPAVLQ SSGLYSLSSVVTVPSSSLGTKTYT CNVDHKPSNTKVDKRVESKYGPP CPPCPAPEAAGGPSVFLFPPKPKD TLMISRTPEVTCVVVDVSQEDPEV QFNWYVDGVEVHNAKTKPREEQ | 110 | QTVVTQEPSLTVSPGGTVTL TCRSSTGAVTTSNYANWVQ QKPGQAPRGLIGGTNKRAPG TPARFSSGSLLGGKAALTLSG VQPEDEAEYYCALWYSNLW VFGGGTKLTVLGQPKAAPS VTLFPPSSEELQANKATLVC LISDFYPGAVTVAWKADSSP VKAGVETTTPSKQSNNKYA ASSYLSLTPEQWKSHRSYSC QVTHEGSTVEKTVAPTECS | 111 |

TABLE 11-continued

Sequences of PSMA X CD3 bispecific antibodies

| Bispecific Ab ID | Heavy Chain Amino acid sequences: PSMA Arm CD3 Arm | SEQ ID NO | Light Chain Amino Acid Sequences: PSMA Arm CD3 Arm | SEQ ID NO |
|---|---|---|---|---|
| | FNSTYRVVSVLTVLHQDWLNGK EYKCKVSNKGLPSSIEKTISKAKG QPREPQVYTLPPSQEEMTKNQVS LTCLVKGFYPSDIAVEWESNGQP ENNYKTTPPVLDSDGSFLLYSKLT VDKSRWQEGNVFSCSVMHEALH NHYTQKSLSLSLGK | | | |
| PS3B20 (PSMB120 X CD3B219) | EVQLVQSGAEVKKPGESLKISCK GSGYSFTSYWIGWVRQMPGKGL EWMGIIYPGDSDTRYSPSFQGQVT ISADKSISTAYLQWSSLKASDTAM YYCARGWAYDRGLDYWGQGTL VTVSSASTKGPSVFPLAPCSRSTSE STAALGCLVKDYFPEPVTVSWNS GALTSGVHTFPAVLQSSGLYSLSS VVTVPSSSLGTKTYTCNVDHKPS NTKVDKRVESKYGPPCPPCPAPE AAGGPSVFLFPPKPKDTLMISRTP EVTCVVVDVSQEDPEVQFNWYV DGVEVHNAKTKPREEQFNSTYRV VSVLTVLHQDWLNGKEYKCKVS NKGLPSSIEKTISKAKGQPREPQV YTLPPSQEEMTKNQVSLTCLVKG FYPSDIAVEWESNGQPENNYKTT PPVLDSDGSFFLYSRLTVDKSRW QEGNVFSCSVMHEALHNHYTQK SLSLSLGK | 99 | DIVMTQSPDSLAVSLGERATI NCKSSQSVLYSSNNKNYLA WYQQKPGQPPKLLIYWAST RESGVPDRFSGSGSGTDFTL TISSLQAEDVAVYYCQQYS TPLTFGQGTKVEIKRTVAAP SVFIFPPSDEQLKSGTASVVC LLNNFYPREAKVQWKVDNA LQSGNSQESVTEQDSKDSTY SLSSTLTLSKADYEKHKVYA CEVTHQGLSSPVTKSPNRGE C | 100 |
| | EVQLVESGGGLVQPGGSLRLSCA ASGFTFNTYAMNWVRQAPGKGL EWVARIRSKYNNYATYYAASVK GRFTISRDDSKNSLYLQMNSLKTE DTAVYYCARHGNFGNSYVSWFA YWGQGTLVTVSSASTKGPSVFPL APCSRSTSESTAALGCLVKDYFPE PVTVSWNSGALTSGVHTFPAVLQ SSGLYSLSSVVTVPSSSLGTKTYT CNVDHKPSNTKVDKRVESKYGPP CPPCPAPEAAGGPSVFLFPPKPKD TLMISRTPEVTCVVVDVSQEDPEV QFNWYVDGVEVHNAKTKPREEQ FNSTYRVVSVLTVLHQDWLNGK EYKCKVSNKGLPSSIEKTISKAKG QPREPQVYTLPPSQEEMTKNQVS LTCLVKGFYPSDIAVEWESNGQP ENNYKTTPPVLDSDGSFLLYSKLT VDKSRWQEGNVFSCSVMHEALH NHYTQKSLSLSLGK | 110 | QTVVTQEPSLTVSPGGTVTL TCRSSTGAVTTSNYANWVQ QKPGQAPRGLIGGTNKRAPG TPARFSSGSLLGGKAALTLSG VQPEDEAEYYCALWYSNLW VFGGGTKLTVLGQPKAAPS VTLFPPSSEELQANKATLVC LISDFYPGAVTVAWKADSSP VKAGVETTTPSKQSNNKYA ASSYLSLTPEQWKSHRSYSC QVTHEGSTVEKTVAPTECS | 111 |
| PS3B19 (PSMB119 X CD3B219) | EVQLVQSGAEVKKPGESLKISCK GSGYSETSYWIGWVRQMPGKGL EWMGIIYPGDSDTRYSPSFQGQVT ISADKSISTAYLQWSSLKASDTAM YYCARAYHYSKGLDYWGQGTLV TVSSASTKGPSVFPLAPCSRSTSES TAALGCLVKDYFPEPVTVSWNSG ALTSGVHTFPAVLQSSGLYSLSSV VTVPSSSLGTKTYTCNVDHKPSN TKVDKRVESKYGPPCPPCPAPEA AGGPSVFLFPPKPKDTLMISRTPE VTCVVVDVSQEDPEVQFNWYVD GVEVHNAKTKPREEQFNSTYRVV SVLTVLHQDWLNGKEYKCKVSN KGLPSSIEKTISKAKGQPREPQVY TLPPSQEEMTKNQVSLTCLVKGF YPSDIAVEWESNGQPENNYKTTP PVLDSDGSFFLYSRLTVDKSRWQ EGNVFSCSVMHEALHNHYTQKSL SLSLGK | 101 | DIVMTQSPDSLAVSLGERATI NCKSSQSVLYSSNNKNYLA WYQQKPGQPPKLLIYWAST RESGVPDRFSGSGSGTDFTL TISSLQAEDVAVYYCQQYS TPLTFGQGTKVEIKRTVAAP SVFIFPPSDEQLKSGTASVVC LLNNFYPREAKVQWKVDNA LQSGNSQESVTEQDSKDSTY SLSSTLTLSKADYEKHKVYA CEVTHQGLSSPVTKSFNRGE C | 100 |
| | EVQLVESGGGLVQPGGSLRLSCA ASGFTFNTYAMNWVRQAPGKGL | 110 | QTVVTQEPSLTVSPGGTVTL TCRSSTGAVTTSNYANWVQ | 111 |

TABLE 11-continued

Sequences of PSMA X CD3 bispecific antibodies

| Bispecific Ab ID | Heavy Chain Amino acid sequences: PSMA Arm CD3 Arm | SEQ ID NO | Light Chain Amino Acid Sequences: PSMA Arm CD3 Arm | SEQ ID NO |
|---|---|---|---|---|
| | EWVARIRSKYNNYATYYAASVK GRFTISRDDSKNSLYLQMNSLKTE DTAVYYCARHGNFGNSYVSWFA YWGQGTLVTVSSASTKGPSVFPL APCSRSTSESTAALGCLVKDYFPE PVTVSWNSGALTSGVHTFPAVLQ SSGLYSLSSVVTVPSSSLGTKTYT CNVDHKPSNTKVDKRVESKYGPP CPPCPAPEAAGGPSVFLFPPKPKD TLMISRTPEVTCVVVDVSQEDPEV QFNWYVDGVEVHNAKTKPREEQ FNSTYRVVSVLTVLHQDWLNGK EYKCKVSNKGLPSSIEKTISKAKG QPREPQVYTLPPSQEEMTKNQVS LTCLVKGFYPSDIAVEWESNGQP ENNYKTTPPVLDSDGSFLLYSKLT VDKSRWQEGNVFSCSVMHEALH NHYTQKSLSLSLGK | | QKPGQAPRGLIGGTNKRAPG TPARFSSGSLLGGKAALTLSG VQPEDEAEYYCALWYSNLW VFGGGTKLTVLGQPKAAPS VTLFPPSSEELQANKATLVC LISDFYPGAVTVAWKADSSP VKAGVETTTPSKQSNNKYA ASSYLSLTPEQWKSHRSYSC QVTHEGSTVEKTVAPTECS | |

TABLE 12

VH/VL Sequences of PSMA x CD3 bispecific antibodies

| Bispecific antibody | ARM 1 | SEQ ID NO: VH | SEQ ID NO: VL | ARM 2 | SEQ ID NO: (VH; VL IgG4PAA F405L, R409K) VH | SEQ ID NO: (VH; VL IgG4PAA F405L, R409K) VL |
|---|---|---|---|---|---|---|
| PS3B2 | PSMB120 (FAB PSMB25) | 77 | 78 | CD3B217 | 102 | 103 |
| PS3B3 | PSMB121 (FAB PSMB49) | 75 | 76 | CD3B217 | 102 | 103 |
| PS3B4 | PSMB122 (FAB PSMB51) | 74 | 61 | CD3B217 | 102 | 103 |
| PS3B5 | PSMB123 (FAB PSMB55) | 75 | 76 | CD3B217 | 102 | 103 |
| PS3B7 | PSMB87 (FAB PSMB58) | 160 | 64 | CD3B217 | 102 | 103 |
| PS3B8 | PSMB126 (FAB PSMB80) | 68 | 69 | CD3B217 | 102 | 103 |
| PS3B9 | PSMB127 (FAB PSMB83) | 66 | 67 | CD3B217 | 102 | 103 |
| PS3B10 | PSMB128 (FAB PSMB84) | 64 | 65 | CD3B217 | 102 | 103 |
| PS3B11 | PSMB129 (FAB PSMB109) | 60 | 61 | CD3B217 | 102 | 103 |
| PS3B12 | PSMB130 (FAB PSMB86) | 62 | 63 | CD3B217 | 102 | 103 |
| PS3B19 | PSMB119 (FAB PSMB18) | 79 | 78 | CD3B219 | 104 | 105 |
| PS3B20 | PSMB120 (FAB PSMB25) | 77 | 178 | CD3B219 | 104 | 105 |
| PS3B21 | PSMB121 (FAB PSMB49) | 75 | 76 | CD3B219 | 104 | 105 |
| PS3B22 | PSMB122 (FAB PSMB51) | 74 | 61 | CD3B219 | 104 | 105 |
| PS3B23 | PSMB123 (FAB PSMB55) | 75 | 76 | CD3B219 | 104 | 105 |
| PS3B24 | PSMB124 (FAB PSMB56) | 70 | 71 | CD3B219 | 104 | 105 |
| PS3B25 | PSMB87 (FAB PSMB58) | 160 | 65 | CD3B219 | 104 | 105 |
| PS3B26 | PSMB126 (FAB PSMB80) | 68 | 69 | CD3B219 | 104 | 105 |
| PS3B27 | PSMB127 (FAB PSMB83) | 66 | 67 | CD3B219 | 104 | 105 |
| PS3B28 | PSMB128 (FAB PSMB84) | 64 | 65 | CD3B219 | 104 | 105 |
| PS3B29 | PSMB129 (FAB PSMB109) | 60 | 61 | CD3B219 | 104 | 105 |
| PS3B30 | PSMB130 (FAB PSMB86) | 62 | 63 | CD3B219 | 104 | 105 |

Example 7. Characterization by Cell-Binding

PSMAxCD3 bispecific antibodies were tested for binding to PSMA positive cell lines LNCAP, human PSMA-HEK, Chimpanzee-PSMA-HEK and Cynomolgous monkey PSMA-HEK. To assess the binding capabilities of the PSMA bispecific antibodies, the cell-binding assay was utilized (described previously). Briefly, PSMA expressing tumor cells are bound by bispecific antibodies at known concentrations and the bound antibody is detected by an anti-human kappa light chain PE conjugated detection reagent (Invitrogen). The Mean Fluorescents Intensity (MFI) is the measure of bound bispecific antibody. The MFI is converted to a relative $EC_{50}$. $EC_{50}$ is a commonly used dose-response curve, where the half maximal effective concentration or the $EC_{50}$ point is defined as the inflection point of the curve. $EC_{50}$ s were determined by measuring cell bound bispecific and known concentrations. High concentrations resulted in maximum target antigen binding i.e. full binding saturation. The dose response curves were then diluted down to that of background or no bispecific binding. The inflection point of this curve reflects the $EC_{50}$ point. The calculated $EC_{50}$ is determined by taking the ug/ml amount of bispecific antibody at the $EC_{50}$ point and converting it to a molarity value based on the MW of the bispecific antibody. Bispecific antibodies were normalized for protein concentration and then incubated with the same number of cells expressing either human or cyno PSMA. The MFI at each concentration was collected by flow cytometry and plotted as a function of concentration. Data was transformed via log 10 and then plotted. Nonlinear regression of binding curves was done to determine $EC_{50}$ s. These relative values were used for ranking PSMA binding to target cells. Table 12 contains the relative $EC_{50}$ binding values for whole cell binding studies using LNCaP, cyno and chimp PSMA-expressing cell lines.

Figure 12:
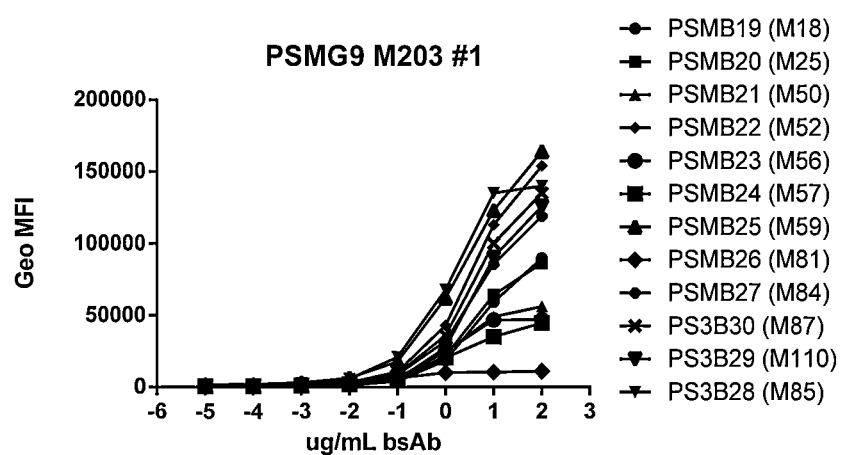
FIG. 12 shows titration curves for PSMA×CD3 bispecific antibodies binding to Chimpanzee PSMA-expressing HEK cells.
Figure 13:
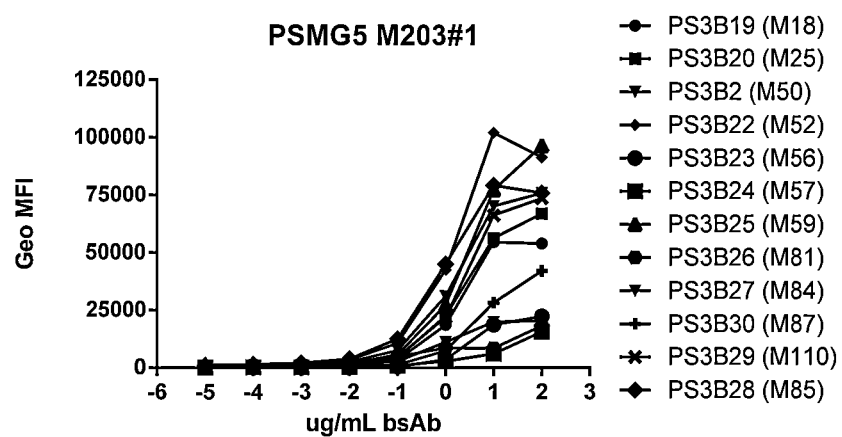
FIG. 13 shows titration curves for PSMA×CD3 bispecific antibodies binding to Cynomolgus monkey PSMA-expressing HEK cells.
Figure 14:
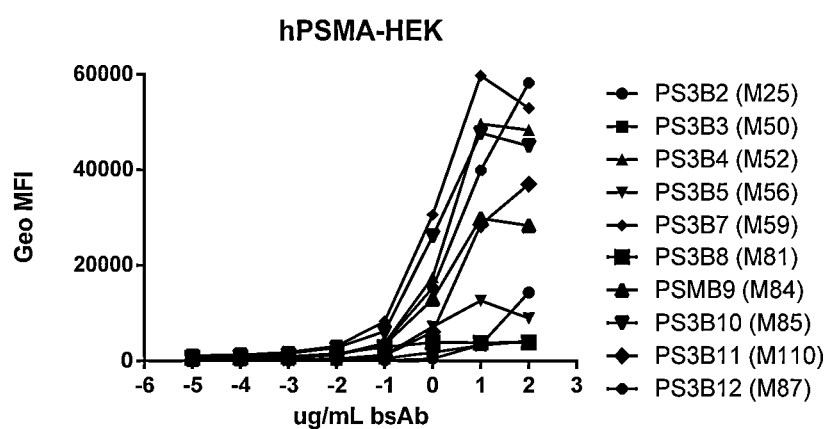
FIG. 14 shows titration curves for PSMA×CD3 bispecific antibodies binding to human PSMA-expressing HEK cells.

FIG. 11 shows LNCAP binding of all bispecific antibodies prepared. The binding data suggests that 3 populations of binding are observed: 1) strong binding, 2) medium binding, and 3) weak/no binding. The PSMAxnull arm bispecific antibodies maintain binding to LNCAP cells (FIG. 11E), but there is no binding observed for the nullxCD3 arm bispecific antibodies (FIG. 11F). The medium affinity and high affinity CD3 arm bispecific antibodies with the same PSMA arm bind similarly. For the remaining assays, only bispecific antibodies that were positive LNCaP binders were used to assess binding activity to Chimp PSMA-HEK (FIG. 12), Cyno PSMA-HEK (FIG. 13), Human-PSMA-HEK (FIG. 14), or Parental HEK293 (data not shown). For each cell line, either the high-affinity or medium affinity CD3 binders were tested. The hPSMA-HEK binding data suggests that there may be subtle differences between LNCaP and this cell line; however, the same overall order of binding is evident. PS3B19, derived from LNCaP panning, appears to bind as strongly to hPSMA-HEK cells. The bispecific antibodies show a wide range of binding profiles on Chimp-PSMA HEK. Interestingly, hits that were panned on the Chimp-PSMA HEK cell line have a stronger binding profile, while those that were panned on LNCaP show weaker binding. There was no binding observed to the parental HEK cells in this experiment (data not shown).

Following recombination into bispecific antibodies, several clones consistently outperform others and bind cross-species. These bispecific antibodies are PS3B21, PS3B22, PS3B26, PS3B27, PS3B28 and PS3B30 which correspond to mAbs PSMB121, PSMB122, PSMB126, PSMB127, PSMB128 and PSMB130. Cell based binding $EC_{50}$'s and calculated $EC_{50}$'s are shown in Table 13.

TABLE 13

Cell Based Binding $EC_{50}$'s.

| | LNCaP | | Cyno | | Chimp | |
| --- | --- | --- | --- | --- | --- | --- |
| bsAb | $EC_{50}$ (ug/mL) | Calculated $EC_{50}$ (nM) | $EC_{50}$ (ug/mL) | Calculated $EC_{50}$ (nM) | $EC_{50}$ (ug/mL) | Calculated $EC_{50}$ (nM) |
| PS3B19 | too weak | N/A | 1.757 | 12.4 | 5.10 | 35.93 |
| PS3B20 | 122.7 | 864.1 | 2.003 | 14.1 | 3.33 | 23.44 |
| PS3B21 | 0.7368 | 5.2 | 0.8604 | 6.1 | 1.25 | 8.81 |
| PS3B22 | 2.603 | 18.3 | 1.137 | 8 | 3.02 | 21.23 |
| PS3B23 | too weak | N/A | 3.744 | 26.4 | 0.88 | 6.18 |
| PS3B24 | too weak | N/A | 18.22 | 128.3 | 1.10 | 7.75 |
| PS3B26 | 0.07147 | 0.5 | 0.3706 | 2.6 | 0.05 | 0.34 |
| PS3B27 | 2.07 | 14.6 | 1.403 | 9.9 | 3.24 | 22.83 |
| PS3B28 | 1.157 | 8.1 | 0.6879 | 4.8 | 1.01 | 7.08 |
| PS3B29 | 7.766 | 54.7 | 2.539 | 17.9 | 4.11 | 28.93 |
| PS3B30 | 1.203 | 8.5 | 5.37 | 37.8 | 3.29 | 23.19 |

All bispecific antibodies maintained the ability to bind PSMA positive cell lines. Several of the antibodies bound well to chimp and cyno PSMA-expressing cells, but only weakly to LNCaP cells. LNCAP binding $EC_{50}$'s ranged from 0.5 nM to 864 nM, whereas Cyno PSMA expressing HEK binding $EC_{50}$'s ranged from 0.9 to 128 nM and Chimp PSMA HEK binding ranged from 36-0.3 nM (Table 12). Based on cell binding $EC_{50}$'s several of the anti-PSMA bispecific antibodies met the criteria of 20 nM or tighter binding for human PSMA, and 50 nM or tighter binding for cyno PSMA.

Example 8. Affinity Characterization by Proteon and Biacore

To further evaluate the antibodies, the rates of chimp PSMA ECD association and dissociation were measured for the hits that were carried forward from Cell-binding assays. The interactions of PSMAxCD3 bispecific mAbs with target (recombinant Chimp, PSMA) were studied by Surface Plasmon Resonance (SPR) using a ProteOn XPR36 system (BioRad). A biosensor surface was prepared by coupling anti-Human IgG Fc (Jackson ImmunoResearch Laboratory, cat #109-005-098) to the modified alginate polymer layer surface of a GLC chip (BioRad, cat #176-5011) using the manufacturer instructions for amine-coupling chemistry. Approximately 4400 RU (response units) of anti-Human IgG Fc antibodies were immobilized. The kinetic experiments were performed at 25° C. in running buffer (DPBS+ 0.03% P20+100 µg/ml BSA). To perform kinetic experiments, 100 RU of bispecific antibodies were captured followed by injections of analytes (recombinant Chimp PSMA ECD) at concentrations ranging from 3.7 nM to 300 nM (in a 3-fold serial dilution). The association phase was monitored for 3 minutes at 50 µL/min, then followed by 15 minutes of buffer flow (dissociation phase). The chip surface was regenerated with two 18 second pulses of 100 mM Phosphoric acid ($H_3PO_4$, Sigma, cat #7961) at 100 µL/min.

The collected data were processed using ProteOn Manager software. First, the data was corrected for background using inter-spots. Then, double reference subtraction of the data was performed by using the buffer injection for analyte injections. The kinetic analysis of the data was performed using a Langmuir 1:1 binding model. The result for each bispecific antibody was reported in the format of $k_a$ (On-rate), $k_d$ (Off-rate) and $K_D$ (equilibrium dissociation constant). Results are shown in Tables 14-18.

Results:

TABLE 14

Summary of kinetics and affinity for PS3B25 and PS3B27 binding to recombinant human PSMA (3.7-300 nM). The parameters reported in this table were obtained from a 1:1 Langmuir binding model. Affinity, $K_D = k_d/k_a$.

| AKA | Bispecific Ab Protein ID | $k_a$ (1/Ms) $10^5$ | $k_d$ (1/s) $10^{-03}$ | $K_D$ (nM) |
|---|---|---|---|---|
| PSMB87 × CD3B219 | PS3B25 | 1.88 ± 0.13 | 1.01 ± 0.05 | 5.38 ± 0.55 |
| PSMB127 × CD3B219 | PS3B27 | 2.87 ± 0.36 | 2.89 ± 0.70 | 10.3 ± 3.2 | n = 3 independent experiments with 2 replicates. Results listed as average ± standard deviation.

TABLE 15

Summary of kinetics and affinity for PS3B25 and PS3B27 binding to recombinant chimp PSMA (3.7-300 nM). The parameters reported in this table were obtained from a 1:1 Langmuir binding model. Affinity, $K_D = k_d/k_a$.

| AKA | Bispecific Ab Protein ID | $k_a$ (1/Ms) $10^5$ | $k_d$ (1/s) $10^{-03}$ | $K_D$ (nM) |
|---|---|---|---|---|
| PSMB87 × CD3B219 | PS3B25 | 2.81 ± 0.08 | 0.99 ± 0.04 | 3.54 ± 0 25 |
| PSMB127 × CD3B219 | PS3B27 | 2.08 ± 0.38 | 1.56 ± 0.37 | 7.48 ± 0.97 | n = 3 independent experiments with 2 replicates. Results listed as average ± standard deviation.

TABLE 16

Summary of kinetics and affinity for PS3B25 and PS3B27 binding to recombinant cyno PSMA (3.7-300 nM). The parameters reported in this table were obtained from a 1:1 Langmuir binding model. Affinity, $K_D = k_d/k_a$.

| AKA | Bispecific Ab Protein ID | $k_a$ (1/Ms) $10^5$ | $k_d$ (1/s) $10^{-03}$ | $K_D$ (nM) |
|---|---|---|---|---|
| PSMB87 × CD3B219 | PS3B25 | 0.98 ± 0.04 | 7.97 ± 0.34 | 81.1 ± 3.3 |
| PSMB127 × CD3B219 | PS3B27 | 1.59 ± 0.12 | 1.10 ± 0.04 | 7.00 ± 0.68 | n = 3 independent experiments with 2 replicates. Results listed as average ± standard deviation.

TABLE 17

Comparing the Human, Chimp and Cyno binding affinity of PS3B25 and PS3B27. Affinity, $K_D = k_d/k_a$.

| Sample | Human $K_D$ (nM) | Chimp $K_D$ (nM) | Cyno $K_D$ (nM) |
|---|---|---|---|
| PS3B25 | 5.38 ± 0.55 | 3.54 ± 0.25 | 81.1 ± 3.3 |
| PS3B27 | 10.3 ± 3.2 | 7.48 ± 0.97 | 7.00 ± 0.68 |

TABLE 18

Summary of kinetics and affinity for bispecific mAbs binding to recombinant chimp PSMA (3.7-300 nM). The parameters reported in this table were obtained from a 1:1 Langmuir binding model. Affinity, $K_D = k_d/k_a$.

| Bispecific Ab Protein ID | ka(1/Ms) | kd(1/s) | KD (nM) |
|---|---|---|---|
| PS3B19 | 1.26E+04 | 2.98E−04 | 23.6 |
| PS3B20 | 1.76E+04 | 3.78E−04 | 21.4 |
| PS3B21 | 6.70E+04 | 4.73E−04 | 7.1 |
| PS3B22 | 6.51E+04 | 1.24E−03 | 19 |
| PS3B23 | 9.89E+05 | 1.76E−03 | 1.8 |
| PS3B24 | 6.26E+03 | 2.52E−04 | 40.3 |
| PS3B25 | 1.95E+05 | 1.06E−03 | 5.5 |
| PS3B26 | | | No binding |
| PS3B27 | 1.70E+05 | 1.76E−03 | 10.4 |
| PS3B28 | 1.341+05 | 2.33E−03 | 17.4 |
| PS3B29 | 6.71E+04 | 6.80E−03 | 101 |
| PS3B30 | 7.34E+04 | 1.65E−03 | 22.4 |
| PS3B31 | | | No binding |
| PS3B32 | | | No binding |
| PS3B33 | | | No binding |
| PS3B34 | | | No binding |
| PSMA null | | | No binding |

For the most part, Proteon binding parallels the cell-binding. However, one of the bispecific antibodies showed no binding to recombinant chimp PSMA ECD although it bound to chimp PSMA expressed on the cell surface of HEK cells. This antibody, PS3B26, is a cell only binder and was culled from subsequent binding experiments. One of the positive binders, PS3B23 showed biphasic binding and did not fit well to the 1:1 binding model. Ten of the bispecific antibodies were positive binders to recombinant Chimp PSMA ECD by Proteon and their affinity was further profiled by BIACORE.

Binding to recombinant Chimp PSMA by Biacore. The Affinity measurements using Surface Plasmon Resonance (SPR) were performed using a Biacore 3000 optical biosensor (Biacore-GE Healthcare). A biosensor surface was prepared by coupling anti-Human IgG Fc (Jackson ImmunoResearch Laboratory, cat #109-005-098) to the carboxymethylated dextran surface of a CM-5 chip (Biacore, cat #BR-1000-12) using the manufacturer instructions for amine-coupling chemistry. Approximately 16,000 RU (response units) of anti-Human IgG Fc antibodies were immobilized in each of four flow cells. The kinetic experiments were performed at 25° C. in running buffer (DPBS+ 0.03% P20+100 g/ml BSA). Dilutions of antigen (recombinant Chimp PSMA, concentration either from 1.2-300 nM or 3.7-900 nM in a 3-fold serial dilution) were prepared in running buffer. About 100 RU of PSMA×CD3 bispecific mAbs were captured on flow cell 2 to 4 of the sensor chip. Flow cell 1 was used as reference surface. Capture of PSMA×CD3 bispecific mAb was followed by a 3 or 5-minute injection (association phase) of antigen (recombinant Chimp PSMA) at 50 μl/min, followed by 15 or 20 minutes of buffer flow (dissociation phase). The chip surface was regenerated by two 18-second injections of 100 mM Phosphoric acid ($H_3PO_4$, Sigma, cat #7961) at 50 μl/min.

The collected data were processed using BIAevaluation software (Biacore). First, double reference subtraction of the data was performed by subtracting the curves generated by buffer injection from the reference-subtracted curves for analyte injections. Then kinetic analysis of the data was performed using a Langmuir 1:1 binding model with global fit. The result for each PSMA×CD3 bispecific mAb was reported in the format of $k_a$ (On-rate), $k_d$ (Off-rate) and $K_D$ (Equilibrium dissociation constant).

TABLE 19

Summary of kinetics and affinity for Bispecific mAbs binding to recombinant chimp PSMA ECD by Biacore

|  | ka (1/Ms) | kd(1/s) | KD (nM) |
|---|---|---|---|
| PS3B19 | 6.24E+03 | 4.14E−04 | 66.3 |
| PS3B20 | 7.82E+03 | 4.61E−04 | 59.1 |
| PS3B21 | 1.10E+04 | 4.89E−04 | 44.4 |
| PS3B22 | 1.66E+04 | 1.00E−03 | 60.4 |
| PS3B23 | 1.34E+05 | 1.22E−03 | 9.1 |
| PS3B24 | 2.35E+04 | 9.07E−04 | 38.6 |
| PS3B25 | 6.59E+04 | 1.08E−03 | 16.4 |
| PS3B27 | 8.90E+04 | 2.00E−03 | 22.4 |
| PS3B28 | 6.20E+04 | 1.91E−03 | 30.8 |
| PS3B29 | 2.74E+04 | 1.59E−03 | 58.1 |
| PS3B30 | 3.48E+04 | 1.82E−03 | 52.3 |

All bispecific antibodies that bound to Chimp PSMA ECD by Proteon, also bound via Biacore. Binding affinities were somewhat weaker by Biacore.

Example 9. Evaluation of PSMA×CD3 Bispecific Abs in Functional Cell Killing Assay T cell mediated cytotoxicity assays were used as a functional screen of bispecific antibody activity. Bispecifics were tested for the ability to lyse human PSMA overexpressing HEK cells, as well as the human prostate cancer cell line LNCAP. In addition, bispecifics were tested for the ability to kill cyno PSMA HEK cells to confirm species cross reactivity A Chromium-51 release assay was used to measure cytotoxicity of individual bispecific antibodies. Cytotoxicity is measured by the amount of chromium release into the culture medium as a result of cell lysis in the presence of activated T-cells. The amount of release is compared to spontaneous release of chromium in target cells only and maximum release via total target cell lysis with Triton-X.

Human Pan T-cells (CD3+) from multiple donors were pre-activated overnight with OKT3 coated flasks (1 ug/ml) and IL-2 at 20 U/ml. T-cells were washed 2×. The target cell line was labelled for 1 hr with Chromium-51. T-cells and target cells were cultured at a 5:1 ratio for 18-24 hours before culture supernantant was harvested and analyzed. All points were run in triplicate and reported as a Cytoxicity Mean of the triplicate and SEM. Dilutions of bispecific antibody from 10 ug/ml-0,00001 ug/ml were used.

Figure 15A:
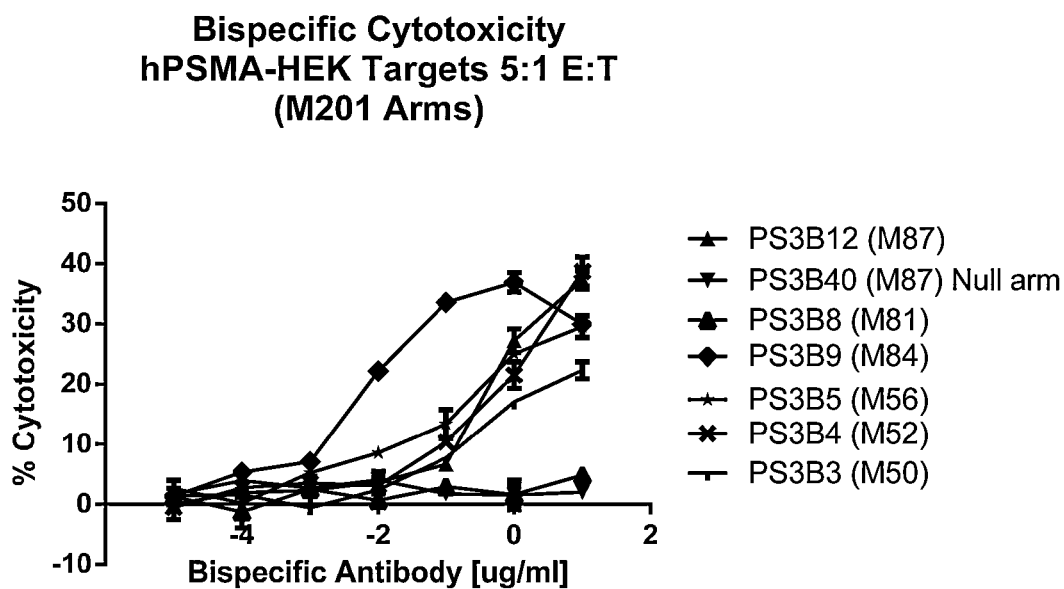
FIG. 15A and FIG. 15B show titration curves for PSMA×CD3 bispecific antibodies for human PSMA-expressing HEK cells in a T-cell-mediated chromium release toxicity assay.
Figure 15B:
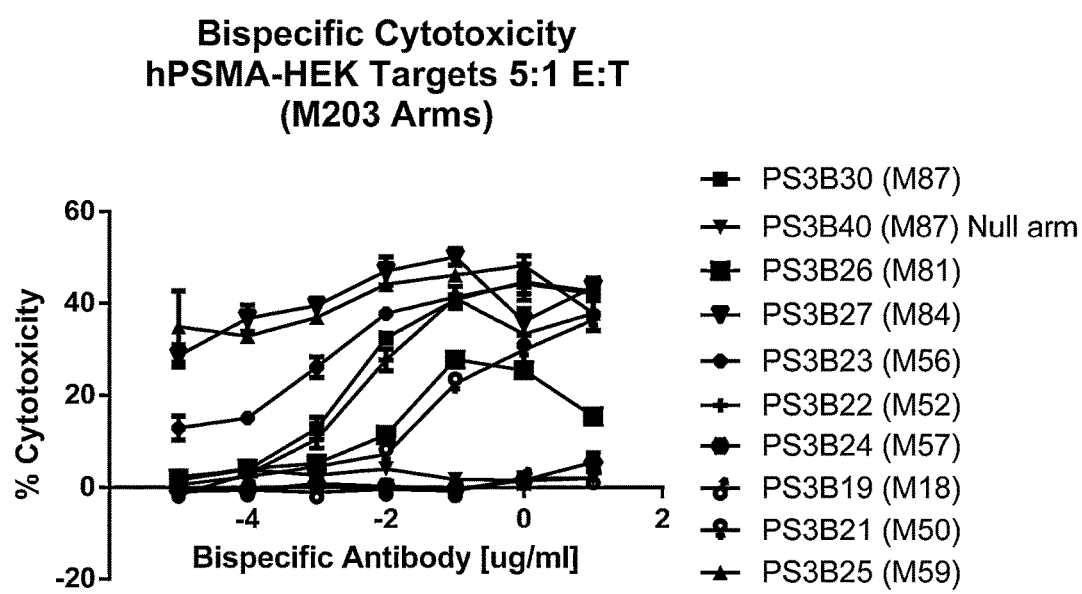
Figure 16A:
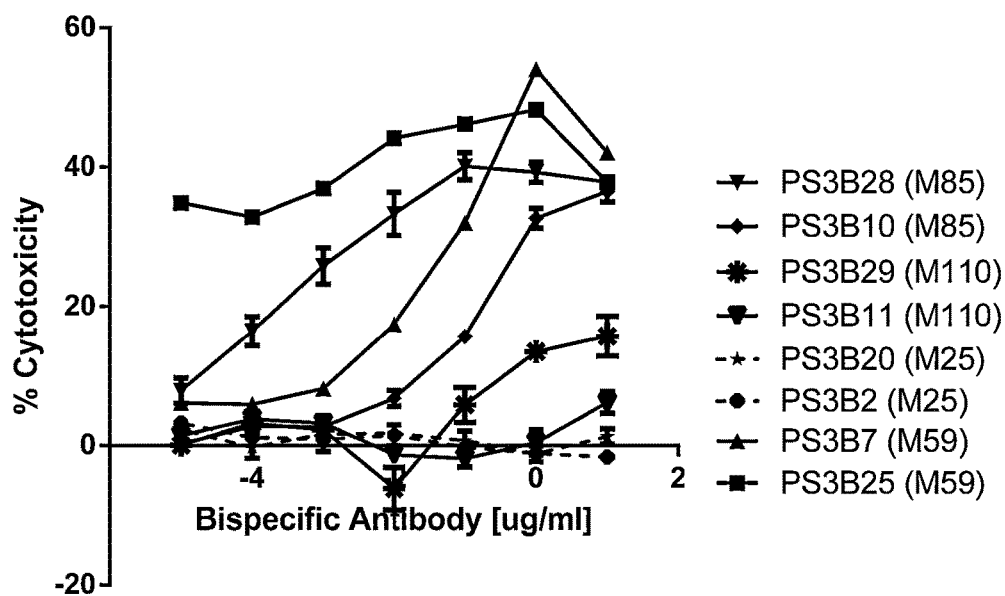
FIG. 16A and FIG. 16B show the comparison of medium vs high affinity CD3 arms in PSMA×CD3 bispecific antibodies in a T-cell-mediated chromium release toxicity assay for human PSMA-expressing HEK cells.
Figure 16B:
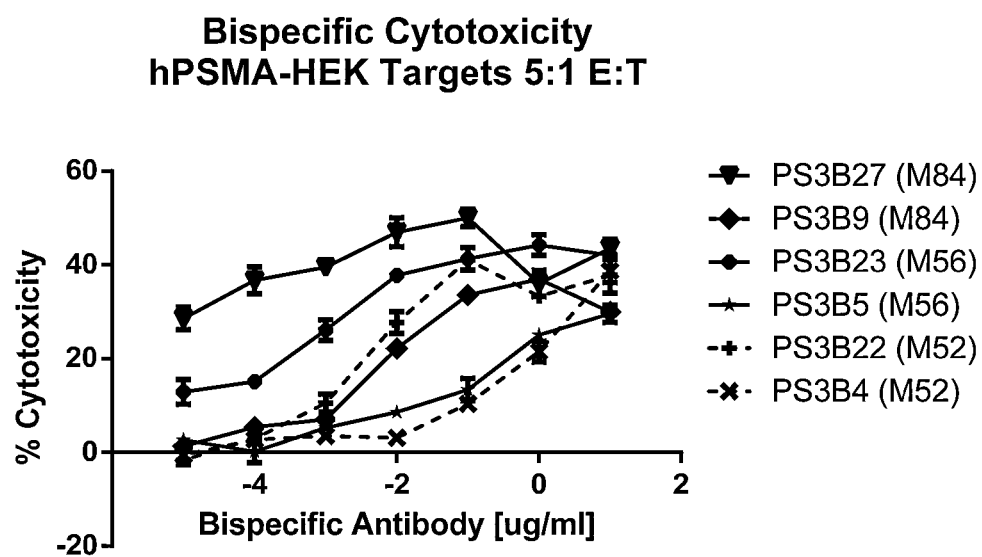

FIG. 15A and FIG. 15B show T cell mediated killing for all PSMA×CD3 bispecific antibodies against hPSMA-HEK cells. For this experiment, the medium and high affinity CD3 arm bispecific antibodies were tested. Cell killing is evident for most of the high affinity CD3 arm molecules, with several of the bispecific antibodies showing killing at the lowest concentration tested. PS3B9 was the only medium affinity bispecific antibody that showed significant cell killing at lower concentrations. FIG. 16A and FIG. 16B show T cell mediated killing for several pairs of bispecific antibodies. From this data it is clear that the high affinity CD3 binding bispecific antibodies generate the most cell killing and these were the subject of further cell killing experiments.

Figure 17:
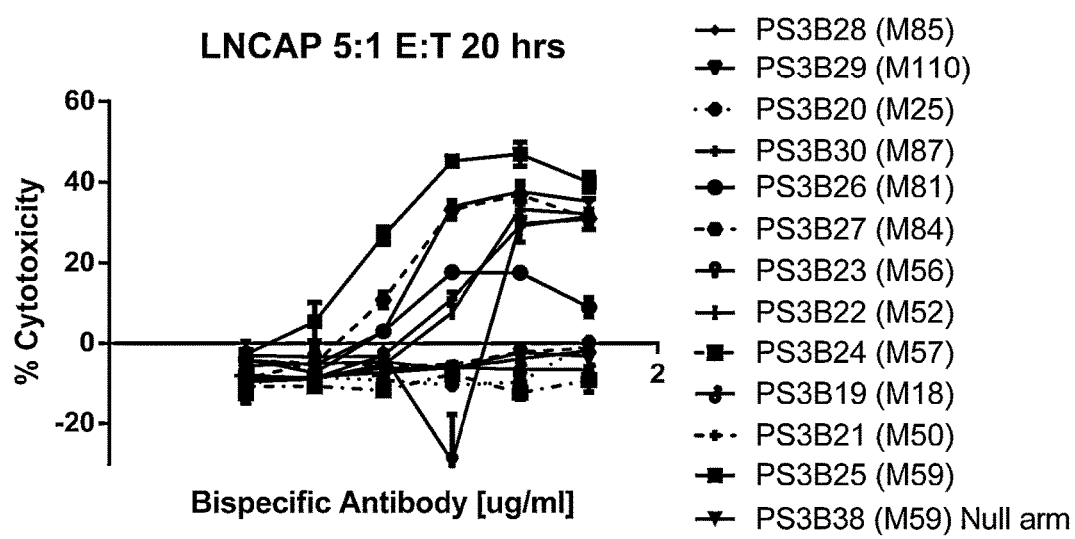
FIG. 17 shows titration curves for PSMA×CD3 bispecific antibodies for LNCaP cells in a T-cell-mediated chromium release toxicity assay.

FIG. 17 shows cell killing data for PSMA×CD3 bispecific antibodies with the high affinity CD3 arm generated against LNCAP cells. PS3B25, PS3B27, PS3B28, PS3B30, PS3B23 and PSB22 all had T cell redirection activity. PS3B29 showed activity on hPSMA-HEK cell at the highest concentrations but not on LNCAPs suggesting that because it is a weak PSMA binder, it is not able to bind well when PSMA expression levels are low. In contrast, PS3B25, PS3B27 and PS3B28 showed the highest LNCAP tumor cell lysis. A bispecific antibody PS3B38 consisting of PSMB125 and a null arm against RSV protein did not have cytolytic activity as expected due to inability to bind T cells.

Figure 18:
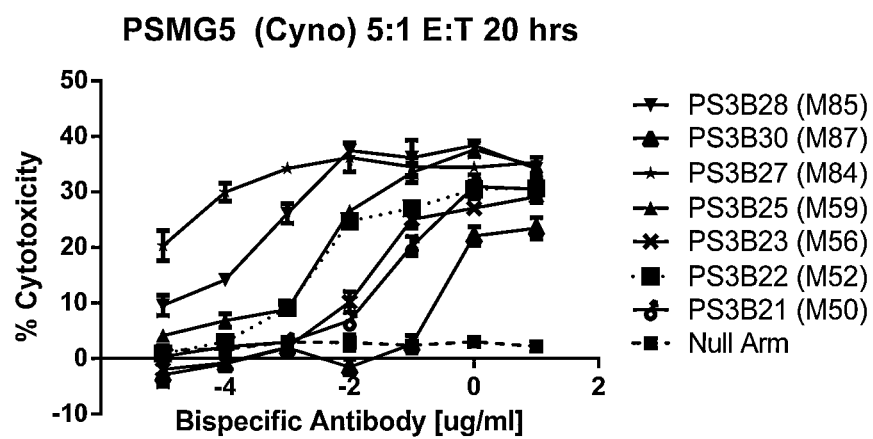
FIG. 18 shows titration curves for PSMA×CD3 bispecific antibodies for Cynomolgus monkey PSMA-expressing HEK cells in a T-cell-mediated chromium release toxicity assay.

To confirm cyno PSMA T cell redirection function Bispecific antibodies were tested for cyno PSMA-HEK cell lysis, shown on FIG. 18. All Bispecific antibodies tested were able to kill cells expressing cyno PSMA with PS3B27 and PS3B28 having the highest activity. From previous cell binding studies these anti-PSMA arms had higher affinity for cyno versus human PSMA and this observation was also reflected in cyno PSMA target cell killing. PS3B27 and PS3B30 were tested for killing of the parental HEK cell line and did not lyse the HEK parent cell line (data not shown).

The PSMA antibodies PSMB127 and PSMB130, which generate the PSMA×CD3 Bispecific antibodies PS3B27 and PS3B30, respectively, were selected for further analysis. PS3B27 and PS3B30 killed both human and cyno PSMA targets and had the high affinity CD3 arm. PS3B27 bound human PSMA expressing cell lines with substantially the same, $EC_{50}$'s of ~14.6 nM and cyno of ~9.9 nM. PS3B30 bound human PSMA with approximately 5-6 fold affinity difference, with $EC_{50}$'s of ~8-8.5 nM and cyno PSMA at ~37.8-57 nM. Although the difference between human and cyno binding may be greater than 5-fold, PS3B27 showed functional killing of both human and cyno targets.

The interactions of PS3B27 with recombinant Chimp PSMA ECD was repeated and interactions with recombinant Cyno PSMA ECD and Human PSMA ECD were studied by Surface Plasmon Resonance (SPR) using a ProteOn XPR36 system (BioRad) as described previously for recombinant chimp PSMA ECD. Summary of kinetics and affinity for binding to chimp, cyno and human PSMA ECD are shown in Table 20. This bispecific antibody binds all targets with substantially the same affinity.

TABLE 20

Summary of kinetics and affinity for PS3B25 and PS3B27 binding to recombinant target PSMA ECDs

|  | $k_a$ (1/Ms) $10^5$ | | $k_d$ (1/s) $10^{-03}$ | | $K_D$ (nM) | |
|---|---|---|---|---|---|---|
| target | PS3B25 | PS3B27 | PS3B25 | PS3B27 | PS3B25 | PS3B27 |
| Chimp | 2.81 ± 0.08 | 2.08 ± 0.38 | 0.99 ± 0.04 | 1.56 ± 0.37 | 3.54 ± 0.25 | 7.48 ± 0.97 |
| Cyno | 0.98 ± 0.04 | 1.59 ± 0.12 | 7.97 ± 0.34 | 1.10 ± 0.04 | 81.1 ± 3.3 | 7.00 ± 0.68 |
| Human | 1.88 ± 0.13 | 2.87 ± 0.36 | 1.01 ± 0.05 | 2.89 ± 0.70 | 5.38 ± 0.55 | 10.3 ± 3.2 |

Evaluation of bispecific antibody, PS3B27 in a caspase assay. T-cell mediated killing of PS3B27 was measured using a second cell toxicity assay. The caspase cytotoxicity assay indirectly measures cell killing via cleavage of a fluorescent substrate by active caspase 3/7. Cleavage of the substrate results in a fluorescent DNA dye, with fluorescence restricted to the cell nucleus. Repeated fluorescence measurements are taken in each well throughout the course of the assay, using a motorized 1 OX objective, capable of precisely imaging well(s) at the same coordinates. Target cell populations are identified based on defined size restrictions and/or through the use of a secondary label.

Frozen Pan CD3+ T-cells (purchased from Biological Specialty Corporation, Colmar, Pa.) were isolated by negative selection from normal healthy donors. Prostate cancer cells expressing PSMA (LNCaP, C42) were cultured in RPMI 1640 with 10% HI FBS+supplements (purchased from Life Technologies).

T-cells and target cells were combined at an effector to target ratio (E:T) of 3:1 in Phenol Red free RPMI+10% FBS and supplements (Life Technologies), without selection reagents, and 0.6 uL of NucView caspase reagent (Essen Bioscience) was added to each mL of cells, per manufacturer guidelines. A total volume of 0.1 mL cells were added to appropriate wells of a clear, 96-well flat-bottom plate (BD Falcon). PS3B27 (CD3×PSMA), CD3B288 (CD3×Null) or PS3B46 (PSMA×Null) Bispecific antibodies were prepared at 2× final concentration in Phenol Red free RPMI, prepared as indicated above, and 0.1 mL of compounds were added to each well. After a 30 minute incubation at room temperature to minimize cell aggregation at the edge of wells, plates were transferred to the Zoom Incucyte instrument (Essen Bioscience). The Incucyte Instrument resides in a humidified incubator set at 37° C., 5% CO2.

Processing definitions on the Incucyte were designed for each cell line tested, per manufacture guidelines. Measurements were taken every six hours, until a plateau in the caspase signal was observed, and followed by three or more successive decreases from the maximum signal in the well(s) containing the highest concentration of the test compound(s).

Figure 19A:
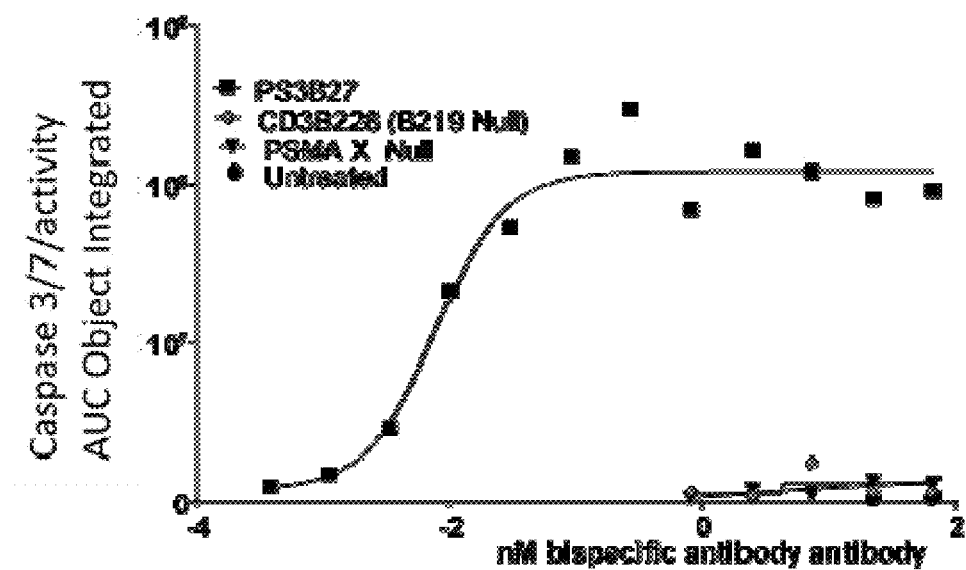
FIG. 19A shows titration curves for PS3B27 and control bispecific antibodies for human PSMA-expressing HEK cells in a T-cell-mediated Caspase 3/7 toxicity assay.
Figure 19B:
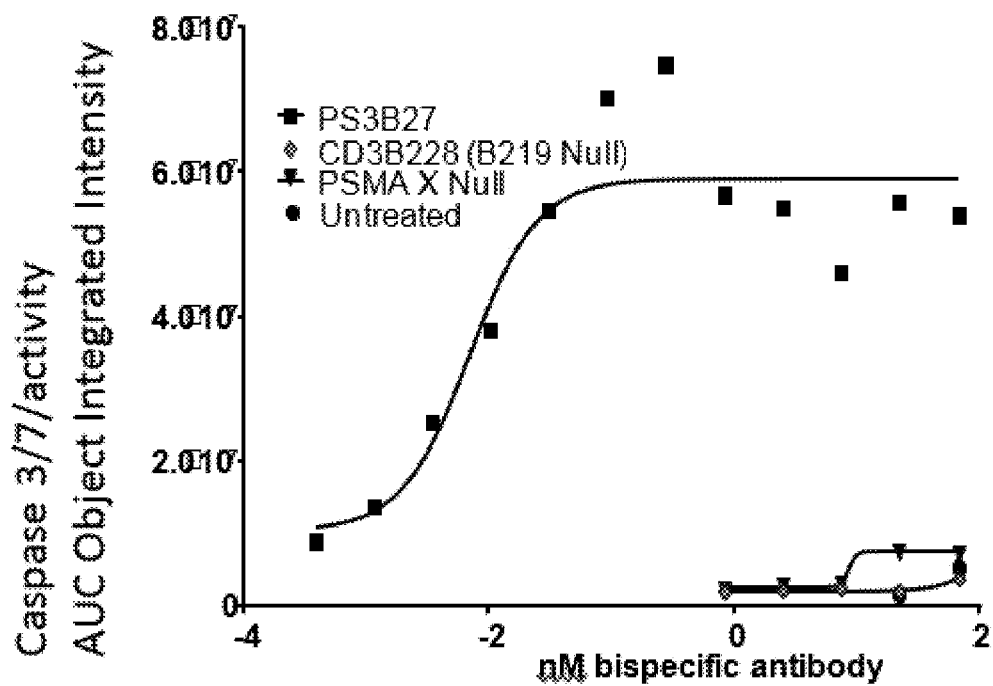
FIG. 19B shows titration curves for PS3B27 and control bispecific antibodies for Cynomolgus monkey PSMA-expressing HEK cells in a T-cell-mediated Caspase 3/7 toxicity assay.
Figure 19C:
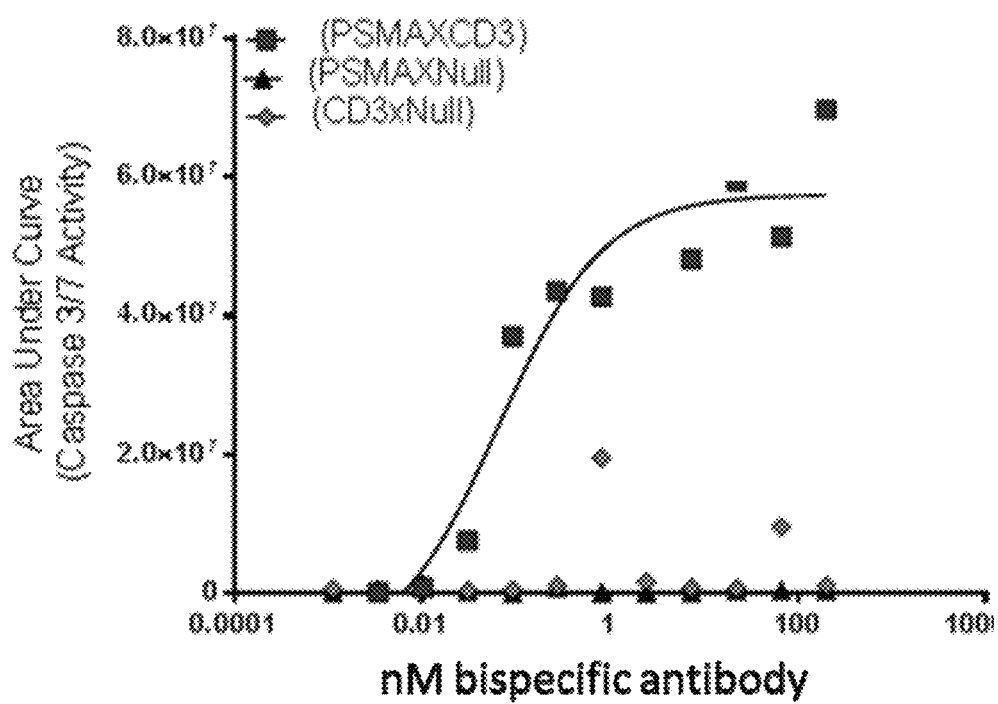
FIG. 19C show titration curves for PS3B27 and control bispecific antibodies for LNCaP cells in a T-cell-mediated Caspase 3/7 toxicity assay.

After the assay was complete, each plate was analyzed using the appropriate processing definition. Raw fluorescent data was exported from the Incucyte Zoom software, and pasted into GraphPad Prism (GraphPad Software, Inc., La Jolla, Calif.). Caspase 3/7 activity was determined by calculating the area under the curve (AUC) for each well in GraphPad. AUC values were plotted as a function of Log 10 nM compound. The $EC_{50}$ for each dose curve, in nanomolar (nM), was reported following non-linear regression analysis (4 parameter fit, least ordinary squares). Each assay contained a minimum of three biologic replicates, and each cell line was tested with five healthy donors. Data were further analyzed by non-clinical statistics using a non-linear regression model. Examples of graphs are shown in FIG. 19A-C. Calculated results are found in Table 21.

TABLE 21

Summary of $EC_{50}$ Values for T-Cell Dependent Cytotoxicity Assay

| Donor | LNCaP FGc | C-42B |
|---|---|---|
| M2550 | 0.27 nM | 0.11 nM |
| M5524 | 0.09 nM | 0.06 nM |
| M5772 | 0.04 nM | 0.03 nM |
| M7259 | 0.05 nM | 0.06 nM |
| M7444 | 0.09 nM | 0.05 nM |

Example 10. T-Cell Activation by PS3B27 in PSMA Positive Cell Lines

Figure 20:
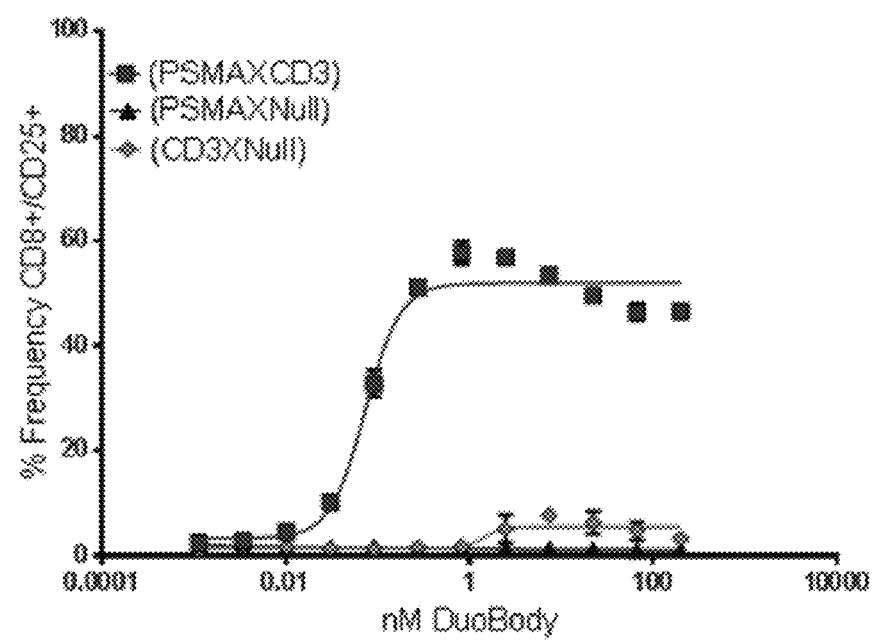
FIG. 20 shows T-cell activation by PS3B27.

Purified Pan CD3+ T-cells were obtained from normal, healthy donors by Biological Specialty Corporation by negative selection of leukapheresed white blood cells, and stored frozen at −80° C. or in Liquid Nitrogen until ready for use. Naïve, unactivated T-cells were combined with target cells and CD3×PSMA bispecific antibodies or null controls (CD3×Null or PSMA×Null) at a 3:1 Effector:Target ratio. Following a 48-hour incubation, supernatants were analyzed for cytokine secretion by sandwich enzyme-linked immunosorbent assay (ELISA) (Meso Scale Discovery). Expression of the T-cell activation marker CD25 was measured by flow cytometry by staining T-cells for CD45, CD8, CD25, and a live/dead near-IR stain. Populations of CD8+/CD25+ were determined by first gating on a gross cell population (FSC-A vs. SSC-A) to exclude debris and cell aggregates. The cell gate subset was further narrowed for cells determined to be live, by exclusion of the live/dead stain. Live cells were then gated for CD45+/CD8+ cells. Finally, the CD8+/CD25+ positive subset was identified. The $EC_{50}$ of PS3B27 or control was derived by plotting the percentage of CD8+/CD25+ against Log 10 nM bispecific antibody or control, followed by a Non-linear regression (4 Parameter fit, least squares method) (FIG. 20). All data analysis was performed in GraphPad Prism.

Example 11. Anti-Tumor Efficacy of in Tumorigenesis Prevention of HEK293-PSMA Xenografts in PBMC-Humanized NSG Mice All in vivo experiments were performed in accordance with The Guide for the Care and Use of Laboratory Animals and approved by the Institutional Animal Care and Use Committee of Janssen R & D, Spring House, Pa.

Efficacy of PS3B27 (PSMA×CD3 Bispecific antibody) was evaluated by prevention of tumorigenesis (prophylactic model) of HEK293-PSMA human xenografts using inoculated human donor peripheral blood mononuclear cells (PBMC) in male NSG mice (NOD.Cg-Prkdc$^{scid}$IL2rg$^{tm1Wjl}$/SzJ or NOD SCID Gamma, Jackson Laboratories, Bar Harbor, Me.). Mice were injected intravenously (iv) in the lateral tail vein with 1×10$^7$ human PBMCs 7 days prior to tumor cell implantation. Mice were subsequently implanted subcutaneously (sc) with 1×10$^7$ HEK293-PSMA cells in the right hind flank. Beginning on the day of tumor implantation PBS (phosphate buffered saline) control, PS3B27, CD3B288 (CD3×Null) or PS3B46 (PSMA×Null) were administered iv at 0.4 mg/kg q2d-q3d for a total of 5 doses on days 0, 3, 5, 7 and 10.

Tumor volume was calculated using the formula:
Tumor Volume (mm$^3$)=(a×b$^2$/2); where 'a' represents the length, and 'b' the width of the tumor as determined by caliper measurements, and monitored twice weekly throughout the study. Percent tumor growth inhibition (TGI) was defined as the difference between mean tumor volumes of the treated and control (PBS) groups, calculated as TGI= [((TVc−TVt)/TVc)*100] where TVc is the mean tumor volume of a given control group and TVt is the mean tumor volume of the treated group. As defined by NCI criteria, ≥60% TGI is considered biologically significant (Johnson, et al (2001) Br J Cancer 84(10) 1424-31). Animals were removed from studies when a maximum tumor volume of 1500 mm$^3$ was reached.

Engraftment of human PBMC eventually leads to graft-versus-host disease (GvHD) in the mice, where the engrafted donor T cells become activated and infiltrate the host tissues, leading to body weight loss, organ failure, and inevitably, death. To monitor the onset and severity of GvHD, body weight was recorded twice weekly and expressed in grams (g). Percent body weight change was calculated using the formula:

Body weight change=$[((B_t-B_0)/B_0)*100]$ where $B_t$ is the body weight on a given day of study and $B_0$ is the body weight at the initiation of treatment. Animals with sustained body weight loss greater than 20% of the initial body weight were considered moribund and removed from the study.

Figure 21:
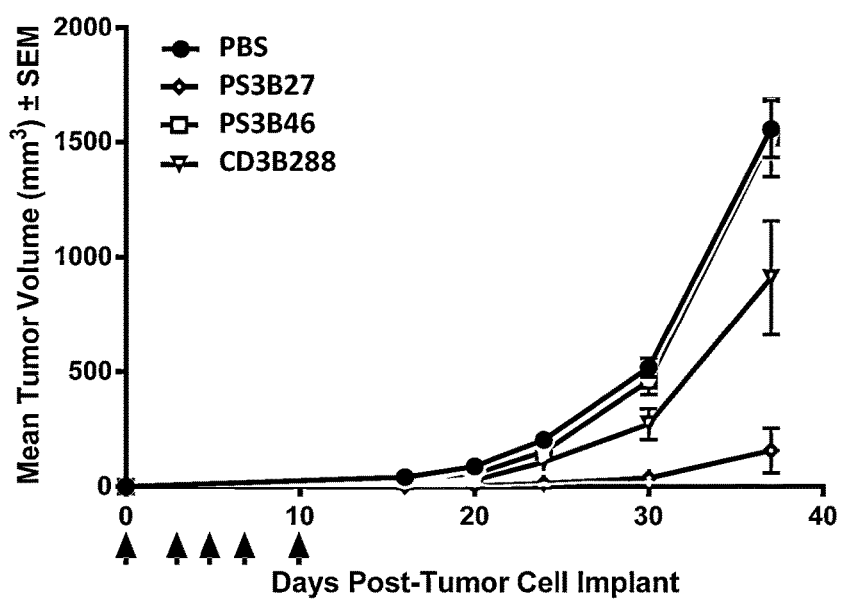
FIG. 21 shows prevention of tumorigenesis of HEK293-PSMA xenografts treated with PS3B27 or control bispecific antibodies in PBMC humanized NSG mice.

Statistical significance was evaluated using a 1-way ANOVA with multiple comparisons using Dunnett's multiple comparisons test using Graph Pad Prism software (version 6). PS3B27 treatment effectively delayed HEK293-PSMA tumorigenesis and tumor growth (FIG. 21). Small but palpable HEK293-PSMA tumors were detectable in seven of eight mice in the PBS treated group on study day 16 (6 days post last therapeutic treatment), whereas only one mouse out of eight in the PS3B27 treated group had a tumor. Five out of eight mice had palpable tumors in the CD3B288 treatment group and two out of eight mice had small tumors in the PS3B46 group. Tumor growth inhibition was assessed 27 days following cessation of treatment (day 37 post-tumor implantation), when each group had a minimum of 7 animals. Tumor growth in the PSMA×CD3 bispecific antibody (PS3B27) treated group was inhibited by 90% as compared to PBS-treated controls (n=8/group, p<0.001). The PSMA×Null bispecific antibody (PS3B46) also inhibited tumorigenesis and growth in a statistically significant fashion (TGI=42%, n=7) vs. PBS control, (p<0.05), although it was not considered to be a biologically significant effect based on NCI criteria [1].

Figure 22:
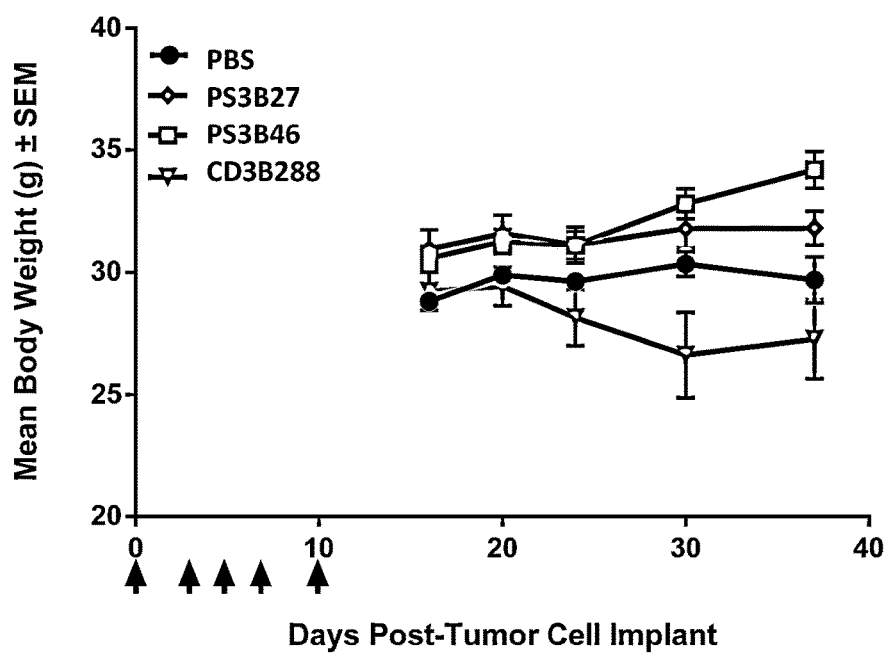
FIG. 22 shows Mean body weights of PBMC-humanized NSG mice bearing HEK293-PSMA xenografts with PS3B27 and control bispecific antibody treatment.

Animal groups receiving PBMCs eventually succumb to progressive GvHD, however body weight loss was slight in the current study. No significant difference was observed between mean body weights of animals treated with 0.4 mg/kg PS3B27 vs PBS as shown in FIG. 22 up to day 37 post-tumor implant (p>0.05). Therefore PS3B27-mediated T cell redirection did not further contribute towards GvHD-related body weight loss.

Despite minor weight loss in the current study, sporadic GvHD-related deaths were noted. One mouse in the PSMA×Null bispecific antibody PS3B46 group was euthanized due to excessive GVHD-related (>20%) body weight loss on day 30-post tumor implant. By day 42 post-tumor implant, additional GvHD-related deaths were noted in the PBS (n=1), and PSMA×Null bispecific antibody PS3B46 groups (n=2), and several additional mice were removed from the study due to reaching the 1500 mm³ tumor volume endpoint, at which time the entire study was terminated.

Example 12. Efficacy of PS3B27 in Tumorigenesis Prevention of Admixture HEK293-PSMA/T Cell Xenografts in Male CD1 Nude Mice Efficacy of PS3B27 was evaluated in an admixture xenograft model where human CD3+ pan T cells and tumor cells were co-injected into male CD1 nude mice (NU-Foxn1nu, Charles River Laboratories, Wilmington, Mass.).

Human PSMA×human CD3 bispecific antibody PS3B27, or control bispecific antibodies were administered iv every 2-3 days (q2d or q3d) for a total of 5 doses as indicated. Mice were monitored (body weight and tumor caliper measurement) twice weekly throughout the studies. Drug doses expressed as μg/animal were converted to mg/kg based on a 25 g body weight (example: 10 μg/animal=0.4 mg/kg). Drug doses administered as mg/kg, were dosed 10 mL/kg based on body weight (example: 25 g mouse=0.25 mL).

Tumor volume was calculated using the formula: Tumor Volume (mm3)=(a×b2/2); where 'a' represents the length, and 'b' the width of the tumor as determined by caliper measurements], and monitored twice weekly throughout the study. Percent tumor growth inhibition (TGI) was defined as the difference between mean tumor volumes of the treated and control (PBS) groups, calculated as TGI=[((TVc−TVt)/TVc)*100] where TVc is the mean tumor volume of a given control group and TVt is the mean tumor volume of the treated group. As defined by NCI criteria, ≥60% TGI is considered biologically significant [1]. Animals were removed from studies when a maximum tumor volume of 1500 mm3 was reached.

The tolerability of PS3B27 could not be assessed with respect to CD3 binding in host tissues due to lack of cross-reactivity of the CD3 arm to corresponding mouse antigens. The T cell injected with the tumor cells do however express human CD3 and can bind PS3B27 and CD3×Null controls. Percent body weight change was calculated using the formula: Body weight change=$[((Bt B0)/B0)*100]$ where Bt is the body weight on a given day of study and B0 is the body weight at the initiation of treatment.

Statistical significance was evaluated using a 1-way ANOVA with multiple comparisons using Dunnett's multiple comparisons test using Graph Pad Prism software (version 6).

Efficacy of PS3B27 was evaluated by prevention of tumorigenesis of admixture xenografts containing HEK293-PSMA cells and activated and expanded CD3 positive pan T-cells in a 1:5 effector to target ratio in male CD1 nude mice (ELN ref: CD3-PSMA-2013-00003). T-cells were activated and expanded in vitro using the T-cell activation/expansion kit in IL-2 containing media (Miltenyi Biotech, Auburn, Calif., catalog #130-091-441, 130-097-743) for 12 days. Mice were implanted sc with an admixture of 5×106 HEK293-PSMA cells and 1×106 activated and expanded T-cells per mouse in 50% Cultrex (Trevigen, Gaithersburg, Md., catalog #3433-005-01) and 50% serum-free RPMI 1640 media in the right hind flank. Beginning on the same day as tumor implantation, PBS, PS3B27 at 0.005-0.5 mg/kg, CD3B288 (CD3×Null bispecific antibody) 0.5 mg/kg or PS3B46 (PSMA×Null bispecific antibody) 0.5 mg/kg were administered iv, by body weight, q2d-q3d for a total of 5 doses on days 0, 2, 4, 7 and 9. (n=10/group). Treatment with PS3B27 was also evaluated with ip administration (data not shown). One animal was removed each on days 46 and 49 in the PBS control group for excessive tumor burden. Tumor volume data was plotted up to day 64 after which half of the control animals were removed from study due to excessive tumor volume.

Figure 23:
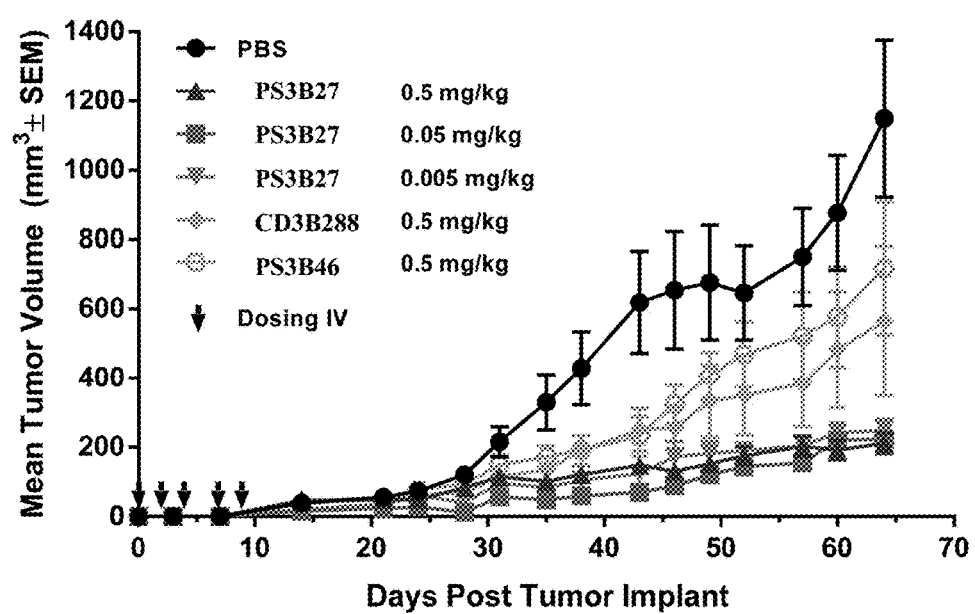
FIG. 23 shows efficacy of PS3B27 and control bispecific antibodies in tumorigenesis prevention of admixture HEK293-PSMA/T cell xenografts in male CD1 nude mice.

As shown in FIG. 23, tumorigenesis and growth were evaluated for 55 days following cessation of treatment (up to day 64). Treatment with PS3B27 significantly inhibited tumorigenesis and delayed growth compared to PBS control at all doses (0.005, 0.05 or 0.5 mg/kg) resulting in TGI of 73%, 81% and 82%, respectively (p<0.001, P<0.0001, P<0.001, respectively) on day 64. Treatment of PS3B27 by ip administration showed similar efficacy as iv administration (data not shown). Animals treated with CD3B288 (CD3×Null bispecific antibody) or PS3B46 (PSMA×Null Bispecific antibody) showed some anti-tumor activity with 51% and 38% TGI, respectively on day 64 (p<0.05, p=ns, respectively), however this is not considered biologically significant based on the NCI criteria of 60% TGI, demonstrating the requirement for both CD3 and PSMA binding of the bispecific antibody to achieve efficacy.

Figure 24:
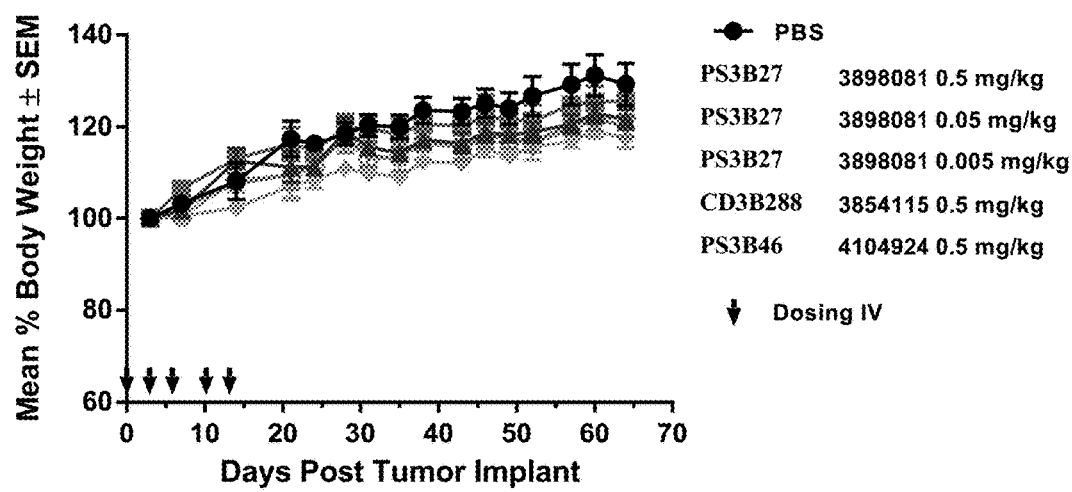
FIG. 24 shows Body Weight of CD1 male nude mice bearing Admixture HEK293-PSMA/T cell Xenografts Treated with PS3B27 and control bispecific antibodies.

There was no body weight loss over the course of the study, however, animals treated with PS3B27 at 0.5 and 0.005 mg/kg did have significantly less increase in body weight compared to PBS (p<0.001, p<0.0001, respectively, FIG. 24), however this could be due to a lower tumor burden in these animals.

Example 13. Crystal Structure of Human PSMA ECD Bound to Anti-PSMA Fab Arm of Bispecific Antibody PS3B27

PSMA is a homodimeric protein expressed on the cell surface. PSMA is a type II integral glycoprotein of 750 residues per monomer, comprised of a large ECD domain (705 residues) with peptidase activity, a single pass TM domain, and a short 19 residue intracellular domain. The crystal structure of the extracellular region (ECD) of human PSMA bound to the anti-PSMA Fab arm of bispecific antibody PS3B27 was determined to 3.15 Å resolution to better understand the combining site between PSMA and the antibody.

The extracellular region of human PSMA (residues 44-750) was expressed in High Five™ insect cells with an N-terminal gp67 signal peptide followed by a cleavable hexahistidine tag (SEQ ID NO: 158). The secreted protein was purified from supernatant by a three-step procedure comprising of an initial $Ni^{2+}$-NTA affinity capture, TEV-mediated cleavage of the histidine tag followed by an inverse affinity chromatography step, and a final size-exclusion chromatography step. Purified PSMA-ECD was flash-frozen in liquid nitrogen and stored at −80° C. in 10 mM HEPES pH 7.4, 150 mM NaCl, 2 mM $CaCl_2$), 0.1 mM $ZnCl_2$ The Fab of PSMB83, which is the parental anti-PSMA Fab arm in bispecific antibody PS3B27, was expressed in HEK293 Expi cells with a hexahistidine tag (SEQ ID NO: 158) and purified using affinity (HisTrap, GE Healthcare) and size-exclusion chromatography (SEC-300, Phenomenex Yarra). The Fab was stored at 4° C. in 50 mM NaCl, 20 mM Tris pH 7.4

The human PSMA ECD/PSMB83 Fab complex was prepared by a three-step procedure. First, the Fab was buffer exchanged into 20 mM MES pH 6.0, 150 mM NaCl. Then, the Fab and PSMA were mixed (1.5 molar excess Fab over PSMA monomer) and incubated overnight at 4° C. while dialyzing into 20 mM MES pH 6.0. Finally, the complex was bound to a monoS 5/50 column in 20 mM MES pH 6.0 and eluted with a NaCl gradient.

Crystals suitable for X-ray diffraction were obtained using the sitting drop vapor-diffusion method at 20° C. and a Mosquito LCP robot (TTP Labtech). Crystals of PSMB83 Fab bound to human PSMA ECD were grown from 18% PEG 3 kDa, 0.2 M $(NH_4)_2SO_4$, 0.1 M Tris pH 8.5 with micro-seeds and the PSMA/Fab complex initially at 7.3 mg/mL. Crystals of free PSMB83 Fab were obtained from 25% PEG 3 kDa, 0.2 M LiCl, 0.1 M acetate pH 4.5 with the Fab initially at 8.8 mg/mL.

The structures were solved by molecular replacement (MR) with Phaser (Phaser Crystallographic Software, University of Cambridge). The MR search model for the PSMB83 Fab structure was PDB code 4M60. The PSMA/Fab complex structure was solved using the crystal structures of PSMA (PDB code: 2C6G) and PSMB83 Fab (structure at 1.93 Å resolution; data not shown) as MR search models. The structures were refined with PHENIX (Adams, et al, 2004) and model adjustments were carried out using COOT (Emsley and Cowtan, 2004). All other crystallographic calculations were performed with the CCP4 suite of programs (Collaborative Computational Project Number 4, 1994). All molecular graphics were generated with PyMol (PyMOL Molecular Graphics System, Version 1.4.1, Schrödinger, LLC.) and complementarity determining regions (CDRs) were determined using the Kabat definition.

The PSMA/Fab structure includes Fab light chain residues 1-211, Fab heavy chain residues 1-224 (except for residues 138-146, which are disordered) and PSMA residues 56-750, which corresponds to the protease (residues 56-116 and 352-590), apical (residues 117-351) and helical (residues 591-750) domains, and seven of ten possible N-linked glycans (in Asn-76, -121, -140, -195, -459, -476, and -638) per PSMA dimer subunit. The PSMA active site is located at the interface between the three domains and it contains two zinc atoms coordinated by histidine (H377 and H553) and glutamate/aspartate (D387, catalytic E424, E425, and D453) residues and a water molecule. The crystal asymmetric unit contains one PSMA dimer with each subunit bound in a similar manner to a PSMB83 Fab. The Fab/PSMA combining site is well defined by the electron density map, which allows reliable positioning of the binding residues. The Fab and PSMA molecules are numbered sequentially in FIGS. 25-30

Figure 25:
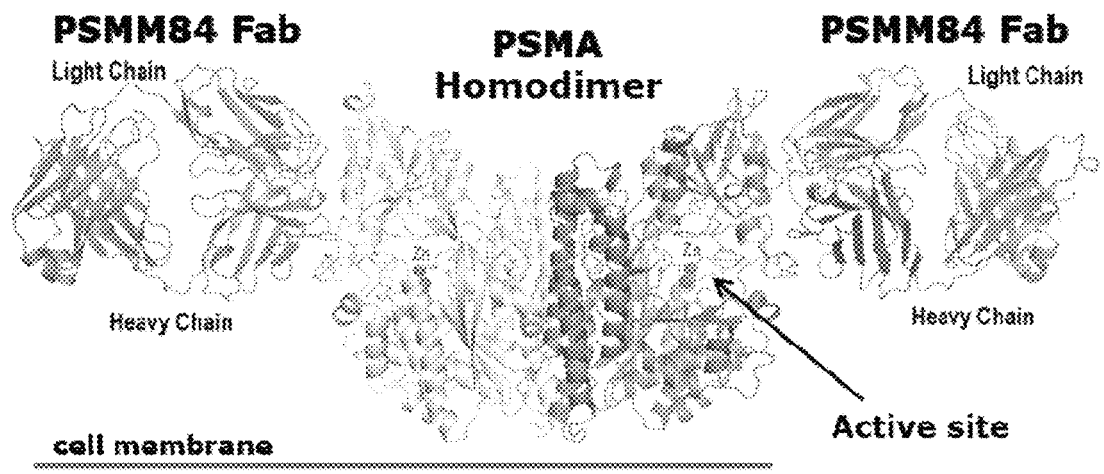
FIG. 25 shows the overall structure of PSMB83 (AKA "PSMM84") Fab bound to human PSMA ECD homodimer.
Figure 26:
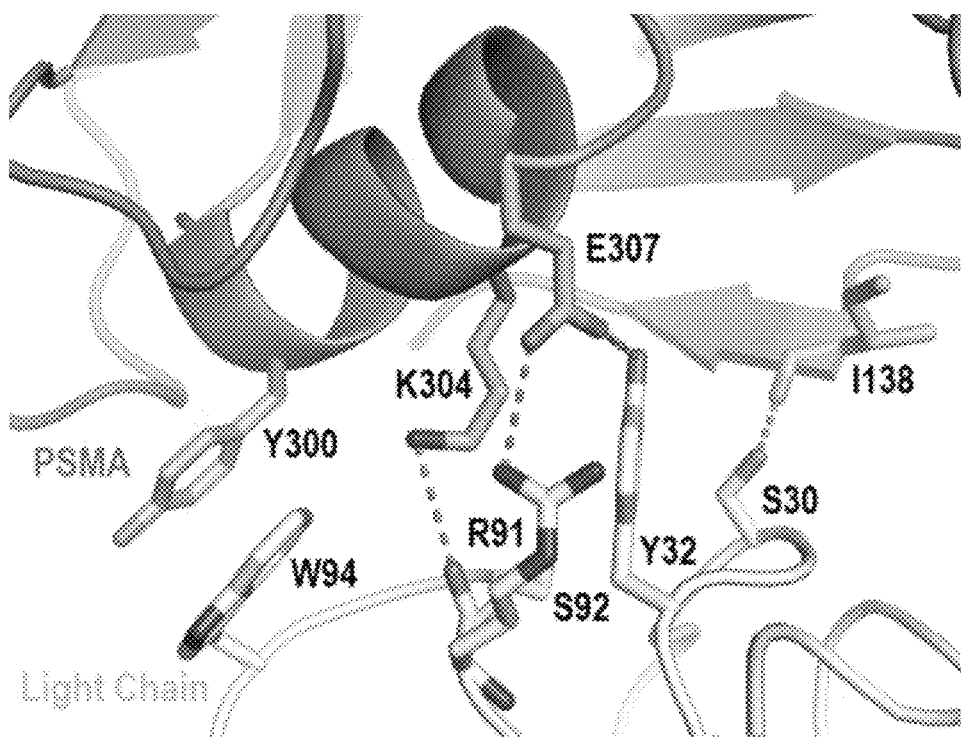
FIG. 26 shows a close view of PSMA main interactions with the PSMB83 (AKA "PSMM84") Light Chain.
Figure 27:
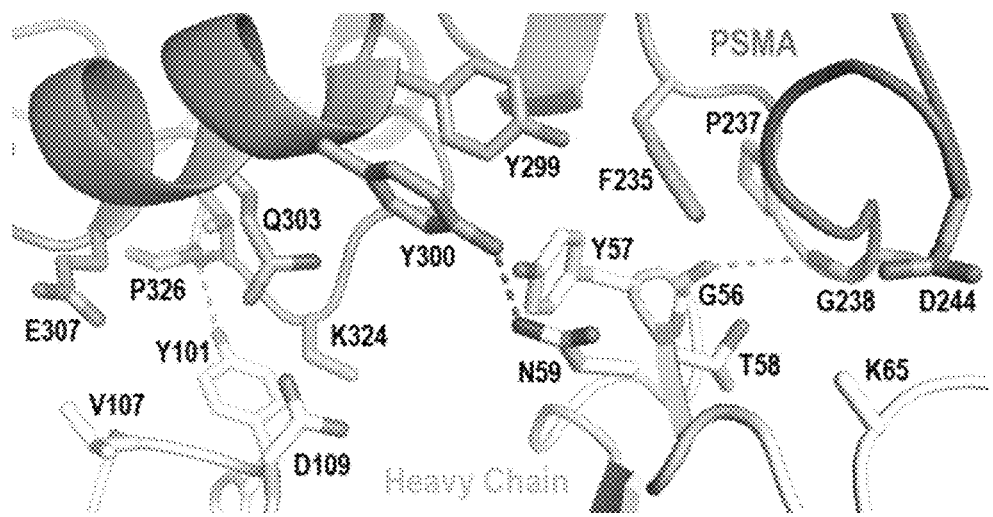
FIG. 27 shows a close view of PSMA main interactions with the PSMB83 (AKA "PSMM84") Heavy Chain.
Figure 30:
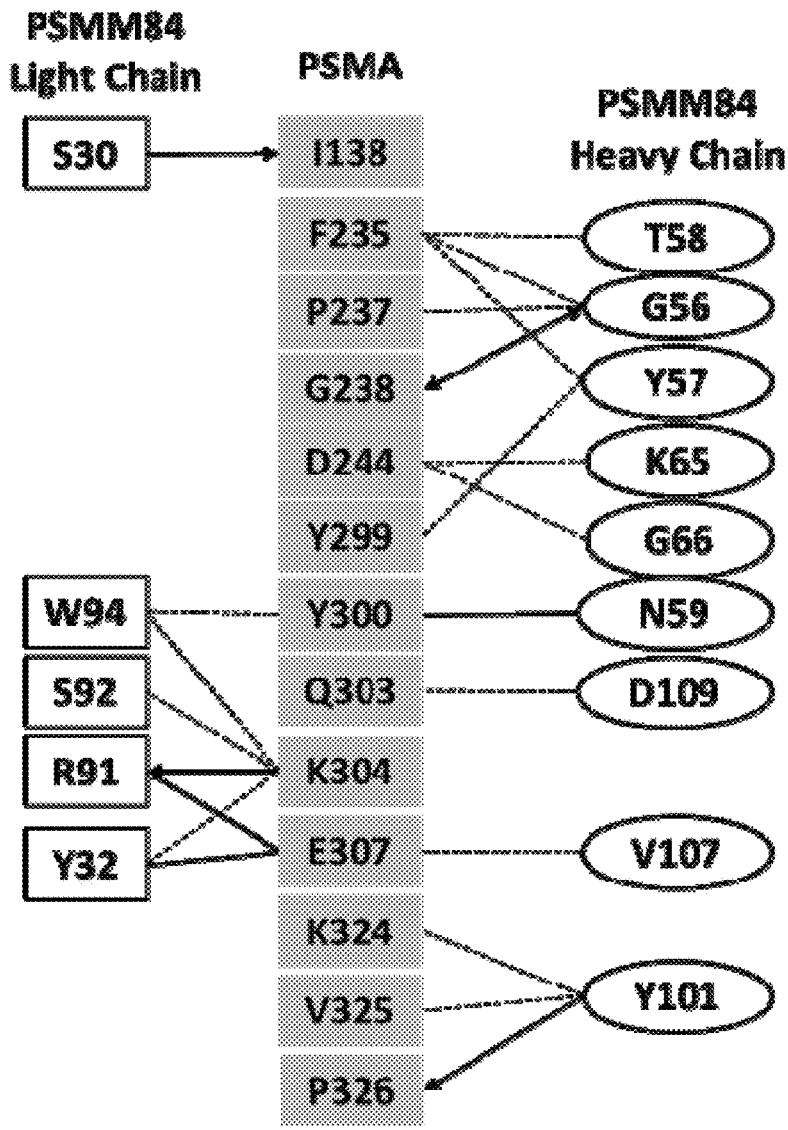
FIG. 30 shows an interaction map with direct contacts made between PSMA and PSMB83 (AKA "PSMM84"). Van der Waals interactions are shown as dashed lines and H-bonds are solid lines with arrows pointing to the backbone atoms.

The PSMB83 epitope, paratope and interactions. PSMB83, which is the parental anti-PSMA Fab arm in bispecific antibody PS3B27, recognizes a conformational and discontinuous epitope in the apical domain of PSMA (FIG. 25). The PSMA surface area buried by the Fab is around 700 $Å^2$. Specifically, the PSMB83 epitope residues are I138, F235, P237, G238, D244, Y299, Y300, Q303, K304, E307, and K324-P326. Helix α7 (residues Y299-E307) is a prevalent region of the epitope and binds across the Fab heavy and light chain CDRs. At one end of the helix, Y299 and Y300 form an aromatic cluster with Fab residues $Y57^H$, $W94^L$ and PSMA residues F235 and P237, while E307, at the other helix end, forms a salt bridge with $R91^L$ and hydrogen bonds $Y32^L$. FIGS. 26 and 27 show the main interactions of PSMA with the PSMB83 light and heavy chains. The PSMB83 epitope residues are conserved between human and cynomolgus monkey (FIG. 28) and the bispecific antibody PS3B27 was demonstrated to bind with similar affinity to human and cyno PSMA. In contrast, the human to mouse G238A and, especially. Y300D epitope mutations are expected to lower PSMB83 binding affinity to mouse PSMA in comparison to human. The Y300D mutation disrupts a hydrogen bond contact with $N59^H$ and a π stacking interaction with $W94^L$. The PSMB83 paratope is composed of residues from all CDRs except CDR-L2 and CDR-H1 (FIG. 29). Specifically, the paratope residues are light chain $S30^L$, $Y32^L$, $R91^L$, $S92^L$, $W94^L$, and heavy chain $G56H-N59^H$, $K65^H$, $G66^H$, $Y101^H$, $V107^H$, and $D109^H$. FIG. 30 shows the interaction contacts between PSMA and PSMB83. The accessible location of the epitope facilitates binding of the PSMB83 Fab arm in the PS3B27 bispecific antibody to membrane-bound PSMA, while the other Fab arm is still bound to CD3 in the T-cell membrane. PSMB83 is not expected to inhibit PSMA enzymatic activity since the antibody binds away from the active site and does not cause any significant structural changes in PSMA that could affect enzymatic function, such as loop movements that close the active site or displacement of catalytic residues (RMSD of 0.3 Å for Cα superposition of PSMA molecules in Fab bound and unbound (Barinka et al, 2007) structures)

Example 14. Anti-PSMA Affinity Maturation

Affinity maturation was performed on anti-PSMA Fab phage clones from two PSMA affinity maturation libraries to identify an antibody with increased binding affinity compared to the parental PSMB127 (fab ID=PSMB83). Two libraries were generated for affinity maturation of PSMB127. In the first library heavy chain CDR1 and CDR2 were randomized according to the design in Table 22 (PH9H9L1). The H-CDR3 fragment was PCR amplified from pDR000024032 and digested with SacII+XhoI. This fragment was cloned into the PH9H9L1/PH9L3 library. This was transformed into E. coli MC1061F' cells and phage was generated displaying this Fab library. In the second library light chain CDRs were randomized according to the design in Table 25 (PH9L3L3). The heavy chain from PSMB83 (PSMH360) was PCR amplified and digested with NcoI+XhoI. This fragment was cloned into the PH9L3L3 library DNA (ELN: De Novo 2010 phage library SRI-021). This was transformed into E. coli MC1061F' cells and phage was generated displaying this Fab library.

TABLE 22

PH9H9L1 Library design

| Position | Parent AA | Library AA |
|---|---|---|
| 30 | S | D, K, S |
| 31 | S | D, N, S, T |
| 32 | Y | A, D, S, Y |
| 33 | A | A, D, G, S, W, Y |
| 35 | S | H, N, S |
| 50 | A | A, E, L, N, R, T, W, Y |
| 52 | S | A, D, L, N, R, S |
| 54 | S | A, E, N, S, Y |
| 57 | S | D, N, R, S, T, Y |
| 59 | Y | E, G, N, Q, R, Y |

TABLE 23

PH9L3L3 Library design

| Position | Parent AA | Library AA |
|---|---|---|
| 30 | S | D, N, R, S |
| 31 | S | N, S, T |
| 32 | Y | D, N, R, S, Y |
| 49 | Y | E, H, K, Y |
| 50 | D | D, G, S, W, Y |
| 53 | N | D, N, S, T, Y |
| 91 | R | A, D, E, G, H, N, R, S, W, Y |
| 92 | S | A, D, E, G, H, N, R, S, W, Y |
| 93 | N | A, D, E, G, H, N, R, S, W, Y |
| 94 | W | A, D, E, G, H, N, R, S, W, Y |
| 96 | L | F, I, L, N, R, W, Y |

A solution panning of the PSMA affinity maturation Fab-pIX libraries was performed against biotinylated human PSMA ECD for three rounds. The phage-bound antigen was captured on neutravidin beads (GE HealthCare Life Science Cat #78152104011150) according to the manufacturer's protocol, followed by extensive washes in 1×PBST (0.05% tween 20) and an hour-long incubation with unlabeled PSMA ECD in 500-fold molar excess of the biotinylated antigen. This panning yielded the clones, PSMXP46R3_59H09, PSMXP46R3_59H06, PSMXP46R3_59E03, PSMXP46R3_59C09, PSMXP46R3_59H01, PSMXP46R3_59F11, and PSMXP46R3_59F07.

Figure 31:
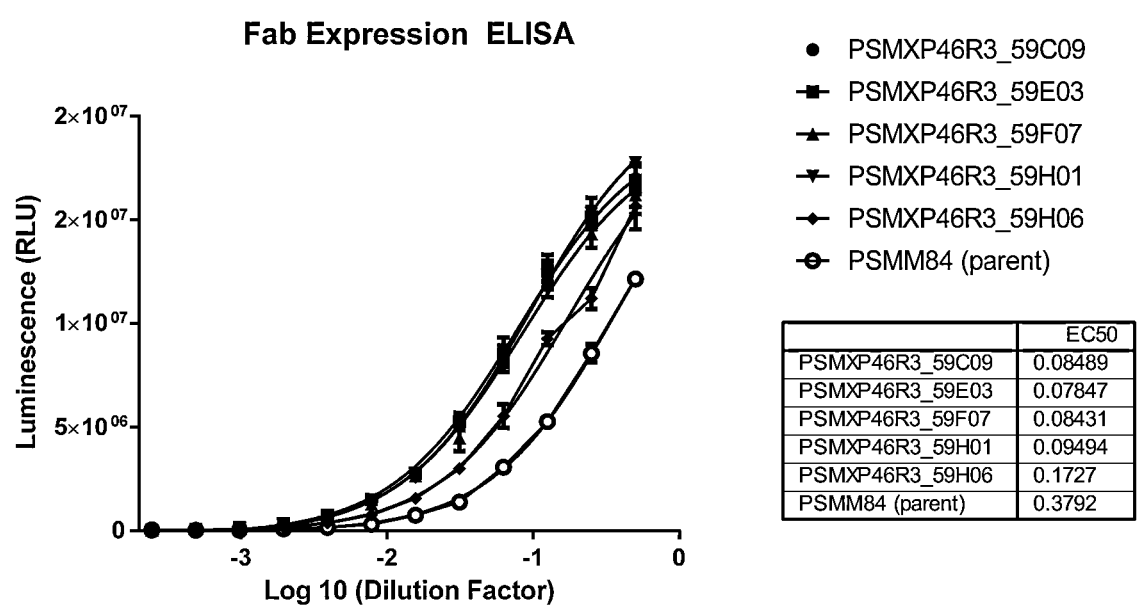
FIG. 31 shows expression levels of anti-PSMA Fab clones derived from PSMB83 as compared to expression of parent PSMB83. Raw luminescence numbers were plotted against the log concentration.

To determine the expression level of the anti-PSMA fab clones, 96 well Maxisorb plates were coated overnight at 4 C with anti-human Fd IgG, washed, and blocked with 3% milk-PBS-0.05% Tween for 1 hour. The phage supernatant samples were serially diluted 2-fold for 11 dilutions in blocking buffer with the final well blank. 100 ul of these solutions were captured on the coated plates for 1 hour. The plates were washed and 100 ul of anti-F(ab')2-HRP antibody was added for 1 hour. Plates were washed and developed with 100 ul of peroxidase reagent and luminescence was read on the Envision (FIG. 31).

Figure 32:
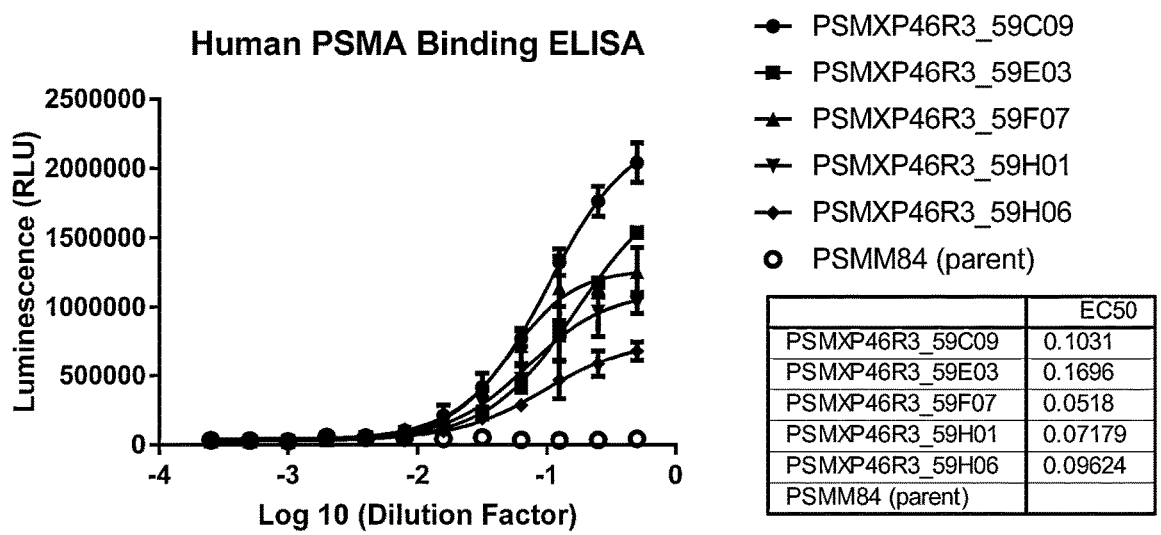
FIG. 32 shows binding to human PSMA of anti-PSMA Fab clones derived from PSMB83 as compared to binding of parent PSMB83. Raw luminescence numbers were plotted against the log concentration.
Figure 33:
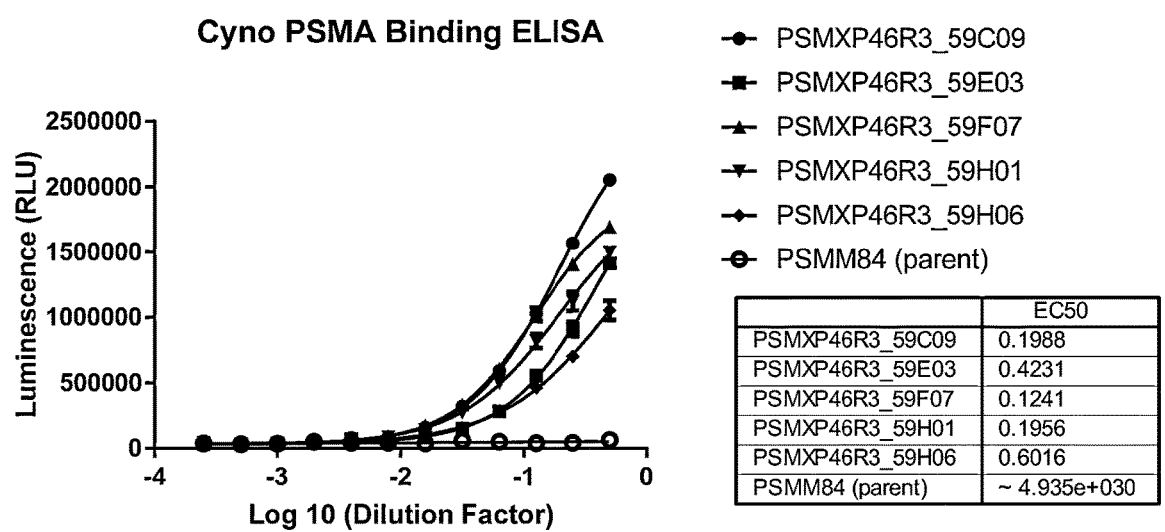
FIG. 33 shows binding to cyno PSMA of anti-PSMA Fab clones derived from PSMB83 as compared to binding of parent PSMB83. Raw luminescence numbers were plotted against the log concentration.

To determine the binding of the anti-PSMA fab clones to human and cynomolgus recombinant protein, 96 well Maxisorb plates were coated with 100 ul of 5 ug/ml neutravidin overnight at 4 C. The plates were washed and blocked with 3% milk-PBS-0.05% Tween for 1 hour. Recombinant biotinylated human and cynomolgus PSMA proteins were captured at 2.5 ug/ml for 1 hour at room temperature. The plates were washed and 100 ul of 2-fold serially diluted fab supernatant was capture for 1 hour at RT. The plate was washed and then there was a 2.5-hour incubation with 200 ul 0.3% milk in PBST to wash away some of the weak affinity fabs. Then there was another 30 minute incubation with fresh 200 ul 0.3% milk in PBST to remove more weak affinity fabs. The plates were washed and 100 ul of anti-F(ab')2-HRP antibody was added for 1 hour. Plates were washed and developed with 100 ul of peroxidase reagent and luminescence was read on the Envision (FIG. 32 and FIG. 33). FIG. 31 demonstrates that the protein expression of the parental Fab and affinity matured Fabs were similar. The y axis values represent the luminescence of the detection reagent which equates to the abundance of fab protein over the dilution curve; the higher the luminescence reading, the more protein in the well which decreased with successive two-fold dilutions. There was more protein in the wells with affinity mature fabs but the increase over the parental is at most five times greater as demonstrated by the $EC_{50}$ values (which is the concentration of protein that gives half of the maximal response). These data demonstrate the difference in PSMA binding profiles in FIG. 32 and FIG. 33 is not due to a difference in Fab concentration.

FIG. 32 demonstrates improved binding of the affinity matured Fabs to the human recombinant antigen over the parental anti-PSMA Fab (PSMB83). Again, the y axis of the graph represents luminescence values. In this case the larger the value means more Fab bound to the human PSMA protein. This is a measure of binding as increased concentrations of Fab (along the x axis) generate higher luminescence values. There was negligible binding of the parental Fab under these conditions as demonstrated by the absence of signal even at high concentrations (open circles along the x axis). Binding of the affinity matured fabs was observed over the concentrations tested which equates to stronger binding capacity to the human PSMA protein. Given that parental Fab binding to human PSMA protein was zero, no $EC_{50}$ could be generated.

FIG. 33 demonstrates improved binding of the affinity matured Fabs to the cynomolgus recombinant antigen over the parental anti-PSMA Fab (PSMB83). Again, the y axis of the graph represents luminescence values. In this case the larger the value means more Fab bound to the cynomolgus PSMA protein. This is a measure of binding as increased concentrations of Fab (along the x axis) generate higher luminescence values. There was negligible binding of the parental Fab under these conditions as demonstrated by the absence of signal even at high concentrations (open circles along the x axis). Binding of the affinity matured Fabs was observed over the concentrations tested which equates to stronger binding capacity to the human PSMA protein. Given that parental Fab binding to human PSMA protein was zero, no $EC_{50}$ could be generated for direct comparison.

Figure 34:
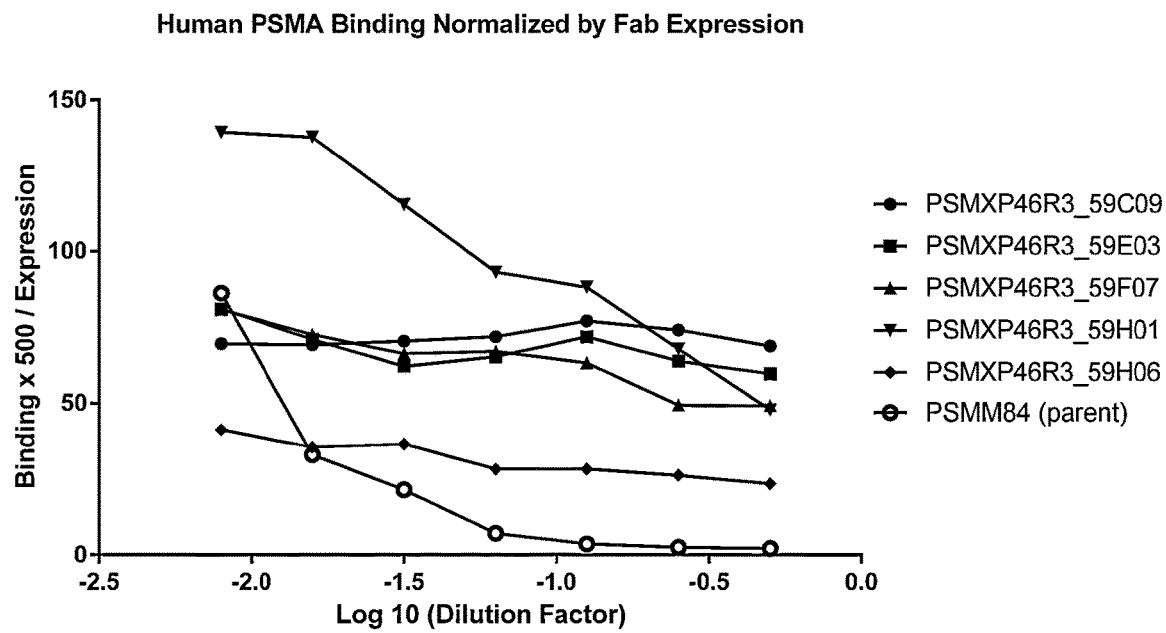
FIG. 34 shows binding to human PSMA of anti-PSMA Fab clones derived from PSMB83 as compared to binding of parent PSMB83. Raw luminescence numbers were normalized by Fab expression levels.
Figure 35:
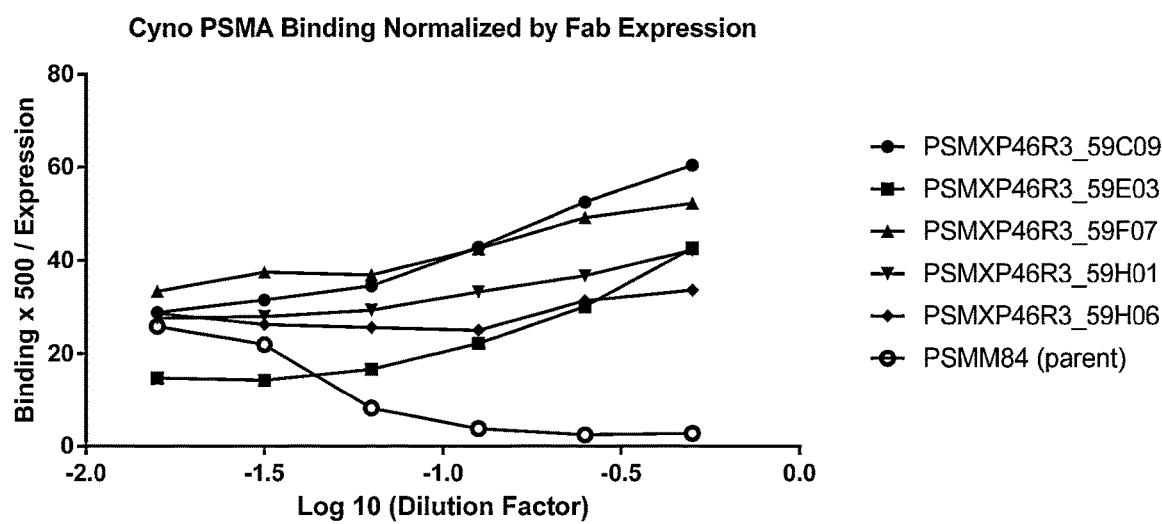
FIG. 35 shows binding to cyno PSMA of anti-PSMA Fab clones derived from PSMB83 as compared to binding of parent PSMB83. Raw luminescence numbers were normalized by Fab expression levels.

Overall, the phages' Fab binding profiles demonstrate improved binding to the human and cynomolgus recombinant antigen over the parental anti-PSMA mAb (PSMB127). This improvement is not a result of differences in Fab expression profiles, as demonstrated by FIG. 34 and FIG. 35, showing binding of affinity mature Fabs normalized to Fab expression levels. The top five Fab candidates identified from the ELISA screen were produced in monoclonal antibody format on IgG4 PAA. Table 24 lists the subsequent Mab identifiers and Tables 25 and 26 provide sequence information.

TABLE 24

Top five affinity mature antibodies identified based on the ELISA

| Well ID | HC SEQ ID | LC SEQ ID | MAB protein IDs |
|---|---|---|---|
| PSMXP46R3_59C09 | PSMH859 | PSML160 | PSMB346 |
| PSMXP46R3_59E03 | PSMH859 | PSML159 | PSMB345 |
| PSMXP46R3_59F07 | PSMH862 | PSML158 | PSMB349 |
| PSMXP46R3_59H01 | PSMH860 | PH9L3 | PSMB347 |
| PSMXP46R3_59H06 | PSMH859 | PH9L3 | PSMB344 |

TABLE 25

VH and VL sequences of top five PSMA Fab candidates

| MAB ID | VH Amino acid sequence | SEQ ID NO | VL Amino Acid Sequence | SEQ ID NO |
|---|---|---|---|---|
| PSMB344 | EVQLLESGGGLVQPGGSLRLSCAASG FTFKSDAMHWVRQAPGKGLEWVSEIS GSGGYTNYADSMKGRFTISRDNSKNT LYLQMNSLRAEDTAVYYCARDSYDSS LYVGDYFDYWGQGTLVTVSS | 138 | EIVLTQSPATLSLSPGE RATLSCRASQSVSSYLA WYQQKPGQAPRLLIYDA SNRATGIPARFSGSGSG TDFTLTISSLEPEDFAV YYCQQRSNWPLTFGQGT KVEIK | 67 |
| PSMB345 | EVQLLESGGGLVQPGGSLRLSCAASG FTFKSDAMHWVRQAPGKGLEWVSEIS GSGGYTNYADSMKGRFTISRDNSKNT LYLQMNSLRAEDTAVYYCARDSYDSS LYVGDYFDYWGQGTLVTVSS | 138 | EIVLTQSPATLSLSPGE RATLSCRASQSVSNYLA WYQQKPGQAPRLLIHDA SNRATGIPARFSGSGSG TDFTLTISSLEPEDFAV YYCQQRRNWPLTFGQGT KVEIK | 142 |
| PSMB346 | EVQLLESGGGLVQPGGSLRLSCAASG FTFKSDAMHWVRQAPGKGLEWVSEIS GSGGYTNYADSMKGRFTISRDNSKNT LYLQMNSLRAEDTAVYYCARDSYDSS LYVGDYFDYWGQGTLVTVSS | 138 | EIVLTQSPATLSLSPGE RATLSCRASQSVSSYLA WYQQKPGQAPRLLIYDA SYRATGIPARFSGSGSG TDFTLTISSLEPEDFAV YYCQQRRNWPLTFGQGT KVEIK | 143 |
| PSMB347 | EVQLLESGGGLVQPGGSLRLSCAASG FTFKSDAMHWVRQAPGKGLEWVSEIS GSGGYTNYADSMKSRFTISRDNSKNT LYLQMNSLRAEDTAVYYCARDSYDSS LYVGDYFDYWGQGTLVTVSS | 139 | EIVLTQSPATLSLSPGE RATLSCRASQSVSSYLA WYQQKPGQAPRLLIYDA SNRATGIPARFSGSGSG TDFTLTISSLEPEDFAV YYCQQRSNWPLTFGQGT KVEIK | 67 |
| PSMB349 | EVQLLESGGGLVQPGGSLRLSCAASG FTFKSDAMHWVRQAPGKGLEWVSEIS GSGGYTNYADSLKGRFTISRDNSKNT LYLQMNSLRAEDTAVYYCARDSYDSS LYVGDYFDYWGQGTLVTVSS | 140 | EIVLTQSPATLSLSPGE RATLSCRASQSVSSYLA WYQQKPGQAPRLLIYDA SNRATGIPARFSGSGSG TDFTLTISSLEPEDFAV YYCQQRGNWPLTFGQGT KVEIK | 144 |

TABLE 26

Heavy Chain and Light Chain sequences of top five PSMA candidates in monoclonal antibody format on IgG4 PAA

| mAb ID | Heavy Chain Amino acid sequence | SEQ ID NO | Light Chain Amino Acid Sequence | SEQ ID NO |
|---|---|---|---|---|
| PSMB344 | EVQLLESGGGLVQPGGSLRLSCAA SGFTFKSDAMHWVRQAPGKGLEWV SEISGSGGYTNYADSMKGRFTISR DNSKNTLYLQMNSLRAEDTAVYYC ARDSYDSSLYVGDYFDYWGQGTLV TVSSASTKGPSVFPLAPCSRSTSE STAALGCLVKDYFPEPVTVSWNSG ALTSGVHTFPAVLQSSGLYSLSSV VTVPSSSLGTKTYTCNVDHKPSNT KVDKRVESKYGPPCPPCPAPEAAG GPSVFLFPPKPKDTLMISRTPEVT CVVVDVSQEDPEVQFNWYVDGVEV HNAKTKPREEQFNSTYRVVSVLTV LHQDWLNGKEYKCKVSNKGLPSSI EKTISKAKGQPREPQVYTLPPSQE EMTKNQVSLTCLVKGFYPSDIAVE WESNGQPENNYKTTPPVLDSDGSF FLYSRLTVDKSRWQEGNVFSCSVM HEALHNHYTQKSLSLSLGK | 145 | EIVLTQSPATLSLSPGERATLS CRASQSVSSYLAWYQQKPGQAP RLLIYDASNRATGIPARFSGSG SGTDFTLTISSLEPEDFAVYYC QQRSNWPLTFGQGTKVEIKRTV AAPSVFIFPPSDEQLKSGTASV VCLLNNFYPREAKVQWKVDNAL QSGNSQESVTEQDSKDSTYSLS STLTLSKADYEKHKVYACEVTH QGLSSPVTKSFNRGEC | 89 |
| PSMB345 | EVQLLESGGGLVQPGGSLRLSCAA SGFTFKSDAMHWVRQAPGKGLEWV SEISGSGGYTNYADSMKGRFTISR DNSKNTLYLQKNSLRAEDTAVYYC ARDSYDSSLYVGDYFDYWGQGTLV TVSSASTKGPSVFPLAPCSRSTSE STAALGCLVKDYFPEPVTVSWNSG ALTSGVHTFPAVLQSSGLYSLSSV VTVPSSSLGTKTYTCNVDHKPSNT KVDKRVESKYGPPCPPCPAPEAAG GPSVFLFPPKPKDTLMISRTPEVT CVVVDVSQEDPEVQFNWYVDGVEV HNAKTKPREEQFNSTYRVVSVLTV LHQDWLNGKEYKCKVSNKGLPSSI EKTISKAKGQPREPQVYTLPPSQE EMTKNQVSLTCLVKGFYPSDIAVE WESNGQPENNYKTTPPVLDSDGSF FLYSRLTVDKSRWQEGNVFSCSVM HEALHNHYTQKSLSLSLGK | 145 | EIVLTQSPATLSLSPGERATLS CRASQSVSNYLAWYQQKPGQAP RLLIHDASNRATGIPARFSGSG SGTDFTLTISSLEPEDFAVYYC QQRRNWPLTFGQGTKVEIKRTV AAPSVFIFPPSDEQLKSGTASV VCLLNNFYPREAKVQWKVDNAL QSGNSQESVTEQDSKDSTYSLS STLTLSKADYEKHKVYACEVTH QGLSSPVTKSFNRGEC | 148 |
| PSMB346 | EVQLLESGGGLVQPGGSLRLSC AASGFTFKSDAMHWVRQAPGKG LEWVSEISGSGGYTNYADSMKG RFTISRDNSKNTLYLQMNSLRA EDTAVYYCARDSYDSSLYVGDY FDYWGQGTLVTVSSASTKGPSV FPLAPCSRSTSESTAALGCLVK DYFPEPVTVSWNSGALTSGVHT FPAVLQSSGLYSLSSVVTVPSS SLGTKTYTCNVDHKPSNTKVDK RVESKYGPPCPPCPAPEAAGGP SVFLFPPKPKDTLMISRTPEVT CVVVDVSQEDPEVQFNWYVDGV EVHNAKTKPRESQFNSTYRVVS VLTVLHQDWLNGKEYKCKVSNK GLPSSIEKTISKAKGQPREPQV YTLPPSQEEMTKNQVSLTCLVK GFYPSDIAVEWESNGQFENNYK TTPPVLDSDGSFFLYSRLTVDK SRWQEGNVFSCSVMHEALHNHY TQKSLSLSLGK | 145 | EIVLTQSPATLSLSPGERAT LSCRASQSVSSYLAWYQQKP GQAPRLLIYDASYRATGIPA RFSGSGSGTDFTLTISSLEP EDFAVYYCQQRRNWPLTFGQ GTKVEIKRTVAAPSVFIFPP SDEQLKSGTASVVCLLNNFY PREAKVQWKVDNALQSGNSQ ESVTEQDSKDSTYSLSSTLT LSKADYEKHKVYACEVTHQG LSSPVTKSFNRGEC | 149 |
| PSMB347 | EVQLLESGGGLVQPGGSLRLSC AASGFTFKSDAMHWVRQAPGKG LEWVSEISGSGGYTNYADSMKS RFTISRDNSKNTLYLQMNSLRA EDTAVYYCARDSYDSSLYVGDY FDYWGQGTLVTVSSASTKGPSV FPLAPCSRSTSESTAALGCLVK DYFPEPVTVSWNSGALTSGVHT FPAVLQSSGLYSLSSVVTVPSS SLGTKTYTCNVDHKPSNTKVDK RVESKYGPPCPPCPAPEAAGGP SVFLFPPKPKDTLMISRTPEVT | 146 | EIVLTQSPATLSLSPGERAT LSCRASQSVSSYLAWYQQKP GQAPRLLIYDASNRATGIPA RFSGSGSGTDFTLTISSLEP EDFAVYYCQQRSNWPLTFGQ GTKVEIKRTVAAPSVFIFPP SDEQLKSGTASVVCLLNNFY PREAKVQWKVDNALQSGNSQ ESVTEQDSKDSTYSLSSTLT LSKADYEKHKVYACEVTHQG LSSPVTKSFNRGEC | 89 |

TABLE 26-continued

Heavy Chain and Light Chain sequences of top five PSMA candidates in monoclonal antibody format on IgG4 PAA

| mAb ID | Heavy Chain Amino acid sequence | SEQ ID NO | Light Chain Amino Acid Sequence | SEQ ID NO |
|---|---|---|---|---|
| | CVVVDVSQEDPEVQFNWYVDGV EVHNAKTKPREEQFNSTYRVVS VLTVLHQDWLNGK5YKCKVSNK GLPSSIEKTISKAKGQPREPQV YTLPPSQEEMTKNQVSLTCLVK GFYPSDIAVEWESNGQPENNYK TTPPVLDSDGSFFLYSRLTVDK SRWQEGNVFSCSVMHEALHNHY TQKSLSLSLGK | | | |
| PSMB349 | EVQLLESGGGLVQPGGSLRLSC AASGFTFKSDAMHWVRQAPGKG LEWVSEISGSGGYTNYADSLKG RFTISRDNSKNTLYLQMNSLRA EDTAVYYCARDSYDSSLYVGDY FDYWGQGTLVTVSSASTKGPSV FPLAPCSRSTSESTAALGCLVK DYFPEPVTVSWNSGALTSGVHT FPAVLQSSGLYSLSSVVTVPSS SLGTKTYTCNVDHKPSNTKVDK RVESKYGPPCPPCPAPEAAGGP SVFLFPPKPKDTLMXSRTPEVT CVVVDVSQEDPEVQFNWYVDGV EVHNAKTKPREEQFNSTYRVVS VLTVLHQDWLNGKEYKCKVSNK GLPSSIEKTISKAKGQPREPQV YTLPPSQEEMTKNQVSLTCLVK GFYPSDIAVEWESNGQPENNYK TTPPVLDSDGSFFLYSRLTVDK SRWQEGNVFSCSVMHEALHNHY TQKSLSLSLGK | 147 | EIVLTQSPATLSLSPGERAT LSCRASQSVSSYLAWYQQK GQAPRLLIYDASNRATGIPA RFSGSGSGTDFTLTISSLEP EDFAVYYCQQRGNWPLTFGQ GTKVEIKRTVAAPSVFIFPP SDEQLKSGTASVVCLLNNFY PREAKVQWKVDNALQSGNSQ ESVTEQDSKDSTYSLSSTLT LSKADYEKHKVYACEVTHQG LSSPVTKSFNRGEC | 150 |

The 3 different HC and 4 different LC were combined in a matrix format to expand the diversity of hits (Table 26). Given that the methionine in the CDR2 of PSMH860 is a posttranslational risk, a new sequence was generated with M64L and identified as PSMH865. PSMH865 was paired with PSML160 to generate Mab PSMB365. Tables 27 and 28 provide sequence information.

TABLE 26

Matrix format of the 3 heavy chains and 4 light chains combined

| | PSMH859 | PSMH860 | PSMH862 |
|---|---|---|---|
| PH9L3 | PSMB344 | PSMB347 | PSMB358 |
| PSML158 | — | PSMB361 | PSMB349 |
| PSML159 | PSMB345 | PSMB362 | PSMB359 |
| PSML160 | PSMB346 | PSMB363 | PSMB360 |

TABLE 27

VH and VL sequences of matrix recombined PSMA hits

| MAB ID | VH Amino acid sequence | SEQ ID NO | VL Amino Acid Sequence | SEQ ID NO |
|---|---|---|---|---|
| PSMB358 | EVQLLESGGGLVQPGGSLRLSCAASG FTFKSDAMHWVRQAPGKGLEWVSEIS GSGGYTNYADSLKGRFTISRDNSKNT LYLQMNSLRAEDTAVYYCARDSYDSS LYVGDYFDYWGQGTLVTVSS | 140 | EIVLTQSPATLSLSPGE RATLSCRASQSVSSYLA WYQQKPGQAPRLLIYDA SNRATGIPARFSGSGSG TDFTLTISSLEPEDFAV YYCQQRSNWPLTFGQGT KVEIK | 67 |
| PSMB359 | EVQLLESGGGLVQPGGSLRLSCAASG FTFKSDAMHWVRQAPGKGLEWVSEIS GSGGYTNYADSLKGRFTISRDNSKNT LYLQMNSLRAEDTAVYYCARDSYDSS LYVGDYFDYWGQGTLVTVSS | 140 | EIVLTQSPATLSLSPGE RATLSCRASQSVSNYLA WYQQKPGQAPRLLIHDA SNRATGIPARFSGSGSG TDFTLTISSLEPEDFAV YYCQQRRNWPLTFGQGT KVEIK | 142 |

TABLE 27-continued

VH and VL sequences of matrix recombined PSMA hits

| MAB ID | VH Amino acid sequence | SEQ ID NO | VL Amino Acid Sequence | SEQ ID NO |
|---|---|---|---|---|
| PSMB360 | EVQLLESGGGLVQPGGSLRLSCAASG FTFKSDAMHWVRQAPGKGLEWVSEIS GSGGYTNYADSLKGRFTISRDNSKNT LYLQMNSLRAEDTAVYYCARDSYDSS LYVGDYFDYWGQGTLVTVSS | 140 | EIVLTQSPATLSLSPGE RATLSCRASQSVSSYLA WYQQKPGQAPRLLIYDA SYRATGIPARFSGSGSG TDFTLTISSLEPEDFAV YYCQQRRNWPLTFGQGT KVEIK | 143 |
| PSMB361 | EVQLLESGGGLVQPGGSLRLSCAASG FTFKSDAMHWVRQAPGKGLEWVSEIS GSGGYTNYADSMKSRFTISRDNSKNT LYLQMNSLRAEDTAVYYCARDSYDSS LYVGDYFDYWGQGTLVTVSS | 139 | EIVLTQSPATLSLSPGE RATLSCRASQSVSSYLA WYQQKPGQAPRLLIYDA SNRATGIPARFSGSGSG TDFTLTISSLEPEDFAV YYCQQRGNWPLTFGQGT KVEIK | 144 |
| PSMB362 | EVQLLESGGGLVQPGGSLRLSCAASG FTFKSDAMHWVRQAPGKGLEWVSEIS GSGGYTNYADSMKSRFTISRDNSKNT LYLQMNSLRAEDTAVYYCARDSYDSS LYVGDYFDYWGQGTLVTVSS | 139 | EIVLTQSPATLSLSPGE RATLSCRASQSVSNYLA WYQQKPGQAPRLLIHDA SNRATGIPARFSGSGSG TDFTLTISSLEPEDFAV YYCQQRRNWPLTFGQGT KVEIK | 142 |
| PSMB363 | EVQLLESGGGLVQPGGSLRLSCAASG FTFKSDAMHWVRQAPGKGLEWVSEIS GSGGYTNYADSMKSRFTISRDNSKNT LYLQMNSLRAEDTAVYYCARDSYDSS LYVGDYFDYWGQGTLVTVSS | 139 | EIVLTQSPATLSLSPGE RATLSCRASQSVSSYLA WYQQKPGQAPRLLIYDA SYRATGIPARFSGSGSG TDFTLTISSLEPEDFAV YYCQQRRNWPLTFGQGT KVEIK | 143 |
| PSMB365 | EVQLLESGGGLVQPGGSLRLSCAASG FTFKSDAMHWVRQAPGKGLEWVSEIS GSGGYTNYADSLKSRFTISRDNSKNT LYLQMNSLRAEDTAVYYCARDSYDSS LYVGDYFDYWGQGTLVTVSS | 141 | EIVLTQSPATLSLSPGE RATLSCRASQSVSSYLA WYQQKPGQAPRLLIYDA SYRATGIPARFSGSGSG TDFTLTISSLEPEDFAV YYCQQRRNWPLTFGQGT KVEIK | 143 |

TABLE 28

Heavy Chain and Light Chain sequences of matrix recombined PSMA hits

| MAB ID | Heavy Chain Amino acid sequence | SEQ ID NO | Light Chain Amino Acid Sequence | SEQ ID NO |
|---|---|---|---|---|
| PSMB358 | EVQLLESGGGLVQPGGSLRLSCAASG FTFKSDAMHWVRQAPGKGLEWVSEIS GSGGYTNYADSLKGRFTISRDNSKNT LYLQMNSLRAEDTAVYYCARDSYDSS LYVGDYFDYWGQGTLVTVSSASTKGP SVFPLAPCSRSTSESTAALGCLVKDY FPEPVTVSWNSGALTSGVHTFPAVLQ SSGLYSLSSVVTVPSSSLGTKTYTCN VDHKPSNTKVDKRVESKYGPPCPPCP APEAAGGPSVFLFPPKPKDTLMISRT PEVTCVVVDVSQEDPEVQFNWYVDGV EVHNAKTKPREEQFNSTYRVVSVLTV LHQDWLNGKEYKCKVSNKGLPSSIEK TISKAKGQPREPQVYTLPPSQEEMTK NQVSLTCLVKGFYPSDIAVEWESNGQ PENNYKTTPPVLDSDGSFFLYSRLTV DKSRWQEGNVFSCSVMHEALHNHYTQ KSLSLSLGK | 147 | EIVLTQSPATLSLSPGE RATLSCRASQSVSSYLA WYQQKPGQAPRLLIYDA SNRATGIPARFSGSGSG TDFTLTISSLEPEDFAV YYCQQRSNWPLTFGQGT KVEIKRTVAAPSVFIFP PSDEQLKSGTASVVCLL NNFYPREAKVQWKVDNA LQSGNSQESVTEQDSKD STYSLSSTLTLSKADYE KHKVYACEVTHQGLSSP VTKSFNRGEC | 89 |
| PSMB359 | EVQLLESGGGLVQPGGSLRLSCAASG FTFKSDAMHWVRQAPGKGLEWVSEIS GSGGYTNYADSLKGRFTISRDNSKNT LYLQMNSLRAEDTAVYYCARDSYDSS LYVGDYFDYWGQGTLVTVSSASTKGP SVFPLAPCSRSTSESTAALGCLVKDY | 147 | EIVLTQSPATLSLSPGE RATLSCRASQSVSNYLA WYQQKPGQAPRLLIHDA SNRATGIPARFSGSGSG TDFTLTISSLEPEDFAV YYCQQRRNWPLTFGQGT | 148 |

TABLE 28-continued

Heavy Chain and Light Chain sequences of matrix recombined PSMA hits

| MAB ID | Heavy Chain Amino acid sequence | SEQ ID NO | Light Chain Amino Acid Sequence | SEQ ID NO |
|---|---|---|---|---|
| | FPEPVTVSWNSGALTSGVHTFPAVLQ SSGLYSLSSVVTVPSSSLGTKTYTCN VDHKPSNTKVDKRVESKYGPPCPPCP APEAAGGPSVFLFPPKPKDTLMISRT PEVTCVVVDVSQEDPEVQFNWYVDGV EVHNAKTKPREEQFNSTYRVVSVLTV LHQDWLNGKEYKCKVSNKGLPSSIEK TISKAKGQPREPQVYTLPPSQEEMTK NQVSLTCLVKGFYPSDIAVEWESNGQ PENNYKTTPPVLDSDGSFFLYSRLTV DKSRWQEGNVFSCSVMHEALHNHYTQ KSLSLSLGK | | KVEIKRTVAAPSVFIFP PSDEQLKSGTASVVCLL NNFYPREAKVQWKVDNA LQSGNSQESVTEQDSKD STYSLSSTLTLSKADYE KHKVYACEVTHQGLSSP VTKSFNRGEC | |
| PSMB360 | EVQLLESGGGLVQPGGSLRLSCAASG FTFKSDAMHWVRQAPGKGLEWVSEIS GSGGYTNYADSLKGRFTISRDNSKNT LYLQMNSLRAEDTAVYYCARDSYDSS LYVGDYFDYWGQGTLVTVSSASTKGP SVFPLAPCSRSTSESTAALGCLVKDY FPEPVTVSWNSGALTSGVHTFPAVLQ SSGLYSLSSVVTVPSSSLGTKTYTCN VDHKPSNTKVDKRVESKYGPPCPPCP APEAAGGPSVFLFPPKPKDTLMISRT PEVTCVVVDVSQEDPEVQFNWYVDGV EVHNAKTKPREEQFNSTYRVVSVLTV LHQDWLNGKEYKCKVSNKGLPSSIEK TISKAKGQPREPQVYTLPPSQEEMTK NQVSLTCLVKGFYPSDIAVEWESNGQ PENNYKTTPPVLDSDGSFFLYSRLTV DKSRWQEGNVFSCSVMHEALHNHYTQ KSLSLSLGK | 147 | EIVLTQSPATLSLSPGE RATLSCRASQSVSSYLA WYQQKPGQAPRLLIYDA SYRATGIPARFSGSGSG TDFTLTISSLEPEDFAV YYCQQRRNWPLTFGQGT KVEIKRTVAAPSVFIFP PSDEQLKSGTASVVCLL NNFYPREAKVQWKVDNA LQSGNSQESVTEQDSKD STYSLSSTLTLSKADYE KHKVYACEVTHQGLSSP VTKSFNRGEC | 149 |
| PSMB361 | EVQLLESGGGLVQPGGSLRLSCAASG FTFKSDAMHWVRQAPGKGLEWVSEIS GSGGYTNYADSMKSRFTISRDNSKNT LYLQMNSLRAEDTAVYYCARDSYDSS LYVGDYFDYWGQGTLVTVSSASTKGP SVFPLAPCSRSTSESTAALGCLVKDY FPEPVTVSWNSGALTSGVHTFPAVLQ SSGLYSLSSVVTVPSSSLGTKTYTCN VDHKPSNTKVDKRVESKYGPPCPPCP APEAAGGPSVFLFPPKPKDTLMISRT PEVTCVVVDVSQEDPEVQFNWYVDGV EVHNAKTKPREEQFNSTYRVVSVLTV LHQDWLNGKEYKCKVSNKGLPSSIEK TISKAKGQPREPQVYTLPPSQEEMTK NQVSLTCLVKGFYPSDIAVEWESNGQ PENNYKTTPPVLDSDGSFFLYSRLTV DKSRWQEGNVFSCSVMHEALHNHYTQ KSLSLSLGK | 146 | EIVLTQSPATLSLSPGE RATLSCRASQSVSSYLA WYQQKPGQAPRLLIYDA SNRATGIPARFSGSGSG TDFTLTISSLEPEDFAV YYCQQRGNWPLTFGQGT KVEIKRTVAAPSVFIFP PSDEQLKSGTASVVCLL NNFYPREAKVQWKVDNA LQSGNSQESVTEQDSKD STYSLSSTLTLSKADYE KHKVYACEVTHQGLSSP VTKSFNRGEC | 150 |
| PSMB362 | EVQLLESGGGLVQPGGSLRLSCAASG FTFKSDAMHWVRQAPGKGLEWVSEIS GSGGYTNYADSMKSRFTISRDNSKNT LYLQMNSLRAEDTAVYYCARDSYDSS LYVGDYFDYWGQGTLVTVSSASTKGP SVFPLAPCSRSTSESTAALGCLVKDY FPEPVTVSWNSGALTSGVHTFPAVLQ SSGLYSLSSVVTVPSSSLGTKTYTCN VDHKPSNTKVDKRVESKYGPPCPPCP APEAAGGPSVFLFPPKPKDTLMISRT PEVTCVVVDVSQEDPEVQFNWYVDGV EVHNAKTKPREEQFNSTYRVVSVLTV LHQPWLNGKEYKCKVSNKGLPSSIEK TISKAKGQPREPQVYTLPPSQEEMTK NQVSLTCLVKGFYPSDIAVEWESNGQ PENNYKTTPPVLDSDGSFFLYSRLTV DKSRWQEGNVFSCSVMHEALHNHYTQ KSLSLSLGK | 146 | EIVLTQSPATLSLSPGE RATLSCRASQSVSNYLA WYQQKPGQAPRLLIHDA SNRATGIPARFSGSGSG TDFTLTISSLEPEDFAV YYCQQRRNWPLTFGQGT KVEIKRTVAAPSVFIFP PSDEQLKSGTASVVCLL NNFYPREAKVQWKVDNA LQSGNSQESVTEQDSKD STYSLSSTLTLSKADYE KHKVYACEVTHQGLSSP VTKSFNRGEC | 148 |
| PSMB363 | EVQLLESGGGLVQPGGSLRLSCAASG FTFKSDAMHWVRQAPGKGLEWVSEIS GSGGYTNYADSMKSRFTISRDNSKNT LYLQMNSLRAEDTAVYYCARDSYDSS LYVGDYFDYWGQGTLVTVSSASTKGP | 146 | EIVLTQSPATLSLSPGE RATLSCRASQSVSSYLA WYQQKPGQAPRLLIYDA SYRATGIPARFSGSGSG TDFTLTISSLEPEDFAV | 143 |

TABLE 28-continued

Heavy Chain and Light Chain sequences of matrix recombined PSMA hits

| MAB ID | Heavy Chain Amino acid sequence | SEQ ID NO | Light Chain Amino Acid Sequence | SEQ ID NO |
|---|---|---|---|---|
| | SVFPLAPCSRSTSESTAALGCLVKDY FPEPVTVSWNSGALTSGVHTFPAVLQ SSGLYSLSSVVTVPSSSLGTKTYTCN VDHKPSNTKVDKRVESKYGPPCPPCP APEAAGGPSVFLFPPKPKDTLMISRT PEVTCVVVDVSQEDPEVQFNWYVDGV EVHNAKTKPREEQFNSTYRVVSVLTV LHQDWLNGKEYKCKVSNKGLPSSIEK TISKAKGQPREPQVYTLPPSQEEMTK NQVSLTCLVKGFYPSDIAVEWESNGQ PENNYKTTPPVLDSDGSFFLYSRLTV DKSRWQEGNVFSCSVMHEALHNHYTQ KSLSLSLGK | | YYCQQRRNWPLTFGQGT KVEIKRTVAAPSVFIFP PSDEQLKSGTASVVCLL NNFYPREAKVQWKVDNA LQSGNSQESVTEQDSKD STYSLSSTLTLSKADYE KHKVYACEVTHQGLSSP VTKSFNRGEC | |
| PSMB365 | EVQLLESGGGLVQPGGSLRLSCAASG FTFKSDAMHWVRQAPGKGLEWVSEIS GSGGGYTNYADSLKSRFTISRDNSKNT LYLQMNSLRAEDTAVYYCARDSYDSS LYVGDYFDYWGQGTLVTVSSASTKGP SVFPLAPCSRSTSESTAALGCLVKDY FPEPVTVSWNSGALTSGVHTFPAVLQ SSGLYSLSSVVTVPSSSLGTKTYTCN VDHKPSNTKVDKRVESKYGPPCPPCP APEAAGGPSVFLFPPKPKDTLMISRT PEVTCVVVDVSQEDPEVQFNWYVDGV EVHNAKTKPREEQFNSTYRVVSVLTV LHQDWLNGKEYKCKVSNKGLPSSIEK TISKAKGQPREPQVYTLPPSQEEMTK NQVSLTCLVKGFYPSDIAVEWESNGQ PENNYKTTPPVLDSDGSFFLYSRLTV DKSRWQEGNVFSCSVMHEALHNHYTQ KSLSLSLGK | 151 | EIVLTQSPATLSLSPGE RATLSCRASQSVSSYLA WYQQKPGQAPRLLIYDA SYRATGIPARFSGSGSG TDFTLTISSLEPEDFAV YYCQQRRNWPLTFGQGT KVEIKRTVAAPSVFIFP PSDEQLKSGTASVVCLL NNFYPREAKVQWKVDNA LQSGNSQESVTEQDSKD STYSLSSTLTLSKADYE KHKVYACEVTHQGLSSP VTKSFNRGEC | 149 |

Table 29 provides the CDRs for all for the affinity-matured hits.

TABLE 29

CDR sequences of affinity-matured PSMA hits

| MAB ID | | CDR1 | CDR2 | CDR3 |
|---|---|---|---|---|
| PSMB344 | HC | SDAMH (25) | EISGSGGYTNYADSMKG (130) | DSYDSSLYVGDYFDY (27) |
| | LC | RASQSVSSYLA (28) | DASNRAT (29) | QQRSNWPLT (30) |
| PSMB345 | HC | SDAMH (25) | EISGSGGYTNYADSMKG (130) | DSYDSSLYVGDYFDY (27) |
| | LC | RASQSVSNYLA (131) | DASNRAT (29) | QQRRNWPLT (132) |
| PSMB346 | HC | SDAMH (25) | EISGSGGYTNYADSMKG (130) | DSYDSSLYVGDYFDY (27) |
| | LC | RASQSVSSYLA (28) | DASYRAT (133) | QQRRNWPLT (132) |
| PSMB347 | HC | SDAMH (25) | EISGSGGYTNYADSMKS (134) | DSYDSSLYVGDYFDY (27) |
| | LC | RASQSVSSYLA (28) | DASNRAT (29) | QQRSNWPLT (30) |
| PSMB349 | HC | SDAMH (25) | EISGSGGYTNYADSLKG (135) | DSYDSSLYVGDYFDY (27) |
| | LC | RASQSVSSYLA (28) | DASNRAT (29) | QQRGNWPLT (136) |
| PSMB358 | HC | SDAMH (25) | EISGSGGYTNYADSLKG (135) | DSYDSSLYVGDYFDY (27) |

TABLE 29-continued

CDR sequences of affinity-matured PSMA hits

| MAB ID | | CDR1 | CDR2 | CDR3 |
|---|---|---|---|---|
| | | CDRs (SEQ ID NO:) | | |
| | LC | RASQSVSSYLA (28) | DASNRAT (29) | QQRSNWPLT (30) |
| PSMB359 | HC | SDAMH (25) | EISGSGGYTNYADSLKG (135) | DSYDSSLYVGDYFDY (27) |
| | LC | RASQSVSNYLA (131) | DASNRAT (29) | QQRRNWPLT (132) |
| PSMB360 | HC | SDAMH (25) | EISGSGGYTNYADSLKG (135) | DSYDSSLYVGDYFDY (27) |
| | LC | RASQSVSSYLA (28) | DASYRAT (133) | QQRRNWPLT (132) |
| PSMB361 | HC | SDAMH (25) | EISGSGGYTNYADSMKS (134) | DSYDSSLYVGDYFDY (27) |
| | LC | RASQSVSSYLA (28) | DASNRAT (29) | QQRGNWPLT (136) |
| PSMB362 | HC | SDAMH (25) | EISGSGGYTNYADSMKS (134) | DSYDSSLYVGDYFDY (27) |
| | LC | RASQSVSNYLA (131) | DASNRAT (29) | QQRRNWPLT (132) |
| PSMB363 | HC | SDAMH (25) | EISGSGGYTNYADSMKS (134) | DSYDSSLYVGDYFDY (27) |
| | LC | RASQSVSSYLA (28) | DASYRAT (133) | QQRRNWPLT (132) |
| PSMB365 | HC | SDAMH (25) | EISGSGGYTNYADSLKS (137) | DSYDSSLYVGDYFDY (27) |
| | LC | RASQSVSSYLA (28) | DASYRAT (133) | QQRRNWPLT (132) |

Example 15. Generation of Affinity-Matured PSMA×CD3 Bispecific

Two types of affinity-matured PSMA×CD3 bispecific antibodies were generated, one specific for the targeting arm (e.g. affinity matured anti-PSMA) recombined with a high affinity CD3 arm [CD3B219 (VH SEQ ID NO: 104, VL SEQ ID NO: 105; HC SEQ ID NO: 110, LC SEQ ID NO: 111)] or a low affinity CD3 arm called CD3B376 [CD3B376 (VH SEQ ID NO: 152, VL SEQ ID NO: 153; HC SEQ ID NO: 154, LC SEQ ID NO: 155)].

TABLE 30

Sequences for the low affinity CD3 arm (CD3B376)

| MAB ID | VH Amino acid sequence | SEQ ID NO | VL Amo Acid Sequence | SEQ ID NO |
|---|---|---|---|---|
| CD3B376 | QVQLQQSGPRLVRPSQTLSLTCAISG DSVFNNNAAWSWIRQSPSRGLEWL GRTYYRSKWLYDYAVSVKSRITVNPD TSRNQFTLQLNSVTPEDTALYYCARG YSSSFDYWGQGTLVTVSS | 152 | QSALTQPASVSGSPGQSITISCT GTSSNIGTYKFVSWYQQHPDKA PKVLLYEVSKRPSGVSSRFSGSKS GNTASLTISGLQAEDQADYHCV SYAGSGTLLFGGGTKLTVL | 153 |
| | Heavy Chain amino acid sequence | | Light Chain amino Acid Sequence | |
| | MAWVWTLLFLMAAAQSIQAQVQL QQSGPRLVRPSQTLSLTCAISGDSVF NNNAAWSWIRQSPSRGLEWLGRTY YRSKWLYDYAVSVKSRITVNPDTSRN QFTLQLNSVTPEDTALYYCARGYSSSF DYWGQGTLVTVSSASTKGPSVFPLA PCSRSTSESTAALGCLVKDYFPEPVTV SWNSGALTSGVHTFPAVLQSSGLYSL SSVVTVPSSSLGTKTYTCNVDHKPSN TKVDKRVESKYGPPCPPCPAPEAAG GPSVFLFPPKPKDTLMISRTPEVTCVV VDVSQEDPEVQFNWYVDGVEVHNA KIKPREEQFNSTYRVVSVLIVLHQD WLNGKEYKCKVSNKGLPSSIEKTISKA | 154 | MARSALLILALLLLGLFSPGAWG QSALTQPASVSGSPGQSITISCT GTSSNIGTYKFVSWYQQHPDKA PKVLLYEVSKRPSGVSSRFSGSKS GNTASLTISGLQAEDQADYHCV SYAGSGTLLFGGGTKLTVLGQPK AAPSVTLFPPSSEELQANKATLV CLISDFYPGAVTVAWKADSSPV KAGVETTTPSKQSNNKYAASSYL SLTPEQWKSHRSYSCQVTHEGS TVEKTVAPTECS | 155 |

TABLE 30-continued

Sequences for the low affinity CD3 arm (CD3B376)

KGQPREPQVYTLPPSQEEMTKNQVS
LTCLVKGFYPSDIAVEWESNGQPEN
NYKTTPPVLDSDGSFLLYSKLTVDKSR
WQEGNVFSCSVMHEALHNHYTQKS
LSLSLGK

These parental mAbs are in the GenMab format (Labrijn et al, 2013) where the targeting parent (PSMA) contains the 409R GenMab mutation (native amino acid for IgG4), while the killing parent (CD3) contains the F405L GenMab mutation and R409K mutation. The monospecific anti-CD3 antibody was expressed as IgG4, having Fc substitutions S228P, F234A, L235A, F405L, and R409K (CD3 arm) (numbering according to EU index) in their Fc regions. The targeting parent (PSMA) is on human IgG4 with Fc substitutions S228P, F234A, L235A. The monospecific antibodies were expressed in HEK cell lines under CMV promoters.

The parental PSMA and CD3 antibodies were purified using a protein A column with an elution buffer of 100 mM NaAc pH3.5 and a neutralization buffer of 2.5M Tris, pH 7.2. The neutralized parental mAbs were used to make PSMA×CD3 bispecific antibodies. A portion of parental mabs were further buffer exchanged into D-PBS, pH 7.2 buffer for analytical measurements and assays.

Post purification, controlled Fab-arm exchange was performed to make bispecific antibodies as described in Example 6.

The final bispecific antibodies produced, along with the parental mAbs (i.e. PSMA, CD3, or Null) used in the recombination reactions are listed in Table 27 and 28.

Selected PSMA hits were also paired with a non-killing arm (Null) to create negative controls for testing purposes. For control bispecific antibodies, B2M1, an RSV antibody in the IgG4 PAA format was generated, purified and, combined with either the CD3 arm CD3B219-F405L, R409K to generate CD3B288 (CD3×null) or PSMA arms, PSMB122, PSMB126, PSMB130 to generate PS3B37, PS3B39 and PS3B40 respectively (PSMA×null). These PSMA specific affinity matured Mabs were crossed (as in methods above) to CD3B219 and CD3B376 to generate the bispecific antibodies shown in Table 31.

TABLE 31

Generation of affinity-matured PSMA x CD3 bispecific antibodies generated from affinity matured PSMB127

| ID | Arm 1 | HC SEQ ID: | LC SEQ ID: | Arm 2 | HC SEQ ID: | LC SEQ ID: |
|---|---|---|---|---|---|---|
| PS3B60 | PSMB344 | 145 | 89 | CD3B219 | 110 | 111 |
| PS3B61 | PSMB345 | 145 | 148 | CD3B219 | 110 | 111 |
| PS3B62 | PSMB346 | 145 | 149 | CD3B219 | 110 | 111 |
| PS3B63 | PSMB347 | 146 | 89 | CD3B219 | 110 | 111 |
| PS3B64 | PSMB349 | 147 | 150 | CD3B219 | 110 | 111 |
| PS3B70 | PSMB358 | 147 | 89 | CD3B219 | 110 | 111 |
| PS3B71 | PSMB359 | 147 | 148 | CD3B219 | 110 | 111 |
| PS3B72 | PSMB360 | 147 | 149 | CD3B219 | 110 | 111 |
| PS3B73 | PSMB361 | 146 | 150 | CD3B219 | 110 | 111 |
| PS3B74 | PSMB362 | 146 | 148 | CD3B219 | 110 | 111 |
| PS3B75 | PSMB363 | 146 | 149 | CD3B219 | 110 | 111 |
| PS3B76 | PSMB358 | 151 | 149 | CD3B376 | 154 | 155 |
| PS3B77 | PSMB349 | 145 | 89 | CD3B376 | 154 | 155 |
| PS3B78 | PSMB359 | 145 | 148 | CD3B376 | 154 | 155 |
| PS3B79 | PSMB360 | 145 | 149 | CD3B376 | 154 | 155 |
| PS3B80 | PSMB347 | 146 | 89 | CD3B376 | 154 | 155 |
| PS3B81 | PSMB361 | 147 | 150 | CD3B376 | 154 | 155 |
| PS3B82 | PSMB362 | 147 | 89 | CD3B376 | 154 | 155 |
| PS3B83 | PSMB363 | 147 | 148 | CD3B376 | 154 | 155 |
| PS3B84 | PSMB344 | 147 | 149 | CD3B376 | 154 | 155 |
| PS3B85 | PSMB345 | 146 | 150 | CD3B376 | 154 | 155 |
| PS3B86 | PSMB346 | 146 | 148 | CD3B376 | 154 | 155 |
| PS3B90 | PSMB365 | 146 | 149 | CD3B376 | 154 | 155 |

Figure 36:
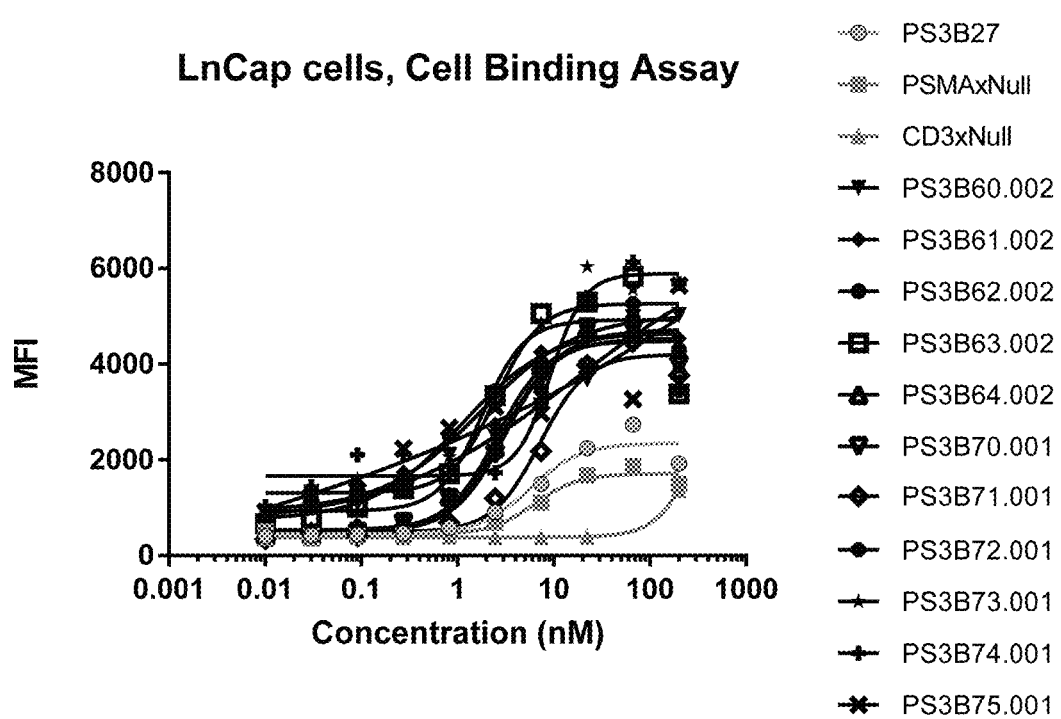
FIG. 36 shows LNCAP cell binding of a subset of affinity-matured PSMA×CD3 bispecific antibodies.
Figure 37:
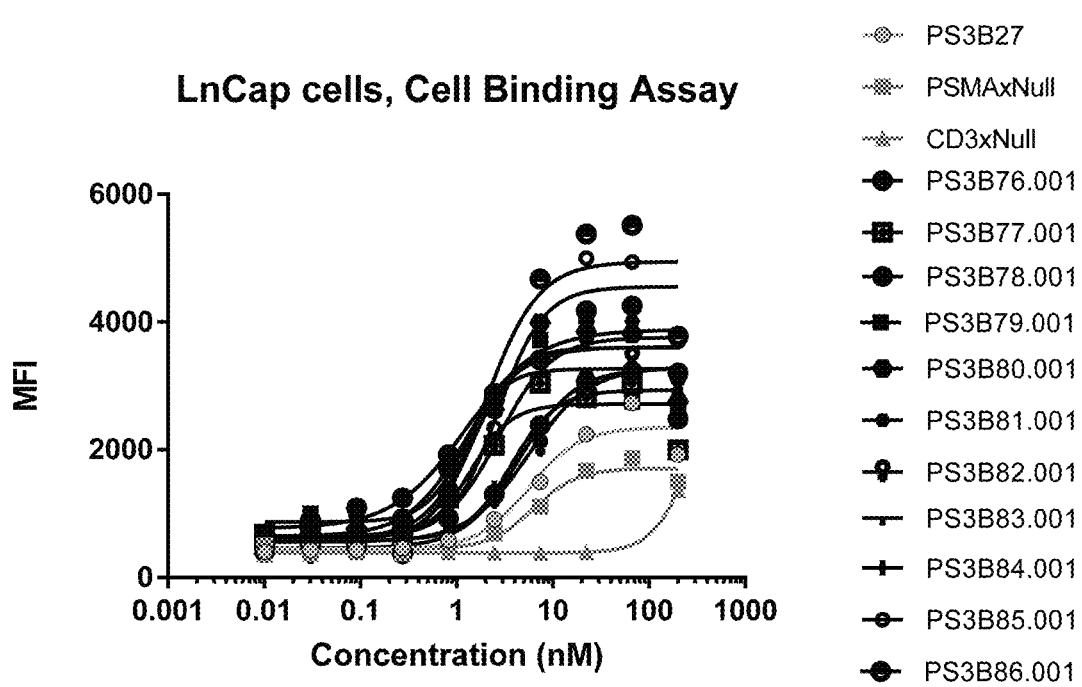
FIG. 37 shows LNCAP cell binding of a subset of affinity-matured PSMA×CD3 bispecific antibodies.
Figure 38:
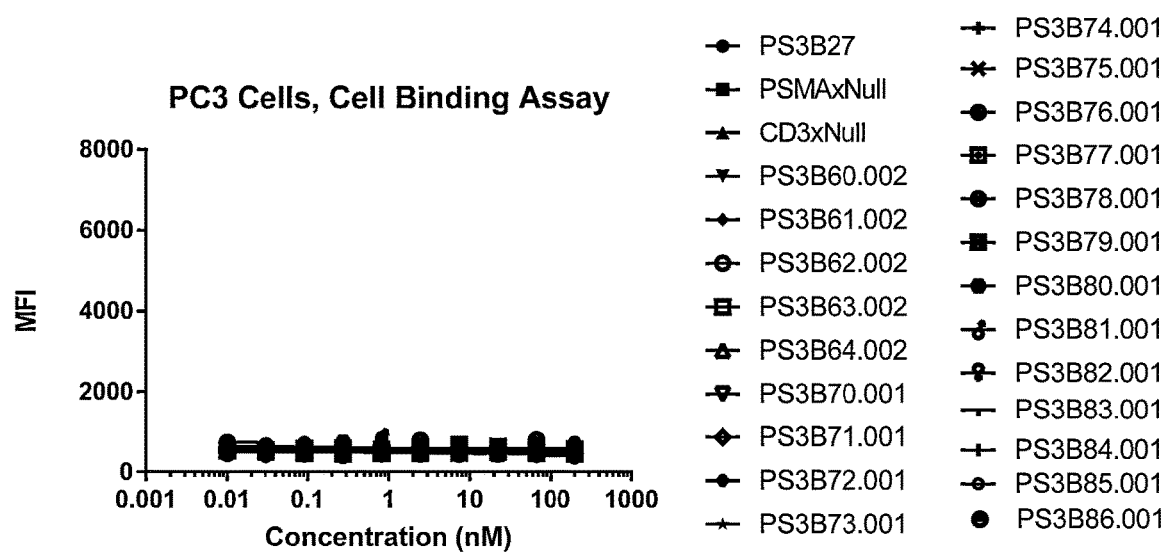
FIG. 38 shows PSMA-negative PC3 cell binding results of affinity-matured PSMA×CD3 bispecific antibodies.

PSMA×CD3 bispecific antibodies were tested for binding to PSMA positive cell line, LNCAP, to PSMA negative cell line, PC3. To assess the binding capabilities of the PSMA bispecific antibodies, the cell-binding assay was utilized (described previously). Bispecific antibodies were normalized for protein concentration and then incubated with the same number of cells expressing either human or cyno PSMA. The MFI at each concentration was collected by flow cytometry and plotted as a function of concentration. Data was transformed via log 10 and then plotted. Nonlinear regression of binding curves was done to determine $EC_{50}$ s. These relative values were used for ranking PSMA binding to target cells. FIGS. 36-38 show LNCAP binding of all bispecific antibodies prepared. In FIG. 38, none of the constructs demonstrated binding to the PSMA negative cell line. In FIG. 36 and FIG. 37, all of the affinity matured hits demonstrated increased binding affinity through left shifted curves and increased cMax as compared to the parental Mab, PS2B27.

The interactions of the affinity matured bispecific antibodies with recombinant Cyno PSMA ECD and Human PSMA ECD were studied by Surface Plasmon Resonance (SPR) using a ProteOn XPR36 system (BioRad) as described previously for recombinant chimp PSMA ECD. All of the bispecific antibodies bind both targets with substantially the same affinity, KDs ranging from 0.05 nM to 0.27 nM for human PSMA ECD and from 0.05 nM to 0.23 nM from cyno PSMA ECD.

Example 16. Evaluation of PSMA×CD3 Affinity Matured Bispecific Abs in Functional Cell Killing Assay Based on the above data, affinity measurements and sequence identity, three PSMA antibodies, PSMB347, PSMB360 and PSMB365 as bispecifics with either CD3B219 or CD3B376, were further characterized for the ability to mediate PSMA specific, redirected T cell cytotoxicity. T-cell mediated killing was measured using a caspase cytotoxicity assay, which indirectly measures cell killing via cleavage of a fluorescent substrate by active caspase 3/7. Cleavage of the substrate results in a fluorescent DNA dye, with fluorescence restricted to the cell nucleus. Repeated fluorescence measurements are taken in each well throughout the course of the assay, using a motorized 10× objective, capable of precisely imaging well(s) at the same coordinates. Target cell populations are identified based on defined size restrictions and/or through the use of a secondary label. Frozen Pan CD3+ T-cells (purchased from Biological Specialty Corporation, Colmar, Pa.) were isolated by negative selection from normal healthy donors. Prostate cancer cells, expressing PSMA, (LNCaP, C42) were cultured in RPMI 1640 with 10% HI FBS+supplements (purchased from Life Technologies).

T-cells and target cells were combined at an effector to target ratio (E:T) of 3:1 in Phenol Red free RPMI+10% FBS and supplements (Life Technologies), without selection reagents, and 0.6 uL of NucView caspase reagent (Essen Bioscience) was added to each mL of cells, per manufacturer guidelines. A total volume of 0.1 mL cells were added to appropriate wells of a clear, 96-well flat-bottom plate (BD Falcon). PS3B27 (CD3×PSMA), CD3B288 (CD3×Null) or PS3B46 (PSMA×Null) Bispecific antibodies were prepared at 2× final concentration in Phenol Red free RPMI, prepared as indicated above, and 0.1 mL of compounds were added to each well. After 30 minute incubation at room temperature to minimize cell aggregation at the edge of wells, plates were transferred to the Zoom Incucyte instrument (Essen Bioscience). The Incucyte Instrument resides in a humidified incubator set at 37° C., 5% CO2.

Figure 39:
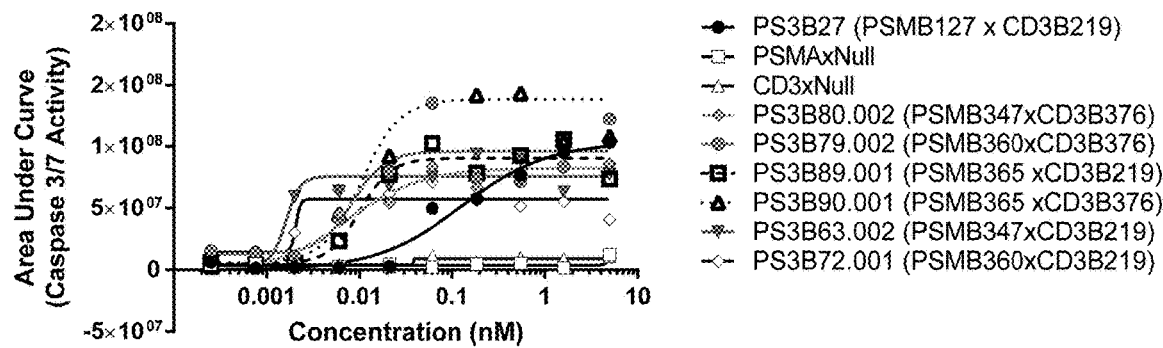
FIG. 39 shows results of PSMA×CD3 Affinity Matured Bispecific Abs in a Functional Cell Killing Assay.

Processing definitions on the Incucyte were designed for each cell line tested, per manufacture guidelines. Measurements were taken every six hours, until a plateau in the caspase signal was observed, and followed by three or more successive decreases from the maximum signal in the well(s) containing the highest concentration of the test compound(s). As the data shows in FIG. 39, the curves for PS3B80, PS3B79, PS3B89, PS3B90, PS3B63, and PS3B72 are left shifted indicating increased potency over PS3B27. The null arm controls did not induce cell death as expected.

Figure 40:
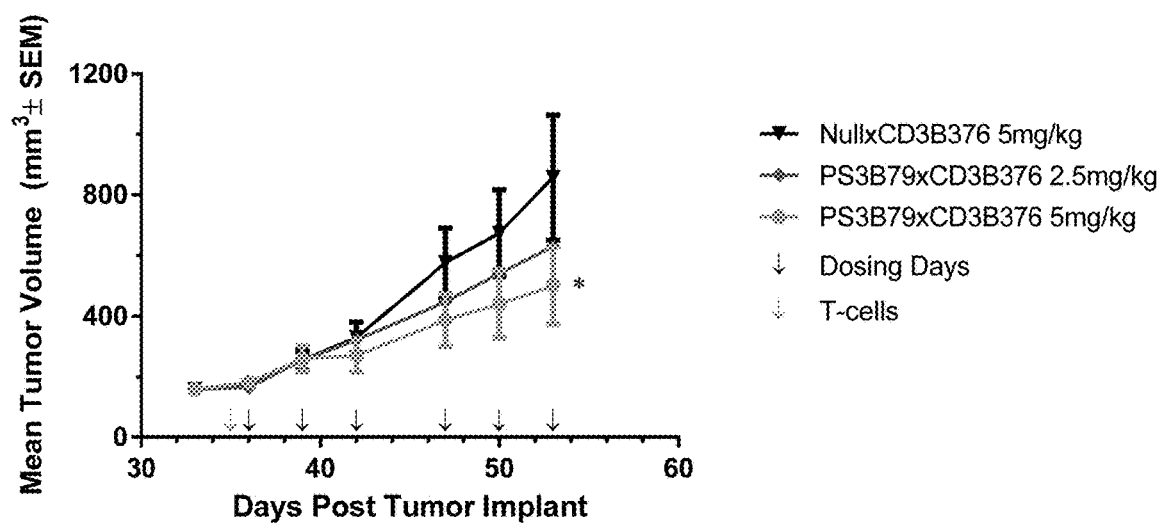
FIG. 40 shows anti-tumor efficacy of PS3B79 in LnCAP AR.TB human prostate xenografts in T cell humanized NSG mice. Subcutaneous LnCAP AR.TB tumors were measured twice weekly and the results presented as the mean tumor volume, expressed in mm$^3$±SEM (*, p<0.0001).
Figure 41:
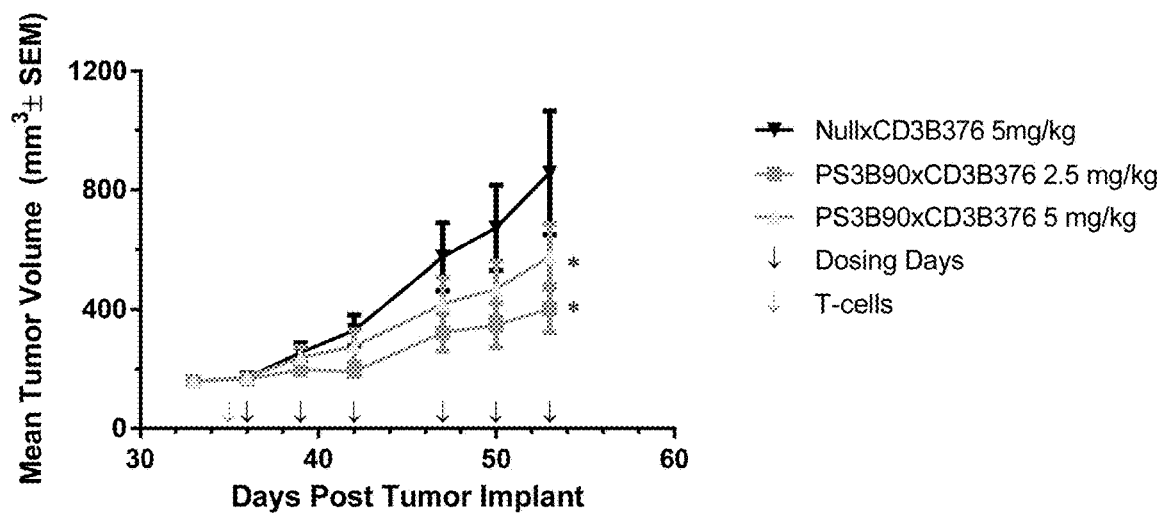
FIG. 41 shows anti-tumor efficacy of PS3B90 in LnCAP AR.TB human prostate xenografts in T cell humanized NSG mice. Subcutaneous LnCAP AR.TB tumors were measured twice weekly and the results presented as the mean tumor volume, expressed in mm$^3$±SEM (*, p<0.001).

Example 17. Anti-Tumor Efficacy in Tumorigenesis Prevention of LnCaP Xenografts in Humanized NSG Mice Efficacy of PS3B79 and PS3B90 was evaluated in established 3D LnCaP AR.TB human prostate cancer xenografts in male NOD.Cg-Prkdc$^{scid}$ Il2rg$^{tm1Wjl}$/SzJ (NSG) mice humanized intraperitoneally (ip) with human T cells. PS3B79 and PS3B90 at 2.5 and 5 mg/kg or Null×CD3B376 antibody control was dosed q3d-q4d on Days 36, 39, 43, 47, 50, 53, 56, 60, and 63 for a total of 8 doses. On day 53 post-tumor implant, which was the last date of the study when nine (9) animals remained per group, tumor growth inhibition (% TGI) was calculated. Statistically significant tumor growth inhibition was observed for PS3B79 at 5 mg/kg with 42% TGI (Two-way ANOVA with Bonferroni test, *p<0.0001, FIG. 40), and for PS3B90 at 2.5 and 5 mg/kg with 53% and 33% respectively compared to Null× CD3 control (Two-way ANOVA with Bonferroni test, *p<0.001, FIG. 41). Thus, CD3B376 is able to induce T cell activation and cytotoxicity in vivo and result in tumor growth inhibition in a bispecific format with high affinity PSMA binding arms, PSMB360 and PSMB365.

Figure 42:
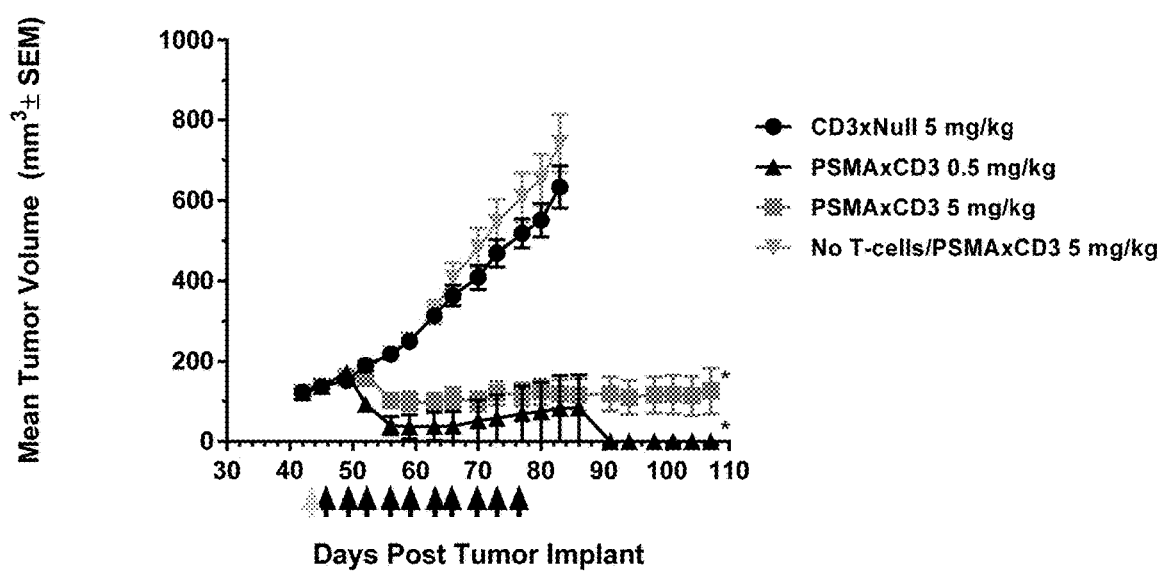
FIG. 42 shows the effect of PS3B72 (PSMA×CD3) on Established Patient-Derived Xenograft LuCaP 86.2 Prostate Tumor Model in T-Cell Humanized NSG Mice. Subcutaneous LuCaP 86.2 tumors were measured twice weekly and the results presented as the mean tumor volume, expressed in mm$^3$±SEM (*, p<0.0001).

Example 18. Efficacy of PSMA×CD3 in the Established Patient-Derived Xenograft LuCaP 86.2 Prostate Tumor Model in T-Cell Humanized NSG Mice The Antitumor Efficacy of PS3B72 was evaluated in the established patient-derived xenograft (PDX) LuCaP 86.2 prostate tumor model in male NOD.Cg-Prkdc$^{scid}$ Il2rg$^{tm1Wjl}$/SzJ (NSG) mice humanized intraperitoneally (ip) with human pan-T cells. PS3B72 at 0.5 and 5 mg/kg or Null×CD3 antibody control was dosed q3d-q4d on Days 45, 49, 52, 56, 59, 63, 66, 70, 73, and 77 post-tumor implantation for a total of 10 doses. On day 83 post-tumor implant, which was the last day of the study when all ten animals remained per group, tumor growth inhibition (% TGI) was calculated. Statistically significant tumor growth inhibition was observed for PSMA×CD3 at both 0.5 and 5 mg/kg, with 108% and 101% ΔTGI (linear mixed-effect analysis using FDR adjustment, *p<0.0001, FIG. 42), respectively compared to the Null×CD3 control. By the end of the 5 week-dosing period, 9 of 10 complete regressions (CR) were observed in the PSMA×CD3 at 0.5 mg/kg group. These 9 mice remained tumor-free until study termination. At study termination 4 of 10 CR were observed in the PS3B72 at 5 mg/kg group. When mice were dosed with PS3B72 at 5 mg/kg in the absence of T cell humanization, no antitumor efficacy was observed.

What is claimed:

1. An isolated recombinant anti-PSMA antibody or an antigen-binding fragment thereof comprising the HCDR1, the HCDR2, the HCDR3, the LCDR1, the LCDR2 and the LCDR3 of SEQ ID NOs: 14, 15, 16, 17, 18 and 19, respectively.

2. An isolated recombinant anti-PSMA antibody or an antigen-binding fragment thereof comprising the HCDR1, the HCDR2, the HCDR3, the LCDR1, the LCDR2 and the LCDR3 of SEQ ID NOs: 20, 21, 22, 23, 12 and 24, respectively.

3. An isolated recombinant anti-PSMA antibody or an antigen-binding fragment thereof comprising the HCDR1, the HCDR2, the HCDR3, the LCDR1, the LCDR2 and the LCDR3 of SEQ ID NOs: 25, 26, 27, 28, 29 and 30, respectively.

4. An isolated recombinant anti-PSMA antibody or an antigen-binding fragment thereof comprising the HCDR1, the HCDR2, the HCDR3, the LCDR1, the LCDR2 and the LCDR3 of SEQ ID NOs: 36, 37, 38, 39, 40 and 41, respectively.

5. An isolated recombinant anti-PSMA antibody or an antigen-binding fragment thereof comprising the HCDR1, the HCDR2, the HCDR3, the LCDR1, the LCDR2 and the LCDR3 of SEQ ID NOs: 31, 42, 43, 11, 12 and 13, respectively.

6. An isolated recombinant anti-PSMA antibody or an antigen-binding fragment thereof comprising the HCDR1, the HCDR2, the HCDR3, the LCDR1, the LCDR2 and the LCDR3 of SEQ ID NOs: 31, 44, 45, 46, 29 and 47, respectively.

7. An isolated recombinant anti-PSMA antibody or an antigen-binding fragment thereof comprising the HCDR1, the HCDR2, the HCDR3, the LCDR1, the LCDR2 and the LCDR3 of SEQ ID NOs: 36, 37, 48, 49, 50 and 51, respectively.

8. An isolated recombinant anti-PSMA antibody or an antigen-binding fragment thereof comprising the HCDR1, the HCDR2, the HCDR3, the LCDR1, the LCDR2 and the LCDR3 of SEQ ID NOs: 36, 37, 52, 49, 50 and 51, respectively.

9. An isolated recombinant anti-PSMA antibody or an antigen-binding fragment thereof comprising the HCDR1, the HCDR2, the HCDR3, the LCDR1, the LCDR2 and the LCDR3 of SEQ ID NOs: 8, 9, 10, 11, 12 and 13, respectively.

10. An isolated recombinant anti-PSMA antibody or an antigen-binding fragment thereof comprising the HCDR1, the HCDR2, the HCDR3, the LCDR1, the LCDR2 and the LCDR3 of SEQ ID NOs: 31, 32, 33, 34, 12 and 35, respectively.

11. An isolated recombinant anti-PSMA antibody or an antigen-binding fragment thereof comprising the HCDR1, the HCDR2, the HCDR3, the LCDR1, the LCDR2 and the LCDR3 of SEQ ID NOs: 53, 54, 55, 23, 12 and 35, respectively.

12. An isolated recombinant anti-PSMA antibody or an antigen-binding fragment thereof comprising the HCDR1, the HCDR2, the HCDR3, the LCDR1, the LCDR2 and the LCDR3 of SEQ ID NOs: 122, 123, 124, 23, 12 and 24, respectively.

13. The isolated recombinant anti-PSMA antibody or the antigen-binding fragment thereof of claim 3, comprising a heavy chain variable region (VH) of SEQ ID NO: 66 and a light chain variable region (VL) of SEQ ID NO: 67.

14. The isolated recombinant anti-PSMA antibody or the antigen-binding fragment thereof of claim 1, comprising the VH of SEQ ID NO: 62 and the VL of SEQ ID NO: 63.

15. The isolated recombinant anti-PSMA antibody or the antigen-binding fragment thereof of claim 2, comprising the VH of SEQ ID NO: 64 and the VL of SEQ ID NO: 65.

16. The isolated recombinant anti-PSMA antibody or the antigen-binding fragment thereof of claim 4, comprising the VH of SEQ ID NO: 72 and the VL of SEQ ID NO: 73.

17. The isolated recombinant anti-PSMA antibody or the antigen-binding fragment thereof of claim 5, comprising the VH of SEQ ID NO: 74 and the VL of SEQ ID NO: 61.

18. The isolated recombinant anti-PSMA antibody or the antigen-binding fragment thereof of claim 6, comprising the VH of SEQ ID NO: 75 and the VL of SEQ ID NO: 76.

19. The isolated recombinant anti-PSMA antibody or the antigen-binding fragment thereof claim 7, comprising the VH of SEQ ID NO: 77 and the VL of SEQ ID NO: 78.

20. The isolated recombinant anti-PSMA antibody or the antigen-binding fragment thereof of claim 8, comprising the VH of SEQ ID NO: 79 and the VL of SEQ ID NO: 78.

21. The isolated recombinant anti-PSMA antibody or the antigen-binding fragment thereof of claim 12, comprising the VH of SEQ ID NO: 160 and the VL of SEQ ID NO: 65.

22. The isolated recombinant anti-PSMA antibody or the antigen-binding fragment thereof of claim 9, comprising the VH of SEQ ID NO: 60 and the VL of SEQ ID NO: 61.

23. The isolated recombinant anti-PSMA antibody or the antigen-binding fragment thereof of claim 11, comprising the VH of SEQ ID NO: 68 and the VL of SEQ ID NO: 69.

24. An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 31, 42, 43, 11, 12 and 13, respectively.

25. The isolated recombinant anti-PSMA antibody or the antigen-binding fragment thereof of claim 24, wherein the antibody comprises the VH of SEQ ID NO:74 and the VL of SEQ ID NO: 61.

26. An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 14, 15, 16, 17, 18 and 19, respectively.

27. The isolated recombinant anti-PSMA antibody or the antigen-binding fragment thereof of claim 26, wherein the antibody comprises the VH of SEQ ID NO: 62 and the VL of SEQ ID NO: 63.

28. An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 36, 37, 38, 39, 40 and 41, respectively.

29. The isolated recombinant anti-PSMA antibody or the antigen-binding fragment thereof of claim 28, wherein the antibody comprises the VH of SEQ ID NO: 72 and the VL of SEQ ID NO: 73.

30. An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 122, 123, 124, 23, 12, and 24, respectively.

31. The isolated recombinant anti-PSMA antibody or the antigen-binding fragment thereof of claim 30, wherein the antibody comprises the VH of SEQ ID NO: 160 and the VL of SEQ ID NO: 65.

32. An isolated recombinant anti-PSMA antibody or antigen-binding fragment thereof, comprising the HCDR1, the HCDR2, the HCDR3, the LCDR1, the LCDR2 and the LCDR3 of SEQ ID NOs:8, 9, 10, 11, 12, and 13, respectively.

33. The isolated recombinant anti-PSMA antibody or the antigen-binding fragment thereof of claim 32, wherein the antibody comprises the VH of SEQ ID NO:60 and the VL of SEQ ID NO:61.

34. An isolated recombinant anti-PSMA antibody or antigen-binding fragment thereof, comprising the HCDR1, the HCDR2, the HCDR3, the LCDR1, the LCDR2 and the LCDR3 of SEQ ID NOs:20, 21, 22, 23, 12, and 24, respectively.

35. The isolated recombinant anti-PSMA antibody or the antigen-binding fragment thereof of claim 34, wherein the antibody comprises the VH of SEQ ID NO:64 and the VL of SEQ ID NO:65.

36. An isolated recombinant anti-PSMA antibody or antigen-binding fragment thereof, comprising the HCDR1, the HCDR2, the HCDR3, the LCDR1, the LCDR2 and the LCDR3 of SEQ ID NOs:31, 32, 33, 34, 12, and 35, respectively.

37. The isolated recombinant anti-PSMA antibody or the antigen-binding fragment thereof of claim 36, wherein the antibody comprises the VH of SEQ ID NO:70 and the VL of SEQ ID NO:71.

38. An isolated recombinant anti-PSMA antibody or antigen-binding fragment thereof, comprising the HCDR1, the HCDR2, the HCDR3, the LCDR1, the LCDR2 and the LCDR3 of SEQ ID NOs:31, 44, 45, 46, 29, and 47, respectively.

39. The isolated recombinant anti-PSMA antibody or the antigen-binding fragment thereof of claim 38, wherein the antibody comprises the VH of SEQ ID NO:75 and the VL of SEQ ID NO:76.

40. An isolated recombinant anti-PSMA antibody or antigen-binding fragment thereof, comprising the HCDR1, the HCDR2, the HCDR3, the LCDR1, the LCDR2 and the LCDR3 of SEQ ID NOs:36, 37, 48, 49, 50, and 51, respectively.

41. The isolated recombinant anti-PSMA antibody or the antigen-binding fragment thereof of claim 40, wherein the antibody comprises the VH of SEQ ID NO:77 and the VL of SEQ ID NO:78.

42. An isolated recombinant anti-PSMA antibody or antigen-binding fragment thereof, comprising the HCDR1, the HCDR2, the HCDR3, the LCDR1, the LCDR2 and the LCDR3 of SEQ ID NOs:36, 37, 52, 49, 50, and 51, respectively.

43. The isolated recombinant anti-PSMA antibody or the antigen-binding fragment thereof of claim 42, wherein the antibody comprises the VH of SEQ ID NO:79 and the VL of SEQ ID NO:78.

44. An isolated recombinant anti-PSMA antibody or antigen-binding fragment thereof, comprising the HCDR1, the HCDR2, the HCDR3, the LCDR1, the LCDR2 and the LCDR3 of SEQ ID NOs:53, 54, 55, 23, 12, and 35, respectively.

45. The isolated recombinant anti-PSMA antibody or the antigen-binding fragment thereof of claim 44, wherein the antibody comprises the VH of SEQ ID NO:68 and the VL of SEQ ID NO:69.

46. An isolated recombinant anti-PSMA antibody or antigen-binding fragment thereof, comprising the HCDR1, the HCDR2, the HCDR3, the LCDR1, the LCDR2 and the LCDR3 of SEQ ID NOs:25, 130, 27, 28, 29, and 30, respectively.

47. The isolated recombinant anti-PSMA antibody or the antigen-binding fragment thereof of claim 46, wherein the antibody comprises the VH of SEQ ID NO:138 and the VL of SEQ ID NO:67.

48. An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 25, 130, 27, 131, 29, and 132, respectively.

49. The isolated recombinant anti-PSMA antibody or the antigen-binding fragment thereof of claim 48, wherein the antibody comprises the VH of SEQ ID NO:138 and the VL of SEQ ID NO:142.

50. An isolated recombinant anti-PSMA antibody or antigen-binding fragment thereof, comprising the HCDR1, the HCDR2, the HCDR3, the LCDR1, the LCDR2 and the LCDR3 of SEQ ID NOs:25, 130, 27, 28, 133, and 132, respectively.

51. The isolated recombinant anti-PSMA antibody or the antigen-binding fragment thereof of claim 50, wherein the antibody comprises the VH of SEQ ID NO:138 and the VL of SEQ ID NO:143.

52. An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 25, 134, 27, 28, 29, and 30, respectively.

53. The isolated recombinant anti-PSMA antibody or the antigen-binding fragment thereof of claim 52, wherein the antibody comprises the VH of SEQ ID NO:139 and the VL of SEQ ID NO:67.

54. An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 25, 135, 27, 28, 29, and 136, respectively.

55. The isolated recombinant anti-PSMA antibody or the antigen-binding fragment thereof of claim 54, wherein the antibody comprises the VH of SEQ ID NO:140 and the VL of SEQ ID NO:144.

56. An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 25, 135, 27, 28, 29, and 30, respectively.

57. The isolated recombinant anti-PSMA antibody or the antigen-binding fragment thereof of claim 56, wherein the antibody comprises the VH of SEQ ID NO:140 and the VL of SEQ ID NO:67.

58. An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 25, 135, 27, 131, 29, and 132, respectively.

59. The isolated recombinant anti-PSMA antibody or the antigen-binding fragment thereof of claim 58, wherein the antibody comprises the VH of SEQ ID NO:140 and the VL of SEQ ID NO:142.

60. An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 25, 135, 27, 28, 133, and 132, respectively.

61. The isolated recombinant anti-PSMA antibody or the antigen-binding fragment thereof of claim 60, wherein the antibody comprises the VH of SEQ ID NO:140 and the VL of SEQ ID NO:143.

62. An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 25, 134, 27, 28, 29, and 136, respectively.

63. The isolated recombinant anti-PSMA antibody or the antigen-binding fragment thereof of claim 62, wherein the antibody comprises the VH of SEQ ID NO:139 and the VL of SEQ ID NO:144.

64. An isolated recombinant anti-PSMA antibody or antigen-binding fragment thereof, comprising the HCDR1, the HCDR2, the HCDR3, the LCDR1, the LCDR2 and the LCDR3 of SEQ ID NOs: 25, 134, 27, 131, 29, and 132, respectively.

65. The isolated recombinant anti-PSMA antibody or the antigen-binding fragment thereof of claim 64, wherein the antibody comprises the VH of SEQ ID NO:139 and the VL of SEQ ID NO:142.

66. An isolated recombinant anti-PSMA antibody or antigen-binding fragment thereof, comprising the HCDR1, the HCDR2, the HCDR3, the LCDR1, the LCDR2 and the LCDR3 of SEQ ID NOs:25, 134, 27, 28, 133, and 132, respectively.

67. The isolated recombinant anti-PSMA antibody or the antigen-binding fragment thereof of claim 66, wherein the antibody comprises the VH of SEQ ID NO:139 and the VL of SEQ ID NO:143.

68. An isolated recombinant anti-PSMA antibody or antigen-binding fragment thereof, comprising the HCDR1, the HCDR2, the HCDR3, the LCDR1, the LCDR2 and the LCDR3 of SEQ ID NOs:25, 137, 27, 28, 133, and 132, respectively.

69. The isolated recombinant anti-PSMA antibody or the antigen-binding fragment thereof of claim 68, wherein the antibody comprises the VH of SEQ ID NO:141 and the VL of SEQ ID NO:143.

70. The isolated recombinant anti-PSMA antibody or the antigen-binding fragment thereof of any one of claims 3 and 13, wherein the antibody is of IgG4 isotype.

71. The isolated recombinant anti-PSMA antibody or the antigen-binding fragment thereof of claim 70, comprising S228P, F234A and L235A substitutions, wherein residue numbering is according to the EU Index.

72. A bispecific antibody comprising a first domain that specifically binds PSMA, wherein the first domain comprises:
 a) the HCDR1, the HCDR2, the HCDR3, the LCDR1, the LCDR2 and the LCDR3 of SEQ ID NOs: 31, 42, 43, 11, 12 and 13, respectively;
 b) the HCDR1, the HCDR2, the HCDR3, the LCDR1, the LCDR2 and the LCDR3 of SEQ ID NOs: 14, 15, 16, 17, 18 and 19, respectively;
 c) the HCDR1, the HCDR2, the HCDR3, the LCDR1, the LCDR2 and the LCDR3 of SEQ ID NOs: 25, 26, 27, 28, 29 and 30, respectively;
 d) the HCDR1, the HCDR2, the HCDR3, the LCDR1, the LCDR2 and the LCDR3 of SEQ ID NOs: 36, 37, 38, 39, 40 and 41, respectively;

e) the HCDR1, the HCDR2, the HCDR3, the LCDR1, the LCDR2 and the LCDR3 of SEQ ID NOs: 122, 123, 124, 23, 12, and 24, respectively;
f) the HCDR1, the HCDR2, the HCDR3, the LCDR1, the LCDR2 and the LCDR3 of SEQ ID NOs:8, 9, 10, 11, 12, and 13, respectively;
g) the HCDR1, the HCDR2, the HCDR3, the LCDR1, the LCDR2 and the LCDR3 of SEQ ID NOs:14, 15, 16, 17, 18, and 19, respectively;
h) the HCDR1, the HCDR2, the HCDR3, the LCDR1, the LCDR2 and the LCDR3 of SEQ ID NOs:20, 21, 22, 23, 12, and 24, respectively;
i) the HCDR1, the HCDR2, the HCDR3, the LCDR1, the LCDR2 and the LCDR3 of SEQ ID NOs:31, 32, 33, 34, 12, and 35, respectively;
j) the HCDR1, the HCDR2, the HCDR3, the LCDR1, the LCDR2 and the LCDR3 of SEQ ID NOs:31, 44, 45, 46, 29, and 47, respectively;
k) the HCDR1, the HCDR2, the HCDR3, the LCDR1, the LCDR2 and the LCDR3 of SEQ ID NOs:36, 37, 48, 49, 50, and 51, respectively;
l) the HCDR1, the HCDR2, the HCDR3, the LCDR1, the LCDR2 and the LCDR3 of SEQ ID NOs:53, 54, 55, 23, 12, and 35, respectively;
m) the HCDR1, the HCDR2, the HCDR3, the LCDR1, the LCDR2 and the LCDR3 of SEQ ID NOs:25, 130, 27, 28, 29, and 30, respectively;
n) the HCDR1, the HCDR2, the HCDR3, the LCDR1, the LCDR2 and the LCDR3 of SEQ ID NOs:25, 130, 27, 131, 29, and 132, respectively;
o) the HCDR1, the HCDR2, the HCDR3, the LCDR1, the LCDR2 and the LCDR3 of SEQ ID NOs:25, 130, 27, 28, 133, and 132, respectively;
p) the HCDR1, the HCDR2, the HCDR3, the LCDR1, the LCDR2 and the LCDR3 of SEQ ID NOs:25, 134, 27, 28, 29, and 30, respectively;
q) the HCDR1, the HCDR2, the HCDR3, the LCDR1, the LCDR2 and the LCDR3 of SEQ ID NOs:25, 135, 27, 28, 29, and 136, respectively;
r) the HCDR1, the HCDR2, the HCDR3, the LCDR1, the LCDR2 and the LCDR3 of SEQ ID NOs:25, 135, 27, 28, 29, and 30, respectively;
s) the HCDR1, the HCDR2, the HCDR3, the LCDR1, the LCDR2 and the LCDR3 of SEQ ID NOs:25, 135, 27, 131, 29, and 132, respectively;
t) the HCDR1, the HCDR2, the HCDR3, the LCDR1, the LCDR2 and the LCDR3 of SEQ ID NOs:25, 135, 27, 28, 133, and 132, respectively;
u) the HCDR1, the HCDR2, the HCDR3, the LCDR1, the LCDR2 and the LCDR3 of SEQ ID NOs:25, 134, 27, 28, 29, and 136, respectively;
v) the HCDR1, the HCDR2, the HCDR3, the LCDR1, the LCDR2 and the LCDR3 of SEQ ID NOs:25, 134, 27, 131, 29, and 132, respectively;
w) the HCDR1, the HCDR2, the HCDR3, the LCDR1, the LCDR2 and the LCDR3 of SEQ ID NOs:25, 134, 27, 28, 133, and 132, respectively; or
x) the HCDR1, the HCDR2, the HCDR3, the LCDR1, the LCDR2 and the LCDR3 of SEQ ID NOs:25, 137, 27, 28, 133, and 132, respectively.

73. The bispecific antibody of claim 72, wherein the first domain comprises:
a) the HCDR1, the HCDR2, the HCDR3, the LCDR1, the LCDR2 and the LCDR3 of SEQ ID NOs: 31, 42, 43, 11, 12 and 13, respectively, and the VH of SEQ ID NO: 74 and the VL of SEQ ID NO: 61;
b) the HCDR1, the HCDR2, the HCDR3, the LCDR1, the LCDR2 and the LCDR3 of SEQ ID NOs: 14, 15, 16, 17, 18 and 19, respectively, and the VH of SEQ ID NO: 62 and the VL of SEQ ID NO: 63;
c) the HCDR1, the HCDR2, the HCDR3, the LCDR1, the LCDR2 and the LCDR3 of SEQ ID NOs: 25, 26, 27, 28, 29 and 30, respectively, and the VH of SEQ ID NO: 66 and the VL of SEQ ID NO: 67;
d) the HCDR1, the HCDR2, the HCDR3, the LCDR1, the LCDR2 and the LCDR3 of SEQ ID NOs: 36, 37, 38, 39, 40 and 41, respectively, and the VH of SEQ ID NO: 72 and the VL of SEQ ID NO: 73;
e) the HCDR1, the HCDR2, the HCDR3, the LCDR1, the LCDR2 and the LCDR3 of SEQ ID NOs: 122, 123, 124, 23, 12, and 24, respectively, and the VH of SEQ ID NO: 160 and the VL of SEQ ID NO: 65;
f) the HCDR1, the HCDR2, the HCDR3, the LCDR1, the LCDR2 and the LCDR3 of SEQ ID NOs:8, 9, 10, 11, 12, and 13, respectively, and the VH of SEQ ID NO:60 and the VL of SEQ ID NO:61;
g) the HCDR1, the HCDR2, the HCDR3, the LCDR1, the LCDR2 and the LCDR3 of SEQ ID NOs:14, 15, 16, 17, 18, and 19, respectively, and the VH of SEQ ID NO:62 and the VL of SEQ ID NO:63;
h) the HCDR1, the HCDR2, the HCDR3, the LCDR1, the LCDR2 and the LCDR3 of SEQ ID NOs:20, 21, 22, 23, 12, and 24, respectively, and VH of SEQ ID NO:64 and the VL of SEQ ID NO:65;
i) the HCDR1, the HCDR2, the HCDR3, the LCDR1, the LCDR2 and the LCDR3 of SEQ ID NOs:31, 32, 33, 34, 12, and 35, respectively, and the VH of SEQ ID NO:70 and the VL of SEQ ID NO:71;
j) the HCDR1, the HCDR2, the HCDR3, the LCDR1, the LCDR2 and the LCDR3 of SEQ ID NOs:31, 44, 45, 46, 29, and 47, respectively, the VH of SEQ ID NO:75 and the VL of SEQ ID NO:76;
k) the HCDR1, the HCDR2, the HCDR3, the LCDR1, the LCDR2 and the LCDR3 of SEQ ID NOs:36, 37, 48, 49, 50, and 51, respectively, and the VH of SEQ ID NO:77 and the VL of SEQ ID NO:78;
l) the HCDR1, the HCDR2, the HCDR3, the LCDR1, the LCDR2 and the LCDR3 of SEQ ID NOs:53, 54, 55, 23, 12, and 35, respectively, and the VH of SEQ ID NO:68 and the VL of SEQ ID NO:69;
m) the HCDR1, the HCDR2, the HCDR3, the LCDR1, the LCDR2 and the LCDR3 of SEQ ID NOs:25, 130, 27, 28, 29, and 30, respectively, and the VH of SEQ ID NO:138 and the VL of SEQ ID NO:67;
n) the HCDR1, the HCDR2, the HCDR3, the LCDR1, the LCDR2 and the LCDR3 of SEQ ID NOs: 25, 130, 27, 131, 29, and 132, respectively, and the VH of SEQ ID NO:138 and the VL of SEQ ID NO:142;
o) the HCDR1, the HCDR2, the HCDR3, the LCDR1, the LCDR2 and the LCDR3 of SEQ ID NOs:25, 130, 27, 28, 133, and 132, respectively, and the VH of SEQ ID NO:138 and the VL of SEQ ID NO:143;
p) the HCDR1, the HCDR2, the HCDR3, the LCDR1, the LCDR2 and the LCDR3 of SEQ ID NOs:25, 134, 27, 28, 29, and 30, respectively, and the VH of SEQ ID NO: 139 and the VL of SEQ ID NO:67;
q) the HCDR1, the HCDR2, the HCDR3, the LCDR1, the LCDR2 and the LCDR3 of SEQ ID NOs:25, 135, 27, 28, 29, and 136, respectively, and the VH of SEQ ID NO:140 and the VL of SEQ ID NO:144;
r) the HCDR1, the HCDR2, the HCDR3, the LCDR1, the LCDR2 and the LCDR3 of SEQ ID NOs:25, 135, 27, 28, 29, and 30, respectively, and the VH of SEQ ID NO:140 and the VL of SEQ ID NO: 67;

s) the HCDR1, the HCDR2, the HCDR3, the LCDR1, the LCDR2 and the LCDR3 of SEQ ID NOs:25, 135, 27, 131, 29, and 132, respectively and the VH of SEQ ID NO:140 and the VL of SEQ ID NO:142;

t) the HCDR1, the HCDR2, the HCDR3, the LCDR1, the LCDR2 and the LCDR3 of SEQ ID NOs:25, 135, 27, 28, 133, and 132, respectively, and the VH of SEQ ID NO:140 and the VL of SEQ ID NO:143;

u) the HCDR1, the HCDR2, the HCDR3, the LCDR1, the LCDR2 and the LCDR3 of SEQ ID NOs:25, 134, 27, 28, 29, and 136, respectively; and the VH of SEQ ID NO:139 and the VL of SEQ ID NO:144;

v) the HCDR1, the HCDR2, the HCDR3, the LCDR1, the LCDR2 and the LCDR3 of SEQ ID NOs:25, 134, 27, 131, 29, and 132, respectively, and the VH of SEQ ID NO:139 and the VL of SEQ ID NO:142;

w) the HCDR1, the HCDR2, the HCDR3, the LCDR1, the LCDR2 and the LCDR3 of SEQ ID NOs:25, 134, 27, 28, 133, and 132, respectively, and the VH of SEQ ID NO:139 and the VL of SEQ ID NO:143; or x) the HCDR1, the HCDR2, the HCDR3, the LCDR1, the LCDR2 and the LCDR3 of SEQ ID NOs:25, 137, 27, 28, 133, and 132, respectively and the VH of SEQ ID NO:141 and the VL of SEQ ID NO:143.

74. The bispecific antibody of claim 73, wherein the bispecific antibody further comprises a second domain that specifically binds CD3, wherein:

a) the first domain comprises a heavy chain variable region (VH) of SEQ ID NO: 62 and a light chain variable region (VL) of SEQ ID NO: 63, and the second domain comprises the VH of SEQ ID NO: 104 and the VL of SEQ ID NO: 105;

b) the first domain comprises the VH of SEQ ID NO: 64 and the VL of SEQ ID NO: 65, and the second domain comprises the VH of SEQ ID NO: 104 and the VL of SEQ ID NO: 105;

c) the first domain comprises the VH of SEQ ID NO: 66 and the VL of SEQ ID NO: 67, and the second domain comprises the VH of SEQ ID NO: 104 and the VL of SEQ ID NO: 105;

d) the first domain comprises the VH of SEQ ID NO: 75 and the VL of SEQ ID NO: 76, and the second domain comprises the VH of SEQ ID NO: 104 and the VL of SEQ ID NO: 105;

e) the first domain comprises the VH of SEQ ID NO: 74 and the VL of SEQ ID NO: 61, and the second domain comprises the VH of SEQ ID NO: 104 and the VL of SEQ ID NO: 105; or f) the first domain comprises the VH of SEQ ID NO: 160 and the VL of SEQ ID NO: 65, and the second domain comprises the VH of SEQ ID NO: 104 and the VL of SEQ ID NO: 105.

75. The bispecific antibody of claim 74, comprising a first heavy chain (HC1), a first light chain (LC1), a second heavy chain (HC2) and a second light chain (LC2), wherein the HC1 and the LC1 comprise the amino acid sequences of a) SEQ ID NOs: 84 and 85, respectively;
b) SEQ ID NOs: 86 and 87, respectively;
c) SEQ ID NOs: 88 and 89, respectively;
d) SEQ ID NOs: 125 and 91, respectively;
e) SEQ ID NOs: 94 and 95, respectively; or
f) SEQ ID NOs: 96 and 83, respectively.

76. The bispecific antibody of claim 75, wherein the HC2 and the LC2 comprises SEQ ID NOs: 110 and 111, respectively.

77. The bispecific antibody of claim 76, comprising the HC1, the LC1, the HC2 and the LC2 of a) SEQ ID NOs: 84, 85, 110 and 111, respectively;
b) SEQ ID NOs: 86, 87, 110 and 111, respectively;
c) SEQ ID NOs: 88, 89, 110, 111, respectively;
d) SEQ ID NOs: 125, 91, 110 and 111, respectively;
e) SEQ ID NOs: 94, 95, 110 and 111, respectively; or
f) SEQ ID NOs: 96, 83, 110 and 111, respectively.

78. The bispecific antibody of any one of claims 72, 73, 74, 75, 76, and 77, wherein the antibody is of IgG4 isotype.

79. The bispecific antibody of claim 78, comprising at least one substitution in an antibody CH3 constant domain.

80. The bispecific antibody of claim 79, wherein the substitution in the antibody CH3 constant domain is R409K, F405L or F405L/R409K substitution, wherein residue numbering is according to the EU Index.

81. The isolated recombinant anti-PSMA antibody or the antigen-binding fragment thereof of claim 10, comprising the VH of SEQ ID NO: 70 and the VL of SEQ ID NO: 71.

* * * * *

SEQUENCE LISTING

```
<160> NUMBER OF SEQ ID NOS: 162

<210> SEQ ID NO 1
<211> LENGTH: 750
<212> TYPE: PRT
<213> ORGANISM: Pan troglodytes

<400> SEQUENCE: 1

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80
```

```
Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
130                 135                 140

Glu Pro Pro Pro Pro Gly Tyr Glu Asn Val Leu Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg His Gly Ile Ala Glu Ala Val Gly
        275                 280                 285

Leu Pro Ser Ile Pro Val His Pro Ile Gly Tyr Tyr Asp Ala Gln Lys
        290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
        370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
        450                 455                 460

Asp Cys Thr Pro Leu Met Tyr Ser Leu Val Tyr Asn Leu Thr Lys Glu
465                 470                 475                 480

Leu Lys Ser Pro Asp Glu Gly Phe Glu Gly Lys Ser Leu Tyr Glu Ser
                485                 490                 495
```

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Gln Arg Leu
        515                 520                 525

Gly Ile Ala Ser Gly Arg Ala Arg Tyr Thr Lys Asn Trp Glu Thr Asn
            530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
            595                 600                 605

Asp Lys Ile Tyr Asn Ile Ser Met Lys His Pro Gln Glu Met Lys Thr
            610                 615                 620

Tyr Ser Val Ser Phe Asp Ser Leu Phe Ser Ala Val Lys Asn Phe Thr
625                 630                 635                 640

Glu Ile Ala Ser Lys Phe Thr Glu Arg Leu Gln Asp Phe Asp Lys Ser
                645                 650                 655

Asn Pro Ile Leu Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr Ala Gly Glu Ser
            690                 695                 700

Phe Pro Gly Ile Tyr Asp Ala Leu Phe Asp Ile Glu Ser Lys Val Asp
705                 710                 715                 720

Pro Ser Lys Ala Trp Gly Asp Val Lys Arg Gln Ile Ser Val Ala Ala
                725                 730                 735

Phe Thr Val Gln Ala Ala Ala Glu Thr Leu Ser Glu Val Ala
            740                 745                 750

<210> SEQ ID NO 2
<211> LENGTH: 750
<212> TYPE: PRT
<213> ORGANISM: Macaca fascicularis

<400> SEQUENCE: 2

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
                20                  25                  30

Phe Leu Leu Gly Phe Leu Phe Gly Trp Phe Ile Lys Ser Ser Ser Glu
            35                  40                  45

Ala Thr Asn Ile Thr Pro Lys His Asn Met Lys Ala Phe Leu Asp Glu
        50                  55                  60

Leu Lys Ala Glu Asn Ile Lys Lys Phe Leu His Asn Phe Thr Gln Ile
65              70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Thr His
            100                 105                 110

Tyr Asp Val Leu Leu Ser Tyr Pro Asn Lys Thr His Pro Asn Tyr Ile
        115                 120                 125

```
Ser Ile Ile Asn Glu Asp Gly Asn Glu Ile Phe Asn Thr Ser Leu Phe
        130             135             140
Glu Pro Pro Ala Gly Tyr Glu Asn Val Ser Asp Ile Val Pro Pro
145             150             155             160
Phe Ser Ala Phe Ser Pro Gln Gly Met Pro Glu Gly Asp Leu Val Tyr
                165             170             175
Val Asn Tyr Ala Arg Thr Glu Asp Phe Phe Lys Leu Glu Arg Asp Met
            180             185             190
Lys Ile Asn Cys Ser Gly Lys Ile Val Ile Ala Arg Tyr Gly Lys Val
        195             200             205
Phe Arg Gly Asn Lys Val Lys Asn Ala Gln Leu Ala Gly Ala Thr Gly
210             215             220
Val Ile Leu Tyr Ser Asp Pro Asp Asp Tyr Phe Ala Pro Gly Val Lys
225             230             235             240
Ser Tyr Pro Asp Gly Trp Asn Leu Pro Gly Gly Val Gln Arg Gly
                245             250             255
Asn Ile Leu Asn Leu Asn Gly Ala Gly Asp Pro Leu Thr Pro Gly Tyr
            260             265             270
Pro Ala Asn Glu Tyr Ala Tyr Arg Arg Gly Met Ala Glu Ala Val Gly
            275             280             285
Leu Pro Ser Ile Pro Val His Pro Ile Gly Tyr Tyr Asp Ala Gln Lys
290             295             300
Leu Leu Glu Lys Met Gly Gly Ser Ala Ser Pro Asp Ser Ser Trp Arg
305             310             315             320
Gly Ser Leu Lys Val Pro Tyr Asn Val Gly Pro Gly Phe Thr Gly Asn
                325             330             335
Phe Ser Thr Gln Lys Val Lys Met His Ile His Ser Thr Ser Glu Val
            340             345             350
Thr Arg Ile Tyr Asn Val Ile Gly Thr Leu Arg Gly Ala Val Glu Pro
            355             360             365
Asp Arg Tyr Val Ile Leu Gly Gly His Arg Asp Ser Trp Val Phe Gly
        370             375             380
Gly Ile Asp Pro Gln Ser Gly Ala Ala Val Val His Glu Ile Val Arg
385             390             395             400
Ser Phe Gly Met Leu Lys Lys Glu Gly Trp Arg Pro Arg Arg Thr Ile
                405             410             415
Leu Phe Ala Ser Trp Asp Ala Glu Glu Phe Gly Leu Leu Gly Ser Thr
            420             425             430
Glu Trp Ala Glu Glu Asn Ser Arg Leu Leu Gln Glu Arg Gly Val Ala
        435             440             445
Tyr Ile Asn Ala Asp Ser Ser Ile Glu Gly Asn Tyr Thr Leu Arg Val
450             455             460
Asp Cys Thr Pro Leu Met Tyr Ser Leu Val Tyr Asn Leu Thr Lys Glu
465             470             475             480
Leu Glu Ser Pro Asp Glu Gly Phe Glu Gly Lys Ser Leu Tyr Glu Ser
                485             490             495
Trp Thr Lys Lys Ser Pro Ser Pro Glu Phe Ser Gly Met Pro Arg Ile
            500             505             510
Ser Lys Leu Gly Ser Gly Asn Asp Phe Glu Val Phe Phe Gln Arg Leu
        515             520             525
Gly Ile Ala Ser Gly Arg Ala Arg Tyr Thr Lys Asn Trp Glu Thr Asn
530             535             540
```

```
Lys Phe Ser Ser Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
            565                 570                 575

Ala Gln Val Arg Gly Gly Met Val Phe Glu Leu Ala Asn Ser Val Val
        580                 585                 590

Leu Pro Phe Asp Cys Arg Asp Tyr Ala Val Val Leu Arg Lys Tyr Ala
    595                 600                 605

Asp Lys Ile Tyr Asn Ile Ser Met Lys His Pro Gln Glu Met Lys Thr
610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Arg Asp Phe Asp Lys Ser
                645                 650                 655

Asn Pro Ile Leu Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
        675                 680                 685

His Val Ile Tyr Ala Pro Ser Ser His Asn Lys Tyr Ala Gly Glu Ser
690                 695                 700

Phe Pro Gly Ile Tyr Asp Ala Leu Phe Asp Ile Glu Ser Lys Val Asp
705                 710                 715                 720

Pro Ser Gln Ala Trp Gly Glu Val Lys Arg Gln Ile Ser Ile Ala Thr
                725                 730                 735

Phe Thr Val Gln Ala Ala Ala Glu Thr Leu Ser Glu Val Ala
                740                 745                 750

<210> SEQ ID NO 3
<211> LENGTH: 750
<212> TYPE: PRT
<213> ORGANISM: Homo sapiens

<400> SEQUENCE: 3

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175
```

```
Val Asn Tyr Ala Arg Thr Glu Asp Phe Phe Lys Leu Glu Arg Asp Met
                180                 185                 190

Lys Ile Asn Cys Ser Gly Lys Ile Val Ile Ala Arg Tyr Gly Lys Val
            195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly His Arg Asp Ser Trp Val Phe Gly
    370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
    450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
    530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590
```

```
Leu Pro Phe Asp Cys Arg Asp Tyr Ala Val Val Leu Arg Lys Tyr Ala
            595                 600                 605

Asp Lys Ile Tyr Ser Ile Ser Met Lys His Pro Gln Glu Met Lys Thr
        610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
        675                 680                 685

His Val Ile Tyr Ala Pro Ser Ser His Asn Lys Tyr Ala Gly Glu Ser
    690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
            740                 745                 750

<210> SEQ ID NO 4
<211> LENGTH: 749
<212> TYPE: PRT
<213> ORGANISM: Artificial Sequence
<220> FEATURE:
<223> OTHER INFORMATION: Description of Artificial Sequence: Synthetic
      Extracellular domain of Pan troglodytes PSMA with
      purification tags

<400> SEQUENCE: 4

Met Ala Trp Val Trp Thr Leu Leu Phe Leu Met Ala Ala Ala Gln Ser
1               5                   10                  15

Ile Gln Ala Gly Leu Asn Asp Ile Phe Glu Ala Gln Lys Ile Glu Trp
            20                  25                  30

His Glu His His His His His His Gly Ser Lys Ser Ser Asn Glu Ala
        35                  40                  45

Thr Asn Ile Thr Pro Lys His Asn Met Lys Ala Phe Leu Asp Glu Leu
    50                  55                  60

Lys Ala Glu Asn Ile Lys Lys Phe Leu Tyr Asn Phe Thr Gln Ile Pro
65                  70                  75                  80

His Leu Ala Gly Thr Glu Gln Asn Phe Gln Leu Ala Lys Gln Ile Gln
                85                  90                  95

Ser Gln Trp Lys Glu Phe Gly Leu Asp Ser Val Glu Leu Ala His Tyr
            100                 105                 110

Asp Val Leu Leu Ser Tyr Pro Asn Lys Thr His Pro Asn Tyr Ile Ser
        115                 120                 125

Ile Ile Asn Glu Asp Gly Asn Glu Ile Phe Asn Thr Ser Leu Phe Glu
    130                 135                 140

Pro Pro Pro Pro Gly Tyr Glu Asn Val Leu Asp Ile Val Pro Pro Phe
145                 150                 155                 160

Ser Ala Phe Ser Pro Gln Gly Met Pro Glu Gly Asp Leu Val Tyr Val
                165                 170                 175

Asn Tyr Ala Arg Thr Glu Asp Phe Phe Lys Leu Glu Arg Asp Met Lys
            180                 185                 190
```

-continued

```
Ile Asn Cys Ser Gly Lys Ile Val Ile Ala Arg Tyr Gly Lys Val Phe
        195                 200                 205

Arg Gly Asn Lys Val Lys Asn Ala Gln Leu Ala Gly Ala Lys Gly Val
    210                 215                 220

Ile Leu Tyr Ser Asp Pro Ala Asp Tyr Phe Ala Pro Gly Val Lys Ser
225                 230                 235                 240

Tyr Pro Asp Gly Trp Asn Leu Pro Gly Gly Val Gln Arg Gly Asn
                245                 250                 255

Ile Leu Asn Leu Asn Gly Ala Gly Asp Pro Leu Thr Pro Gly Tyr Pro
        260                 265                 270

Ala Asn Glu Tyr Ala Tyr Arg His Gly Ile Ala Glu Ala Val Gly Leu
        275                 280                 285

Pro Ser Ile Pro Val His Pro Ile Gly Tyr Tyr Asp Ala Gln Lys Leu
        290                 295                 300

Leu Glu Lys Met Gly Gly Ser Ala Pro Pro Asp Ser Ser Trp Arg Gly
305                 310                 315                 320

Ser Leu Lys Val Pro Tyr Asn Val Gly Pro Gly Phe Thr Gly Asn Phe
                325                 330                 335

Ser Thr Gln Lys Val Lys Met His Ile His Ser Thr Asn Glu Val Thr
            340                 345                 350

Arg Ile Tyr Asn Val Ile Gly Thr Leu Arg Gly Ala Val Glu Pro Asp
            355                 360                 365

Arg Tyr Val Ile Leu Gly Gly His Arg Asp Ser Trp Val Phe Gly Gly
        370                 375                 380

Ile Asp Pro Gln Ser Gly Ala Ala Val Val His Glu Ile Val Arg Ser
385                 390                 395                 400

Phe Gly Thr Leu Lys Lys Glu Gly Trp Arg Pro Arg Arg Thr Ile Leu
                405                 410                 415

Phe Ala Ser Trp Asp Ala Glu Glu Phe Gly Leu Leu Gly Ser Thr Glu
            420                 425                 430

Trp Ala Glu Glu Asn Ser Arg Leu Leu Gln Glu Arg Gly Val Ala Tyr
        435                 440                 445

Ile Asn Ala Asp Ser Ser Ile Glu Gly Asn Tyr Thr Leu Arg Val Asp
        450                 455                 460

Cys Thr Pro Leu Met Tyr Ser Leu Val Tyr Asn Leu Thr Lys Glu Leu
465                 470                 475                 480

Lys Ser Pro Asp Glu Gly Phe Glu Gly Lys Ser Leu Tyr Glu Ser Trp
                485                 490                 495

Thr Lys Lys Ser Pro Ser Pro Glu Phe Ser Gly Met Pro Arg Ile Ser
            500                 505                 510

Lys Leu Gly Ser Gly Asn Asp Phe Glu Val Phe Phe Gln Arg Leu Gly
        515                 520                 525

Ile Ala Ser Gly Arg Ala Arg Tyr Thr Lys Asn Trp Glu Thr Asn Lys
        530                 535                 540

Phe Ser Gly Tyr Pro Leu Tyr His Ser Val Tyr Glu Thr Tyr Glu Leu
545                 550                 555                 560

Val Glu Lys Phe Tyr Asp Pro Met Phe Lys Tyr His Leu Thr Val Ala
                565                 570                 575

Gln Val Arg Gly Gly Met Val Phe Glu Leu Ala Asn Ser Ile Val Leu
            580                 585                 590

Pro Phe Asp Cys Arg Asp Tyr Ala Val Val Leu Arg Lys Tyr Ala Asp
            595                 600                 605
```

```
Lys Ile Tyr Asn Ile Ser Met Lys His Pro Gln Glu Met Lys Thr Tyr
    610                 615                 620

Ser Val Ser Phe Asp Ser Leu Phe Ser Ala Val Lys Asn Phe Thr Glu
625                 630                 635                 640

Ile Ala Ser Lys Phe Thr Glu Arg Leu Gln Asp Phe Asp Lys Ser Asn
                645                 650                 655

Pro Ile Leu Leu Arg Met Met Asn Asp Gln Leu Met Phe Leu Glu Arg
                660                 665                 670

Ala Phe Ile Asp Pro Leu Gly Leu Pro Asp Arg Pro Phe Tyr Arg His
                675                 680                 685

Val Ile Tyr Ala Pro Ser Ser His Asn Lys Tyr Ala Gly Glu Ser Phe
        690                 695                 700

Pro Gly Ile Tyr Asp Ala Leu Phe Asp Ile Glu Ser Lys Val Asp Pro
705                 710                 715                 720

Ser Lys Ala Trp Gly Asp Val Lys Arg Gln Ile Ser Val Ala Ala Phe
                725                 730                 735

Thr Val Gln Ala Ala Ala Glu Thr Leu Ser Glu Val Ala
                740                 745

<210> SEQ ID NO 5
<211> LENGTH: 749
<212> TYPE: PRT
<213> ORGANISM: Artificial Sequence
<220> FEATURE:
<223> OTHER INFORMATION: Description of Artificial Sequence: Synthetic
      Extracellular domain of Macaca fascicularis PSMA with
      purification tags

<400> SEQUENCE: 5

Met Ala Trp Val Trp Thr Leu Leu Phe Leu Met Ala Ala Ala Gln Ser
1               5                   10                  15

Ile Gln Ala Gly Leu Asn Asp Ile Phe Glu Ala Gln Lys Ile Glu Trp
            20                  25                  30

His Glu His His His His His His Gly Ser Lys Ser Ser Ser Glu Ala
        35                  40                  45

Thr Asn Ile Thr Pro Lys His Asn Met Lys Ala Phe Leu Asp Glu Leu
    50                  55                  60

Lys Ala Glu Asn Ile Lys Lys Phe Leu His Asn Phe Thr Gln Ile Pro
65                  70                  75                  80

His Leu Ala Gly Thr Glu Gln Asn Phe Gln Leu Ala Lys Gln Ile Gln
                85                  90                  95

Ser Gln Trp Lys Glu Phe Gly Leu Asp Ser Val Glu Leu Thr His Tyr
            100                 105                 110

Asp Val Leu Leu Ser Tyr Pro Asn Lys Thr His Pro Asn Tyr Ile Ser
        115                 120                 125

Ile Ile Asn Glu Asp Gly Asn Glu Ile Phe Asn Thr Ser Leu Phe Glu
    130                 135                 140

Pro Pro Pro Ala Gly Tyr Glu Asn Val Ser Asp Ile Val Pro Pro Phe
145                 150                 155                 160

Ser Ala Phe Ser Pro Gln Gly Met Pro Glu Gly Asp Leu Val Tyr Val
                165                 170                 175

Asn Tyr Ala Arg Thr Glu Asp Phe Phe Lys Leu Glu Arg Asp Met Lys
            180                 185                 190

Ile Asn Cys Ser Gly Lys Ile Val Ile Ala Arg Tyr Gly Lys Val Phe
        195                 200                 205
```

```
Arg Gly Asn Lys Val Lys Asn Ala Gln Leu Ala Gly Ala Thr Gly Val
    210                 215                 220

Ile Leu Tyr Ser Asp Pro Asp Asp Tyr Phe Ala Pro Gly Val Lys Ser
225                 230                 235                 240

Tyr Pro Asp Gly Trp Asn Leu Pro Gly Gly Val Gln Arg Gly Asn
                245                 250                 255

Ile Leu Asn Leu Asn Gly Ala Gly Asp Pro Leu Thr Pro Gly Tyr Pro
                260                 265                 270

Ala Asn Glu Tyr Ala Tyr Arg Arg Gly Met Ala Glu Ala Val Gly Leu
            275                 280                 285

Pro Ser Ile Pro Val His Pro Ile Gly Tyr Tyr Asp Ala Gln Lys Leu
    290                 295                 300

Leu Glu Lys Met Gly Gly Ser Ala Ser Pro Asp Ser Ser Trp Arg Gly
305                 310                 315                 320

Ser Leu Lys Val Pro Tyr Asn Val Gly Pro Gly Phe Thr Gly Asn Phe
                325                 330                 335

Ser Thr Gln Lys Val Lys Met His Ile His Ser Thr Ser Glu Val Thr
                340                 345                 350

Arg Ile Tyr Asn Val Ile Gly Thr Leu Arg Gly Ala Val Glu Pro Asp
            355                 360                 365

Arg Tyr Val Ile Leu Gly Gly His Arg Asp Ser Trp Val Phe Gly Gly
    370                 375                 380

Ile Asp Pro Gln Ser Gly Ala Ala Val Val His Glu Ile Val Arg Ser
385                 390                 395                 400

Phe Gly Met Leu Lys Lys Glu Gly Trp Arg Pro Arg Arg Thr Ile Leu
                405                 410                 415

Phe Ala Ser Trp Asp Ala Glu Glu Phe Gly Leu Leu Gly Ser Thr Glu
                420                 425                 430

Trp Ala Glu Glu Asn Ser Arg Leu Leu Gln Glu Arg Gly Val Ala Tyr
            435                 440                 445

Ile Asn Ala Asp Ser Ser Ile Glu Gly Asn Tyr Thr Leu Arg Val Asp
    450                 455                 460

Cys Thr Pro Leu Met Tyr Ser Leu Val Tyr Asn Leu Thr Lys Glu Leu
465                 470                 475                 480

Glu Ser Pro Asp Glu Gly Phe Glu Gly Lys Ser Leu Tyr Glu Ser Trp
                485                 490                 495

Thr Lys Lys Ser Pro Ser Pro Glu Phe Ser Gly Met Pro Arg Ile Ser
                500                 505                 510

Lys Leu Gly Ser Gly Asn Asp Phe Glu Val Phe Phe Gln Arg Leu Gly
            515                 520                 525

Ile Ala Ser Gly Arg Ala Arg Tyr Thr Lys Asn Trp Glu Thr Asn Lys
    530                 535                 540

Phe Ser Ser Tyr Pro Leu Tyr His Ser Val Tyr Glu Thr Tyr Glu Leu
545                 550                 555                 560

Val Glu Lys Phe Tyr Asp Pro Met Phe Lys Tyr His Leu Thr Val Ala
                565                 570                 575

Gln Val Arg Gly Gly Met Val Phe Glu Leu Ala Asn Ser Val Val Leu
            580                 585                 590

Pro Phe Asp Cys Arg Asp Tyr Ala Val Val Leu Arg Lys Tyr Ala Asp
    595                 600                 605

Lys Ile Tyr Asn Ile Ser Met Lys His Pro Gln Glu Met Lys Thr Tyr
610                 615                 620
```

```
Ser Val Ser Phe Asp Ser Leu Phe Ser Ala Val Lys Asn Phe Thr Glu
625                 630                 635                 640

Ile Ala Ser Lys Phe Ser Glu Arg Leu Arg Asp Phe Asp Lys Ser Asn
                645                 650                 655

Pro Ile Leu Leu Arg Met Met Asn Asp Gln Leu Met Phe Leu Glu Arg
                660                 665                 670

Ala Phe Ile Asp Pro Leu Gly Leu Pro Asp Arg Pro Phe Tyr Arg His
            675                 680                 685

Val Ile Tyr Ala Pro Ser Ser His Asn Lys Tyr Ala Gly Glu Ser Phe
            690                 695                 700

Pro Gly Ile Tyr Asp Ala Leu Phe Asp Ile Glu Ser Lys Val Asp Pro
705                 710                 715                 720

Ser Gln Ala Trp Gly Glu Val Lys Arg Gln Ile Ser Ile Ala Thr Phe
                725                 730                 735

Thr Val Gln Ala Ala Glu Thr Leu Ser Glu Val Ala
                740                 745
```

<210> SEQ ID NO 6
<211> LENGTH: 967
<212> TYPE: PRT
<213> ORGANISM: Artificial Sequence
<220> FEATURE:
<223> OTHER INFORMATION: Description of Artificial Sequence: Synthetic
      Chimeric protein with Macaca fascicularis PSMA, purification
      tags and human Fc

<400> SEQUENCE: 6

```
Met Ala Trp Val Trp Thr Leu Leu Phe Leu Met Ala Ala Ala Gln Ser
1               5                   10                  15

Ile Gln Ala His Ala Cys Pro Pro Cys Pro Ala Pro Glu Leu Leu Gly
                20                  25                  30

Gly Pro Ser Val Phe Leu Phe Pro Pro Lys Pro Lys Asp Thr Leu Met
            35                  40                  45

Ile Ser Arg Thr Pro Glu Val Thr Cys Val Val Val Asp Val Ser His
        50                  55                  60

Glu Asp Pro Glu Val Lys Phe Asn Trp Tyr Val Asp Gly Val Glu Val
65                  70                  75                  80

His Asn Ala Lys Thr Lys Pro Arg Glu Glu Gln Tyr Asn Ser Thr Tyr
                85                  90                  95

Arg Val Val Ser Val Leu Thr Val Leu His Gln Asp Trp Leu Asn Gly
                100                 105                 110

Lys Glu Tyr Lys Cys Lys Val Ser Asn Lys Ala Leu Pro Ala Pro Ile
            115                 120                 125

Glu Lys Thr Ile Ser Lys Ala Lys Gly Gln Pro Arg Glu Pro Gln Val
        130                 135                 140

Tyr Thr Leu Pro Pro Ser Arg Asp Glu Leu Thr Lys Asn Gln Val Ser
145                 150                 155                 160

Leu Thr Cys Leu Val Lys Gly Phe Tyr Pro Ser Asp Ile Ala Val Glu
                165                 170                 175

Trp Glu Ser Asn Gly Gln Pro Glu Asn Asn Tyr Lys Thr Thr Pro Pro
                180                 185                 190

Val Leu Asp Ser Asp Gly Ser Phe Phe Leu Tyr Ser Lys Leu Thr Val
            195                 200                 205

Asp Lys Ser Arg Trp Gln Gln Gly Asn Val Phe Ser Cys Ser Val Met
        210                 215                 220
```

-continued

His Glu Ala Leu His Asn His Tyr Thr Gln Lys Ser Leu Ser Leu Ser
225                 230                 235                 240

Ala Ser Gly Gly Gly Ser Gly Gly Gly Ser Leu Glu Val Leu
            245                 250                 255

Phe Gln Gly Pro Lys Ser Ser Glu Ala Thr Asn Ile Thr Pro Lys
        260                 265                 270

His Asn Met Lys Ala Phe Leu Asp Glu Leu Lys Ala Glu Asn Ile Lys
    275                 280                 285

Lys Phe Leu His Asn Phe Thr Gln Ile Pro His Leu Ala Gly Thr Glu
        290                 295                 300

Gln Asn Phe Gln Leu Ala Lys Gln Ile Gln Ser Gln Trp Lys Glu Phe
305                 310                 315                 320

Gly Leu Asp Ser Val Glu Leu Thr His Tyr Asp Val Leu Leu Ser Tyr
                325                 330                 335

Pro Asn Lys Thr His Pro Asn Tyr Ile Ser Ile Ile Asn Glu Asp Gly
            340                 345                 350

Asn Glu Ile Phe Asn Thr Ser Leu Phe Glu Pro Pro Ala Gly Tyr
        355                 360                 365

Glu Asn Val Ser Asp Ile Val Pro Pro Phe Ser Ala Phe Ser Pro Gln
370                 375                 380

Gly Met Pro Glu Gly Asp Leu Val Tyr Val Asn Tyr Ala Arg Thr Glu
385                 390                 395                 400

Asp Phe Phe Lys Leu Glu Arg Asp Met Lys Ile Asn Cys Ser Gly Lys
                405                 410                 415

Ile Val Ile Ala Arg Tyr Gly Lys Val Phe Arg Gly Asn Lys Val Lys
                420                 425                 430

Asn Ala Gln Leu Ala Gly Ala Thr Gly Val Ile Leu Tyr Ser Asp Pro
            435                 440                 445

Asp Asp Tyr Phe Ala Pro Gly Val Lys Ser Tyr Pro Asp Gly Trp Asn
        450                 455                 460

Leu Pro Gly Gly Gly Val Gln Arg Gly Asn Ile Leu Asn Leu Asn Gly
465                 470                 475                 480

Ala Gly Asp Pro Leu Thr Pro Gly Tyr Pro Ala Asn Glu Tyr Ala Tyr
                485                 490                 495

Arg Arg Gly Met Ala Glu Ala Val Gly Leu Pro Ser Ile Pro Val His
            500                 505                 510

Pro Ile Gly Tyr Tyr Asp Ala Gln Lys Leu Leu Glu Lys Met Gly Gly
        515                 520                 525

Ser Ala Ser Pro Asp Ser Ser Trp Arg Gly Ser Leu Lys Val Pro Tyr
530                 535                 540

Asn Val Gly Pro Gly Phe Thr Gly Asn Phe Ser Thr Gln Lys Val Lys
545                 550                 555                 560

Met His Ile His Ser Thr Ser Glu Val Thr Arg Ile Tyr Asn Val Ile
                565                 570                 575

Gly Thr Leu Arg Gly Ala Val Glu Pro Asp Arg Tyr Val Ile Leu Gly
            580                 585                 590

Gly His Arg Asp Ser Trp Val Phe Gly Gly Ile Asp Pro Gln Ser Gly
        595                 600                 605

Ala Ala Val Val His Glu Ile Val Arg Ser Phe Gly Met Leu Lys Lys
            610                 615                 620

Glu Gly Trp Arg Pro Arg Arg Thr Ile Leu Phe Ala Ser Trp Asp Ala
625                 630                 635                 640

```
Glu Glu Phe Gly Leu Leu Gly Ser Thr Glu Trp Ala Glu Glu Asn Ser
                645                 650                 655
Arg Leu Leu Gln Glu Arg Gly Val Ala Tyr Ile Asn Ala Asp Ser Ser
            660                 665                 670
Ile Glu Gly Asn Tyr Thr Leu Arg Val Asp Cys Thr Pro Leu Met Tyr
        675                 680                 685
Ser Leu Val Tyr Asn Leu Thr Lys Glu Leu Glu Ser Pro Asp Glu Gly
    690                 695                 700
Phe Glu Gly Lys Ser Leu Tyr Glu Ser Trp Thr Lys Lys Ser Pro Ser
705                 710                 715                 720
Pro Glu Phe Ser Gly Met Pro Arg Ile Ser Lys Leu Gly Ser Gly Asn
                725                 730                 735
Asp Phe Glu Val Phe Phe Gln Arg Leu Gly Ile Ala Ser Gly Arg Ala
            740                 745                 750
Arg Tyr Thr Lys Asn Trp Glu Thr Asn Lys Phe Ser Ser Tyr Pro Leu
        755                 760                 765
Tyr His Ser Val Tyr Glu Thr Tyr Glu Leu Val Glu Lys Phe Tyr Asp
    770                 775                 780
Pro Met Phe Lys Tyr His Leu Thr Val Ala Gln Val Arg Gly Gly Met
785                 790                 795                 800
Val Phe Glu Leu Ala Asn Ser Val Val Leu Pro Phe Asp Cys Arg Asp
                805                 810                 815
Tyr Ala Val Val Leu Arg Lys Tyr Ala Asp Lys Ile Tyr Asn Ile Ser
            820                 825                 830
Met Lys His Pro Gln Glu Met Lys Thr Tyr Ser Val Ser Phe Asp Ser
        835                 840                 845
Leu Phe Ser Ala Val Lys Asn Phe Thr Glu Ile Ala Ser Lys Phe Ser
    850                 855                 860
Glu Arg Leu Arg Asp Phe Asp Lys Ser Asn Pro Ile Leu Leu Arg Met
865                 870                 875                 880
Met Asn Asp Gln Leu Met Phe Leu Glu Arg Ala Phe Ile Asp Pro Leu
                885                 890                 895
Gly Leu Pro Asp Arg Pro Phe Tyr Arg His Val Ile Tyr Ala Pro Ser
            900                 905                 910
Ser His Asn Lys Tyr Ala Gly Glu Ser Phe Pro Gly Ile Tyr Asp Ala
        915                 920                 925
Leu Phe Asp Ile Glu Ser Lys Val Asp Pro Ser Gln Ala Trp Gly Glu
    930                 935                 940
Val Lys Arg Gln Ile Ser Ile Ala Thr Phe Thr Val Gln Ala Ala Ala
945                 950                 955                 960
Glu Thr Leu Ser Glu Val Ala
                965

<210> SEQ ID NO 7
<211> LENGTH: 749
<212> TYPE: PRT
<213> ORGANISM: Artificial Sequence
<220> FEATURE:
<223> OTHER INFORMATION: Description of Artificial Sequence: Synthetic
      Extracellular domain of human PSMA with purification tags

<400> SEQUENCE: 7

Met Ala Trp Val Trp Thr Leu Leu Phe Leu Met Ala Ala Ala Gln Ser
1               5                   10                  15
Ile Gln Ala Gly Leu Asn Asp Ile Phe Glu Ala Gln Lys Ile Glu Trp
            20                  25                  30
```

```
His Glu His His His His His Gly Ser Lys Ser Asn Glu Ala
         35                  40                  45

Thr Asn Ile Thr Pro Lys His Asn Met Lys Ala Phe Leu Asp Glu Leu
 50                  55                  60

Lys Ala Glu Asn Ile Lys Lys Phe Leu Tyr Asn Phe Thr Gln Ile Pro
 65                  70                  75                  80

His Leu Ala Gly Thr Glu Gln Asn Phe Gln Leu Ala Lys Gln Ile Gln
                 85                  90                  95

Ser Gln Trp Lys Glu Phe Gly Leu Asp Ser Val Glu Leu Ala His Tyr
                100                 105                 110

Asp Val Leu Leu Ser Tyr Pro Asn Lys Thr His Pro Asn Tyr Ile Ser
            115                 120                 125

Ile Ile Asn Glu Asp Gly Asn Glu Ile Phe Asn Thr Ser Leu Phe Glu
130                 135                 140

Pro Pro Pro Pro Gly Tyr Glu Asn Val Ser Asp Ile Val Pro Pro Phe
145                 150                 155                 160

Ser Ala Phe Ser Pro Gln Gly Met Pro Glu Gly Asp Leu Val Tyr Val
                165                 170                 175

Asn Tyr Ala Arg Thr Glu Asp Phe Phe Lys Leu Glu Arg Asp Met Lys
            180                 185                 190

Ile Asn Cys Ser Gly Lys Ile Val Ile Ala Arg Tyr Gly Lys Val Phe
            195                 200                 205

Arg Gly Asn Lys Val Lys Asn Ala Gln Leu Ala Gly Ala Lys Gly Val
            210                 215                 220

Ile Leu Tyr Ser Asp Pro Ala Asp Tyr Phe Ala Pro Gly Val Lys Ser
225                 230                 235                 240

Tyr Pro Asp Gly Trp Asn Leu Pro Gly Gly Gly Val Gln Arg Gly Asn
                245                 250                 255

Ile Leu Asn Leu Asn Gly Ala Gly Asp Pro Leu Thr Pro Gly Tyr Pro
            260                 265                 270

Ala Asn Glu Tyr Ala Tyr Arg Arg Gly Ile Ala Glu Ala Val Gly Leu
            275                 280                 285

Pro Ser Ile Pro Val His Pro Ile Gly Tyr Tyr Asp Ala Gln Lys Leu
            290                 295                 300

Leu Glu Lys Met Gly Gly Ser Ala Pro Pro Asp Ser Ser Trp Arg Gly
305                 310                 315                 320

Ser Leu Lys Val Pro Tyr Asn Val Gly Pro Gly Phe Thr Gly Asn Phe
                325                 330                 335

Ser Thr Gln Lys Val Lys Met His Ile His Ser Thr Asn Glu Val Thr
            340                 345                 350

Arg Ile Tyr Asn Val Ile Gly Thr Leu Arg Gly Ala Val Glu Pro Asp
            355                 360                 365

Arg Tyr Val Ile Leu Gly Gly His Arg Asp Ser Trp Val Phe Gly Gly
370                 375                 380

Ile Asp Pro Gln Ser Gly Ala Ala Val Val His Glu Ile Val Arg Ser
385                 390                 395                 400

Phe Gly Thr Leu Lys Lys Glu Gly Trp Arg Pro Arg Arg Thr Ile Leu
                405                 410                 415

Phe Ala Ser Trp Asp Ala Glu Glu Phe Gly Leu Leu Gly Ser Thr Glu
            420                 425                 430

Trp Ala Glu Glu Asn Ser Arg Leu Leu Gln Glu Arg Gly Val Ala Tyr
            435                 440                 445
```

```
Ile Asn Ala Asp Ser Ser Ile Glu Gly Asn Tyr Thr Leu Arg Val Asp
    450                 455                 460

Cys Thr Pro Leu Met Tyr Ser Leu Val His Asn Leu Thr Lys Glu Leu
465                 470                 475                 480

Lys Ser Pro Asp Glu Gly Phe Glu Gly Lys Ser Leu Tyr Glu Ser Trp
                485                 490                 495

Thr Lys Lys Ser Pro Ser Pro Glu Phe Ser Gly Met Pro Arg Ile Ser
                500                 505                 510

Lys Leu Gly Ser Gly Asn Asp Phe Glu Val Phe Phe Gln Arg Leu Gly
                515                 520                 525

Ile Ala Ser Gly Arg Ala Arg Tyr Thr Lys Asn Trp Glu Thr Asn Lys
530                 535                 540

Phe Ser Gly Tyr Pro Leu Tyr His Ser Val Tyr Glu Thr Tyr Glu Leu
545                 550                 555                 560

Val Glu Lys Phe Tyr Asp Pro Met Phe Lys Tyr His Leu Thr Val Ala
                565                 570                 575

Gln Val Arg Gly Gly Met Val Phe Glu Leu Ala Asn Ser Ile Val Leu
                580                 585                 590

Pro Phe Asp Cys Arg Asp Tyr Ala Val Val Leu Arg Lys Tyr Ala Asp
                595                 600                 605

Lys Ile Tyr Ser Ile Ser Met Lys His Pro Gln Glu Met Lys Thr Tyr
610                 615                 620

Ser Val Ser Phe Asp Ser Leu Phe Ser Ala Val Lys Asn Phe Thr Glu
625                 630                 635                 640

Ile Ala Ser Lys Phe Ser Glu Arg Leu Gln Asp Phe Asp Lys Ser Asn
                645                 650                 655

Pro Ile Val Leu Arg Met Met Asn Asp Gln Leu Met Phe Leu Glu Arg
                660                 665                 670

Ala Phe Ile Asp Pro Leu Gly Leu Pro Asp Arg Pro Phe Tyr Arg His
                675                 680                 685

Val Ile Tyr Ala Pro Ser Ser His Asn Lys Tyr Ala Gly Glu Ser Phe
690                 695                 700

Pro Gly Ile Tyr Asp Ala Leu Phe Asp Ile Glu Ser Lys Val Asp Pro
705                 710                 715                 720

Ser Lys Ala Trp Gly Glu Val Lys Arg Gln Ile Tyr Val Ala Ala Phe
                725                 730                 735

Thr Val Gln Ala Ala Glu Thr Leu Ser Glu Val Ala
                740                 745

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      HC CDR 1 of PSMM110

<400> SEQUENCE: 8

Asn Ala Trp Ile Ser
1               5

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      HC CDR 2 of PSMM110
```

-continued

<400> SEQUENCE: 9

Trp Ile Asn Pro Glu Ser Gly Arg Ala Asn Tyr Ala Gln Lys Phe Gln
1               5                   10                  15
Gly

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      HC CDR 3 of PSMM110

<400> SEQUENCE: 10

Glu Leu Tyr Tyr Leu Val Tyr Ser Thr Tyr Tyr Tyr Ala Phe Asp Tyr
1               5                   10                  15

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      LC CDR 1 of PSMM110, 52

<400> SEQUENCE: 11

Arg Ala Ser Gln Ser Ile Asp Arg Trp Leu Asn
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      LC CDR 2 of PSMM110, 85, 57, 52, 81

<400> SEQUENCE: 12

Ala Ala Ser Ser Leu Gln Ser
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      LC CDR 3 of PSMM110, 52

<400> SEQUENCE: 13

Gln Gln Ser Pro Arg Tyr Pro Leu Thr
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      HC CDR 1 of PSMM87

<400> SEQUENCE: 14

Ser Tyr Asp Ile Ser
1               5

```
<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      HC CDR 2 of PSMM87

<400> SEQUENCE: 15

Gly Ile Ile Pro Ile Glu Gly Thr Ala Asn Tyr Ala Gln Lys Phe Gln
1               5                   10                  15

Gly

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      HC CDR 3 of PSMM87

<400> SEQUENCE: 16

Asp Tyr Pro Ala Gly Tyr Gly Phe Asp Tyr
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      LC CDR 1 of PSMM87

<400> SEQUENCE: 17

Arg Ala Ser Gln Ser Val Ser Ser Ser Tyr Leu Ala
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      LC CDR 2 of PSMM87

<400> SEQUENCE: 18

Gly Ala Ser Ser Arg Ala Thr
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      LC CDR 3 of PSMM87

<400> SEQUENCE: 19

Gln Gln Tyr Gly Ser Ser Pro Leu Thr
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      HC CDR 1 of PSMM85
```

```
<400> SEQUENCE: 20

Ser Asp Trp Met Ser
1               5

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      HC CDR 2 of PSMM85

<400> SEQUENCE: 21

Ala Ile Ser Gly Asn Gly Gly Ser Thr Glu Tyr Ala Asp Ser Val Lys
1               5                   10                  15

Gly

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      HC CDR 3 of PSMM85

<400> SEQUENCE: 22

Asp Pro Tyr Tyr Tyr Tyr Asp Gly Asp Ser Tyr Tyr Gly Met Asp Val
1               5                   10                  15

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      LC CDR 1 of PSMM85, 81

<400> SEQUENCE: 23

Arg Ala Ser Gln Ser Ile Ser Ser Tyr Leu Asn
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      LC CDR 3 of PSMM85

<400> SEQUENCE: 24

Gln Gln Ser Tyr Ser Thr Pro
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      HC CDR 1 of PSMM84

<400> SEQUENCE: 25

Ser Asp Ala Met His
1               5
```

```
<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      HC CDR 2 of PSMM84

<400> SEQUENCE: 26

Glu Ile Ser Gly Ser Gly Gly Tyr Thr Asn Tyr Ala Asp Ser Val Lys
1               5                   10                  15

Gly

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      HC CDR 3 of PSMM84

<400> SEQUENCE: 27

Asp Ser Tyr Asp Ser Ser Leu Tyr Val Gly Asp Tyr Phe Asp Tyr
1               5                   10                  15

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      LC CDR 1 of PSMM84

<400> SEQUENCE: 28

Arg Ala Ser Gln Ser Val Ser Ser Tyr Leu Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      LC CDR 2 of PSMM84, 50

<400> SEQUENCE: 29

Asp Ala Ser Asn Arg Ala Thr
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      LC CDR 3 of PSMM84

<400> SEQUENCE: 30

Gln Gln Arg Ser Asn Trp Pro Leu Thr
1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      HC CDR 1 of PSMM57, 52, 50
```

```
<400> SEQUENCE: 31

Ser Tyr Ala Ile Ser
1               5

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      HC CDR 2 of PSMM57

<400> SEQUENCE: 32

Trp Ile Ser Pro Tyr Asn Gly Asn Ala Asn Tyr Ala Gln Lys Phe Gln
1               5                   10                  15

Gly

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      HC CDR 3 of PSMM57

<400> SEQUENCE: 33

Asp Ser Asp Arg Ser Tyr Asn Leu Asp Tyr
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      LC CDR 1 of PSMM57

<400> SEQUENCE: 34

Arg Ala Ser Gln Ser Ile Ser Gly Trp Leu Asn
1               5                   10

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      LC CDR 3 of PSMM57, 81

<400> SEQUENCE: 35

Gln Gln Ser Tyr Ser Thr Pro Leu Thr
1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      HC CDR 1 of PSMM56, 25, 18

<400> SEQUENCE: 36

Ser Tyr Trp Ile Gly
1               5
```

```
<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      HC CDR 2 of PSMM56, 25, 18

<400> SEQUENCE: 37

Ile Ile Tyr Pro Gly Asp Ser Asp Thr Arg Tyr Ser Pro Ser Phe Gln
1               5                   10                  15

Gly

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      HC CDR 3 of PSMM56

<400> SEQUENCE: 38

Gly Leu Pro Ile Trp Tyr Leu Asp Tyr
1               5

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      LC CDR 1 of PSMM56

<400> SEQUENCE: 39

Arg Ala Ser Gln Ser Val Ala Ser Asp Leu Ala
1               5                   10

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      LC CDR 2 of PSMM56

<400> SEQUENCE: 40

Phe Ala Ser Asn Arg Ala Thr
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      LC CDR 3 of PSMM56

<400> SEQUENCE: 41

Gln Gln Ser Ile Thr Trp Pro Phe Thr
1               5

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      HC CDR 2 of PSMM52
```

```
<400> SEQUENCE: 42

Trp Ile Ile Pro Tyr Asn Gly Asn Ala Asn Tyr Ala Gln Lys Phe Gln
1               5                   10                  15

Gly

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      HC CDR 3 of PSMM52

<400> SEQUENCE: 43

Val Asn Ser Ala Ala Leu Val Trp Glu Arg Leu Asp Tyr
1               5                   10

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      HC CDR 2 of PSMM50

<400> SEQUENCE: 44

Gly Ile Ile Pro Ile Phe Gly Thr Ala Asn Tyr Ala Gln Lys Phe Gln
1               5                   10                  15

Gly

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      HC CDR 3 of PSMM50

<400> SEQUENCE: 45

Ala Ser Arg Val Trp His Ala Ser Tyr Gly Tyr Leu Asp Tyr
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      LC CDR 1 of PSMM50

<400> SEQUENCE: 46

Arg Ala Ser Gln Ser Val Ser Lys Trp Leu Ala
1               5                   10

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      LC CDR 3 of PSMM50

<400> SEQUENCE: 47

Gln Gln Arg Phe Thr Ala Pro Trp Thr
1               5
```

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      HC CDR 3 of PSMM25

<400> SEQUENCE: 48

Gly Trp Ala Tyr Asp Arg Gly Leu Asp Tyr
1               5                   10

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      LC CDR 1 of PSMM25, 18

<400> SEQUENCE: 49

Lys Ser Ser Gln Ser Val Leu Tyr Ser Ser Asn Asn Lys Asn Tyr Leu
1               5                   10                  15

Ala

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      LC CDR 2 of PSMM25, 18

<400> SEQUENCE: 50

Trp Ala Ser Thr Arg Glu Ser
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      LC CDR 3 of PSMM25, 18

<400> SEQUENCE: 51

Gln Gln Tyr Tyr Ser Thr Pro Leu Thr
1               5

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      HC CDR 3 of PSMM18

<400> SEQUENCE: 52

Ala Tyr His Tyr Ser Lys Gly Leu Asp Tyr
1               5                   10

<210> SEQ ID NO 53
<211> LENGTH: 5
<212> TYPE: PRT
<213> ORGANISM: Artificial Sequence
<220> FEATURE:

```
<223> OTHER INFORMATION: Description of Artificial Sequence: Synthetic
      HC CDR 1 of PSMM81

<400> SEQUENCE: 53

Asp Tyr Ala Ile Ser
1               5

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      HC CDR 2 of PSMM81

<400> SEQUENCE: 54

Arg Ile Asp Pro Ile Glu Gly Thr Ala Asn Tyr Ala Gln Lys Phe Gln
1               5                   10                  15

Gly

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      HC CDR 3 of PSMM81

<400> SEQUENCE: 55

Asp Arg Tyr Tyr Tyr Asp Gly Val Tyr Trp Tyr Ser Asp Tyr Phe Asp
1               5                   10                  15

Tyr

<210> SEQ ID NO 56
<211> LENGTH: 19
<212> TYPE: PRT
<213> ORGANISM: Artificial Sequence
<220> FEATURE:
<223> OTHER INFORMATION: Description of Artificial Sequence: Synthetic
      Signal sequence

<400> SEQUENCE: 56

Met Ala Trp Val Trp Thr Leu Leu Phe Leu Met Ala Ala Ala Gln Ser
1               5                   10                  15

Ile Gln Ala

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      Avi tag

<400> SEQUENCE: 57

Gly Leu Asn Asp Ile Phe Glu Ala Gln Lys Ile Glu Trp His Glu
1               5                   10                  15

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

<400> SEQUENCE: 58

His His His His His His
1               5

<210> SEQ ID NO 59
<211> LENGTH: 321
<212> TYPE: PRT
<213> ORGANISM: Artificial Sequence
<220> FEATURE:
<223> OTHER INFORMATION: Description of Artificial Sequence: Synthetic
      BirA protein sequence

<400> SEQUENCE: 59

Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
            20                  25                  30

Arg Ala Ala Ile Asn Lys His Ile Gln Thr Leu Arg Asp Trp Gly Val
        35                  40                  45

Asp Val Phe Thr Val Pro Gly Lys Gly Tyr Ser Leu Pro Glu Pro Ile
    50                  55                  60

Gln Leu Leu Asn Ala Lys Gln Ile Leu Gly Gln Leu Asp Gly Gly Ser
65                  70                  75                  80

Val Ala Val Leu Pro Val Ile Asp Ser Thr Asn Gln Tyr Leu Leu Asp
                85                  90                  95

Arg Ile Gly Glu Leu Lys Ser Gly Asp Ala Cys Ile Ala Glu Tyr Gln
            100                 105                 110

Gln Ala Gly Arg Gly Arg Arg Gly Arg Lys Trp Phe Ser Pro Phe Gly
        115                 120                 125

Ala Asn Leu Tyr Leu Ser Met Phe Trp Arg Leu Glu Gln Gly Pro Ala
    130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
            180                 185                 190

Gly Lys Thr Gly Asp Ala Ala Gln Ile Val Ile Gly Ala Gly Ile Asn
        195                 200                 205

Met Ala Met Arg Arg Val Glu Glu Ser Val Val Asn Gln Gly Trp Ile
    210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
            260                 265                 270

Asn Arg Pro Val Lys Leu Ile Ile Gly Asp Lys Glu Ile Phe Gly Ile
        275                 280                 285

Ser Arg Gly Ile Asp Lys Gln Gly Ala Leu Leu Leu Glu Gln Asp Gly
    290                 295                 300

Ile Ile Lys Pro Trp Met Gly Gly Glu Ile Ser Leu Arg Ser Ala Glu
305                 310                 315                 320

Lys

```
<210> SEQ ID NO 60
<211> LENGTH: 122
<212> TYPE: PRT
<213> ORGANISM: Artificial Sequence
<220> FEATURE:
<223> OTHER INFORMATION: Description of Artificial Sequence: Synthetic
      PSMM110 VH

<400> SEQUENCE: 60
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Trp Ile Ser Pro Tyr Asn Gly Asn Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Ser Ala Ala Leu Val Trp Glu Arg Leu Asp Tyr Trp
            100                 105                 110

Gly Gln Gly Thr Leu Val Thr Val Ser Ser
        115                 120

```
<210> SEQ ID NO 61
<211> LENGTH: 107
<212> TYPE: PRT
<213> ORGANISM: Artificial Sequence
<220> FEATURE:
<223> OTHER INFORMATION: Description of Artificial Sequence: Synthetic
      PSMM110 VL

<400> SEQUENCE: 61
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Arg Trp
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Pro Arg Tyr Pro Leu
                85                  90                  95

Thr Phe Gly Gln Gly Thr Lys Val Glu Ile Lys
            100                 105

```
<210> SEQ ID NO 62
<211> LENGTH: 119
<212> TYPE: PRT
<213> ORGANISM: Artificial Sequence
<220> FEATURE:
<223> OTHER INFORMATION: Description of Artificial Sequence: Synthetic
      PSMM87VH

<400> SEQUENCE: 62
```

Gln Val Gln Leu Val Gln Ser Gly Ala Glu Val Lys Lys Pro Gly Ser
1               5                   10                  15

```
Ser Val Lys Val Ser Cys Lys Ala Ser Gly Gly Thr Phe Lys Ser Tyr
            20                  25                  30

Asp Ile Ser Trp Val Arg Gln Ala Pro Gly Gln Gly Leu Glu Trp Met
        35                  40                  45

Gly Gly Ile Ile Pro Ile Glu Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Pro Ala Gly Tyr Gly Phe Asp Tyr Trp Gly Gln Gly
                100                 105                 110

Thr Leu Val Thr Val Ser Ser
        115

<210> SEQ ID NO 63
<211> LENGTH: 108
<212> TYPE: PRT
<213> ORGANISM: Artificial Sequence
<220> FEATURE:
<223> OTHER INFORMATION: Description of Artificial Sequence: Synthetic
      PSMM87 VL

<400> SEQUENCE: 63

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys
                100                 105

<210> SEQ ID NO 64
<211> LENGTH: 125
<212> TYPE: PRT
<213> ORGANISM: Artificial Sequence
<220> FEATURE:
<223> OTHER INFORMATION: Description of Artificial Sequence: Synthetic
      PSMM85 VH

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Ser Asp
            20                  25                  30

Trp Met Ser Trp Val Arg Gln Ala Pro Gly Lys Gly Leu Glu Trp Val
        35                  40                  45

Ser Ala Ile Ser Gly Asn Gly Gly Ser Thr Glu Tyr Ala Asp Ser Val
50                  55                  60

Lys Gly Arg Phe Thr Ile Ser Arg Asp Asn Ser Lys Asn Thr Leu Tyr
65                  70                  75                  80
```

-continued

Leu Gln Met Asn Ser Leu Arg Ala Glu Asp Thr Ala Val Tyr Tyr Cys
                85                  90                  95

Ala Arg Asp Pro Tyr Tyr Tyr Asp Gly Asp Ser Tyr Tyr Gly Met
            100                 105                 110

Asp Val Trp Gly Gln Gly Thr Leu Val Thr Val Ser Ser
        115                 120                 125

<210> SEQ ID NO 65
<211> LENGTH: 107
<212> TYPE: PRT
<213> ORGANISM: Artificial Sequence
<220> FEATURE:
<223> OTHER INFORMATION: Description of Artificial Sequence: Synthetic
      PSMM85 VL

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 66
<211> LENGTH: 124
<212> TYPE: PRT
<213> ORGANISM: Artificial Sequence
<220> FEATURE:
<223> OTHER INFORMATION: Description of Artificial Sequence: Synthetic
      PSMM84 VH

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ser Asp
            20                  25                  30

Ala Met His Trp Val Arg Gln Ala Pro Gly Lys Gly Leu Glu Trp Val
        35                  40                  45

Ser Glu Ile Ser Gly Ser Gly Gly Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Tyr Asp Ser Ser Leu Tyr Val Gly Asp Tyr Phe Asp
            100                 105                 110

Tyr Trp Gly Gln Gly Thr Leu Val Thr Val Ser Ser
        115                 120

<210> SEQ ID NO 67

```
<211> LENGTH: 107
<212> TYPE: PRT
<213> ORGANISM: Artificial Sequence
<220> FEATURE:
<223> OTHER INFORMATION: Description of Artificial Sequence: Synthetic
      PSMM84 VL

<400> SEQUENCE: 67

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys
            100                 105

<210> SEQ ID NO 68
<211> LENGTH: 126
<212> TYPE: PRT
<213> ORGANISM: Artificial Sequence
<220> FEATURE:
<223> OTHER INFORMATION: Description of Artificial Sequence: Synthetic
      PSMM81 VH

<400> SEQUENCE: 68

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asp Asp Tyr
            20                  25                  30

Ala Ile Ser Trp Val Arg Gln Ala Pro Gly Gln Gly Leu Glu Trp Met
        35                  40                  45

Gly Arg Ile Asp Pro Ile Glu Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Tyr Tyr Tyr Asp Gly Val Tyr Trp Tyr Ser Asp Tyr
            100                 105                 110

Phe Asp Tyr Trp Gly Gln Gly Thr Leu Val Thr Val Ser Ser
        115                 120                 125

<210> SEQ ID NO 69
<211> LENGTH: 107
<212> TYPE: PRT
<213> ORGANISM: Artificial Sequence
<220> FEATURE:
<223> OTHER INFORMATION: Description of Artificial Sequence: Synthetic
      PSMM81 VL

<400> SEQUENCE: 69

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105
```

<210> SEQ ID NO 70
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Trp Ile Ser Pro Tyr Asn Gly Asn Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Asp Arg Ser Tyr Asn Leu Asp Tyr Trp Gly Gln Gly
            100                 105                 110

Thr Leu Val Thr Val Ser Ser
        115
```

<210> SEQ ID NO 71
<211> LENGTH: 107
<212> TYPE: PRT
<213> ORGANISM: Artificial Sequence
<220> FEATURE:
<223> OTHER INFORMATION: Description of Artificial Sequence: Synthetic
      PSMM57 VL

<400> SEQUENCE: 71

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Gly Trp
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 72
<211> LENGTH: 118
<212> TYPE: PRT
<213> ORGANISM: Artificial Sequence
<220> FEATURE:
<223> OTHER INFORMATION: Description of Artificial Sequence: Synthetic
      PSMM56 VH

<400> SEQUENCE: 72

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Leu Pro Ile Trp Tyr Leu Asp Tyr Trp Gly Gln Gly Thr
            100                 105                 110

Leu Val Thr Val Ser Ser
        115

<210> SEQ ID NO 73
<211> LENGTH: 107
<212> TYPE: PRT
<213> ORGANISM: Artificial Sequence
<220> FEATURE:
<223> OTHER INFORMATION: Description of Artificial Sequence: Synthetic
      PSMM56 VL

<400> SEQUENCE: 73

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ala Ser Asp
            20                  25                  30

Leu Ala Trp Tyr Gln Gln Lys Pro Gly Gln Ala Pro Arg Leu Leu Ile
        35                  40                  45

Tyr Phe Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ile Thr Trp Pro Phe
                85                  90                  95

Thr Phe Gly Gln Gly Thr Lys Val Glu Ile Lys
            100                 105

<210> SEQ ID NO 74
<211> LENGTH: 122
<212> TYPE: PRT
<213> ORGANISM: Artificial Sequence
<220> FEATURE:

<223> OTHER INFORMATION: Description of Artificial Sequence: Synthetic
      PSMM52 VH

<400> SEQUENCE: 74

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Trp Ile Ile Pro Tyr Asn Gly Asn Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Ser Ala Ala Leu Val Trp Glu Arg Leu Asp Tyr Trp
            100                 105                 110

Gly Gln Gly Thr Leu Val Thr Val Ser Ser
        115                 120

<210> SEQ ID NO 75
<211> LENGTH: 123
<212> TYPE: PRT
<213> ORGANISM: Artificial Sequence
<220> FEATURE:
<223> OTHER INFORMATION: Description of Artificial Sequence: Synthetic
      PSMM50 VH

<400> SEQUENCE: 75

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Arg Val Trp His Ala Ser Tyr Gly Tyr Leu Asp Tyr
            100                 105                 110

Trp Gly Gln Gly Thr Leu Val Thr Val Ser Ser
        115                 120

<210> SEQ ID NO 76
<211> LENGTH: 107
<212> TYPE: PRT
<213> ORGANISM: Artificial Sequence
<220> FEATURE:
<223> OTHER INFORMATION: Description of Artificial Sequence: Synthetic
      PSMM50 VL

<400> SEQUENCE: 76

Glu Ile Val Leu Thr Gln Ser Pro Ala Thr Leu Ser Leu Ser Pro Gly
1               5                   10                  15

```
Glu Arg Ala Thr Leu Ser Cys Arg Ala Ser Gln Ser Val Ser Lys Trp
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Phe Thr Ala Pro Trp
                85                  90                  95

Thr Phe Gly Gln Gly Thr Lys Val Glu Ile Lys
            100                 105

<210> SEQ ID NO 77
<211> LENGTH: 119
<212> TYPE: PRT
<213> ORGANISM: Artificial Sequence
<220> FEATURE:
<223> OTHER INFORMATION: Description of Artificial Sequence: Synthetic
      PSMM25 VH

<400> SEQUENCE: 77

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Trp Ala Tyr Asp Arg Gly Leu Asp Tyr Trp Gly Gln Gly
            100                 105                 110

Thr Leu Val Thr Val Ser Ser
        115

<210> SEQ ID NO 78
<211> LENGTH: 113
<212> TYPE: PRT
<213> ORGANISM: Artificial Sequence
<220> FEATURE:
<223> OTHER INFORMATION: Description of Artificial Sequence: Synthetic
      PSMM25 VL

<400> SEQUENCE: 78

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
65                  70                  75                  80
```

```
Ile Ser Ser Leu Gln Ala Glu Asp Val Ala Val Tyr Tyr Cys Gln Gln
                85                  90                  95

Tyr Tyr Ser Thr Pro Leu Thr Phe Gly Gln Gly Thr Lys Val Glu Ile
            100                 105                 110

Lys

<210> SEQ ID NO 79
<211> LENGTH: 119
<212> TYPE: PRT
<213> ORGANISM: Artificial Sequence
<220> FEATURE:
<223> OTHER INFORMATION: Description of Artificial Sequence: Synthetic
      PSMM18 VH

<400> SEQUENCE: 79

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ala Tyr His Tyr Ser Lys Gly Leu Asp Tyr Trp Gly Gln Gly
            100                 105                 110

Thr Leu Val Thr Val Ser Ser
        115

<210> SEQ ID NO 80
<211> LENGTH: 19
<212> TYPE: PRT
<213> ORGANISM: Mus musculus

<400> SEQUENCE: 80

Met Ala Trp Val Trp Thr Leu Leu Phe Leu Met Ala Ala Ala Gln Ser
1               5                   10                  15

Ile Gln Ala

<210> SEQ ID NO 81
<211> LENGTH: 222
<212> TYPE: PRT
<213> ORGANISM: Homo sapiens

<400> SEQUENCE: 81

His Ala Cys Pro Pro Cys Pro Ala Pro Glu Leu Leu Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80
```

```
Ser Val Leu Thr Val Leu His Gln Asp Trp Leu Asn Gly Lys Glu Tyr
            85                  90                  95

Lys Cys Lys Val Ser Asn Lys Ala Leu Pro Ala Pro Ile Glu Lys Thr
                100                 105                 110

Ile Ser Lys Ala Lys Gly Gln Pro Arg Glu Pro Gln Val Tyr Thr Leu
            115                 120                 125

Pro Pro Ser Arg Asp Glu Leu Thr Lys Asn Gln Val Ser Leu Thr Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
                180                 185                 190

Arg Trp Gln Gln Gly Asn Val Phe Ser Cys Ser Val Met His Glu Ala
                195                 200                 205

Leu His Asn His Tyr Thr Gln Lys Ser Leu Ser Leu Ser Ala
            210                 215                 220

<210> SEQ ID NO 82
<211> LENGTH: 449
<212> TYPE: PRT
<213> ORGANISM: Artificial Sequence
<220> FEATURE:
<223> OTHER INFORMATION: Description of Artificial Sequence: Synthetic
      PSMM169 HC

<400> SEQUENCE: 82

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Trp Ile Ser Pro Tyr Asn Gly Asn Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Ser Ala Ala Leu Val Trp Glu Arg Leu Asp Tyr Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
            195                 200                 205
```

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
    435                 440                 445

Lys

<210> SEQ ID NO 83
<211> LENGTH: 214
<212> TYPE: PRT
<213> ORGANISM: Artificial Sequence
<220> FEATURE:
<223> OTHER INFORMATION: Description of Artificial Sequence: Synthetic
      PSMM169 LC

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Arg Trp
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Pro Arg Tyr Pro Leu
                85                  90                  95

Thr Phe Gly Gln Gly Thr Lys Val Glu Ile Lys Arg Thr Val Ala Ala
            100                 105                 110

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 84
<211> LENGTH: 446
<212> TYPE: PRT
<213> ORGANISM: Artificial Sequence
<220> FEATURE:
<223> OTHER INFORMATION: Description of Artificial Sequence: Synthetic
      PSMM170 HC

<400> SEQUENCE: 84

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Lys Ser Tyr
            20                  25                  30

Asp Ile Ser Trp Val Arg Gln Ala Pro Gly Gln Gly Leu Glu Trp Met
        35                  40                  45

Gly Gly Ile Ile Pro Ile Glu Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Pro Ala Gly Tyr Gly Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240
```

```
Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 85
<211> LENGTH: 215
<212> TYPE: PRT
<213> ORGANISM: Artificial Sequence
<220> FEATURE:
<223> OTHER INFORMATION: Description of Artificial Sequence: Synthetic
      PSMM170 LC

<400> SEQUENCE: 85

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140
```

```
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 86
<211> LENGTH: 452
<212> TYPE: PRT
<213> ORGANISM: Artificial Sequence
<220> FEATURE:
<223> OTHER INFORMATION: Description of Artificial Sequence: Synthetic
      PSMM168 HC

<400> SEQUENCE: 86

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Ser Asp
            20                  25                  30

Trp Met Ser Trp Val Arg Gln Ala Pro Gly Lys Gly Leu Glu Trp Val
        35                  40                  45

Ser Ala Ile Ser Gly Asn Gly Gly Ser Thr Glu Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Tyr Tyr Tyr Asp Gly Asp Ser Tyr Tyr Gly Met
            100                 105                 110

Asp Val Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270
```

```
Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450

<210> SEQ ID NO 87
<211> LENGTH: 214
<212> TYPE: PRT
<213> ORGANISM: Artificial Sequence
<220> FEATURE:
<223> OTHER INFORMATION: Description of Artificial Sequence: Synthetic
      PSMM168 LC

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

-continued

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 88
<211> LENGTH: 451
<212> TYPE: PRT
<213> ORGANISM: Artificial Sequence
<220> FEATURE:
<223> OTHER INFORMATION: Description of Artificial Sequence: Synthetic
      PSMM167 HC

<400> SEQUENCE: 88

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ser Asp
            20                  25                  30

Ala Met His Trp Val Arg Gln Ala Pro Gly Lys Gly Leu Glu Trp Val
        35                  40                  45

Ser Glu Ile Ser Gly Ser Gly Gly Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Tyr Asp Ser Ser Leu Tyr Val Gly Asp Tyr Phe Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

```
His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450

<210> SEQ ID NO 89
<211> LENGTH: 214
<212> TYPE: PRT
<213> ORGANISM: Artificial Sequence
<220> FEATURE:
<223> OTHER INFORMATION: Description of Artificial Sequence: Synthetic
      PSMM167 LC

<400> SEQUENCE: 89

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 90
<211> LENGTH: 453
<212> TYPE: PRT
<213> ORGANISM: Artificial Sequence
<220> FEATURE:
<223> OTHER INFORMATION: Description of Artificial Sequence: Synthetic
      PSMM166 HC

<400> SEQUENCE: 90

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Asp Asp Tyr
            20                  25                  30

Ala Ile Ser Trp Val Arg Gln Ala Pro Gly Gln Gly Leu Glu Trp Met
            35                  40                  45

Gly Arg Ile Asp Pro Ile Glu Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Asp Arg Tyr Tyr Asp Gly Val Tyr Trp Tyr Ser Asp Tyr
            100                 105                 110

Phe Asp Tyr Trp Gly Gln Gly Thr Leu Val Thr Val Ser Ser Ala Ser
            115                 120                 125

Thr Lys Gly Pro Ser Val Phe Pro Leu Ala Pro Cys Ser Arg Ser Thr
130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
            165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
            195                 200                 205

Cys Asn Val Asp His Lys Pro Ser Asn Thr Lys Val Asp Lys Arg Val
            210                 215                 220

Glu Ser Lys Tyr Gly Pro Pro Cys Pro Pro Cys Pro Ala Pro Glu Ala
225                 230                 235                 240

Ala Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
            275                 280                 285

Glu Val His Asn Ala Lys Thr Lys Pro Arg Glu Glu Gln Phe Asn Ser
            290                 295                 300
```

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
            325                 330                 335

Ser Ile Glu Lys Thr Ile Ser Lys Ala Lys Gly Gln Pro Arg Glu Pro
        340                 345                 350

Gln Val Tyr Thr Leu Pro Pro Ser Gln Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
            435                 440                 445

Leu Ser Leu Gly Lys
    450

<210> SEQ ID NO 91
<211> LENGTH: 214
<212> TYPE: PRT
<213> ORGANISM: Artificial Sequence
<220> FEATURE:
<223> OTHER INFORMATION: Description of Artificial Sequence: Synthetic
      PSMM166 LC

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 92
<211> LENGTH: 446
<212> TYPE: PRT
<213> ORGANISM: Artificial Sequence
<220> FEATURE:
<223> OTHER INFORMATION: Description of Artificial Sequence: Synthetic
      PSMM164 HC

<400> SEQUENCE: 92

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Trp Ile Ser Pro Tyr Asn Gly Asn Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Asp Arg Ser Tyr Asn Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

```
Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445
```

<210> SEQ ID NO 93
<211> LENGTH: 214
<212> TYPE: PRT
<213> ORGANISM: Artificial Sequence
<220> FEATURE:
<223> OTHER INFORMATION: Description of Artificial Sequence: Synthetic
      PSMM164 LC

<400> SEQUENCE: 93

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Gly Trp
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

-continued

```
<210> SEQ ID NO 94
<211> LENGTH: 445
<212> TYPE: PRT
<213> ORGANISM: Artificial Sequence
<220> FEATURE:
<223> OTHER INFORMATION: Description of Artificial Sequence: Synthetic
      PSMM163 HC

<400> SEQUENCE: 94

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Leu Pro Ile Trp Tyr Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365
```

-continued

```
Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 95
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ala Ser Asp
            20                  25                  30

Leu Ala Trp Tyr Gln Gln Lys Pro Gly Gln Ala Pro Arg Leu Leu Ile
        35                  40                  45

Tyr Phe Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ile Thr Trp Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 96
<211> LENGTH: 449
<212> TYPE: PRT
<213> ORGANISM: Artificial Sequence
<220> FEATURE:
<223> OTHER INFORMATION: Description of Artificial Sequence: Synthetic
      PSMM162 HC
```

<400> SEQUENCE: 96

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Trp Ile Ile Pro Tyr Asn Gly Asn Ala Asn Tyr Ala Gln Lys Phe
50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Val Asn Ser Ala Ala Leu Val Trp Glu Arg Leu Asp Tyr Trp
            100                 105                 110
Gly Gln Gly Thr Leu Val Thr Val Ser Ser Ala Ser Thr Lys Gly Pro
        115                 120                 125
Ser Val Phe Pro Leu Ala Pro Cys Ser Arg Ser Thr Ser Glu Ser Thr
130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Lys Thr Tyr Thr Cys Asn Val Asp
        195                 200                 205
His Lys Pro Ser Asn Thr Lys Val Asp Lys Arg Val Glu Ser Lys Tyr
210                 215                 220
Gly Pro Pro Cys Pro Pro Cys Pro Ala Pro Glu Ala Ala Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser Gln Glu Asp
            260                 265                 270
Pro Glu Val Gln Phe Asn Trp Tyr Val Asp Gly Val Glu Val His Asn
        275                 280                 285
Ala Lys Thr Lys Pro Arg Glu Glu Gln Phe Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Gln Glu Glu Met Thr Lys Asn Gln Val Ser Leu Thr
        355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
```

-continued

```
Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 97
<211> LENGTH: 450
<212> TYPE: PRT
<213> ORGANISM: Artificial Sequence
<220> FEATURE:
<223> OTHER INFORMATION: Description of Artificial Sequence: Synthetic
      PSMM161 HC

<400> SEQUENCE: 97

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Arg Val Trp His Ala Ser Tyr Gly Tyr Leu Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
            435                 440                 445

Gly Lys
    450

<210> SEQ ID NO 98
<211> LENGTH: 214
<212> TYPE: PRT
<213> ORGANISM: Artificial Sequence
<220> FEATURE:
<223> OTHER INFORMATION: Description of Artificial Sequence: Synthetic
      PSMM161 LC

<400> SEQUENCE: 98

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Lys Trp
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Phe Thr Ala Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
            195                 200                 205

Phe Asn Arg Gly Glu Cys
    210

<210> SEQ ID NO 99
<211> LENGTH: 446
<212> TYPE: PRT
<213> ORGANISM: Artificial Sequence
<220> FEATURE:
<223> OTHER INFORMATION: Description of Artificial Sequence: Synthetic
      PSMM160 HC

<400> SEQUENCE: 99

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Trp Ala Tyr Asp Arg Gly Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320
```

```
Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
            435                 440                 445

<210> SEQ ID NO 100
<211> LENGTH: 220
<212> TYPE: PRT
<213> ORGANISM: Artificial Sequence
<220> FEATURE:
<223> OTHER INFORMATION: Description of Artificial Sequence: Synthetic
      PSMM160 LC

<400> SEQUENCE: 100

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
            50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
            85                  90                  95

Tyr Tyr Ser Thr Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220
```

```
<210> SEQ ID NO 101
<211> LENGTH: 446
<212> TYPE: PRT
<213> ORGANISM: Artificial Sequence
<220> FEATURE:
<223> OTHER INFORMATION: Description of Artificial Sequence: Synthetic
      PSMM159 HC

<400> SEQUENCE: 101
```

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ala Tyr His Tyr Ser Lys Gly Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
            435                 440                 445

<210> SEQ ID NO 102
<211> LENGTH: 125
<212> TYPE: PRT
<213> ORGANISM: Artificial Sequence
<220> FEATURE:
<223> OTHER INFORMATION: Description of Artificial Sequence: Synthetic
      CD38217 VH

<400> SEQUENCE: 102

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 103
<211> LENGTH: 109
<212> TYPE: PRT
<213> ORGANISM: Artificial Sequence
<220> FEATURE:
<223> OTHER INFORMATION: Description of Artificial Sequence: Synthetic
      CD38217 VL

<400> SEQUENCE: 103

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Cys Ala Leu Trp Tyr Ser Asn
                85                  90                  95

```
Leu Trp Val Phe Gly Gly Gly Thr Lys Leu Thr Val Leu
            100                 105

<210> SEQ ID NO 104
<211> LENGTH: 125
<212> TYPE: PRT
<213> ORGANISM: Artificial Sequence
<220> FEATURE:
<223> OTHER INFORMATION: Description of Artificial Sequence: Synthetic
      CD38219 VH

<400> SEQUENCE: 104

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 105
<211> LENGTH: 109
<212> TYPE: PRT
<213> ORGANISM: Artificial Sequence
<220> FEATURE:
<223> OTHER INFORMATION: Description of Artificial Sequence: Synthetic
      CD38219 VL

<400> SEQUENCE: 105

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 106
<211> LENGTH: 120
<212> TYPE: PRT
<213> ORGANISM: Artificial Sequence
<220> FEATURE:
<223> OTHER INFORMATION: Description of Artificial Sequence: Synthetic
      B2M1 VH
```

```
<400> SEQUENCE: 106

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Phe Thr Tyr Gly Phe Ala Tyr Trp Gly Gln
            100                 105                 110

Gly Thr Leu Val Thr Val Ser Ser
            115                 120

<210> SEQ ID NO 107
<211> LENGTH: 111
<212> TYPE: PRT
<213> ORGANISM: Artificial Sequence
<220> FEATURE:
<223> OTHER INFORMATION: Description of Artificial Sequence: Synthetic
      B2M1 VL

<400> SEQUENCE: 107

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Asp Tyr Asn
            20                  25                  30

Gly Ile Ser Tyr Met His Trp Tyr Gln Gln Lys Pro Gly Gln Pro Pro
        35                  40                  45

Lys Leu Leu Ile Tyr Ala Ala Ser Asn Pro Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ile Ile
                85                  90                  95

Glu Asp Pro Trp Thr Phe Gly Gln Gly Thr Lys Val Glu Ile Lys
            100                 105                 110

<210> SEQ ID NO 108
<211> LENGTH: 452
<212> TYPE: PRT
<213> ORGANISM: Artificial Sequence
<220> FEATURE:
<223> OTHER INFORMATION: Description of Artificial Sequence: Synthetic
      CD3B217 HC

<400> SEQUENCE: 108

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45
```

```
Ala Arg Ile Arg Ser Lys Tyr Asn Asn Tyr Ala Thr Tyr Tyr Ala Asp
    50              55              60

Ser Val Lys Gly Arg Phe Thr Ile Ser Arg Asp Asn Ser Lys Asn Thr
65              70              75              80

Leu Tyr Leu Gln Met Asn Ser Leu Arg Ala Glu Asp Thr Ala Val Tyr
                85              90              95

Tyr Cys Val Lys His Gly Asn Phe Gly Asn Ser Tyr Val Ser Trp Phe
            100             105             110

Ala Tyr Trp Gly Gln Gly Thr Leu Val Thr Val Ser Ser Ala Ser Thr
        115             120             125

Lys Gly Pro Ser Val Phe Pro Leu Ala Pro Cys Ser Arg Ser Thr Ser
    130             135             140

Glu Ser Thr Ala Ala Leu Gly Cys Leu Val Lys Asp Tyr Phe Pro Glu
145             150             155             160

Pro Val Thr Val Ser Trp Asn Ser Gly Ala Leu Thr Ser Gly Val His
                165             170             175

Thr Phe Pro Ala Val Leu Gln Ser Ser Gly Leu Tyr Ser Leu Ser Ser
            180             185             190

Val Val Thr Val Pro Ser Ser Leu Gly Thr Lys Thr Tyr Thr Cys
        195             200             205

Asn Val Asp His Lys Pro Ser Asn Thr Lys Val Asp Lys Arg Val Glu
    210             215             220

Ser Lys Tyr Gly Pro Pro Cys Pro Pro Cys Pro Ala Pro Glu Ala Ala
225             230             235             240

Gly Gly Pro Ser Val Phe Leu Phe Pro Pro Lys Pro Lys Asp Thr Leu
                245             250             255

Met Ile Ser Arg Thr Pro Glu Val Thr Cys Val Val Val Asp Val Ser
            260             265             270

Gln Glu Asp Pro Glu Val Gln Phe Asn Trp Tyr Val Asp Gly Val Glu
        275             280             285

Val His Asn Ala Lys Thr Lys Pro Arg Glu Glu Gln Phe Asn Ser Thr
    290             295             300

Tyr Arg Val Val Ser Val Leu Thr Val Leu His Gln Asp Trp Leu Asn
305             310             315             320

Gly Lys Glu Tyr Lys Cys Lys Val Ser Asn Lys Gly Leu Pro Ser Ser
                325             330             335

Ile Glu Lys Thr Ile Ser Lys Ala Lys Gly Gln Pro Arg Glu Pro Gln
            340             345             350

Val Tyr Thr Leu Pro Pro Ser Gln Glu Glu Met Thr Lys Asn Gln Val
        355             360             365

Ser Leu Thr Cys Leu Val Lys Gly Phe Tyr Pro Ser Asp Ile Ala Val
    370             375             380

Glu Trp Glu Ser Asn Gly Gln Pro Glu Asn Asn Tyr Lys Thr Thr Pro
385             390             395             400

Pro Val Leu Asp Ser Asp Gly Ser Phe Leu Leu Tyr Ser Lys Leu Thr
                405             410             415

Val Asp Lys Ser Arg Trp Gln Glu Gly Asn Val Phe Ser Cys Ser Val
            420             425             430

Met His Glu Ala Leu His Asn His Tyr Thr Gln Lys Ser Leu Ser Leu
        435             440             445

Ser Leu Gly Lys
    450
```

<210> SEQ ID NO 109
<211> LENGTH: 215
<212> TYPE: PRT
<213> ORGANISM: Artificial Sequence
<220> FEATURE:
<223> OTHER INFORMATION: Description of Artificial Sequence: Synthetic
      CD3B217 LC

<400> SEQUENCE: 109

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 110
<211> LENGTH: 452
<212> TYPE: PRT
<213> ORGANISM: Artificial Sequence
<220> FEATURE:
<223> OTHER INFORMATION: Description of Artificial Sequence: Synthetic
      CD3B219 HC

<400> SEQUENCE: 110

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Ala
    50                  55                  60

Ser Val Lys Gly Arg Phe Thr Ile Ser Arg Asp Asp Ser Lys Asn Ser
65                  70                  75                  80

```
Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
130             135                 140

Glu Ser Thr Ala Ala Leu Gly Cys Leu Val Lys Asp Tyr Phe Pro Glu
145             150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
            210                 215                 220

Ser Lys Tyr Gly Pro Pro Cys Pro Pro Cys Pro Ala Pro Glu Ala Ala
225             230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
            290                 295                 300

Tyr Arg Val Val Ser Val Leu Thr Val Leu His Gln Asp Trp Leu Asn
305             310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385             390                 395                 400

Pro Val Leu Asp Ser Asp Gly Ser Phe Leu Leu Tyr Ser Lys Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
            435                 440                 445

Ser Leu Gly Lys
    450

<210> SEQ ID NO 111
<211> LENGTH: 215
<212> TYPE: PRT
<213> ORGANISM: Artificial Sequence
```

```
<220> FEATURE:
<223> OTHER INFORMATION: Description of Artificial Sequence: Synthetic
      CD3B219 LC

<400> SEQUENCE: 111

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 112
<211> LENGTH: 346
<212> TYPE: PRT
<213> ORGANISM: Escherichia coli

<400> SEQUENCE: 112

Met Ala Trp Val Trp Thr Leu Leu Phe Leu Met Ala Ala Ala Gln Ser
1               5                   10                  15

Ile Gln Ala Met Lys Asp Asn Thr Val Pro Leu Lys Leu Ile Ala Leu
            20                  25                  30

Leu Ala Asn Gly Glu Phe His Ser Gly Glu Gln Leu Gly Glu Thr Leu
        35                  40                  45

Gly Met Ser Arg Ala Ala Ile Asn Lys His Ile Gln Thr Leu Arg Asp
    50                  55                  60

Trp Gly Val Asp Val Phe Thr Val Pro Gly Lys Gly Tyr Ser Leu Pro
65                  70                  75                  80

Glu Pro Ile Gln Leu Leu Asn Ala Lys Gln Ile Leu Gly Gln Leu Asp
                85                  90                  95

Gly Gly Ser Val Ala Val Leu Pro Val Ile Asp Ser Thr Asn Gln Tyr
            100                 105                 110

Leu Leu Asp Arg Ile Gly Glu Leu Lys Ser Gly Asp Ala Cys Ile Ala
        115                 120                 125
```

Glu Tyr Gln Gln Ala Gly Arg Gly Arg Arg Gly Arg Lys Trp Phe Ser
        130                 135                 140

Pro Phe Gly Ala Asn Leu Tyr Leu Ser Met Phe Trp Arg Leu Glu Gln
145                 150                 155                 160

Gly Pro Ala Ala Ala Ile Gly Leu Ser Leu Val Ile Gly Ile Val Met
                165                 170                 175

Ala Glu Val Leu Arg Lys Leu Gly Ala Asp Lys Val Arg Val Lys Trp
                180                 185                 190

Pro Asn Asp Leu Tyr Leu Gln Asp Arg Lys Leu Ala Gly Ile Leu Val
                195                 200                 205

Glu Leu Thr Gly Lys Thr Gly Asp Ala Ala Gln Ile Val Ile Gly Ala
        210                 215                 220

Gly Ile Asn Met Ala Met Arg Arg Val Glu Glu Ser Val Val Asn Gln
225                 230                 235                 240

Gly Trp Ile Thr Leu Gln Glu Ala Gly Ile Asn Leu Asp Arg Asn Thr
                245                 250                 255

Leu Ala Ala Met Leu Ile Arg Glu Leu Arg Ala Ala Leu Glu Leu Phe
                260                 265                 270

Glu Gln Glu Gly Leu Ala Pro Tyr Leu Ser Arg Trp Glu Lys Leu Asp
        275                 280                 285

Asn Phe Ile Asn Arg Pro Val Lys Leu Ile Ile Gly Asp Lys Glu Ile
290                 295                 300

Phe Gly Ile Ser Arg Gly Ile Asp Lys Gln Gly Ala Leu Leu Leu Glu
305                 310                 315                 320

Gln Asp Gly Ile Ile Lys Pro Trp Met Gly Gly Glu Ile Ser Leu Arg
                325                 330                 335

Ser Ala Glu Lys Asp Tyr Lys Asp Glu Leu
                340                 345

<210> SEQ ID NO 113
<211> LENGTH: 455
<212> TYPE: PRT
<213> ORGANISM: Mus musculus

<400> SEQUENCE: 113

Glu Val Lys Leu Leu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ala Ala Thr Thr
            115                 120                 125

Thr Ala Pro Ser Val Tyr Pro Leu Val Pro Gly Cys Ser Asp Thr Ser
        130                 135                 140

Gly Ser Ser Val Thr Leu Gly Cys Leu Val Lys Gly Tyr Phe Pro Glu
145                 150                 155                 160

Pro Val Thr Val Lys Trp Asn Tyr Gly Ala Leu Ser Ser Gly Val Arg
                165                 170                 175

Thr Val Ser Ser Val Leu Gln Ser Ala Phe Tyr Ser Leu Ser Ser Leu
            180                 185                 190

Val Thr Val Pro Ser Ser Thr Trp Pro Ser Gln Thr Val Ile Cys Asn
        195                 200                 205

Val Ala His Pro Ala Ser Lys Thr Glu Leu Ile Lys Arg Ile Glu Pro
210                 215                 220

Arg Ile Pro Lys Pro Ser Thr Pro Pro Gly Ser Ser Cys Pro Pro Gly
225                 230                 235                 240

Asn Ile Leu Gly Gly Pro Ser Val Phe Ile Phe Pro Pro Lys Pro Lys
                245                 250                 255

Asp Ala Leu Met Ile Ser Leu Thr Pro Lys Val Thr Cys Val Val Val
            260                 265                 270

Asp Val Ser Glu Asp Asp Pro Asp Val His Val Ser Trp Phe Val Asp
        275                 280                 285

Asn Lys Glu Val His Thr Ala Trp Thr Gln Pro Arg Glu Ala Gln Tyr
290                 295                 300

Asn Ser Thr Phe Arg Val Val Ser Ala Leu Pro Ile Gln His Gln Asp
305                 310                 315                 320

Trp Met Arg Gly Lys Glu Phe Lys Cys Lys Val Asn Asn Lys Ala Leu
                325                 330                 335

Pro Ala Pro Ile Glu Arg Thr Ile Ser Lys Pro Lys Gly Arg Ala Gln
            340                 345                 350

Thr Pro Gln Val Tyr Thr Ile Pro Pro Pro Arg Glu Gln Met Ser Lys
        355                 360                 365

Lys Lys Val Ser Leu Thr Cys Leu Val Thr Asn Phe Phe Ser Glu Ala
370                 375                 380

Ile Ser Val Glu Trp Glu Arg Asn Gly Glu Leu Glu Gln Asp Tyr Lys
385                 390                 395                 400

Asn Thr Pro Pro Ile Leu Asp Ser Asp Gly Thr Tyr Phe Leu Tyr Ser
                405                 410                 415

Lys Leu Thr Val Asp Thr Asp Ser Trp Leu Gln Gly Glu Ile Phe Thr
            420                 425                 430

Cys Ser Val Val His Glu Ala Leu His Asn His His Thr Gln Lys Asn
        435                 440                 445

Leu Ser Arg Ser Pro Gly Lys
    450                 455

<210> SEQ ID NO 114
<211> LENGTH: 215
<212> TYPE: PRT
<213> ORGANISM: Mus musculus

<400> SEQUENCE: 114

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

```
Leu Ile Gly Gly Thr Asn Lys Arg Ala Pro Gly Val Pro Ala Arg Phe
         50                  55                  60

Ser Gly Ser Leu Ile Gly Asp Lys Ala Ala Leu Thr Ile Thr Gly Ala
 65              70                  75                  80

Gln Thr Glu Asp Glu Ala Ile Tyr Phe Cys Ala Leu Trp Tyr Ser Asn
                 85                  90                  95

Leu Trp Val Phe Gly Gly Gly Thr Lys Leu Thr Val Leu Gly Gln Pro
            100                 105                 110

Lys Ser Ser Pro Ser Val Thr Leu Phe Pro Pro Ser Ser Glu Glu Leu
        115                 120                 125

Glu Thr Asn Lys Ala Thr Leu Val Cys Thr Ile Thr Asp Phe Tyr Pro
    130                 135                 140

Gly Val Val Thr Val Asp Trp Lys Val Asp Gly Thr Pro Val Thr Gln
145                 150                 155                 160

Gly Met Glu Thr Thr Gln Pro Ser Lys Gln Ser Asn Asn Lys Tyr Met
                165                 170                 175

Ala Ser Ser Tyr Leu Thr Leu Thr Ala Arg Ala Trp Glu Arg His Ser
            180                 185                 190

Ser Tyr Ser Cys Gln Val Thr His Glu Gly His Thr Val Glu Lys Ser
        195                 200                 205

Leu Ser Arg Ala Asp Cys Ser
    210                 215

<210> SEQ ID NO 115
<211> LENGTH: 125
<212> TYPE: PRT
<213> ORGANISM: Artificial Sequence
<220> FEATURE:
<223> OTHER INFORMATION: Description of Artificial Sequence: Synthetic
      CD3H143

<400> SEQUENCE: 115

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asn Thr Tyr
             20                  25                  30

Ala Met Asn Trp Val Arg Gln Ala Pro Gly Lys Gly Leu Glu Trp Val
         35                  40                  45

Ala Arg Ile Arg Ser Lys Tyr Asn Asn Tyr Ala Thr Tyr Tyr Ala Asp
     50                  55                  60

Ser Val Lys Gly Arg Phe Thr Ile Ser Arg Asp Asn Ser Lys Asn Thr
 65              70                  75                  80

Leu Tyr Leu Gln Met Asn Ser Leu Arg Ala Glu Asp Thr Ala Val Tyr
                 85                  90                  95

Tyr Cys Val Lys His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 116
<211> LENGTH: 125
<212> TYPE: PRT
<213> ORGANISM: Artificial Sequence
<220> FEATURE:
<223> OTHER INFORMATION: Description of Artificial Sequence: Synthetic
      CD3H144
```

<400> SEQUENCE: 116

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Gly Arg Ile Arg Ser Lys Tyr Asn Gly Tyr Ala Thr Tyr Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 117
<211> LENGTH: 109
<212> TYPE: PRT
<213> ORGANISM: Artificial Sequence
<220> FEATURE:
<223> OTHER INFORMATION: Description of Artificial Sequence: Synthetic
      CD3L64

<400> SEQUENCE: 117

Gln Ser Val Leu Thr Gln Pro Pro Ser Val Ser Ala Ala Pro Gly Gln
1               5                   10                  15

Lys Val Thr Ile Ser Cys Arg Ser Ser Thr Gly Ala Val Thr Thr Ser
            20                  25                  30

Asn Tyr Ala Asn Trp Val Gln Gln Leu Pro Gly Thr Ala Pro Lys Gly
        35                  40                  45

Leu Ile Gly Gly Thr Asn Lys Arg Ala Pro Gly Ile Pro Asp Arg Phe
    50                  55                  60

Ser Gly Ser Lys Ser Gly Thr Ser Ala Thr Leu Gly Ile Thr Gly Leu
65                  70                  75                  80

Gln Thr Gly Asp Glu Ala Asp Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 118
<211> LENGTH: 447
<212> TYPE: PRT
<213> ORGANISM: Artificial Sequence
<220> FEATURE:
<223> OTHER INFORMATION: Description of Artificial Sequence: Synthetic
      G11 heavy chain

<400> SEQUENCE: 118

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Gly Ile Asn Gly Gly Gly Ser Lys Tyr Tyr Ala Asp Ser Val
    50              55                  60

Lys Gly Arg Phe Thr Ile Ser Arg Asp Asn Ser Lys Asn Thr Leu Tyr
 65              70                  75                  80

Leu Gln Met Asn Ser Leu Arg Ala Glu Asp Thr Ala Val Tyr Tyr Cys
                85                  90                  95

Ala Lys Thr Ser Ala Gln Arg Phe Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 119
<211> LENGTH: 213
<212> TYPE: PRT

<213> ORGANISM: Artificial Sequence
<220> FEATURE:
<223> OTHER INFORMATION: Description of Artificial Sequence: Synthetic G11 light chain

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Ala Pro Lys Leu Leu Ile Tyr
        35                  40                  45

Ala Ala Ser Ser Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Ser Tyr Ser Leu Pro Leu Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 120
<211> LENGTH: 450
<212> TYPE: PRT
<213> ORGANISM: Artificial Sequence
<220> FEATURE:
<223> OTHER INFORMATION: Description of Artificial Sequence: Synthetic CD3B94 heavy chain

<400> SEQUENCE: 120

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

```
Ala Arg Asp Pro Ala Arg Leu Tyr Ser Tyr Tyr Phe Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Leu Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 121
<211> LENGTH: 214
<212> TYPE: PRT
<213> ORGANISM: Artificial Sequence
<220> FEATURE:
<223> OTHER INFORMATION: Description of Artificial Sequence: Synthetic
      CD3B94 Light chain
```

-continued

<400> SEQUENCE: 121

Asp Ile Gln Met Thr Gln Ser Pro Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 122
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ser Tyr Trp Ile Ser
1               5

<210> SEQ ID NO 123
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ile Ile Tyr Pro Gly Asp Ser Tyr Thr Arg Tyr Ser Pro Ser Phe Gln
1               5                   10                  15

Gly

<210> SEQ ID NO 124
<211> LENGTH: 13
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 124

Asp Tyr Glu Trp Glu Leu Phe Asp Ser Arg Leu Asp Tyr
1               5                   10

<210> SEQ ID NO 125
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Ser Trp Val Arg Gln Met Pro Gly Lys Gly Leu Glu Trp Met
            35                  40                  45

Gly Ile Ile Tyr Pro Gly Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Glu Trp Glu Leu Phe Asp Ser Arg Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 126
<211> LENGTH: 750
<212> TYPE: PRT
<213> ORGANISM: Macaca fascicularis

<400> SEQUENCE: 126

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Ser Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu His Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Thr His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Ala Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Thr Gly
    210                 215                 220

Val Ile Leu Tyr Ser Asp Pro Asp Tyr Phe Ala Pro Gly Val Lys
225                 230                 235                 240
```

Ser Tyr Pro Asp Gly Trp Asn Leu Pro Gly Gly Val Gln Arg Gly
            245                 250                 255

Asn Ile Leu Asn Leu Asn Gly Ala Gly Asp Pro Leu Thr Pro Gly Tyr
        260                 265                 270

Pro Ala Asn Glu Tyr Ala Tyr Arg Arg Gly Met Ala Glu Ala Val Gly
            275                 280                 285

Leu Pro Ser Ile Pro Val His Pro Ile Gly Tyr Tyr Asp Ala Gln Lys
        290                 295                 300

Leu Leu Glu Lys Met Gly Gly Ser Ala Ser Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Ser Glu Val
            340                 345                 350

Thr Arg Ile Tyr Asn Val Ile Gly Thr Leu Arg Gly Ala Val Glu Pro
            355                 360                 365

Asp Arg Tyr Val Ile Leu Gly Gly His Arg Asp Ser Trp Val Phe Gly
        370                 375                 380

Gly Ile Asp Pro Gln Ser Gly Ala Ala Val Val His Glu Ile Val Arg
385                 390                 395                 400

Ser Phe Gly Met Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
        450                 455                 460

Asp Cys Thr Pro Leu Met Tyr Ser Leu Val Tyr Asn Leu Thr Lys Glu
465                 470                 475                 480

Leu Glu Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
        530                 535                 540

Lys Phe Ser Ser Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Val Val
            580                 585                 590

Leu Pro Phe Asp Cys Arg Asp Tyr Ala Val Val Leu Arg Lys Tyr Ala
        595                 600                 605

Asp Lys Ile Tyr Asn Ile Ser Met Lys His Pro Gln Glu Met Lys Thr
        610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Arg Asp Phe Asp Lys Ser
                645                 650                 655

Asn Pro Ile Leu Leu Arg Met Met Asn Asp Gln Leu Met Phe Leu Glu
             660                 665                 670

Arg Ala Phe Ile Asp Pro Leu Gly Leu Pro Asp Arg Pro Phe Tyr Arg
         675                 680                 685

His Val Ile Tyr Ala Pro Ser Ser His Asn Lys Tyr Ala Gly Glu Ser
     690                 695                 700

Phe Pro Gly Ile Tyr Asp Ala Leu Phe Asp Ile Glu Ser Lys Val Asp
705                 710                 715                 720

Pro Ser Gln Ala Trp Gly Glu Val Lys Arg Gln Ile Ser Ile Ala Thr
                 725                 730                 735

Phe Thr Val Gln Ala Ala Ala Glu Thr Leu Ser Glu Val Ala
             740                 745                 750

<210> SEQ ID NO 127
<211> LENGTH: 750
<212> TYPE: PRT
<213> ORGANISM: Pan troglodytes

<400> SEQUENCE: 127

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
             20                  25                  30

Phe Leu Leu Gly Phe Leu Phe Gly Trp Phe Ile Lys Ser Ser Asn Glu
         35                  40                  45

Ala Thr Asn Ile Thr Pro Lys His Asn Met Lys Ala Phe Leu Asp Glu
     50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                 85                  90                  95

Gln Ser Gln Trp Lys Glu Phe Gly Leu Asp Ser Val Glu Leu Ala His
             100                 105                 110

Tyr Asp Val Leu Leu Ser Tyr Pro Asn Lys Thr His Pro Asn Tyr Ile
         115                 120                 125

Ser Ile Ile Asn Glu Asp Gly Asn Glu Ile Phe Asn Thr Ser Leu Phe
     130                 135                 140

Glu Pro Pro Pro Gly Tyr Glu Asn Val Leu Asp Ile Val Pro Pro
145                 150                 155                 160

Phe Ser Ala Phe Ser Pro Gln Gly Met Pro Glu Gly Asp Leu Val Tyr
                 165                 170                 175

Val Asn Tyr Ala Arg Thr Glu Asp Phe Phe Lys Leu Glu Arg Asp Met
             180                 185                 190

Lys Ile Asn Cys Ser Gly Lys Ile Val Ile Ala Arg Tyr Gly Lys Val
         195                 200                 205

Phe Arg Gly Asn Lys Val Lys Asn Ala Gln Leu Ala Gly Ala Lys Gly
     210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                 245                 250                 255

Asn Ile Leu Asn Leu Asn Gly Ala Gly Asp Pro Leu Thr Pro Gly Tyr
             260                 265                 270

Pro Ala Asn Glu Tyr Ala Tyr Arg His Gly Ile Ala Glu Ala Val Gly
         275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
                340                 345                 350

Thr Arg Ile Tyr Asn Val Ile Gly Thr Leu Arg Gly Ala Val Glu Pro
                355                 360                 365

Asp Arg Tyr Val Ile Leu Gly Gly His Arg Asp Ser Trp Val Phe Gly
    370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
                420                 425                 430

Glu Trp Ala Glu Glu Asn Ser Arg Leu Leu Gln Glu Arg Gly Val Ala
            435                 440                 445

Tyr Ile Asn Ala Asp Ser Ser Ile Glu Gly Asn Tyr Thr Leu Arg Val
    450                 455                 460

Asp Cys Thr Pro Leu Met Tyr Ser Leu Val Tyr Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
                500                 505                 510

Ser Lys Leu Gly Ser Gly Asn Asp Phe Glu Val Phe Phe Gln Arg Leu
            515                 520                 525

Gly Ile Ala Ser Gly Arg Ala Arg Tyr Thr Lys Asn Trp Glu Thr Asn
    530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
                580                 585                 590

Leu Pro Phe Asp Cys Arg Asp Tyr Ala Val Val Leu Arg Lys Tyr Ala
            595                 600                 605

Asp Lys Ile Tyr Asn Ile Ser Met Lys His Pro Gln Glu Met Lys Thr
    610                 615                 620

Tyr Ser Val Ser Phe Asp Ser Leu Phe Ser Ala Val Lys Asn Phe Thr
625                 630                 635                 640

Glu Ile Ala Ser Lys Phe Thr Glu Arg Leu Gln Asp Phe Asp Lys Ser
                645                 650                 655

Asn Pro Ile Leu Leu Arg Met Met Asn Asp Gln Leu Met Phe Leu Glu
                660                 665                 670

Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr Ala Gly Glu Ser
    690                 695                 700

```
Phe Pro Gly Ile Tyr Asp Ala Leu Phe Asp Ile Glu Ser Lys Val Asp
705                 710                 715                 720

Pro Ser Lys Ala Trp Gly Asp Val Lys Arg Gln Ile Ser Val Ala Ala
            725                 730                 735

Phe Thr Val Gln Ala Ala Glu Thr Leu Ser Glu Val Ala
        740                 745                 750

<210> SEQ ID NO 128
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Glu Val Lys Leu Leu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125

<210> SEQ ID NO 129
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 130
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Glu Ile Ser Gly Ser Gly Gly Tyr Thr Asn Tyr Ala Asp Ser Met Lys
1               5                   10                  15
Gly

<210> SEQ ID NO 131
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Arg Ala Ser Gln Ser Val Ser Asn Tyr Leu Ala
1               5                   10

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gln Gln Arg Arg Asn Trp Pro Leu Thr
1               5

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Asp Ala Ser Tyr Arg Ala Thr
1               5

<210> SEQ ID NO 134
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Glu Ile Ser Gly Ser Gly Gly Tyr Thr Asn Tyr Ala Asp Ser Met Lys
1               5                   10                  15
Ser

<210> SEQ ID NO 135
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 135

Glu Ile Ser Gly Ser Gly Gly Tyr Thr Asn Tyr Ala Asp Ser Leu Lys
1               5                   10                  15

Gly

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gln Gln Arg Gly Asn Trp Pro Leu Thr
1               5

<210> SEQ ID NO 137
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Glu Ile Ser Gly Ser Gly Gly Tyr Thr Asn Tyr Ala Asp Ser Leu Lys
1               5                   10                  15

Ser

<210> SEQ ID NO 138
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ser Asp
                20                  25                  30

Ala Met His Trp Val Arg Gln Ala Pro Gly Lys Gly Leu Glu Trp Val
            35                  40                  45

Ser Glu Ile Ser Gly Ser Gly Gly Tyr Thr Asn Tyr Ala Asp Ser Met
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Tyr Asp Ser Ser Leu Tyr Val Gly Asp Tyr Phe Asp
                100                 105                 110

Tyr Trp Gly Gln Gly Thr Leu Val Thr Val Ser Ser
            115                 120

<210> SEQ ID NO 139
<211> LENGTH: 124
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 139

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ser Asp
            20                  25                  30

Ala Met His Trp Val Arg Gln Ala Pro Gly Lys Gly Leu Glu Trp Val
        35                  40                  45

Ser Glu Ile Ser Gly Ser Gly Gly Tyr Thr Asn Tyr Ala Asp Ser Met
    50                  55                  60

Lys Ser Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Tyr Asp Ser Ser Leu Tyr Val Gly Asp Tyr Phe Asp
            100                 105                 110

Tyr Trp Gly Gln Gly Thr Leu Val Thr Val Ser Ser
        115                 120

<210> SEQ ID NO 140
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 140

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ser Asp
            20                  25                  30

Ala Met His Trp Val Arg Gln Ala Pro Gly Lys Gly Leu Glu Trp Val
        35                  40                  45

Ser Glu Ile Ser Gly Ser Gly Gly Tyr Thr Asn Tyr Ala Asp Ser Leu
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Tyr Asp Ser Ser Leu Tyr Val Gly Asp Tyr Phe Asp
            100                 105                 110

Tyr Trp Gly Gln Gly Thr Leu Val Thr Val Ser Ser
        115                 120

<210> SEQ ID NO 141
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 141

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Lys Ser Asp
            20                  25                  30

Ala Met His Trp Val Arg Gln Ala Pro Gly Lys Gly Leu Glu Trp Val
        35                  40                  45

Ser Glu Ile Ser Gly Ser Gly Gly Tyr Thr Asn Tyr Ala Asp Ser Leu
 50                  55                  60

Lys Ser Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ser Tyr Asp Ser Ser Leu Tyr Val Gly Asp Tyr Phe Asp
            100                 105                 110

Tyr Trp Gly Gln Gly Thr Leu Val Thr Val Ser Ser
        115                 120

<210> SEQ ID NO 142
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Asn Tyr
            20                  25                  30

Leu Ala Trp Tyr Gln Gln Lys Pro Gly Gln Ala Pro Arg Leu Leu Ile
        35                  40                  45

His Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Arg Asn Trp Pro Leu
                 85                  90                  95

Thr Phe Gly Gln Gly Thr Lys Val Glu Ile Lys
            100                 105

<210> SEQ ID NO 143
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Tyr Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80
```

Glu Asp Phe Ala Val Tyr Tyr Cys Gln Gln Arg Arg Asn Trp Pro Leu
                85                  90                  95

Thr Phe Gly Gln Gly Thr Lys Val Glu Ile Lys
            100                 105

<210> SEQ ID NO 144
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Gly Asn Trp Pro Leu
                85                  90                  95

Thr Phe Gly Gln Gly Thr Lys Val Glu Ile Lys
            100                 105

<210> SEQ ID NO 145
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ser Asp
            20                  25                  30

Ala Met His Trp Val Arg Gln Ala Pro Gly Lys Gly Leu Glu Trp Val
        35                  40                  45

Ser Glu Ile Ser Gly Ser Gly Gly Tyr Thr Asn Tyr Ala Asp Ser Met
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Tyr Asp Ser Ser Leu Tyr Val Gly Asp Tyr Phe Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450

<210> SEQ ID NO 146
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ser Asp
            20                  25                  30

Ala Met His Trp Val Arg Gln Ala Pro Gly Lys Gly Leu Glu Trp Val
        35                  40                  45

-continued

```
Ser Glu Ile Ser Gly Ser Gly Gly Tyr Thr Asn Tyr Ala Asp Ser Met
     50                  55                  60

Lys Ser Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ser Tyr Asp Ser Ser Leu Tyr Val Gly Asp Tyr Phe Asp
            100                 105                 110

Tyr Trp Gly Gln Gly Thr Leu Val Thr Val Ser Ser Ala Ser Thr Lys
            115                 120                 125

Gly Pro Ser Val Phe Pro Leu Ala Pro Cys Ser Arg Ser Thr Ser Glu
            130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
            195                 200                 205

Val Asp His Lys Pro Ser Asn Thr Lys Val Asp Lys Arg Val Glu Ser
210                 215                 220

Lys Tyr Gly Pro Pro Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
            275                 280                 285

His Asn Ala Lys Thr Lys Pro Arg Glu Glu Gln Phe Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
            435                 440                 445

Leu Gly Lys
450
```

<210> SEQ ID NO 147
<211> LENGTH: 451
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 147

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ser Asp
            20                  25                  30

Ala Met His Trp Val Arg Gln Ala Pro Gly Lys Gly Leu Glu Trp Val
        35                  40                  45

Ser Glu Ile Ser Gly Ser Gly Gly Tyr Thr Asn Tyr Ala Asp Ser Leu
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Tyr Asp Ser Ser Leu Tyr Val Gly Asp Tyr Phe Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

-continued

```
Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450

<210> SEQ ID NO 148
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asn Tyr
            20                  25                  30

Leu Ala Trp Tyr Gln Gln Lys Pro Gly Gln Ala Pro Arg Leu Leu Ile
        35                  40                  45

His Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Arg Asn Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 149
<211> LENGTH: 214
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 149

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Tyr Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Arg Asn Trp Pro Leu
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 150
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Gly Asn Trp Pro Leu
                85                  90                  95

Thr Phe Gly Gln Gly Thr Lys Val Glu Ile Lys Arg Thr Val Ala Ala
                100                 105                 110

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 151
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ser Asp
            20                  25                  30

Ala Met His Trp Val Arg Gln Ala Pro Gly Lys Gly Leu Glu Trp Val
        35                  40                  45

Ser Glu Ile Ser Gly Ser Gly Gly Tyr Thr Asn Tyr Ala Asp Ser Leu
    50                  55                  60

Lys Ser Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Tyr Asp Ser Ser Leu Tyr Val Gly Asp Tyr Phe Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Ala Ala Gly
225                 230                 235                 240
```

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450

<210> SEQ ID NO 152
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Gln Val Gln Leu Gln Gln Ser Gly Pro Arg Leu Val Arg Pro Ser Gln
1               5                   10                  15

Thr Leu Ser Leu Thr Cys Ala Ile Ser Gly Asp Ser Val Phe Asn Asn
            20                  25                  30

Asn Ala Ala Trp Ser Trp Ile Arg Gln Ser Pro Ser Arg Gly Leu Glu
        35                  40                  45

Trp Leu Gly Arg Thr Tyr Tyr Arg Ser Lys Trp Leu Tyr Asp Tyr Ala
    50                  55                  60

Val Ser Val Lys Ser Arg Ile Thr Val Asn Pro Asp Thr Ser Arg Asn
65                  70                  75                  80

Gln Phe Thr Leu Gln Leu Asn Ser Val Thr Pro Glu Asp Thr Ala Leu
                85                  90                  95

Tyr Tyr Cys Ala Arg Gly Tyr Ser Ser Phe Asp Tyr Trp Gly Gln
            100                 105                 110

Gly Thr Leu Val Thr Val Ser Ser
        115                 120

```
<210> SEQ ID NO 153
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153
```

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asn Ile Gly Thr Tyr
            20                  25                  30

Lys Phe Val Ser Trp Tyr Gln Gln His Pro Asp Lys Ala Pro Lys Val
        35                  40                  45

Leu Leu Tyr Glu Val Ser Lys Arg Pro Ser Gly Val Ser Ser Arg Phe
    50                  55                  60

Ser Gly Ser Lys Ser Gly Asn Thr Ala Ser Leu Thr Ile Ser Gly Leu
65                  70                  75                  80

Gln Ala Glu Asp Gln Ala Asp Tyr His Cys Val Ser Tyr Ala Gly Ser
                85                  90                  95

Gly Thr Leu Leu Phe Gly Gly Thr Lys Leu Thr Val Leu
            100                 105                 110

```
<210> SEQ ID NO 154
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154
```

Met Ala Trp Val Trp Thr Leu Leu Phe Leu Met Ala Ala Ala Gln Ser
1               5                   10                  15

Ile Gln Ala Gln Val Gln Leu Gln Gln Ser Gly Pro Arg Leu Val Arg
            20                  25                  30

Pro Ser Gln Thr Leu Ser Leu Thr Cys Ala Ile Ser Gly Asp Ser Val
        35                  40                  45

Phe Asn Asn Asn Ala Ala Trp Ser Trp Ile Arg Gln Ser Pro Ser Arg
    50                  55                  60

Gly Leu Glu Trp Leu Gly Arg Thr Tyr Tyr Arg Ser Lys Trp Leu Tyr
65                  70                  75                  80

Asp Tyr Ala Val Ser Val Lys Ser Arg Ile Thr Val Asn Pro Asp Thr
                85                  90                  95

Ser Arg Asn Gln Phe Thr Leu Gln Leu Asn Ser Val Thr Pro Glu Asp
            100                 105                 110

Thr Ala Leu Tyr Tyr Cys Ala Arg Gly Tyr Ser Ser Ser Phe Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

```
Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Pro Cys Pro Ala Pro Glu Ala Ala Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Gln Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Leu Leu Tyr Ser Lys Leu Thr Val Asp
            420                 425                 430

Lys Ser Arg Trp Gln Glu Gly Asn Val Phe Ser Cys Ser Val Met His
        435                 440                 445

Glu Ala Leu His Asn His Tyr Thr Gln Lys Ser Leu Ser Leu Ser Leu
    450                 455                 460

Gly Lys
465

<210> SEQ ID NO 155
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Met Ala Arg Ser Ala Leu Leu Ile Leu Ala Leu Leu Leu Gly Leu
1               5                   10                  15

Phe Ser Pro Gly Ala Trp Gly Gln Ser Ala Leu Thr Gln Pro Ala Ser
            20                  25                  30

Val Ser Gly Ser Pro Gly Gln Ser Ile Thr Ile Ser Cys Thr Gly Thr
        35                  40                  45

Ser Ser Asn Ile Gly Thr Tyr Lys Phe Val Ser Trp Tyr Gln Gln His
    50                  55                  60
```

```
Pro Asp Lys Ala Pro Lys Val Leu Leu Tyr Glu Val Ser Lys Arg Pro
 65                  70                  75                  80

Ser Gly Val Ser Ser Arg Phe Ser Gly Ser Lys Ser Gly Asn Thr Ala
                 85                  90                  95

Ser Leu Thr Ile Ser Gly Leu Gln Ala Glu Asp Gln Ala Asp Tyr His
            100                 105                 110

Cys Val Ser Tyr Ala Gly Ser Gly Thr Leu Leu Phe Gly Gly Gly Thr
        115                 120                 125

Lys Leu Thr Val Leu Gly Gln Pro Lys Ala Ala Pro Ser Val Thr Leu
130                 135                 140

Phe Pro Pro Ser Ser Glu Glu Leu Gln Ala Asn Lys Ala Thr Leu Val
145                 150                 155                 160

Cys Leu Ile Ser Asp Phe Tyr Pro Gly Ala Val Thr Val Ala Trp Lys
                165                 170                 175

Ala Asp Ser Ser Pro Val Lys Ala Gly Val Glu Thr Thr Thr Pro Ser
            180                 185                 190

Lys Gln Ser Asn Asn Lys Tyr Ala Ala Ser Ser Tyr Leu Ser Leu Thr
        195                 200                 205

Pro Glu Gln Trp Lys Ser His Arg Ser Tyr Ser Cys Gln Val Thr His
210                 215                 220

Glu Gly Ser Thr Val Glu Lys Thr Val Ala Pro Thr Glu Cys Ser
225                 230                 235

<210> SEQ ID NO 156
<211> LENGTH: 4
<212> TYPE: PRT
<213> ORGANISM: Unknown
<220> FEATURE:
<223> OTHER INFORMATION: Description of Unknown:
      'KDEL' family motif peptide

<400> SEQUENCE: 156

Lys Asp Glu Leu
1

<210> SEQ ID NO 157
<211> LENGTH: 752
<212> TYPE: PRT
<213> ORGANISM: Mus musculus

<400> SEQUENCE: 157

Met Trp Asn Ala Leu Gln Asp Arg Asp Ser Ala Glu Val Leu Gly His
1               5                   10                  15

Arg Gln Arg Trp Leu Arg Val Gly Thr Leu Val Leu Ala Leu Thr Gly
                20                  25                  30

Thr Phe Leu Ile Gly Phe Leu Phe Gly Trp Phe Ile Lys Pro Ser Asn
            35                  40                  45

Glu Ala Thr Gly Asn Val Ser His Ser Gly Met Lys Lys Glu Phe Leu
        50                  55                  60

His Glu Leu Lys Ala Glu Asn Ile Lys Lys Phe Leu Tyr Asn Phe Thr
65                  70                  75                  80

Arg Thr Pro His Leu Ala Gly Thr Gln Asn Asn Phe Glu Leu Ala Lys
                85                  90                  95

Gln Ile His Asp Gln Trp Lys Glu Phe Gly Leu Asp Leu Val Glu Leu
            100                 105                 110

Ser His Tyr Asp Val Leu Leu Ser Tyr Pro Asn Lys Thr His Pro Asn
        115                 120                 125
```

```
Tyr Ile Ser Ile Ile Asn Glu Asp Gly Asn Glu Ile Phe Lys Thr Ser
    130                 135                 140

Leu Ser Glu Gln Pro Pro Gly Tyr Glu Asn Ile Ser Asp Val Val
145                 150                 155                 160

Pro Pro Tyr Ser Ala Phe Ser Pro Gln Gly Thr Pro Glu Gly Asp Leu
                165                 170                 175

Val Tyr Val Asn Tyr Ala Arg Thr Glu Asp Phe Phe Lys Leu Glu Arg
            180                 185                 190

Glu Met Lys Ile Ser Cys Ser Gly Lys Ile Val Ile Ala Arg Tyr Gly
        195                 200                 205

Lys Val Phe Arg Gly Asn Met Val Lys Asn Ala Gln Leu Ala Gly Ala
    210                 215                 220

Lys Gly Met Ile Leu Tyr Ser Asp Pro Ala Asp Tyr Phe Val Pro Ala
225                 230                 235                 240

Val Lys Ser Tyr Pro Asp Gly Trp Asn Leu Pro Gly Gly Gly Val Gln
                245                 250                 255

Arg Gly Asn Val Leu Asn Leu Asn Gly Ala Gly Asp Pro Leu Thr Pro
            260                 265                 270

Gly Tyr Pro Ala Asn Glu His Ala Tyr Arg His Glu Leu Thr Asn Ala
        275                 280                 285

Val Gly Leu Pro Ser Ile Pro Val His Pro Ile Gly Tyr Asp Asp Ala
    290                 295                 300

Gln Lys Leu Leu Glu His Met Gly Gly Pro Ala Pro Pro Asp Ser Ser
305                 310                 315                 320

Trp Lys Gly Gly Leu Lys Val Pro Tyr Asn Val Gly Pro Gly Phe Ala
                325                 330                 335

Gly Asn Phe Ser Thr Gln Lys Val Lys Met His Ile His Ser Tyr Thr
            340                 345                 350

Lys Val Thr Arg Ile Tyr Asn Val Ile Gly Thr Leu Lys Gly Ala Leu
        355                 360                 365

Glu Pro Asp Arg Tyr Val Ile Leu Gly Gly His Arg Asp Ala Trp Val
370                 375                 380

Phe Gly Gly Ile Asp Pro Gln Ser Gly Ala Ala Val Val His Glu Ile
385                 390                 395                 400

Val Arg Ser Phe Gly Thr Leu Lys Lys Lys Gly Arg Arg Pro Arg Arg
                405                 410                 415

Thr Ile Leu Phe Ala Ser Trp Asp Ala Glu Glu Phe Gly Leu Leu Gly
            420                 425                 430

Ser Thr Glu Trp Ala Glu Glu His Ser Arg Leu Leu Gln Glu Arg Gly
        435                 440                 445

Val Ala Tyr Ile Asn Ala Asp Ser Ser Ile Glu Gly Asn Tyr Thr Leu
    450                 455                 460

Arg Val Asp Cys Thr Pro Leu Met Tyr Ser Leu Val Tyr Asn Leu Thr
465                 470                 475                 480

Lys Glu Leu Gln Ser Pro Asp Glu Gly Phe Glu Gly Lys Ser Leu Tyr
                485                 490                 495

Asp Ser Trp Lys Glu Lys Ser Pro Ser Pro Glu Phe Ile Gly Met Pro
            500                 505                 510

Arg Ile Ser Lys Leu Gly Ser Gly Asn Asp Phe Glu Val Phe Phe Gln
        515                 520                 525

Arg Leu Gly Ile Ala Ser Gly Arg Ala Arg Tyr Thr Lys Asn Trp Lys
    530                 535                 540
```

```
Thr Asn Lys Val Ser Ser Tyr Pro Leu Tyr His Ser Val Tyr Glu Thr
545                 550                 555                 560

Tyr Glu Leu Val Val Lys Phe Tyr Asp Pro Thr Phe Lys Tyr His Leu
                565                 570                 575

Thr Val Ala Gln Val Arg Gly Ala Met Val Phe Glu Leu Ala Asn Ser
            580                 585                 590

Ile Val Leu Pro Phe Asp Cys Gln Ser Tyr Ala Val Ala Leu Lys Lys
            595                 600                 605

Tyr Ala Asp Thr Ile Tyr Asn Ile Ser Met Lys His Pro Gln Glu Met
            610                 615                 620

Lys Ala Tyr Met Ile Ser Phe Asp Ser Leu Phe Ser Ala Val Asn Asn
625                 630                 635                 640

Phe Thr Asp Val Ala Ser Lys Phe Asn Gln Arg Leu Gln Glu Leu Asp
                645                 650                 655

Lys Ser Asn Pro Ile Leu Leu Arg Ile Met Asn Asp Gln Leu Met Tyr
            660                 665                 670

Leu Glu Arg Ala Phe Ile Asp Pro Leu Gly Leu Pro Gly Arg Pro Phe
            675                 680                 685

Tyr Arg His Ile Ile Tyr Ala Pro Ser Ser His Asn Lys Tyr Ala Gly
690                 695                 700

Glu Ser Phe Pro Gly Ile Tyr Asp Ala Leu Phe Asp Ile Ser Ser Lys
705                 710                 715                 720

Val Asn Ala Ser Lys Ala Trp Asn Glu Val Lys Arg Gln Ile Ser Ile
                725                 730                 735

Ala Thr Phe Thr Val Gln Ala Ala Glu Thr Leu Arg Glu Val Ala
            740                 745                 750

<210> SEQ ID NO 158
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ser Asp
                20                  25                  30

Ala Met His Trp Val Arg Gln Ala Pro Gly Lys Gly Leu Glu Trp Val
            35                  40                  45

Ser Glu Ile Ser Gly Ser Gly Gly Tyr Thr Asn Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Tyr Asp Ser Ser Leu Tyr Val Gly Asp Tyr Phe Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160
```

```
Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
            210                 215                 220

Lys Ser Cys
225

<210> SEQ ID NO 159
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 160
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 160

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Ile Ile Tyr Pro Gly Asp Ser Tyr Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Glu Trp Glu Leu Phe Asp Ser Arg Leu Asp Tyr Trp
                100                 105                 110

Gly Gln Gly Thr Leu Val Thr Val Ser Ser
            115                 120

<210> SEQ ID NO 161
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 161

```
atggcttggg tgtggacctt gctattcctg atggcagctg cccaaagtat acaggccgag     60
gttcagctgc tggaatctgg cggaggattg gttcagcctg gcggctctct gagactgtct    120
tgtgccgctt ctggcttcac cttcaagtcc gacgctatgc actgggtccg acaggcccct    180
ggaaaaggac tggaatgggt gtccgagatc tctggtctg gcggctacac caactacgcc    240
gactccatga agtcccggtt caccatctct cgggacaact ccaagaacac cctgtacctg    300
cagatgaact ccctgagagc cgaggacacc gccgtgtact actgcgccag agactcctac    360
gactccagcc tgtacgtggg cgactacttc gattattggg gccagggcac cctggtcacc    420
gtttcttctg cttccaccaa gggcccatcc gtcttccccc tggcgccctg ctccaggagc    480
acctccgaga gcacagccgc cctgggctgc ctggtcaagg actacttccc cgaaccggtg    540
acggtgtcgt ggaactcagg cgccctgacc agcggcgtgc acaccttccc ggctgtccta    600
cagtcctcag gactctactc cctcagcagc gtggtgaccg tgccctccag cagcttgggc    660
acgaaaacct acacctgcaa cgtagatcac aagcccagca acaccaaggt ggacaagaga    720
gttgagtcca aatatggtcc cccatgccca ccatgcccag cacctgaggc cgccggggga    780
ccatcagtct tcctgttccc cccaaaaccc aaggacactc tcatgatctc ccggacccct    840
gaggtcacgt gcgtggtggt ggacgtgagc caggaagacc ccgaggtcca gttcaactgg    900
tacgtggatg gcgtggaggt gcataatgcc aagacaaagc cgcggggagga gcagttcaac    960
agcacgtacc gtgtggtcag cgtcctcacc gtcctgcacc aggactggct gaacggcaag   1020
gagtacaagt gcaaggtctc caacaaaggc ctcccgtcct ccatcgagaa aaccatctcc   1080
aaagccaaag ggcagccccg agagccacag gtgtacaccc tgcccccatc ccaggaggag   1140
atgaccaaga accaggtcag cctgacctgc ctggtcaaag gcttctaccc cagcgacatc   1200
gccgtggagt gggagagcaa tgggcagccg gagaacaact acaagaccac gcctcccgtg   1260
```

-continued

```
ctggactccg acggctcctt cttcctctac agcaggctaa ccgtggacaa gagcaggtgg    1320
caggagggga atgtcttctc atgctccgtg atgcatgagg ctctgcacaa ccactacaca    1380
cagaagagcc tctccctgtc tctgggtaaa                                     1410
```

<210> SEQ ID NO 162
<211> LENGTH: 699
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 162

```
atggcctggg tgtggaccct gctgttcctg atggccgccg cccagagcat ccaggccgag     60
atcgtgctga cccagagccc cgccaccctg agcctgagcc ccggcgagcg ggccaccctg    120
agctgccggg ccagccagag cgtgagcagc tacctggcct ggtaccagca gaagcccggc    180
caggcccccc ggctgctgat ctacgacgcc agcaaccggg ccaccggcat ccccgcccgg    240
ttcagcggca gcggcagcgg caccgacttc accctgacca tcagcagcct ggagcccgag    300
gacttcgccg tgtactactg ccagcagcgg agcaactggc ccctgacctt cggccagggc    360
accaaggtgg agatcaagcg tacggtggct gcaccatctg tcttcatctt cccgccatct    420
gatgagcagt tgaaatctgg aactgcctct gttgtgtgcc tgctgaataa cttctatccc    480
agagaggcca agtacagtg gaaggtggat aacgccctcc aatcgggtaa ctcccaggag    540
agtgtcacag agcaggacag caaggacagc acctacagcc tcagcagcac cctgacgctg    600
agcaaagcag actacgagaa acacaaagtc tacgcctgcg aagtcaccca tcagggcctg    660
agctcgcccg tcacaaagag cttcaacagg ggagagtgt                            699
```